US011447486B2

United States Patent
Kim et al.

(10) Patent No.: US 11,447,486 B2
(45) Date of Patent: Sep. 20, 2022

(54) 2-AMINO-BENZIMIDAZOLE DERIVATIVES AND THEIR USE AS 5-LIPOXYGENASE AND/OR PROSTAGLANDIN E SYNTHASE INHIBITORS

(71) Applicants: INSTITUT PASTEUR KOREA, Gyeonggi-Do (KR); QURIENT CO., LTD., Gyeonggi-Do (KR)

(72) Inventors: Jaeseung Kim, Seoul (KR); Seohyun Ahn, Gyeonggi-Do (KR); Yeejin Jeon, Seoul (KR); Dongsik Park, Gyeonggi-Do (KR); Young-In Yang, Gyeonggi-Do (KR); Doohyung Lee, Busan (KR); Saeyeon Lee, Gyeonggi-Do (KR); Jiye Ahn, Gyeonggi-Do (KR); Jeongjun Kim, Seoul (KR); Kiyean Nam, Gyeonggi-Do (KR); Sunhee Kang, Gyeonggi-Do (KR); Minjung Seo, Incheon (KR); Mooyoung Seo, Gyeonggi-Do (KR); Jeongjea Seo, Seoul (KR); Sung-Jun Han, Seoul (KR); Jung Hwan Kim, Gyeonggi-Do (KR); Sangchul Lee, Gyeonggi-Do (KR); Gahee Choi, Seoul (KR); Yunmi Lee, Gyeonggi-Do (KR)

(73) Assignees: INSTITUT PASTEUR KOREA, Gyeonggi-Do (KR); QURIENT CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/327,560

(22) PCT Filed: Jul. 31, 2015

(86) PCT No.: PCT/EP2015/067644
§ 371 (c)(1),
(2) Date: Jan. 19, 2017

(87) PCT Pub. No.: WO2016/016421
PCT Pub. Date: Feb. 4, 2016

(65) Prior Publication Data
US 2017/0166563 A1   Jun. 15, 2017

Related U.S. Application Data

(60) Provisional application No. 62/031,337, filed on Jul. 31, 2014.

(51) Int. Cl.
*C07D 471/04* (2006.01)
*C07D 403/12* (2006.01)
(Continued)

(52) U.S. Cl.
CPC ......... *C07D 471/04* (2013.01); *C07D 235/20* (2013.01); *C07D 235/30* (2013.01);
(Continued)

(58) Field of Classification Search
None
See application file for complete search history.

(56) References Cited

U.S. PATENT DOCUMENTS 4,002,623 A * 1/1977 Kadin .................. C07C 335/38
544/132
4,835,161 A * 5/1989 Janssens ............. C07D 401/12
514/255.05
(Continued)

FOREIGN PATENT DOCUMENTS

CN     101489553 A     7/2009
CN     101955483 A     1/2011
(Continued)

OTHER PUBLICATIONS

Database CAPLUS Chemical Abstracts Service, Columbus, Ohio, US; Database Accession No. 1967:482162, Kolodyazhnaya et al., Khimiya Geterotsiklicheskikh Soedinenii (1967), (1), 186-7.*
(Continued)

*Primary Examiner* — Karl J Puttlitz
(74) *Attorney, Agent, or Firm* — Saliwanchik, Lloyd & Eisenschenk

(57) ABSTRACT

The present invention relates to benzimidazole derivatives having the general formula I, wherein n is 0 or 1; $X^1$ and $X^2$ are independently, at each occurrence, $CR^5$ or N; Y is $C_1$-$C_6$ alkylene, wherein alkylene is optionally substituted with one to two $C_1$-$C_3$ alkyl groups; $R^1$ is selected from the group consisting of hydrogen, halogen, $C_1$-$C_6$ alkoxy, —$NH_2$, —$NHR^6$, —$NR^7R^8$ and —NH—$(R^9)_n$—$R^{10}$, n being 0 or 1; $R^2$ is selected from the group consisting of hydrogen, halogen, $C_1$-$C_6$ alkyl, —$NH_2$, —$NHR^6$, —$NR^7R^8$ and —NH—$(R^9)_n$—$R^{10}$; $R^3$ is selected from the group consisting of hydrogen, hydroxyl, $OR^{11}$, —$NR^7R^8$, $C_1$-$C_6$ alkoxy, $C_1$-$C_6$ alkyl, $C_3$-$C_{10}$ cycloalkyl, $C_1$-$C_3$ haloalkyl, —C(O)$NHR^{11}$, aryl, heteroaryl and heterocyclyl, wherein each of said cycloalkyl, aryl, heteroaryl and heterocyclyl is optionally and independently substituted with one to four $R^a$ groups; and $R^4$ is selected from the group consisting of —$NH_2$, —$N(R^{12})(V)_pR^{13}$, —$NH(V)_p$—$OR^{14}$, —NHC(O)$R^{15}$, and groups of formula 1a shown below, and their use in the treatment of diseases, in particular inflammatory diseases, cancer, stroke and/or Alzheimer's disease.

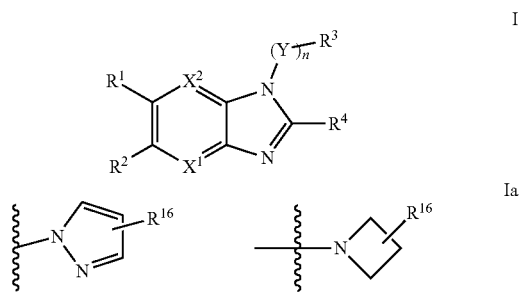

(Continued)

-continued

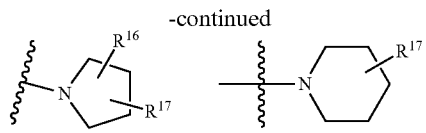

19 Claims, No Drawings

(51) Int. Cl.
| | |
|---|---|
| C07D 401/14 | (2006.01) |
| C07D 405/14 | (2006.01) |
| C07D 413/14 | (2006.01) |
| C07D 401/04 | (2006.01) |
| C07D 401/06 | (2006.01) |
| C07D 401/12 | (2006.01) |
| C07D 403/04 | (2006.01) |
| C07D 403/14 | (2006.01) |
| C07D 405/12 | (2006.01) |
| C07D 409/14 | (2006.01) |
| C07D 413/12 | (2006.01) |
| C07D 417/14 | (2006.01) |
| C07D 235/20 | (2006.01) |
| C07D 235/30 | (2006.01) |

(52) U.S. Cl.
CPC ......... C07D 401/04 (2013.01); C07D 401/06
(2013.01); C07D 401/12 (2013.01); C07D
401/14 (2013.01); C07D 403/04 (2013.01);
C07D 403/12 (2013.01); C07D 403/14
(2013.01); C07D 405/12 (2013.01); C07D
405/14 (2013.01); C07D 409/14 (2013.01);
C07D 413/12 (2013.01); C07D 413/14
(2013.01); C07D 417/14 (2013.01)

(56) References Cited

U.S. PATENT DOCUMENTS

| | | | | |
|---|---|---|---|---|
| 8,258,129 | B2 * | 9/2012 | Engelhardt | C07D 471/04 |
| | | | | 514/217.06 |
| 2005/0234083 | A1 * | 10/2005 | Chamberlain | C07D 401/14 |
| | | | | 514/275 |
| 2007/0066660 | A1 | 3/2007 | Stahle et al. | |
| 2009/0203673 | A1 | 8/2009 | Engelhardt et al. | |
| 2012/0178709 | A1 | 7/2012 | Coquerel et al. | |
| 2013/0079325 | A1 | 3/2013 | Allen et al. | |
| 2013/0136782 | A1 | 5/2013 | Blackwell et al. | |

FOREIGN PATENT DOCUMENTS

| | | |
|---|---|---|
| CN | 10304337 A | 4/2013 |
| CN | 103121969 A | 5/2013 |
| CN | 103450093 A | 12/2013 |
| EP | 0419210 * | 3/1991 |
| EP | 0419210 A1 | 3/1991 |
| JP | 2005524668 A | 8/2005 |
| WO | WO 00/31067 A1 | 6/2000 |
| WO | WO 03/030902 A1 | 4/2003 |
| WO | 2003/074515 A1 | 9/2003 |
| WO | 2004092181 A1 | 10/2004 |
| WO | WO 2004/085425 A1 | 10/2004 |
| WO | WO 2005/042520 A1 | 5/2005 |
| WO | WO 2005/070920 A1 | 8/2005 |
| WO | 2005079791 A1 | 9/2005 |
| WO | 2005092899 A1 | 10/2005 |
| WO | 2008042454 A1 | 4/2008 |
| WO | 2011143495 A1 | 11/2011 |
| WO | WO 2012/076672 A1 | 6/2012 |

OTHER PUBLICATIONS

Database Caplus Chemical Abstracts Service, Columbus, Ohio, US; Database Accession No. 2000:368343, Abstract of U.S. Pat. No. 20020035092, Alexander et al., Celltech Therapeutics Ltd., UK, Mar. 21, 2002.*
Wisastra et al., Cancers 2014, 6, 1500-1521.*
Joshi et al., Front Cell Neurosci. 2014; 8: 436.*
Bonfanti et al., Journal of Medicinal Chemistry, 2008, vol. 51, No. 4.*
Database Caplus Chemical Abstracts Service, Columbus, Ohio, US; Database Accession No. 1971:76370, Abstract of Mokrushina et al., Khimiya Geterotsiklicheskikh Soedinenii (1970), (10), 1397-400.*
Ding et al., Bioorganic & Medicinal Chemistry Letters 24 (2014) 3113-3117.*
Database Caplus Chemical Abstracts Service, Columbus, Ohio, US; Database Accession No. 1988:21891, Abstractor U.S. Pat. No. 4835161, Janssens et al., Janssen Pharmaceutica N. V., Belg., May 30, 1989.*
Irving et al., Journal of the Chemical Society (1959) 2296-8 (Year: 1959).*
Database Caplus Chemical Abstracts Service, Columbus, Ohio, US; Database Accession No. 2003:242160, Abstract of WO 2003024448, MethylGene, Inc., Can., Delorme et al., Mar. 27, 2002 (Year: 2002).*
Database Caplus Chemical Abstracts Service, Columbus, Ohio, US; Database Accession No. 1959:111767, Abstractor Irving et al., Journal of the Chemical Society (1959) 2296-8 (Year: 1959).*
Chemical Abstract citation for 1195517-73-7, 1H-Benzimidazol-2-amine, N,N,1-trimethyl-, hydrochloride (1:2), Dec. 3, 2009 (Year: 2009).*
Database Caplus Chemical Abstracts Service, Columbus, Ohio, US; Database Accession No. 2005:1075803, Abstract of WO 2005092899, MethylGene, Inc., Can., Delorme et al., Jun. 10, 2005 (Year: 2005).*
Zhu et al., Bioorganic & Medicinal Chemistry, vol. 21, Issue 14, Jul. 15, 2013, pp. 4218-4224 (Year: 2013).*
Database Caplus Chemical Abstracts Service, Columbus, Ohio, US; Database Accession No. 1951:6199, Abstract of Mamalis et al., Journal of the Chemical Society (1950) 1600-3 (Year: 1950).*
Database Caplus Chemical Abstracts Service, Columbus, Ohio, US; Database Accession No. 2004:117213, Abstract of EP 1388341, Aventis Pharma Deutschland GmbH, Germany, Strobel et al., Feb. 11, 2004 (Year: 2004).*
Database Caplus Chemical Abstracts Service, Columbus, Ohio, US; Database Accession No. 2002:818378, Abstract of Seth et al., Tetrahedron Letters (2002), 43(41), 7303-7306 (Year: 2002).*
Database Caplus Chemical Abstracts Service, Columbus, Ohio, US; Database Accession No. 2003:719473, Abstractor WO 2003074515, Smithkline Beecham Corporation, USA, Chamberlain et al., Sep. 12, 2003 (Year: 2003).*
Database Caplus Chemical Abstracts Service, Columbus, Ohio, US; Database Accession No. 2008:43697, Abstractor U.S. Pat. No. 8258129, Boehringer Ingelheim International GmbH, Germany, Engelhardt et al., Sep. 4, 2012 (Year: 2012).*
Database Caplus Chemical Abstracts Service, Columbus, Ohio, US; Database Accession No. 1977:171452, Abstractor Kadin et al., U.S. Pat. No. 4,002,623, Jan. 11, 1977 (Year: 1977).*
Database Caplus Chemical Abstracts Service, Columbus, Ohio, US; Database Accession No. 1999:684272, Abstractor DE 19816915, Boehringer Ingelheim Pharma K.-G., Esser et al., Oct. 21, 1999 (Year: 1999).*
Database Caplus Chemical Abstracts Service, Columbus, Ohio, US; Database Accession No. 2011:389341, Abstract or Wang et al., Journal or Organic Chemistry (2011), 76(9), 3174-3180 (Year: 2011).*
Database Caplus Chemical Abstracts Service, Columbus, Ohio, US; Database Registry No. 50844-53-6, Carbamic acid, [1-[[[3-(2-chloro-1,1,2-trifluoroethoxy)phenyl]amino]carbonyl]-5-methyl-1H-benzimidazol-2-yl]- methyl ester, entered 16, Nov. 1984 (Year: 1984).*

(56) References Cited

OTHER PUBLICATIONS

Database Caplus Chemical Abstracts Service, Columbus, Ohio, US; Database Accession No. 2011:636179, Abstract of CN 102060779, Tsinghua University, Peop. Rep. China, May 18, 2011 (Year: 2011).*
Database Caplus Chemical Abstracts Service, Columbus, Ohio, US; Database Accession No. 2005:962038, Abstract of WO 2005079791, Boehringer Ingelheim Pharmaceuticals, Inc., USA (Year: 2005).*
Database Registry, Chemical Abstracts Service, Columbus, Ohio, US; Registry No. 856895-19-7, 3-Pyridinol, 2-[[2-[(cyclohexylmethyl)amino]-5,7-dimethyl-1H-benzimidazol-1-yl]methyl]-6-methyl- (CA Index Name), entered Jul. 25, 2005 (Year: 2005).*
Database Caplus Chemical Abstracts Service, Columbus, Ohio, US; Registration No. 1052524-65-8, 2008 (Year: 2008).*
Database Caplus Chemical Abstracts Service, Columbus, Ohio, US; Accession No. 2013:1944384, Abstractor CN 103450093, China Pharmaceutical Company, Peop. Rep. China, Dec. 18, 2013, Lu et al. (Year: 2013).*
Wang et al., Journal of Organic Chemistry, (2011), 76(9), 3174-3180 (Year: 2011).*
Database Caplus Chemical Abstracts Service, Columbus, Ohio, US; Registration No. 596131-71-4, Carbamic acid, [5-[(2-chloro-4-pyrimidinyl)amino]-1-methyl-1H-benzimidazol-2-yl]-1,1-dimethylethyl ester, entered Oct. 1, 2003 (Year: 2003).*
Database Accession No. 2010:1440246, He et al., Advanced Synthesis & Catalysis (2010), 352(17), 2905-2912, (Abstract) (Year: 2010).*
Database Registry [Online], *Chemical Abstracts Service* (Columbus, Ohio, US), Jul. 9, 2015, Database accession No. 1797682-22-4.
Lee, Jin Ha et al., "A facile synthesis of 2-acyl- and 2-alkylaminobenzimidazoles for 5-lipoxygenase inhibitors." *Heterocycles*, Jan. 1, 2006, 70:571-580.
Deng, X., et al., "Direct, Metal-Free Amination of Heterocyclic Amides/Ureas with NH-Heterocycles and N-Substituted Anilines in POCl3." The Journal of Organic Chemistry, 2011, 76: 8262-8269.
Chassaing, C., et al., "Highly Water-Soluble Prodrugs of Anthelmintic Benzimidazole Carbamates: Synthesis, Pharmacodynamics, and Pharmacokinetics." J. Med. Chem., 2008, 51(5): 1111-1114.
Chen, Q., et al., "Design and synthesis of novel benzoheterocyclic derivatives as human acrosin inhibitors by scaffold hopping." European Journal of Medicinal Chemistry, 2013, 59: 176-182.
Divaeva, L.N., et al., "Synthesis and some conversions of N-substituted benzimidazole-2-sulfonic acids" Chemistry of Heterocyclic Compounds, 2006, 42(4): 463 468.
Fu, R., et al., "Design, synthesis and bioevaluation of dihydropyrazolo[3,4-b]pyridine and benzo[4,5]imidazo[1,2-a]pyrimidine compounds as dual KSP and Aurora-A kinase inhibitors for anti-cancer agents." Bioorg. Med. Chem., 2010, 18(22): 8035-8043.
Hunger, A., et al., "Benzimidazol-Derivate und verwandte Heterocyclen VII. Synthese neuer 2-Amino-benzimidazole." Helvetica Chimica Acta, 1961, 44(5): 1273-1282.
Li, F., et al., "General and efficient method for direct N-monomethylation of aromatic primary amines with methanol." RSC Adv., 2012, 2(23): 8645-8652.
Shalaeva, M., et al., "Integrating Intramolecular Hydrogen Bonding (IMHB) Considerations in Drug Discovery Using AlogP as a Tool." J. Med. Chem., 2013, 56(12): 4870-4879.
Sridevi, G., et al., "Synthesis of 4-Aryl Benzimidazolo[1,2-a]-s-triazin-2-ones and 2-Aroylaminobenzimidazolo[1,2-b]-1,2,4-thiadiazolines." Synthetic Communications, 1989, 19(5-6): 965-972.
Database Registry, Feb. 2014, RN 1541140-87-7, 1538868-99-3, 1536367-51-7, retrieved from STN International [online]; retrieved on Mar. 26, 2019.
Database Registry, Jan. 2014, RN 1533522-00-7, 1529280-72-5, 1528005-29-9, 1525796-75-1, 1522954-74-0, 1519422-08-2, 1519204-85-3, 1518877-77-4, 1515668-46-8, 1515498-66-4, 1511796-36-3, 1508803-33-5, retrieved from STN International [online]; retrieved on Mar. 26, 2019.
Database Registry, 2013, RN 1499579-70-2, Retrieved from STN International [online]; retrieved on Mar. 26, 2019.
Database Registry, Feb. 2014, RN 1542936-92-4, 1541791-05-2, 1540199-07-2, 1538037-44-3, 1536347-19-9, Retrieved from STN International [online]; retrieved on Mar. 26, 2019.
Database Registry, Jan. 2014, RN 1528291-55-5, 1520640-87-2, 1510964-30-3, Retrieved from STN International [online]; retrieved on Mar. 26, 2019.
Database Registry, 2013, RN 1505029-19-5, 1504134-40-0, 1502798-39-1, 1502412-99-8, Retrieved from STN International [online]; retrieved on Mar. 26, 2019.
Database Registry, Jan. 2014, RN 1514001-71-8, RN 1513940-72-1, RN 1513055-12-3, Retrieved from STN International [online]; retrieved on Mar. 26, 2019.
Japanese Office Action dated Apr. 4, 2019 issued in the parallel Japanese Patent Application No. 2017-504727 with an English translation of the Office Action.
Database Registry, Jul. 2014: RN 1616475-67-2, RN 1616475-66-1, Feb. 2013: RN 1418985-68-8, and Nov. 1984: RN 46005-72-5, respectively, retrieved from STN International [online]; all published before Jul. 31, 2014.
3rd Chinese Office Action dated Sep. 6, 2019 in the parallel Chinese Patent Application No. 201580053161X with an English translation of the Office Action.

* cited by examiner

2-AMINO-BENZIMIDAZOLE DERIVATIVES AND THEIR USE AS 5-LIPOXYGENASE AND/OR PROSTAGLANDIN E SYNTHASE INHIBITORS

CROSS REFERENCE TO A RELATED APPLICATION

This application is a National Stage Application of International Application Number PCT/EP2015/067644, filed Jul. 31, 2015; which claims priority to U.S. Provisional Patent Application Ser. No. 62/031,337, filed Jul. 31, 2014; which are incorporated herein by reference in their entirety.

BACKGROUND OF THE INVENTION

The present invention relates to small molecule compounds and their use in the treatment of diseases, in particular inflammatory diseases, cancer, stroke and/or Alzheimer's disease.

The arachidonate5-lipoxygenase (5-LOX, 5-LO, 5-lipoxygenase or Alox5) pathway has been shown to play an important role in the pathophysiology of many inflammatory diseases such as asthma, chronic obstructive pulmonary syndrome (COPD), allergic rhinitis, atherosclerosis, atopic dermatitis and pain by controlling the production of key inflammatory mediators. It has been also reported to be involved in cancer and Alzheimer's disease.

The 5-LOX enzyme is required in the production of LTB4 (leukotriene B4), a primary chemo-attractant and activator for leukocytes. LTB4 is primarily produced in neutrophils and macrophages where the enzyme LTA4 hydrolase converts LTA4 to LTB4. 5-LOX is also involved in the synthesis of LTC4, D4, and E4 (cysteinylleukotrienes; cys-LTs), which are strong bronchoconstrictors and proinflammatory mediators. Cys-LTs are also made from LTA4, a 5-LOX metabolite of arachidonic acid (AA). Another enzyme, LTC4 synthase, present in several cells, including eosinophils, basophils, and mast cells, conjugates LTA4 to glutathione to yield LTC4. LTC4 is further metabolized into LTD4 and LTE4. 5-LOX activity also results in the production of bioactive metabolites 5-hydroxyeicosatetraenoic acid (HETE) and 5-oxo-6,8,11,14-eicosatetraenoic acid (5-oxo-ETE). 5-oxoETE has been shown to induce tissue eosinophilia; thus, it may play a role in asthma and other diseases.

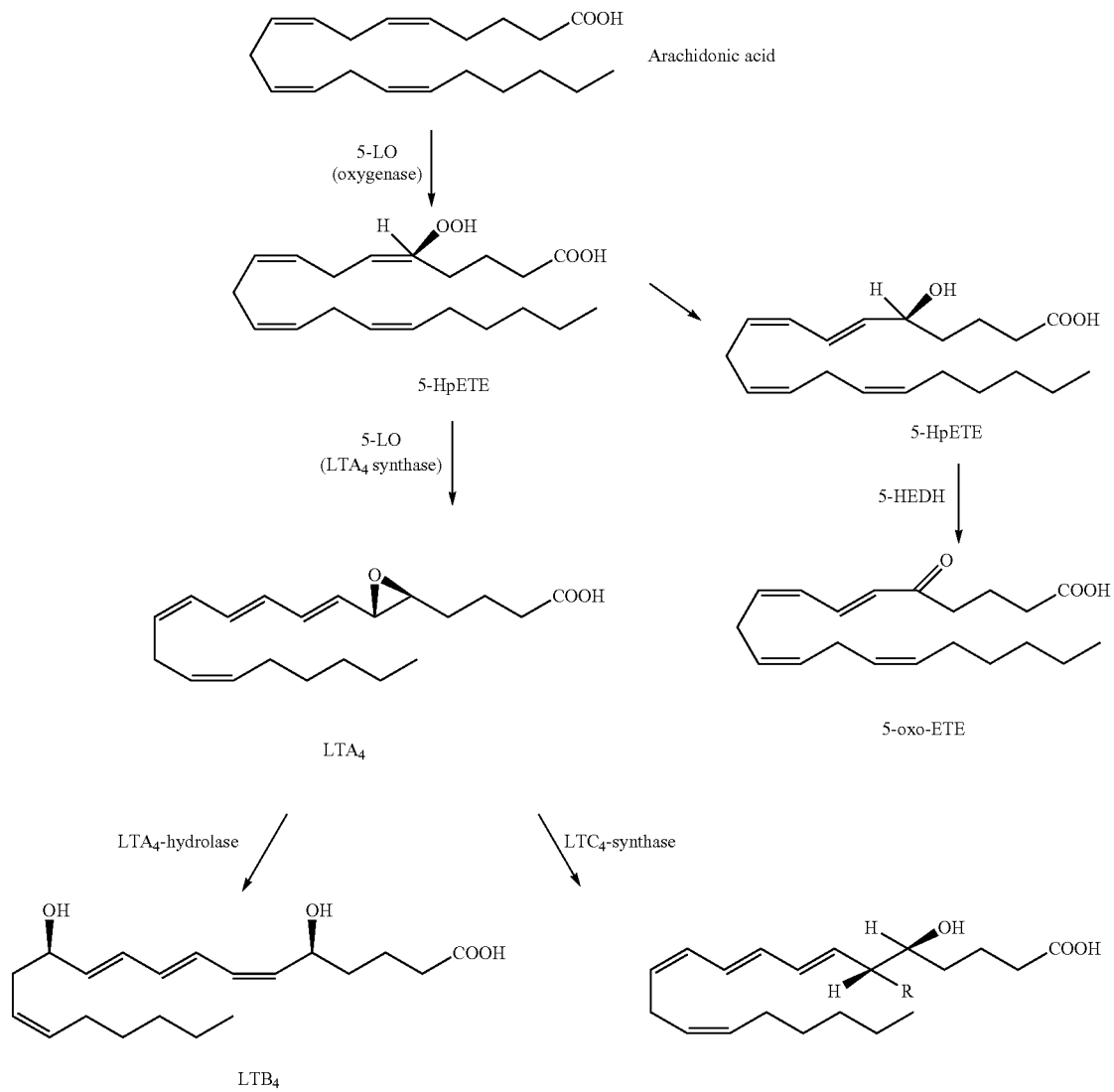

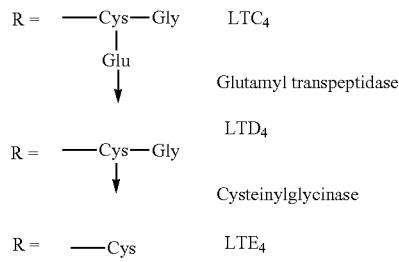

The clinical importance of the leukotriene pathway in inflammatory airway diseases has been demonstrated by the efficacy of various agents in the treatment of asthma and allergic rhinitis. Cys-LT receptor 1 antagonists (e.g., montelukast, zafirlukast, and pranlukast) have shown efficacy in asthma and allergic rhinitis, and the 5-LOX inhibitor zileuton has been shown to be efficacious in the treatment of asthma. 5-LOX inhibitors, which block both Cys-LTs and LTB4 production, have the potential for enhanced efficacy in asthma and allergic rhinitis compared to leukotriene receptor antagonists. 5-LOX inhibitors will block the proinflammatory activity of LTB4 and Cys-LTs as well as other leukotriene such as 5-HETE, and 5-oxo-ETE. Meta-analysis of several clinical trials suggest a better forced expiratory volume in 1 (FEV1) efficacy of zileuton versus the Cys-LT receptor antagonists in patients with severe asthma.

The only marketed 5-LOX inhibitor is zileuton, a redox hydroxyurea compound that chelates a critical active site iron moiety in the 5-LOX enzyme. Its efficacy and medical acceptance have been compromised by an inconvenient dosing regimen (i.e., four times daily), a suboptimal pharmacokinetic and pharmacodynamic profile, and a potential for hepatotoxicity. In addition, efforts to develop non-redox 5-LOX inhibitors have failed due to insufficient efficacy in human. Unmet medical needs therefore exist for more potent, better tolerated, non-hepatotoxic 5-LOX inhibitors that could maximize the benefits of inhibiting the leukotriene pathway and provide superior efficacy than obtained with zileuton and Cys-LT receptor antagonists.

Prostaglandin E synthase (PGES) is an enzyme involved in eicosanoid and glutathione metabolism, catalyzing the reaction from prostaglandin $H_2$ to prostaglandin E. It requires glutathione as an essential cofactor for its activity. It has been implicated in osteoarthritis, rheumatoid arthritis, atherosclerosis, and inflammatory pain.

Furthermore, inflammation-induced microsomal prostaglandin E synthase-1 (mPGES) is the terminal enzyme that synthesize prostaglandin E2 ($PGE_2$) downstream of cyclooxygenase-2 (COX-2). mPGES-1 is up-regulated in response to various pro-inflammatory stimuli with a concomitant increased expression of COX-2. Increase in the coordinate expression of COX-2 and mPGES-1 is reversed by glucocorticoid. The inhibition of PGES provides a rational for exploring mPGES-1 inhibition as a potential novel therapy for the above mentioned diseases. According to data of mPGES-1 knockout (KO) mice, these were less sensitive to inflammatory and neuropathic pain in rodent arthritis models, therefore, mPGES-1 has emerged as a potential target for the development of drugs for treatment of inflammation, pain, cancer, atherosclerosis, and stroke.

Herein are disclosed compounds with anti-inflammatory activity and anti-5-LOX activity and/or anti-PGES-activity.

It was an object of the present invention to identify compounds that interact and interfere with the 5-LOX-pathway and/or the PGES-pathway, in particular compounds having an inhibitory effect against arachidonate 5-lipoxygenase and/or prostaglandin E synthase.

It was also an object of the present invention to identify compounds with an anti-inflammatory activity.

It was furthermore an object of the present invention to identify compounds effective against inflammatory disease, in particular asthma, atherosclerosis, pain, COPD, allergic rhinitis, inflammation post infection, arthritis, dermatitis, pain, allergies, such as hay fever, autoimmune diseases, such as lupus erythematosus, inflammatory bowel diseases, such as Crohn's disease, celiac disease, acne, and against other diseases associated with a pathology of the 5-LOX-pathway and/or the PGES-pathway or diseases with an implication of the 5-LOX-pathway and/or the PGES-pathway, such as cancer and/or Alzheimer's disease and/or stroke.

1. Expert Opin. Ther. Patents (2010) 20(3), 335-375
2. Eur Respir J 2012; 40: 724.741
3. CurrOpin Allergy ClinImmunol. 2010 February; 10(1): 60-66
4. Biochemical Pharmacology 70 (2005) 327-333
5. Int J ClinPract, April 2007, 61, 4, 663-676

DESCRIPTION OF THE INVENTION

In one aspect, the present invention relates to a compound having the general formula I:

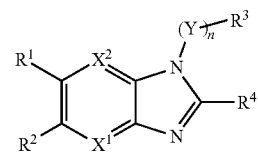

Formula I wherein
n is 0 or 1;
$X^1$ and $X^2$ are independently, at each occurrence, $CR^5$ or N;
Y is $C_1$-$C_6$ alkylene, wherein alkylene is optionally substituted with one to two $C_1$-$C_3$ alkyl groups;
$R^1$ is selected from the group consisting of hydrogen, halogen, $C_1$-$C_6$ alkoxy, $-NH_2$, $-NHR^6$, $-NR^7R^8$ and $-NH-(R^9)_n-R^{10}$, n being 0 or 1;
$R^2$ is selected from the group consisting of hydrogen, halogen, $C_1$-$C_6$ alkyl, $-NH_2$, $-NHR^6$, $-NR^7R^8$ and $-NH-(R^9)_n-R^{10}$ group, n being 0 or 1;
$R^3$ is selected from the group consisting of hydrogen, hydroxyl, $OR^{11}$, $-NR^7R^8$, $C_1$-$C_6$ alkoxy, $C_1$-$C_6$ alkyl, $C_3$-$C_{10}$cycloalkyl, $C_1$-$C_3$ haloalkyl, $-C(O)NHR^{11}$, aryl, heteroaryl and heterocyclyl group, wherein each of said cycloalkyl, aryl, heteroaryl and heterocyclyl is optionally and independently substituted with one to four R$^a$ groups;

R$^4$ is selected from the group consisting of —NH$_2$, —N(R$^{12}$)(V)$_p$R$^{13}$, —NH(V)$_p$—OR$^{14}$, —NHC(O)R$^{15}$, and groups of formula Ia shown below, Formula Ia

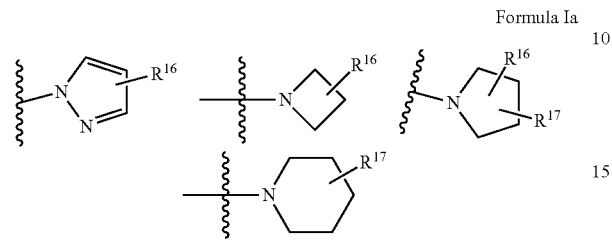

wherein, p is 0 or 1,

V is C$_1$-C$_6$ alkylene, wherein alkylene is optionally substituted with one to three C$_1$-C$_3$ alkyl, C$_3$-C$_6$ cycloalkyl or phenyl groups, or wherein a carbon atom of said alkylene forms part of a C$_3$-C$_6$ cycloalkyl group;

R$^5$ is selected from the group consisting of hydrogen, halogen, C$_1$-C$_6$ alkyl, C$_1$-C$_6$ haloalkyl and C$_1$-C$_6$ alkoxy group;

R$^6$ is selected from the group consisting of C$_1$-C$_6$ alkyl, C$_3$-C$_{10}$cycloalkyl, C$_1$-C$_6$haloalkyl, aryl, heteroaryl and heterocyclyl group, wherein each of said alkyl, cycloalkyl, haloalkyl, aryl, heteroaryl and heterocyclyl is optionally and independently substituted with one to four R$^a$ groups;

R$^7$ and R$^8$ are independently, at each occurrence, C$_1$-C$_6$ alkyl or heterocyclyl; or R$^7$ and R$^8$ are connected to each other to make a four, five or six membered heterocyclyl or heteroaryl group, wherein each of said heterocyclyl and heteroaryl is optionally and independently substituted with one to four R$^a$ groups;

R$^9$ is C$_1$-C$_4$ alkylene, wherein said alkylene is optionally substituted with one to three C$_1$-C$_3$ alkyl groups;

R$^{10}$ is selected from the group consisting of hydroxyl, —OR$^{11}$, —CN, —C(O)OR$^{18}$, —C(O)NH$_2$, —C(NH)NH$_2$, aryl, heteroaryl and heterocyclyl group wherein each of said aryl, heteroaryl and heterocyclyl is optionally and independently substituted with one to four R$^a$ groups;

R$^{11}$ is independently, at each occurrence, selected from the group consisting of aryl, e.g. phenyl or benzyl, heteroaryl and heterocyclyl group wherein each of said aryl, heteroaryl and heterocyclyl is optionally and independently substituted with one to four R$^a$ groups;

R$^{12}$ is selected from the group consisting of hydrogen, C$_1$-C$_6$ alkyl, C$_1$-C$_4$ alkyl-hydroxyl and C$_1$-C$_4$ alkyl-alkoxy;

R$^{13}$ is selected from the group consisting of hydrogen, C$_1$-C$_6$ alkyl, C$_3$-C$_{10}$ cycloalkyl, C$_1$-C$_4$ alkyl-hydroxyl, —OH, —C(O)NH$_2$, —C(O)OR$^{18}$, —CN, C$_1$-C$_3$ haloalkyl and heterocyclyl, and groups of formula Ib shown below, Formula Ib

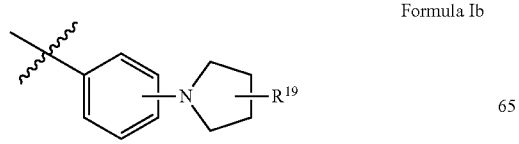

-continued

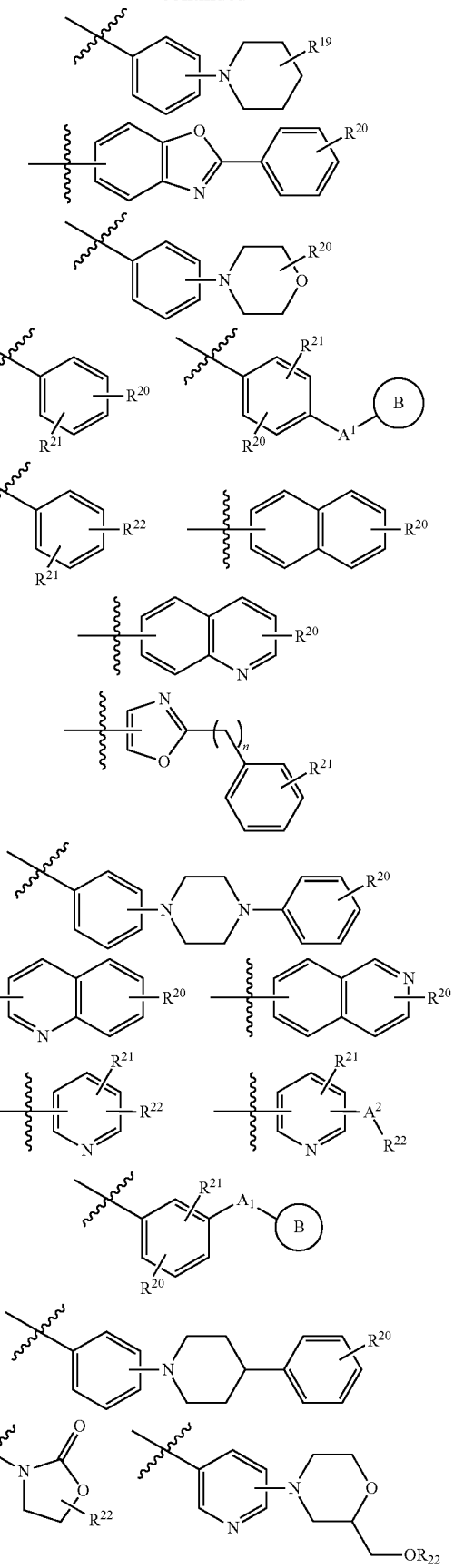

-continued

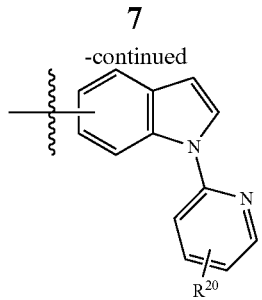

wherein, n is 0 or 1;

$A^1$ is —O—, —$CH_2$O—, —O$CH_2$—, —S—, —$SO_2$—, —$SO_2$NH—, —C(O)—, —C(O)NH—, —C(O)N($R^7$)—, —CH(OH)—, —CH(O$R^7$)—, —NH—, —N($CH_3$)— or —N($CH_2$COO$R^7$)—;

$A^2$ is —O— or NH—;

B is selected from the group consisting of aryl, e.g. phenyl or benzyl, heteroaryl and heterocyclyl group wherein each of said aryl, heteroaryl and heterocyclyl is optionally and independently substituted with one to four $R^a$ groups;

$R^{14}$ is selected from the group consisting of hydrogen, $C_1$-$C_6$ alkyl and aryl, wherein each of said alkyl and aryl is optionally and independently substituted with one to four halogen or $C_1$-$C_3$ haloalkoxy groups;

$R^{15}$ is aryl, wherein aryl is optionally substituted with one to four halogen groups;

$R^{16}$ is selected from the group consisting of hydrogen, halogen, $C_1$-$C_6$ alkyl and hydroxyl;

$R^{17}$ is selected from the group consisting of hydrogen, halogen, $C_1$-$C_6$ alkyl, —C(O)$R^{11}$, —C(O)NH$R^{11}$, —O$R^{11}$ and aryl, wherein each of said alkyl and aryl is optionally and independently substituted with one to four $R^a$ groups;

$R^{18}$ is hydrogen or $C_1$-$C_6$ alkyl;

$R^{19}$ is selected from the group consisting of hydrogen, —O$R^{22}$ and —$CH_2$O$R^{22}$;

$R^{20}$ is selected from the group consisting of hydrogen, halogen, $C_1$-$C_6$ alkyl, $C_1$-$C_6$ alkoxy, —C(O)$R^a$ and $C_1$-$C_6$ haloalkoxy;

$R^{21}$ is selected from the group consisting of hydrogen, halogen and $C_1$-$C_6$ alkyl group;

$R^{22}$ is selected from the group consisting of $C_1$-$C_6$ haloalkyl, aryl, e.g. phenyl or benzyl, and heteroaryl, wherein each of said haloalkyl, aryl and heteroaryl is optionally and independently substituted with one to four $R^a$ groups;

$R^a$ is independently, at each occurrence, selected from the group consisting of hydrogen, halogen, $C_1$-$C_3$ alkyl, $C_3$-$C_{10}$ cycloalkyl, $C_1$-$C_4$ alkoxy, $C_1$-$C_4$ haloalkyl, $C_1$-$C_6$ haloalkoxy, hydroxyl, $C_1$-$C_3$ alkylhydroxyl, —$CH_2$O$R^c$, —O$CH_2R^c$, —O$R^c$, —CN, $NO_2$, —N$R^bR^c$, —C(O)N$R^bR^c$, —C(NH)$NH_2$, —C(O)$R^c$, —C(O)O$R^c$, sulfonyl, sulfoxide, heterocyclyl, heteroaryl and aryl, e.g. phenyl, benzyl, wherein each of said alkyl, haloalkyl, haloalkoxy, alkoxy, cycloalkyl, aryl, heteroaryl and heterocyclyl is optionally and independently substituted with one to four $C_1$-$C_3$ alkyl, $C_1$-$C_4$ alkoxy, halogen, $C_1$-$C_3$ haloalkyl, —CN, —C(O)NH$_2$, —COOH, —$CO_2$Et and heteroaryl;

$R^b$ and $R^c$ are independently, at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_6$ haloalkyl, aryl, e.g. phenyl or benzyl, heteroaryl, and heterocyclyl wherein each of said alkyl, cycloalkyl, alkyl-O-alkyl, alkenyl, alkoxy, cycloalkenyl, alkynyl, haloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH$_2$, —COOH, —COOMe, —COOEt, —CN, —$NO_2$, —NH$_2$; or $R^b$ and $R^c$ are connected to each other to make a four, five or six membered saturated or unsaturated cyclic or heterocyclic ring;

and pharmaceutically acceptable salts thereof.

In a further aspect, the present invention relates to a compound having the general formula II:

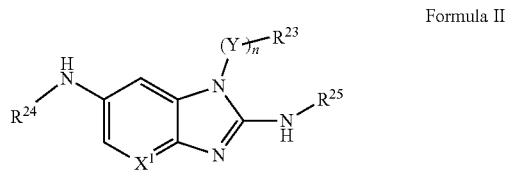

Formula II wherein n is 0 or 1;

$X^1$ is $CR^5$ or N;

Y is $C_1$-$C_6$ alkylene, wherein alkylene is optionally substituted with one to two $C_1$-$C_3$ alkyl groups;

$R^5$ is selected from the group consisting of hydrogen, halogen, $C_1$-$C_6$ alkyl, $C_1$-$C_6$ haloalkyl and $C_1$-$C_6$ alkoxy group;

$R^{23}$ is selected from the group consisting of hydrogen, $C_1$-$C_6$ alkyl, $C_1$-$C_3$ haloalkyl, aryl, heteroaryl and heterocyclyl group, wherein each of said aryl, heteroaryl and heterocyclyl is optionally and independently substituted with one to four $R^a$ groups;

$R^{24}$ is selected from the group consisting of hydrogen, $C_3$-$C_{10}$ cycloalkyl, aryl, heteroaryl and heterocyclyl group, wherein each of said cycloalkyl, aryl, heteroaryl and heterocyclyl is optionally and independently substituted with one to four $R^a$ groups;

$R^{25}$ is selected from the group consisting of hydrogen, —$(V)_p R^{26}$ and —$(V)_p$—O$R^{14}$;

wherein, p is 0 or 1,

V is $C_1$-$C_6$ alkylene, wherein alkylene is optionally substituted with one to three $C_1$-$C_3$ alkyl or phenyl groups, or wherein a carbon atom of said alkylene forms part of a $C_3$-$C_6$ cycloalkyl group;

$R^{14}$ is selected from the group consisting of hydrogen, $C_1$-$C_6$ alkyl and aryl, wherein each of said alkyl and aryl is optionally and independently substituted with one to four halogen or $C_1$-$C_3$ haloalkoxy groups;

$R^{26}$ is selected from the group consisting of hydrogen, $C_1$-$C_6$ alkyl, —CN and $C_1$-$C_3$ haloalkyl, and groups of formula IIa shown below,

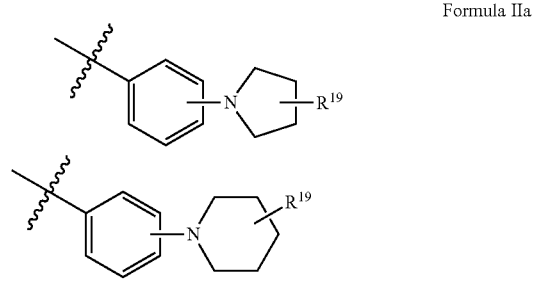

Formula IIa

-continued

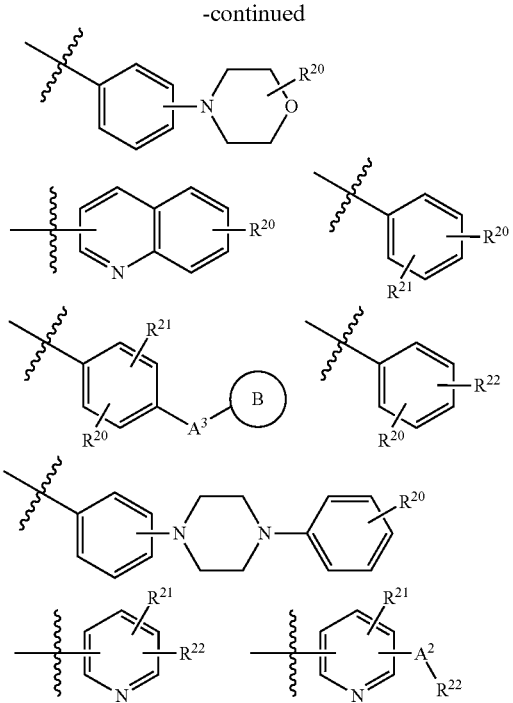

wherein, $A^2$ is —O— or NH—;

$A^3$ is —O—, —CH$_2$O—, —OCH$_2$—, or —NH—;

B is selected from the group consisting of aryl, e.g. phenyl or benzyl, heteroaryl and heterocyclyl group wherein each of said aryl, heteroaryl and heterocyclyl is optionally and independently substituted with one to four $R^a$ groups;

$R^{19}$ is selected from the group consisting of hydrogen, —OR$^{22}$ and —CH$_2$OR$^{22}$;

$R^{20}$ is selected from the group consisting of hydrogen, halogen, C$_1$-C$_6$ alkyl, C$_1$-C$_6$ alkoxy and C$_1$-C$_6$ haloalkoxy;

$R^{21}$ is selected from the group consisting of hydrogen, halogen and C$_1$-C$_6$ alkyl;

$R^{22}$ is selected from the group consisting of aryl, e.g. phenyl or benzyl, and heteroaryl, wherein each of said aryl and heteroaryl is optionally and independently substituted with one to four $R^a$ groups;

$R^a$ is independently, at each occurrence, selected from the group consisting of hydrogen, halogen, C$_1$-C$_3$ alkyl, C$_3$-C$_{10}$ cycloalkyl, C$_1$-C$_4$ alkoxy, C$_1$-C$_4$ haloalkyl, C$_1$-C$_6$ haloalkoxy, hydroxyl, C$_1$-C$_3$ alkylhydroxyl, —CH$_2$OR$^c$, —OCH$_2$R$^c$, —OR$^c$, —CN, NO$_2$, —NR$^b$R$^c$, —C(O)NR$^b$R$^c$, —C(NH)NH$_2$, —C(O)R$^c$, —C(O)OR$^c$, sulfonyl, sulfoxide, heterocyclyl, heteroaryl and aryl, e.g. phenyl, benzyl, wherein each of said alkyl, haloalkyl, haloalkoxy, alkoxy, cycloalkyl, aryl, heteroaryl and heterocyclyl is optionally and independently substituted with one to four C$_1$-C$_3$ alkyl, C$_1$-C$_4$ alkoxy, halogen, C$_1$-C$_3$ haloalkyl, —CN, —C(O)NH$_2$, —COOH, —CO$_2$Et and heteroaryl;

$R^b$ and $R^c$ are independently, at each occurrence, selected from the group consisting of hydrogen, C$_1$-C$_{10}$ alkyl, C$_3$-C$_{10}$ cycloalkyl, C$_1$-C$_6$ alkyl-O-alkyl, C$_2$-C$_{10}$ alkenyl, C$_1$-C$_4$ alkoxy, C$_1$-C$_3$ alkylhydroxyl, C$_3$-C$_{10}$ cycloalkenyl, C$_2$-C$_{10}$ alkynyl, C$_1$-C$_6$ haloalkyl, aryl, e.g. phenyl or benzyl, heteroaryl, and heterocyclyl wherein each of said alkyl, alkyl-O-alkyl, alkenyl, alkoxy, cycloalkenyl, alkynyl, haloalkyl, cycloalkyl, aryl, heteroaryl and heterocyclyl is optionally and independently substituted with one to four C$_1$-C$_3$ alkyl, C$_1$-C$_4$ alkoxy, halogen, C$_1$-C$_6$ haloalkyl, C$_1$-C$_6$ haloalkoxy, hydroxyl, —C(O)NH$_2$, —COOH, —COOMe, —COOEt, —CN, —NO$_2$, —NH$_2$; or $R^b$ and $R^c$ are connected to each other to make a four, five or six membered saturated or unsaturated cyclic or heterocyclic ring;

and pharmaceutically acceptable salts thereof.

In a further aspect, the present invention relates to a compound having the general formula III:

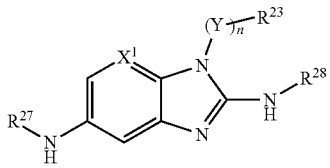

Formula III wherein n is 0 or 1;

$X^1$ is CR$^5$ or N;

Y is C$_1$-C$_6$ alkylene, wherein alkylene is optionally substituted with one to two C$_1$-C$_3$ alkyl groups;

$R^5$ is selected from the group consisting of hydrogen, halogen, C$_1$-C$_6$ alkyl, C$_1$-C$_6$ haloalkyl and C$_1$-C$_6$ alkoxy group;

$R^{23}$ is selected from the group consisting of hydrogen, C$_1$-C$_6$ alkyl, aryl, heteroaryl and heterocyclyl group, wherein each of said aryl, heteroaryl and heterocyclyl is optionally and independently substituted with one to four $R^a$ groups;

$R^{27}$ is selected from the group consisting of hydrogen, —R$^6$, and —R$^9$—R$^{10}$;

wherein, $R^6$ is selected from the group consisting of C$_1$-C$_6$ alkyl, C$_3$-C$_{10}$cycloalkyl, C$_1$-C$_6$haloalkyl, aryl, heteroaryl and heterocyclyl group, wherein said alkyl, cycloalkyl, haloalkyl, aryl, heteroaryl and heterocyclyl is optionally and independently substituted with one to four $R^a$ groups;

$R^9$ is C$_1$-C$_4$ alkylene, wherein said alkylene is optionally substituted with one to three C$_1$-C$_3$ alkyl groups;

$R^{10}$ is selected from the group consisting of hydroxyl, —OR$^{11}$, —C(O)OR$^{18}$, —C(O)NH$_2$, aryl, heteroaryl and heterocyclyl group wherein each of said aryl, heteroaryl and heterocyclyl is optionally and independently substituted with one to four $R^a$ groups;

$R^{11}$ is independently, at each occurrence selected from the group consisting of aryl, e.g. phenyl or benzyl, heteroaryl and heterocyclyl group wherein said aryl, heteroaryl and heterocyclyl is optionally and independently substituted with one to four $R^a$ groups;

$R^{18}$ is hydrogen or C$_1$-C$_6$ alkyl;

$R^{28}$ is selected from the group consisting of hydrogen, —(V)$_p$R$^{29}$ and —(V)$_p$—OR$^{14}$ group;

wherein, p is 0 or 1,

V is C$_1$-C$_6$ alkylene, wherein alkylene is optionally substituted with one to three C$_1$-C$_6$ alkyl or phenyl groups;

$R^{14}$ is selected from the group consisting of hydrogen, C$_1$-C$_6$ alkyl and aryl, wherein each of said alkyl and aryl is optionally and independently substituted with one to four halogen or C$_1$-C$_3$ haloalkoxy groups;

$R^{29}$ is selected from the group consisting of hydrogen, C$_1$-C$_6$ alkyl and C$_1$-C$_3$ haloalkyl, and groups of formula IIIa shown below, Formula IIIa

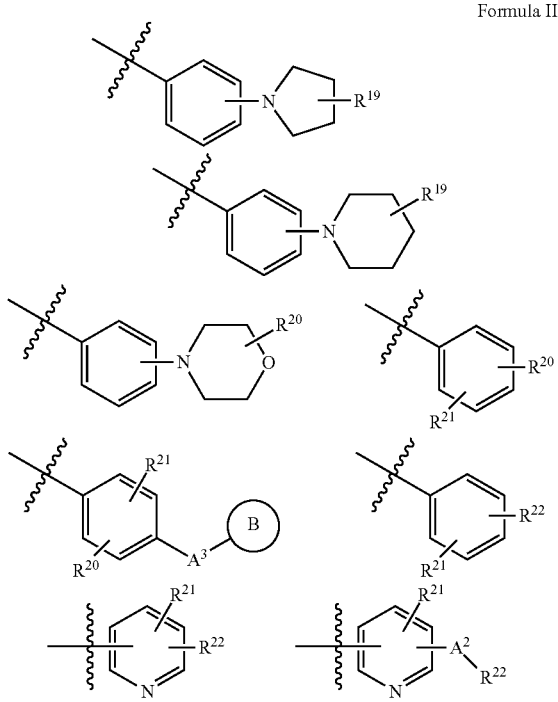

wherein,
$A^2$ is —O— or NH—;
$A^3$ is —O—, —CH$_2$O—, —OCH$_2$—, or —NH—;
B is selected from the group consisting of aryl, e.g. phenyl or benzyl, heteroaryl and heterocyclyl group wherein each of said aryl, heteroaryl and heterocyclyl is optionally and independently substituted with one to four $R^a$ groups;
$R^{19}$ is selected from the group consisting of hydrogen, —OR$^{22}$ and —CH$_2$OR$^{22}$;
$R^{20}$ is selected from the group consisting of hydrogen, halogen, $C_1$-$C_6$ alkyl, $C_1$-$C_6$ alkoxy and $C_1$-$C_6$ haloalkoxy;
$R^{21}$ is selected from the group consisting of hydrogen, halogen and $C_1$-$C_6$ alkyl;
$R^{22}$ is selected from the group consisting of aryl, e.g. phenyl or benzyl, and heteroaryl, wherein said aryl and heteroaryl is optionally and independently substituted with one to four $R^a$ groups;
$R^a$ is independently, at each occurrence, selected from the group consisting of hydrogen, halogen, $C_1$-$C_3$ alkyl, $C_3$-$C_{10}$ cycloalkyl, $C_1$-$C_4$ alkoxy, $C_1$-$C_4$ haloalkyl, $C_1$-$C_6$ haloalkoxy, hydroxyl, $C_1$-$C_3$ alkylhydroxyl, —CH$_2$OR$^c$, —OCH$_2$R$^c$, —OR$^c$, —CN, NO$_2$, —NR$^b$R$^c$, —C(O)NR$^b$R$^c$, —C(NH)NH$_2$, —C(O)R$^c$, —C(O)OR$^c$, sulfonyl, sulfoxide, heterocyclyl, heteroaryl and aryl, e.g. phenyl, benzyl, wherein each of said alkyl, haloalkyl, haloalkoxy, alkoxy, cycloalkyl, aryl, heteroaryl and heterocyclyl is optionally and independently substituted with one to four $C_1$-$C_3$ alkyl, $C_1$-$C_4$ alkoxy, halogen, $C_1$-$C_3$ haloalkyl, —CN, —C(O)NH$_2$, —COOH, —CO$_2$Et and heteroaryl;
$R^b$ and $R^c$ are independently, at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_6$ haloalkyl, alkyl-O-alkyl, alkenyl, alkoxy, cycloalkenyl, alkynyl, haloalkyl, aryl, e.g. phenyl or benzyl, heteroaryl, and heterocyclyl wherein each of said alkyl, cycloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH$_2$, —COOH, —COOMe, —COOEt, —CN, —NO$_2$, —NH$_2$; or
$R^b$ and $R^c$ are connected to each other to make a four, five or six membered saturated or unsaturated cyclic or heterocyclic ring;
and pharmaceutically acceptable salts thereof.

In one embodiment, the compound according to the present invention has one of the formulae 1-556, as shown in tables 1-6 and/or example 7 and/or table 7, or a pharmaceutically acceptable salt thereof, preferably having one of the formulae 1-12, 14-16, 19-21, 24, 28-34, 36-40, 44, 48, 51-54, 56-68, 70, 71, 73-77, 79-81, 84, 86-173, 175-192, 194-234, 236-241, 243, 244, 246-261, 263-278, 280-321, 323-354, 356-385, 387-428, 430-440, 442-446, 449-463, 465-471, 473-487, 489-492, 495-496, 499, 501, 503, 505, 507, 509, 512-514, 525, 529-544, 546-556 as indicated in Tables 1 and 7, or formula 14 as indicated in Tables 2 and 7, or one of the formulae 53, 54, 86, 90, 91, 95, 99, 103, 226 as indicated in Tables 5-7; or one of the formulae 14, 17, 24, 29, 30, 32, 33, 38, 43-46, 48, 49, 51-60, 62, 65-70, 73, 74, 79-81, 84, 86-88, 90-107, 109-113, 116, 118-132, 134-138, 140, 145, 147-150, 152, 153, 155, 160-162, 164-166, 168, 169, 172, 175-177, 179, 180, 184-187, 190-197, 199, 200, 202-220, 223, 224, 226, 227, 229-231, 233-236, 238-255, 257-262, 264, 265, 267-302, 304-306, 313, 316, 322-333, 335, 340, 342, 346, 347, 349, 350, 352, 353, 357-359, 361, 365-369, 372-375, 377-380, 382-384, 387, 389-393, 395-403, 405-407, 410, 412-415, 419-428, 430-432, 434-437, 440, 442, 445-453, 455, 457-458, 460-461, 463-482, 486-487, 489-496, 499, 501-553, 556 as indicated in Tables 3 and 7, or one of the formulae, 11, 12, 14, 24, 30, 32, 48, 52-54, 62, 65, 77, 79-81, 86-88, 92, 94, 97, 98, 101-103, 106, 109-111, 113, 119, 120, 122, 123, 125, 130, 136-138, 145, 147, 149, 155, 165, 166, 176, 177, 184, 193, 195, 199, 204, 211, 226, 227, 229, 231, 233, 234, 238, 239, 243, 249, 251, 253, 256, 268-271, 275, 277, 279, 281, 284, 288, 289, 296, 306, 311, 324, 328, 336, 341, 345, 350, 351, 358, 360, 362, 367-369, 373, 374, 378, 381, 392, 412-415, 430, 431, 433, 447-450, 461, 464-466, 468-471, 473-477, 479, 481, 482, 486, 487, 489-496, 498, 499, 501-506, 508, 509, 512-514, 516-519, 525-538, 540-547, 550, 553-554 as indicated in Tables 4 and 7; or having the formula 211 as indicated in Table 7; or a pharmaceutically acceptable salt thereof.

In one embodiment of the compound having the formula I, $R^4$ is —N(R$^{12}$)(V)$_p$R$^{13}$, $R^{12}$ is H, V is $C_1$-alkylene, p is 1, $R^{13}$ is

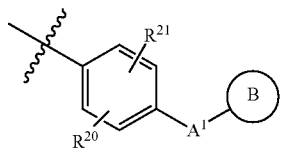

and B is heteroaryl which is optionally substituted with one to four $R^a$ groups.

In one embodiment of the compound having formula I, $R^1$ is —NH$_2$ or —NHR$^6$, $R^6$ is heteroaryl or heterocyclyl wherein each of said heteroaryl and heterocyclyl is optionally and independently substituted with one to four $R^a$ groups.

In a further aspect, the present invention relates to a compound, as defined above, or a pharmaceutically acceptable salt thereof, for use in the treatment of a disease associated with the 5LOX-pathway and/or the prostaglandin E synthase (PGES) pathway, said disease being selected from inflammatory diseases, e.g. asthma, atherosclerosis, pain, or COPD, cancer, stroke and Alzheimer's disease.

In one embodiment, said compound has an inhibitory activity on an enzyme involved in an inflammatory pathway or several inflammatory pathways, e.g. the arachidonate 5-lipoxygenese pathway and/or the prostaglandin E synthase pathway, preferably on arachidonate 5-lipoxygenase (5-lipoxygenase, 5-LO, 5-LOX, Alox5), at a concentration of said compound between 0.001-50 µM, particularly preferably having an $IC_{50}$ on arachidonate 5-lipoxygenase of less than 1 µM and/or having an $EC_{50}$ of less than 10 µM on the production of leukotriene B4 (LTB4) in rat basophilic leucocyte cells (RBL) and/or rat whole blood (RWB), and/or having a 40-70% inhibitory activity, preferably a>70% inhibitory activity on the production of prostaglandin E2 in HeLaS3 cells, stimulated with TNF-α, at a concentration of 10 µM of said compound.

The present invention also relates to a composition comprising a compound or a pharmaceutically acceptable salt thereof, as defined above and a pharmaceutically acceptable carrier.

The present invention also relates to such composition for use in the treatment of a disease associated with the 5LOX-pathway and/or the prostaglandin E synthase (PGES) pathway, said disease being selected from inflammatory diseases, e.g. asthma, atherosclerosis, pain, or COPD, cancer, stroke and Alzheimer's disease.

In one embodiment, said inflammatory disease is one or several of asthma, allergic rhinitis, dermatitis, chronic obstructive pulmonary disease (COPD), inflammation post infection, arthritis, atherosclerosis, allergies, such as hay fever, autoimmune diseases, such as lupus erythematosus, inflammatory bowel diseases, such as Crohn's disease, celiac disease, acne, or pain, e.g. inflammatory and/or neuropathic pain.

In one embodiment, said treatment comprises administering a suitable amount of a compound as defined in any of claims 1-6, or of a composition as defined in claim 9, to a patient in need thereof, suffering from an inflammatory disease, and/or of cancer, and/or of stroke, and/or of Alzheimer's disease.

The present invention also relates to a method of treatment of a disease associated with the 5-LOX-pathway and/or the prostaglandin E synthase (PGES) pathway, said disease being selected from inflammatory diseases, cancer and Alzheimer's disease, said method comprising the application of a suitable amount of a compound as defined above or of a composition as defined above, to a patient in need thereof, suffering from a disease associated with the 5-LOX-pathway and/or the prostaglandin E synthase (PGES) pathway.

In one embodiment, said inflammatory disease is selected from asthma, allergic rhinitis, dermatitis, chronic obstructive pulmonary disease (COPD), inflammation post infection, arthritis, atherosclerosis, allergies, such as hay fever, autoimmune diseases, such as lupus erythematosus, inflammatory bowel diseases, such as Crohn's disease, celiac disease, acne, and pain, e.g. inflammatory and/or neuropathic pain.

In one embodiment, said suitable amount is an amount in the range of 0.01 mg/kg body weight to 1 g/kg body weight of said patient.

The present invention also relates to a compound that competitively inhibits the specific binding of a compound as defined above to arachidonate 5-lipoxygenase (5-lipoxygenase, 5-LO, 5-LOX, Alox5) or to prostaglandin E synthase (PGES). Such competitively inhibiting compound is herein also sometimes referred to as "competitive compound" or "competitively inhibiting compound".

The present invention also relates to a method of treatment of an inflammatory disease, in particular asthma, atherosclerosis, pain, chronic obstructive pulmonary disease (COPD), inflammation post infection, allergic rhinitis, arthritis, pain, e.g. inflammatory or neuropathic pain, allergies, such as hay fever, autoimmune diseases, such as lupus erythematosus, inflammatory bowel diseases, such as Crohn's disease, celiac disease, acne, and/or dermatitis, or a method of treatment of cancer/and or of Alzheimer's disease, said method comprising the application of a suitable amount of a competitively inhibiting compound as defined above, to a patient in need thereof.

In one embodiment, said patient is a patient suffering from an inflammatory disease and/or from cancer and/or from stroke and/or from Alzheimer's disease.

In one aspect, the present invention also relates to the use of a compound according to the present invention or of a composition according to the present invention for the manufacture of a medicament for the treatment of a disease associated with the 5LOX-pathway or the prostaglandin E synthase (PGES) pathway said disease being selected from inflammatory diseases, e.g. asthma, atherosclerosis, pain or COPD, cancer, stroke and Alzheimer's disease, wherein preferably, said inflammatory disease, in particular, is selected from asthma, atherosclerosis, pain, chronic obstructive pulmonary disease (COPD), inflammation post infection, allergic rhinitis, arthritis, pain, e.g. inflammatory or neuropathic pain, allergies, such as hay fever, autoimmune diseases, such as lupus erythematosus, inflammatory bowel diseases, such as Crohn's disease, celiac disease, acne, and/or dermatitis, wherein said treatment comprises the application of a suitable amount of a compound or a composition according to the present invention or composition according to the present invention, as defined above, to a patient in need thereof. The compound and the composition according to the present invention is either a compound according to the formula I, II or III, in particular, a compound according to any of claims 1-6, or it is a compound that is a competitive compound or competitively inhibiting compound, as defined further above.

The term "substituted" as used herein, for example as in "optionally substituted", is meant to indicate that a hydrogen atom attached to a member atom within a group is ("optionally") replaced by a group, such as halogen including fluorine, chlorine, bromine, $C_1$-$C_{10}$ alkyl, $C_1$-$C_3$haloalkyl, $C_3$-$C_7$cycloalkyl, oxo, —OH, —OR$^{23}$, —OC(O)R$^{23}$, —CN, NO$_2$, —N(R$^{23}$)$_2$, —N(R$^{23}$)C(O)R$^{23}$, —R$^{23}$N(R$^{23}$)C(O)R$^{23}$, —C(O)R$^{23}$, —R$^{23}$C(O)R$^{23}$, —C(O)OR$^{23}$, —R$^{23}$C(O)OR$^{23}$, —C(O)N(R$^{23}$)$_2$, —R$^{23}$C(O)N(R$^{23}$)$_2$, —S(O)R$^{23}$, —S(O)$_2$R$^{23}$, —S(O)$_2$N(R$^{23}$)$_2$, phenyl, benzyl, aryl, heteroaryl or heterocyclyl, any of which itself is "optionally substituted"; it should be noted that the term "substituted" as used herein may also refer to several such substitutions in the same moiety.

$R^{23}$ is, at each occurence, independently selected from the group consisting of hydrogen, halogen, $C_1$-$C_{10}$ alkyl, $C_1$-$C_3$ haloalkyl, $C_3$-$C_7$ cycloalkyl, hydroxyl, oxo, —OR$^{24}$, —C(O)OR$^{24}$, —C(O)R$^{24}$, —C(O)N(R$^{24}$)$_2$, —CN, —NO$_2$, —NH$_2$, —N(R$^{24}$)$_2$, —OR$^{24}$HetA, —OR$^{24}$N(R$^{24}$)$_2$, —C(O)N(R$^{24}$)HetA, —C(O)HetA, —C(O)N(R$^{24}$)R$^{24}$S(O)$_2$R$^{24}$; —S(O)$_2$N(R$^{24}$)$_2$, —S(O)$_2$R$^{24}$, —N(R$^{24}$)C(O)R$^{24}$SR$^{24}$, —N(R$^{24}$)R$^{24}$S(O)$_2$R$^{24}$, or —N(R$^{24}$)S(O)$_2$R$^{24}$, aryl, e.g. phenyl, benzyl, heteroaryl, and heterocyclyl, any of which is optionally substituted.

$R^{24}$ is, at each occurrence, independently selected from the group consisting of hydrogen, $C_1$-$C_8$ alkyl optionally substituted with at least one hydroxyl or halogen; $C_3$-$C_7$cycloalkyl, aryl, e.g. phenyl, benzyl, and heterocycyl, any of which is optionally substituted.

In one embodiment, the present invention also relates to pharmaceutically acceptable salts of the compounds according to the present invention, and to such pharmaceutically acceptable salts for use in the treatment of an inflammatory disease and/or of cancer and/or of stroke and/or of Alzheimer's disease.

The term "alkyl" refers to a monovalent straight or branched chain, saturated aliphatic hydrocarbon radical having a number of carbon atoms in the specified range any of which is optionally substituted. Thus, for example, "$C_1$-$C_6$ alkyl" refers to any of the hexyl alkyl and pentyl alkyl isomers as well as n-, iso-, sec-, and t-butyl, n- and isopropyl, ethyl and methyl, any of which is optionally substituted.

The term "alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$alkoxy), 1 to 12 carbon atoms (i.e., $C_1$-$C_{12}$alkoxy), or 1 to 6 carbon atoms (i.e., $C_1$-$C_6$alkoxy). Examples of suitable alkoxy groups include, but are not limited to, methoxy (—O—CH$_3$ or OMe), ethoxy (—OCH$_2$CH$_3$ or —OEt), t-butoxy (—O—C(CH$_3$)$_3$ or —OtBu) and the like. Such alkoxy group may itself be substituted once or several times.

The term "alkenyl" refers to a monovalent straight or branched chain aliphatic hydrocarbon radical containing one carbon-carbon double bond and having a number of carbon atoms in the specified range (and being optionally substituted). Thus, for example, "$C_2$-$C_6$alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "alkynyl" refers to a monovalent straight or branched chain aliphatic hydrocarbon radical containing one carbon-carbon triple bond and having a number of carbon atoms in the specified range. Thus, for example, "$C_2$-$C_6$alkynyl" refers to all of the hexynyl and pentynyl isomers as well as 1-butynyl, 2-butynyl, 3-butynyl, 1-propynyl, 2-propynyl, and ethynyl.

The term "alkylene" refers to a saturated, branched or straight chain or cyclic hydrocarbon radical having two monovalent radical centers derived by the removal of two hydrogen atoms from the same or two different carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

The term "alkenylene" refers to an unsaturated, branched or straight chain or cyclic hydrocarbon radical having two monovalent radical centers derived by the removal of two hydrogen atoms from the same or two different carbon atoms of parent alkene. For example, an alkenylene group can have 1 to 20 carbon atoms, 1 to 10 carbon atoms, or 1 to 6 carbon atoms. Typical alkenylene radicals include, but are not limited to, 1,2-ethenyl (—CH=CH—).

The term "alkynylene" refers to an unsaturated, branched or straight chain or cyclic hydrocarbon radical having two monovalent radical centers derived by the removal of two hydrogen atoms from the same or two different carbon atoms of parent alkyne. For example, an alkynylene group can have 1 to 20 carbon atoms, 1 to 10 carbon atoms or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as —CHF$_2$, —CF$_3$, —CH$_2$—CH$_2$—F, —CH$_2$—CF$_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or thioalkyl group (e.g., —SCH$_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), alkyl amine (e.g., —CH$_2$NHCH$_3$, —CH$_2$N(CH$_3$)$_2$, etc.), or thioalkyl ether (e.g., —CH$_2$—S—CH$_3$).

The term "halogen" refers to fluorine, chlorine, bromine, or iodine.

The term "aryl" refers to (i) optionally substituted phenyl, (ii) optionally substituted 9- or 10 membered bicyclic, fused carbocyclic ring systems in which at least one ring is aromatic, and (iii) optionally substituted 11- to 14-membered tricyclic, fused carbocyclic ring systems in which at least one ring is aromatic. Suitable aryls include, for example, phenyl, biphenyl, naphthyl, tetrahydronaphthyl (tetralinyl), indenyl, anthracenyl, and fluorenyl.

The term "phenyl" as used herein is meant to indicate that optionally substituted or non-substituted phenyl group.

The term "benzyl" as used herein is meant to indicate that optionally substituted or non-substituted benzyl group.

The term "heteroaryl" (herein sometimes also abbreviated as "HetA") refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl.

The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to $S(O)$ or $S(O)_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

In one embodiment, said compound has an inhibitory activity on an enzyme involved in an inflammatory pathway(s), preferably an arachidonate 5-lipoxygenase (5-lipoxygenase, 5-LO, 5-LOX, Alox 5), at a concentration of said compound between 0.001-50 µM, particularly preferably having an $IC_{50}$ on arachidonate 5-lipoxygenase of less than 1 µM and/or having an $EC_{50}$ of less than 10 µM on the production of leukotriene B4 (LTB4) in rat basophilic leukocyte cells (RBL) or rat whole blood (RWB).

The term "5-LOX-Pathway" is meant to refer to the pathway starting from arachidonic acid to LTA4, LTB4, LTC4, LTD4, LTE4 and 5-oxoETE (5-oxo-6,8,11,14-eicosatetraenoic acid). The 5-LOX-pathway involves one or several of the enzymes arachidonate-5-lipoxygenase (5-LOX), LTA4-hydrolase, LTC4-synthase, glutamyltranspeptidase, and 5-hydroxy-6,8,11,14-eicosatetraenoic acid dehydrogenase. In this 5-LOX-pathway one or several enzymes may malfunction and lead to a pathology which, in many instances, manifests itself in a disease or disease state. Such malfunctioning of an enzyme may be a deviation of activity as compared to the normal healthy state (which is not affected by such pathology). Such deviation may be an excess activity of the respective enzyme, or it may be an activity that is below the normal activity of such enzyme in a healthy individual. A "disease associated with the 5-LOX-pathway" may be a disease wherein one or several of the above mentioned enzymes show an excess activity. Preferably, it is the 5-lipoxygenase (5-LOX), which shows a deviant activity, preferably an excess activity in comparison to a healthy, non-pathological state. In one embodiment, the 5-lipoxygenase (5-LOX) is the only enzyme of the 5-LOX-pathway showing a decreased activity. In another embodiment, other enzyme(s) alone or in addition to the 5-lipoxygenase show decreased or increased activity as well. A person skilled in the art knows how to determine whether or not one or several enzymes of the 5-LOX-pathway show a deviant activity. For example this can be easily determined by measurement of one or several leukotrienes which are reaction products of the respective reactions within the 5-LOX-pathway. Measurement of these leukotrienes, for example one or several of LTA4, LTB4, LTC4, LTD4, LTE4, 5-HpETE, 5-HETE and 5-oxo-ETE, may be performed in an appropriate body fluid of a patient, such as blood, nasal secretions, bronchial secretions, urine, semen, spinal fluid, lymph, interstitial fluid, mucosal fluid, fluid extracted from cells or a cell homogenate, vaginal fluid, tears, synovial fluid, sweat, pus, pleural fluid, peritoneal fluid, pericardial fluid, mucus, chyle, breast milk, cerebrospinal fluid, serum, and amniotic fluid. Measurement of such leukotrienes may be done by various means, such as chromatography alone or coupled with mass spectrometry, for example as published by Knapp et al. (N. Engl. J. Med. 1989; 320:1037-1043), Knapp, Prostaglandins 1990; 39:407-423; and Reilly et al. J. Clin. Pathol. 1988; 41:1163-1167; reverse phase-HPLC (Antonelli et al.) Intensive Care Med. 1989; 15(5):296-301, HPLC, as published by Otila et al. Acta Derm. Venereol. 1986; 66(5):381-385, ELISA-Technology, as for example commercially available in the form of a kit for leukotrienes from Oxford Biomedical Research or from Assay Designs Inc., or from Cayman (cat no. 520111), as for example published by Chu et al., American Journal of Pathology, 2011, Volume 178, No. 4, pp. 1762-1769, or by Tardif et al. Circ. Cardiovasc. Imaging, 2010, 298-307. Hence, methodology for determining the levels of leukotrienes and other reaction products/intermediates of the 5-LOX-pathway are available to someone skilled in the art, and hence, a person skilled in the art can easily determine whether or not a disease is associated with the 5-LOX-pathway by determining whether or not the activity of one or several of the enzymes from the 5-LOX-pathway show a deviant activity when compared to the normal/healthy state.

The term "PGES-pathway" is meant to refer to a pathway involving the production of prostaglandin E. The PGES-pathway involves one or several enzymes, including cyclooxygenase-2 (COX-2) and prostaglandin E synthase (PGES). In this PGES-pathway, one or several enzymes may malfunction and lead to a pathology which, in many instances, manifests itself in a disease or disease state. Such malfunctioning of an enzyme may be a deviation of activity as compared to the normal healthy state (which is not effected by such pathology). Such deviation may be an excess activity of the respective enzyme, or it may be an activity that is below the normal activity of such enzyme in a healthy individual. A "disease associated with the PGES-pathway" may be a disease wherein one or several of the above-mentioned enzyme show a deviant activity. Preferably it is the prostaglandin E synthase (PGES) which shows a deviant activity, preferably an excess activity in comparison to a healthy-non-pathological state.

In a preferred embodiment, such a "disease associated with the 5-LOX-pathway" or "a disease associated with the PGES-pathway" is a disease selected from inflammatory diseases, cancer, stroke and Alzheimer's disease. In a preferred embodiment, such disease is associated with an increased level of one or several reaction products or intermediates from the 5-LOX-pathway, such as the above mentioned leukotrienes or 5-HpETE, 5-HETE or 5-oxo-ETE, or one or several reaction products or intermediates from the PGES-pathway. In one embodiment, the inflammatory disease is a disease selected from inflammatory diseases of the respiratory system, such as asthma, allergic rhinitis, chronic obstructive pulmonary disease (COPD), sinusitis, bronchitis, hay fever, inflammatory diseases of the skin, such as dermatitis, psoriasis, acne, inflammatory bowel diseases, such as Crohn's disease, celiac disease, colitis ulcerosa, autoimmune diseases, such as lupus erythematosus arthritis, in particular rheumatoid arthritis, inflammatory diseases of the vascular system, such as atherosclerosis, vasculitis, Wegener granulomatosis, inflammation post infection and pain, e.g. inflammatory or neuropathic pain.

The 5-lipoxygenase pathway has been implicated in various diseases, and 5-lipoxygenase-products/intermediates have been measured for various diseases, as exemplified for atherosclerosis in Tardif et al. Circ. Cardiovasc. Imaging, 2010; 3: 298-307; for Alzheimer's disease in Chu et al. Am. J. Cathol. 2011 April; 178(4); 1762-1769; for cancer in Lim et al. J. Neurooncol. 2010, May; 97(3); 339-346; for asthma in Berger et al. Int. J. Clin. Pract., April 2007, 61, 4, 663-676; for COPD in Cazzola et al. European Respiratory Journal 2012; 40(3); 724-741, for allergic rhinitis in Knapp N. Engl. J. Med. 1990; 323; 1745-1748, for atopic dermatitis in Woodmansee et al. Ann. Allergy Asthma Immunol. 1999; 83:548-552, for Urticaria in Spector et al. J. Allergy Clinc. Immunol. 1998; 101(4)572, for chronic nasal polyposis/sinusitis in Ravikumar, J. Allergy Clin. Immunol. 2005; 115(2) Supplemental S201; A 801, for arthritis, in Lewis et al., N. Engl. J. Med. 1990; 323:645-655, for pain in Noguchi et al. Biol. Pharm. Bull. 2011; 34(8):1163-1169, for autoimmune diseases in J. Rheumatol. 1995 (March); 22(3):462-468, for Crohn's disease in Lewis et al. N. Engl. J. Med. 1990; 323:645-655, for acne in Zouboulis, Dermatoendocrinology 2009 May/June; 1(3):188-192.

In one aspect, the present invention relates to compounds for use in the treatment of a disease associated with the 5-LOX-pathway and/or prostaglandin E synthase (PGES), e.g. an inflammatory disease or cancer or Alzheimer's disease, said compound having one of the formulae 1-415, as shown in Tables 1-6 and/or Example 7 and Table 7, preferably having one of the formulae 1-12, 14-16, 19-21, 24, 28-34, 36-40, 44, 48, 51-54, 56-68, 70, 71, 73-77, 79-81, 84, 86-173, 175-192, 194-234, 236-241, 243, 244, 246-261, 263-278, 280-321, 323-354, 356-385, 387-428, 430-440, 442-446, 449-463, 465-471, 473-487, 489-492, 495-496, 499, 501, 503, 505, 507, 509, 512-514, 525, 529-544, 546-556 as indicated in Tables 1 and 7 or formula 14 as indicated in Tables 2 and 7, or one of the formulae 53, 54, 86, 90, 91, 95, 99, 103, 226 as indicated in Tables 5-7; or one of the formulae 14, 17, 24, 29, 30, 32, 33, 38, 43-46, 48, 49, 51-60, 62, 65-70, 73, 74, 79-81, 84, 86-88, 90-107, 109-113, 116, 118-132, 134-138, 140, 145, 147-150, 152, 153, 155, 160-162, 164-166, 168, 169, 172, 175-177, 179, 180, 184-187, 190-197, 199, 200, 202-220, 223, 224, 226, 227, 229-231, 233-236, 238-255, 257-262, 264, 265, 267-302, 304-306, 313, 316, 322-333, 335, 340, 342, 346, 347, 349, 350, 352, 353, 357-359, 361, 365-369, 372-375, 377-380, 382-384, 387, 389-393, 395-403, 405-407, 410, 412-415, 419-428, 430-432, 434-437, 440, 442, 445-453, 455, 457-458, 460-461, 463-482, 486-487, 489-496, 499, 501-553, 556 as indicated in Tables 3 and 7, or one of the formulae 11, 12, 14, 24, 30, 32, 48, 52-54, 62, 65, 77, 79-81, 86-88, 92, 94, 97, 98, 101-103, 106, 109-111, 113, 119, 120, 122, 123, 125, 130, 136-138, 145, 147, 149, 155, 165, 166, 176, 177, 184, 193, 195, 199, 204, 211, 226, 227, 229, 231, 233, 234, 238, 239, 243, 249, 251, 253, 256, 268-271, 275, 277, 279, 281, 284, 288, 289, 296, 306, 311, 324, 328, 336, 341, 345, 350, 351, 358, 360, 362, 367-369, 373, 374, 378, 381, 392, 412-415, 430, 431, 433, 447-450, 461, 464-466, 468-471, 473-477, 479, 481, 482, 486, 487, 489-496, 498, 499, 501-506, 508, 509, 512-514, 516-519, 525-538, 540-547, 550, 553-554 as indicated in Tables 4 and 7; or the formula 211 as indicated in Table 7; or a pharmaceutically acceptable salt thereof.

Preferably, the compounds as defined above have an inhibitory activity on an enzyme involved in an inflammatory pathway(s) e.g. the arachidonate 5-lipoxygenase pathway and/or the prostaglandin E synthase (PGES) pathway, preferably on arachidonate 5-lipoxygenase (5-lipoxygenase, 5-LO, 5-LOX, Alox5), at a concentration of said compound between 0.001-50 µM, particularly preferably having an $IC_{50}$ on arachidonate 5-lipoxygenase of less than 1 µM and/or having an $EC_{50}$ of less than 10 µM on the production of leukotriene B4 (LTB4) in rat basophilic leukocyte cells (RBL) or rat whole blood (RWB), and/or having a 40-70% inhibitory activity, preferably >70% inhibitory activity on the production of prostaglandin E2 in HeLa S3 cells stimulated with TNF-alpha, at a concentration of 10 µM of said compound.

In one aspect the present invention relates to a composition comprising a compound according to the present invention and a pharmaceutically acceptable carrier, for use in the treatment of a disease associated with the 5-LOX-pathway and/or the PGES-pathway, said disease being selected from inflammatory disease, e.g. asthma or COPD, cancer, stroke and Alzheimer's disease.

In one embodiment, said inflammatory disease is asthma or allergic rhinitis or dermatitis or chronic obstructive pulmonary disease (COPD) or inflammation post infection or arthritis or atherosclerosis or pain. e.g. inflammatory and/or neuropathic pain.

In one embodiment, said treatment comprises administering a suitable amount of a compound or of a composition as defined above to a patient in need thereof, suffering from a disease associated with the 5-LOX-pathway and/or the PGES-pathway, said disease being selected from inflammatory disease, cancer, stroke and Alzheimer's disease.

In a further aspect the present invention relates to a method of treatment of a disease associated with the 5-LOX-pathway and/or the PGES-pathway, said disease being selected from an inflammatory disease, cancer, stroke and Alzheimer's disease, said method comprising the application of a suitable amount of a compound or composition as defined above to a patient in need thereof. In one embodiment said inflammatory disease is asthma or allergic rhinitis or dermatitis or chronic obstructive pulmonary disease (COPD) or inflammation post infection or arthritis or atherosclerosis or pain, e.g. inflammatory and/or neuropathic pain.

In one embodiment, said suitable amount is an amount in the range of 0.01 mg/kg body weight to 1 g/kg body weight of said patient.

The present invention also relates to the use of a compound or composition according to the present invention, as defined above, for the manufacture of an medicament for the treatment of a disease associated with the 5-LOX-pathway/or the PGES-pathway, said disease being selected from an inflammatory disease, cancer, stroke and Alzheimer's disease, said treatment comprising the application of a suitable amount of a compound or a composition as defined above to a patient in need thereof. The inflammatory disease and the suitable amount is as defined further above.

In a further aspect the present invention relates to compound that competitively inhibits the specific binding of a compound according to the present invention as defined above to arachidonate 5-lipoxygenase (5-lipoxygenase, 5-LO, 5-LOX, Alox5) and/or the prostaglandin E synthase (PGES).

In yet a further aspect the present invention relates to method of treatment of a disease associated with the 5-LOX-pathway and/or the PGES-pathway, said disease being selected from an inflammatory disease, in particular asthma, atherosclerosis, pain, COPD, inflammation post infection, allergic rhinitis and/or atopic dermatitis or cancer or stroke or Alzheimer's disease, said method comprising the application of a suitable amount of a compound as just defined, i.e. a compound that competitively inhibits the specific binding of a compound according to the present invention to arachidonate 5-lipoxygenase or to prostaglandin E synthase, to a patient in need thereof.

Such compound that competitively inhibits the specific binding of a compound according to the present invention to 5-LOX or to PGES, is herein also sometimes referred to as a "competitively inhibitory compound".

In one embodiment, such patient is a patient suffering from an inflammatory disease, preferably as defined further above.

The present invention also relates to the use of a competitively inhibitory compound for the manufacturer of a medicament for the treatment of a disease associated with the 5-LOX-pathway or the PGES-pathway, said disease being selected from an inflammatory disease, in particular, asthma, atherosclerosis, pain or COPD, inflammation post-infection, allergic rhinitis and/or arthritis, or cancer or stroke or Alzheimer's disease, said treatment comprising the application of a suitable amount of a compound that competitively inhibits the specific binding as defined above, to a patient in need thereof.

The terms "$IC_{50}$" and "$EC_{50}$" refer to the half-maximal inhibitory concentration and the half-maximal effective concentration, respectively, of a compound with respect to a given activity, for example an inhibition of an enzyme through a compound, or the production of a substance stimulated by a compound. One example of an $IC_{50}$ is the half-maximum inhibitory concentration of a compound on the activity of arachidonate 5-lipoxygenase. One example for an $EC_{50}$-value is the half maximum effective concentration of a compound on the production and/or secretion of leukotriene B4 (LTB4) in a cell or whole blood, for example a rat basophilic leukocyte cell (RBL) or rat whole blood (RWB).

Pharmaceutical Compositions

Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enanthate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphthalene-2-sulphonic acid, the nitrate derived from nitric acid, the oxalate derived from oxalic acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids which may not be considered pharmaceutically acceptable, may be useful in the preparation of salts useful as intermediates in obtaining a chemical compound of the invention and its pharmaceutically acceptable acid addition salt, for use in the treatment of an inflammatory disease.

In another embodiment, the compounds of the invention are used in their respective free base form, for use in the treatment of an inflammatory disease, according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intra-arterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0.001% to 70% per weight of the compound, preferably between 0.01% to 70% per weight of the compound, even more preferred between 0.1% and 70% per weight of the compound. In one embodiment, a suitable amount of compound administered is in the range of 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.) and Remington: The science and practice of pharmacy", Lippincott Williams and Wilkins. Appropriate formulations and ways of manufacturing them are, for example also disclosed in "Arzneiformenlehre, Paul Heinz List, EinLehrbuchfürPharmazeuten, WissenschaftlicheVerlagsgesellschaft Stuttgart, 4. Auflage, 1985", or "The theory and practice of industrial pharmacy" by Lachman et al., Varghese Publishing House, 1987", or "Modern Pharmaceutics", edited by James Swarbrick, 2. Edition".

DESCRIPTION OF THE TABLES

Reference is now made to the tables, wherein

Table 1 summarizes 5-LOX $IC_{50}$ inhibitory activities (uM) as measured by fluorescence wherein the compound number refers to the compounds listed in Example 7;

Table 2 summarizes 5-LOX $IC_{50}$ inhibitory activities (uM) as detected by ELISA wherein the compound number refers to the compounds listed in Example 7;

Table 3 summarizes LTB4 secretion assay ($EC_{50}$, uM) in RBL (rat basophilic leukemia) cells wherein the compound number refers to the compounds listed in Example 7;

Table 4 summarizes LTB4 secretion assay ($EC_{50}$, uM) in RWB (rat whole blood) wherein the compound number refers to the compounds listed in Example 7;

Table 5 summarizes $PGE_2$% inhibition at 10 uM as measured by HTRF (Homogeneous Time Resolved Fluorescence) wherein the compound number refers to the compounds listed in Example 7;

Table 6 summarizes COX-2 (Cyclooxygenase 2) % inhibition at 10 uM as measured by EIA (Enzyme Immunoassay) wherein the compound number refers to the compounds listed in Example 7 and Table 7;

Table 7 summarizes compounds 1-556 the synthesis of which is described in Example 7.

EXAMPLES

The invention is now further described by reference to the following examples which are intended to illustrate, not to limit the scope of the invention.

Example 1

Activity of Compounds Against 5-LOX Enzyme

The activity of compounds against 5-LOX were determined by measuring $LTB_4$ (leukotriene B4) levels and/or by a fluorescence method. Both approaches are outlined in more detail below;

$LTB_4$ Measurement by ELISA:

Human 5-lipoxygenase (5-LOX) (Cayman, Cat #60402) produced in insect cells was pre-incubated with compounds for 5 min at RT in incubation buffer (50 mM Tris-Cl, pH 7.4, 2 mM $CaCl_2$, 0.1 mM ATP, 2% DMSO). Compounds were tested in dose reponse from 0.5 nM to 10 uM. The enzymatic reaction was started by adding arachidonic acid to a final concentration of 3 uM. After 5 min of incubation at 25° C., the reaction was stopped by adding $H_2O_2$ to a final concentration of 1 mM. $LTB_4$ levels were quantified using a $LTB_4$ EIA kit (Cayman, Cat #520111) as instructed.

Fluorescence Method:

Besides the above method for quantifying LTB4 levels, a fluorescence assay measuring 5-hydroperoxyeicosatetraenoic acid (5-HPETE) was introduced for high-throughput screening in a 384 well microplate format (Pufahl et al., 2007) Development of a Fluorescence-based enzyme assay of human 5-lipoxygenase. ANALYTICAL BIOCHEMISTRY 364, 204-212). For nonspecific ester cleavage of the acetate groups in $H_2DCFDA$(2',7'-dichlorodihydrofluorescein diacetate), the insect cell lysate expressing human 5-LOX (Cayman Cat #60402) was incubated with $H_2DCFDA$ (50 mM Tris-Cl, pH 7.5, 2 mM CaCl2, 20 uM $H_2DCFDA$, 600 mU 5-LOX per reaction) for 5 minutes. The compound, in a dose response manner(0.5 nM to 10 uM), and enzyme mixture was pre-incubated for 5 minutes, and the enzymatic reaction was initiated by addition of ATP and arachidonic acid to a final concentration of 100 uM and 3 uM, respectively. After 5 minutes of incubation, fluorescence was measured using Spectramax M5 (Molecular Device, Ex/Em=485 nm/530 nm). All steps were carried out at room temperature.

Example 2

LTB4 Secretion Assay in RBL (Rat Basophilic Leukemia Cells)

Rat basophilic leukemia (RBL) cells (ATCC, Cat #CRL-2256) were maintained in EMEM (ATCC, Cat #30-2003) supplemented with 15% FBS. The day before RBL assay, cells were seeded at a concentration of $2\times10^4$ cells per well in 96-well plates. The media was replaced with 100 ul of EMEM supplemented with 0.5% FBS and compounds in dose response(5 nM to 100 uM) were added. After 15 min of pre-incubation at 37° C., arachidonic acid and calcium ionophore (A23187) were added to give a final concentration of 2.5 uM and 5 uM, respectively. After a further 10 min incubation at 37° C., culture supernatant was transferred and quantification of LTB4 was done with a Leukotriene B4 EIA kit (Cayman, Cat #520111) as instructed.

Example 3

LTB4 Secretion Assay in RWB (Rat Whole Blood)

Rat blood was drawn from caudal vena cava from male Sprague Dawley rat (6-9 weeks old) in vacuette coated with sodium heparin (Greiner bio-one, Cat #455051). The blood was pooled and diluted with RPMI (WelGENE, Cat #LM 011-05) to 1:1. The diluted blood was aliquoted into 96 well plate (200 ul per well) and compounds were added in dose response to a desired concentration ranging from 2.5 nM to 50 uM. After 15 min of pre-incubation at 37° C., calcium ionophore (A23187) was added to the final concentration of 10 uM. After 10 min of further incubation at 37° C., the LTB4 production was stopped by diluting the reaction mixture with ice cold PBS (1:4 dilutions). Cells were removed by centrifugation at 1000×g, 4° C. for 10 min, and the supernatant was transferred and then the quantification of LTB4 was done with Leukotriene B4 EIA kit (Cayman, Cat #520111) as instructed.

Example 4

Inflammation Efficacy in OVA-Induced Airway Inflammation Model in Brown Norway Rats The objective of this study is to determine the efficacy of compounds in the lungs of ovalbumin (OVA) induced in Brown Norway rats. As with most models of induced allergic asthma, animals are systemically sensitized to specific antigens and then, after a period of time, challenged with the same allergen administered via the airway. Ovalbumin had been used as the standard allergen to sensitize and challenge animals in this study.

Thirty (30) male Brown Norway rats were randomized into 5 groups on the basis of body weight. For sensitization, 1% OVA in PBS solution was mixed with alum solution (with volume ratio of 1:9). All rats in groups 1-5 were sensitized by i.p injection (1 mL/rat) of 1% OVA-alum sensitization solution on day 1, 2 and 3. At day 21, rats in groups 1-5 were challenged with 1% OVA in PBS solution with aerosolizing dosing system for 20 min.

Test compounds were administered by p.o. from days 19-21 of the study as per schedule below:
Group 1: sensitized-vehicle,
Group 2: reference drug dexamethasone, 0.3 mg/kg, p.o., Day 19-21, BID,
Group 3: compound 211, 25 mg/kg, p.o., Day 19-21, BID,
Group 4: compound 211, 50 mg/kg, p.o., Day 19-21, BID,
Group 5: compound 211, 100 mg/kg, p.o., Day 19-21, BID, On day 22, bronchoalveolar lavage and lung tissues were harvested. Total cell number and differential cell counts in BALF, leukotriene B4 (LTB4) in BALF and lung tissue, histopathology of lung by H&E staining will be evaluated.

Treatment of rats using compound 211 significantly reduced the increase of inflammatory cells including total cell and eosinophils, reduced LTB4 in BALF and Lung, and significantly reduced inflammation cell infiltration. These data indicate that compound 211 shows antiinflammatory activity in OVA-induced asthma.

Example 5

PGE$_2$ Inhibition Assay

Human epitheloid cervix carcinoma HeLa S3 cells (2×10$^6$cells/ml) were seeded with modified F-12K buffer medium pH 7.4 in tissue culture plate and incubated for overnight at 37° C. and 5% CO$_2$. Then medium was changed into new medium contained 10 uM testing compounds or 0.1% DMSO and incubated overnight. After incubation, cells were stimulated with 30 nM TNF-α (Tumor necrosis factor-α) for 16 h. For determination of PGE$_2$, the supernatant was measured by PGE$_2$ HTRF (Homogeneous Time Resolved Fluorescence) assay kit Inhibition of PGE$_2$ by compounds is calculated as a percentage of activity in the presence of drug versus the activity in the stimulator TNF-α.

Example 6

COX-2 Inhibition Assay

Human recombinant cyclooxygenase-2 expressed in insect Sf21 cells was used. The testing compounds and reference compound (Rofecoxib) were dissolved in DMSO (Sigma, USA) and tested at 10 uM. Test samples were pre-incubated with 0.11 U enzyme in 100 mM modified Tris-HCl buffer pH 7.7 for 15 minutes at 37° C. The reactions were initiated by addition of 0.3 μM arachidonic acid for another 5-minute incubation period, then terminated by further addition of 1 N HCl. An aliquot was then combined with the EIA kit for spectrophotometric determination of the quantity of PGE$_2$ formed. Inhibition % was determined by compared with relative amounts of PGE$_2$ induced by arachidonic acid. The results show that the compounds according to the present, as exemplified by compounds (cpds.) 90 and 95, do not have an inhibitory effect on cyclooxygenase-2 (COX-2), thus lending support to the fact that their inhibitory action on the PGES-pathway occurs at the level of "PGES".

Example 7

Preparation of Compounds

The synthesis of compounds described herein may be accomplished using means described in the chemical literature, using the methods described herein, or by a combination thereof.

Compounds described herein may be synthesized using standard synthetic techniques known to those of skill in the art or using methods known in the art in combination with methods described herein. In addition, solvents, temperatures and other reaction conditions presented herein may vary according to those of skill in the art. The starting material used for the synthesis of the compounds described herein may be synthesized or can be obtained from commercial sources, such as, but not limited to, Aldrich Chemical Co. (Milwaukee, Wis.), or Sigma Chemical Co. (St. Louis, Mo.). The compounds described herein, and other related compounds having different substituents can be synthesized using techniques and materials described herein as well as those that are known to those of skill in the art. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the synthetic method of Schemes may be utilized to prepare a compound described herein.

The compounds (scaffold I, II and III; see Tables 1-7) underwent derivatization according to the methods outlined below (Schemes 1-37), and the synthesized compounds as well as relevant NMR characterization data are shown in Table 7. Resulting derivatives were examined for inhibitory activity (IC$_{50}$, EC$_{50}$, in vivo) using the assays described above (Examples 1, 2, 3, 4, 5 and 6), and the results are summarized in Tables 1, 2, 3, 4, 5 and 6.

Scheme 1. General synthesis 1 of an amine compound

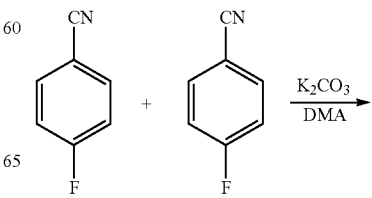

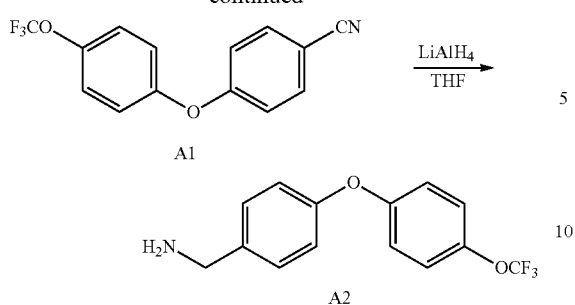

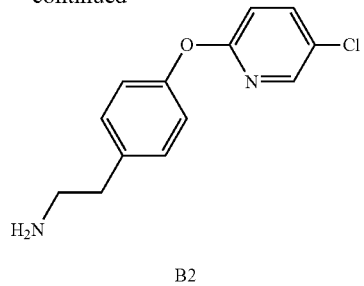

General Procedure for the Synthesis of A1

To a stirred solution of 4-fluorobenzonitrile (5.00 g, 41.3 mmol) and 4-trifluoromethoxy-phenol (8.10 g, 45.5 mmol) in DMA (30 mL) was added $K_2CO_3$ (6.30 g, 45.6 mmol). The resulting mixture was stirred at 120° C. for 16 hours. The mixture was cooled to 50° C. and 100 mL water was added dropwise under good stirring. The mixture was extracted with EtOAc (100 mL×2), the combined organic phase was washed with water (100 mL) and brine (100 mL), dried over anhydrous $Na_2SO_4$ and concentrated under reduced pressure to afford A1.

General Procedure for the Synthesis of A2

To a stirred solution of A1 (3.00 g, 10.7 mmol) in anhydrous THF (30 mL) at 0° C. was added $LiAlH_4$ (1.63 g, 43.0 mmol) in portions, the reaction mixture was stirred at 0° C. for 3 hours, the resulting mixture was stirred at 50° C. for another 16 hours. The mixture was quenched with water (1.6 mL) dropwise at 0° C., then followed NaOH (10%, 3.2 mL) dropwise and water (1.6 mL) to the mixture. The mixture was filtered, the filter cake was washed with EtOAc (30 mL) and the filtrate was concentrated under reduced pressure to afford A2.

General Procedure for the Synthesis of B1

To a stirred solution of 2-(4-hydroxyphenyl)acetonitrile (10.0 g, 75.2 mmol) in DMA (120 mL) were added 2,5-dichloro pyridine (12.2 g, 82.7 mmol), $K_2CO_3$ (15.6 g, 113 mmol) and TBAF (589 mg, 2.26 mmol), then the mixture was stirred at 115° C. for 16 hours. The reaction mixture was poured into water (600 mL) with vigorous stirring for 1 hour. The precipitate was collected by filtration, dried in air for 2 hours and purified by Combi Flash (PE:EtOAc=5:1 to 2:1) to afford B1.

General Procedure for the synthesis of B2

To a stirred solution of B1 (500 mg, 2.04 mmol) in MeOH (15 mL) were added Raney-Ni (400 mg) and $NH_3.H_2O$ (0.5 mL, 28%). The reaction solution was stirred at 15° C. under $H_2$ atmosphere (45 psi) for 6 hours. Then the solution was filtered through a pad of Celite. The filtrate was concentrated and diluted with DCM (30 mL), then dried over anhydrous $Na_2SO_4$, evaporated to afford B2.

Scheme 2. General synthesis 2 of an amine compound

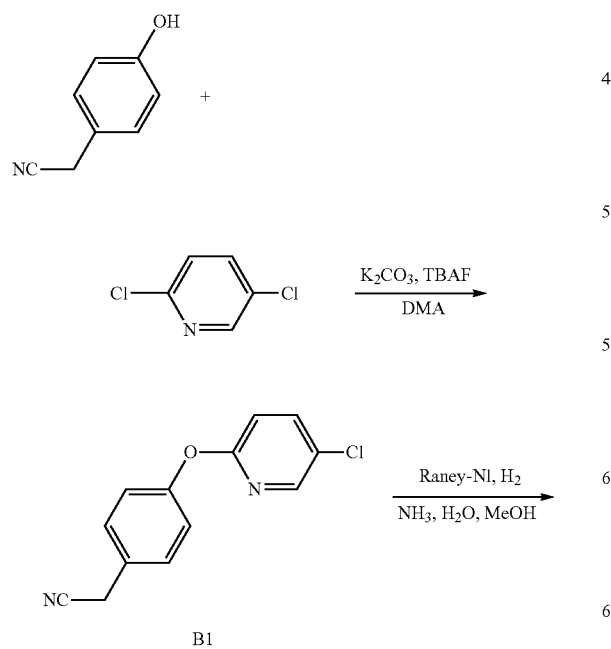

Scheme 3. General synthesis 3 of an amine compound

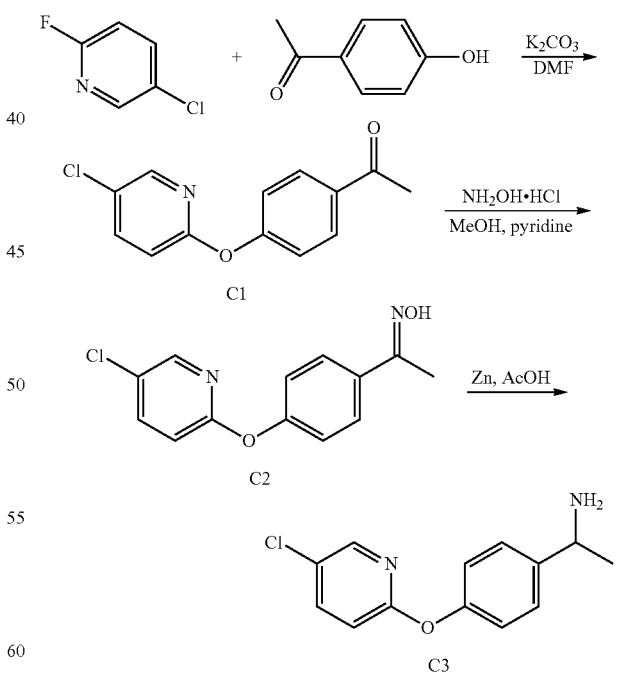

General Procedure for the Synthesis of C1

A mixture of 4'-hydroxyacetophenone (5.00 g, 36.7 mmol), 5-chloro-2-fluoropyridine (5.79 g, 44.0 mmol) and $K_2CO_3$ (10.1 g, 73.4 mmol) in DMF (150 mL) was stirred at 100° C. for 6 hours. After cooling to room temperature, the reaction mixture was diluted with EtOAc (200 mL), then filtered and the filtrate was washed with brine (150 mL×3), dried over anhydrous Na$_2$SO$_4$ and concentrated under reduced pressure to afford a residue. The residue was washed with PE/EtOAc=20/1(40 mL) to afford C1.

General Procedure for the Synthesis of C2

A mixture of C2 (4.50 g, 18.2 mmol) and NH$_2$OH.HCl (1.26 g, 18.2 mmol) in MeOH/pyridine (25 mL/25 mL) was stirred at 8-10° C. for 16 hours. The resulting mixture was concentrated under reduced pressure, acidified with HCl (2 M, 120 mL), extracted with DCM (50 mL×4), the combined organic layer was washed with water (200 mL×3), brine (200 mL), dried over anhydrous Na$_2$SO$_4$ and concentrated under reduced pressure to afford C2.

General Procedure for the Synthesis of C3

A mixture of C2 (4.70 g, 17.9 mmol) and Zn powder (11.6 g, 179 mmol) in AcOH (120 mL) was stirred at 65-75° C. for 28 hours. After cooling to room temperature, the reaction mixture was filtered, washed with EtOAc (10 mL×3) and the combined filtrate was concentrated under reduced pressure to afford a residue. The residue was diluted with saturated NaHCO$_3$ (150 mL), extracted with EtOAc (100 mL×3), the combined organic layer was washed with brine (200 mL×2), dried over anhydrous Na$_2$SO$_4$ and concentrated under reduced pressure to afford C3.

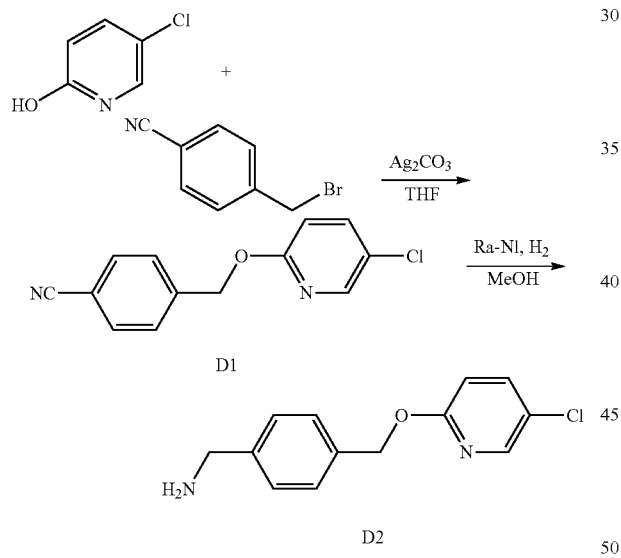

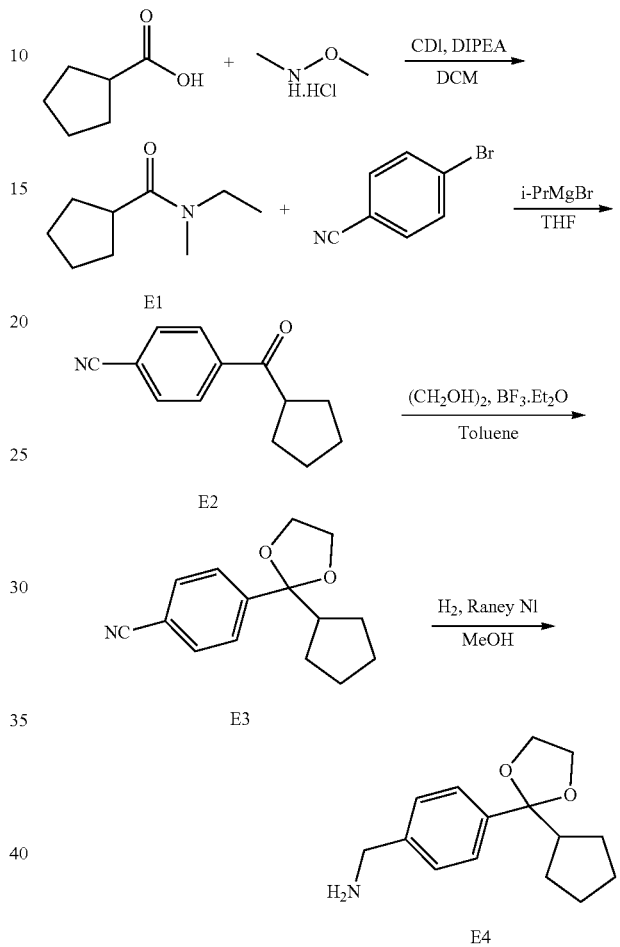

General Procedure for the Synthesis of D1

To a stirred mixture of 5-chloro-2-hydroxypyridine (15.0 g, 76.5 mmol) in anhydrous THF (200 mL) were added 4-cyanobenzyl bromide (8.26 g, 63.8 mmol) and Ag$_2$CO$_3$ (10.5 g, 38.3 mmol). The resulting mixture was refluxed for 16 hours. The mixture was cooled to room temperature and filtered. The filter cake was washed with THF (100 mL). The combined filtrate was concentrated under reduced pressure to afford a residue, which was purified by combi flash (PE/EtOAc=92/8 to 70/30) to afford D1.

General Procedure for the Synthesis of D2

To a stirred solution of D1 (5.00 g, 2.04 mmol) in MeOH (100 mL) were added Raney-Ni (1.00 g) and NH$_3$.H$_2$O (0.5 mL, 28%) under N$_2$ atmosphere. The suspension was degassed under vacuum and purged with H$_2$ for three times. The solution was stirred at 12° C. under H$_2$ (45 psi) atmosphere for 2 hours. The mixture was filtered through a pad of celite, and the pad was washed with MeOH (200 mL). The filtrate was concentrated under reduced pressure to afford D2.

General Procedure for the Synthesis of E1

To a stirred solution of cyclopentanecarboxylic acid (5.00 g, 44.2 mmol) in anhydrous DCM (100 mL) was added CDI (8.10 g, 57.5 mmol) in portions at 28° C. The reaction solution was stirred at 28° C. for 0.5 hour. Then DIEA (8.00 g, 61.9 mmol) and N,O-dimethyl hydroxylamine hydrochloride (5.13 g, 61.9 mmol) were added. The reaction solution was stirred at 28° C. for 16 hours. The reaction solution was diluted with saturated NaHCO$_3$ (50 mL) and separated. The organic layer was dried over anhydrous Na$_2$SO$_4$ and concentrated under reduced pressure. The residue was purified by Combi Flash (PE:EtOAc=5:1 to 2:1) to afford E1.

General Procedure for the Synthesis of E2

To a stirred solution of 4-bromobenzonitrile (1.40 g, 7.69 mmol) in anhydrous THF (15 mL) was added i-PrMgBr (19.2 mL, 19.2 mmol, 1 M in THF) dropwise at −30° C. under N$_2$ atmosphere. Then the mixture was stirred at −30° C. under N$_2$ atmosphere for 30 minutes. A solution of E1 (1.00 g, 6.37 mmol) in anhydrous THF (5 mL) was added dropwise at −30° C. The reaction solution was allowed to warm to 30° C. and stirred at 30° C. for 16 hours. The reaction solution was quenched by saturated NH$_4$Cl solution (15 mL) at 0° C. The organic phase was separated, concentrated under reduced pressure. The residue was purified by Combi Flash (PE:EtOAc=10:1) to afford E2.

General Procedure for the Synthesis of E3

A mixture of E2 (250 mg, 1.26 mmol), BF$_3$.Et$_2$O (0.5 mL), ethylene glycol (1 mL) in toluene (50 mL) was refluxed with azeotropic removal of water for 48 hours. The reaction solution was cooled to room temperature and diluted with saturated Na$_2$CO$_3$ (30 mL). The organic layer was separated, dried over anhydrous Na$_2$SO$_4$ and concentrated under reduced pressure. The residue was purified by prep-TLC (PE:EtOAc=5:1) to afford E3.

General Procedure for the Synthesis of E4

To a stirred solution of E3 (100 mg, 0.410 mmol) in MeOH (5 mL) were added Raney-Ni (100 mg) and ammonia water (0.5 mL, 28%). The reaction solution was stirred at 25° C. under H$_2$ atmosphere (45 psi) for 2 hours. Then the solution was filtered through a pad of Celite. The filtrate was concentrated under reduced pressure to afford E4.

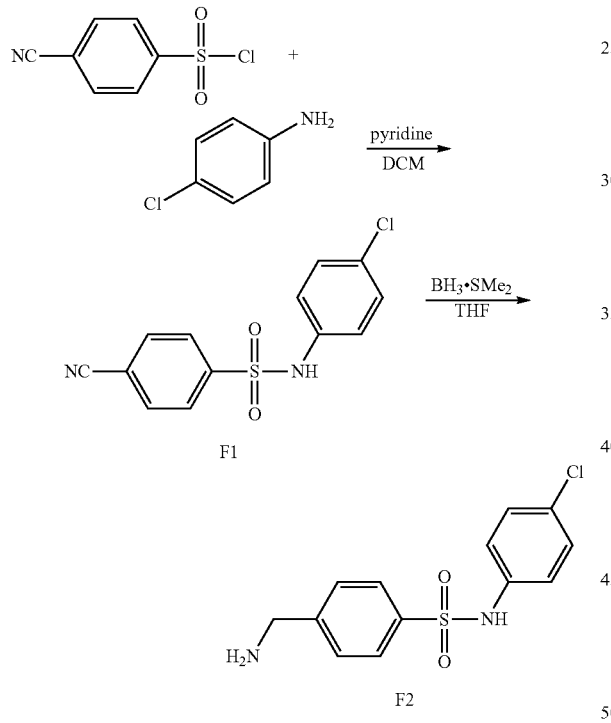

General Procedure for the Synthesis of F1

To a stirred solution of 4-chloroaniline (634 mg, 4.96 mmol) and pyridine (1.17 g, 14.9 mmol) in DCM (10 mL) was added a solution of 4-cyanobenzenesulfonyl chloride (1.00 g, 4.96 mmol) in DCM (5 mL) under ice bath, then the mixture was stirred under N$_2$ atmosphere at 25° C. for 12 hours. The mixture was poured into water (30 mL), extracted with DCM (10 mL×3). The combined extracts was dried over anhydrous Na$_2$SO$_4$ and concentrated under reduced pressure to afford a residue, which was purified by flash column chromatography (eluent: DCM) to afford F1.

General Procedure for the Synthesis of F2

To a stirred solution of F2 (500 mg, 1.71 mmol) in anhydrous THF (2.5 mL) was added BH$_3$/Me$_2$S (1.35 mL, 13.5 mmol, 10M) under ice bath, the mixture was stirred under N$_2$ atmosphere at 25° C. for 12 hours. MeOH (5 mL) was added dropwise carefully to quench the reaction, then the mixture was diluted with water (50 mL), adjusted pH 8 by saturated Na$_2$CO$_3$, extracted with EtOAc (30 mL×3). The combined extract was dried over anhydrous Na$_2$SO$_4$ and concentrated under reduced pressure to afford a residue, which was purified by Combi Flash (eluent: PE/EtOAc=1/1 to EtOAc) to afford F2.

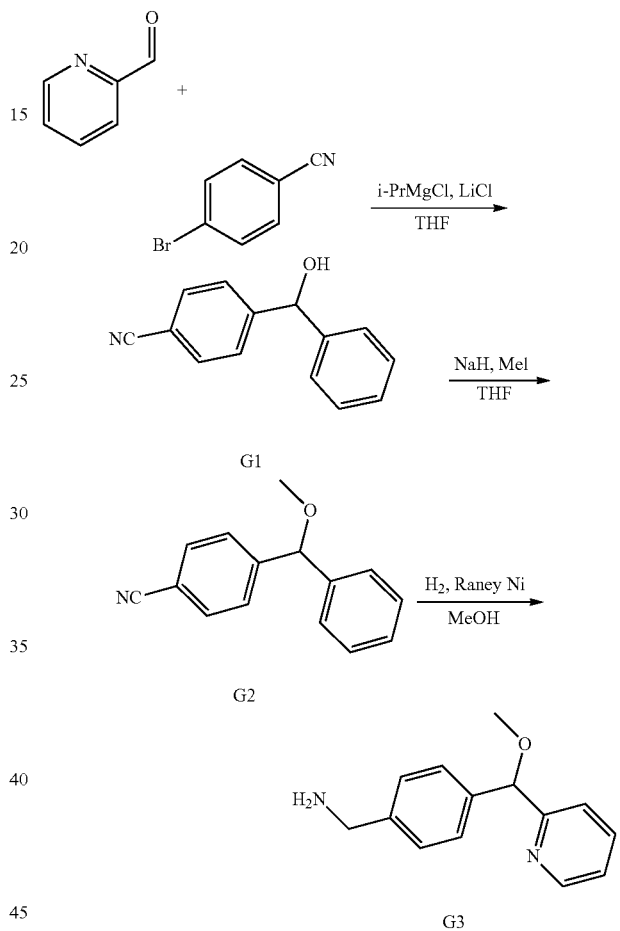

General Procedure for the Synthesis of G1

To a stirred solution of 4-bromobenzonitrile (1.00 g, 5.50 mmol), LiCl (252 mg, 6.00 mmol) in anhydrous THF (10 mL) was added i-PrMgCl (3 mL, 6.0 mmol, 2 M in THF) dropwise at −15° C. under N$_2$ atmosphere. Then the mixture was stirred at −15° C. under N$_2$ atmosphere for 2 hours. Then picolinaldehyde (640 mg, 6.00 mmol) was added dropwise at −15° C. The reaction solution was allowed to warm to 30° C. TLC showed the reaction was complete. The reaction solution was quenched by saturated NH$_4$Cl solution (10 mL) at 0° C. The organic layer was separated and concentrated under reduced pressure. The residue was purified by Combi Flash (PE:EtOAc=5:1 to 2:1) to afford G1.

General Procedure for the Synthesis of G2

To a stirred solution of G2 (400 mg, 1.90 mmol) in anhydrous THF (6 mL) was added NaH (298 mg, 2.10 mmol, 60% dispersion in mineral oil) at 0° C., then the mixture was stirred at 0° C. for 15 minutes. Afterwards, MeI (298 mg, 2.10 mmol) was added to the mixture at 0° C. The mixture was stirred under N$_2$ atmosphere at 25° C. for 1 hour. The reaction mixture was poured into water (10 mL), extracted with EtOAc (10 mL×3). The combined organic layer was washed with brine (10 mL), dried over anhydrous Na₂SO₄ and concentrated under reduced pressure. The residue was purified by Combi Flash (PE:EtOAc=5:1 to 1:1) to afford G2.

General Procedure for the Synthesis of G3

To a stirred solution of G2 (1.50 g, 6.70 mmol) in MeOH (40 mL) were added Raney-Ni (2.0 g) and concentrated ammonia water (4 mL, 28%). The reaction solution was stirred at 25° C. under H₂ atmosphere (45 psi) for 3 hours. Then the solution was filtered through a pad of Celite. The filtrate was concentrated under reduced pressure to afford 1.53 g of residue, which was purified by silica gel column chromatography (DCM:MeOH=10:1) to afford G3.

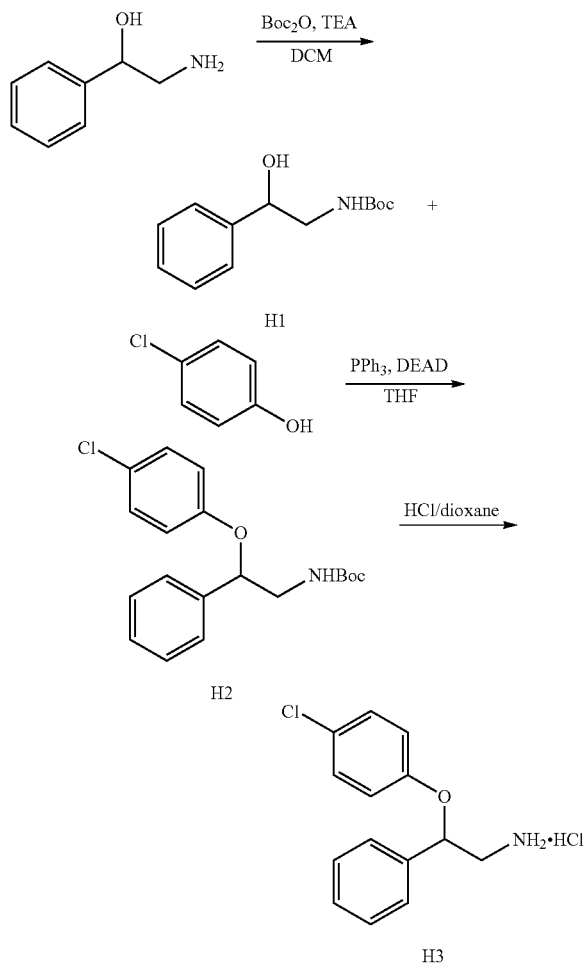

General Procedure for the Synthesis of H1

To a stirred solution of 2-amino-1-phenylethanol (5.00 g, 36.4 mmol) and TEA (5.51 g, 54.6 mmol) in DCM (100 mL) was added Boc₂O (9.54 g, 43.7 mmol), then the resulting mixture was stirred at 27-28° C. for 2 hours. The reaction mixture was concentrated under reduced pressure to remove most of DCM. The residue was diluted with EtOAc (100 mL), then washed with 1% HCl solution (50 mL), brine (50 mL×2), dried over anhydrous Na₂SO₄ and concentrated under reduced pressure. The residue was washed with PE/EtOAc (50 mL/5 mL) to afford H1.

General Procedure for the Synthesis of H2

To a stirred solution of H1 (4.00 g, 16.9 mmol), 4-chlorophenol (4.33 g, 33.7 mmol) and PPh₃ (6.63 g, 25.3 mmol) in anhydrous THF (150 mL) was added dropwise a solution of DEAD (4.40 g, 25.3 mmol) in THF (50 mL) at 0-5° C. The resulting mixture was stirred at 26-30° C. for 16 hours. The reaction mixture was diluted with EtOAc (500 mL), then washed with brine (300 mL×3), dried over anhydrous Na₂SO₄ and concentrated under reduced pressure. The residue was purified by flash column chromatography (PE/EtOAc=20/1 to 5/1), diluted with MTBE (100 mL), then washed with 1 μM NaOH solution (50 mL×3), brine (50 mL×3), dried over anhydrous Na₂SO₄ and concentrated under reduced pressure to afford H2.

General Procedure for the Synthesis of H3

A mixture of H2 (2.00 g, 5.75 mmol) in HCl/dioxane (30 mL, 4.0 M) was stirred at 27° C. for 20 minutes. The reaction mixture was concentrated under reduced pressure to afford H3.

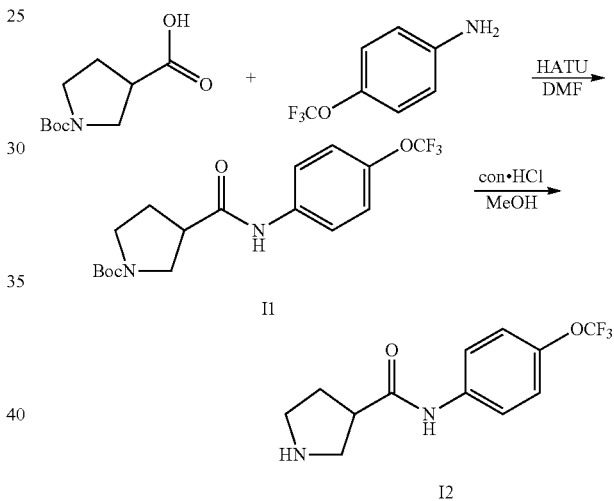

General Procedure for the Synthesis of I1

To a stirred solution of 1-Boc-pyrrolidine-3-carboxylic acid (5.00 g, 23.3 mmol) and 4-(trifluoromethoxy)aniline (3.91 g, 22.1 mmol) in anhydrous DMF (50 mL) was added DIPEA (9.0 g, 69.8 mmol). Then HATU (13.2 g, 34.7 mmol) was added portionwise at 0° C. The reaction mixture was stirred at 25° C. for 4 hours. The mixture was quenched with water (100 mL), extracted with EtOAc (100 mL×2). The combined organic phase was washed with saturated NaHCO₃ (100 mL), dried over anhydrous Na₂SO₄ and concentrated under reduced pressure to afford I1.

General Procedure for the Synthesis of I2

To a stirred solution of I1 (6.00 g, 16.0 mmol) in DCM (120 mL) was added TFA (40 mL) dropwise at 0° C. After the addition, the mixture was stirred at 25° C. for 12 hours. The mixture was concentrated under reduced pressure and the residue was diluted with 100 mL water. Solid K₂CO₃ was added to adjust pH 10 and extracted with EtOAc (200 mL×2). The combined organic phase was dried over anhydrous Na₂SO₄ and concentrated under reduced pressure to afford I2.

Scheme 10. General sythesis 10 of an amine compound

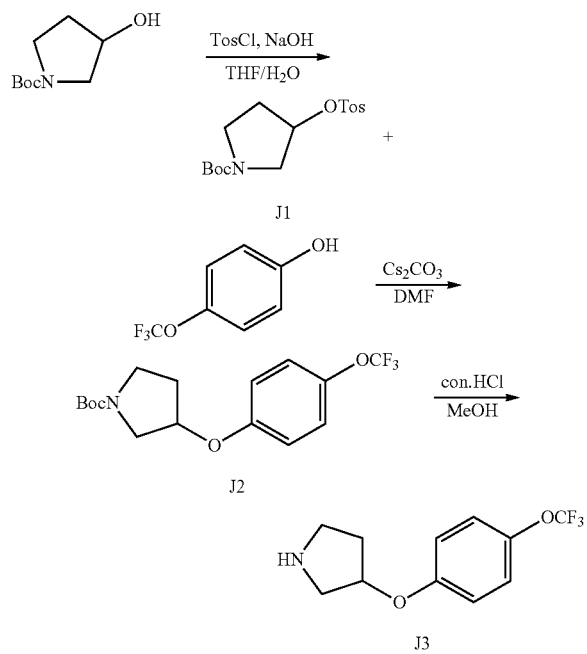

Scheme 11. General synthesis 11 of an amine compound

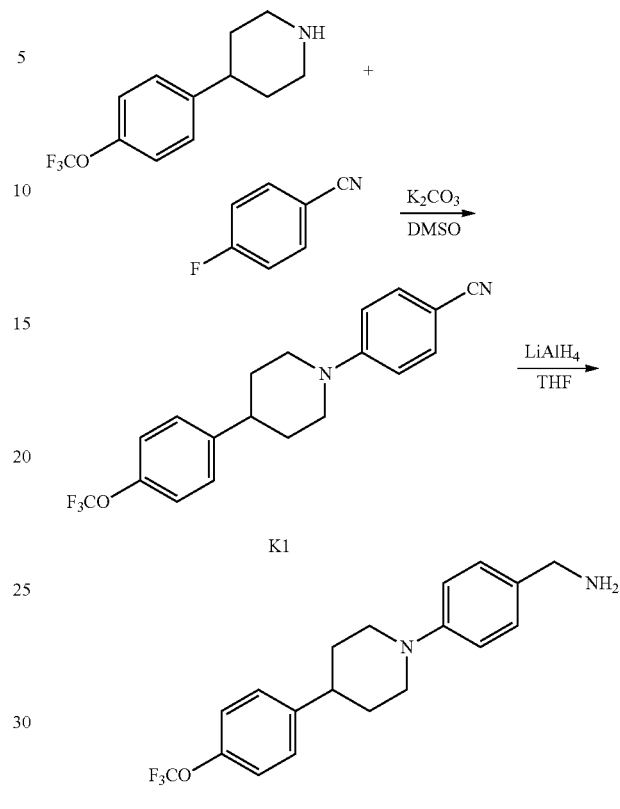

General Procedure for the Synthesis of J1

To a stirred solution of tert-butyl-3-hydroxypyrrolidine-1-carboxylate (10.0 g, 53.4 mmol) in THF (50 mL) was dropwise added aqueous NaOH (5.30 g/134 mmol in 5 mL water) under ice bath (below 10° C.), then TosCl (13.2 g, 68.4 mmol) was added by portions below 10° C. Then the mixture was warmed at 30° C. for 12 hours. THF was concentrated under reduced pressure to afford a residue, the residue was diluted with water (100 mL), extracted with EtOAc (50 mL×3). The combined extract was washed with water (50 mL×2), dried over anhydrous $Na_2SO_4$ and concentrated under reduced pressure to afford a J1.

General Procedure for the Synthesis of J2

A mixture of compound 2 (5.00 g, 14.6 mmol), 4-(trifluoromethoxy)phenol (2.73 g, 15.3 mmol) and $Cs_2CO_3$ (9.50 g, 29.2 mmol) in DMF (25 mL) was stirred at 80-90° C. for 2 hours. The mixture was diluted with water (150 mL), extracted with EtOAc (50 mL×4). The combined extract was dried over anhydrous $Na_2SO_4$ and concentrated to afford a crude, which was purified by flash column chromatography (eluent: EtOAc/PE=1/100 to 1/5) to afford J2

General Procedure for the Synthesis of J3

To a stirred solution of J2 (3.80 g, 10.9 mmol) in MeOH (20 mL) was added aq.HCl (5 mL, 12M) at 10° C., the mixture was stirred at 10° C. for 2 hours. The mixture was concentrated under reduced pressure to afford a residue. The residue was diluted with water (50 mL), adjusted pH=9 by aqueous NaOH (2M), extracted with EtOAc (30 mL×3). The combined extract was dried over anhydrous $Na_2SO_4$ and concentrated under reduced pressure to afford J3.

General Procedure for the Synthesis of K1

To a stirred solution of 4-(4-(trifluoromethoxy)phenyl)piperidine (86.0 g, 0.351 mol) in DMSO (1 L) was added $K_2CO_3$ (121 g, 0.878 mol) and 4-fluorobenzonitrile (63.8 g, 0.527 mol) at 18° C. The reaction mixture was heated to 120° C. for 16 hours under $N_2$. After cooling to room temperature, the mixture was concentrated to about 400 mL over high vacuum. $H_2O$ (2 L) was poured into the mixture and the resulting precipitate was collected by filtration. The crude product was triturated with $H_2O$ (1.5 L), dried over high vacuum, then triturated with EtOAc/PE (800 mL/4 L), dried over high vacuum to afford K1.

General Procedure for the Synthesis of K2

To a stirred solution of K1 (60.0 g, 0.173 mol) in anhydrous THF (1.0 L) was added $LiAlH_4$ (32.9 g, 0.865 mol) at 0° C. The reaction mixture was heated to reflux for 3 hours under $N_2$. After cooling to room temperature, the mixture was quenched carefully with $H_2O$ (33 mL), 10% NaOH solution (33 mL), $H_2O$ (100 mL) in turn. The mixture was filtered, the filter cake was washed with THF (300 mL), and the filtrate was concentrated under high vacuum to afford K2.

Scheme 12. General synthesis of an alkyl halide

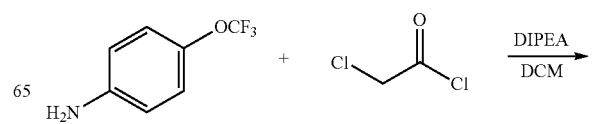

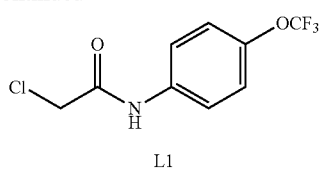

L1

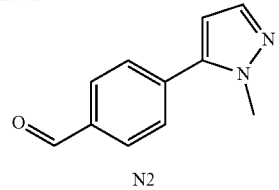

N2

General Procedure for the Synthesis of L1

To a stirred solution of 4-(trifluoromethoxy)aniline (2.00 g, 17.7 mmol), DIPEA (2.51 g, 19.3 mmol) in DCM (80 mL) was added a solution of chloroacetyl chloride (2.00 g, 17.7 mmol) in DCM (8 mL) dropwise at 0° C. The reaction mixture was stirred at 0° C. for 0.5 hour and poured into water (50 mL). The mixture was separated and the organic layer was washed with water (20 mL), dried over anhydrous $Na_2SO_4$ and concentrated under reduced pressure. The residue was purified by recrystallization from PE/EtOAc (1/1) to afford L1.

Scheme 13. General synthesis 1 of an aryl aldehyde

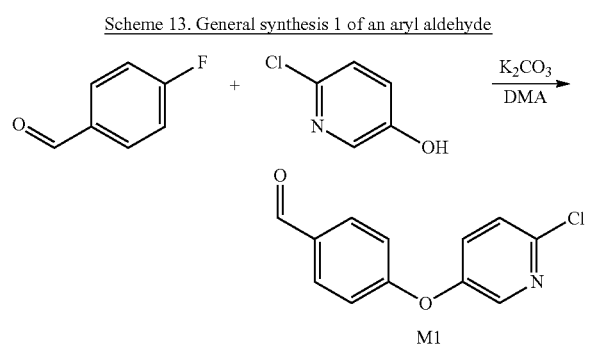

M1

General Procedure for the Synthesis of M1

To a stirred solution of 2-chloro-5-hydroxypyridine (3.00 g, 23.3 mmol) in anhydrous DMA (40 mL) were added 4-fluoro benzaldehyde (2.88 g, 23.3 mmol) and $K_2CO_3$ (6.40 g, 46.6 mmol). The resulting mixture was heated to 130° C. for 16 hours. Water (30 mL) was poured into the mixture, then extracted with EtOAc (40 mL×3). The combined organic phase was washed with brine (40 mL×2), dried over anhydrous $Na_2SO_4$ and concentrated under reduced pressure to afford crude product. The residue was purified by Combi-flash (PE:EtOAc=20:1 to 15:1) to afford M1.

Scheme 14. General synthesis 2 of an aryl aldehyde

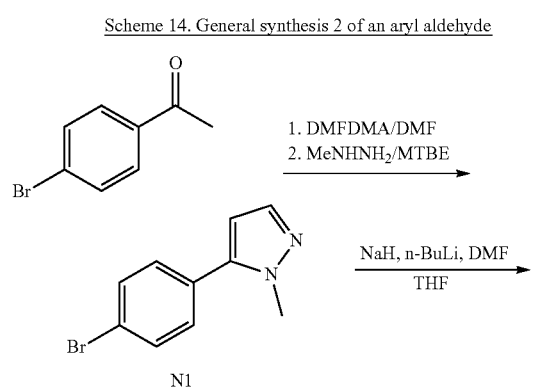

N1

General Procedure for the Synthesis of N1

To a stirred solution of 1-(4-bromophenyl)ethan-1-one (30.0 g, 150 mmol) in DMF (18 mL) was added DMFDMA (43.5 mL, 300 mmol), the resulting mixture was stirred at 110° C. for 4 hours. After cooling to room temperature, MTBE (150 mL) was added to the mixture, then $MeNHNH_2$ (78.9 g, 600 mmol) was added into above mixture, the resulting mixture was stirred at 25° C. for 17 hours. The mixture was diluted with EtOAc (100 mL), filtered and the filter cake was washed with EtOAc (150 mL). The combined organic layer was washed with water (200 mL×3) and brine (200 mL), dried over anhydrous $Na_2SO_4$ and concentrated under reduced pressure to afford a residue. The residue was purified by flash column chromatography (eluted: PE/EtOAc=8/1 to 4/1) to afford N1.

General Procedure for the Synthesis of N2

To a stirred solution of N1 (1.20 g, 5.10 mmol) in anhydrous THF (10 mL) was added NaH (240 mg, 6.00 mmol, 60% dispersion in mineral oil), the resulting mixture was stirred at 0° C. for 1 hour, then n-BuLi (2.3 mL, 5.75 mmol, 2.5 M in hexane) was added into above mixture at −70° C. and stirred at −70° C. for 1 hour, freshly distilled DMF (1.85 g, 25.3 mmol) was added into above mixture and stirred at −70° C. for 1 hour, then the reaction mixture was allowed to warm to 0° C. TLC showed the reaction was completed. The reaction was quenched with water (30 mL) at 0° C., extracted with EtOAc (30 mL×3). The combined organic phase washed with brine (50 mL), dried over anhydrous $Na_2SO_4$ and concentrated under reduced pressure to afford a residue. The residue was purified by flash column chromatography (eluted: PE/EtOAc=2/1) to afford N2.

Scheme 15. General synthesis 3 of an aryl aldehyde

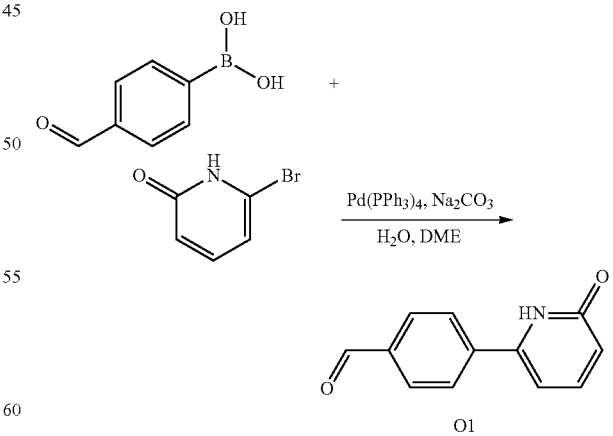

O1

General Procedure for the Synthesis of O1

To a stirred solution of 2-bromo-6-hydroxypyridine (100 mg, 0.57 mmol) and 4-formylphenylboronic acid (72 mg, 0.48 mmol) in DME (2 mL) were added $Pd(PPh_3)_4$ (55 mg, 0.05 mmol) and $Na_2CO_3$ solution (0.63 mL, 2M). The mixture was stirred under N₂ atmosphere maintaining gentle reflux for 16 hours. The mixture was diluted with water (10 mL) extracted with EtOAc (20 mL×3). The combined extracts were washed with brine (20 mL), dried over anhydrous Na₂SO₄ and concentrated under reduced pressure to afford a crude, which was purified by combi flash (eluent: EtOAc) to afford O1.

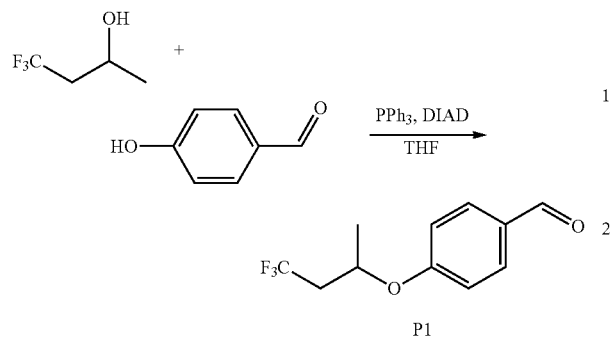

General Procedure for the Synthesis of P1

To a stirred solution of 4,4,4-trifluoro-2-butanol (450 mg, 3.51 mmol) in anhydrous THF (10 mL) were added 4-hydroxybenzaldehyde (390 mg, 3.19 mmol), PPh₃ (1.26 g, 4.28 mmol) and DIAD (967 mg, 4.78 mmol). Then the mixture was stirred at 27-30° C. for 16 hours. Then the mixture was diluted with water (50 mL), extracted with EtOAc (30 mL×2). The combined extracts were washed with brine (50 mL), dried over anhydrous Na₂SO₄ and concentrated under reduced pressure to afford crude residue which was purified by Combi Flash (PE/EtOAc=10/1) to afford P1.

Scheme 17. General synthesis 5 of an aryl aldehyde

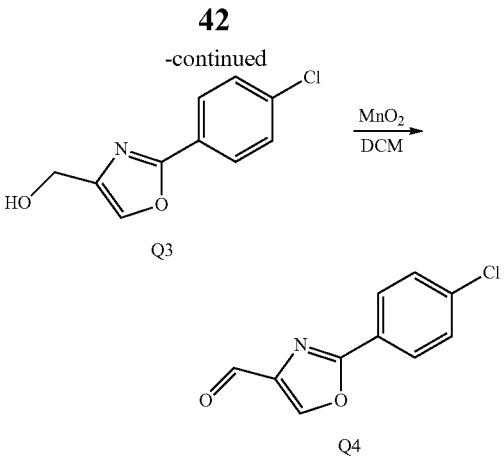

General Procedure for the Synthesis of O1

To a stirred solution of DL-serine methyl ester hydrochloride (11.1 g, 71.4 mmol), MgSO₄ (8.64 g, 71.4 mmol) in anhydrous THF (350 mL) were added 4-chloro-benzaldehyde (10.0 g, 71.4 mmol) and TEA (14.4 g, 143 mmol), then the mixture was stirred at 25-30° C. for 12 hours. The resulting mixture was filtered, washed with MTBE (100 mL×2). The combined filtrate was concentrated under reduced pressure to afford a crude Q1.

General Procedure for the Synthesis of Q2

To a stirred solution of Q1 (13.8 g, crude) in anhydrous DCM (220 mL) were added BrCCl₃ (16.4 mL, 166 mmol) and DBU (25 mL, 166 mmol) at 0° C. The resulting mixture was stirred at 0° C. for 2 hours and then at 25-30° C. for 10 hours. The mixture was concentrated under reduced pressure to dryness. The residue was dissolved in EtOAc (250 mL), washed with water (140 mL×2), brine (80 mL) in turn, dried over anhydrous Na₂SO₄ and concentrated to afford a residue. The residue was washed with EtOAc (20 mL) to afford Q2.

General Procedure for the Synthesis of Q3

To a stirred solution of Q2 (3.46 g, 14.6 mmol) in anhydrous DCM (65 mL) was added DIBAL-H (16.1 mL, 16.1 mmol, 1M in toluene) at −78° C. under N₂ atmosphere. The resulting mixture was stirred at 0° C. for 4 hours. The reaction was quenched with saturated NH₄Cl (25 mL) at 0° C. Then the mixture was warmed to room temperature, adjusted pH 2 by HCl (1M). The mixture was extracted with DCM (50 mL×3), the combined organic layer was dried over anhydrous Na₂SO₄ and concentrated under reduced pressure to afford a residue. The residue was washed with DCM (15 mL) to afford Q3.

General Procedure for the Synthesis of Q4

A mixture of Q3 (1.49 g, 7.13 mmol) and MnO₂ (6.20 g, 71.3 mmol) in DCM (65 mL) was stirred under N₂ atmosphere at 25-30° C. for 18 hours. The mixture was filtered and the filter cake was washed with DCM (10 mL×2), the filtrate was concentrated under reduced pressure to dryness to afford Q4.

Scheme 18. General synthesis 6 of an aryl aldehyde

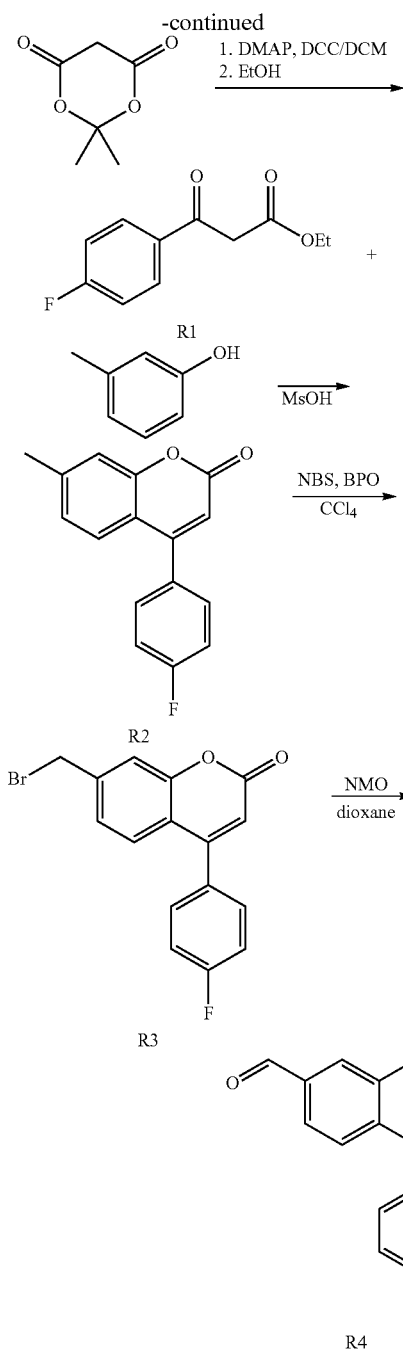

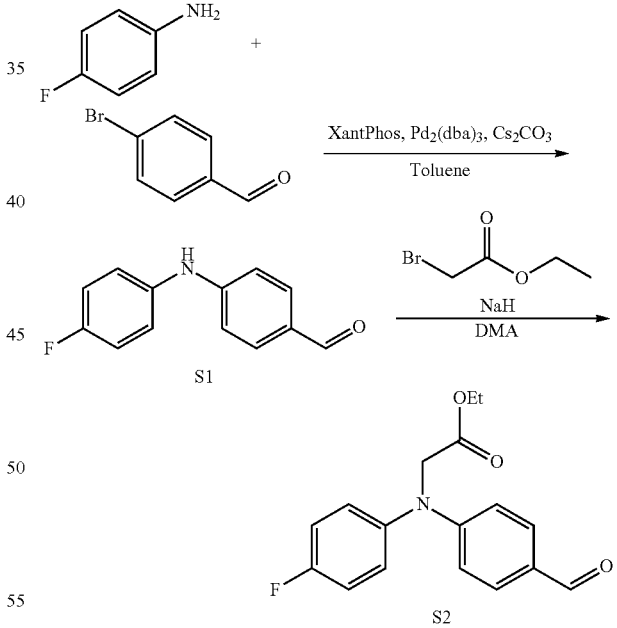

Scheme 19. General synthesis 7 of an aryl aldehyde

General Procedure for the Synthesis of R2

A mixture of R1 (7.50 g, 35.7 mmol) and m-cresol (3.86 g, 35.7 mmol) in MsOH (9.5 mL) was stirred at 40° C. for 17 hours. After cooling to room temperature, the reaction mixture was poured into cooling EtOH (−30° C., 60 mL) and stirred at −30° C. for 1 hour. The precipitate was filtered. The solid was dissolved in EtOAc (50 mL) and then washed with saturated $NaHCO_3$ (50 mL×2), brine (50 mL), dried over $Na_2SO_4$ and concentrated under reduced pressure to afford R2.

General Procedure for the Synthesis of R3

To a stirred solution of R2 (1.00 g, 3.94 mmol) in $CCl_4$ (30 mL) were added NBS (842 mg, 4.73 mmol) and BPO (195 mg, 0.806 mmol), the resulting mixture was stirred at reflux for 48 hours. Then the mixture was filtered, the filtrate was concentrated under reduced pressure to afford a residue, which was purified by flash column chromatography (PE/EtOAc=30/1) to afford R3.

General Procedure for the Synthesis of R4

To a stirred solution of R4 (1.00 g, 3.00 mmol) in dioxane (15 mL) was added NMO (882 mg, 7.53 mmol) and the resulting mixture was stirred at reflux for 6 hours. After cooling to room temperature, the mixture was diluted with water (50 mL), extracted with EtOAc (30 mL×3). The combined organic layer was washed with brine (50 mL), dried over anhydrous $Na_2SO_4$ and concentrated under reduced pressure to afford a residue, which was purified flash column chromatography (PE/EtOAc=20/1) to afford R4.

General Procedure for the Synthesis of R1

To a stirred solution of 4-fluorobenzoic acid (50.0 g, 357 mmol), 2,2-dimethyl-1,3-dioxane-4,6-dione (61.7 g, 428 mmol) and DMAP (65.5 g, 536 mmol) in DCM (1.5 L) was added DCC (97.5 g, 464 mmol) dropwise at 0° C. and stirred at 0° C. for 30 minutes, then stirred at 25° C. for 17 hours. The mixture was filtered, the filtrate was washed with aqueous HCl (1 M, 800 mL×3), washed with brine (800 mL), dried over anhydrous $Na_2SO_4$ and concentrated under reduced pressure to afford a residue. The residue was dissolve in EtOH (600 mL) and stirred at 100° C. for 17 hours. The excessive EtOH was removed under reduced pressure to afford a residue, which was purified by flash column chromatography (eluted: PE/EtOAc=20/1) to afford R1.

General Procedure for the Synthesis of S1

To a stirred solution of 4-fluoro aniline (360 mg, 3.24 mmol), 4-Bromobenzaldehyde (500 mg, 2.70 mmol), XantPhos (60 mg, 0.108 mmol) and $Pd_2(dba)_3$ (25 mg, 0.027 mmol) in anhydrous toluene (15 mL) was added $Cs_2CO_3$ (1.32 g, 4.05 mmol) under $N_2$ atmosphere. The reaction mixture was purged under $N_2$ atmosphere for 3 times, then heated to reflux (oil bath 120° C.) under $N_2$ atmosphere for 16 hours. 40 mL water was poured into the mixture, then extracted with EtOAc (20 mL×2), the combined organic phase was dried over anhydrous Na$_2$SO$_4$ and concentrated under reduced pressure to give crude product. The residue was purified by Combi-flash (PE:EtOAc=20:1 to 9:1) to afford S1.

General Procedure for the Synthesis of S2

To a stirred solution of S1 (200 mg, 0.929 mmol) in anhydrous DMA (20 mL) was added NaH (74 mg, 1.86 mmol, 60% dispersion in mineral oil) at 0° C. for 0.5 hour, then ethyl bromoacetate (186 mg, 1.12 mmol) was added, after 1 hour, the resulting mixture was stirred at 60° C. for another 16 hours. The mixture was quenched with water (20 mL), then extracted with EtOAc (30 mL×2). The combined organic phase was washed with brine (20 mL×2), dried over anhydrous Na$_2$SO$_4$ and concentrated under reduced pressure to afford S2.

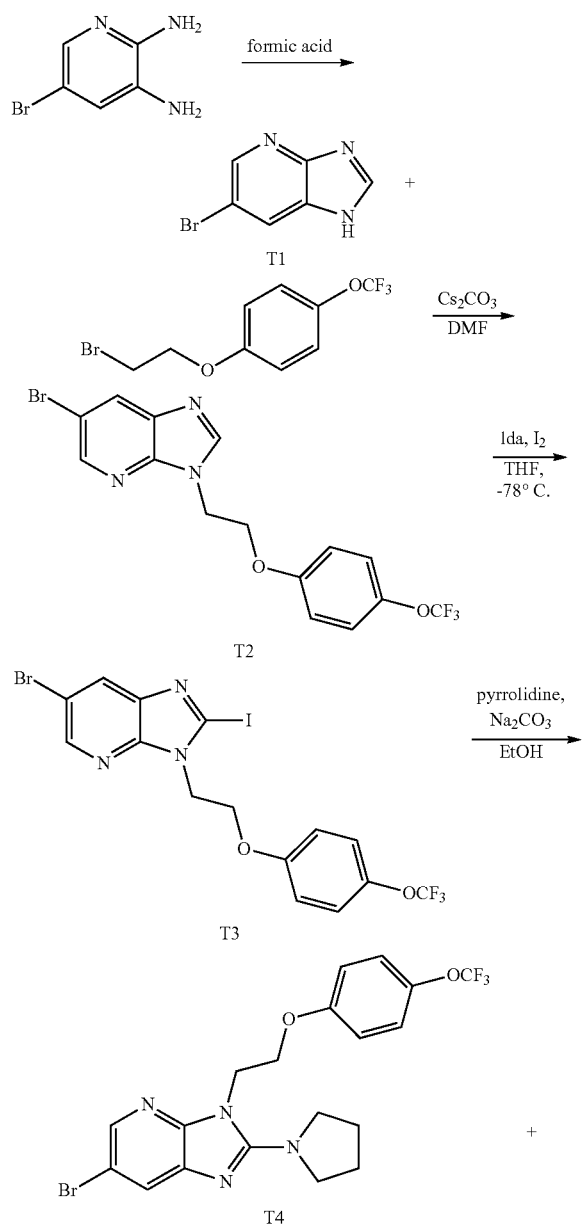

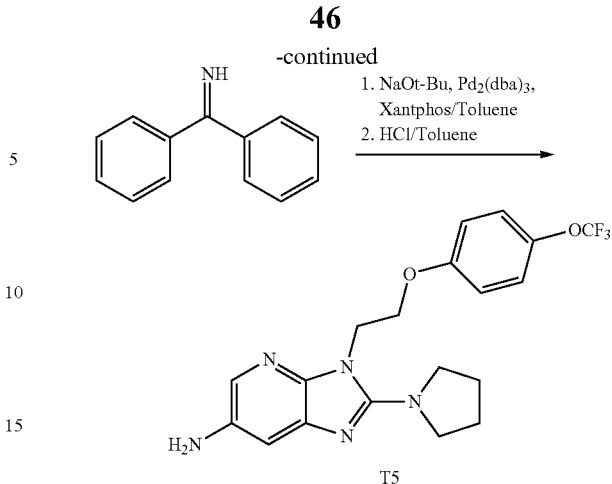

General Procedure for the Synthesis of T1

A mixture of 5-bromopyridine-2, 3-diamine (5.00 g, 26.6 mmol) in formic acid (80 mL) was heated to 110° C. for 16 hours. The reaction solution was concentrated under reduced pressure. The residue was partitioned between 2 N NaOH (200 mL) and DCM (100 mL). The organic phase was separated and the aqueous layer was cooled to 0° C. for 1 hour. The precipitate was collected by filtration, dried over high vacuum to afford T1.

General Procedure for the Synthesis of T2

To a stirred solution of T1 (200 mg, 1.01 mmol) in DMF (4 mL) were added 1-(2-bromoethoxy)-4-(trifluoromethoxy)benzene (432 mg, 1.52 mmol) and Cs$_2$CO$_3$ (823 mg, 2.53 mmol) and stirred at 50° C. for 16 hours. The reaction mixture was poured into water (200 mL) and extracted with EtOAc (20 mL×3). The combined organic layer was washed with water (10 mL×3), brine (10 mL), dried over anhydrous Na$_2$SO$_4$ and concentrated under reduced pressure. The residue was purified by Combi Flash (PE:EtOAc=1:1) to afford T2.

General Procedure for the Synthesis of T3

To a stirred solution of diisopropylamine (0.125 mL, 0.894 mmol) in anhydrous THF (1.5 mL) was added n-BuLi (0.37 mL, 2.5 M in hexane) dropwise at −78° C. The solution was stirred at −78° C. for 30 minutes. Then a solution of T2 (200 mg, 0.447 mmol) in anhydrous THF (0.5 mL) was added dropwise at −78° C. and the solution was stirred at −78° C. for 0.5 hours. Then a solution of iodine (226 mg, 0.894 mmol) in anhydrous THF (0.5 mL) was added dropwise. The reaction solution was stirred at −78° C. for 1.5 hours and warmed to room temperature. The reaction mixture was quenched by saturated Na$_2$S$_2$O$_3$ (1.5 mL) and diluted with EtOAc (20 mL). The organic layer was washed with brine (10 mL), dried over anhydrous Na$_2$SO$_4$ and concentrated under reduced pressure. The residue was recrystallized from PE/EtOAc (3 mL/3 mL) to afford T3.

General Procedure for the Synthesis of T4

A mixture of T3 (70 mg, 0.133 mmol), pyrrolidine (13 µg, 0.159 mmol) and Na$_2$CO$_3$ (21 mg, 0.200 mmol) in EtOH (1 mL) was stirred at 80° C. for 16 hours. The reaction mixture was diluted with EtOAc (20 mL), washed with brine (10 mL), dried over anhydrous Na$_2$SO$_4$ and concentrated under reduced pressure. The residue was purified by prep-TLC (PE:EtOAc=1:1) to afford T4.

General Procedure for the Synthesis of T5

To a stirred solution of XantPhos (5 mg, 0.00847 mmol), Pd$_2$(dba)$_3$ (8 mg, 0.00847 mmol) and NaOt-Bu (20 mg, 0.211 mmol) in anhydrous toluene (1 mL) were added T4

(40 mg, 0.0847 mmol) and benzophenone imine (18 mg, 0.101 mmol). The reaction mixture was stirred at 120° C. under N₂ for 1.5 hours. HCl (1 mL, 4 N) was added to the reaction mixture and the mixture was stirred at 16° C. for 5 minutes. The aqueous layer was basified with NaOH (4 mL, 2 N) and extracted with EtOAc (10 mL×2). The combined extract was washed with brine (10 mL), dried over anhydrous Na₂SO₄, evaporated under reduced pressure. The resulting oil was purified by prep-TLC (DCM/MeOH, 15/1) to afford T5.

Scheme 21. General synthesis of a N⁴ substituted benzimidazole derivative

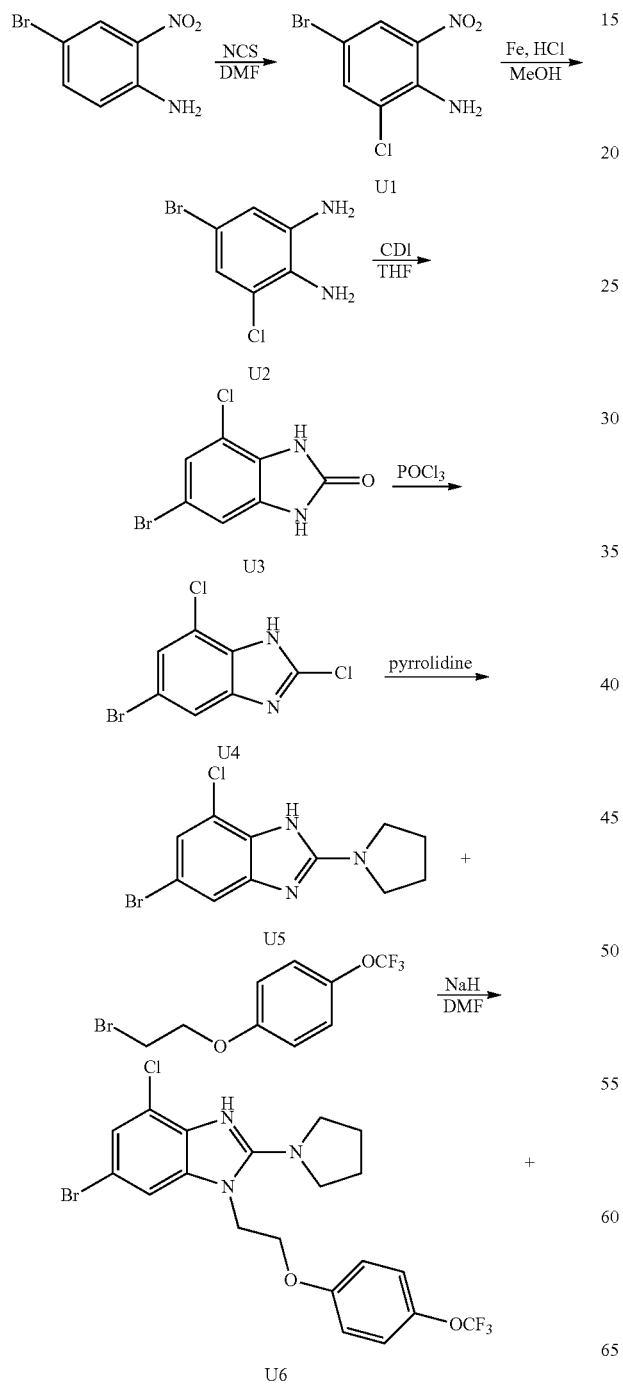

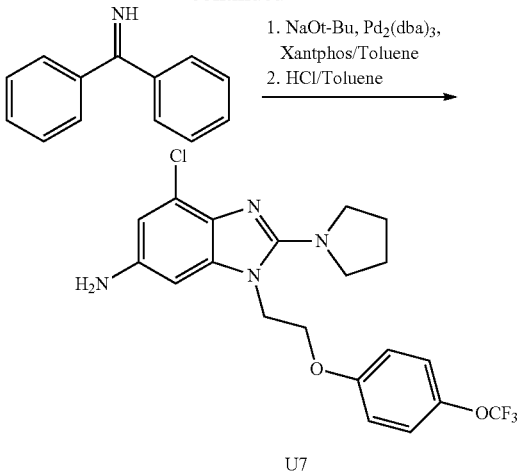

General Procedure for the Synthesis of U1

A mixture of 4-bromo-2-nitroaniline (10.0 g, 0.046 mol) and NCS (6.15 g, 0.046 mol) in DMF (100 mL) was stirred at 120° C. for 16 hours. The mixture was poured into water (100 mL), the precipitate was filtered, washed with water (50 mL) and dried under reduced pressure to afford U1.

General Procedure for the Synthesis of U2

To a stirred solution of U1 in MeOH (100 mL) were added concentrated HCl (9 mL, 108 mmol, 12M) and iron powder (10.0 g, 179 mmol). The reaction mixture was stirred at 8-16° C. for 16 hours. After reaction was completed, the mixture was filtered. The filtrate was neutralized to pH 8 with NaHCO₃ aqueous solution and filtered. The filtrate was extracted with EtOAc (100 mL×2). The combined extracts were washed with brine (200 mL), dried over anhydrous Na₂SO₄ and concentrated under reduced pressure to afford U2.

General Procedure for the Synthesis of U3

A mixture of U2 (7.2 g, 32.5 mmol) and CDI (6.32 g, 39.0 mmol) in anhydrous THF (100 mL) was refluxed for 16 hours. After cooling to room temperature, the white precipitate was collected by filtration and dried under reduced pressure to afford U3.

General Procedure for the Synthesis of U4

A mixture of U3 (4.90 g, 19.8 mmol) in POCl₃ (30 mL) was refluxed for 16 hours. After the mixture was cooled to room temperature, the mixture was poured into water (100 mL) under stirring. The white precipitate was collected by filtration, washed with water (50 mL) and dried under reduced pressure to afford U4.

General Procedure for the Synthesis of U5

A mixture of U4 (2.10 g, 7.90 mmol) in pyrrolidine (20 mL) was refluxed for 16 hours. The mixture was diluted with water (50 mL) and extracted with EtOAc (50 mL×2). The combined extracts were washed with brine (100 mL), dried over anhydrous Na₂SO₄ and concentrated under reduce pressure to afford crude residue which was purified by flash column chromatography (PE/EtOAc=5/1-2/1) to afford U5.

General Procedure for the Synthesis of U6

To a stirred solution of U5 (850 mg, 2.83 mmol) in anhydrous DMF (10 mL) was added NaH (170 mg, 4.24 mmol, 60% in mineral oil) at 0° C. The mixture was stirred at 0° C. for 30 minutes, added a solution of 1-(2-bromoethoxy)-4-(trifluoromethoxy)benzene (1.61 g, 5.66 mmol) in anhydrous DMF (5 mL) and stirred at 60° C. for 16 hours. The mixture was quenched with water (50 mL), extracted with EtOAc (50 mL×2). The combined extracts were washed with brine (50 mL), dried over anhydrous Na$_2$SO$_4$ and concentrated under reduce pressure to afford crude residue which was purified by Combi Flash to afford U6.

General Procedure for the Synthesis of U7

To a stirred solution of U6 (680 mg, 1.35 mmol), benzophenone imine (488 mg, 2.69 mmol), Pd$_2$(dba)$_3$ (124 mg, 0.135 mmol) and XantPhos (156 mg, 0.270 mmol) in anhydrous toluene (10 mL) was added NaOt-Bu (324 mg, 3.38 mmol) under N$_2$ atmosphere. The reaction mixture was purged in N$_2$ atmosphere for three times. The mixture was heated to 80-100° C. for 16 hours. The mixture was concentrated, dissolved in MeOH (2 mL), added HCl (3 M, 2 mL) and stirred at 20-25° C. for 2 hours. Then the mixture was neutralized to pH 8 with NaHCO$_3$ aqueous solution and extracted with EtOAc (30 mL×2), the combined extracts were washed with brine (50 mL), dried over anhydrous Na$_2$SO$_4$ and concentrated under reduced pressure to afford crude residue, which was purified by prep-HPLC (0.05% HCl) to afford U7.

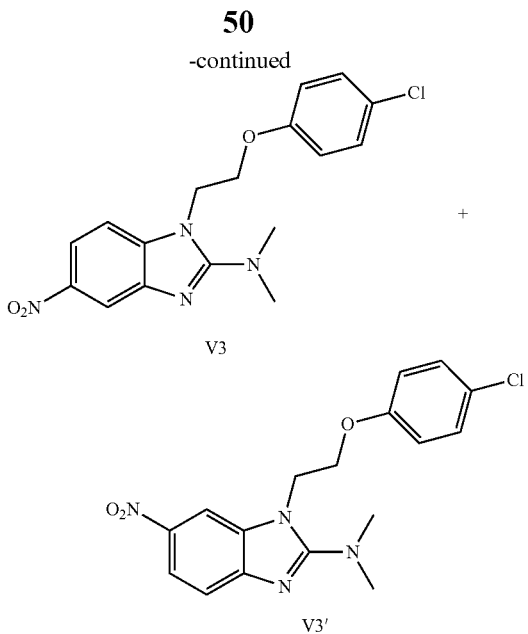

General Procedure for the Synthesis of V2

To a stirred solution of compound 2 (538 mg, 2.61 mmol) in DMA (10 mL) was added NaH (125 mg, 3.13 mmol, 60% dispersion in mineral oil) portionwise. The mixture was stirred at 0° C. under N$_2$ atmosphere for 5 minutes. Then a solution of 1-(2-bromoethoxy)-4-chlorobenzene (908 mg, 3.90 mmol) in DMA (8 mL) was added to the mixture and the solution was stirred at 60° C. under N$_2$ for 24 hours. The mixture was diluted with water (80 mL) and extracted with EtOAc (40 mL×3), the combined extracts were washed with water (20 mL×2), brine (10 mL), dried over anhydrous Na$_2$SO$_4$ and concentrated under reduced pressure to afford the crude product, which was recrystallized from EtOAc (5 mL) to afford a mixture of V2 and V2'.

General Procedure for the Synthesis of V3

To a stirred solution of a mixture of V2 and V2' (100 mg, 0.302 mmol) in MeOH were added Zn powder (98.2 mg, 1.51 mmol) and NH$_4$Cl (326 mg, 6004 mmol) at 19° C. The mixture was stirred at 45° C. for 16 hours. The reaction solution was diluted with EtOAc (10 mL) and filtered. The filtrate was concentrated under reduced pressure. The resulting oil was purified by prep-TLC (DCM/MeOH, 20/1) to afford V3.

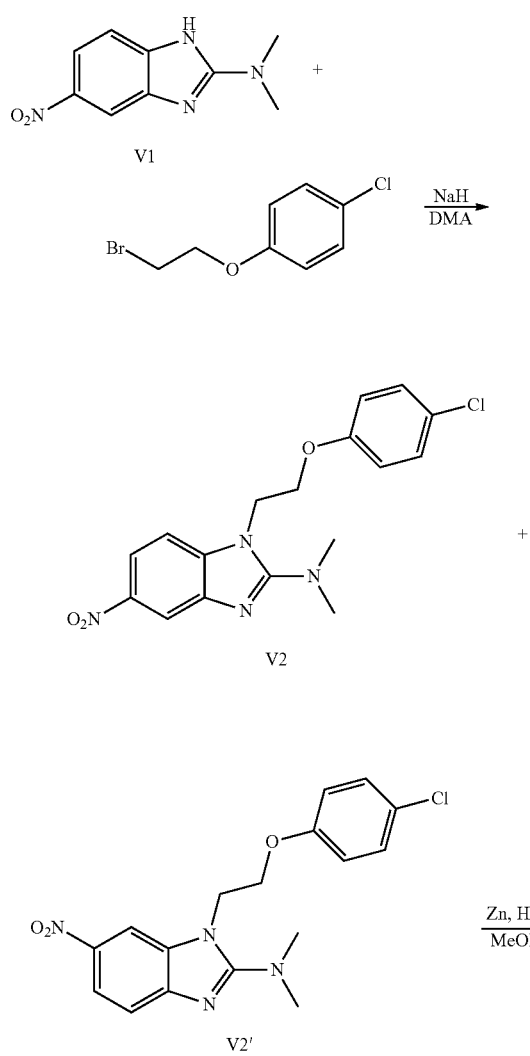

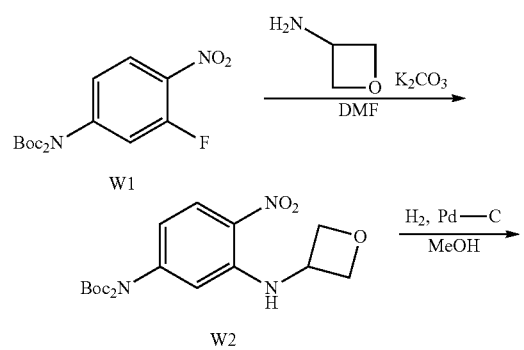

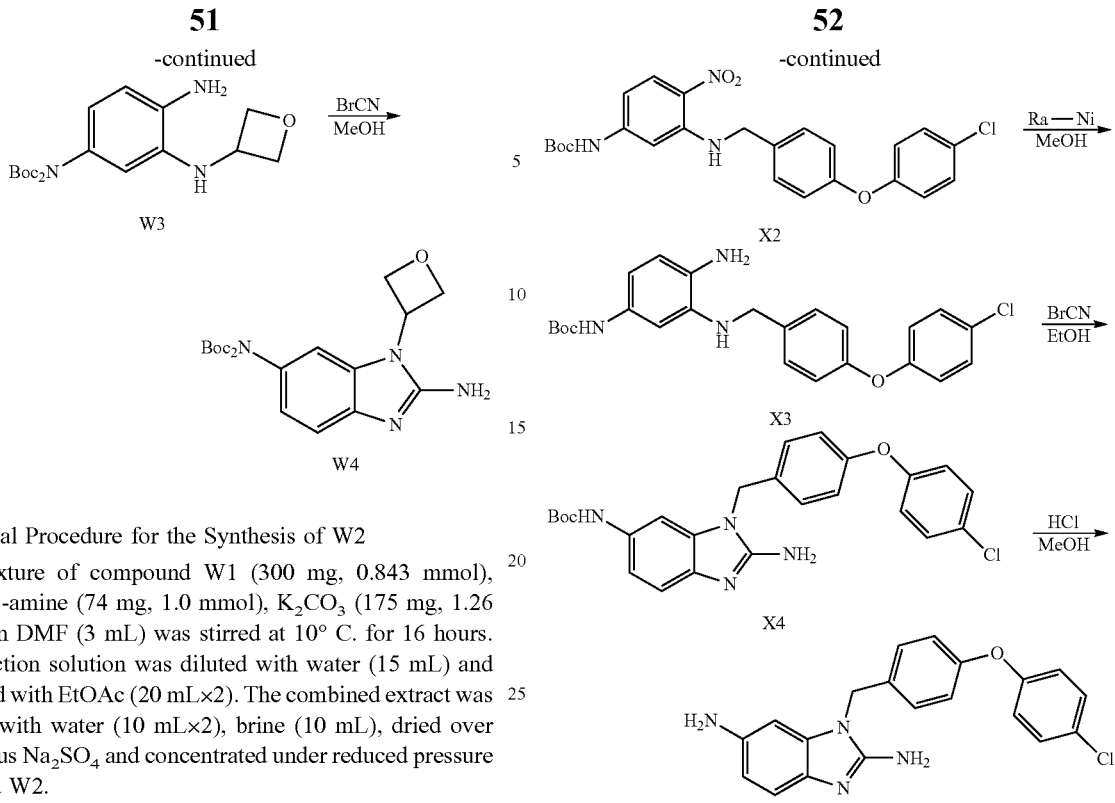

General Procedure for the Synthesis of W2

A mixture of compound W1 (300 mg, 0.843 mmol), oxetan-3-amine (74 mg, 1.0 mmol), $K_2CO_3$ (175 mg, 1.26 mmol) in DMF (3 mL) was stirred at 10° C. for 16 hours. The reaction solution was diluted with water (15 mL) and extracted with EtOAc (20 mL×2). The combined extract was washed with water (10 mL×2), brine (10 mL), dried over anhydrous $Na_2SO_4$ and concentrated under reduced pressure to afford W2.

General Procedure for the Synthesis of W4

To a stirred solution of W2 (500 mg, 1.22 mmol) in MeOH (20 mL) was added Pd/C (50 mg, 5%, 60% wet) in $N_2$ atmosphere. The suspension was degassed under vacuum and purged with $H_2$ several times. The mixture was stirred under $H_2$ atmosphere (1 atm) for 1.5 hours. The reaction mixture was filtered through a pad of Celite. To the filtrate (W3 in MeOH) was added BrCN (261 mg, 2.44 mmol). The reaction solution was stirred at 10° C. for 16 hours. The reaction solution was concentrated under reduced pressure. The residue was diluted with water (30 mL) and EtOAc (30 mL). Then solid $Na_2CO_3$ was added with stirring until aqueous layer was basified to pH 9. The organic layer was separated and dried over anhydrous $Na_2SO_4$ and concentrated under reduced pressure to afford W4.

Scheme 24. General synthesis 3 of a $N^1$ substituted benzimidazole derivative

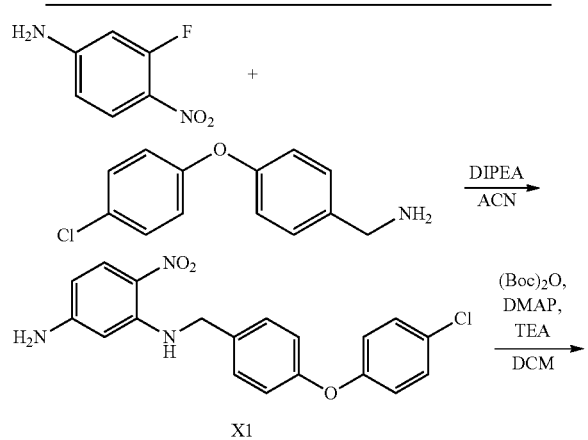

General Procedure for the Synthesis of X1

A mixture of 3-fluoro-4-nitroaniline (1.00 g, 6.40 mmol), (4-(4-chlorophenoxy)phenyl) methanamine (1.79 g, 7.28 mmol), and DIPEA (1.65 g, 12.8 mmol) in ACN (15 mL) was refluxed 16 hours. The mixture was cooled to room temperature and diluted with water (40 mL). The mixture was extracted with EtOAc (40 mL×2). The combined extracts was dried over anhydrous $Na_2SO_4$ and concentrated under reduced pressure to afford 3.42 g of crude residue, which was purified by Combi Flash to afford X1.

General Procedure for the Synthesis of X2

To a stirred solution of X1 (1.50 g, 4.06 mmol), di-tert-butyl dicarbonate (1.15 g, 5.27 mmol) in DCM (20 mL) were added DMAP (248 mg, 2.03 mmol) and TEA (413 mg, 4.06 mmol). The mixture was stirred at 20° C. for 16 hours. The mixture was diluted with water (50 mL) and extracted with EtOAc (40 mL×2). The combined extracts were washed with brine (100 mL×2), dried over anhydrous $Na_2SO_4$ and concentrated under reduced pressure to afford 3.00 g of crude residue, which was purified by Combi flash (PE/EtOAc=25/1 to 20/1 to 15/1) to afford X2.

General Procedure for the Synthesis of X3

To a stirred solution of X2 (100 mg, 0.213 mmol) in MeOH (5 mL) was added Raney-Ni (20 mg) under Ar. The suspension was degassed under vacuum and purged with $H_2$ for three times. The solution was stirred at 28° C. under $H_2$ (50 psi) for 16 hours. The mixture was filtered through a pad of celite, and the pad was washed with MeOH (200 mL). The filtrate was concentrated under reduced pressure to afford X3.

General Procedure for the Synthesis of X4

A mixture of X3 (80 mg, 182 mmol), cyanogen bromide (29 mg, 0.273 mmol) in EtOH (4 mL) was stirred at 25° C. for 16 hours. The mixture was basified to pH 9 with $Na_2CO_3$ aqueous solution, diluted with water (20 mL) and extracted with EtOAc (20 mL×2). The combined extracts was washed with brine (40 mL×2), dried over anhydrous $Na_2SO_4$ and concentrated under reduced pressure to afford X4.

General Procedure for the Synthesis of X5

To a stirred solution of X4 (80 mg, 0.172 mmol) in MeOH (2 mL) was added HCl solution of MeOH (4M, 2 mL). The resulting solution was stirred at 25° C. for 2 hours. The mixture was diluted with water (20 mL), basified to pH 9 with $Na_2CO_3$ aqueous solution and extracted with EtOAc (20 mL×2). The combined extracts was washed with brine (40 mL×2), dried over anhydrous $Na_2SO_4$ and concentrated under reduced pressure to afford crude residue, which was purified by prep-HPLC (0.01% $NH_3.H_2O$) to afford X5.

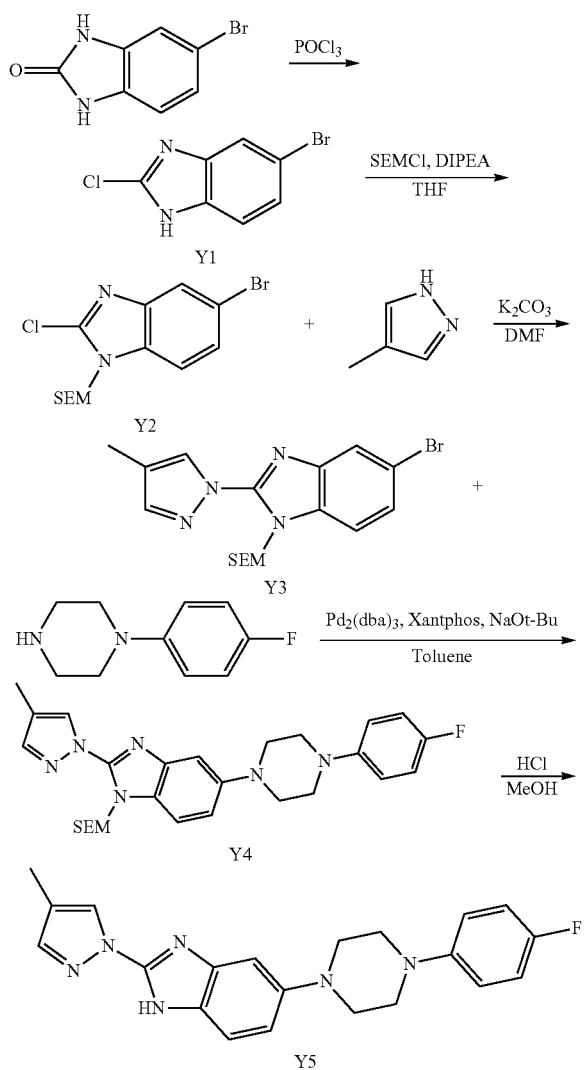

General Procedure for the Synthesis of Y1

A mixture of 5-bromo-1,3-dihydro-2H-benzo[d]imidazol-2-one (5.00 g, 23.5 mmol) and $POCl_3$ (80 mL) was refluxed for 16 hours. After cooled to room temperature, the mixture was poured into water (300 mL) and NaOH aqueous solution (5 M, 80 mL) was added. The precipitate was filtered and washed with water. The filtrate was dried over high vacuum to afford Y1.

General Procedure for the Synthesis of Y2

To a stirred solution of Y1 (500 mg, 2.16 mmol) and DIPEA (558 mg, 4.32 mmol) in THF (5 mL) was added SEMCl (540 mg, 3.24 mmol) at 0° C. and the resulting mixture was stirred at 35° C. for 16 hours. The mixture was diluted with water (50 mL), extracted with EtOAc (50 mL×2). The combined extracts were washed with brine (50 mL), dried over anhydrous $Na_2SO_4$ and concentrated under reduce pressure to afford a residue. The residue was purified by flash column chromatography to afford Y2.

General Procedure for the Synthesis of Y3

A mixture of Y2 (480 mg, 1.33 mmol), 4-methyl-1H-pyrazole (109 mg, 1.33 mmol) and $K_2CO_3$ (275 mg, 1.99 mmol) in DMF (5 mL) was stirred at 100° C. for 16 hours. The mixture was diluted with water (50 mL), extracted with EtOAc (50 mL×2). The combined extracts were washed with brine (50 mL), dried over anhydrous $Na_2SO_4$ and concentrated under reduce pressure to afford a residue. The residue was purified by flash column chromatography to afford Y3.

General Procedure for the Synthesis of Y4

A mixture of Y3 (500 mg, 1.23 mmol), 1-(4-fluorophenyl)piperazine (243 mg, 1.35 mmol), NaOt-Bu (236 mg, 2.45 mmol), $Pd_2(dba)_3$ (112 mg, 0.123 mmol) and Xantphos (71 mg, 0.12 mmol) in toluene (5 mL) was stirred at 120° C. for 16 hours. The mixture was diluted with water (50 mL), extracted with EtOAc (50 mL×2). The combined extracts were washed with brine (50 mL), dried over anhydrous $Na_2SO_4$ and concentrated under reduce pressure to afford a residue. The residue was purified by flash column chromatography to afford Y4.

General Procedure for the Synthesis of Y5

A mixture of Y4 (160 mg, 0.316 mmol) and conc.HCl (2 mL) in MeOH (6 mL) was stirred at 32° C. for 16 hours. The mixture was diluted with water (50 mL), neutralized with NaOH aqueous solution and extracted with EtOAc (50 mL×2). The combined extracts were washed with brine (50 mL), dried over anhydrous $Na_2SO_4$ and concentrated under reduce pressure to afford Y5.

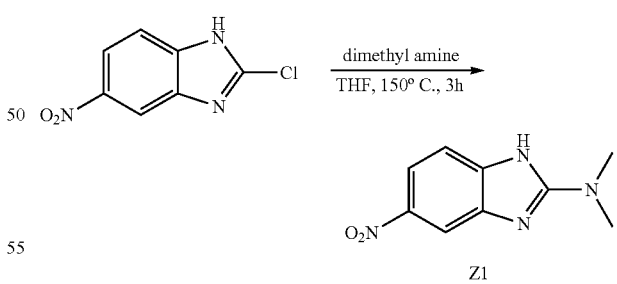

General Procedure for the Synthesis of Z1

To a stirred solution of dimethyl amine in THF (18 mL, 2 N) was added 2-chloro-5-nitro-1H-benzo[d]imidazole (1.80 g, 9.1 mmol) at 20° C. The reaction solution was stirred at 150° C. in a sealed tube for 3 hours. The reaction solution was poured into water (20 mL) and extracted with EtOAc (10 mL×3). The combined organic layer was washed with brine (10 mL), dried over anhydrous $Na_2SO_4$ and concentrated under reduced pressure to afford Z1.

Scheme 27. General coupling reaction 1 of a benzimidazole N² amine

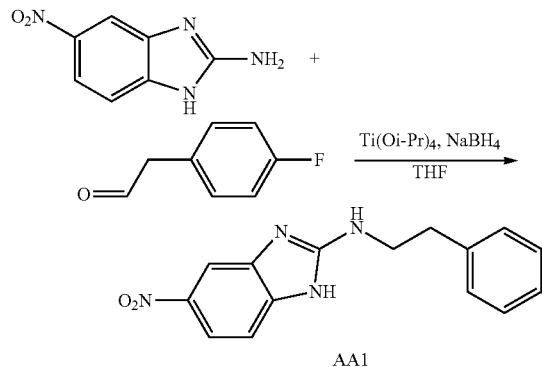

AA1

General Procedure for the Synthesis of AA1

A mixture of 5-nitro-1H-benzo[d]imidazol-2-amine (200 mg, 1.12 mmol), (4-fluoro-phenyl)-acetaldehyde (388 mg, 2.80 mmol) and Ti(Oi-Pr)$_4$ (637 mg, 2.24 mmol) in anhydrous THF (5 mL) was stirred at 60° C. for 30 minutes, then cooled to 20° C. and kept at this temperature for 30 minutes under stirring. Then NaBH$_4$ (213 mg, 5.60 mmol) was added into the mixture at 0° C. and stirred at 20° C. for 3 hours, then at 60° C. for 16 hours. The mixture was cooled and quenched with aqueous NH$_3$.H$_2$O (2M, 10 mL). The precipitate was filtered and washed with THF (20 mL). The filtrate was diluted with water (20 mL) and extracted with EtOAc (20 mL×2). The combined extracts were washed with brine (50 mL×2), dried over anhydrous Na$_2$SO$_4$ and concentrated under reduced pressure to afford crude product, which was purified by prep-HPLC (0.01% NH$_3$.H$_2$O) to afford AA1.

Scheme 28. General coupling reaction 2 of a benzimidazole N² amine

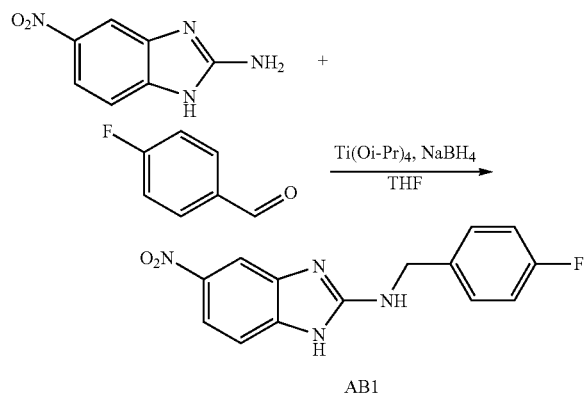

AB1

General Procedure for the Synthesis of AB1

A mixture of 5-nitro-1H-benzo[d]imidazol-2-amine (1.00 g, 5.60 mmol), 4-fluorobenzaldehyde (2.78 g, 22.4 mmol) and Ti(Oi-Pr)$_4$ (3.18 g, 11.2 mmol) in THF (6 mL) was stirred at 60° C. for 30 minutes, the mixture was cooled to 20° C. and kept at this temperature for 30 minutes. Then NaBH$_4$ (851 mg, 22.4 mmol) was added into the mixture at 0° C. and stirred at 20° C. for 3 hours and at 60° C. for 16 hours. The mixture was cooled to 20° C. and quenched with aqueous NH$_3$.H$_2$O (2M, 15 mL). The precipitate was filtered, washed with THF (50 mL). The filtrate was diluted with water (50 mL) and extracted with EtOAc (50 mL×2). The combined extracts were washed with brine (100 mL×2), dried over anhydrous Na$_2$SO$_4$ and concentrated under reduced pressure to afford crude product, which was purified by prep-HPLC (0.01% NH$_3$.H$_2$O) to afford AB1.

Scheme 29. General coupling reaction 3 of a benzimidazole N² amine

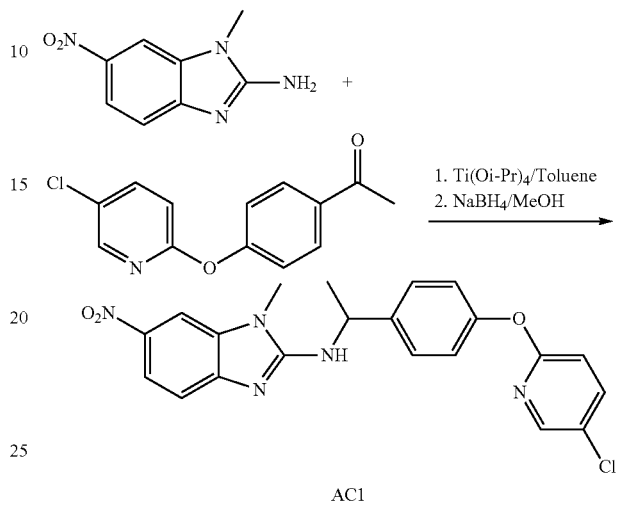

AC1

General Procedure for the Synthesis of AC1

To a stirred solution of 1-methyl-6-nitro-1H-benzo[d]imidazol-2-amine (900 mg, 3.63 mmol) and acetophenone (700 mg, 3.64 mmol) in anhydrous toluene (150 mL) was added Ti(Oi-Pr)$_4$ (3.13 g, 10.9 mmol). The resulting mixture was stirred under reflux under N$_2$ atmosphere for 24 hours. After cooling to room temperature, NaBH$_4$ (290 mg, 7.26 mmol) was added to the mixture followed by MeOH (5 mL). The resulting mixture was stirred at 12° C. for 2 hours. The mixture was diluted with EtOAc (200 mL), washed with brine (200 mL) and water (200 mL×2), dried over anhydrous Na$_2$SO$_4$ and concentrated under reduced pressure to afford crude product, which was purified by flash column chromatography (eluted with PE/EtOAc=50/1 to 5/1) to afford AC1.

Scheme 30. General coupling reaction 4 of a benzimidazole N² amine

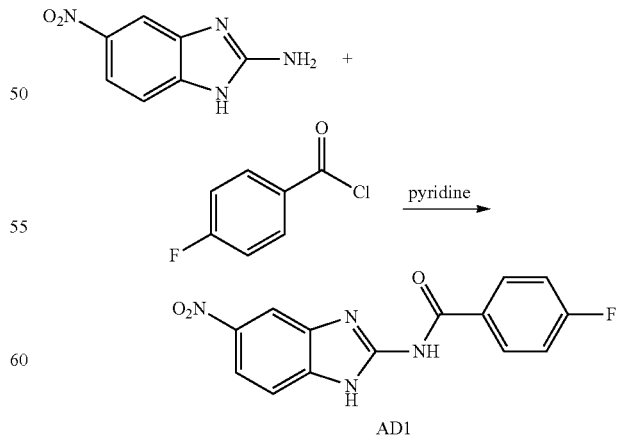

AD1

General Procedure for the Synthesis of AD1

A mixture of 5-nitro-1H-benzo[d]imidazol-2-amine (3.00 g, 16.8 mmol) and 4-fluorobenzoyl chloride (8.10 g, 53.6 mmol) in pyridine (30 mL) was stirred at 20° C. for 10 minutes. The mixture was diluted with water (150 mL) and filtered. The filter cake was washed with water (100 mL) and dried over high vacuum to afford a crude residue which was purified by flash column chromatography to afford AD1.

Scheme 31. General coupling reaction 5 of a benzimidazole N² amine

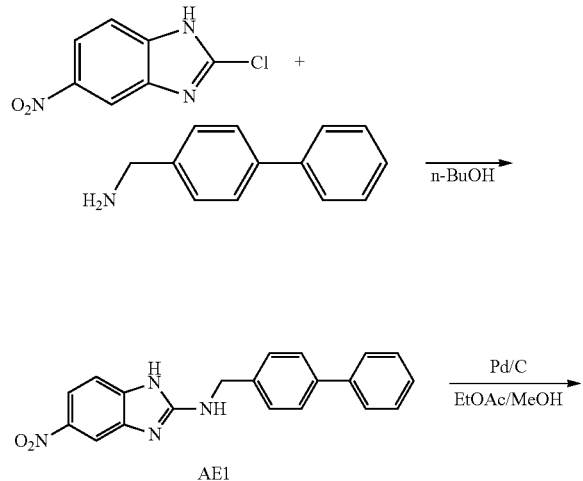

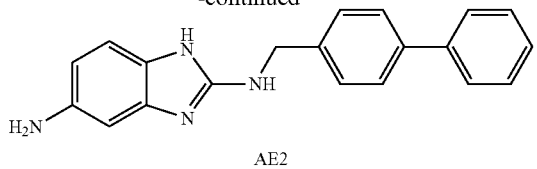

AE2

General Procedure for the Synthesis of AE1

A mixture of 2-chloro-5-nitro-1H-benzo[d]imidazole (500 mg, 2.53 mmol), 4-phenylbenzylamine (696 mg, 3.80 mmol) in n-BuOH (8 mL) was refluxed for 36 hours. After reaction was complete, the mixture was diluted with water (50 mL) and extracted with EtOAc (50 mL×2). The combined extracts were washed with brine (100 mL×2), dried over anhydrous $Na_2SO_4$ and concentrated under reduced pressure to afford crude residue, which was purified by combi flash (PE/EtOAc=3/1 to 2/1 to 1/1) to afford AE1.

General Procedure for the Synthesis of AE2

To a stirred solution of AE1 (150 mg, 0.436 mmol) in EtOAc/MeOH (8 mL/2 mL) was added Pd/C (30 mg, 10%) under $N_2$. The suspension was degassed under vacuum and purged with $H_2$ for three times. The solution was stirred at 22° C. under $H_2$ balloon for 16 hours. The mixture was filtered through a pad of celite and washed with EtOAc (30 mL). The filtrate was concentrated under reduced pressure to afford crude residue which was purified by washing with EtOAc/MeOH (5 mL/1 mL) to afford AE2.

Scheme 32. General coupling reaction 1 of a benzimidazole N⁶ amine

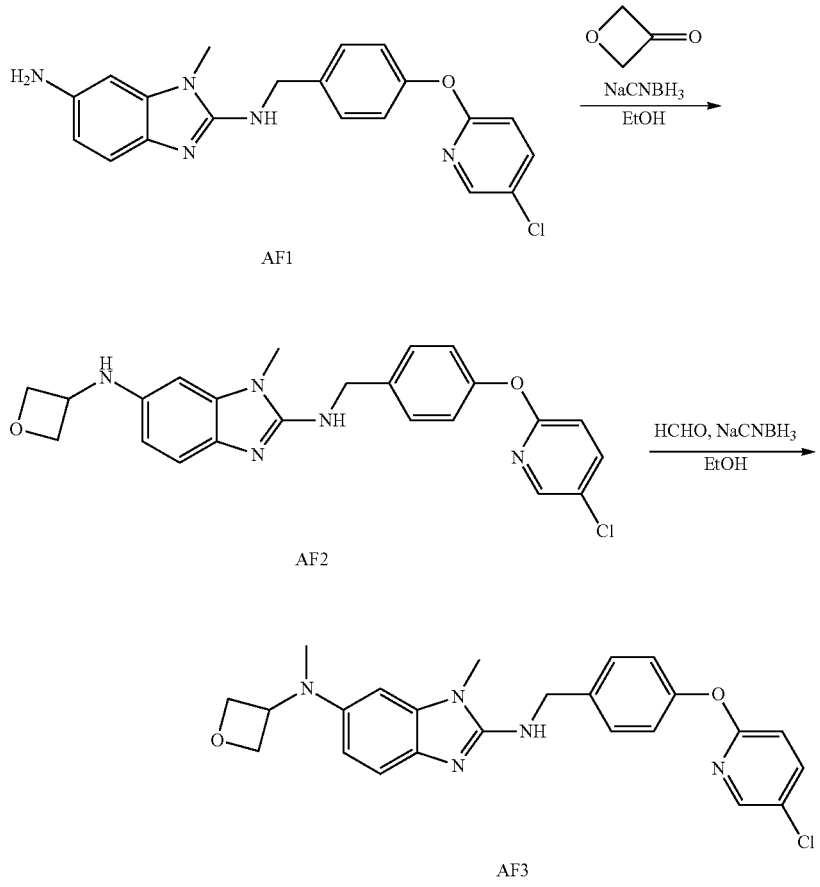

General Procedure for the Synthesis of AF2

A mixture of A1 (200 mg, 0.488 mmol), AcOH (0.3 mL) and 3-oxetanone (42 mg, 0.59 mmol) in absolute EtOH (3 mL) was stirred at 18-22° C. for 16 hours. Then to the reaction mixture was added NaBH$_3$CN (92 mg, 1.5 mmol), the resulting mixture was stirred at 18-20° C. for 4 hours. The reaction mixture was diluted with EtOAc (50 mL), then washed with water (40 mL) and brine (40 mL×3), dried over anhydrous Na$_2$SO$_4$ and concentrated under reduced pressure. The residue was purified by prep-HPLC (0.01% NH$_3$.H$_2$O as additive) to afford AF2.

General Procedure for the Synthesis of AF3

A mixture of AF2 (100 mg, 0.229 mmol) and formaldehyde (86 mg, 1.15 mmol, 40% aqueous solution in water) in EtOH (5 mL) was added AcOH (adjusted to pH 4 of reaction mixture). The resulting mixture was stirred at 10° C. for 16 hours. NaBH$_3$CN (72 mg, 1.15 mmol) was added to the mixture and the reaction mixture was stirred at 10° C. for 4 hours. The mixture was diluted with water (20 mL) and extracted with EtOAc (20 mL×2), the combined extracts were washed with brine (40 mL×2), dried over anhydrous Na$_2$SO$_4$ and concentrated under reduced pressure to afford a residue, which was purified by prep-HPLC (0.01% NH$_3$.H$_2$O) to afford AF3.

Scheme 33. General coupling reaction 2 of a benzimidazole N$^6$ amine

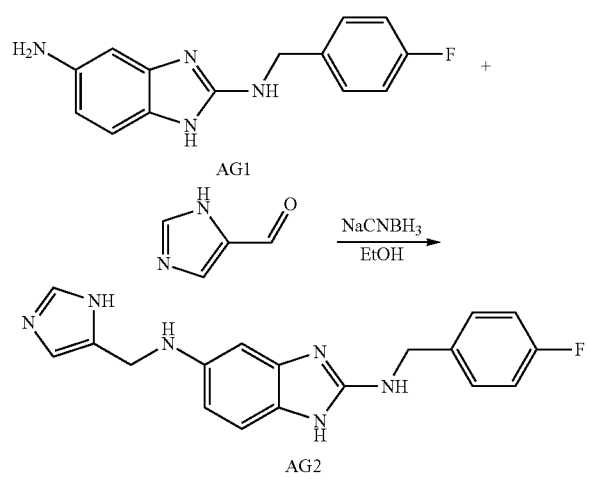

General Procedure for the Synthesis of AG2

To a stirred solution of AG1 (150 mg, 0.583 mmol), 1H-imidazole-5-carbaldehyde (39 mg, 0.416 mmol) in EtOH (3 mL) was added AcOH (adjusted to pH 4 of reaction mixture). The resulting mixture was stirred at 20° C. for 16 hours. Then NaBH$_3$CN (73 mg, 1.17 mmol) was added and the mixture was stirred at 20° C. for 16 hours. The mixture was neutralized with Na$_2$CO$_3$, diluted with water (20 mL) and extracted with EtOAc (20 mL×2). The combined extracts were washed with brine (40 mL×2), dried over anhydrous Na$_2$SO$_4$ and concentrated under reduced pressure to afford crude residue, which was purified by prep-HPLC (0.01% NH$_3$.H$_2$O) to afford AG2.

Scheme 34. General coupling reaction 3 of a benzimidazole N$^6$ amine

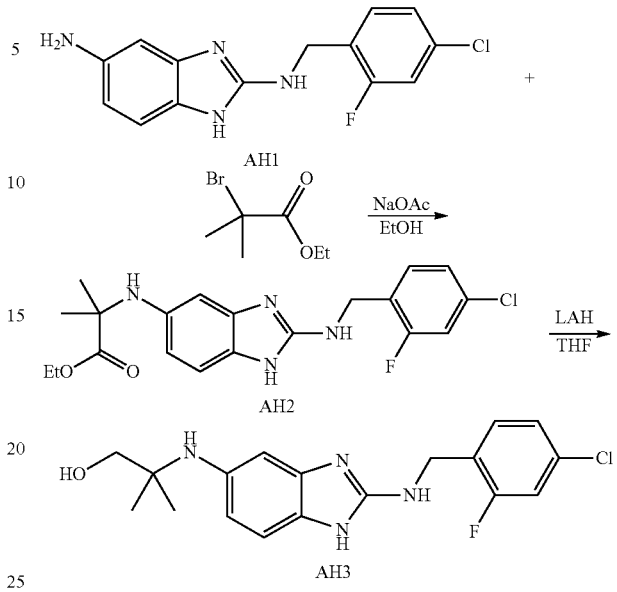

General Procedure for the Synthesis of AH2

To a stirred solution of AH1 (200 mg, 0.69 mmol) and ethyl 2-bromoisobutyrate (537 mg, 2.75 mmol) in EtOH (10 mL) was added NaOAc (226 mg, 2.75 mmol). The mixture was refluxed under N$_2$ for 16 hours. The mixture was diluted with water (10 mL) and extracted with EtOAc (10 mL×2). The combined extracts were washed with brine (10 mL×2), dried over anhydrous Na$_2$SO$_4$ and concentrated under reduced pressure afford a crude AH2.

General Procedure for the Synthesis of AH3

To a stirred solution of compound AH2 (200 mg, crude) in anhydrous THF (5 mL) was added LiAlH$_4$ (75 mg, 1.98 mmol) at 0° C. After stirred at 0° C. for 2 hours, the mixture was allowed to stir at 25° C. under N$_2$ for 16 hours. The mixture was quenched with NaOH aqueous solution (5 M, 0.2 mL) and filtered. The filtrate was diluted with water (10 mL) and extracted with EtOAc (10 mL×2), the combined extracts were washed with brine, dried over anhydrous Na$_2$SO$_4$ and concentrated under reduced pressure to afford crude product, which was purified by prep-TLC (MeOH: DCM=1:10) to afford AH3.

Scheme 35. General synthesis of a N$^6$ substituted benzimidazole derivative

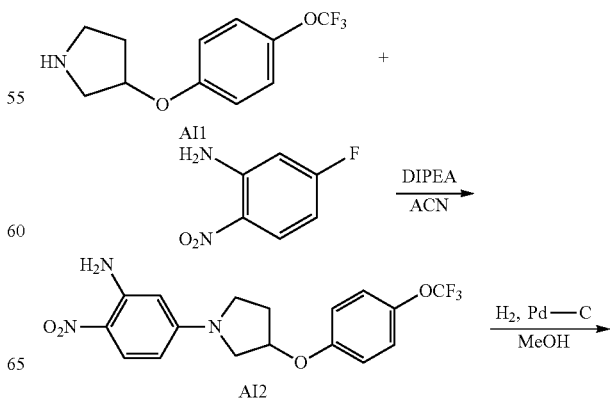

-continued

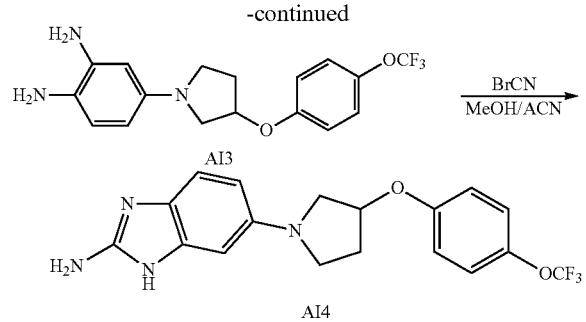

General Procedure for the Synthesis of AI2

A mixture of AI1 (1.00 g, 4.05 mmol), 5-fluoro-2-nitroaniline (631 mg, 4.05 mmol) and DIPEA (1.55 g, 12.2 mmol) in ACN (10 mL) was heated to reflux for 12 hours. The mixture was concentrated under reduced pressure to afford a residue, which was purified by silica gel column (eluent: EtOAc/PE=1/10 to DCM to DCM/EtOAc=1/1) to afford AI2.

General Procedure for the Synthesis of AI3

A mixture of compound AI2 (1.30 g, 3.39 mmol) and Pd—C (200 mg, 10%) in MeOH (30 mL) was stirred at 10° C. under $H_2$ (1 atm) for 2 hours. The mixture was filtered, the filtrate was concentrated under reduced pressure to afford a crude AI3.

General Procedure for the Synthesis of AI4

To a stirred solution of compound AI3 (100 mg, 0.283 mmol) in MeOH (5 mL) was added BrCN (31 mg, in 0.5 mL ACN) with ice bath, the mixture was stirred at 10° C. for 1 hour. The reaction solution was purified by prep-HPLC (0.01% HCl) to afford AI4.

Scheme 36. General coupling reaction 4 of a benzimidazole $N^6$ amine

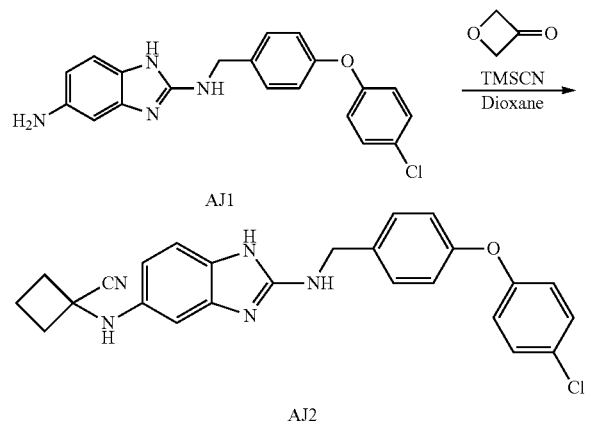

General Procedure for the Synthesis of AJ2

To a stirred solution of AJ1 (100 mg, 0.274 mmol) in anhydrous dioxane (3 mL) were added cyclobutanone (23 mg, 0.329 mmol) and TMSCN (38 mg, 0.384 mmol), the resulting mixture was stirred at 50° C. under $N_2$ atmosphere for 16 hours. The mixture was diluted with water (15 mL) and extracted with EtOAc (15 mL×2), the combined extracts were washed with brine (30 mL×2), dried over anhydrous $Na_2SO_4$ and concentrated under reduced pressure to afford 90 mg of crude residue, which was purified by prep-HPLC (0.05% HCl) to afford AJ2.

Scheme 37. General coupling reaction 5 of a benzimidazole $N^6$ amine

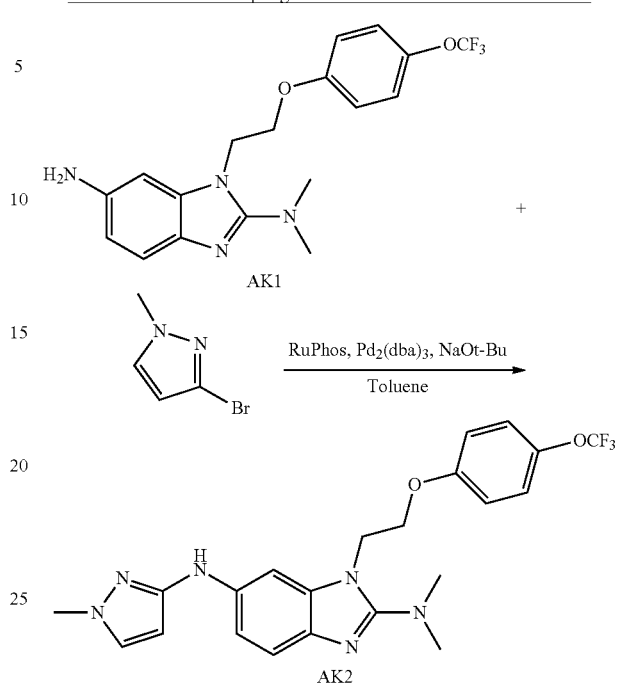

General Procedure for the Synthesis of AK2

To a stirred solution of AK1 (100 mg, 0.244 mmol) in anhydrous toluene (5 mL) were added RuPhos (12 mg, 0.0244 mmol), $Pd_2(dba)_3$ (23 mg, 0.0244 mmol), 3-bromo-1-methyl-1H-pyrazole (47 mg, 0.293 mmol) and NaOt-Bu (58 mg, 0.610 mmol). The mixture was stirred at 110° C. under $N_2$ for 16 hours. The reaction was diluted with brine (5 mL) and filtered. The filtrate was extracted with EtOAc (5 mL×3). The combined extract was washed with brine (5 mL), dried over $Na_2SO_4$, evaporated under reduced pressure. The resulting oil was purified by prep-HPLC (0.01% $NH_3.H_2O$ as additive) to afford AK2.

Using the above procedures, compounds 1-556 as shown in Table 7 (further below) were synthesized.

TABLE 1

5-LO activity by fluorescence method

| # cpds | 5-LO (IC$_{50}$, uM) |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | ++ |
| 14 | +++ |
| 15 | +++ |
| 16 | +++ |
| 17 | ++ |
| 18 | ++ |
| 19 | +++ |
| 20 | +++ |

TABLE 1-continued

5-LO activity by fluorescence method

| # cpds | 5-LO (IC$_{50}$, uM) |
|---|---|
| 21 | +++ |
| 22 | + |
| 23 | ++ |
| 24 | +++ |
| 25 | + |
| 26 | ++ |
| 27 | ++ |
| 28 | +++ |
| 29 | +++ |
| 30 | +++ |
| 31 | +++ |
| 32 | +++ |
| 33 | +++ |
| 34 | +++ |
| 35 | ++ |
| 36 | +++ |
| 37 | +++ |
| 38 | +++ |
| 39 | +++ |
| 40 | +++ |
| 41 | ++ |
| 42 | ++ |
| 43 | ++ |
| 44 | +++ |
| 45 | + |
| 46 | + |
| 47 | + |
| 48 | +++ |
| 49 | + |
| 50 | ++ |
| 51 | +++ |
| 52 | +++ |
| 53 | +++ |
| 54 | +++ |
| 55 | ++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | ++ |
| 70 | +++ |
| 71 | +++ |
| 72 | + |
| 73 | +++ |
| 74 | +++ |
| 75 | +++ |
| 76 | +++ |
| 77 | +++ |
| 78 | + |
| 79 | +++ |
| 80 | +++ |
| 81 | +++ |
| 82 | + |
| 83 | ++ |
| 84 | +++ |
| 85 | ++ |
| 86 | +++ |
| 87 | +++ |
| 88 | +++ |
| 89 | +++ |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | +++ |
| 112 | +++ |
| 113 | +++ |
| 114 | +++ |
| 115 | +++ |
| 116 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | +++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |
| 156 | +++ |
| 157 | +++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |

TABLE 1-continued

5-LO activity by fluorescence method

| # cpds | 5-LO (IC$_{50}$, uM) |
|---|---|
| 173 | +++ |
| 174 | ++ |
| 175 | +++ |
| 176 | +++ |
| 177 | +++ |
| 178 | +++ |
| 179 | +++ |
| 180 | +++ |
| 181 | +++ |
| 182 | +++ |
| 183 | +++ |
| 184 | +++ |
| 185 | +++ |
| 186 | +++ |
| 187 | +++ |
| 188 | +++ |
| 189 | +++ |
| 190 | +++ |
| 191 | +++ |
| 192 | +++ |
| 193 | + |
| 194 | +++ |
| 195 | +++ |
| 196 | +++ |
| 197 | +++ |
| 198 | +++ |
| 199 | +++ |
| 200 | +++ |
| 201 | +++ |
| 202 | +++ |
| 203 | +++ |
| 204 | +++ |
| 205 | +++ |
| 206 | +++ |
| 207 | +++ |
| 208 | +++ |
| 209 | +++ |
| 210 | +++ |
| 211 | +++ |
| 212 | +++ |
| 213 | +++ |
| 214 | +++ |
| 215 | +++ |
| 216 | +++ |
| 217 | +++ |
| 218 | +++ |
| 219 | +++ |
| 220 | +++ |
| 221 | +++ |
| 222 | +++ |
| 223 | +++ |
| 224 | +++ |
| 225 | +++ |
| 226 | +++ |
| 227 | +++ |
| 228 | +++ |
| 229 | +++ |
| 230 | +++ |
| 231 | +++ |
| 232 | +++ |
| 233 | +++ |
| 234 | +++ |
| 235 | + |
| 236 | +++ |
| 237 | +++ |
| 238 | +++ |
| 239 | +++ |
| 240 | +++ |
| 241 | +++ |
| 242 | ++ |
| 243 | +++ |
| 244 | +++ |
| 245 | + |
| 246 | +++ |
| 247 | +++ |
| 248 | +++ |
| 249 | +++ |
| 250 | +++ |
| 251 | +++ |
| 252 | +++ |
| 253 | +++ |
| 254 | +++ |
| 255 | +++ |
| 256 | +++ |
| 257 | +++ |
| 258 | +++ |
| 259 | +++ |
| 260 | +++ |
| 261 | +++ |
| 262 | + |
| 263 | +++ |
| 264 | +++ |
| 265 | +++ |
| 266 | +++ |
| 267 | +++ |
| 268 | +++ |
| 269 | +++ |
| 270 | +++ |
| 271 | +++ |
| 272 | +++ |
| 273 | +++ |
| 274 | +++ |
| 275 | +++ |
| 276 | +++ |
| 277 | +++ |
| 278 | +++ |
| 279 | ++ |
| 280 | +++ |
| 281 | +++ |
| 282 | +++ |
| 283 | +++ |
| 284 | +++ |
| 285 | +++ |
| 286 | +++ |
| 287 | +++ |
| 288 | +++ |
| 289 | +++ |
| 290 | +++ |
| 291 | +++ |
| 292 | +++ |
| 293 | +++ |
| 294 | +++ |
| 295 | +++ |
| 296 | +++ |
| 297 | +++ |
| 298 | +++ |
| 299 | +++ |
| 300 | +++ |
| 301 | +++ |
| 302 | +++ |
| 303 | +++ |
| 304 | +++ |
| 305 | +++ |
| 306 | +++ |
| 307 | +++ |
| 308 | +++ |
| 309 | +++ |
| 310 | +++ |
| 311 | +++ |
| 312 | +++ |
| 313 | +++ |
| 314 | +++ |
| 315 | +++ |
| 316 | +++ |
| 317 | +++ |
| 318 | +++ |
| 319 | +++ |
| 320 | +++ |
| 321 | +++ |
| 322 | + |
| 323 | +++ |
| 324 | +++ |

TABLE 1-continued

5-LO activity by fluorescence method

| # cpds | 5-LO (IC$_{50}$, uM) |
|---|---|
| 325 | +++ |
| 326 | +++ |
| 327 | +++ |
| 328 | +++ |
| 329 | +++ |
| 330 | +++ |
| 331 | +++ |
| 332 | +++ |
| 333 | +++ |
| 334 | +++ |
| 335 | +++ |
| 336 | +++ |
| 337 | +++ |
| 338 | +++ |
| 339 | +++ |
| 340 | +++ |
| 341 | +++ |
| 342 | +++ |
| 343 | +++ |
| 344 | +++ |
| 345 | +++ |
| 346 | +++ |
| 347 | +++ |
| 348 | +++ |
| 349 | +++ |
| 350 | +++ |
| 351 | +++ |
| 352 | +++ |
| 353 | +++ |
| 354 | +++ |
| 355 | ++ |
| 356 | +++ |
| 357 | +++ |
| 358 | +++ |
| 359 | +++ |
| 360 | +++ |
| 361 | +++ |
| 362 | +++ |
| 363 | +++ |
| 364 | +++ |
| 365 | +++ |
| 366 | +++ |
| 367 | +++ |
| 368 | +++ |
| 369 | +++ |
| 370 | +++ |
| 371 | +++ |
| 372 | +++ |
| 373 | +++ |
| 374 | +++ |
| 375 | +++ |
| 376 | +++ |
| 377 | +++ |
| 378 | +++ |
| 379 | +++ |
| 380 | +++ |
| 381 | +++ |
| 382 | +++ |
| 383 | +++ |
| 384 | +++ |
| 385 | +++ |
| 386 | ++ |
| 387 | +++ |
| 388 | +++ |
| 389 | +++ |
| 390 | +++ |
| 391 | +++ |
| 392 | +++ |
| 393 | +++ |
| 394 | +++ |
| 395 | +++ |
| 396 | +++ |
| 397 | +++ |
| 398 | +++ |
| 399 | +++ |
| 400 | +++ |
| 401 | +++ |
| 402 | +++ |
| 403 | +++ |
| 404 | +++ |
| 405 | +++ |
| 406 | +++ |
| 407 | +++ |
| 408 | +++ |
| 409 | +++ |
| 410 | +++ |
| 411 | +++ |
| 412 | +++ |
| 413 | +++ |
| 414 | +++ |
| 415 | +++ |
| 416 | +++ |
| 417 | +++ |
| 418 | +++ |
| 419 | +++ |
| 420 | +++ |
| 421 | +++ |
| 422 | +++ |
| 423 | +++ |
| 424 | +++ |
| 425 | +++ |
| 426 | +++ |
| 427 | +++ |
| 428 | +++ |
| 429 | + |
| 430 | +++ |
| 431 | +++ |
| 432 | +++ |
| 433 | +++ |
| 434 | +++ |
| 435 | +++ |
| 436 | +++ |
| 437 | +++ |
| 438 | +++ |
| 439 | +++ |
| 440 | +++ |
| 441 | + |
| 442 | +++ |
| 443 | +++ |
| 444 | +++ |
| 445 | +++ |
| 446 | +++ |
| 447 | ++ |
| 448 | ++ |
| 449 | +++ |
| 450 | +++ |
| 451 | +++ |
| 452 | +++ |
| 453 | +++ |
| 454 | +++ |
| 455 | +++ |
| 456 | +++ |
| 457 | +++ |
| 458 | +++ |
| 459 | +++ |
| 460 | +++ |
| 461 | +++ |
| 462 | +++ |
| 463 | +++ |
| 464 | ++ |
| 465 | +++ |
| 466 | +++ |
| 467 | +++ |
| 468 | +++ |
| 469 | +++ |
| 470 | +++ |
| 471 | +++ |
| 472 | ++ |
| 473 | +++ |
| 474 | +++ |
| 475 | +++ |
| 476 | +++ |

TABLE 1-continued

5-LO activity by fluorescence method

| # cpds | 5-LO (IC$_{50}$, uM) |
|---|---|
| 477 | +++ |
| 478 | +++ |
| 479 | +++ |
| 480 | +++ |
| 481 | +++ |
| 482 | +++ |
| 483 | +++ |
| 484 | +++ |
| 485 | +++ |
| 486 | +++ |
| 487 | +++ |
| 488 | ++ |
| 489 | +++ |
| 490 | +++ |
| 491 | +++ |
| 492 | +++ |
| 493 | ++ |
| 494 | ++ |
| 495 | +++ |
| 496 | +++ |
| 497 | ++ |
| 498 | + |
| 499 | +++ |
| 500 | ++ |
| 501 | +++ |
| 502 | ++ |
| 503 | +++ |
| 504 | ++ |
| 505 | +++ |
| 506 | + |
| 507 | +++ |
| 508 | ++ |
| 509 | +++ |
| 510 | + |
| 511 | + |
| 512 | +++ |
| 513 | +++ |
| 514 | +++ |
| 515 | + |
| 516 | + |
| 517 | ++ |
| 518 | + |
| 519 | + |
| 520 | + |
| 521 | ++ |
| 522 | + |
| 523 | + |
| 524 | + |
| 525 | +++ |
| 526 | ++ |
| 527 | + |
| 528 | + |
| 529 | +++ |
| 530 | +++ |
| 531 | +++ |
| 532 | +++ |
| 533 | +++ |
| 534 | +++ |
| 535 | +++ |
| 536 | +++ |
| 537 | +++ |
| 538 | +++ |
| 539 | +++ |
| 540 | +++ |
| 541 | +++ |
| 542 | +++ |
| 543 | +++ |
| 544 | +++ |
| 545 | ++ |
| 546 | +++ |
| 547 | +++ |
| 548 | +++ |
| 549 | +++ |
| 550 | +++ |
| 551 | +++ |
| 552 | +++ |
| 553 | +++ |
| 554 | +++ |
| 555 | +++ |
| 556 | +++ |

Activity range: +++ indicates <1 uM, ++ indicates between 1-10 uM, + indicates >10 uM

TABLE 2

5-LO activity by ELISA method

| # cpds | 5LO (IC$_{50}$, uM) |
|---|---|
| 14 | +++ |
| 48 | ++ |
| 49 | ++ |

Activity range: +++ indicates <1 uM, ++ indicates between 1-20 uM, + indicates >20 uM

TABLE 3

LTB4 secretion assay in RBL

| # cpds | RBL (EC$_{50}$, uM) |
|---|---|
| 14 | +++ |
| 17 | +++ |
| 24 | +++ |
| 26 | + |
| 27 | + |
| 28 | ++ |
| 29 | +++ |
| 30 | +++ |
| 31 | + |
| 32 | +++ |
| 33 | +++ |
| 34 | ++ |
| 35 | + |
| 36 | ++ |
| 37 | + |
| 38 | +++ |
| 39 | ++ |
| 40 | ++ |
| 41 | ++ |
| 42 | ++ |
| 43 | +++ |
| 44 | +++ |
| 45 | +++ |
| 46 | +++ |
| 47 | + |
| 48 | +++ |
| 49 | +++ |
| 50 | ++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | ++ |
| 62 | +++ |
| 63 | ++ |
| 64 | + |
| 65 | +++ |
| 66 | +++ |
| 67 | +++ |
| 68 | +++ |
| 69 | +++ |

TABLE 3-continued

LTB4 secretion assay in RBL

| # cpds | RBL (EC$_{50}$, uM) |
|---|---|
| 70 | +++ |
| 71 | ++ |
| 72 | + |
| 73 | +++ |
| 74 | +++ |
| 75 | ++ |
| 76 | + |
| 77 | ++ |
| 78 | ++ |
| 79 | +++ |
| 80 | +++ |
| 81 | +++ |
| 82 | ++ |
| 83 | + |
| 84 | +++ |
| 85 | + |
| 86 | +++ |
| 87 | +++ |
| 88 | +++ |
| 89 | + |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | + |
| 109 | +++ |
| 110 | +++ |
| 111 | +++ |
| 112 | +++ |
| 113 | +++ |
| 114 | ++ |
| 115 | + |
| 116 | +++ |
| 117 | ++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | ++ |
| 134 | +++ |
| 135 | +++ |
| 136 | +++ |
| 137 | +++ |
| 138 | +++ |
| 139 | + |
| 140 | +++ |
| 141 | + |
| 142 | ++ |
| 143 | ++ |
| 144 | ++ |
| 145 | +++ |
| 146 | ++ |
| 147 | +++ |
| 148 | +++ |
| 149 | +++ |
| 150 | +++ |
| 151 | + |
| 152 | +++ |
| 153 | +++ |
| 154 | + |
| 155 | +++ |
| 156 | ++ |
| 157 | + |
| 158 | + |
| 159 | + |
| 160 | +++ |
| 161 | +++ |
| 162 | +++ |
| 163 | + |
| 164 | +++ |
| 165 | +++ |
| 166 | +++ |
| 167 | + |
| 168 | +++ |
| 169 | +++ |
| 170 | ++ |
| 171 | + |
| 172 | +++ |
| 173 | + |
| 174 | + |
| 175 | +++ |
| 176 | +++ |
| 177 | +++ |
| 178 | ++ |
| 179 | +++ |
| 180 | +++ |
| 181 | + |
| 182 | ++ |
| 183 | + |
| 184 | +++ |
| 185 | +++ |
| 186 | +++ |
| 187 | +++ |
| 188 | + |
| 189 | + |
| 190 | +++ |
| 191 | +++ |
| 192 | +++ |
| 193 | +++ |
| 194 | +++ |
| 195 | +++ |
| 196 | +++ |
| 197 | +++ |
| 198 | ++ |
| 199 | +++ |
| 200 | +++ |
| 201 | + |
| 202 | +++ |
| 203 | +++ |
| 204 | +++ |
| 205 | +++ |
| 206 | +++ |
| 207 | +++ |
| 208 | +++ |
| 209 | +++ |
| 210 | +++ |
| 211 | +++ |
| 212 | +++ |
| 213 | +++ |
| 214 | +++ |
| 215 | +++ |
| 216 | +++ |
| 217 | +++ |
| 218 | +++ |
| 219 | +++ |
| 220 | +++ |
| 221 | + |

TABLE 3-continued

LTB4 secretion assay in RBL

| # cpds | RBL (EC$_{50}$, uM) |
|---|---|
| 222 | ++ |
| 223 | +++ |
| 224 | +++ |
| 225 | + |
| 226 | +++ |
| 227 | +++ |
| 228 | + |
| 229 | +++ |
| 230 | +++ |
| 231 | +++ |
| 232 | + |
| 233 | +++ |
| 234 | +++ |
| 235 | +++ |
| 236 | +++ |
| 237 | + |
| 238 | +++ |
| 239 | +++ |
| 240 | +++ |
| 241 | +++ |
| 242 | +++ |
| 243 | +++ |
| 244 | +++ |
| 245 | +++ |
| 246 | +++ |
| 247 | +++ |
| 248 | +++ |
| 249 | +++ |
| 250 | +++ |
| 251 | +++ |
| 252 | +++ |
| 253 | +++ |
| 254 | +++ |
| 255 | +++ |
| 256 | ++ |
| 257 | +++ |
| 258 | +++ |
| 259 | +++ |
| 260 | +++ |
| 261 | +++ |
| 262 | +++ |
| 263 | ++ |
| 264 | +++ |
| 265 | +++ |
| 266 | ++ |
| 267 | +++ |
| 268 | +++ |
| 269 | +++ |
| 270 | +++ |
| 271 | +++ |
| 272 | +++ |
| 273 | +++ |
| 274 | +++ |
| 275 | +++ |
| 276 | +++ |
| 277 | +++ |
| 278 | +++ |
| 279 | +++ |
| 280 | +++ |
| 281 | +++ |
| 282 | +++ |
| 283 | +++ |
| 284 | +++ |
| 285 | +++ |
| 286 | +++ |
| 287 | +++ |
| 288 | +++ |
| 289 | +++ |
| 290 | +++ |
| 291 | +++ |
| 292 | +++ |
| 293 | +++ |
| 294 | +++ |
| 295 | +++ |
| 296 | +++ |
| 297 | +++ |
| 298 | +++ |
| 299 | +++ |
| 300 | +++ |
| 301 | +++ |
| 302 | +++ |
| 303 | + |
| 304 | +++ |
| 305 | +++ |
| 306 | +++ |
| 307 | ++ |
| 308 | + |
| 309 | + |
| 310 | + |
| 311 | + |
| 312 | + |
| 313 | +++ |
| 314 | ++ |
| 315 | ++ |
| 316 | +++ |
| 317 | + |
| 318 | + |
| 319 | + |
| 320 | + |
| 321 | ++ |
| 322 | +++ |
| 323 | +++ |
| 324 | +++ |
| 325 | +++ |
| 326 | +++ |
| 327 | +++ |
| 328 | +++ |
| 329 | +++ |
| 330 | +++ |
| 331 | +++ |
| 332 | +++ |
| 333 | +++ |
| 334 | ++ |
| 335 | +++ |
| 336 | ++ |
| 337 | ++ |
| 338 | + |
| 339 | ++ |
| 340 | +++ |
| 341 | ++ |
| 342 | +++ |
| 343 | + |
| 344 | + |
| 345 | + |
| 346 | +++ |
| 347 | +++ |
| 348 | + |
| 349 | +++ |
| 350 | +++ |
| 351 | ++ |
| 352 | +++ |
| 353 | +++ |
| 354 | + |
| 355 | + |
| 356 | ++ |
| 357 | +++ |
| 358 | +++ |
| 359 | +++ |
| 360 | ++ |
| 361 | +++ |
| 362 | ++ |
| 363 | + |
| 364 | + |
| 365 | +++ |
| 366 | +++ |
| 367 | +++ |
| 368 | +++ |
| 369 | +++ |
| 370 | ++ |
| 371 | ++ |
| 372 | +++ |
| 373 | +++ |

TABLE 3-continued

LTB4 secretion assay in RBL

| # cpds | RBL (EC$_{50}$, uM) |
|---|---|
| 374 | +++ |
| 375 | +++ |
| 376 | + |
| 377 | +++ |
| 378 | +++ |
| 379 | +++ |
| 380 | +++ |
| 381 | + |
| 382 | +++ |
| 383 | +++ |
| 384 | +++ |
| 385 | ++ |
| 386 | + |
| 387 | +++ |
| 388 | ++ |
| 389 | +++ |
| 390 | +++ |
| 391 | +++ |
| 392 | +++ |
| 393 | +++ |
| 394 | ++ |
| 395 | +++ |
| 396 | +++ |
| 397 | +++ |
| 398 | +++ |
| 399 | +++ |
| 400 | +++ |
| 401 | +++ |
| 402 | +++ |
| 403 | +++ |
| 404 | + |
| 405 | +++ |
| 406 | +++ |
| 407 | +++ |
| 408 | + |
| 409 | + |
| 410 | +++ |
| 411 | + |
| 412 | +++ |
| 413 | +++ |
| 414 | +++ |
| 415 | +++ |
| 416 | ++ |
| 417 | + |
| 418 | + |
| 419 | +++ |
| 420 | +++ |
| 421 | +++ |
| 422 | +++ |
| 423 | +++ |
| 424 | +++ |
| 425 | +++ |
| 426 | +++ |
| 427 | +++ |
| 428 | +++ |
| 429 | ++ |
| 430 | +++ |
| 431 | +++ |
| 432 | +++ |
| 433 | ++ |
| 434 | +++ |
| 435 | +++ |
| 436 | +++ |
| 437 | +++ |
| 438 | ++ |
| 439 | ++ |
| 440 | +++ |
| 441 | + |
| 442 | +++ |
| 443 | + |
| 444 | ++ |
| 445 | +++ |
| 446 | +++ |
| 447 | +++ |
| 448 | +++ |
| 449 | +++ |
| 450 | +++ |
| 451 | +++ |
| 452 | +++ |
| 453 | +++ |
| 454 | ++ |
| 455 | +++ |
| 456 | + |
| 457 | +++ |
| 458 | +++ |
| 459 | ++ |
| 460 | +++ |
| 461 | +++ |
| 462 | + |
| 463 | +++ |
| 464 | +++ |
| 465 | +++ |
| 466 | +++ |
| 467 | +++ |
| 468 | +++ |
| 469 | +++ |
| 470 | +++ |
| 471 | +++ |
| 472 | +++ |
| 473 | +++ |
| 474 | +++ |
| 475 | +++ |
| 476 | +++ |
| 477 | +++ |
| 478 | +++ |
| 479 | +++ |
| 480 | +++ |
| 481 | +++ |
| 482 | +++ |
| 483 | + |
| 484 | + |
| 485 | ++ |
| 486 | +++ |
| 487 | +++ |
| 488 | + |
| 489 | +++ |
| 490 | +++ |
| 491 | +++ |
| 492 | +++ |
| 493 | +++ |
| 494 | +++ |
| 495 | +++ |
| 496 | +++ |
| 497 | + |
| 498 | + |
| 499 | +++ |
| 500 | ++ |
| 501 | +++ |
| 502 | +++ |
| 503 | +++ |
| 504 | +++ |
| 505 | +++ |
| 506 | +++ |
| 507 | +++ |
| 508 | +++ |
| 509 | +++ |
| 510 | +++ |
| 511 | +++ |
| 512 | +++ |
| 513 | +++ |
| 514 | +++ |
| 515 | +++ |
| 516 | +++ |
| 517 | +++ |
| 518 | +++ |
| 519 | +++ |
| 520 | +++ |
| 521 | +++ |
| 522 | +++ |
| 523 | +++ |
| 524 | +++ |
| 525 | +++ |

TABLE 3-continued

LTB4 secretion assay in RBL

| # cpds | RBL (EC$_{50}$, uM) |
|---|---|
| 526 | +++ |
| 527 | +++ |
| 528 | +++ |
| 529 | +++ |
| 530 | +++ |
| 531 | +++ |
| 532 | +++ |
| 533 | +++ |
| 534 | +++ |
| 535 | +++ |
| 536 | +++ |
| 537 | +++ |
| 538 | +++ |
| 539 | +++ |
| 540 | +++ |
| 541 | +++ |
| 542 | +++ |
| 543 | +++ |
| 544 | +++ |
| 545 | +++ |
| 546 | +++ |
| 547 | +++ |
| 548 | +++ |
| 549 | +++ |
| 550 | +++ |
| 551 | +++ |
| 552 | +++ |
| 553 | +++ |
| 554 | ++ |
| 555 | ++ |
| 556 | +++ |

Activity range: +++ indicates <10 uM, ++ indicates between 10-20 uM, + indicates >20 uM

TABLE 4

LTB4 secretion assay in Rat whole blood (RWB)

| # cpds | RWB (EC$_{50}$, uM) |
|---|---|
| 1 | + |
| 3 | + |
| 4 | + |
| 5 | ++ |
| 6 | + |
| 7 | + |
| 8 | + |
| 9 | ++ |
| 10 | ++ |
| 11 | +++ |
| 12 | +++ |
| 13 | + |
| 14 | +++ |
| 15 | + |
| 16 | + |
| 17 | + |
| 20 | + |
| 21 | + |
| 22 | + |
| 23 | ++ |
| 24 | +++ |
| 30 | +++ |
| 32 | +++ |
| 38 | + |
| 43 | + |
| 44 | + |
| 48 | +++ |
| 49 | ++ |
| 51 | ++ |
| 52 | +++ |
| 53 | +++ |
| 54 | +++ |
| 55 | + |
| 56 | ++ |
| 57 | + |
| 58 | + |
| 59 | + |
| 62 | +++ |
| 65 | +++ |
| 66 | + |
| 67 | + |
| 68 | + |
| 70 | + |
| 73 | ++ |
| 74 | ++ |
| 75 | + |
| 77 | +++ |
| 79 | +++ |
| 80 | +++ |
| 81 | +++ |
| 86 | +++ |
| 87 | +++ |
| 88 | +++ |
| 90 | ++ |
| 91 | ++ |
| 92 | +++ |
| 93 | + |
| 94 | +++ |
| 97 | +++ |
| 98 | +++ |
| 99 | + |
| 101 | +++ |
| 102 | +++ |
| 103 | +++ |
| 104 | + |
| 105 | + |
| 106 | +++ |
| 107 | + |
| 108 | + |
| 109 | +++ |
| 110 | +++ |
| 111 | +++ |
| 112 | ++ |
| 113 | +++ |
| 114 | + |
| 116 | ++ |
| 118 | + |
| 119 | +++ |
| 120 | +++ |
| 121 | + |
| 122 | +++ |
| 123 | +++ |
| 125 | +++ |
| 126 | + |
| 127 | + |
| 128 | + |
| 129 | + |
| 130 | +++ |
| 132 | + |
| 135 | ++ |
| 136 | +++ |
| 137 | +++ |
| 138 | +++ |
| 145 | +++ |
| 147 | +++ |
| 148 | + |
| 149 | +++ |
| 150 | + |
| 152 | ++ |
| 154 | + |
| 155 | +++ |
| 160 | + |
| 161 | ++ |
| 164 | + |
| 165 | +++ |
| 166 | +++ |
| 172 | ++ |
| 175 | + |
| 176 | +++ |
| 177 | +++ |

TABLE 4-continued

LTB4 secretion assay in Rat whole blood (RWB)

| # cpds | RWB (EC$_{50}$, uM) |
|---|---|
| 184 | +++ |
| 190 | + |
| 191 | + |
| 193 | +++ |
| 195 | +++ |
| 196 | ++ |
| 197 | + |
| 199 | +++ |
| 202 | + |
| 203 | + |
| 204 | +++ |
| 211 | +++ |
| 219 | + |
| 226 | +++ |
| 227 | +++ |
| 229 | +++ |
| 231 | +++ |
| 233 | +++ |
| 234 | +++ |
| 238 | +++ |
| 239 | +++ |
| 241 | + |
| 243 | +++ |
| 245 | ++ |
| 249 | +++ |
| 251 | +++ |
| 253 | +++ |
| 256 | +++ |
| 268 | +++ |
| 269 | +++ |
| 270 | +++ |
| 271 | +++ |
| 273 | ++ |
| 275 | +++ |
| 277 | +++ |
| 279 | +++ |
| 281 | +++ |
| 284 | +++ |
| 288 | +++ |
| 289 | +++ |
| 291 | ++ |
| 294 | + |
| 296 | +++ |
| 298 | + |
| 300 | ++ |
| 302 | ++ |
| 303 | + |
| 305 | + |
| 306 | +++ |
| 307 | + |
| 309 | + |
| 311 | +++ |
| 315 | + |
| 324 | +++ |
| 328 | +++ |
| 336 | +++ |
| 337 | ++ |
| 341 | +++ |
| 343 | ++ |
| 344 | ++ |
| 345 | +++ |
| 350 | +++ |
| 351 | +++ |
| 357 | ++ |
| 358 | +++ |
| 360 | +++ |
| 362 | +++ |
| 364 | + |
| 367 | +++ |
| 368 | +++ |
| 369 | +++ |
| 371 | ++ |
| 373 | +++ |
| 374 | +++ |
| 378 | +++ |
| 381 | +++ |
| 383 | + |
| 392 | +++ |
| 394 | + |
| 409 | + |
| 412 | +++ |
| 413 | +++ |
| 414 | +++ |
| 415 | +++ |
| 417 | + |
| 418 | + |
| 430 | +++ |
| 431 | +++ |
| 433 | +++ |
| 447 | +++ |
| 448 | +++ |
| 449 | +++ |
| 450 | +++ |
| 459 | ++ |
| 461 | +++ |
| 464 | +++ |
| 465 | +++ |
| 466 | +++ |
| 468 | +++ |
| 469 | +++ |
| 470 | +++ |
| 471 | +++ |
| 473 | +++ |
| 474 | +++ |
| 475 | +++ |
| 476 | +++ |
| 477 | +++ |
| 479 | +++ |
| 481 | +++ |
| 482 | +++ |
| 486 | +++ |
| 487 | +++ |
| 489 | +++ |
| 490 | +++ |
| 491 | +++ |
| 492 | +++ |
| 493 | +++ |
| 494 | +++ |
| 495 | +++ |
| 496 | +++ |
| 497 | + |
| 498 | +++ |
| 499 | +++ |
| 501 | +++ |
| 502 | +++ |
| 503 | +++ |
| 504 | +++ |
| 505 | +++ |
| 506 | +++ |
| 507 | ++ |
| 508 | +++ |
| 509 | +++ |
| 512 | +++ |
| 513 | +++ |
| 514 | +++ |
| 516 | +++ |
| 517 | +++ |
| 518 | +++ |
| 519 | +++ |
| 523 | ++ |
| 524 | ++ |
| 525 | +++ |
| 526 | +++ |
| 527 | +++ |
| 528 | +++ |
| 529 | +++ |
| 530 | +++ |
| 531 | +++ |
| 532 | +++ |
| 533 | +++ |
| 534 | +++ |
| 535 | +++ |

TABLE 4-continued

LTB4 secretion assay in Rat whole blood (RWB)

| # cpds | RWB (EC$_{50}$, uM) |
|---|---|
| 536 | +++ |
| 537 | +++ |
| 538 | +++ |
| 540 | +++ |
| 541 | +++ |
| 542 | +++ |
| 543 | +++ |
| 544 | +++ |
| 545 | +++ |
| 546 | +++ |
| 547 | +++ |
| 550 | +++ |
| 552 | ++ |
| 553 | +++ |
| 554 | +++ |
| 555 | ++ |

Activity range: +++ indicates <10 uM, ++ indicates between 10-20 uM, + indicates >20 uM

TABLE 5

| PGE$_2$ inhibition assay | |
|---|---|
| # cpds | Inhibition (%, 10 uM) |
| 44 | ++ |
| 53 | +++ |
| 54 | +++ |
| 86 | +++ |
| 90 | +++ |
| 91 | +++ |
| 95 | +++ |
| 99 | +++ |
| 103 | +++ |
| 195 | + |
| 211 | ++ |
| 226 | +++ |

Activity range: +++ indicates >70%, ++ indicates between 40-70%, + indicates <40%

TABLE 6

| COX-2 inhibition assay | |
|---|---|
| # cpds | Inhibition (%, 10 uM) |
| 90 | NA |
| 95 | NA |

NA: not active (<1%)

| No. | Structure |
|---|---|
| 1 | 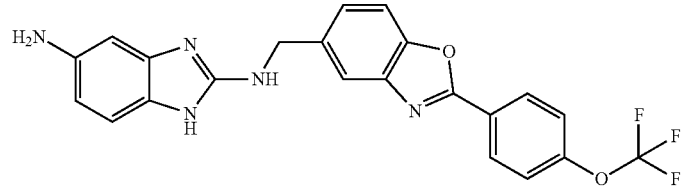 [SMILES: Nc1ccc2[nH]c(NCc3ccc4oc(-c5ccc(OC(F)(F)F)cc5)nc4c3)nc2c1] |
| 2 | 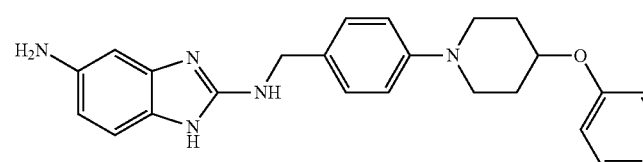 |
| 3 | 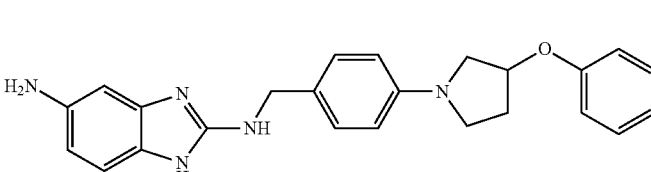 |
| 4 | 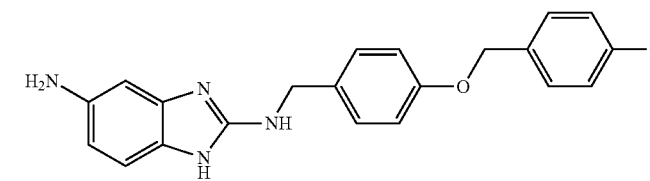 |

5 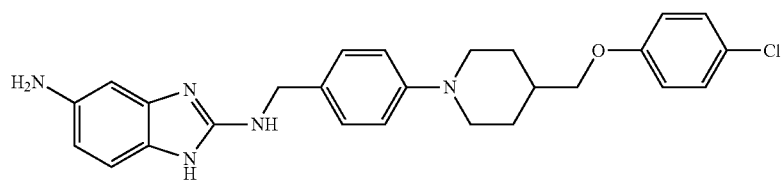 [SMILES: Nc1ccc2[nH]c(NCc3ccc(N4CCC(COc5ccc(Cl)cc5)CC4)cc3)nc2c1]
6 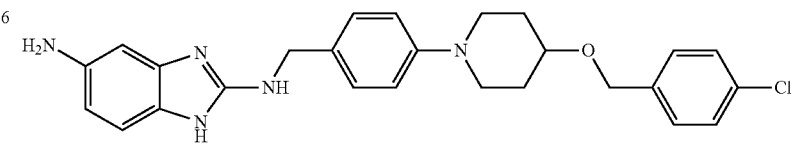
7 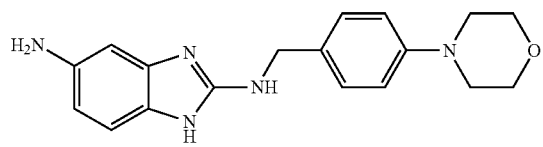 [SMILES: Nc1ccc2[nH]c(NCc3ccc(N4CCOCC4)cc3)nc2c1]
8 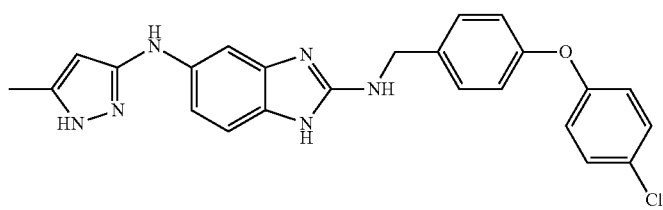 [SMILES: Cc1cc(Nc2ccc3[nH]c(NCc4ccc(Oc5ccc(Cl)cc5)cc4)nc3c2)n[nH]1]
9 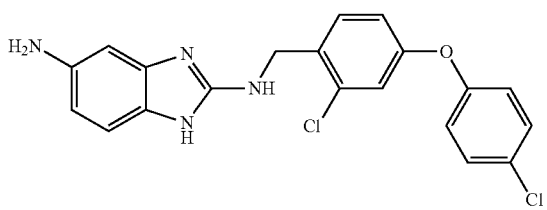 [SMILES: Nc1ccc2[nH]c(NCc3ccc(Oc4ccc(Cl)cc4)cc3Cl)nc2c1]
10 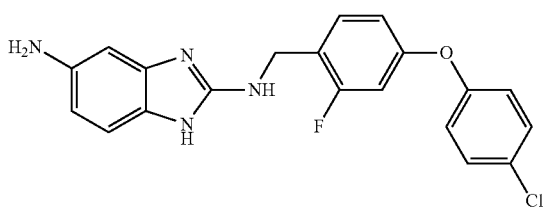 [SMILES: Nc1ccc2[nH]c(NCc3ccc(Oc4ccc(Cl)cc4)cc3F)nc2c1]
11 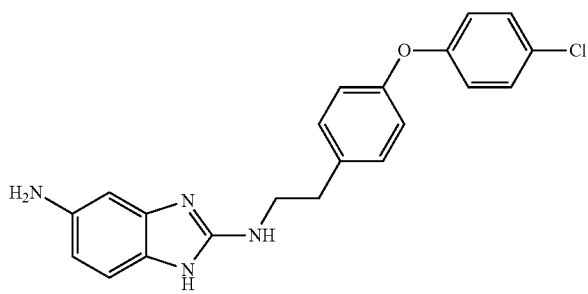 [SMILES: Nc1ccc2[nH]c(NCCc3ccc(Oc4ccc(Cl)cc4)cc3)nc2c1]

-continued
| | |
|---|---|
| 12 | 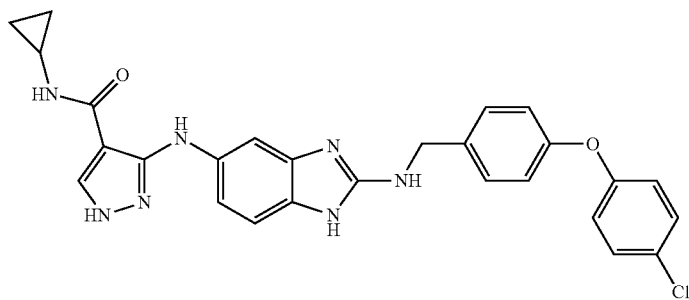 [SMILES: O=C(NC1CC1)c1c[nH]nc1Nc1ccc2[nH]c(NCc3ccc(Oc4ccc(Cl)cc4)cc3)nc2c1] |
| 13 | 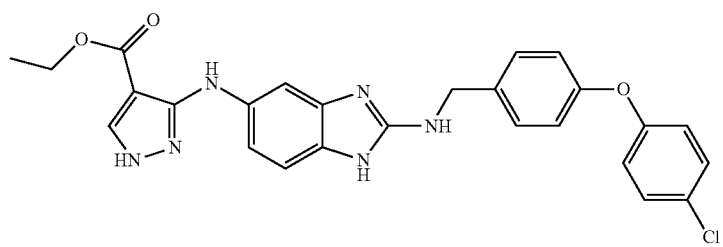 [SMILES: CCOC(=O)c1c[nH]nc1Nc1ccc2[nH]c(NCc3ccc(Oc4ccc(Cl)cc4)cc3)nc2c1] |
| 14 | 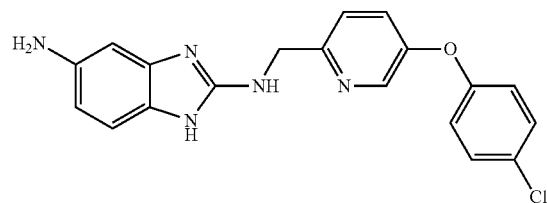 [SMILES: Nc1ccc2[nH]c(NCc3ccc(Oc4ccc(Cl)cc4)cn3)nc2c1] |
| 15 | 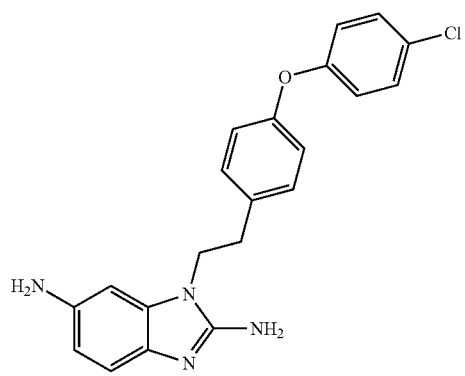 [SMILES: Nc1ccc2nc(N)n(CCc3ccc(Oc4ccc(Cl)cc4)cc3)c2c1] |
| 16 | 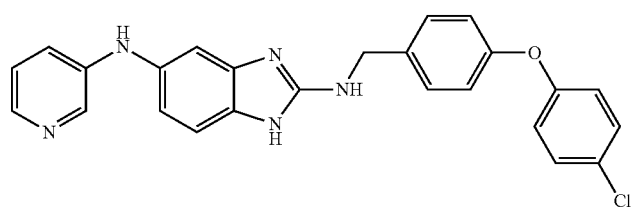 [SMILES: Clc1ccc(Oc2ccc(CNc3nc4cc(Nc5cccnc5)ccc4[nH]3)cc2)cc1] |

17
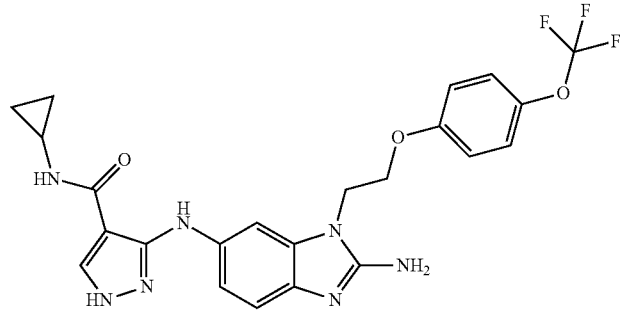 [SMILES: Nc1nc2ccc(Nc3n[nH]cc3C(=O)NC3CC3)cc2n1CCOc1ccc(OC(F)(F)F)cc1]
18
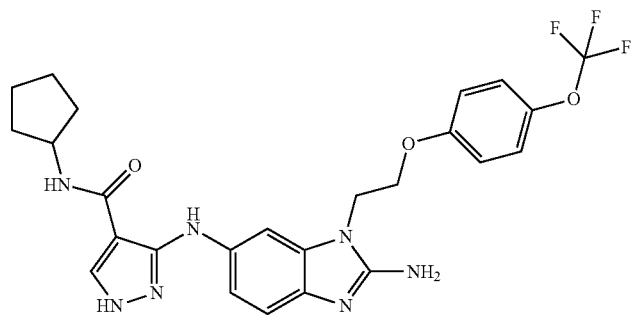 [SMILES: Nc1nc2ccc(Nc3n[nH]cc3C(=O)NC3CCCC3)cc2n1CCOc1ccc(OC(F)(F)F)cc1]
19
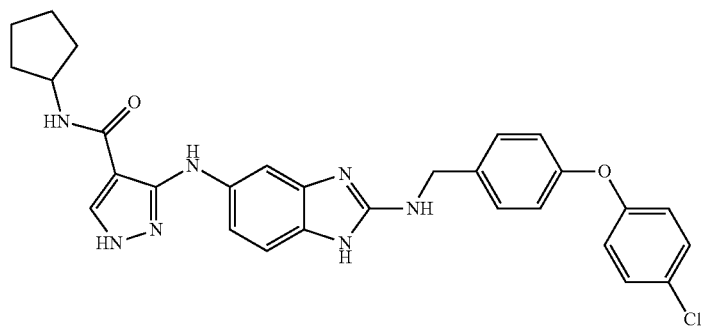 [SMILES: O=C(NC1CCCC1)c1c[nH]nc1Nc1ccc2[nH]c(NCc3ccc(Oc4ccc(Cl)cc4)cc3)nc2c1]
20
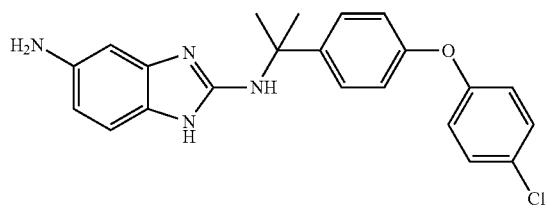 [SMILES: CC(C)(Nc1nc2cc(N)ccc2[nH]1)c1ccc(Oc2ccc(Cl)cc2)cc1]
21
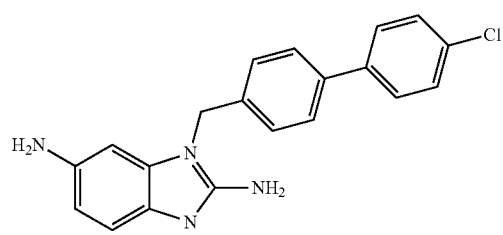

| | |
|---|---|
| 22 | 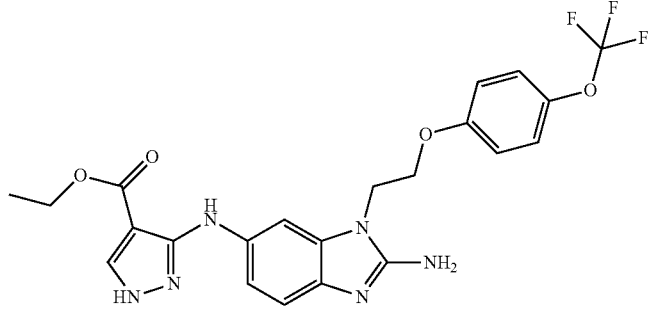 [SMILES: CCOC(=O)c1c[nH]nc1Nc1ccc2nc(N)n(CCOc3ccc(OC(F)(F)F)cc3)c2c1] |
| 23 | 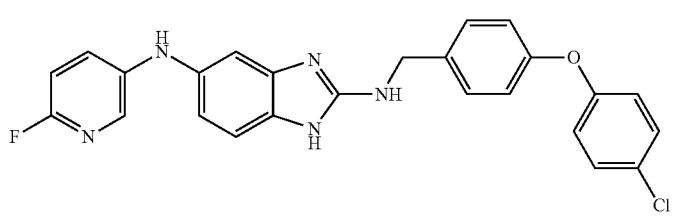 [SMILES: Fc1ccc(Nc2ccc3[nH]c(NCc4ccc(Oc5ccc(Cl)cc5)cc4)nc3c2)cn1] |
| 24 | 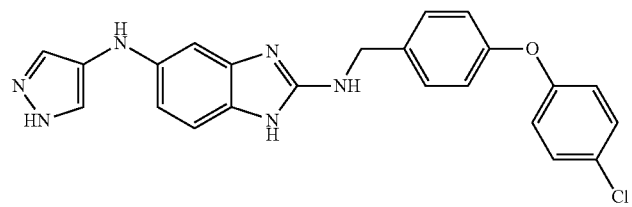 [SMILES: Clc1ccc(Oc2ccc(CNc3nc4cc(Nc5cn[nH]c5)ccc4[nH]3)cc2)cc1] |
| 25 | 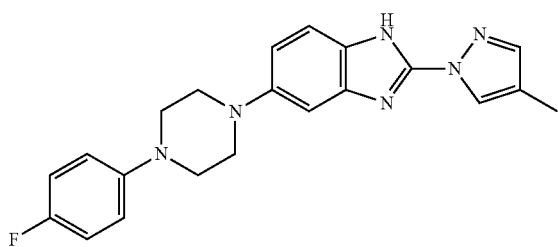 [SMILES: Cc1cnn(-c2nc3cc(N4CCN(c5ccc(F)cc5)CC4)ccc3[nH]2)c1] |
| 26 | 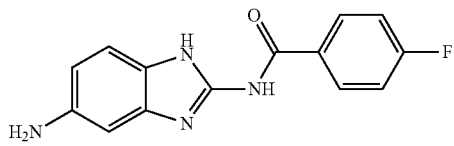 [SMILES: Nc1ccc2[nH]c(NC(=O)c3ccc(F)cc3)nc2c1] |
| 27 | 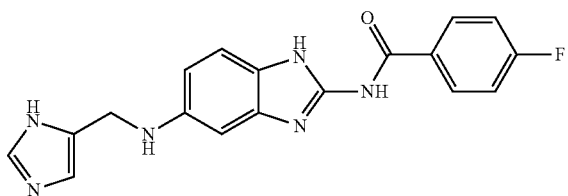 [SMILES: O=C(Nc1nc2cc(NCc3cnc[nH]3)ccc2[nH]1)c1ccc(F)cc1] |
| 28 | 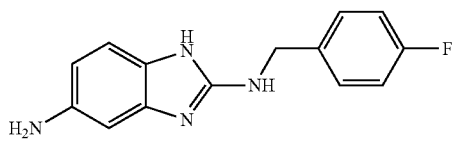 [SMILES: Nc1ccc2[nH]c(NCc3ccc(F)cc3)nc2c1] |

29 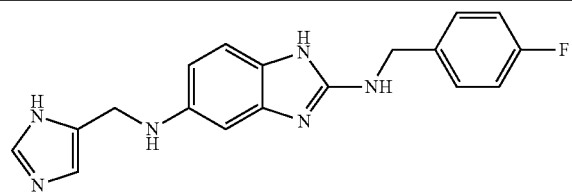
30 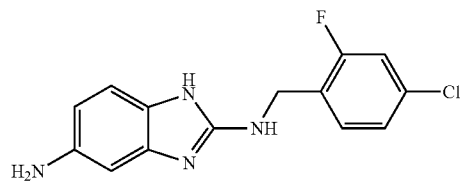
31 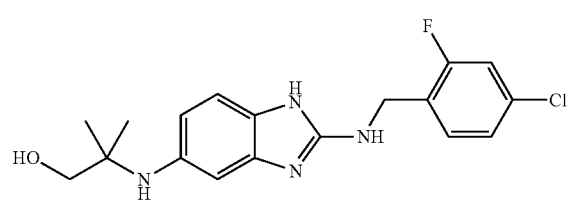 [SMILES: CC(C)(CO)Nc1ccc2[nH]c(NCc3ccc(Cl)cc3F)nc2c1]
32 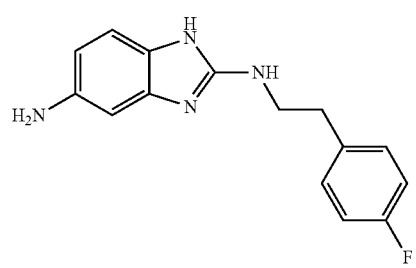 [SMILES: Nc1ccc2[nH]c(NCCc3ccc(F)cc3)nc2c1]
33 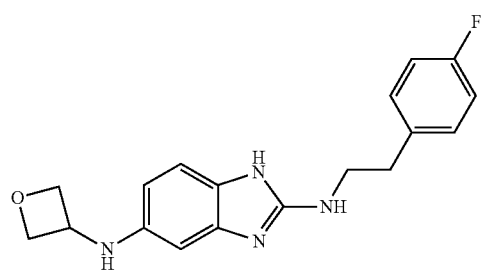 [SMILES: Fc1ccc(CCNc2nc3cc(NC4COC4)ccc3[nH]2)cc1]
34 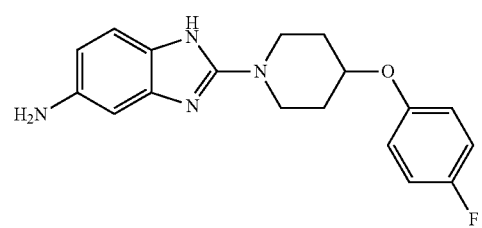 [SMILES: Nc1ccc2[nH]c(N3CCC(Oc4ccc(F)cc4)CC3)nc2c1]
35 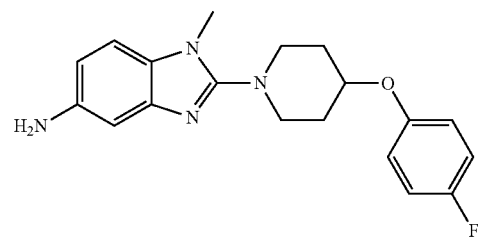 [SMILES: Cn1c(N2CCC(Oc3ccc(F)cc3)CC2)nc2cc(N)ccc21]

| | |
|---|---|
| 36 | 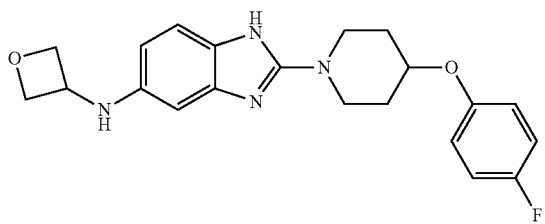 [SMILES: Fc1ccc(OC2CCN(c3nc4cc(NC5COC5)ccc4[nH]3)CC2)cc1] |
| 37 | 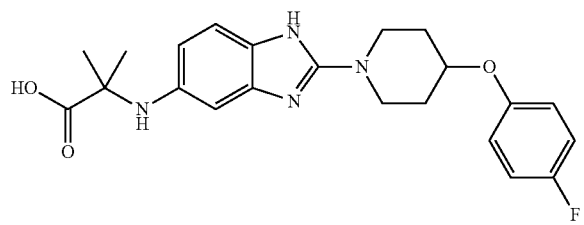 [SMILES: CC(C)(Nc1ccc2[nH]c(N3CCC(Oc4ccc(F)cc4)CC3)nc2c1)C(=O)O] |
| 38 | 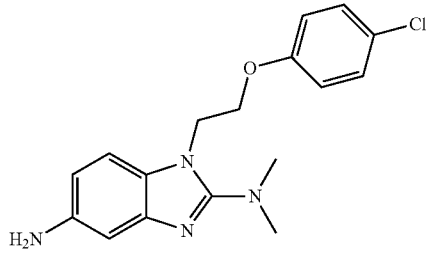 [SMILES: CN(C)c1nc2cc(N)ccc2n1CCOc1ccc(Cl)cc1] |
| 39 | 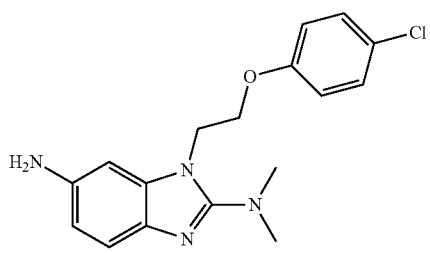 [SMILES: CN(C)c1nc2ccc(N)cc2n1CCOc1ccc(Cl)cc1] |
| 40 | 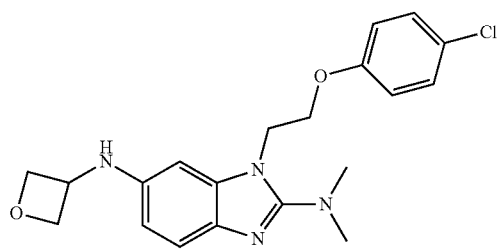 [SMILES: CN(C)c1nc2ccc(NC3COC3)cc2n1CCOc1ccc(Cl)cc1] |
| 41 | 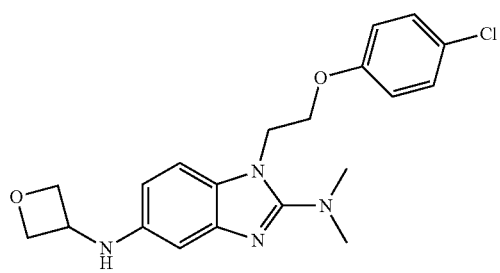 [SMILES: CN(C)c1nc2cc(NC3COC3)ccc2n1CCOc1ccc(Cl)cc1] |

42 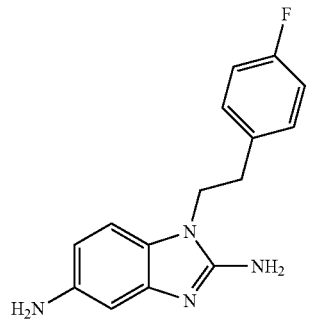 [SMILES: Nc1ccc2c(c1)nc(N)n2CCc1ccc(F)cc1]
43 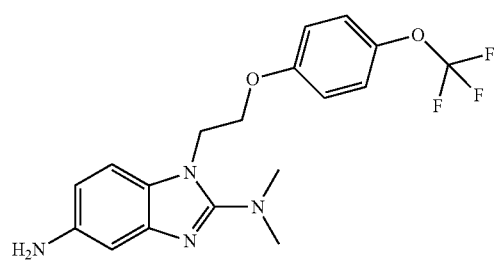 [SMILES: CN(C)c1nc2cc(N)ccc2n1CCOc1ccc(OC(F)(F)F)cc1]
44 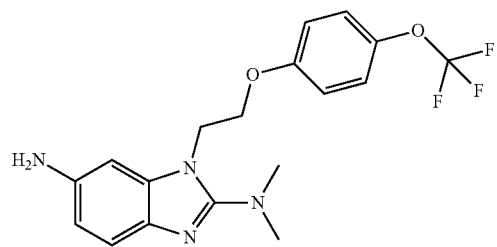 [SMILES: CN(C)c1nc2ccc(N)cc2n1CCOc1ccc(OC(F)(F)F)cc1]
45 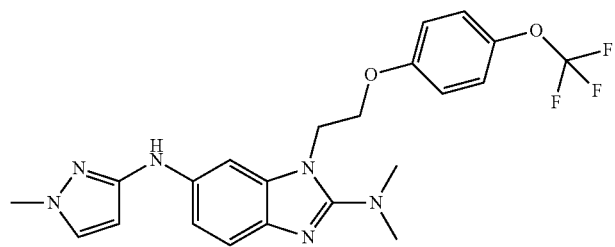 [SMILES: CN(C)c1nc2ccc(Nc3ccn(C)n3)cc2n1CCOc1ccc(OC(F)(F)F)cc1]
46 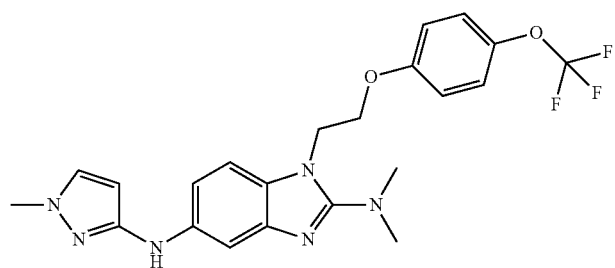 [SMILES: CN(C)c1nc2cc(Nc3ccn(C)n3)ccc2n1CCOc1ccc(OC(F)(F)F)cc1]

-continued
| | |
|---|---|
| 47 | 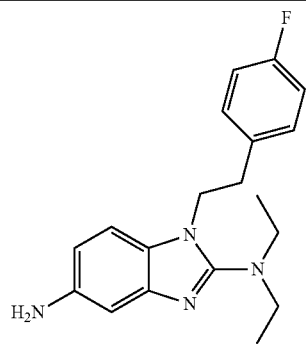 |
| 48 | 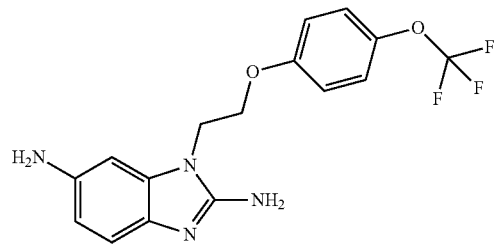 [SMILES: Nc1ccc2nc(N)n(CCOc3ccc(OC(F)(F)F)cc3)c2c1] |
| 49 | 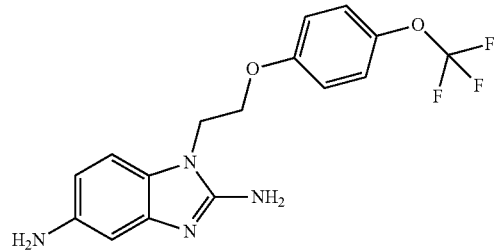 [SMILES: Nc1ccc2c(c1)nc(N)n2CCOc1ccc(OC(F)(F)F)cc1] |
| 50 | 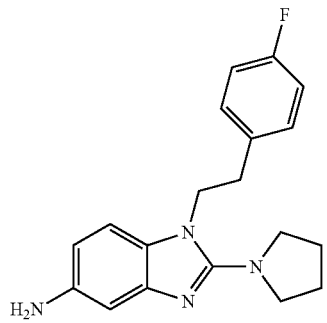 [SMILES: Nc1ccc2c(c1)nc(N1CCCC1)n2CCc1ccc(F)cc1] |
| 51 | 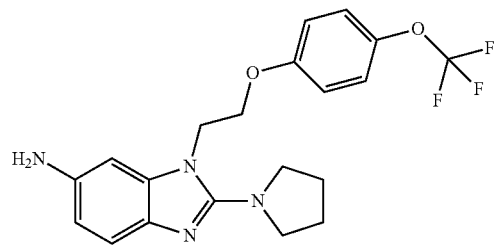 [SMILES: Nc1ccc2nc(N3CCCC3)n(CCOc3ccc(OC(F)(F)F)cc3)c2c1] |
| 52 | 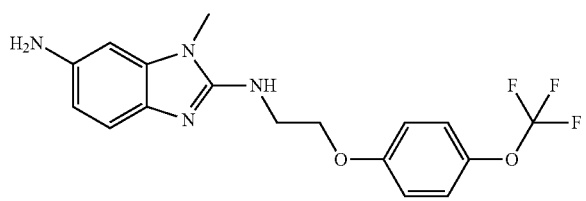 [SMILES: Cn1c(NCCOc2ccc(OC(F)(F)F)cc2)nc2ccc(N)cc21] |

53 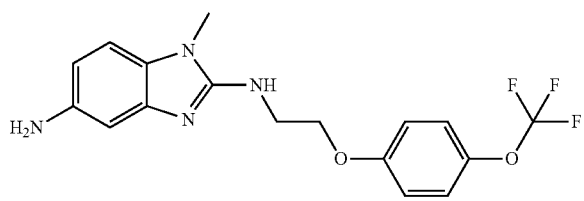 [SMILES: Cn1c(NCCOc2ccc(OC(F)(F)F)cc2)nc2cc(N)ccc21]
54 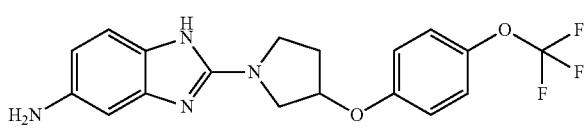 [SMILES: Nc1ccc2[nH]c(N3CCC(Oc4ccc(OC(F)(F)F)cc4)C3)nc2c1]
55 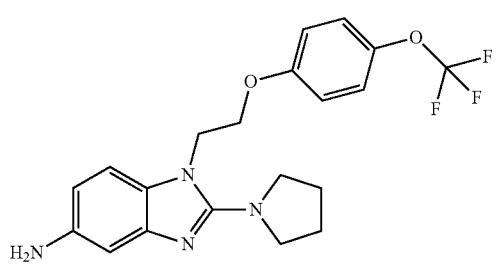 [SMILES: Nc1ccc2c(c1)nc(N1CCCC1)n2CCOc1ccc(OC(F)(F)F)cc1]
56 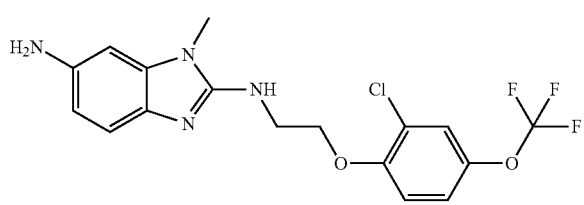 [SMILES: Cn1c(NCCOc2ccc(OC(F)(F)F)cc2Cl)nc2ccc(N)cc21]
57 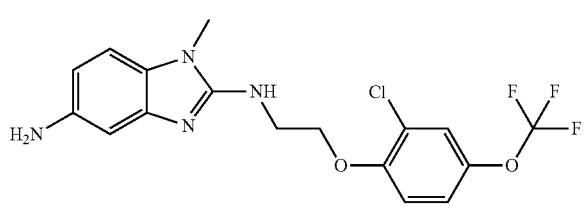 [SMILES: Cn1c(NCCOc2ccc(OC(F)(F)F)cc2Cl)nc2cc(N)ccc21]
58 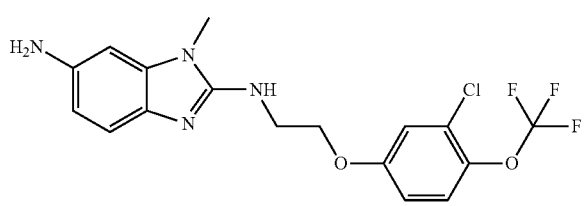 [SMILES: Cn1c(NCCOc2ccc(OC(F)(F)F)c(Cl)c2)nc2ccc(N)cc21]
59 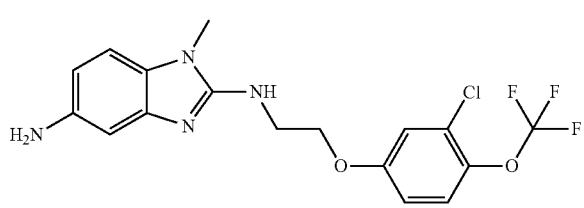 [SMILES: Cn1c(NCCOc2ccc(OC(F)(F)F)c(Cl)c2)nc2cc(N)ccc21]
60 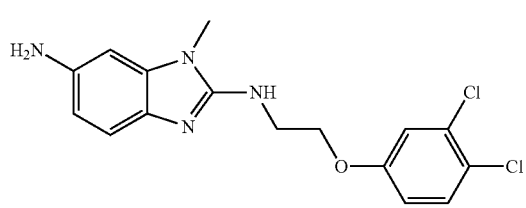 [SMILES: Cn1c(NCCOc2ccc(Cl)c(Cl)c2)nc2ccc(N)cc21]

-continued
61 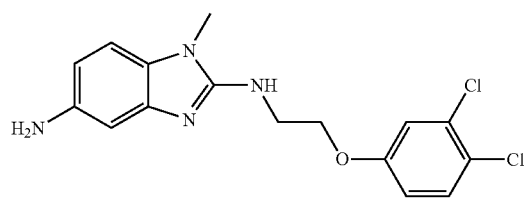 [SMILES: Cn1c(NCCOc2ccc(Cl)c(Cl)c2)nc2cc(N)ccc21]
62 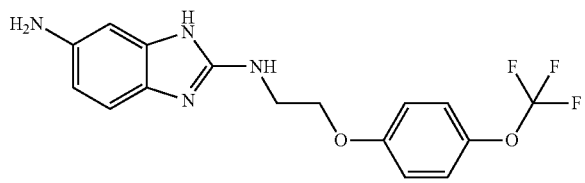 [SMILES: Nc1ccc2nc(NCCOc3ccc(OC(F)(F)F)cc3)[nH]c2c1]
63 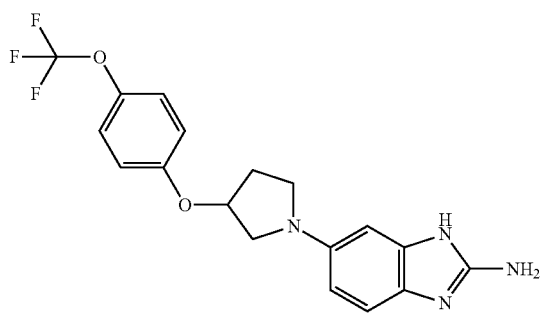 [SMILES: Nc1nc2ccc(N3CCC(Oc4ccc(OC(F)(F)F)cc4)C3)cc2[nH]1]
64 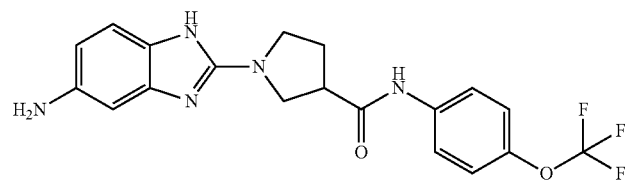 [SMILES: Nc1ccc2[nH]c(N3CCC(C(=O)Nc4ccc(OC(F)(F)F)cc4)C3)nc2c1]
65 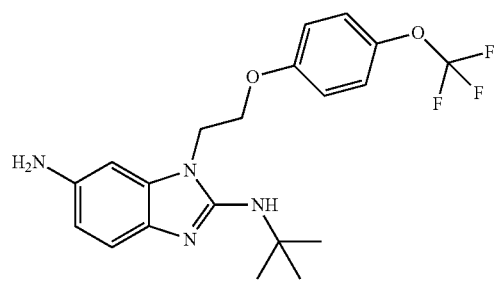 [SMILES: CC(C)(C)Nc1nc2ccc(N)cc2n1CCOc1ccc(OC(F)(F)F)cc1]
66 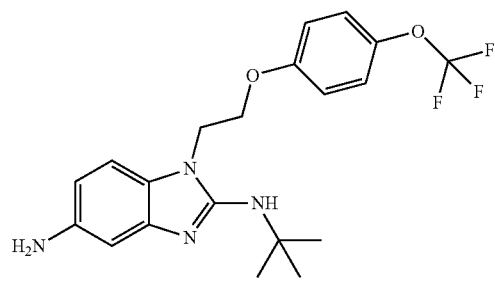 [SMILES: CC(C)(C)Nc1nc2cc(N)ccc2n1CCOc1ccc(OC(F)(F)F)cc1]

-continued
| | |
|---|---|
| 67 | 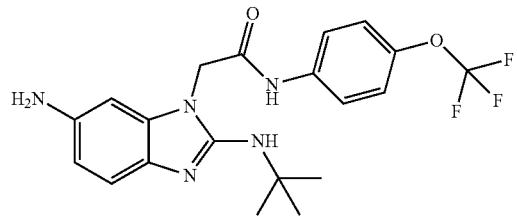 [SMILES: CC(C)(C)Nc1nc2ccc(N)cc2n1CC(=O)Nc1ccc(OC(F)(F)F)cc1] |
| 68 | 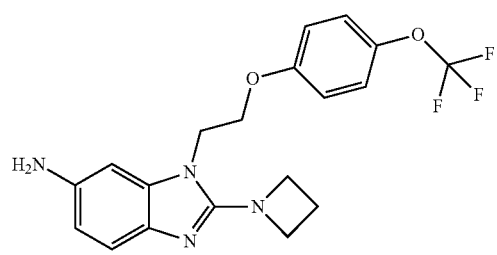 [SMILES: Nc1ccc2nc(N3CCC3)n(CCOc3ccc(OC(F)(F)F)cc3)c2c1] |
| 69 | 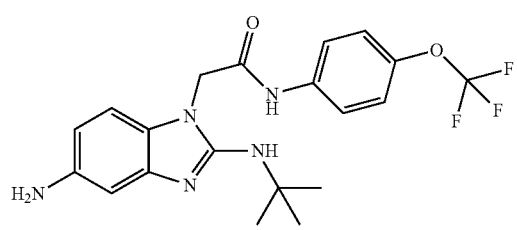 [SMILES: CC(C)(C)Nc1nc2cc(N)ccc2n1CC(=O)Nc1ccc(OC(F)(F)F)cc1] |
| 70 | 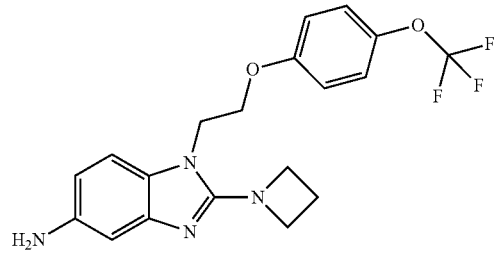 [SMILES: Nc1ccc2c(c1)nc(N1CCC1)n2CCOc1ccc(OC(F)(F)F)cc1] |
| 71 | 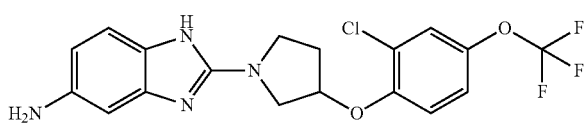 [SMILES: Nc1ccc2[nH]c(N3CCC(Oc4ccc(OC(F)(F)F)cc4Cl)C3)nc2c1] |
| 72 | 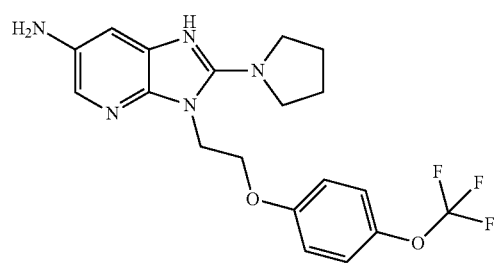 |
| 73 | 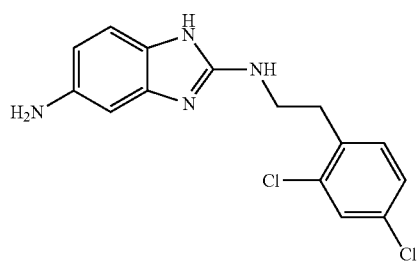 [SMILES: Nc1ccc2[nH]c(NCCc3ccc(Cl)cc3Cl)nc2c1] |

| | |
|---|---|
| 74 | 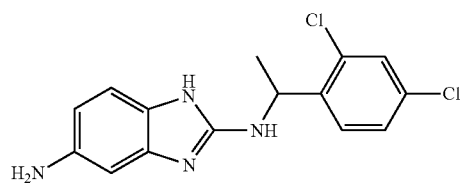 [SMILES: CC(Nc1nc2cc(N)ccc2[nH]1)c1ccc(Cl)cc1Cl] |
| 75 | 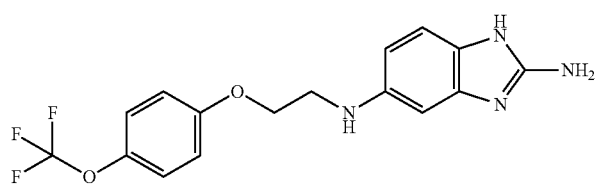 [SMILES: Nc1nc2cc(NCCOc3ccc(OC(F)(F)F)cc3)ccc2[nH]1] |
| 76 | 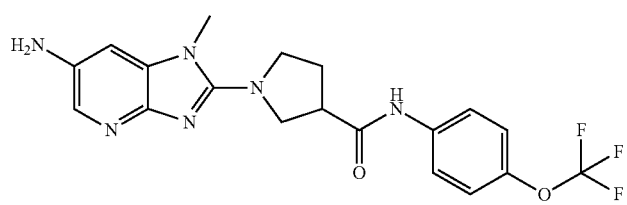 [SMILES: Cn1c(N2CCC(C(=O)Nc3ccc(OC(F)(F)F)cc3)C2)nc2ncc(N)cc21] |
| 77 | 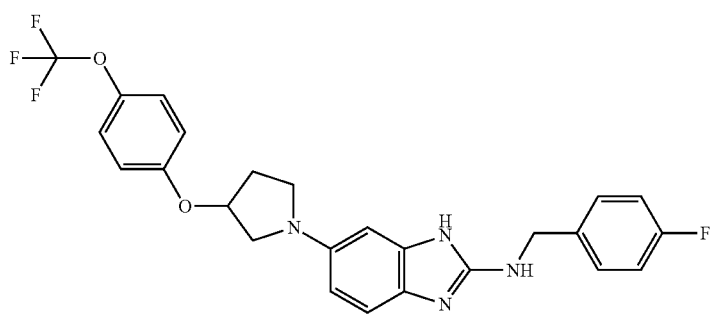 [SMILES: Fc1ccc(CNc2nc3ccc(N4CCC(Oc5ccc(OC(F)(F)F)cc5)C4)cc3[nH]2)cc1] |
| 78 | 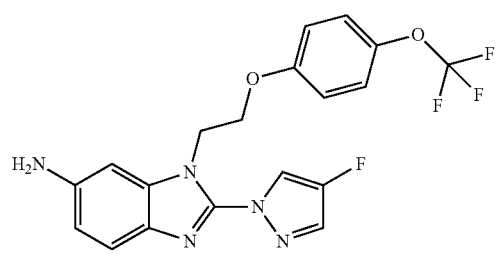 [SMILES: Nc1ccc2nc(-n3cc(F)cn3)n(CCOc3ccc(OC(F)(F)F)cc3)c2c1] |
| 79 | 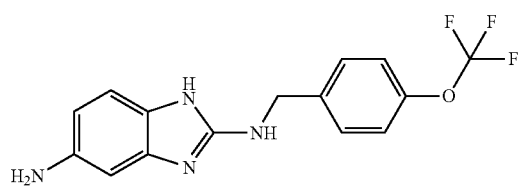 |
| 80 | 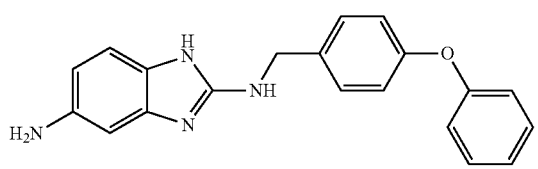 [SMILES: Nc1ccc2[nH]c(NCc3ccc(Oc4ccccc4)cc3)nc2c1] |

| | |
|---|---|
| 81 | 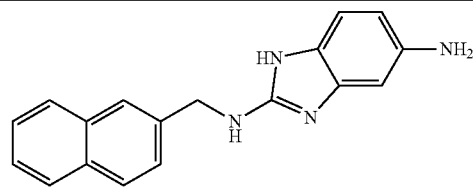 |
| 82 | 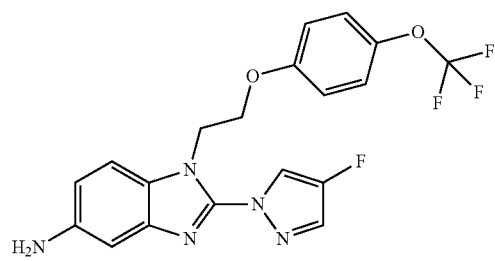 [SMILES: Nc1ccc2c(c1)nc(-n1cc(F)cn1)n2CCOc1ccc(OC(F)(F)F)cc1] |
| 83 | 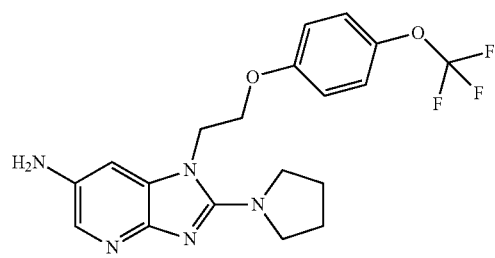 [SMILES: Nc1cnc2nc(N3CCCC3)n(CCOc3ccc(OC(F)(F)F)cc3)c2c1] |
| 84 | 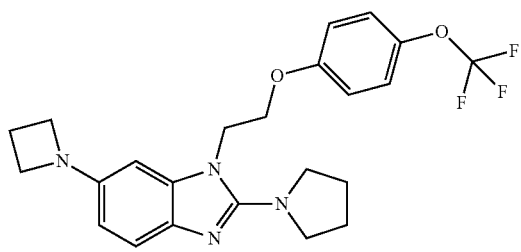 [SMILES: FC(F)(F)Oc1ccc(OCCn2c(N3CCCC3)nc3ccc(N4CCC4)cc32)cc1] |
| 85 | 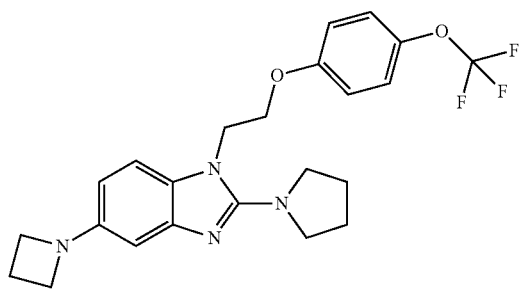 [SMILES: FC(F)(F)Oc1ccc(OCCn2c(N3CCCC3)nc3cc(N4CCC4)ccc32)cc1] |
| 86 | 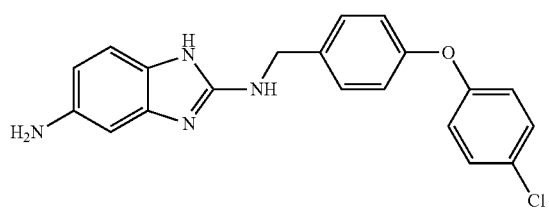 |
| 87 | 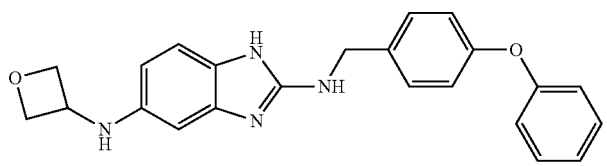 [SMILES: c1ccc(Oc2ccc(CNc3nc4cc(NC5COC5)ccc4[nH]3)cc2)cc1] |

88 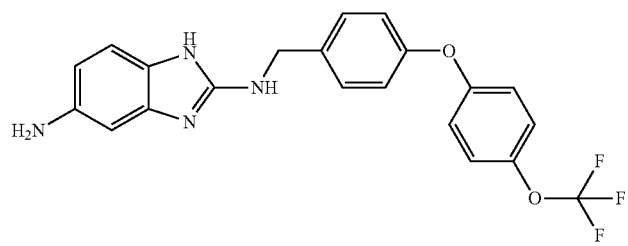 [SMILES: Nc1ccc2[nH]c(NCc3ccc(Oc4ccc(OC(F)(F)F)cc4)cc3)nc2c1]
89 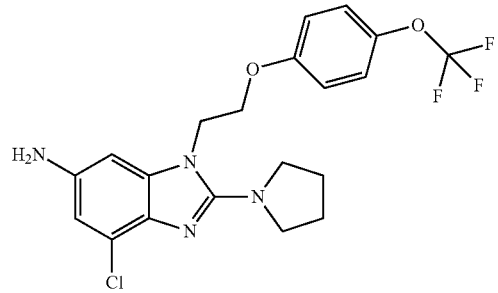 [SMILES: Nc1cc(Cl)c2nc(N3CCCC3)n(CCOc3ccc(OC(F)(F)F)cc3)c2c1]
90 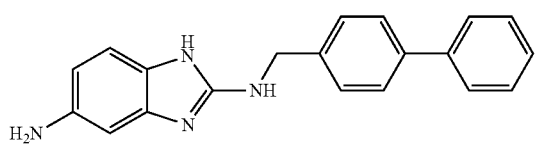 [SMILES: Nc1ccc2[nH]c(NCc3ccc(-c4ccccc4)cc3)nc2c1]
91 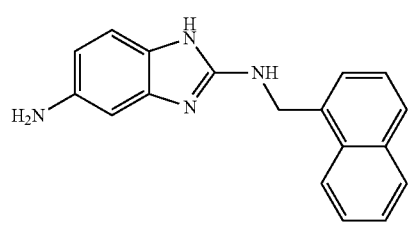 [SMILES: Nc1ccc2[nH]c(NCc3cccc4ccccc34)nc2c1]
92 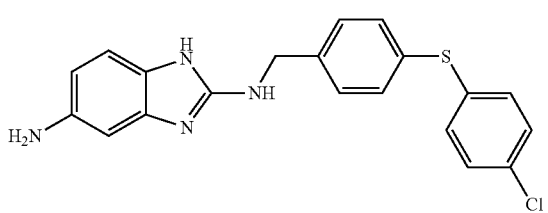 [SMILES: Nc1ccc2[nH]c(NCc3ccc(Sc4ccc(Cl)cc4)cc3)nc2c1]
93 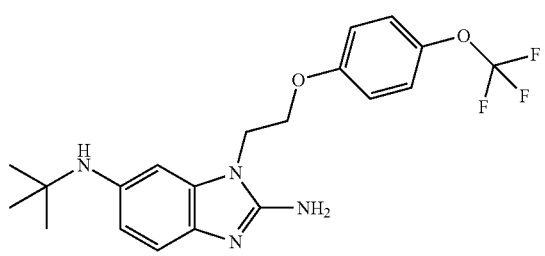 [SMILES: CC(C)(C)Nc1ccc2nc(N)n(CCOc3ccc(OC(F)(F)F)cc3)c2c1]
94 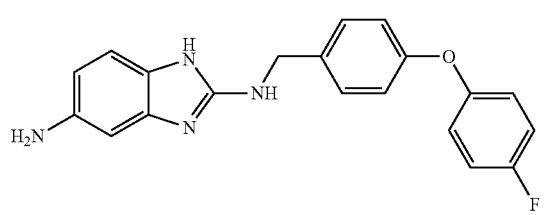 [SMILES: Nc1ccc2[nH]c(NCc3ccc(Oc4ccc(F)cc4)cc3)nc2c1]

-continued
| | |
|---|---|
| 95 | 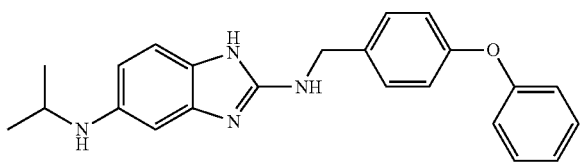 [SMILES: CC(C)Nc1ccc2[nH]c(NCc3ccc(Oc4ccccc4)cc3)nc2c1] |
| 96 | 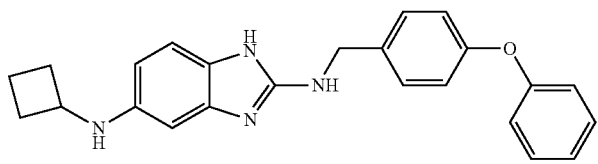 [SMILES: c1ccc(Oc2ccc(CNc3nc4cc(NC5CCC5)ccc4[nH]3)cc2)cc1] |
| 97 | 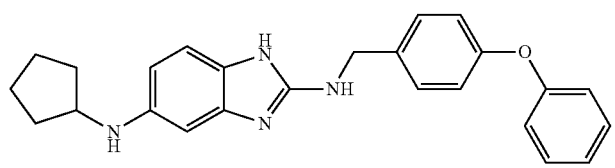 [SMILES: c1ccc(Oc2ccc(CNc3nc4cc(NC5CCCC5)ccc4[nH]3)cc2)cc1] |
| 98 | 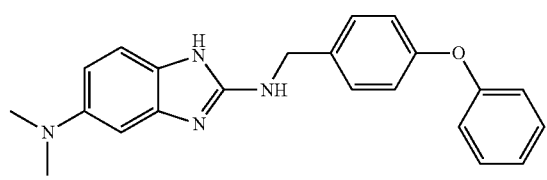 [SMILES: CN(C)c1ccc2[nH]c(NCc3ccc(Oc4ccccc4)cc3)nc2c1] |
| 99 | 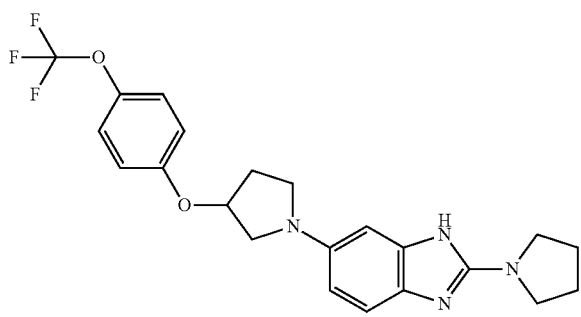 [SMILES: FC(F)(F)Oc1ccc(OC2CCN(c3ccc4nc(N5CCCC5)[nH]c4c3)C2)cc1] |
| 100 | 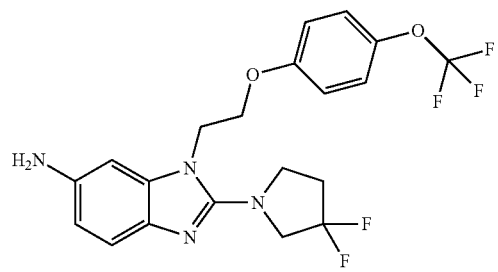 [SMILES: Nc1ccc2nc(N3CCC(F)(F)C3)n(CCOc3ccc(OC(F)(F)F)cc3)c2c1] |
| 101 | 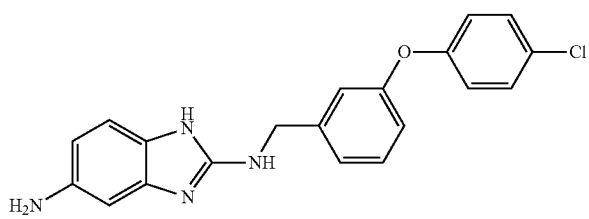 [SMILES: Nc1ccc2[nH]c(NCc3cccc(Oc4ccc(Cl)cc4)c3)nc2c1] |

| | |
|---|---|
| 102 | 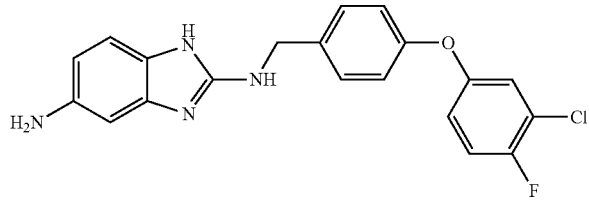 [SMILES: Nc1ccc2[nH]c(NCc3ccc(Oc4ccc(F)c(Cl)c4)cc3)nc2c1] |
| 103 | 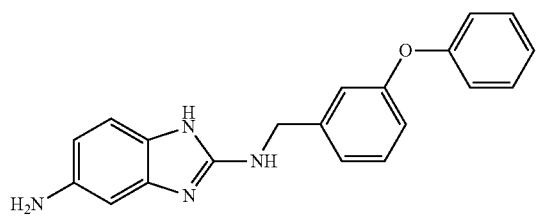 [SMILES: Nc1ccc2[nH]c(NCc3cccc(Oc4ccccc4)c3)nc2c1] |
| 104 | 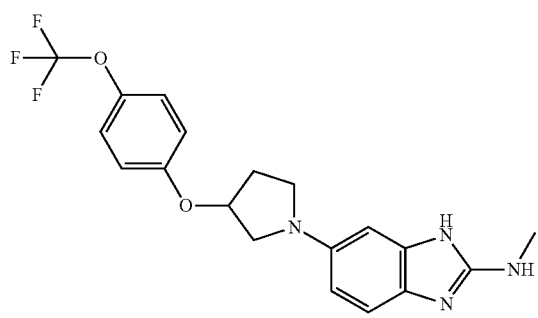 [SMILES: CNc1nc2ccc(N3CCC(Oc4ccc(OC(F)(F)F)cc4)C3)cc2[nH]1] |
| 105 | 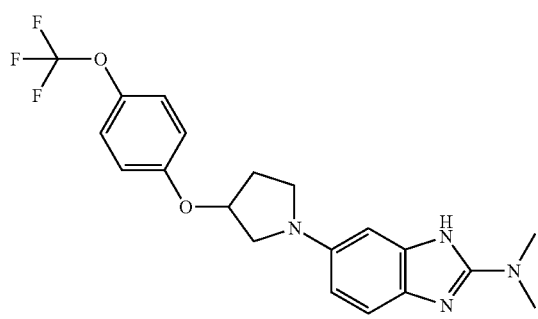 [SMILES: CN(C)c1nc2ccc(N3CCC(Oc4ccc(OC(F)(F)F)cc4)C3)cc2[nH]1] |
| 106 | 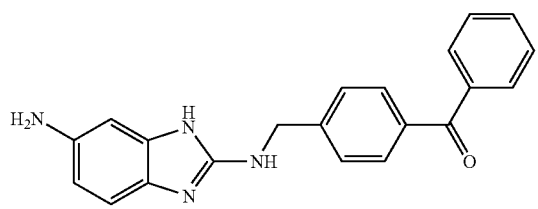 [SMILES: Nc1ccc2nc(NCc3ccc(C(=O)c4ccccc4)cc3)[nH]c2c1] |
| 107 | 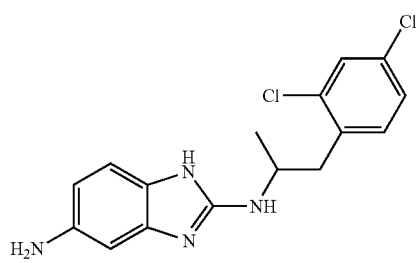 [SMILES: CC(Cc1ccc(Cl)cc1Cl)Nc1nc2cc(N)ccc2[nH]1] |

-continued
108
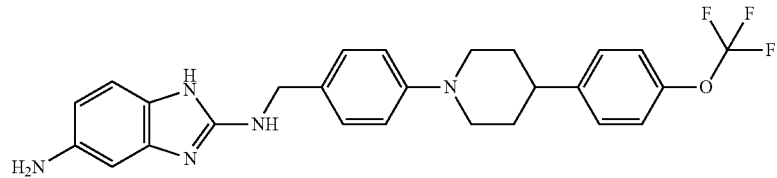 [SMILES: Nc1ccc2[nH]c(NCc3ccc(N4CCC(c5ccc(OC(F)(F)F)cc5)CC4)cc3)nc2c1]
109
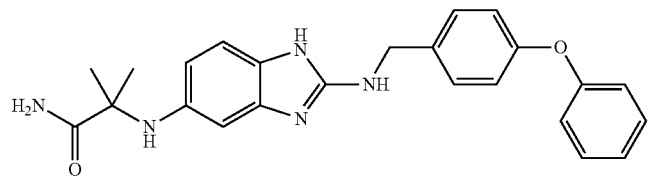 [SMILES: CC(C)(Nc1ccc2[nH]c(NCc3ccc(Oc4ccccc4)cc3)nc2c1)C(N)=O]
110
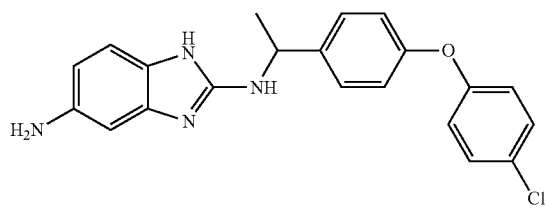
111
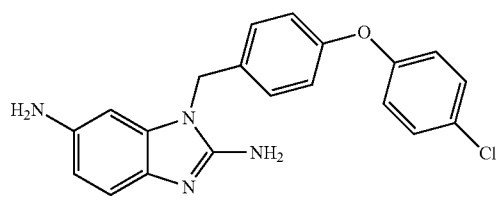 [SMILES: Nc1ccc2nc(N)n(Cc3ccc(Oc4ccc(Cl)cc4)cc3)c2c1]
112
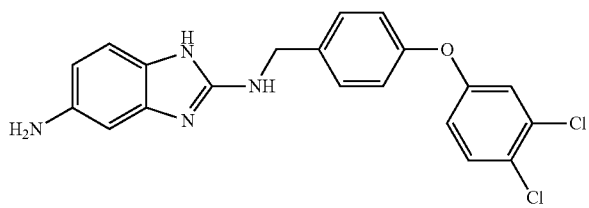 [SMILES: Nc1ccc2[nH]c(NCc3ccc(Oc4ccc(Cl)c(Cl)c4)cc3)nc2c1]
113
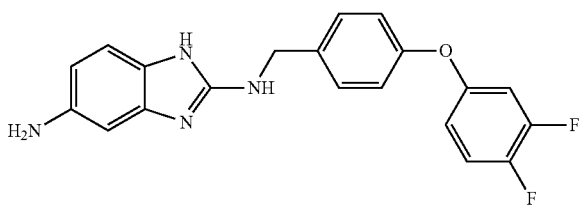 [SMILES: Nc1ccc2[nH]c(NCc3ccc(Oc4ccc(F)c(F)c4)cc3)nc2c1]
114
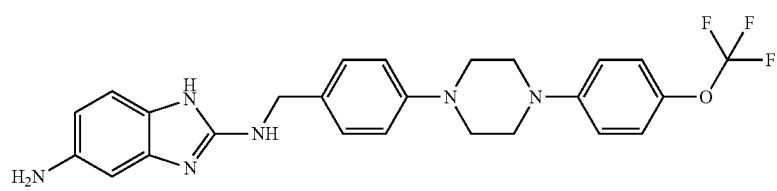 [SMILES: Nc1ccc2[nH]c(NCc3ccc(N4CCN(c5ccc(OC(F)(F)F)cc5)CC4)cc3)nc2c1]
115
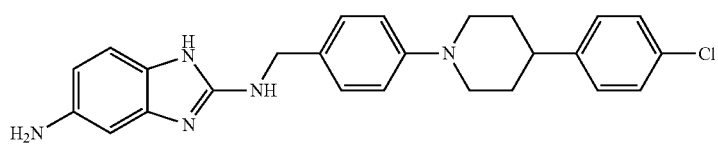 [SMILES: Nc1ccc2[nH]c(NCc3ccc(N4CCC(c5ccc(Cl)cc5)CC4)cc3)nc2c1]

-continued
116
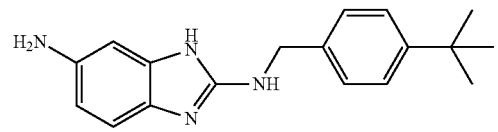 [SMILES: CC(C)(C)c1ccc(CNc2nc3ccc(N)cc3[nH]2)cc1]
117
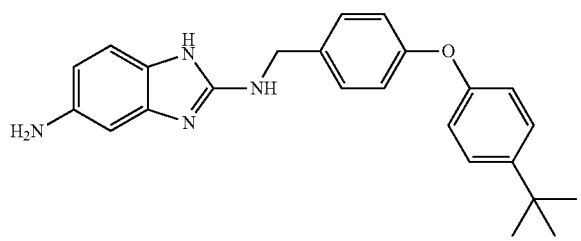 [SMILES: CC(C)(C)c1ccc(Oc2ccc(CNc3nc4cc(N)ccc4[nH]3)cc2)cc1]
118
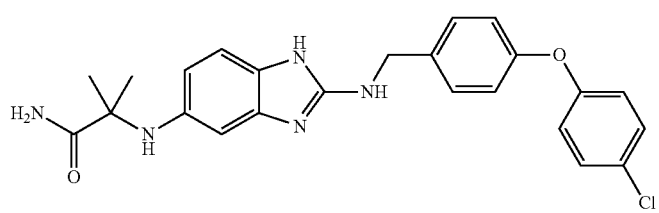 [SMILES: CC(C)(Nc1ccc2[nH]c(NCc3ccc(Oc4ccc(Cl)cc4)cc3)nc2c1)C(N)=O]
119
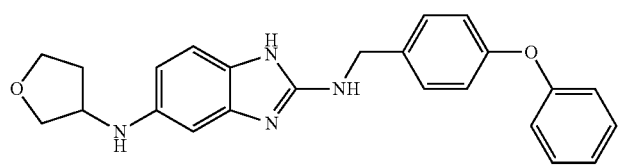 [SMILES: c1ccc(Oc2ccc(CNc3nc4cc(NC5CCOC5)ccc4[nH]3)cc2)cc1]
120
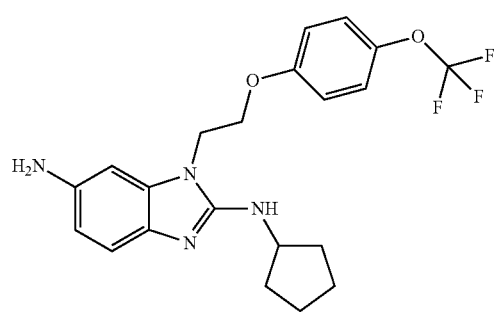 [SMILES: Nc1ccc2nc(NC3CCCC3)n(CCOc3ccc(OC(F)(F)F)cc3)c2c1]
121
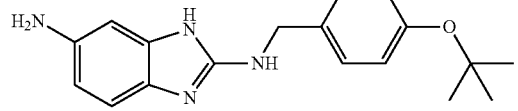
122
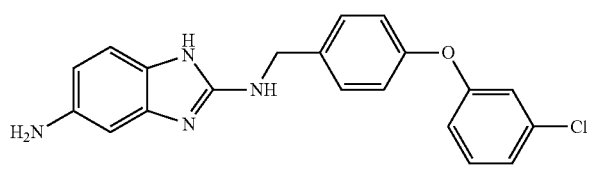 [SMILES: Nc1ccc2[nH]c(NCc3ccc(Oc4cccc(Cl)c4)cc3)nc2c1]
123
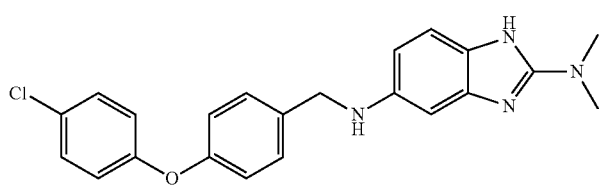 [SMILES: CN(C)c1nc2cc(NCc3ccc(Oc4ccc(Cl)cc4)cc3)ccc2[nH]1]

-continued
| 124 | 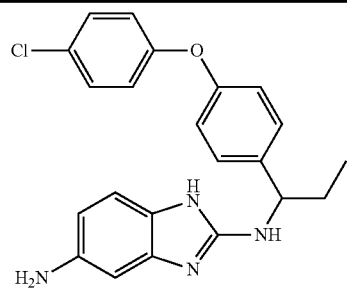 |
| 125 | 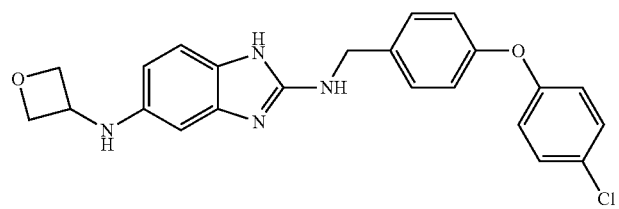 [SMILES: Clc1ccc(Oc2ccc(CNc3nc4cc(NC5COC5)ccc4[nH]3)cc2)cc1] |
| 126 | 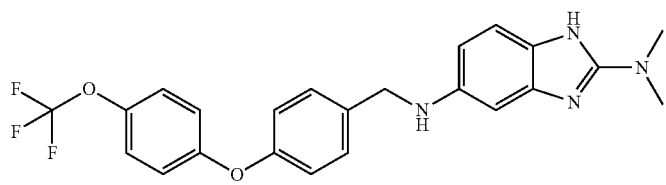 [SMILES: CN(C)c1nc2cc(NCc3ccc(Oc4ccc(OC(F)(F)F)cc4)cc3)ccc2[nH]1] |
| 127 | 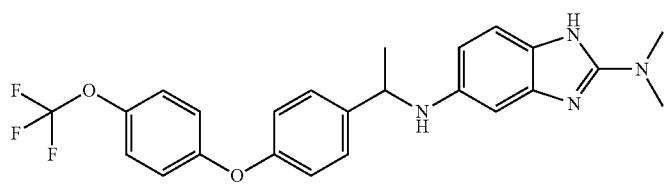 |
| 128 | 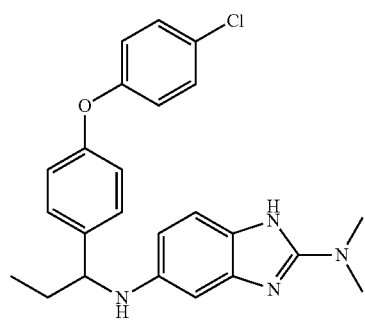 [SMILES: CCC(Nc1ccc2[nH]c(N(C)C)nc2c1)c1ccc(Oc2ccc(Cl)cc2)cc1] |
| 129 | 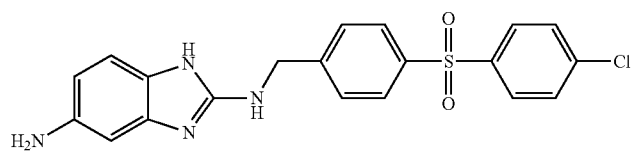 |
| 130 | 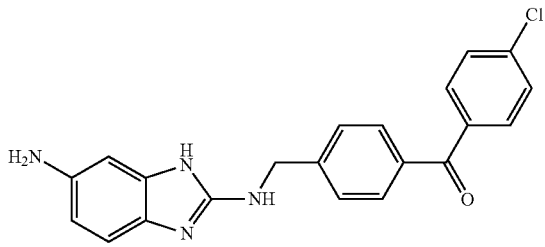 [SMILES: Nc1ccc2nc(NCc3ccc(C(=O)c4ccc(Cl)cc4)cc3)[nH]c2c1] |

-continued
| | |
|---|---|
| 131 | 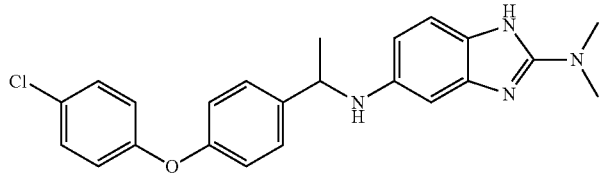 [SMILES: CC(Nc1ccc2[nH]c(N(C)C)nc2c1)c1ccc(Oc2ccc(Cl)cc2)cc1] |
| 132 | 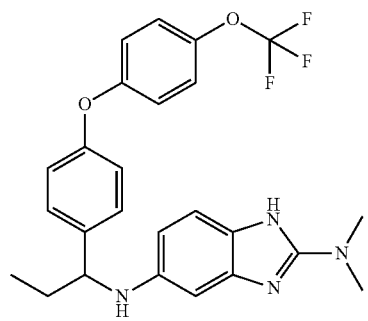 [SMILES: CCC(Nc1ccc2[nH]c(N(C)C)nc2c1)c1ccc(Oc2ccc(OC(F)(F)F)cc2)cc1] |
| 133 | 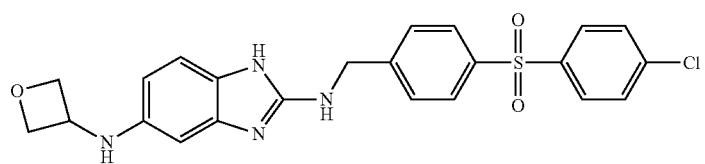 [SMILES: O=S(=O)(c1ccc(Cl)cc1)c1ccc(CNc2nc3cc(NC4COC4)ccc3[nH]2)cc1] |
| 134 | 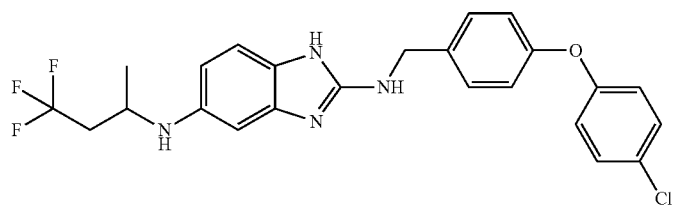 [SMILES: CC(CC(F)(F)F)Nc1ccc2[nH]c(NCc3ccc(Oc4ccc(Cl)cc4)cc3)nc2c1] |
| 135 | 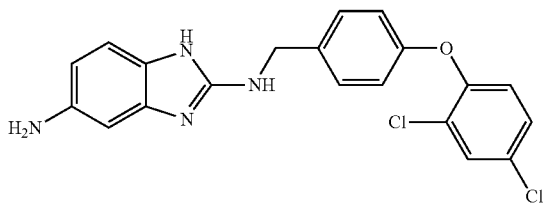 [SMILES: Nc1ccc2[nH]c(NCc3ccc(Oc4ccc(Cl)cc4Cl)cc3)nc2c1] |
| 136 | 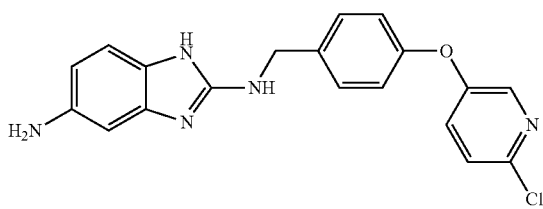 [SMILES: Nc1ccc2[nH]c(NCc3ccc(Oc4ccc(Cl)nc4)cc3)nc2c1] |
| 137 | 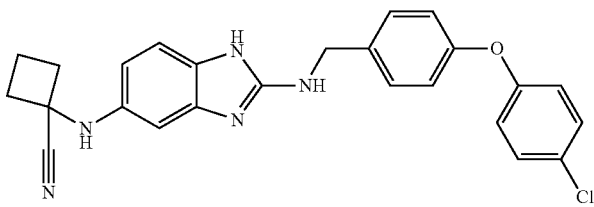 [SMILES: N#CC1(Nc2ccc3[nH]c(NCc4ccc(Oc5ccc(Cl)cc5)cc4)nc3c2)CCC1] |

138 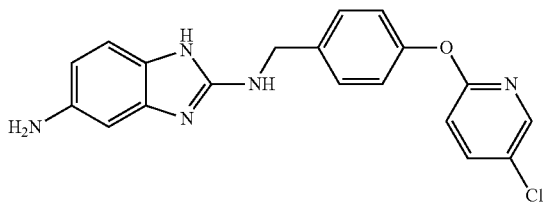 [SMILES: Nc1ccc2[nH]c(NCc3ccc(Oc4ccc(Cl)cn4)cc3)nc2c1]
139 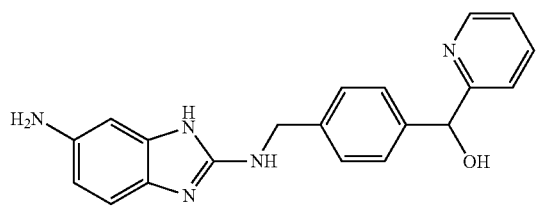 [SMILES: Nc1ccc2nc(NCc3ccc(C(O)c4ccccn4)cc3)[nH]c2c1]
140 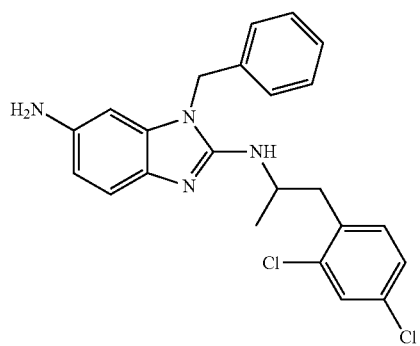 [SMILES: CC(Cc1ccc(Cl)cc1Cl)Nc1nc2ccc(N)cc2n1Cc1ccccc1]
141 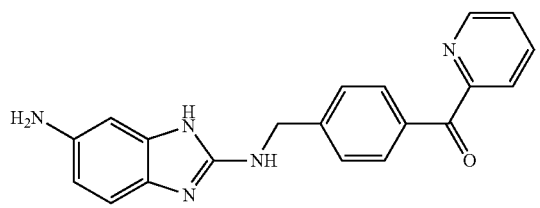 [SMILES: Nc1ccc2nc(NCc3ccc(C(=O)c4ccccn4)cc3)[nH]c2c1]
142 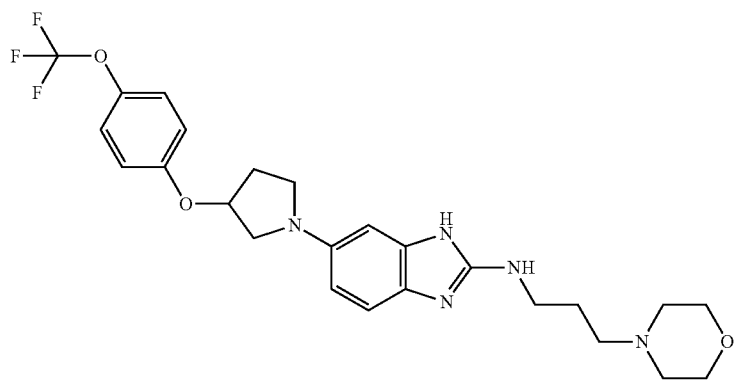 [SMILES: FC(F)(F)Oc1ccc(OC2CCN(c3ccc4nc(NCCCN5CCOCC5)[nH]c4c3)C2)cc1]

-continued
143 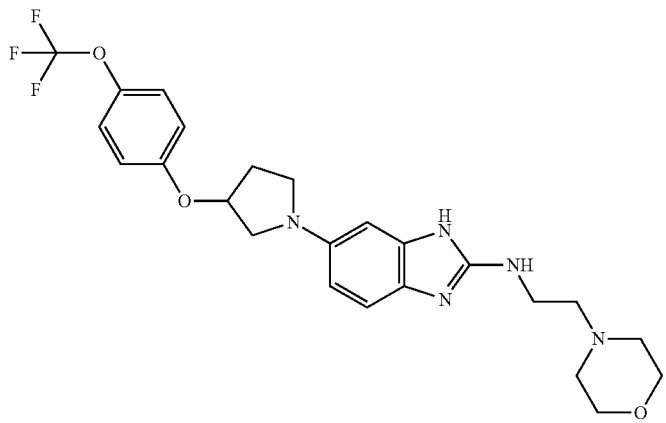 [SMILES: FC(F)(F)Oc1ccc(OC2CCN(c3ccc4nc(NCCN5CCOCC5)[nH]c4c3)C2)cc1]
144 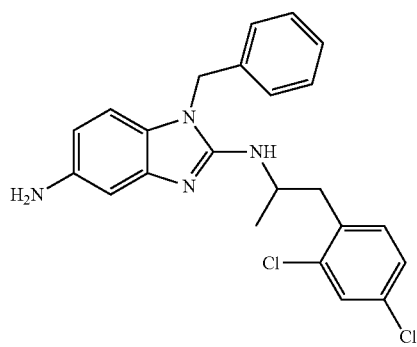 [SMILES: CC(Cc1ccc(Cl)cc1Cl)Nc1nc2cc(N)ccc2n1Cc1ccccc1]
145 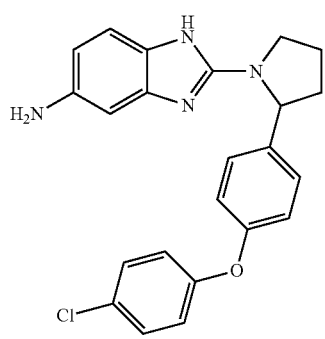 [SMILES: Nc1ccc2[nH]c(N3CCCC3c3ccc(Oc4ccc(Cl)cc4)cc3)nc2c1]
146 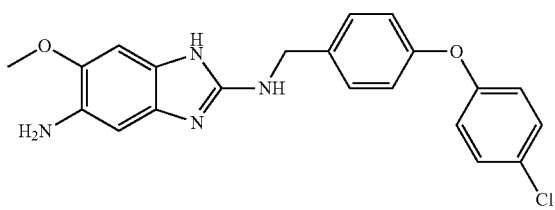 [SMILES: COc1cc2[nH]c(NCc3ccc(Oc4ccc(Cl)cc4)cc3)nc2cc1N]
147 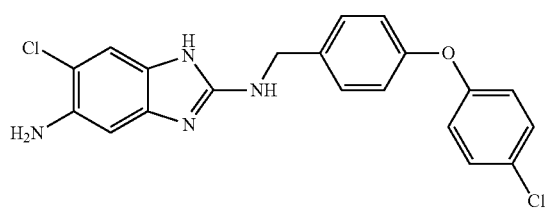 [SMILES: Nc1cc2nc(NCc3ccc(Oc4ccc(Cl)cc4)cc3)[nH]c2cc1Cl]

| 148 | 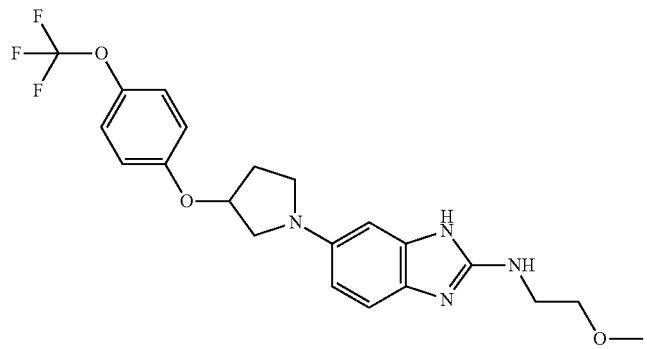 [SMILES: COCCNc1nc2ccc(N3CCC(Oc4ccc(OC(F)(F)F)cc4)C3)cc2[nH]1] |
| 149 | 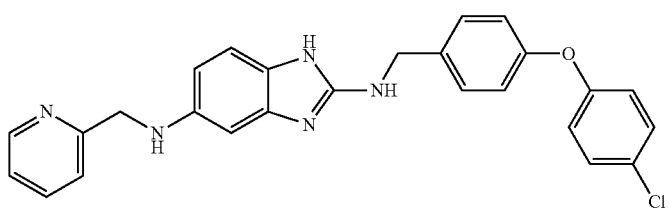 [SMILES: Clc1ccc(Oc2ccc(CNc3nc4cc(NCc5ccccn5)ccc4[nH]3)cc2)cc1] |
| 150 | 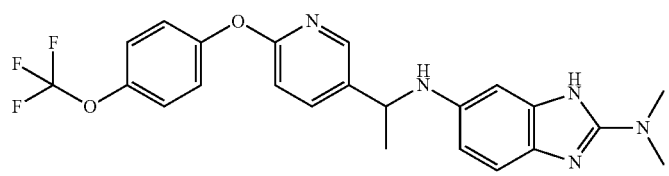 [SMILES: CC(Nc1ccc2nc(N(C)C)[nH]c2c1)c1ccc(Oc2ccc(OC(F)(F)F)cc2)nc1] |
| 151 | 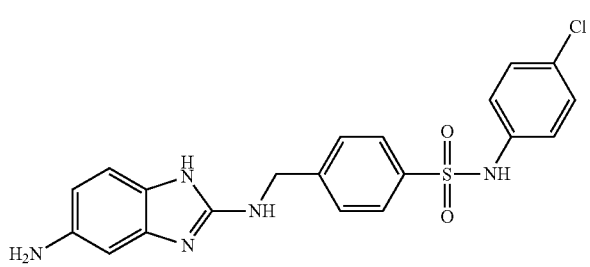 [SMILES: Nc1ccc2[nH]c(NCc3ccc(S(=O)(=O)Nc4ccc(Cl)cc4)cc3)nc2c1] |
| 152 | 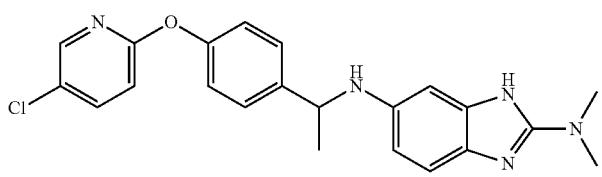 [SMILES: CC(Nc1ccc2nc(N(C)C)[nH]c2c1)c1ccc(Oc2ccc(Cl)cn2)cc1] |
| 153 | 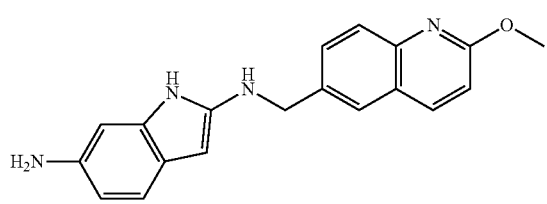 [SMILES: COc1ccc2cc(CNc3cc4ccc(N)cc4[nH]3)ccc2n1] |
| 154 | 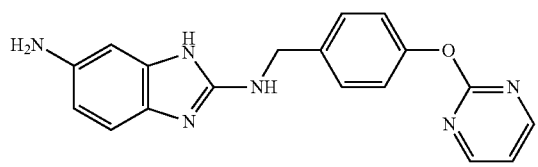 [SMILES: Nc1ccc2nc(NCc3ccc(Oc4ncccn4)cc3)[nH]c2c1] |

-continued
| | |
|---|---|
| 155 | 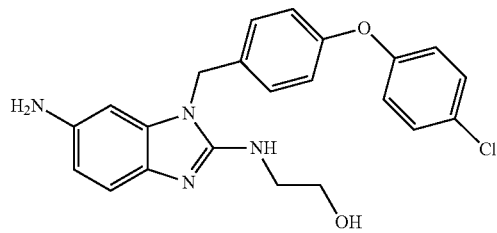 |
| 156 | 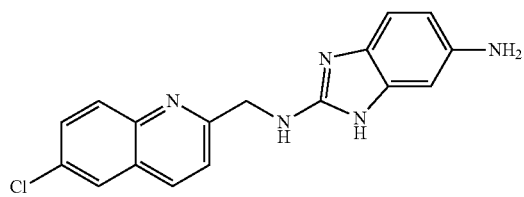 [SMILES: Nc1ccc2nc(NCc3ccc4cc(Cl)ccc4n3)[nH]c2c1] |
| 157 | 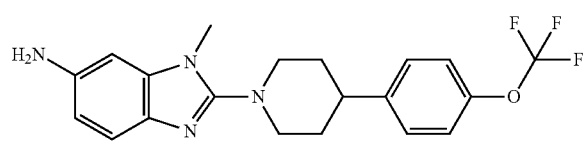 [SMILES: Cn1c(N2CCC(c3ccc(OC(F)(F)F)cc3)CC2)nc2ccc(N)cc21] |
| 158 | 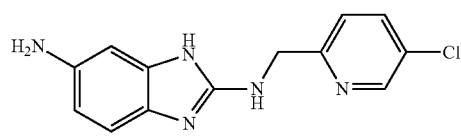 [SMILES: Nc1ccc2nc(NCc3ccc(Cl)cn3)[nH]c2c1] |
| 159 | 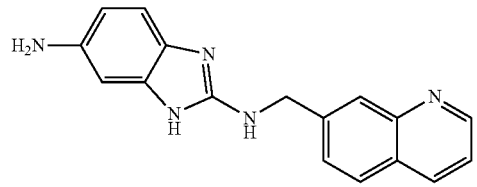 [SMILES: Nc1ccc2nc(NCc3ccc4cccnc4c3)[nH]c2c1] |
| 160 | 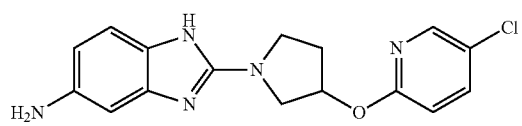 [SMILES: Nc1ccc2[nH]c(N3CCC(Oc4ccc(Cl)cn4)C3)nc2c1] |
| 161 | 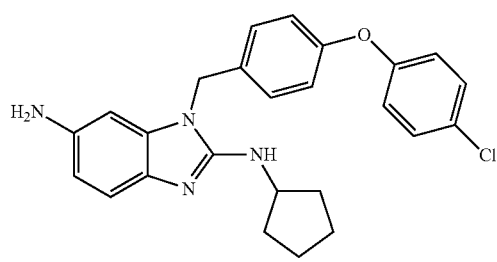 [SMILES: Nc1ccc2nc(NC3CCCC3)n(Cc3ccc(Oc4ccc(Cl)cc4)cc3)c2c1] |
| 162 | 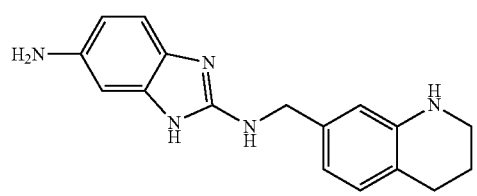 [SMILES: Nc1ccc2nc(NCc3ccc4c(c3)NCCC4)[nH]c2c1] |

-continued
163
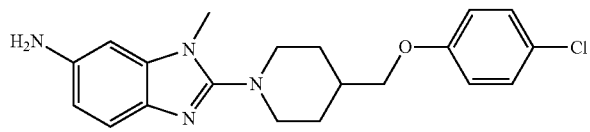 [SMILES: Cn1c(N2CCC(COc3ccc(Cl)cc3)CC2)nc2ccc(N)cc21]
164
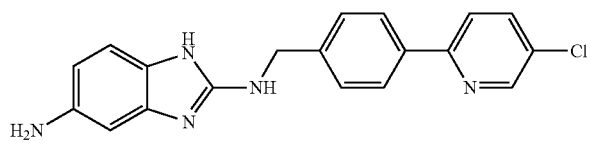
165
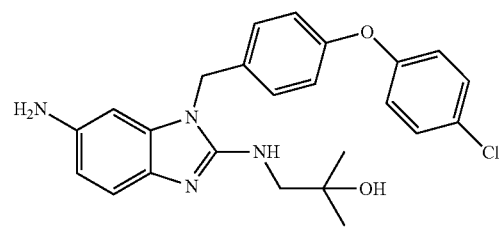 [SMILES: CC(C)(O)CNc1nc2ccc(N)cc2n1Cc1ccc(Oc2ccc(Cl)cc2)cc1]
166
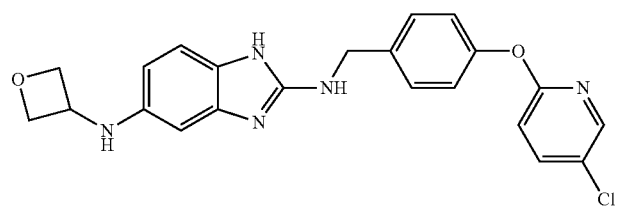 [SMILES: Clc1ccc(Oc2ccc(CNc3nc4cc(NC5COC5)ccc4[nH]3)cc2)nc1]
167
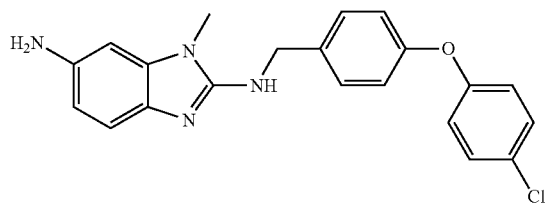
168
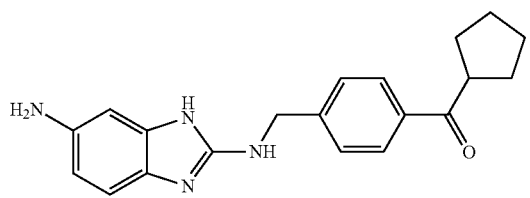 [SMILES: Nc1ccc2nc(NCc3ccc(C(=O)C4CCCC4)cc3)[nH]c2c1]
169
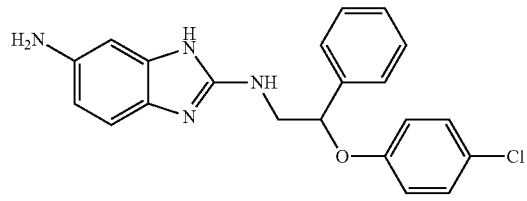 [SMILES: Nc1ccc2nc(NCC(Oc3ccc(Cl)cc3)c3ccccc3)[nH]c2c1]
170
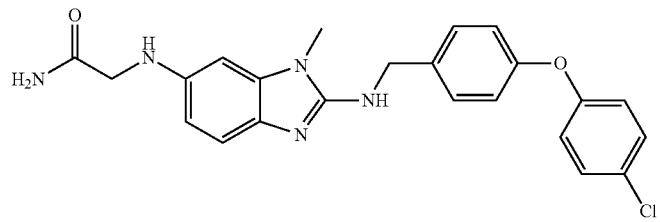 [SMILES: Cn1c(NCc2ccc(Oc3ccc(Cl)cc3)cc2)nc2ccc(NCC(N)=O)cc21]

-continued
| | |
|---|---|
| 171 | 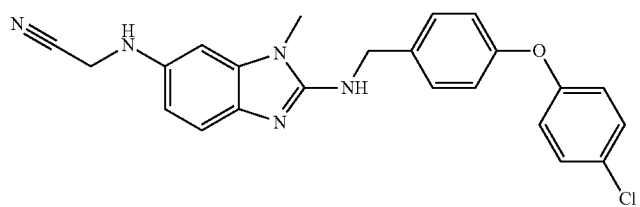 [SMILES: Cn1c(NCc2ccc(Oc3ccc(Cl)cc3)cc2)nc2ccc(NCC#N)cc21] |
| 172 | 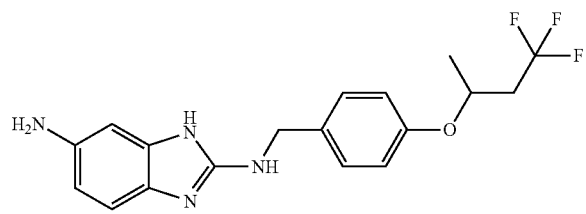 [SMILES: CC(CC(F)(F)F)Oc1ccc(CNc2nc3ccc(N)cc3[nH]2)cc1] |
| 173 | 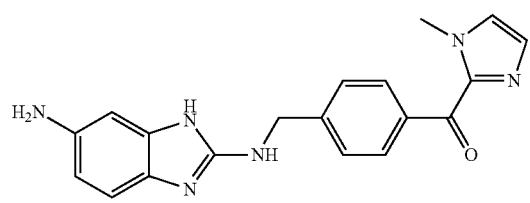 [SMILES: Cn1ccnc1C(=O)c1ccc(CNc2nc3ccc(N)cc3[nH]2)cc1] |
| 174 | 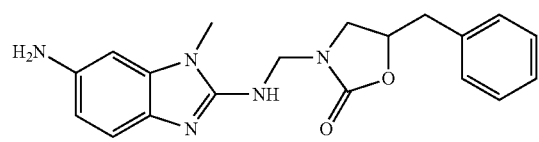 [SMILES: Cn1c(NCN2CC(Cc3ccccc3)OC2=O)nc2ccc(N)cc21] |
| 175 | 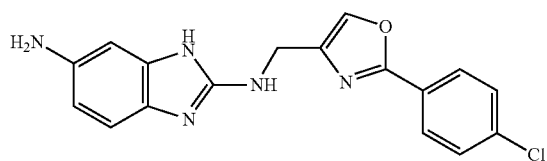 [SMILES: Nc1ccc2nc(NCc3coc(-c4ccc(Cl)cc4)n3)[nH]c2c1] |
| 176 | 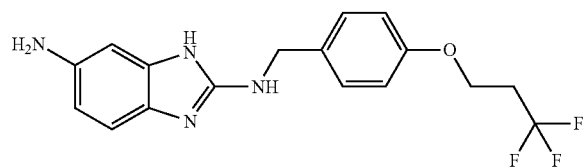 [SMILES: Nc1ccc2nc(NCc3ccc(OCCC(F)(F)F)cc3)[nH]c2c1] |
| 177 | 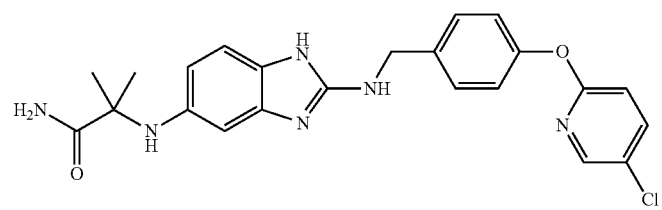 |
| 178 | 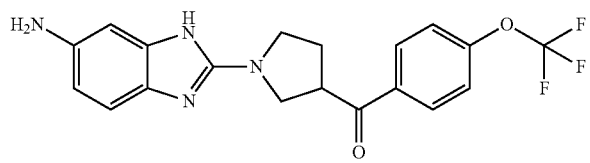 [SMILES: Nc1ccc2nc(N3CCC(C(=O)c4ccc(OC(F)(F)F)cc4)C3)[nH]c2c1] |

| | |
|---|---|
| 179 | 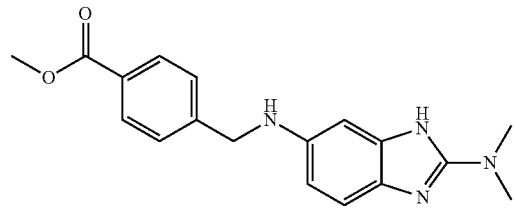 |
| 180 | 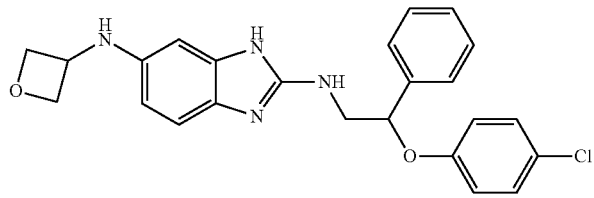 [SMILES: Clc1ccc(OC(CNc2nc3ccc(NC4COC4)cc3[nH]2)c2ccccc2)cc1] |
| 181 | 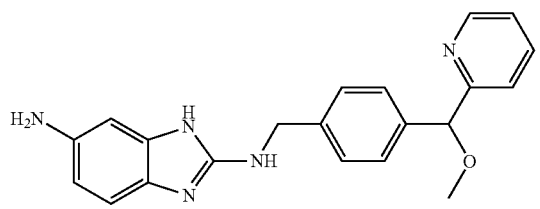 [SMILES: COC(c1ccc(CNc2nc3ccc(N)cc3[nH]2)cc1)c1ccccn1] |
| 182 | 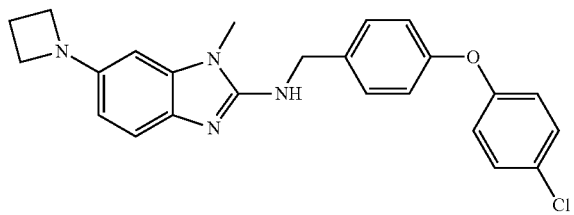 [SMILES: Cn1c(NCc2ccc(Oc3ccc(Cl)cc3)cc2)nc2ccc(N3CCC3)cc21] |
| 183 | 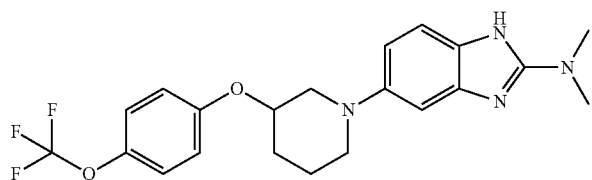 [SMILES: CN(C)c1nc2cc(N3CCCC(Oc4ccc(OC(F)(F)F)cc4)C3)ccc2[nH]1] |
| 184 | 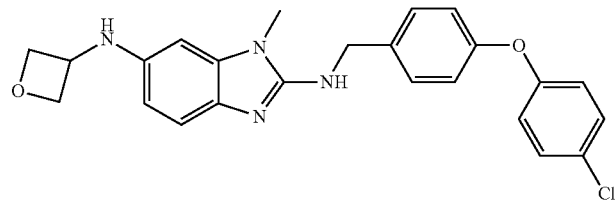 [SMILES: Cn1c(NCc2ccc(Oc3ccc(Cl)cc3)cc2)nc2ccc(NC3COC3)cc21] |
| 185 | 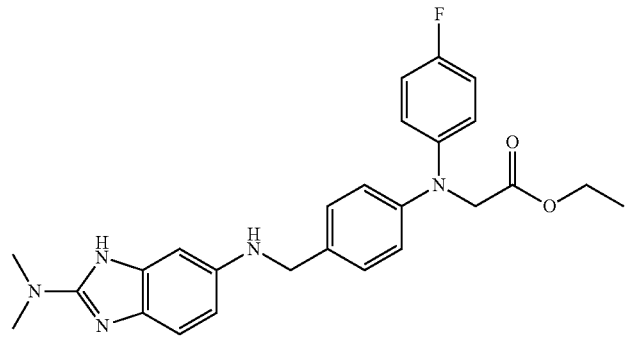 [SMILES: CCOC(=O)CN(c1ccc(F)cc1)c1ccc(CNc2ccc3nc(N(C)C)[nH]c3c2)cc1] |

186 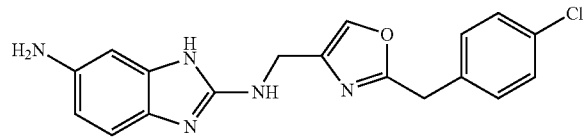 [SMILES: Nc1ccc2nc(NCc3coc(Cc4ccc(Cl)cc4)n3)[nH]c2c1]
187 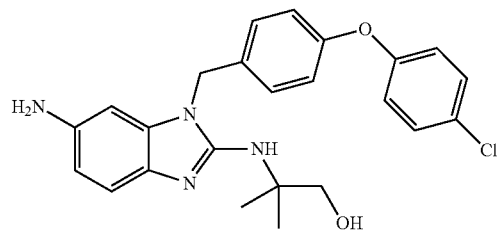 [SMILES: CC(C)(CO)Nc1nc2ccc(N)cc2n1Cc1ccc(Oc2ccc(Cl)cc2)cc1]
188 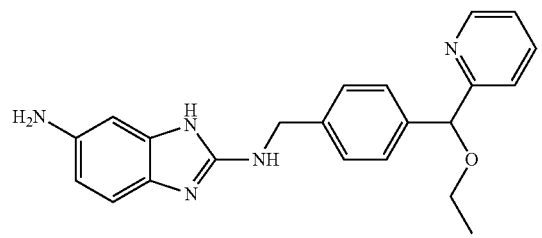 [SMILES: CCOC(c1ccc(CNc2nc3ccc(N)cc3[nH]2)cc1)c1ccccn1]
189 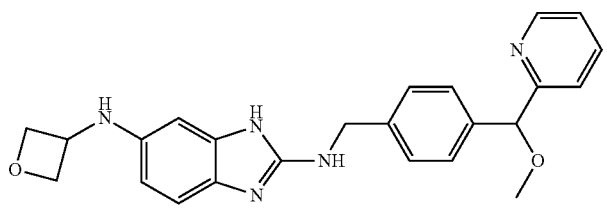 [SMILES: COC(c1ccc(CNc2nc3ccc(NC4COC4)cc3[nH]2)cc1)c1ccccn1]
190 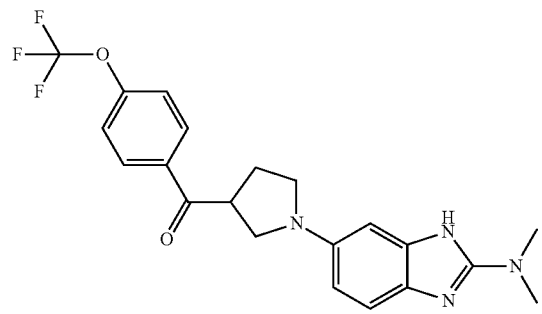 [SMILES: CN(C)c1nc2ccc(N3CCC(C(=O)c4ccc(OC(F)(F)F)cc4)C3)cc2[nH]1]
191 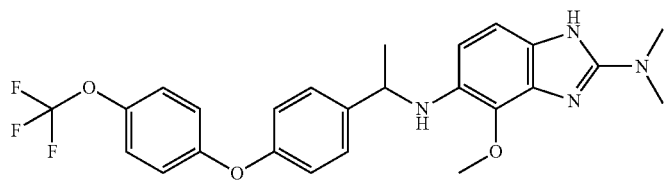 [SMILES: COc1c(NC(C)c2ccc(Oc3ccc(OC(F)(F)F)cc3)cc2)ccc2[nH]c(N(C)C)nc12]
192 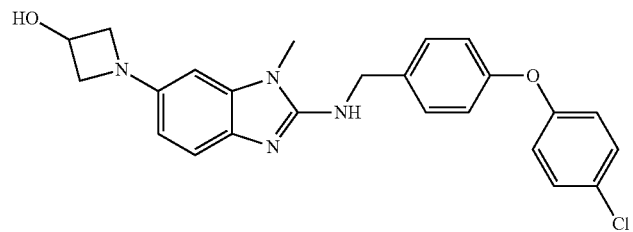 [SMILES: Cn1c(NCc2ccc(Oc3ccc(Cl)cc3)cc2)nc2ccc(N3CC(O)C3)cc21]

| | |
|---|---|
| 193 | 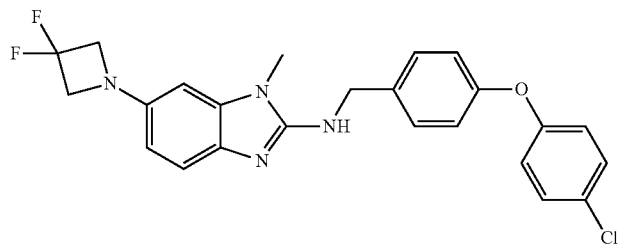 |
| 194 | 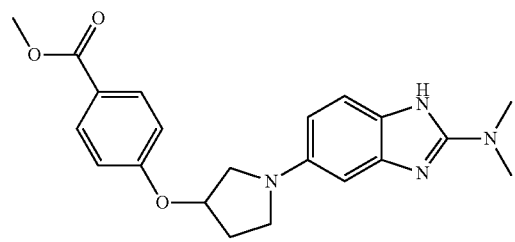 |
| 195 | 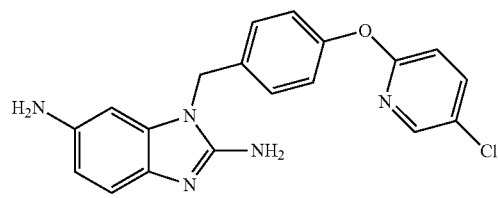 [SMILES: Nc1ccc2nc(N)n(Cc3ccc(Oc4ccc(Cl)cn4)cc3)c2c1] |
| 196 | 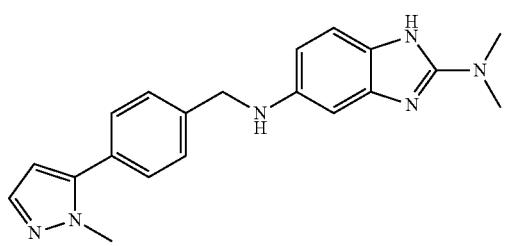 [SMILES: CN(C)c1nc2cc(NCc3ccc(-c4ccnn4C)cc3)ccc2[nH]1] |
| 197 | 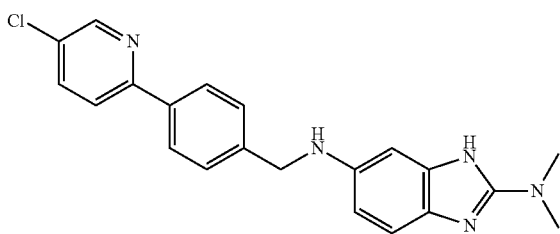 [SMILES: CN(C)c1nc2ccc(NCc3ccc(-c4ccc(Cl)cn4)cc3)cc2[nH]1] |
| 198 | 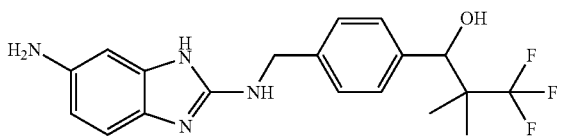 [SMILES: CC(C)(C(O)c1ccc(CNc2nc3ccc(N)cc3[nH]2)cc1)C(F)(F)F] |
| 199 | 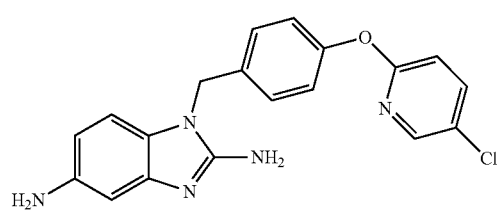 [SMILES: Nc1ccc2c(c1)nc(N)n2Cc1ccc(Oc2ccc(Cl)cn2)cc1] |

-continued
200
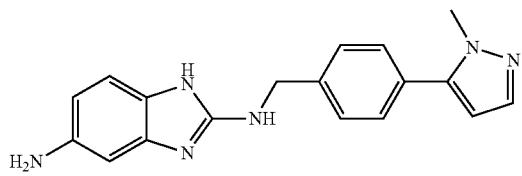 [SMILES: Cn1nccc1-c1ccc(CNc2nc3cc(N)ccc3[nH]2)cc1]
201
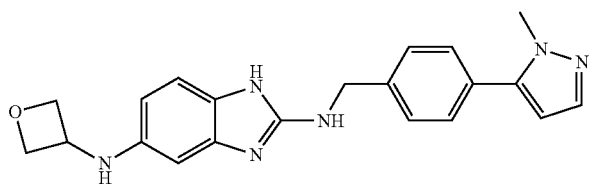 [SMILES: Cn1nccc1-c1ccc(CNc2nc3cc(NC4COC4)ccc3[nH]2)cc1]
202
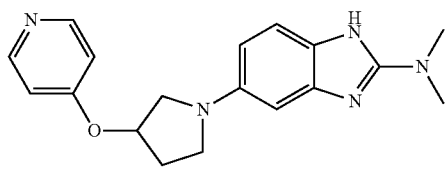 [SMILES: CN(C)c1nc2cc(N3CCC(Oc4ccncc4)C3)ccc2[nH]1]
203
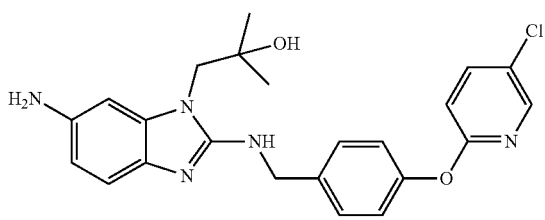 [SMILES: CC(C)(O)Cn1c(NCc2ccc(Oc3ccc(Cl)cn3)cc2)nc2ccc(N)cc21]
204
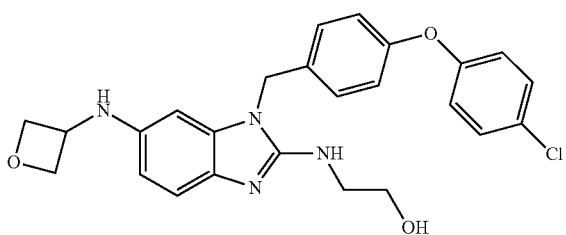 [SMILES: OCCNc1nc2ccc(NC3COC3)cc2n1Cc1ccc(Oc2ccc(Cl)cc2)cc1]
205
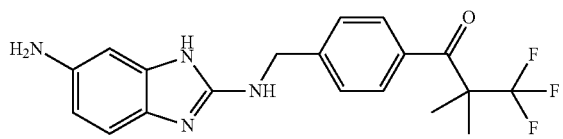 [SMILES: CC(C)(C(=O)c1ccc(CNc2nc3ccc(N)cc3[nH]2)cc1)C(F)(F)F]
206
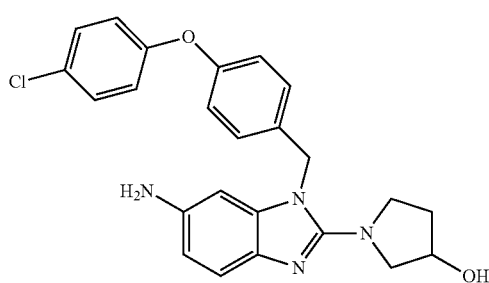 [SMILES: Nc1ccc2nc(N3CCC(O)C3)n(Cc3ccc(Oc4ccc(Cl)cc4)cc3)c2c1]

143 -continued
207
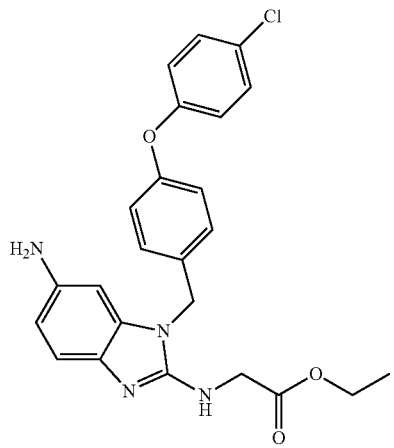 [SMILES: CCOC(=O)CNc1nc2ccc(N)cc2n1Cc1ccc(Oc2ccc(Cl)cc2)cc1]
208
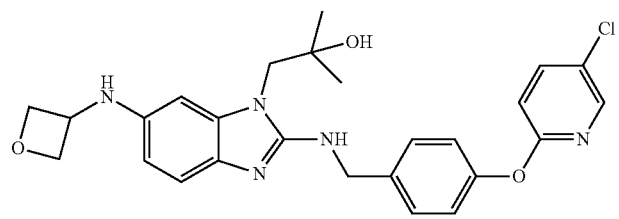 [SMILES: CC(C)(O)Cn1c(NCc2ccc(Oc3ccc(Cl)cn3)cc2)nc2ccc(NC3COC3)cc21]
209
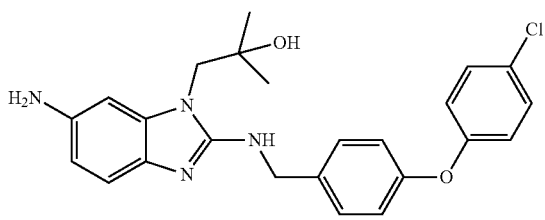
210
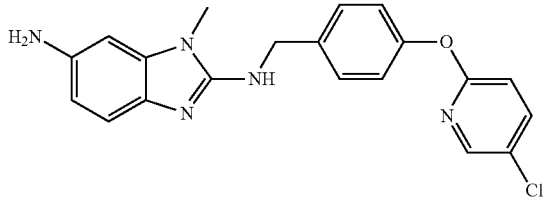
211
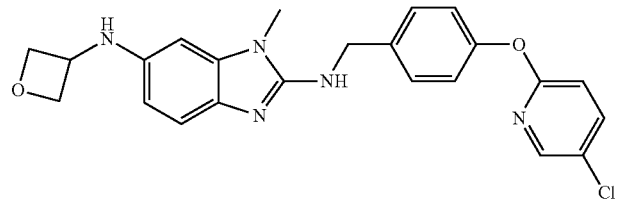
212
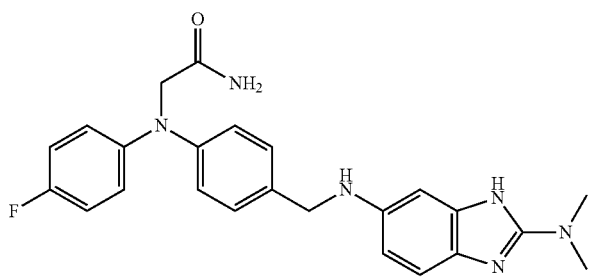 [SMILES: CN(C)c1nc2ccc(NCc3ccc(N(CC(N)=O)c4ccc(F)cc4)cc3)cc2[nH]1]

-continued
213 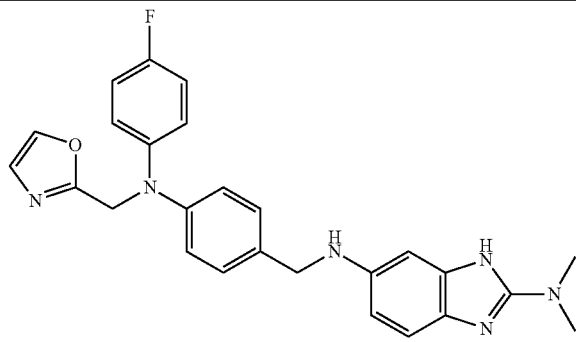
214 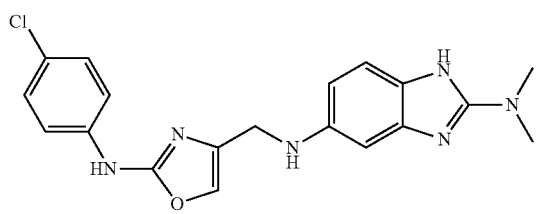 [SMILES: CN(C)c1nc2cc(NCc3coc(Nc4ccc(Cl)cc4)n3)ccc2[nH]1]
215 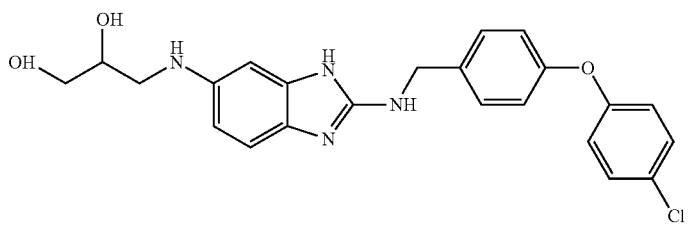 [SMILES: OCC(O)CNc1ccc2nc(NCc3ccc(Oc4ccc(Cl)cc4)cc3)[nH]c2c1]
216 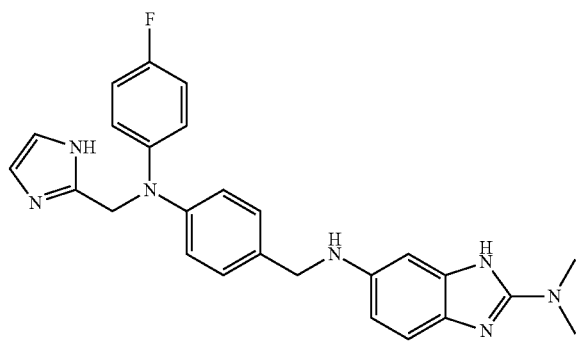 [SMILES: CN(C)c1nc2ccc(NCc3ccc(N(Cc4ncc[nH]4)c4ccc(F)cc4)cc3)cc2[nH]1]
217 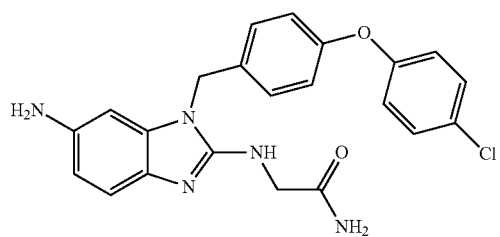 [SMILES: NC(=O)CNc1nc2ccc(N)cc2n1Cc1ccc(Oc2ccc(Cl)cc2)cc1]
218 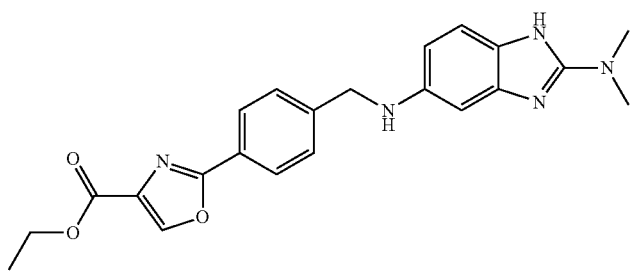 [SMILES: CCOC(=O)c1coc(-c2ccc(CNc3ccc4[nH]c(N(C)C)nc4c3)cc2)n1]

-continued
219
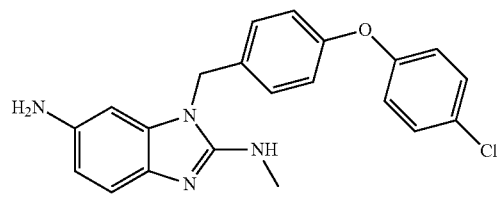 [SMILES: CNc1nc2ccc(N)cc2n1Cc1ccc(Oc2ccc(Cl)cc2)cc1]
220
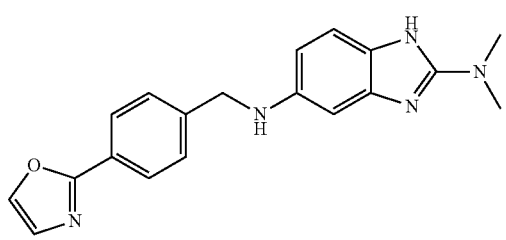 [SMILES: CN(C)c1nc2cc(NCc3ccc(-c4ncco4)cc3)ccc2[nH]1]
221
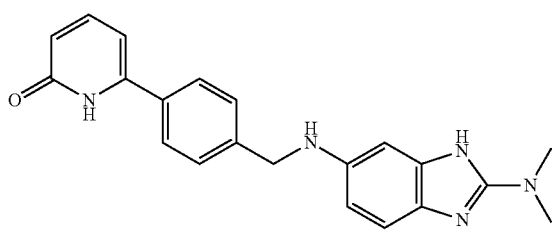 [SMILES: CN(C)c1nc2ccc(NCc3ccc(-c4cccc(=O)[nH]4)cc3)cc2[nH]1]
222
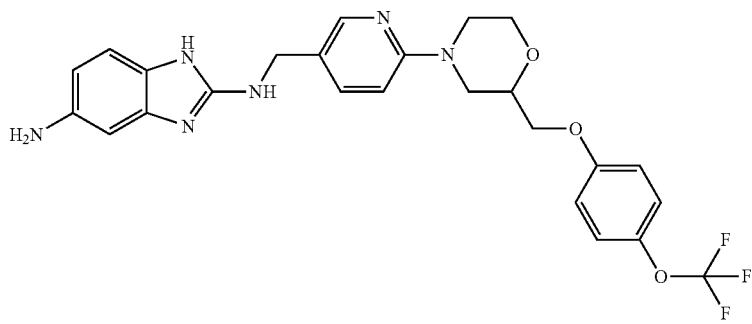 [SMILES: Nc1ccc2[nH]c(NCc3ccc(N4CCOC(COc5ccc(OC(F)(F)F)cc5)C4)nc3)nc2c1]
223
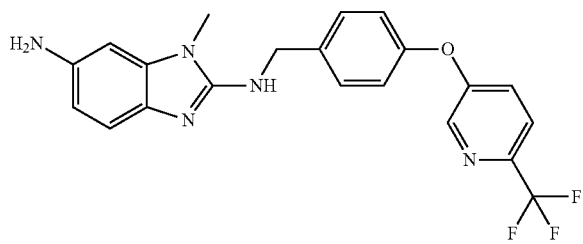 [SMILES: Cn1c(NCc2ccc(Oc3ccc(C(F)(F)F)nc3)cc2)nc2ccc(N)cc21]
224
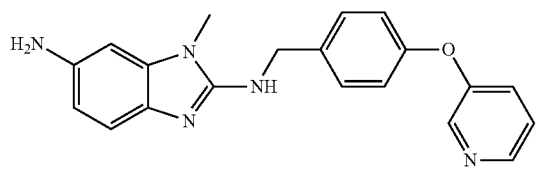

225 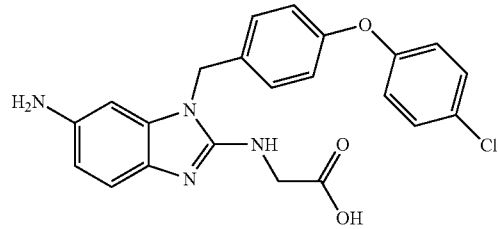 [SMILES: Nc1ccc2nc(NCC(=O)O)n(Cc3ccc(Oc4ccc(Cl)cc4)cc3)c2c1]
226 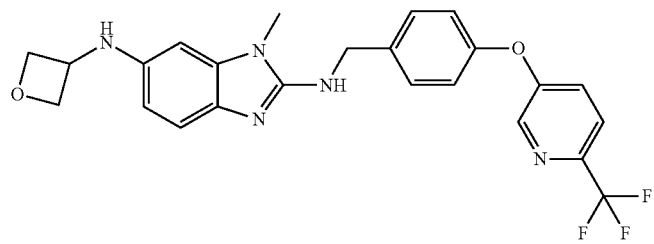
227 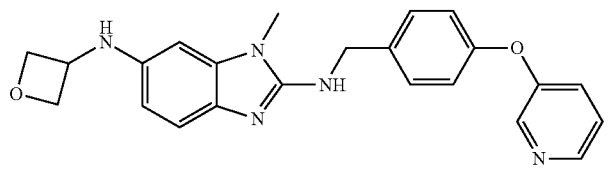
228 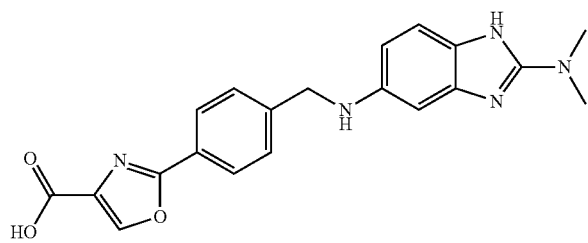 [SMILES: CN(C)c1nc2cc(NCc3ccc(-c4nc(C(=O)O)co4)cc3)ccc2[nH]1]
229 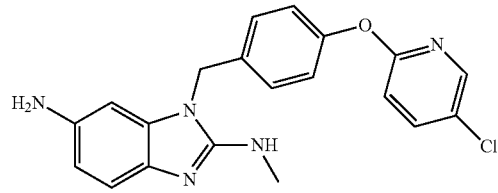 [SMILES: CNc1nc2ccc(N)cc2n1Cc1ccc(Oc2ccc(Cl)cn2)cc1]
230 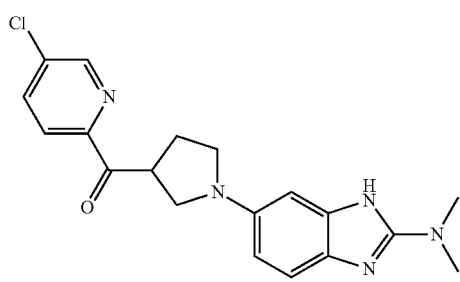 [SMILES: CN(C)c1nc2ccc(N3CCC(C(=O)c4ccc(Cl)cn4)C3)cc2[nH]1]
231 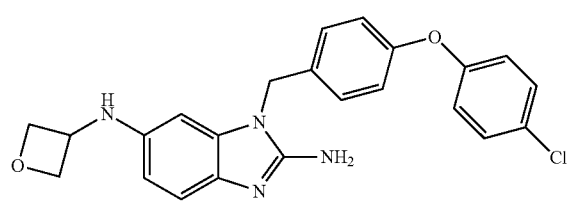

| | |
|---|---|
| 232 | 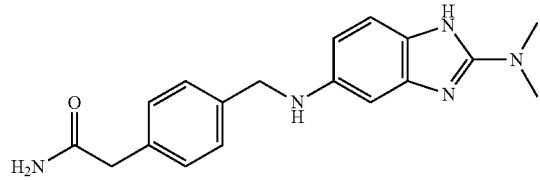 [SMILES: CN(C)c1nc2cc(NCc3ccc(CC(N)=O)cc3)ccc2[nH]1] |
| 233 | 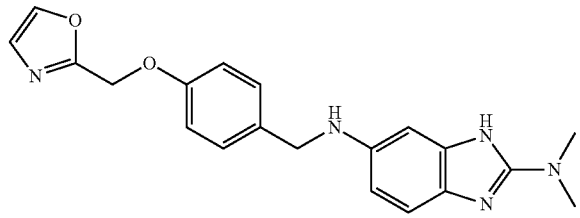 [SMILES: CN(C)c1nc2ccc(NCc3ccc(OCc4ncco4)cc3)cc2[nH]1] |
| 234 | 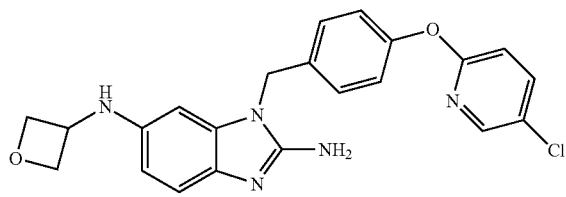 [SMILES: Nc1nc2ccc(NC3COC3)cc2n1Cc1ccc(Oc2ccc(Cl)cn2)cc1] |
| 235 | 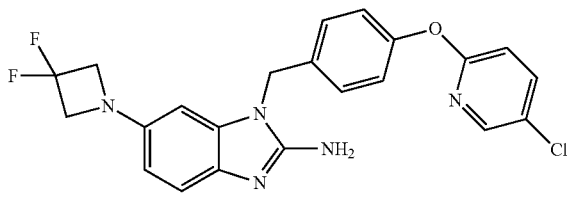 [SMILES: Nc1nc2ccc(N3CC(F)(F)C3)cc2n1Cc1ccc(Oc2ccc(Cl)cn2)cc1] |
| 236 | 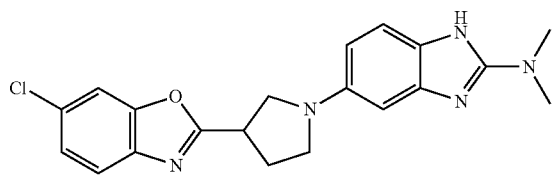 [SMILES: CN(C)c1nc2cc(N3CCC(c4nc5ccc(Cl)cc5o4)C3)ccc2[nH]1] |
| 237 | 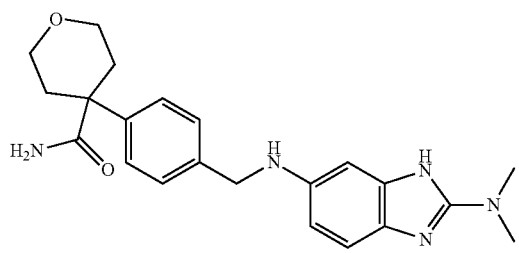 [SMILES: CN(C)c1nc2ccc(NCc3ccc(C4(C(N)=O)CCOCC4)cc3)cc2[nH]1] |
| 238 | 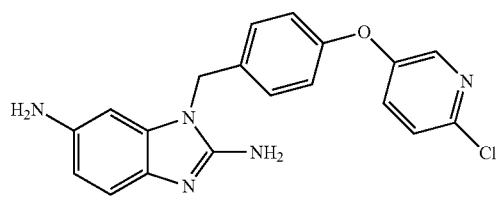 |

-continued
239
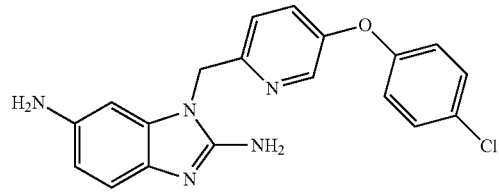
240
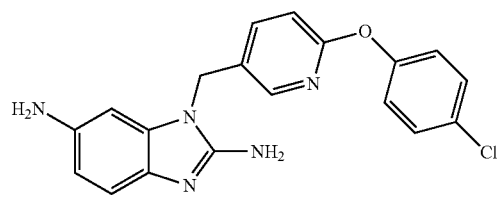 [SMILES: Nc1ccc2nc(N)n(Cc3ccc(Oc4ccc(Cl)cc4)nc3)c2c1]
241
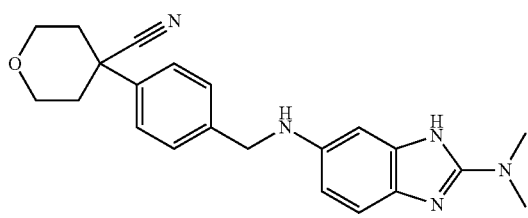 [SMILES: CN(C)c1nc2ccc(NCc3ccc(C4(C#N)CCOCC4)cc3)cc2[nH]1]
242
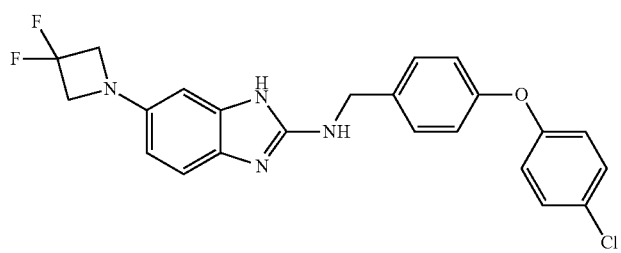
243
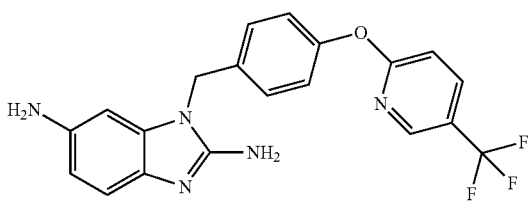 [SMILES: Nc1ccc2nc(N)n(Cc3ccc(Oc4ccc(C(F)(F)F)cn4)cc3)c2c1]
244
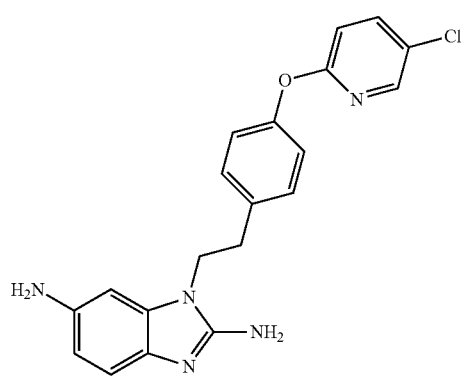 [SMILES: Nc1ccc2nc(N)n(CCc3ccc(Oc4ccc(Cl)cn4)cc3)c2c1]

-continued
| | |
|---|---|
| 245 | 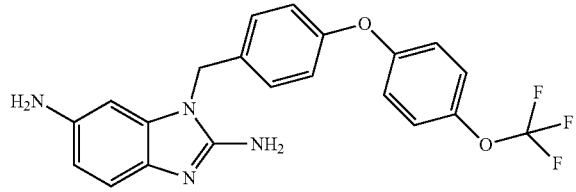 [SMILES: Nc1ccc2nc(N)n(Cc3ccc(Oc4ccc(OC(F)(F)F)cc4)cc3)c2c1] |
| 246 | 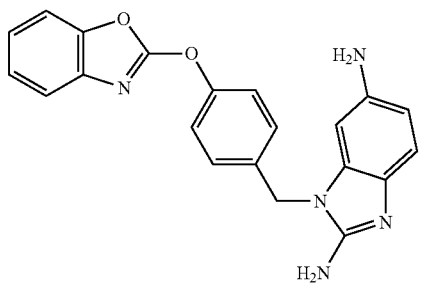 [SMILES: Nc1ccc2nc(N)n(Cc3ccc(Oc4nc5ccccc5o4)cc3)c2c1] |
| 247 | 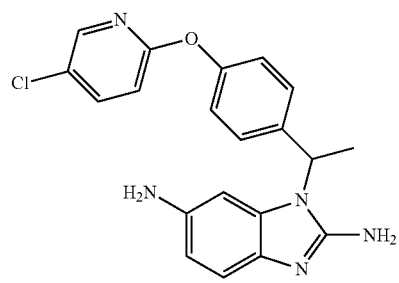 [SMILES: CC(c1ccc(Oc2ccc(Cl)cn2)cc1)n1c(N)nc2ccc(N)cc21] |
| 248 | 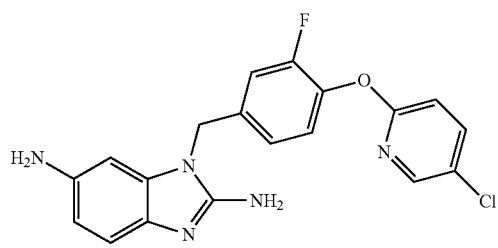 [SMILES: Nc1ccc2nc(N)n(Cc3ccc(Oc4ccc(Cl)cn4)c(F)c3)c2c1] |
| 249 | 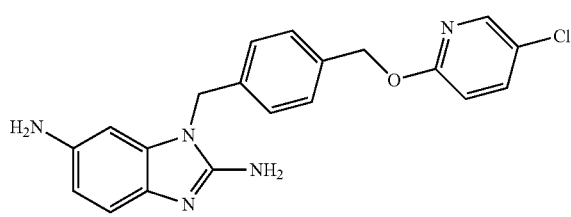 [SMILES: Nc1ccc2nc(N)n(Cc3ccc(COc4ccc(Cl)cn4)cc3)c2c1] |
| 250 | 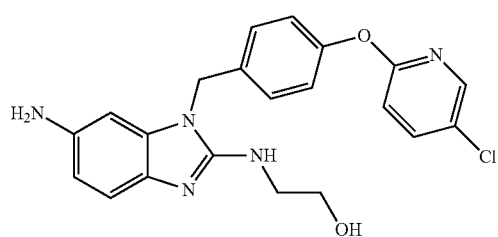 |

251 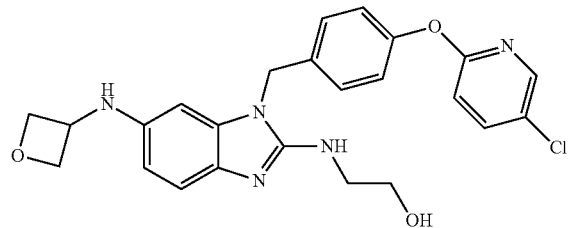 [SMILES: OCCNc1nc2ccc(NC3COC3)cc2n1Cc1ccc(Oc2ccc(Cl)cn2)cc1]
252 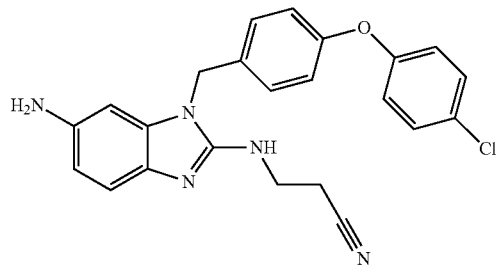 [SMILES: N#CCCNc1nc2ccc(N)cc2n1Cc1ccc(Oc2ccc(Cl)cc2)cc1]
253 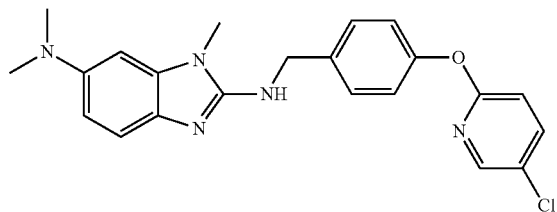 [SMILES: CN(C)c1ccc2nc(NCc3ccc(Oc4ccc(Cl)cn4)cc3)n(C)c2c1]
254 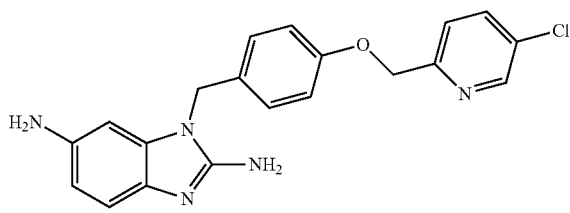 [SMILES: Nc1ccc2nc(N)n(Cc3ccc(OCc4ccc(Cl)cn4)cc3)c2c1]
255 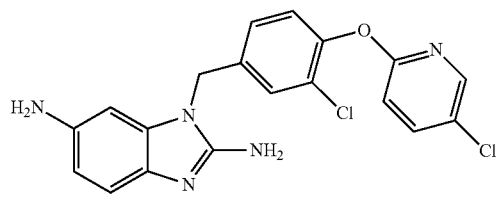 [SMILES: Nc1ccc2nc(N)n(Cc3ccc(Oc4ccc(Cl)cn4)c(Cl)c3)c2c1]
256 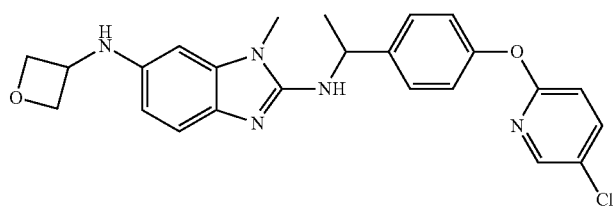 [SMILES: CC(Nc1nc2ccc(NC3COC3)cc2n1C)c1ccc(Oc2ccc(Cl)cn2)cc1]
257 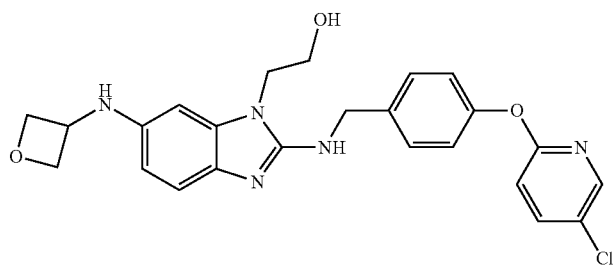 [SMILES: OCCn1c(NCc2ccc(Oc3ccc(Cl)cn3)cc2)nc2ccc(NC3COC3)cc21]

258 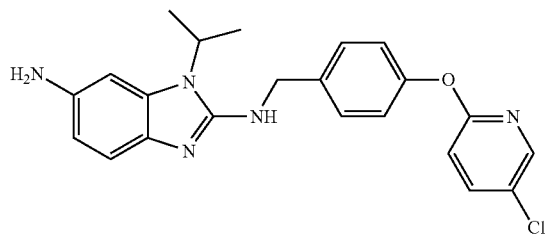 [SMILES: CC(C)n1c(NCc2ccc(Oc3ccc(Cl)cn3)cc2)nc2ccc(N)cc21]
259 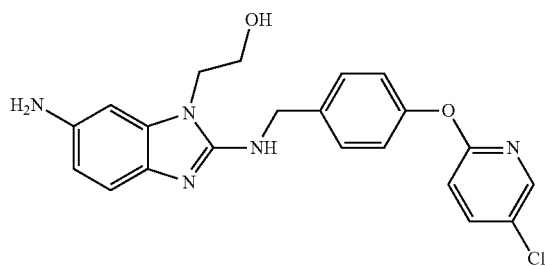 [SMILES: Nc1ccc2nc(NCc3ccc(Oc4ccc(Cl)cn4)cc3)n(CCO)c2c1]
260 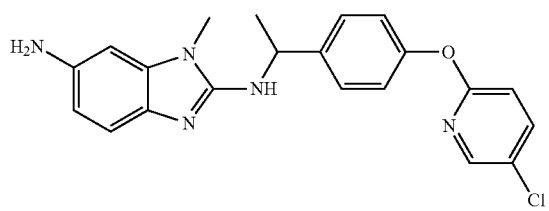 [SMILES: CC(Nc1nc2ccc(N)cc2n1C)c1ccc(Oc2ccc(Cl)cn2)cc1]
261 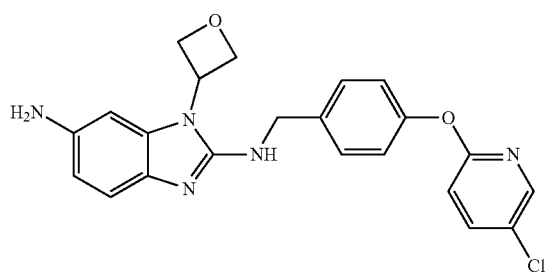 [SMILES: Nc1ccc2nc(NCc3ccc(Oc4ccc(Cl)cn4)cc3)n(C3COC3)c2c1]
262 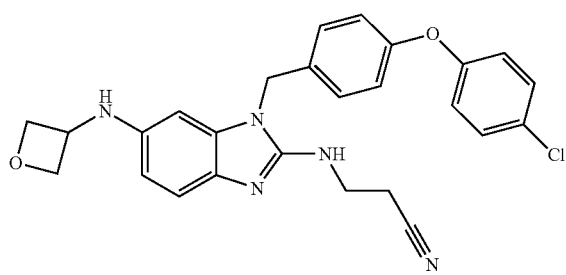 [SMILES: N#CCCNc1nc2ccc(NC3COC3)cc2n1Cc1ccc(Oc2ccc(Cl)cc2)cc1]
263 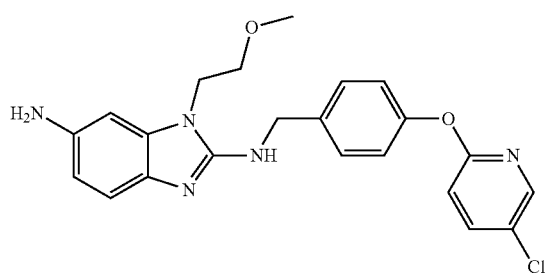 [SMILES: COCCn1c(NCc2ccc(Oc3ccc(Cl)cn3)cc2)nc2ccc(N)cc21]

| | |
|---|---|
| 264 | 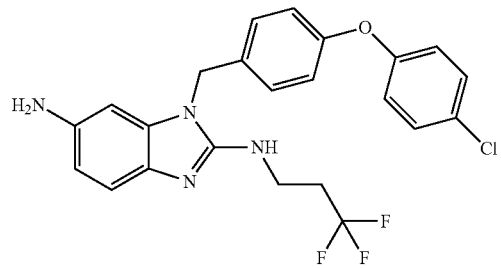 [SMILES: Nc1ccc2nc(NCCC(F)(F)F)n(Cc3ccc(Oc4ccc(Cl)cc4)cc3)c2c1] |
| 265 | 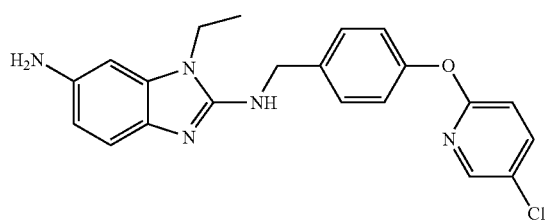 [SMILES: CCn1c(NCc2ccc(Oc3ccc(Cl)cn3)cc2)nc2ccc(N)cc21] |
| 266 | 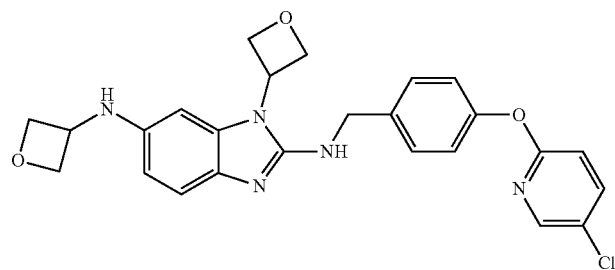 [SMILES: Clc1ccc(Oc2ccc(CNc3nc4ccc(NC5COC5)cc4n3C3COC3)cc2)nc1] |
| 267 | 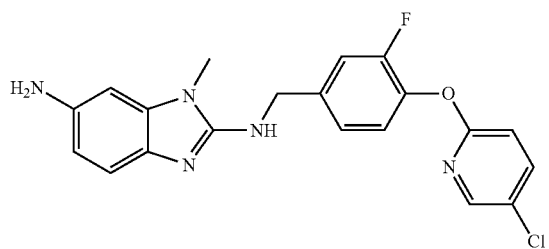 [SMILES: Cn1c(NCc2ccc(Oc3ccc(Cl)cn3)c(F)c2)nc2ccc(N)cc21] |
| 268 | 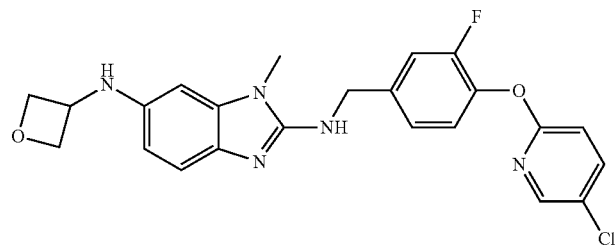 |
| 269 | 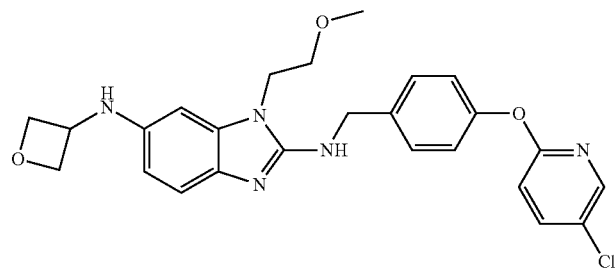 [SMILES: COCCn1c(NCc2ccc(Oc3ccc(Cl)cn3)cc2)nc2ccc(NC3COC3)cc21] |

| 270 | 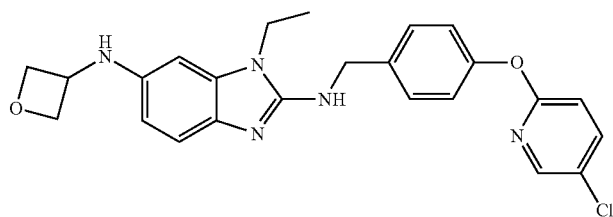 [SMILES: CCn1c(NCc2ccc(Oc3ccc(Cl)cn3)cc2)nc2ccc(NC3COC3)cc21] |
| --- | --- |
| 271 | 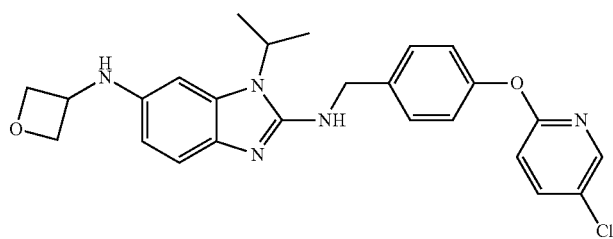 [SMILES: CC(C)n1c(NCc2ccc(Oc3ccc(Cl)cn3)cc2)nc2ccc(NC3COC3)cc21] |
| 272 | 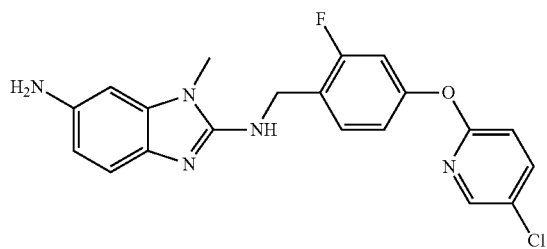 |
| 273 | 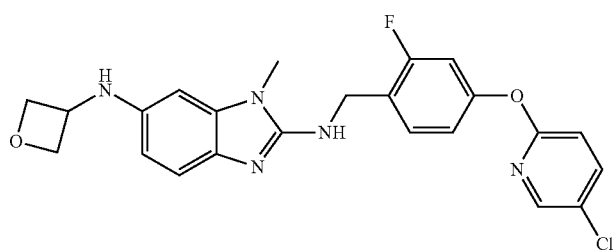 |
| 274 | 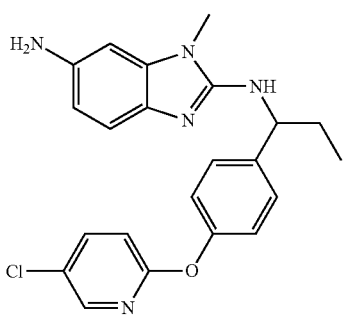 [SMILES: CCC(Nc1nc2ccc(N)cc2n1C)c1ccc(Oc2ccc(Cl)cn2)cc1] |
| 275 | 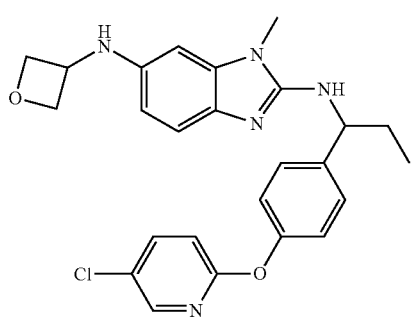 [SMILES: CCC(Nc1nc2ccc(NC3COC3)cc2n1C)c1ccc(Oc2ccc(Cl)cn2)cc1] |

276 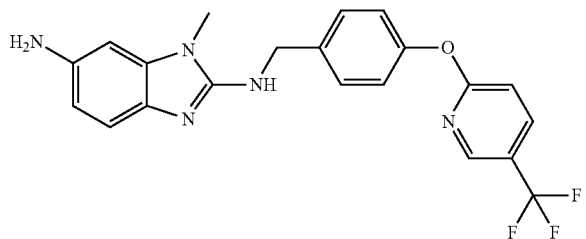
277 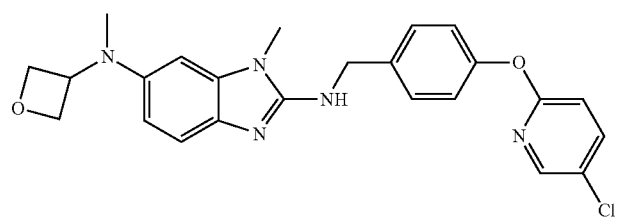 [SMILES: CN(c1ccc2nc(NCc3ccc(Oc4ccc(Cl)cn4)cc3)n(C)c2c1)C1COC1]
278 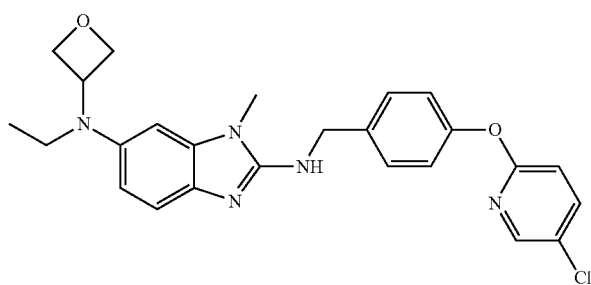 [SMILES: CCN(c1ccc2nc(NCc3ccc(Oc4ccc(Cl)cn4)cc3)n(C)c2c1)C1COC1]
279 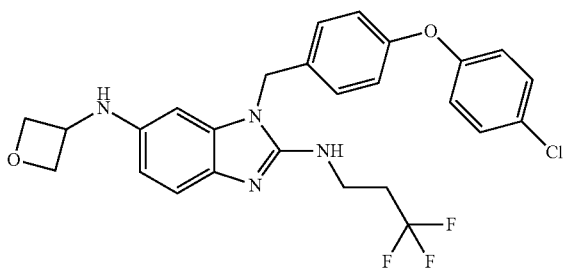 [SMILES: FC(F)(F)CCNc1nc2ccc(NC3COC3)cc2n1Cc1ccc(Oc2ccc(Cl)cc2)cc1]
280 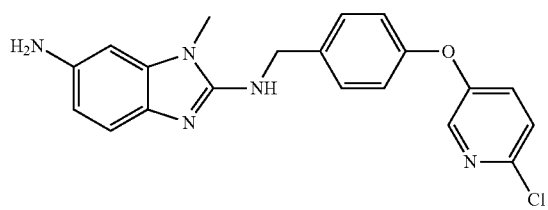 [SMILES: Cn1c(NCc2ccc(Oc3ccc(Cl)nc3)cc2)nc2ccc(N)cc21]
281 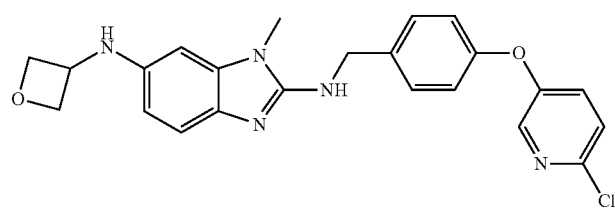

-continued
282 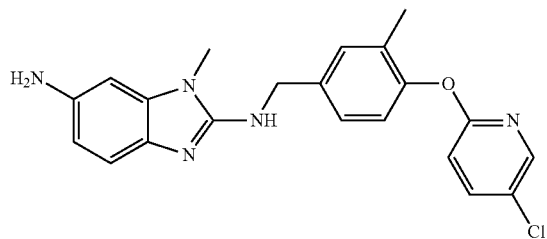 [SMILES: Cc1cc(CNc2nc3ccc(N)cc3n2C)ccc1Oc1ccc(Cl)cn1]
283 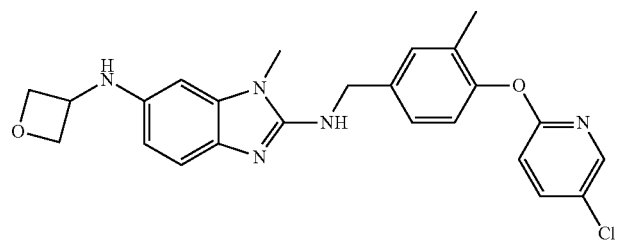
284 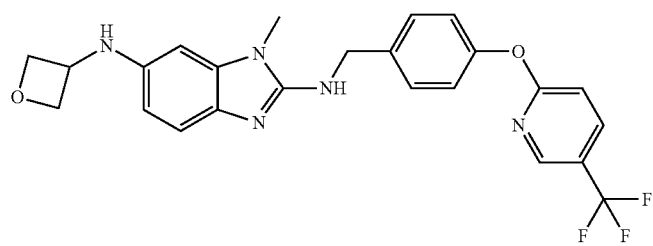 [SMILES: Cn1c(NCc2ccc(Oc3ccc(C(F)(F)F)cn3)cc2)nc2ccc(NC3COC3)cc21]
285 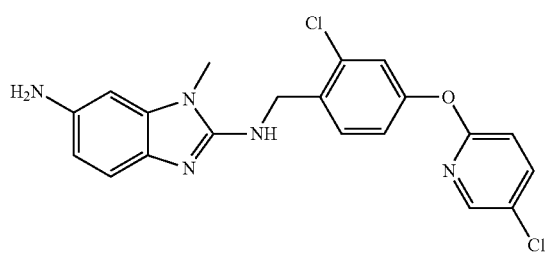 [SMILES: Cn1c(NCc2ccc(Oc3ccc(Cl)cn3)cc2Cl)nc2ccc(N)cc21]
286 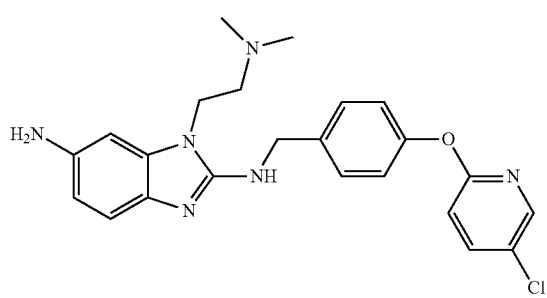 [SMILES: CN(C)CCn1c(NCc2ccc(Oc3ccc(Cl)cn3)cc2)nc2ccc(N)cc21]
287 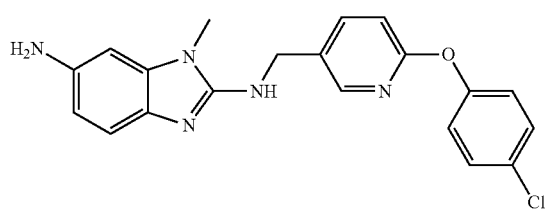

| | |
|---|---|
| 288 | 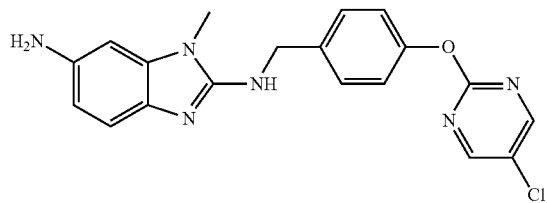 |
| 289 | 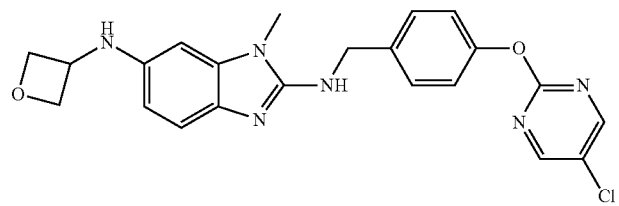 |
| 290 | 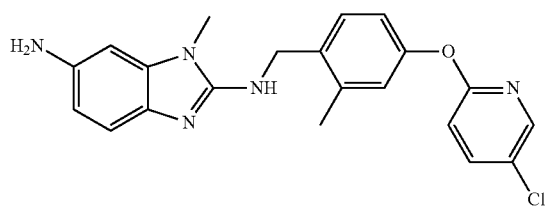 |
| 291 | 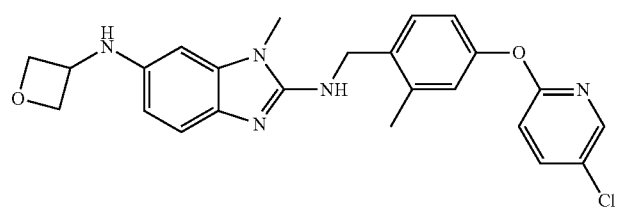 [SMILES: Cc1cc(Oc2ccc(Cl)cn2)ccc1CNc1nc2ccc(NC3COC3)cc2n1C] |
| 292 | 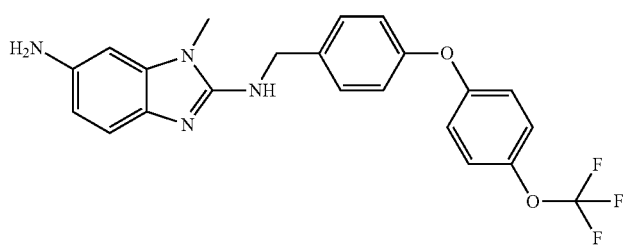 |
| 293 | 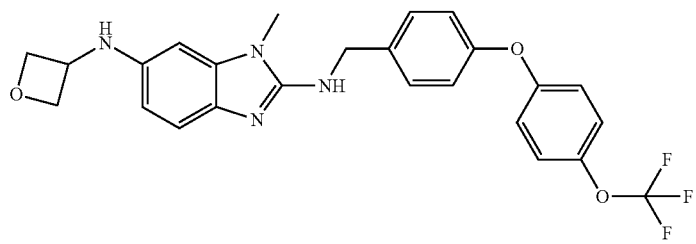 [SMILES: Cn1c(NCc2ccc(Oc3ccc(OC(F)(F)F)cc3)cc2)nc2ccc(NC3COC3)cc21] |
| 294 | 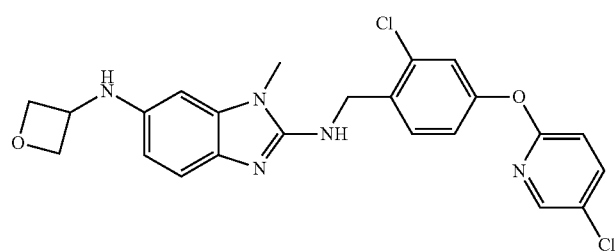 [SMILES: Cn1c(NCc2ccc(Oc3ccc(Cl)cn3)cc2Cl)nc2ccc(NC3COC3)cc21] |

295 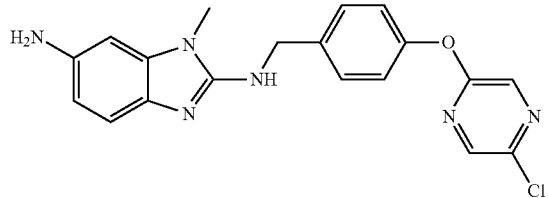
296 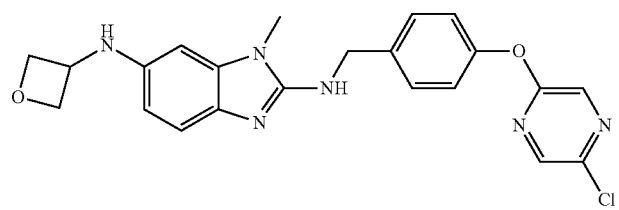
297 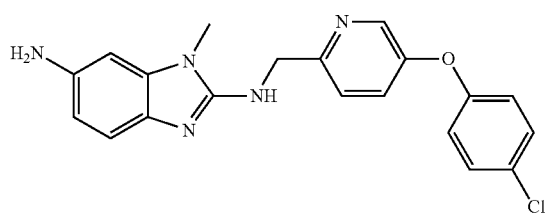 [SMILES: Cn1c(NCc2ccc(Oc3ccc(Cl)cc3)cn2)nc2ccc(N)cc21]
298 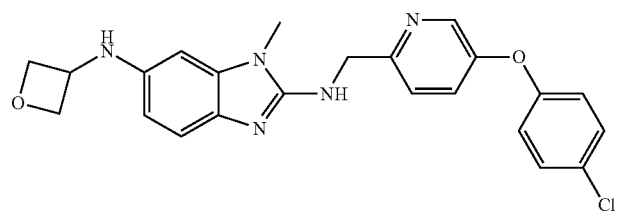
299 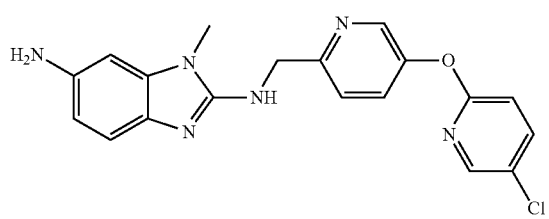 [SMILES: Cn1c(NCc2ccc(Oc3ccc(Cl)cn3)cn2)nc2ccc(N)cc21]
300 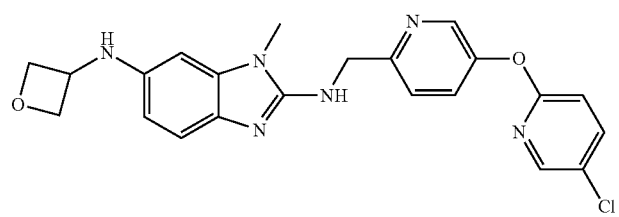
301 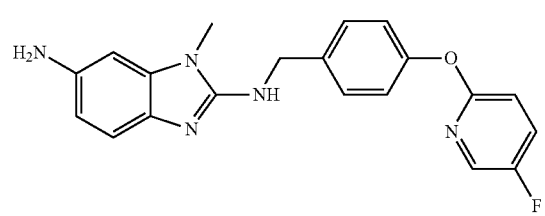

-continued
302 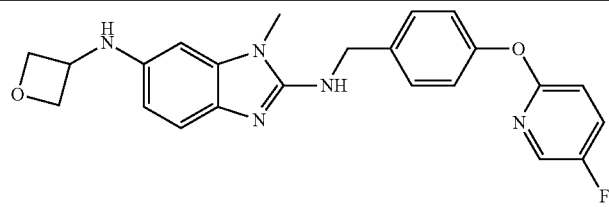
303 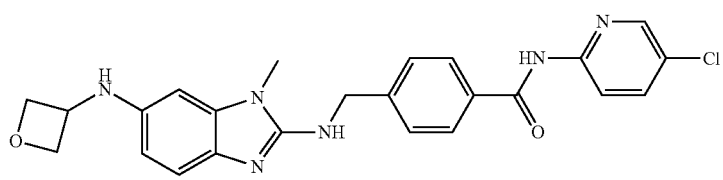 [SMILES: Cn1c(NCc2ccc(C(=O)Nc3ccc(Cl)cn3)cc2)nc2ccc(NC3COC3)cc21]
304 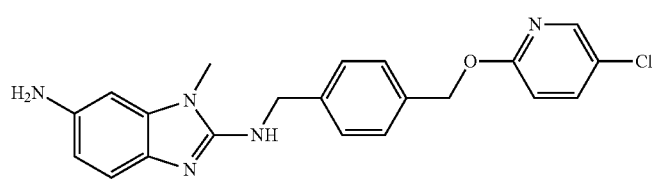 [SMILES: Cn1c(NCc2ccc(COc3ccc(Cl)cn3)cc2)nc2ccc(N)cc21]
305 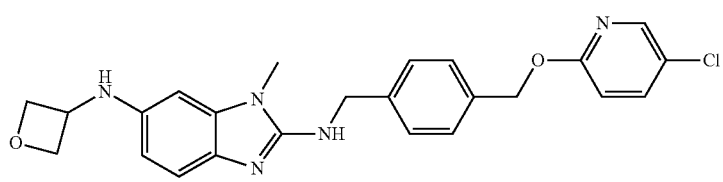
306 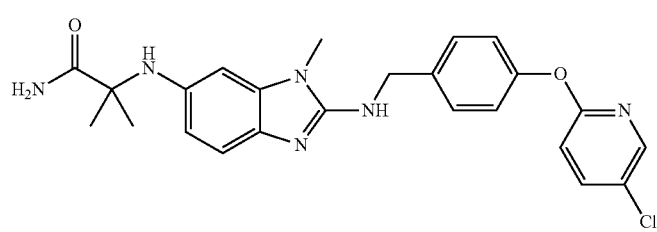
307 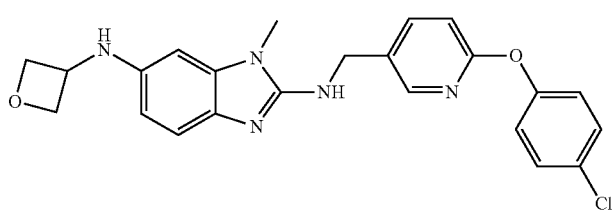 [SMILES: Cn1c(NCc2ccc(Oc3ccc(Cl)cc3)nc2)nc2ccc(NC3COC3)cc21]
308 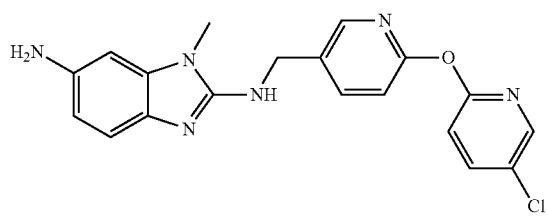 [SMILES: Cn1c(NCc2ccc(Oc3ccc(Cl)cn3)nc2)nc2ccc(N)cc21]
309 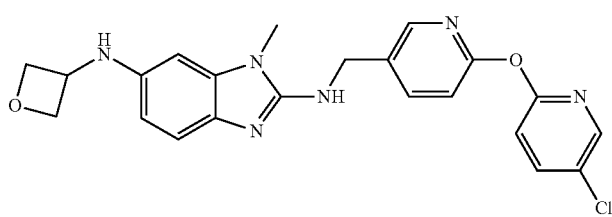 [SMILES: Cn1c(NCc2ccc(Oc3ccc(Cl)cn3)nc2)nc2ccc(NC3COC3)cc21]

-continued
| | |
|---|---|
| 310 | 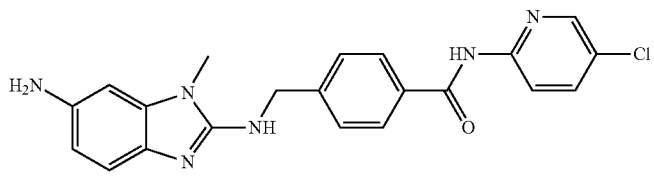 [SMILES: Cn1c(NCc2ccc(C(=O)Nc3ccc(Cl)cn3)cc2)nc2ccc(N)cc21] |
| 311 | 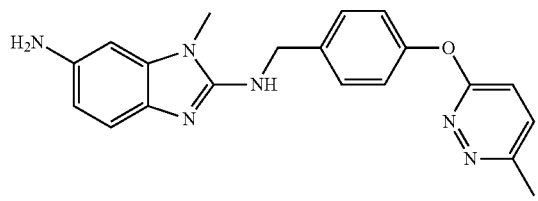 [SMILES: Cc1ccc(Oc2ccc(CNc3nc4ccc(N)cc4n3C)cc2)nn1] |
| 312 | 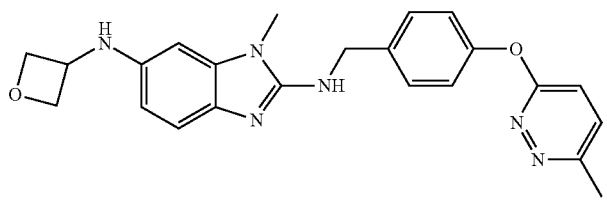 [SMILES: Cc1ccc(Oc2ccc(CNc3nc4ccc(NC5COC5)cc4n3C)cc2)nn1] |
| 313 | 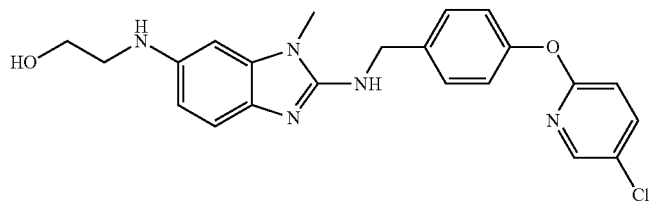 [SMILES: Cn1c(NCc2ccc(Oc3ccc(Cl)cn3)cc2)nc2ccc(NCCO)cc21] |
| 314 | 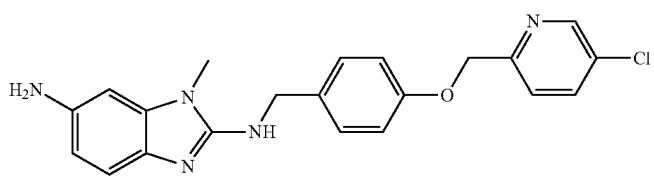 [SMILES: Cn1c(NCc2ccc(OCc3ccc(Cl)cn3)cc2)nc2ccc(N)cc21] |
| 315 | 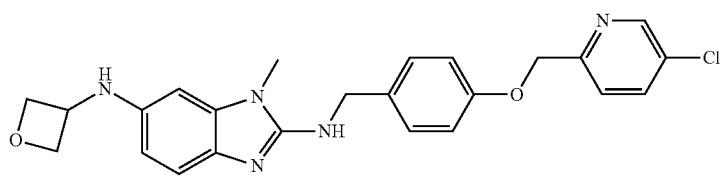 |
| 316 | 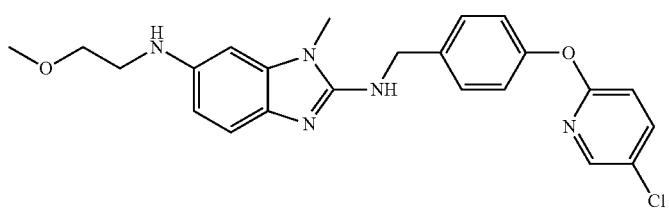 [SMILES: COCCNc1ccc2nc(NCc3ccc(Oc4ccc(Cl)cn4)cc3)n(C)c2c1] |

317 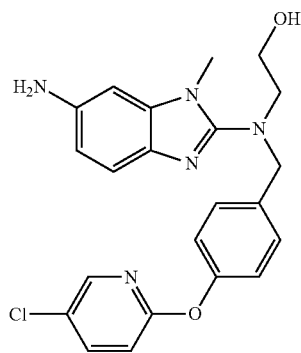 [SMILES: Cn1c(N(CCO)Cc2ccc(Oc3ccc(Cl)cn3)cc2)nc2ccc(N)cc21]
318 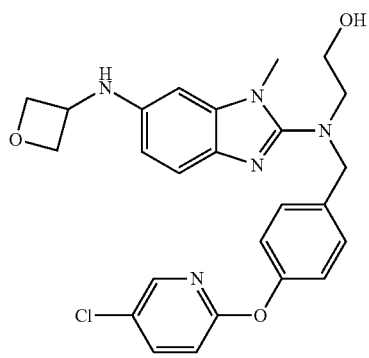 [SMILES: Cn1c(N(CCO)Cc2ccc(Oc3ccc(Cl)cn3)cc2)nc2ccc(NC3COC3)cc21]
319 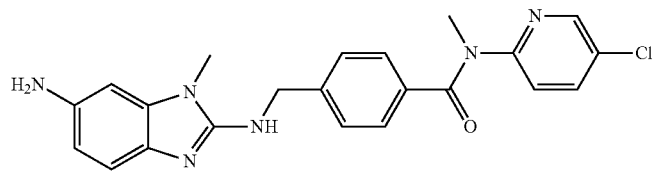 [SMILES: CN(C(=O)c1ccc(CNc2nc3ccc(N)cc3n2C)cc1)c1ccc(Cl)cn1]
320 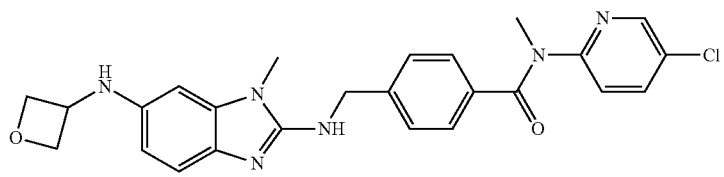 [SMILES: CN(C(=O)c1ccc(CNc2nc3ccc(NC4COC4)cc3n2C)cc1)c1ccc(Cl)cn1]
321 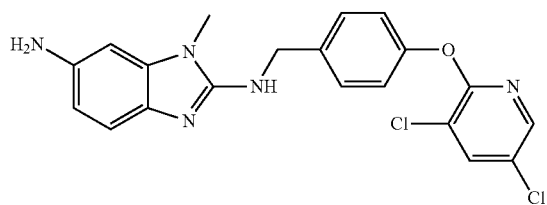 [SMILES: Cn1c(NCc2ccc(Oc3ncc(Cl)cc3Cl)cc2)nc2ccc(N)cc21]
322 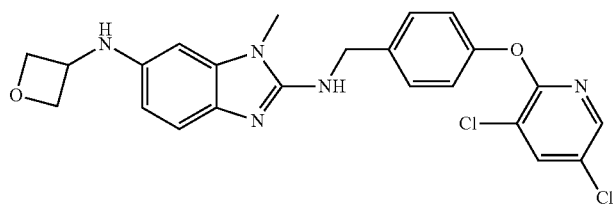 [SMILES: Cn1c(NCc2ccc(Oc3ncc(Cl)cc3Cl)cc2)nc2ccc(NC3COC3)cc21]

-continued
| 323 | 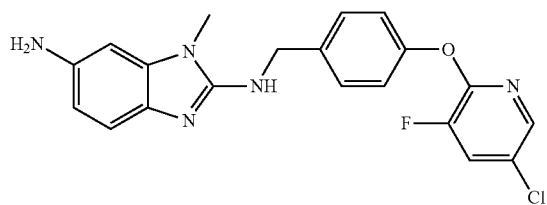 |
| 324 | 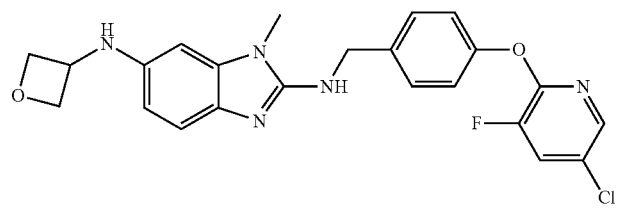 |
| 325 | 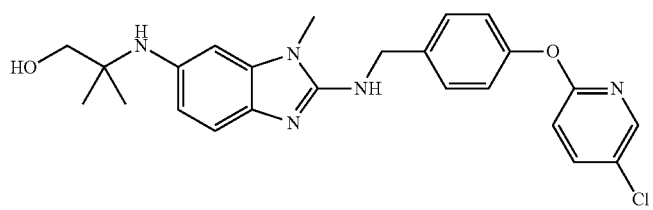 [SMILES: Cn1c(NCc2ccc(Oc3ccc(Cl)cn3)cc2)nc2ccc(NC(C)(C)CO)cc21] |
| 326 |  |
| 327 | 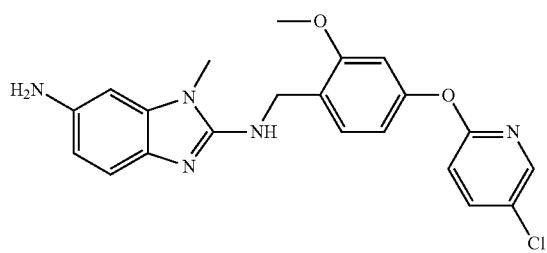 [SMILES: COc1cc(Oc2ccc(Cl)cn2)ccc1CNc1nc2ccc(N)cc2n1C] |
| 328 | 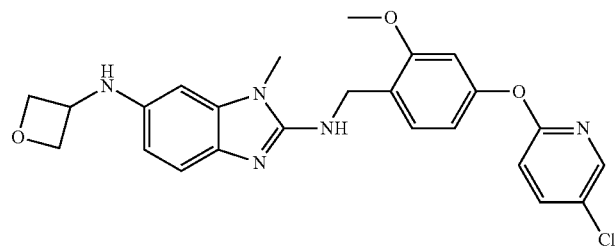 [SMILES: COc1cc(Oc2ccc(Cl)cn2)ccc1CNc1nc2ccc(NC3COC3)cc2n1C] |
| 329 | 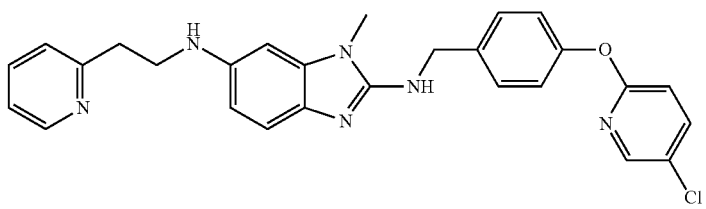 [SMILES: Cn1c(NCc2ccc(Oc3ccc(Cl)cn3)cc2)nc2ccc(NCCc3ccccn3)cc21] |

-continued
| | |
|---|---|
| 330 | 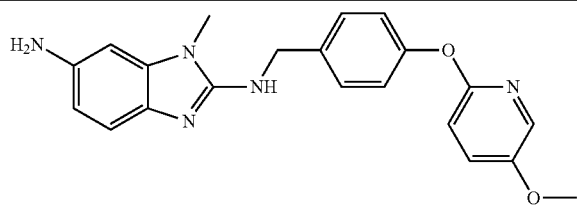 |
| 331 | 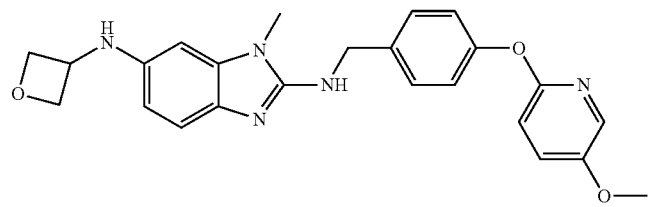 [SMILES: COc1ccc(Oc2ccc(CNc3nc4ccc(NC5COC5)cc4n3C)cc2)nc1] |
| 332 | 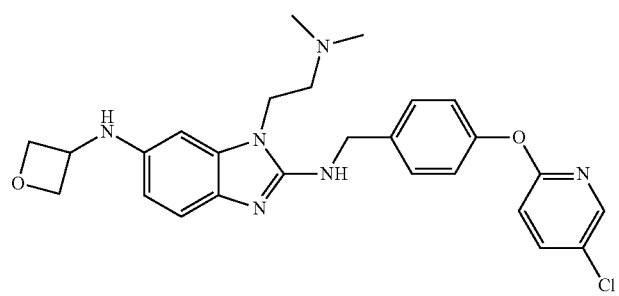 [SMILES: CN(C)CCn1c(NCc2ccc(Oc3ccc(Cl)cn3)cc2)nc2ccc(NC3COC3)cc21] |
| 333 | 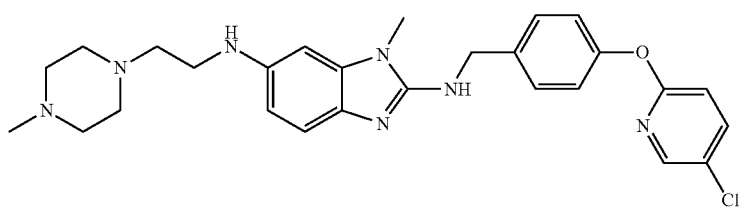 [SMILES: CN1CCN(CCNc2ccc3nc(NCc4ccc(Oc5ccc(Cl)cn5)cc4)n(C)c3c2)CC1] |
| 334 | 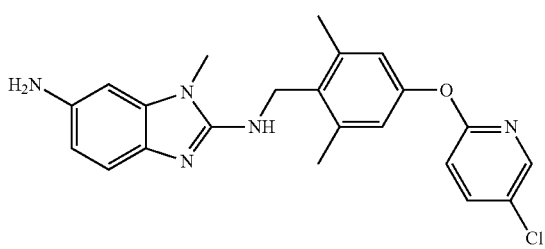 [SMILES: Cc1cc(Oc2ccc(Cl)cn2)cc(C)c1CNc1nc2ccc(N)cc2n1C] |
| 335 | 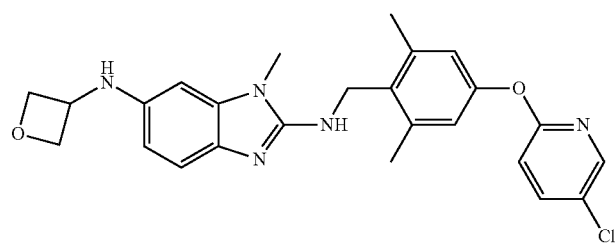 [SMILES: Cc1cc(Oc2ccc(Cl)cn2)cc(C)c1CNc1nc2ccc(NC3COC3)cc2n1C] |
| 336 | 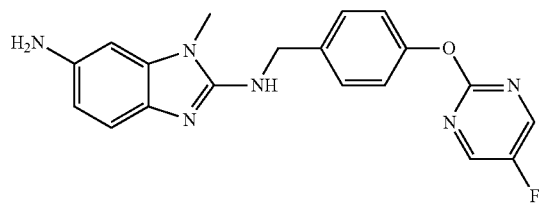 [SMILES: Cn1c(NCc2ccc(Oc3ncc(F)cn3)cc2)nc2ccc(N)cc21] |

| | |
|---|---|
| 337 | 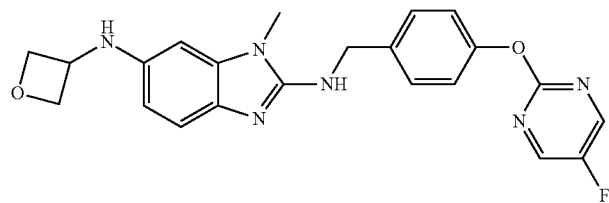 [SMILES: Cn1c(NCc2ccc(Oc3ncc(F)cn3)cc2)nc2ccc(NC3COC3)cc21] |
| 338 | 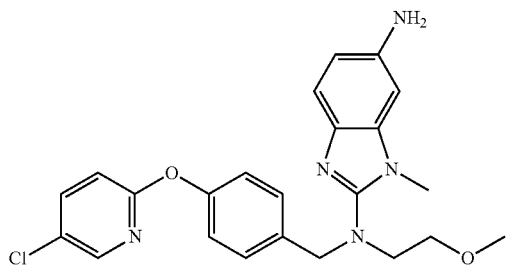 [SMILES: COCCN(Cc1ccc(Oc2ccc(Cl)cn2)cc1)c1nc2ccc(N)cc2n1C] |
| 339 | 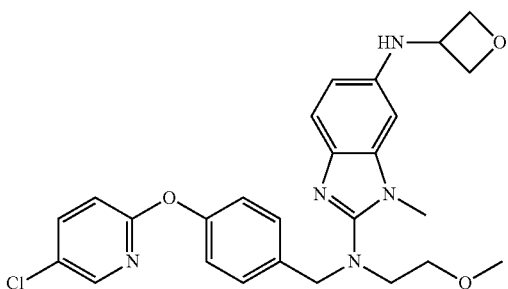 [SMILES: COCCN(Cc1ccc(Oc2ccc(Cl)cn2)cc1)c1nc2ccc(NC3COC3)cc2n1C] |
| 340 | 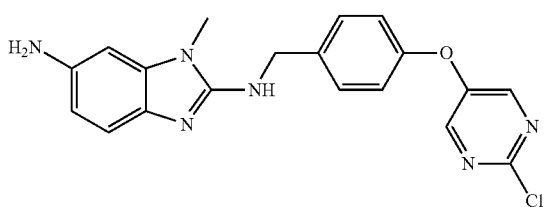 [SMILES: Cn1c(NCc2ccc(Oc3cnc(Cl)nc3)cc2)nc2ccc(N)cc21] |
| 341 | 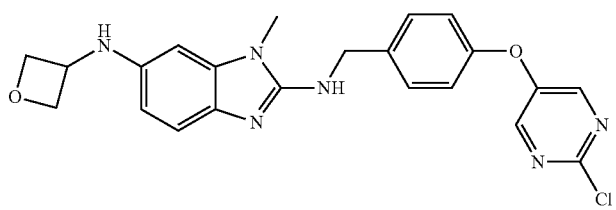 |
| 342 | 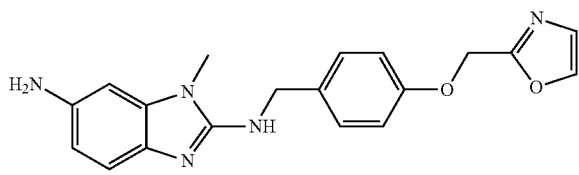 [SMILES: Cn1c(NCc2ccc(OCc3ncco3)cc2)nc2ccc(N)cc21] |
| 343 | 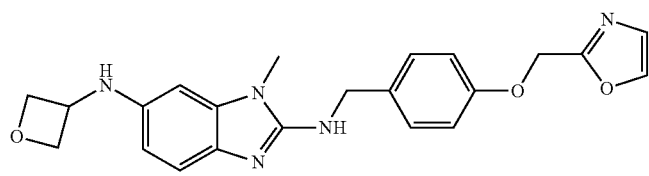 [SMILES: Cn1c(NCc2ccc(OCc3ncco3)cc2)nc2ccc(NC3COC3)cc21] |

| | |
|---|---|
| 344 | 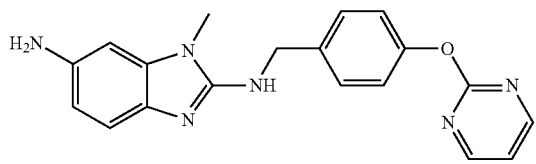 [SMILES: Cn1c(NCc2ccc(Oc3ncccn3)cc2)nc2ccc(N)cc21] |
| 345 | 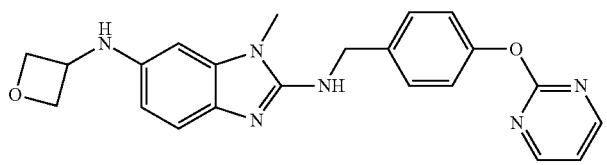 [SMILES: Cn1c(NCc2ccc(Oc3ncccn3)cc2)nc2ccc(NC3COC3)cc21] |
| 346 | 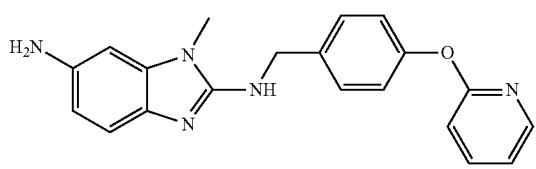 [SMILES: Cn1c(NCc2ccc(Oc3ccccn3)cc2)nc2ccc(N)cc21] |
| 347 | 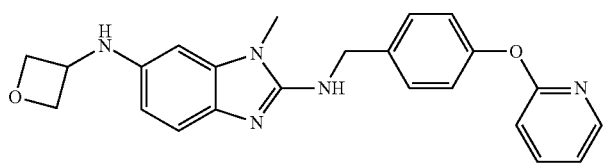 [SMILES: Cn1c(NCc2ccc(Oc3ccccn3)cc2)nc2ccc(NC3COC3)cc21] |
| 348 | 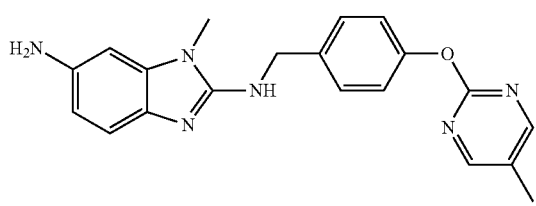 |
| 349 | 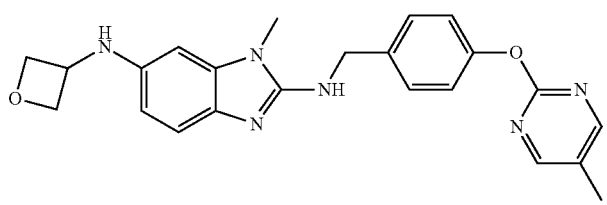 |
| 350 | 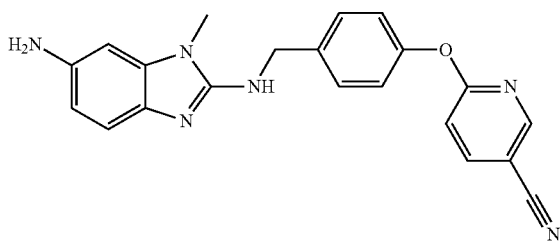 [SMILES: Cn1c(NCc2ccc(Oc3ccc(C#N)cn3)cc2)nc2ccc(N)cc21] |
| 351 | 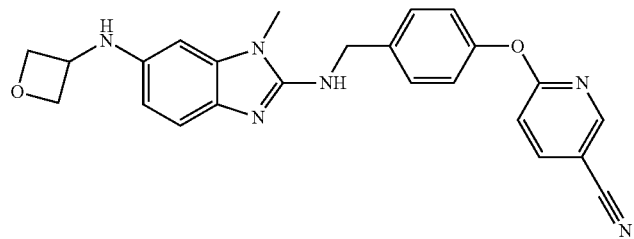 [SMILES: Cn1c(NCc2ccc(Oc3ccc(C#N)cn3)cc2)nc2ccc(NC3COC3)cc21] |

| | |
|---|---|
| 352 | 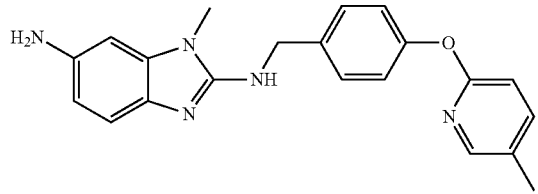 |
| 353 | 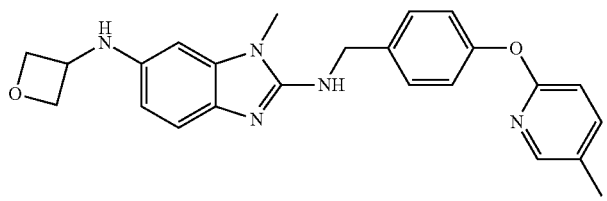 |
| 354 | 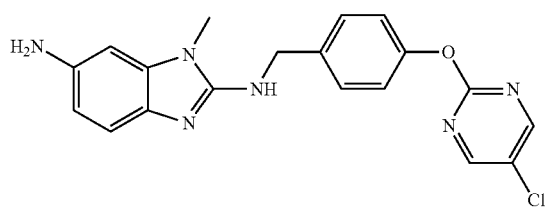 [SMILES: Cn1c(NCc2ccc(Oc3ncc(Cl)cn3)cc2)nc2ccc(N)cc21] |
| 355 | 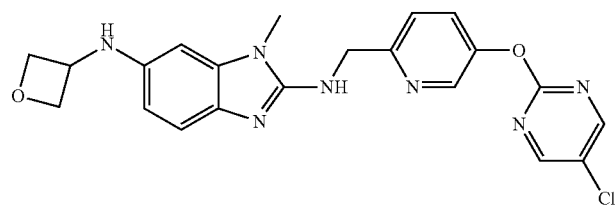 [SMILES: Cn1c(NCc2ccc(Oc3ncc(Cl)cn3)cn2)nc2ccc(NC3COC3)cc21] |
| 356 | 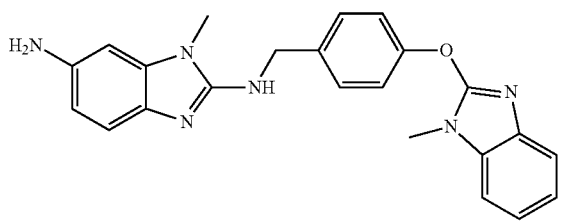 [SMILES: Cn1c(NCc2ccc(Oc3nc4ccccc4n3C)cc2)nc2ccc(N)cc21] |
| 357 | 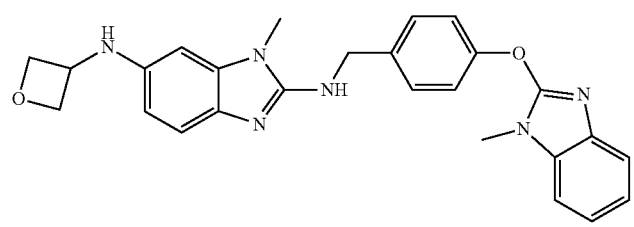 [SMILES: Cn1c(NCc2ccc(Oc3nc4ccccc4n3C)cc2)nc2ccc(NC3COC3)cc21] |
| 358 | 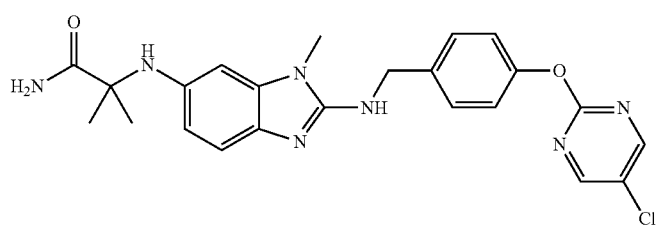 [SMILES: Cn1c(NCc2ccc(Oc3ncc(Cl)cn3)cc2)nc2ccc(NC(C)(C)C(N)=O)cc21] |

| | |
|---|---|
| 359 | 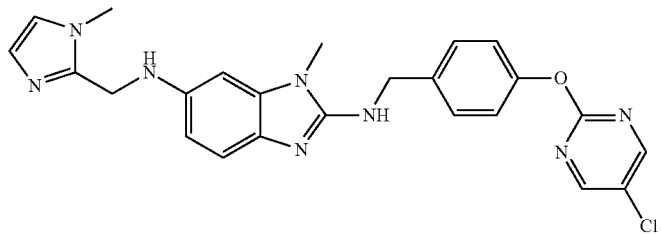 [SMILES: Cn1ccnc1CNc1ccc2nc(NCc3ccc(Oc4ncc(Cl)cn4)cc3)n(C)c2c1] |
| 360 | 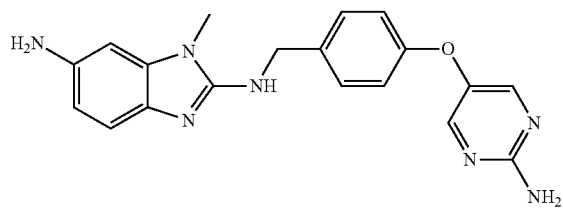 [SMILES: Cn1c(NCc2ccc(Oc3cnc(N)nc3)cc2)nc2ccc(N)cc21] |
| 361 | 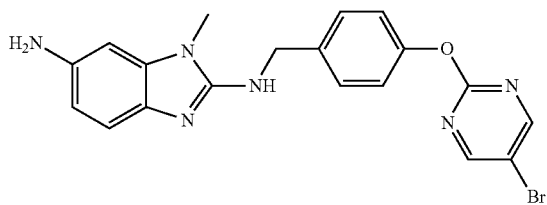 [SMILES: Cn1c(NCc2ccc(Oc3ncc(Br)cn3)cc2)nc2ccc(N)cc21] |
| 362 | 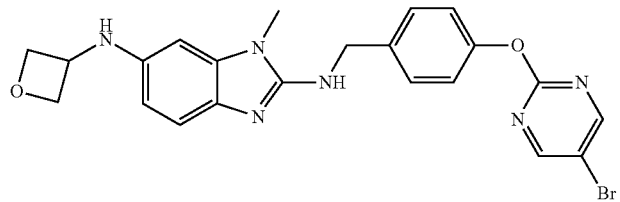 |
| 363 | 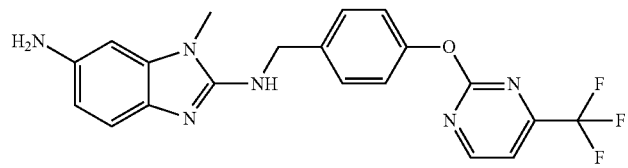 [SMILES: Cn1c(NCc2ccc(Oc3nccc(C(F)(F)F)n3)cc2)nc2ccc(N)cc21] |
| 364 | 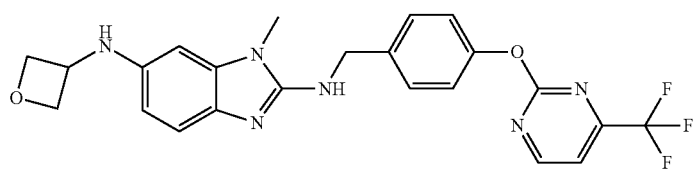 [SMILES: Cn1c(NCc2ccc(Oc3nccc(C(F)(F)F)n3)cc2)nc2ccc(NC3COC3)cc21] |
| 365 | 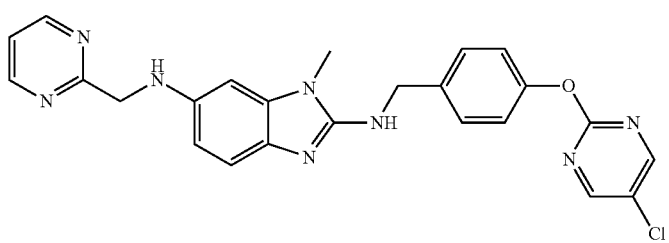 [SMILES: Cn1c(NCc2ccc(Oc3ncc(Cl)cn3)cc2)nc2ccc(NCc3ncccn3)cc21] |

-continued
| | |
|---|---|
| 366 | 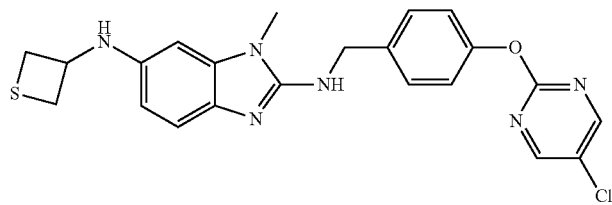 [SMILES: Cn1c(NCc2ccc(Oc3ncc(Cl)cn3)cc2)nc2ccc(NC3CSC3)cc21] |
| 367 | 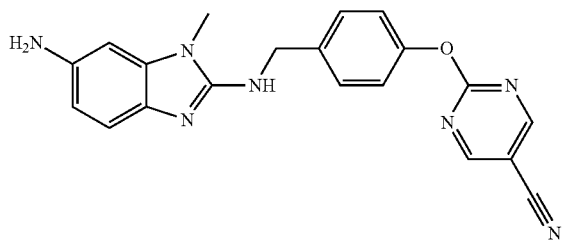 [SMILES: Cn1c(NCc2ccc(Oc3ncc(C#N)cn3)cc2)nc2ccc(N)cc21] |
| 368 | 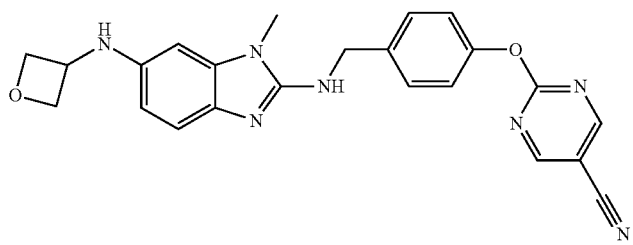 |
| 369 | 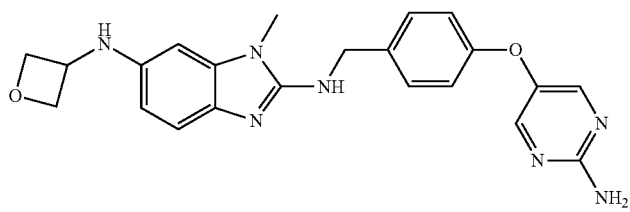 [SMILES: Cn1c(NCc2ccc(Oc3cnc(N)nc3)cc2)nc2ccc(NC3COC3)cc21] |
| 370 | 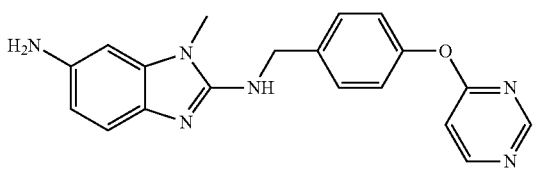 [SMILES: Cn1c(NCc2ccc(Oc3ccncn3)cc2)nc2ccc(N)cc21] |
| 371 | 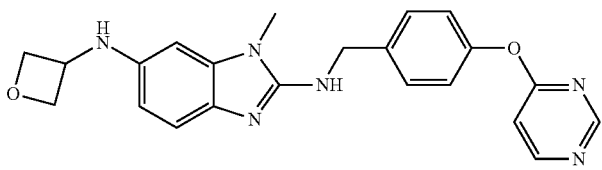 [SMILES: Cn1c(NCc2ccc(Oc3ccncn3)cc2)nc2ccc(NC3COC3)cc21] |
| 372 | 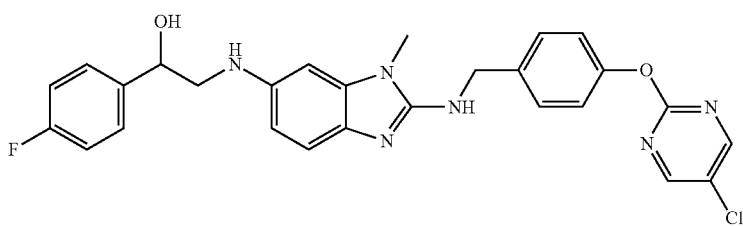 |

373 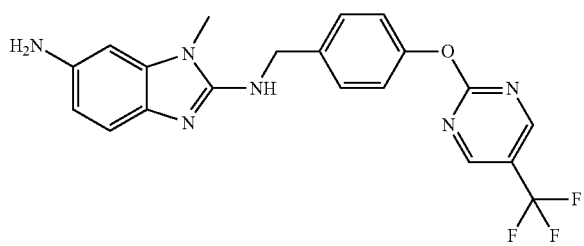
374 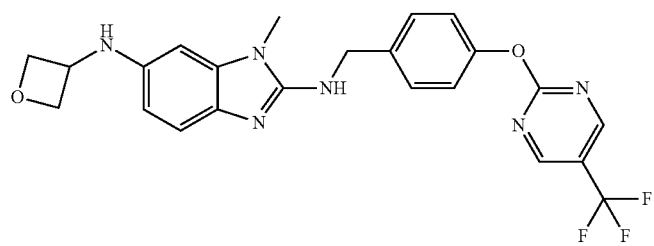
375 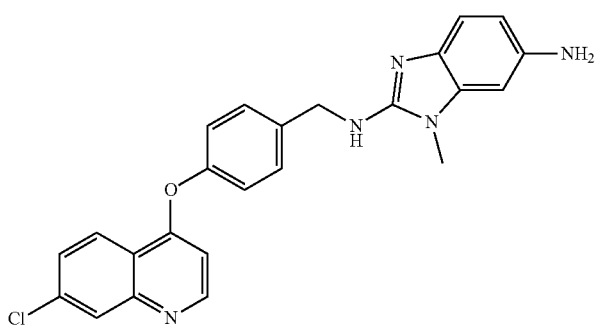 [SMILES: Cn1c(NCc2ccc(Oc3ccnc4cc(Cl)ccc34)cc2)nc2ccc(N)cc21]
376 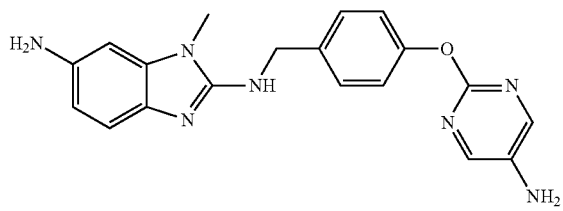
377 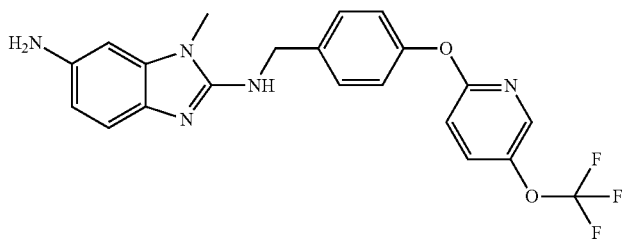 [SMILES: Cn1c(NCc2ccc(Oc3ccc(OC(F)(F)F)cn3)cc2)nc2ccc(N)cc21]
378 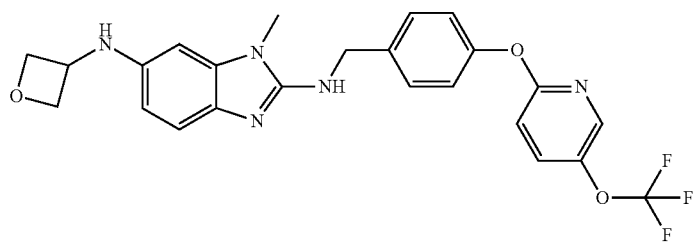

-continued
379 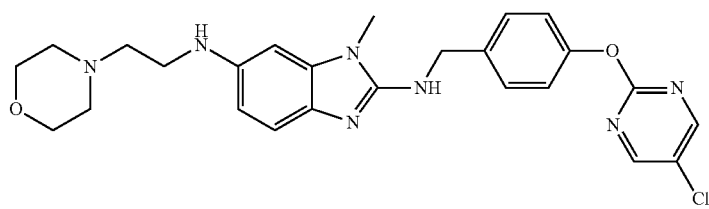 [SMILES: Cn1c(NCc2ccc(Oc3ncc(Cl)cn3)cc2)nc2ccc(NCCN3CCOCC3)cc21]
380 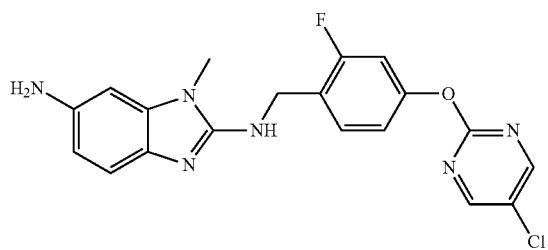 [SMILES: Cn1c(NCc2ccc(Oc3ncc(Cl)cn3)cc2F)nc2ccc(N)cc21]
381 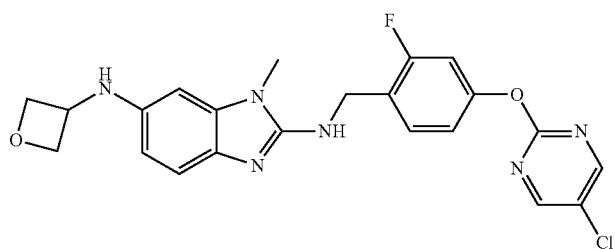
382 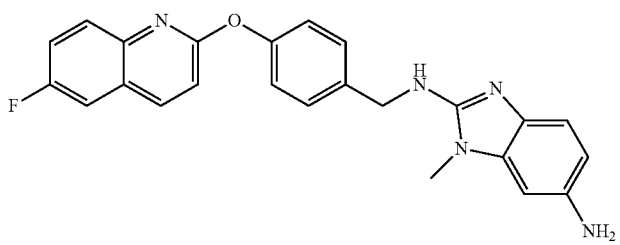 [SMILES: Cn1c(NCc2ccc(Oc3ccc4cc(F)ccc4n3)cc2)nc2ccc(N)cc21]
383 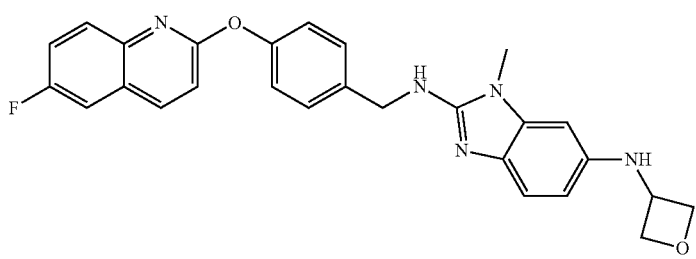 [SMILES: Cn1c(NCc2ccc(Oc3ccc4cc(F)ccc4n3)cc2)nc2ccc(NC3COC3)cc21]
384 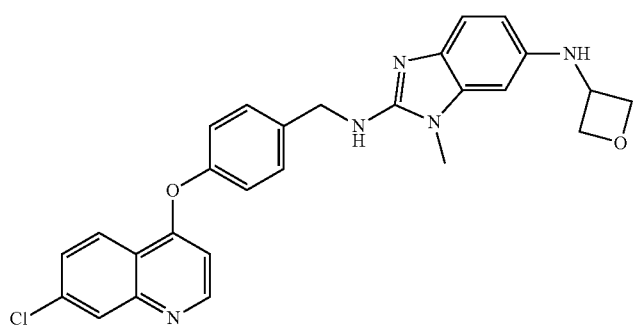 [SMILES: Cn1c(NCc2ccc(Oc3ccnc4cc(Cl)ccc34)cc2)nc2ccc(NC3COC3)cc21]

-continued
| | |
|---|---|
| 385 | 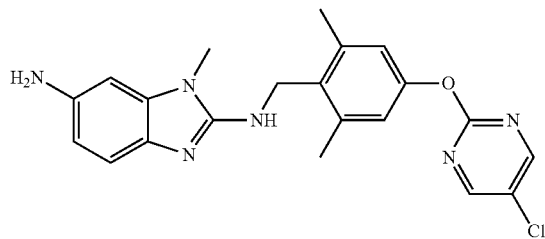 [SMILES: Cc1cc(Oc2ncc(Cl)cn2)cc(C)c1CNc1nc2ccc(N)cc2n1C] |
| 386 | 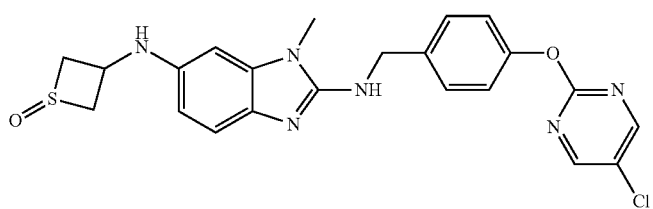 [SMILES: Cn1c(NCc2ccc(Oc3ncc(Cl)cn3)cc2)nc2ccc(NC3CS(=O)C3)cc21] |
| 387 | 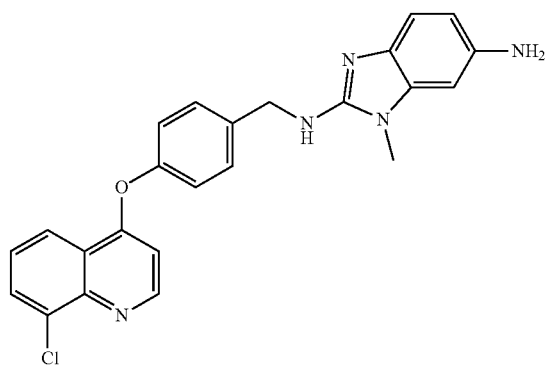 [SMILES: Cn1c(NCc2ccc(Oc3ccnc4c(Cl)cccc34)cc2)nc2ccc(N)cc21] |
| 388 | 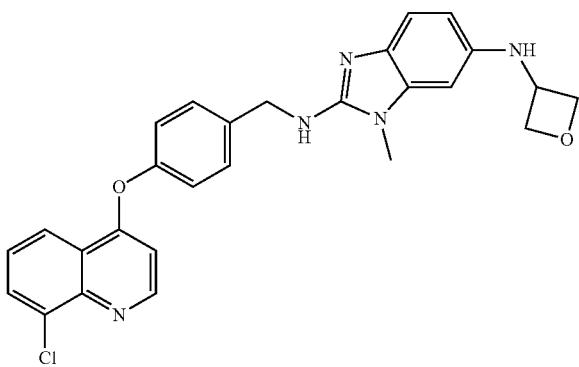 [SMILES: Cn1c(NCc2ccc(Oc3ccnc4c(Cl)cccc34)cc2)nc2ccc(NC3COC3)cc21] |
| 389 | 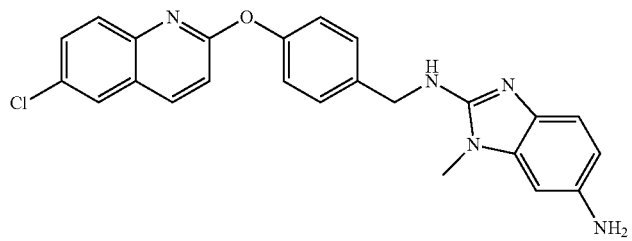 [SMILES: Cn1c(NCc2ccc(Oc3ccc4cc(Cl)ccc4n3)cc2)nc2ccc(N)cc21] |

| | |
|---|---|
| 390 | 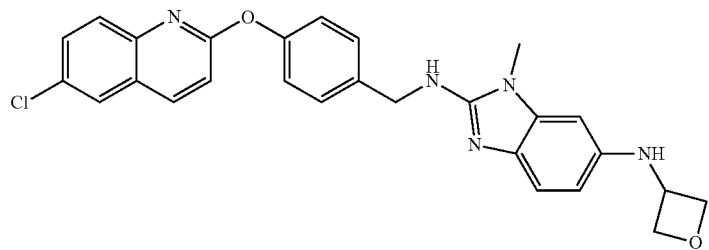 [SMILES: Cn1c(NCc2ccc(Oc3ccc4cc(Cl)ccc4n3)cc2)nc2ccc(NC3COC3)cc21] |
| 391 | 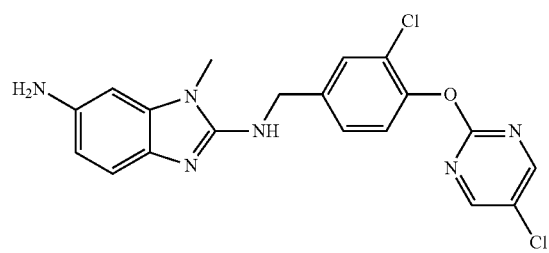 [SMILES: Cn1c(NCc2ccc(Oc3ncc(Cl)cn3)c(Cl)c2)nc2ccc(N)cc21] |
| 392 | 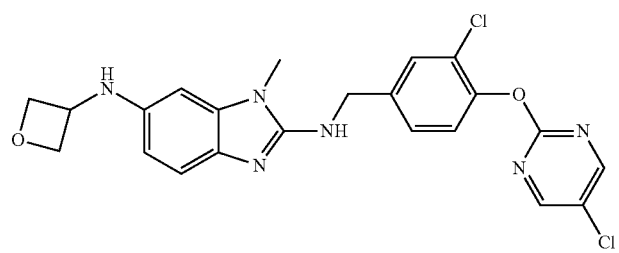 [SMILES: Cn1c(NCc2ccc(Oc3ncc(Cl)cn3)c(Cl)c2)nc2ccc(NC3COC3)cc21] |
| 393 | 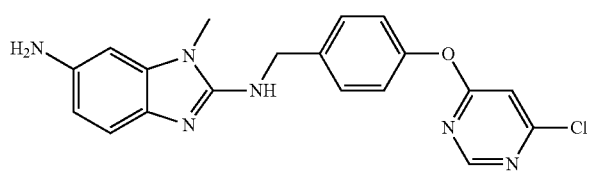 [SMILES: Cn1c(NCc2ccc(Oc3cc(Cl)ncn3)cc2)nc2ccc(N)cc21] |
| 394 | 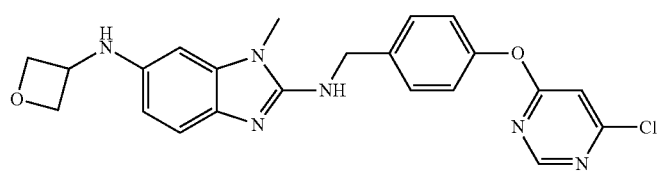 [SMILES: Cn1c(NCc2ccc(Oc3cc(Cl)ncn3)cc2)nc2ccc(NC3COC3)cc21] |
| 395 | 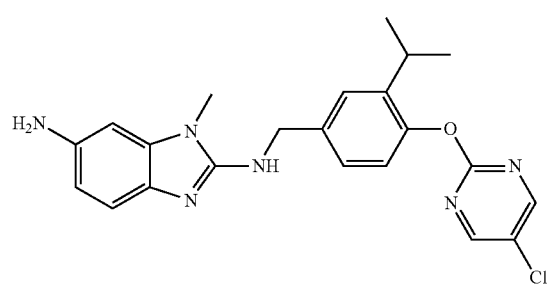 [SMILES: CC(C)c1cc(CNc2nc3ccc(N)cc3n2C)ccc1Oc1ncc(Cl)cn1] |

-continued
| | |
|---|---|
| 396 | 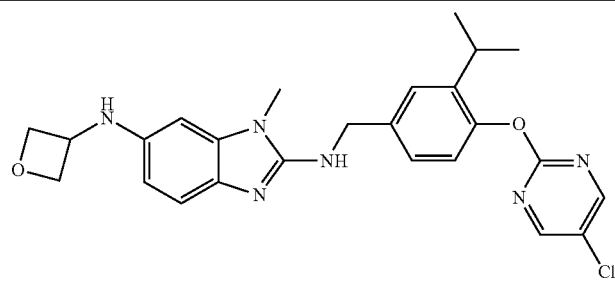 |
| 397 | 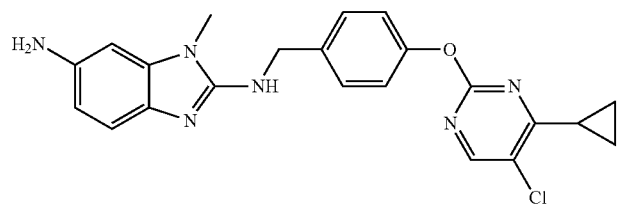 [SMILES: Cn1c(NCc2ccc(Oc3ncc(Cl)c(C4CC4)n3)cc2)nc2ccc(N)cc21] |
| 398 | 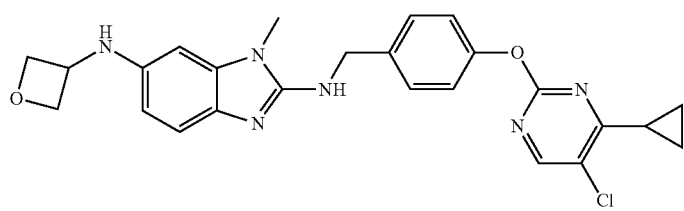 [SMILES: Cn1c(NCc2ccc(Oc3ncc(Cl)c(C4CC4)n3)cc2)nc2ccc(NC3COC3)cc21] |
| 399 | 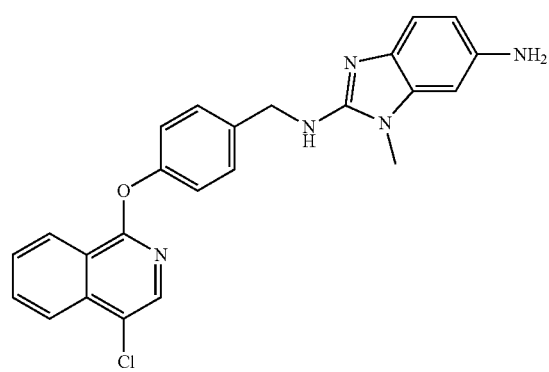 [SMILES: Cn1c(NCc2ccc(Oc3ncc(Cl)c4ccccc34)cc2)nc2ccc(N)cc21] |
| 400 | 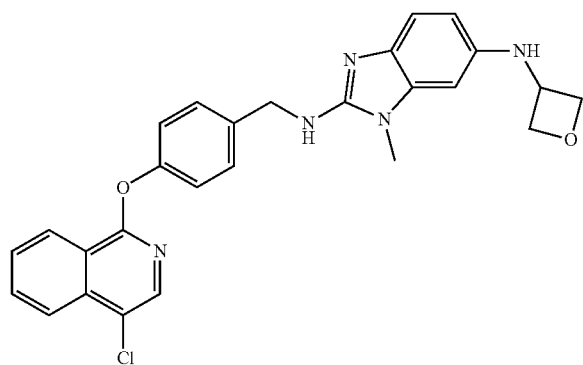 [SMILES: Cn1c(NCc2ccc(Oc3ncc(Cl)c4ccccc34)cc2)nc2ccc(NC3COC3)cc21] |
| 401 | 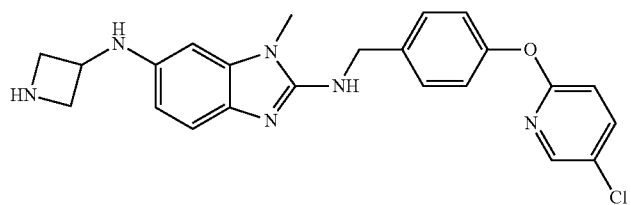 [SMILES: Cn1c(NCc2ccc(Oc3ccc(Cl)cn3)cc2)nc2ccc(NC3CNC3)cc21] |

402 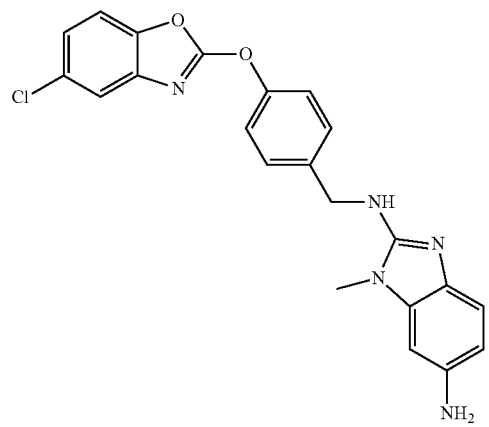 [SMILES: Cn1c(NCc2ccc(Oc3nc4cc(Cl)ccc4o3)cc2)nc2ccc(N)cc21]
403 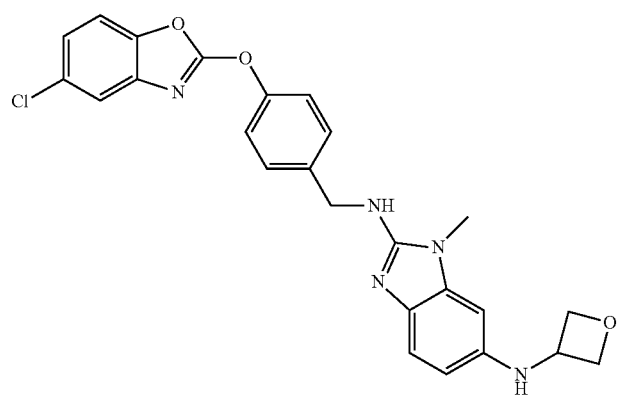 [SMILES: Cn1c(NCc2ccc(Oc3nc4cc(Cl)ccc4o3)cc2)nc2ccc(NC3COC3)cc21]
404 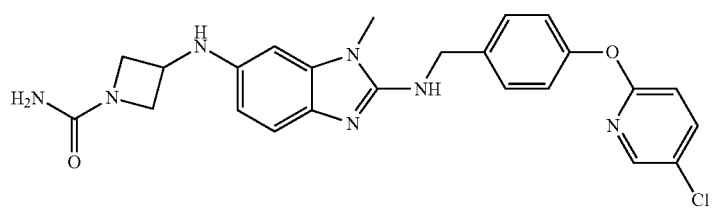 [SMILES: Cn1c(NCc2ccc(Oc3ccc(Cl)cn3)cc2)nc2ccc(NC3CN(C(N)=O)C3)cc21]
405 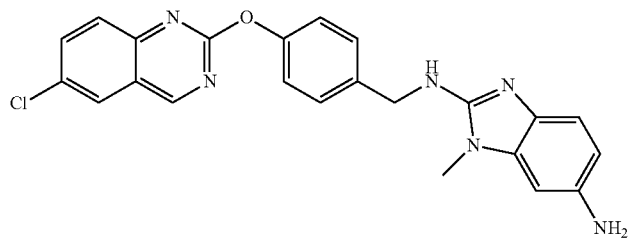 [SMILES: Cn1c(NCc2ccc(Oc3ncc4cc(Cl)ccc4n3)cc2)nc2ccc(N)cc21]
406 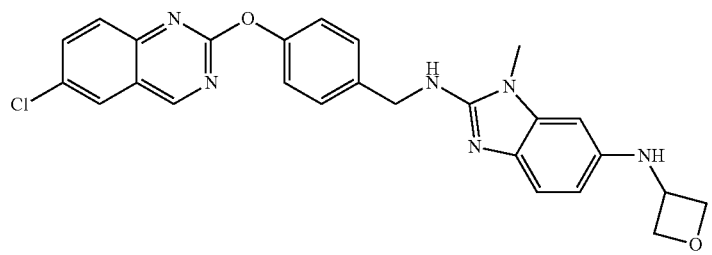 [SMILES: Cn1c(NCc2ccc(Oc3ncc4cc(Cl)ccc4n3)cc2)nc2ccc(NC3COC3)cc21]

-continued
| | |
|---|---|
| 407 | 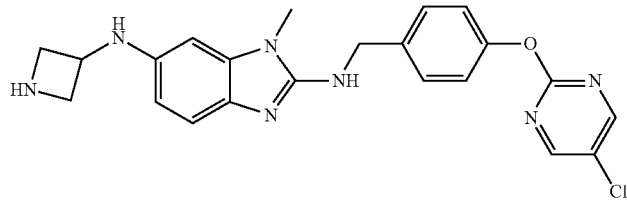 [SMILES: Cn1c(NCc2ccc(Oc3ncc(Cl)cn3)cc2)nc2ccc(NC3CNC3)cc21] |
| 408 | 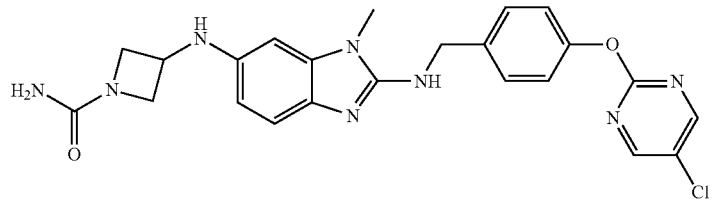 |
| 409 | 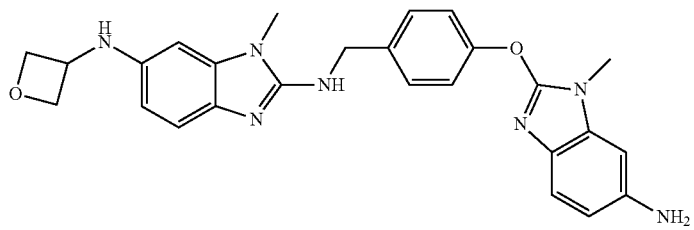 [SMILES: Cn1c(NCc2ccc(Oc3nc4ccc(N)cc4n3C)cc2)nc2ccc(NC3COC3)cc21] |
| 410 | 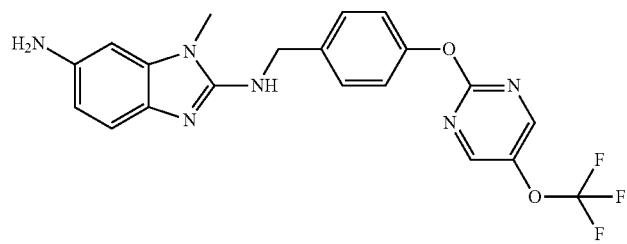 [SMILES: Cn1c(NCc2ccc(Oc3ncc(OC(F)(F)F)cn3)cc2)nc2ccc(N)cc21] |
| 411 | 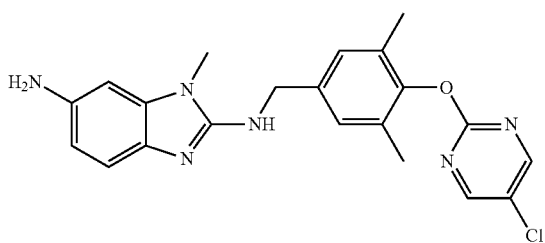 [SMILES: Cc1cc(CNc2nc3ccc(N)cc3n2C)cc(C)c1Oc1ncc(Cl)cn1] |
| 412 | 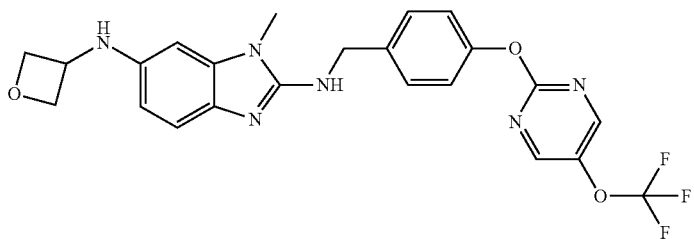 |
| 413 | 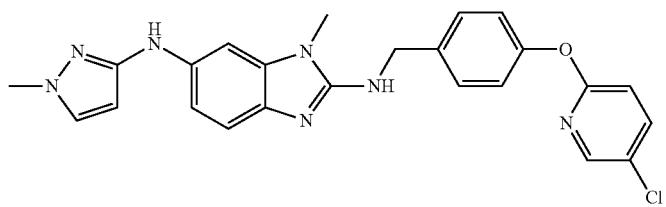 [SMILES: Cn1ccc(Nc2ccc3nc(NCc4ccc(Oc5ccc(Cl)cn5)cc4)n(C)c3c2)n1] |

-continued
| 414 | 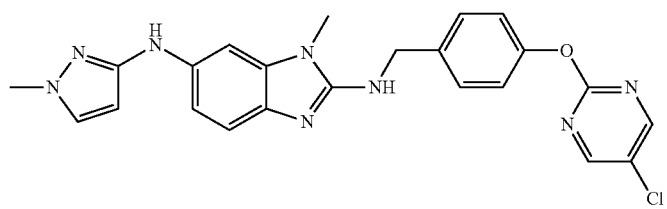 [SMILES: Cn1ccc(Nc2ccc3nc(NCc4ccc(Oc5ncc(Cl)cn5)cc4)n(C)c3c2)n1] |
| 415 | 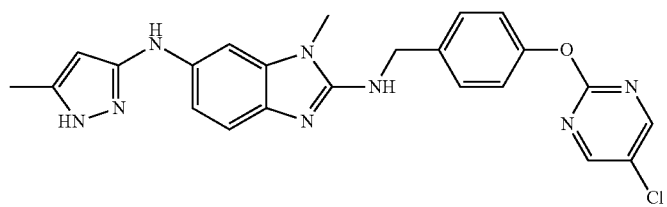 |
| 416 | 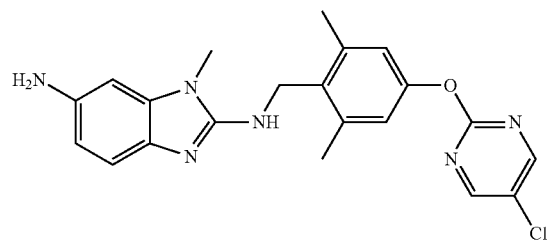 |
| 417 | 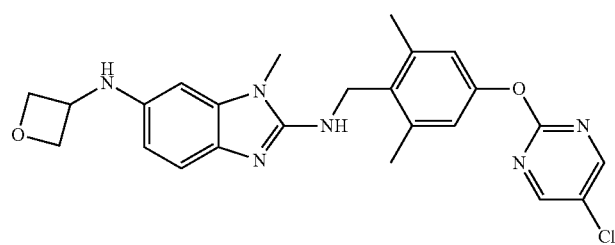 |
| 418 | 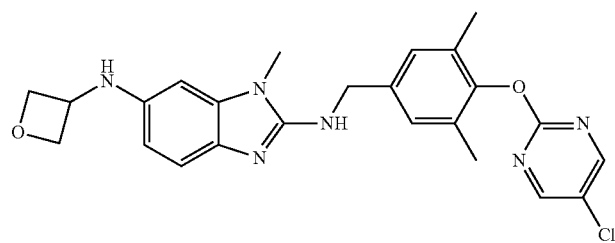 [SMILES: Cc1cc(CNc2nc3ccc(NC4COC4)cc3n2C)cc(C)c1Oc1ncc(Cl)cn1] |
| 419 | 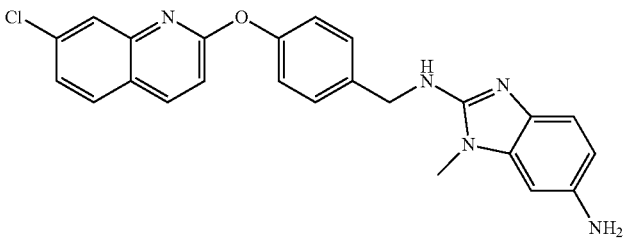 [SMILES: Cn1c(NCc2ccc(Oc3ccc4ccc(Cl)cc4n3)cc2)nc2ccc(N)cc21] |

-continued
| 420 | 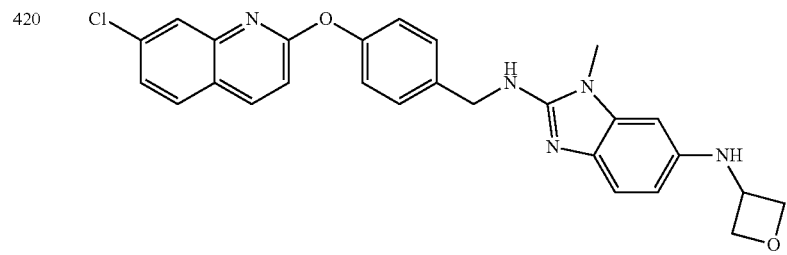 |
| --- | --- |
| 421 | 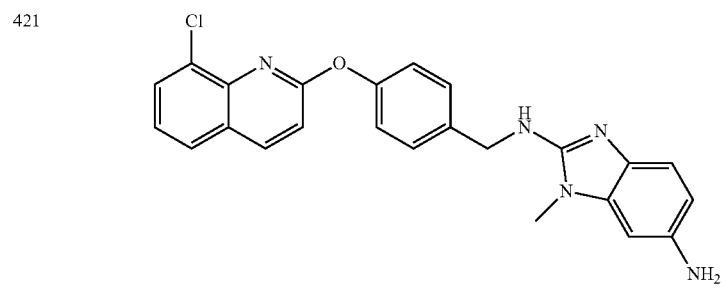 |
| 422 | 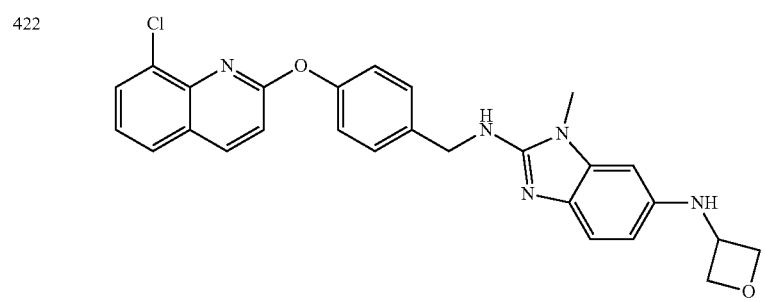 |
| 423 | 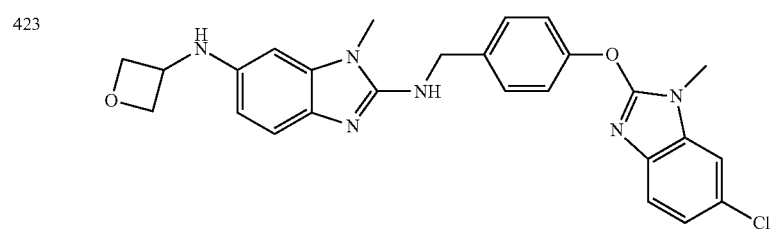 |
| 424 | 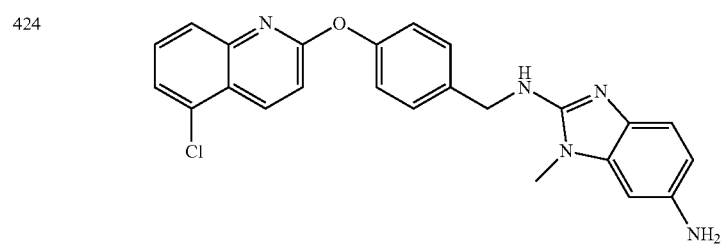 |
| 425 | 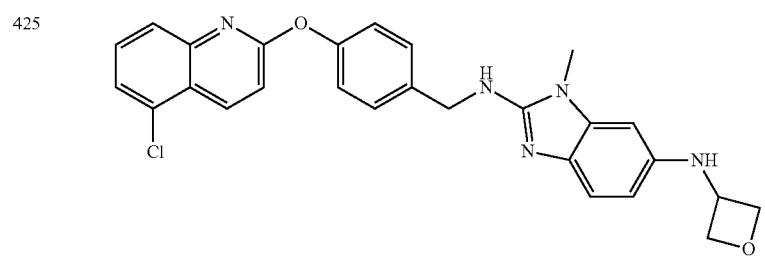 |

| | |
|---|---|
| 426 | 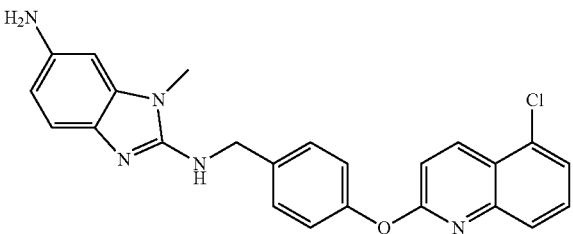 [SMILES: Cn1c(NCc2ccc(Oc3ccc4c(Cl)cccc4n3)cc2)nc2ccc(N)cc21] |
| 427 | 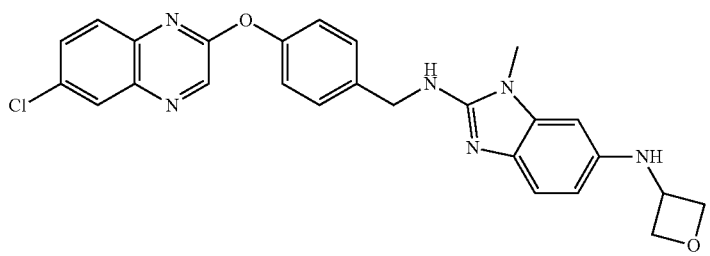 [SMILES: Cn1c(NCc2ccc(Oc3cnc4cc(Cl)ccc4n3)cc2)nc2ccc(NC3COC3)cc21] |
| 428 | 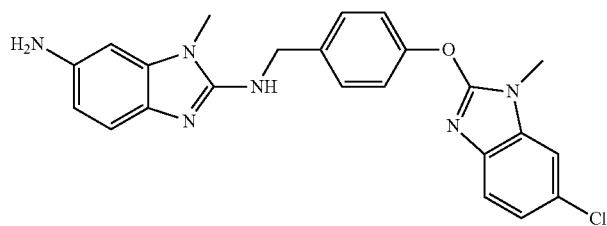 [SMILES: Cn1c(NCc2ccc(Oc3nc4ccc(Cl)cc4n3C)cc2)nc2ccc(N)cc21] |
| 429 | 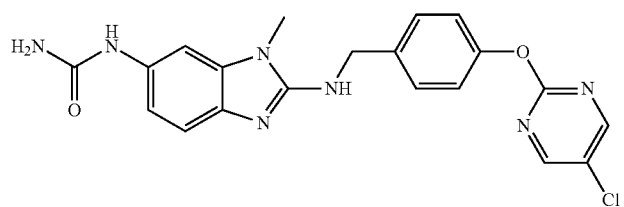 [SMILES: Cn1c(NCc2ccc(Oc3ncc(Cl)cn3)cc2)nc2ccc(NC(N)=O)cc21] |
| 430 | 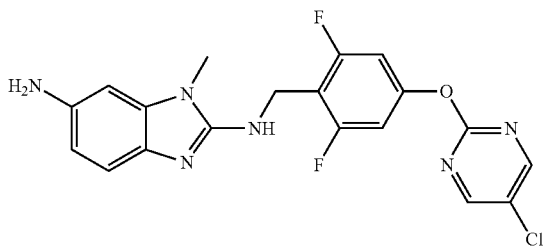 [SMILES: Cn1c(NCc2c(F)cc(Oc3ncc(Cl)cn3)cc2F)nc2ccc(N)cc21] |
| 431 | 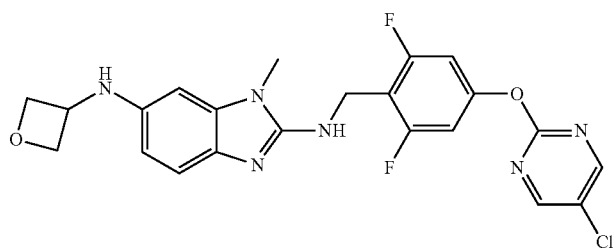 [SMILES: Cn1c(NCc2c(F)cc(Oc3ncc(Cl)cn3)cc2F)nc2ccc(NC3COC3)cc21] |

-continued
432
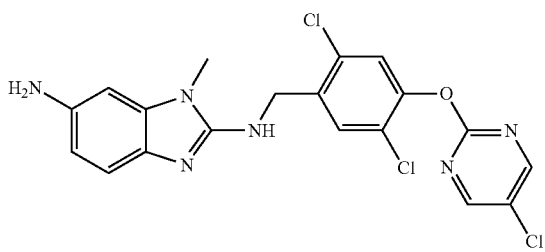 [SMILES: Cn1c(NCc2cc(Cl)c(Oc3ncc(Cl)cn3)cc2Cl)nc2ccc(N)cc21]
433
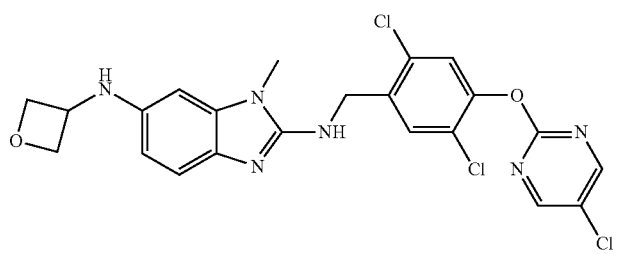
434
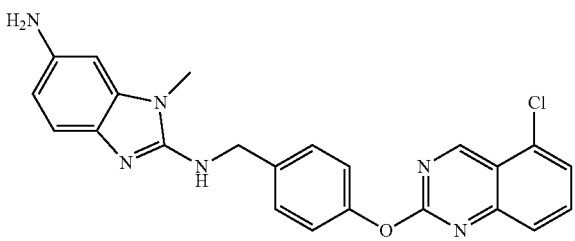 [SMILES: Cn1c(NCc2ccc(Oc3ncc4c(Cl)cccc4n3)cc2)nc2ccc(N)cc21]
435
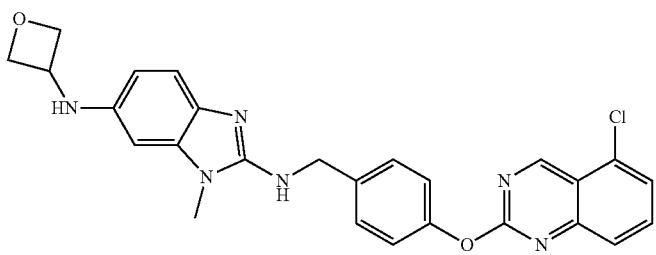 [SMILES: Cn1c(NCc2ccc(Oc3ncc4c(Cl)cccc4n3)cc2)nc2ccc(NC3COC3)cc21]
436
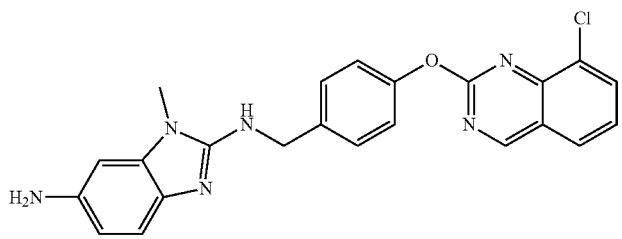 [SMILES: Cn1c(NCc2ccc(Oc3ncc4cccc(Cl)c4n3)cc2)nc2ccc(N)cc21]
437
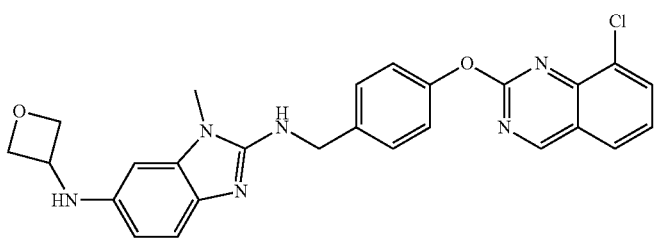 [SMILES: Cn1c(NCc2ccc(Oc3ncc4cccc(Cl)c4n3)cc2)nc2ccc(NC3COC3)cc21]

-continued
438
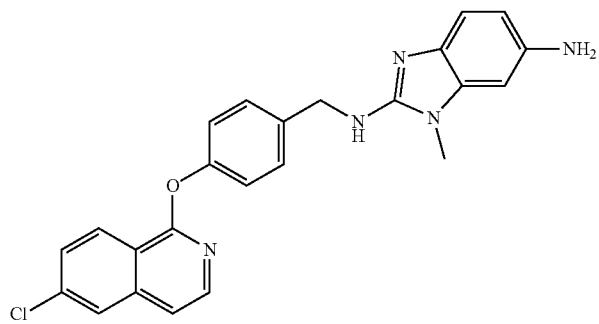
439
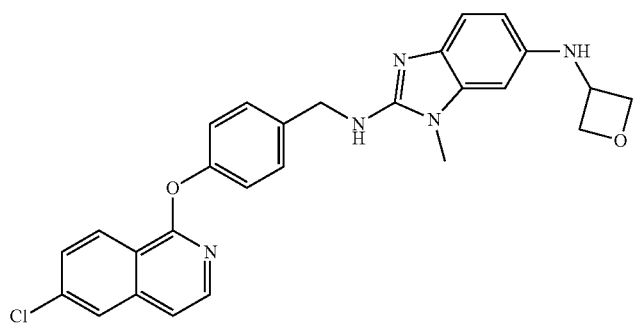 [SMILES: Cn1c(NCc2ccc(Oc3nccc4cc(Cl)ccc34)cc2)nc2ccc(NC3COC3)cc21]
440
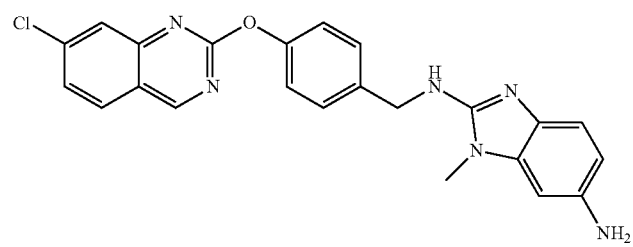
441
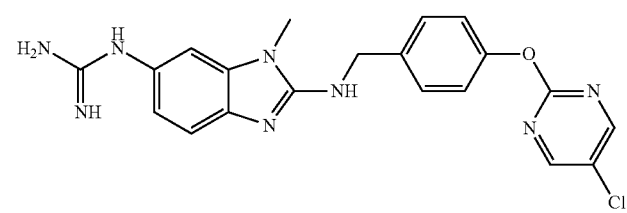 [SMILES: Cn1c(NCc2ccc(Oc3ncc(Cl)cn3)cc2)nc2ccc(NC(=N)N)cc21]
442
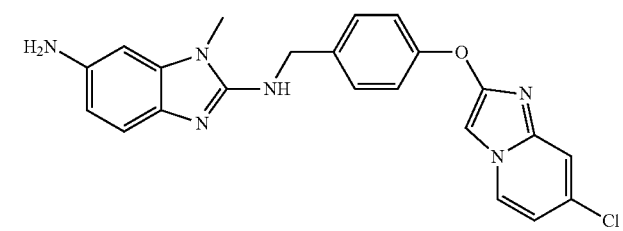 [SMILES: Cn1c(NCc2ccc(Oc3cn4ccc(Cl)cc4n3)cc2)nc2ccc(N)cc21]
443
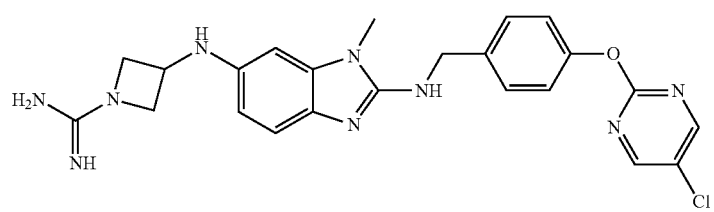 [SMILES: Cn1c(NCc2ccc(Oc3ncc(Cl)cn3)cc2)nc2ccc(NC3CN(C(=N)N)C3)cc21]

444 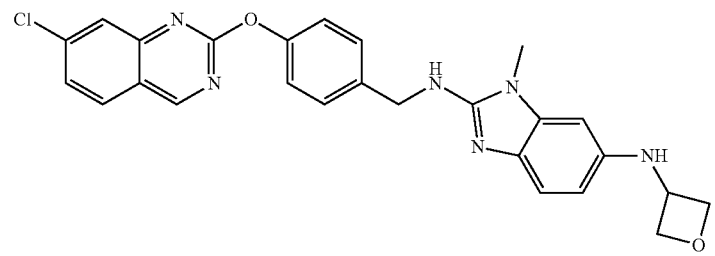
445 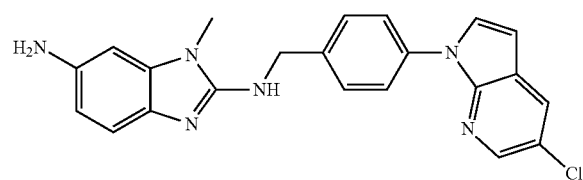 [SMILES: Cn1c(NCc2ccc(-n3ccc4cc(Cl)cnc43)cc2)nc2ccc(N)cc21]
446 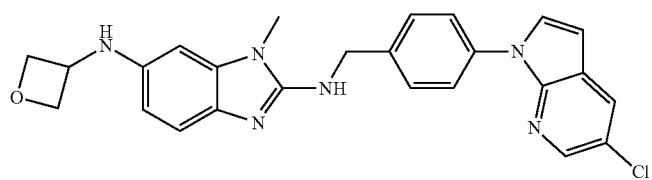 [SMILES: Cn1c(NCc2ccc(-n3ccc4cc(Cl)cnc43)cc2)nc2ccc(NC3COC3)cc21]
447 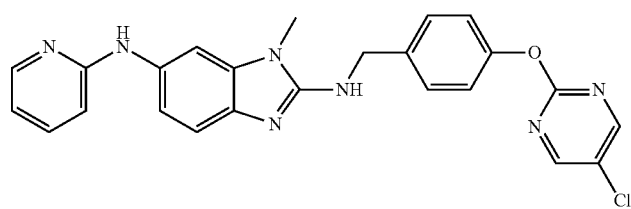
448 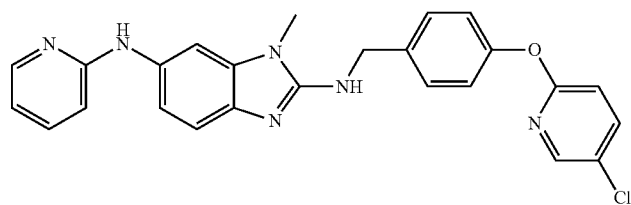
449 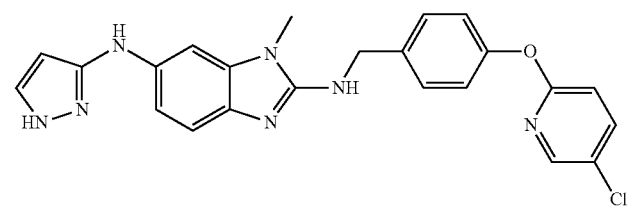 [SMILES: Cn1c(NCc2ccc(Oc3ccc(Cl)cn3)cc2)nc2ccc(Nc3cc[nH]n3)cc21]
450 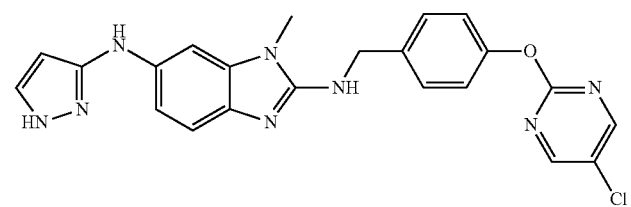 [SMILES: Cn1c(NCc2ccc(Oc3ncc(Cl)cn3)cc2)nc2ccc(Nc3cc[nH]n3)cc21]

451 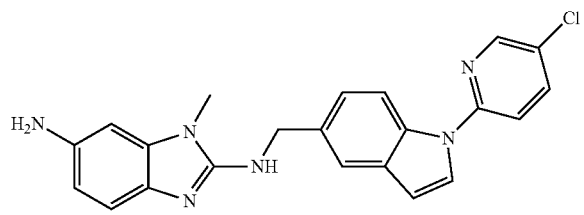 [SMILES: Cn1c(NCc2ccc3c(ccn3-c3ccc(Cl)cn3)c2)nc2ccc(N)cc21]
452 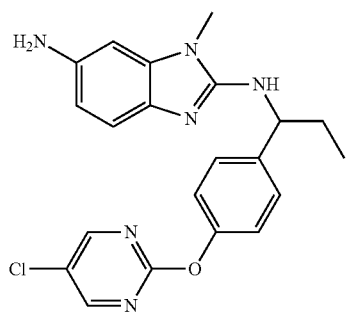 [SMILES: CCC(Nc1nc2ccc(N)cc2n1C)c1ccc(Oc2ncc(Cl)cn2)cc1]
453 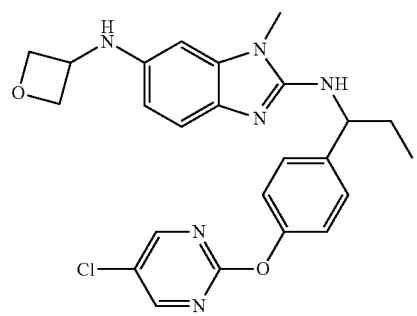 [SMILES: CCC(Nc1nc2ccc(NC3COC3)cc2n1C)c1ccc(Oc2ncc(Cl)cn2)cc1]
454 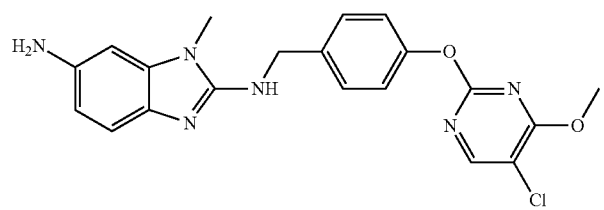 [SMILES: COc1nc(Oc2ccc(CNc3nc4ccc(N)cc4n3C)cc2)ncc1Cl]
455 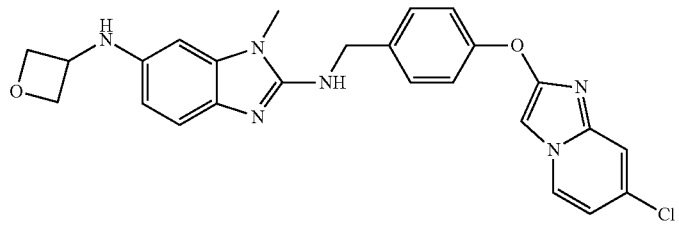 [SMILES: Cn1c(NCc2ccc(Oc3cn4ccc(Cl)cc4n3)cc2)nc2ccc(NC3COC3)cc21]
456 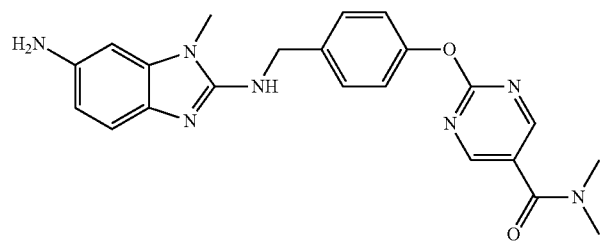

| | |
|---|---|
| 457 | 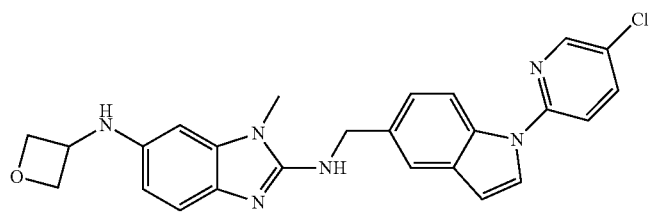 [SMILES: Cn1c(NCc2ccc3c(ccn3-c3ccc(Cl)cn3)c2)nc2ccc(NC3COC3)cc21] |
| 458 | 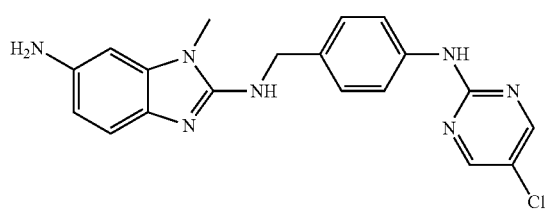 |
| 459 | 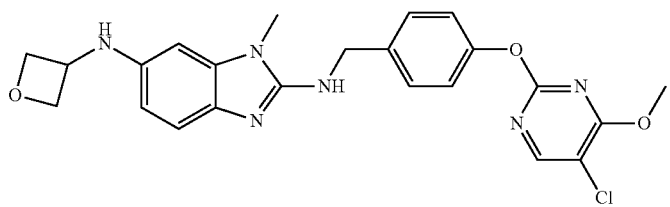 |
| 460 | 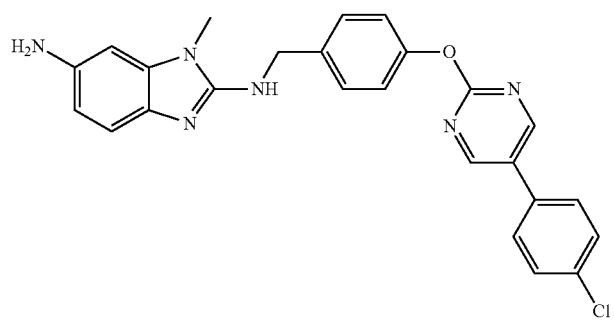 [SMILES: Cn1c(NCc2ccc(Oc3ncc(-c4ccc(Cl)cc4)cn3)cc2)nc2ccc(N)cc21] |
| 461 | 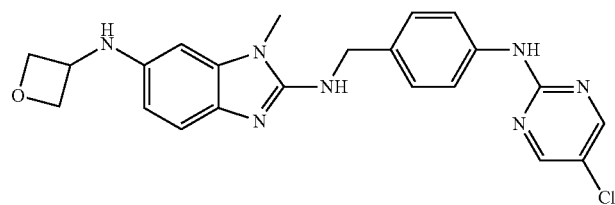 [SMILES: Cn1c(NCc2ccc(Nc3ncc(Cl)cn3)cc2)nc2ccc(NC3COC3)cc21] |
| 462 | 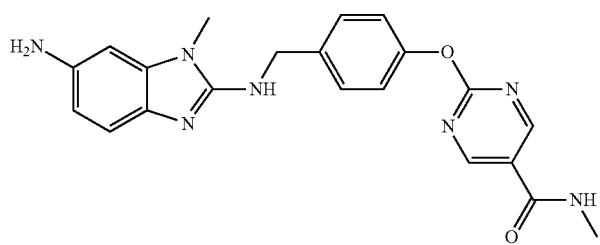 [SMILES: CNC(=O)c1cnc(Oc2ccc(CNc3nc4ccc(N)cc4n3C)cc2)nc1] |

| | |
|---|---|
| 463 | 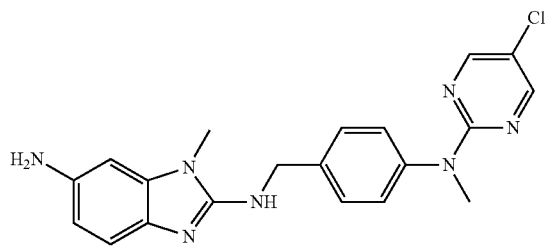 [SMILES: CN(c1ccc(CNc2nc3ccc(N)cc3n2C)cc1)c1ncc(Cl)cn1] |
| 464 | 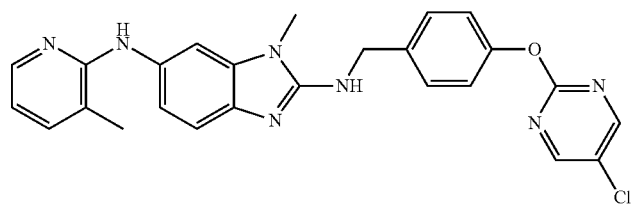 |
| 465 | 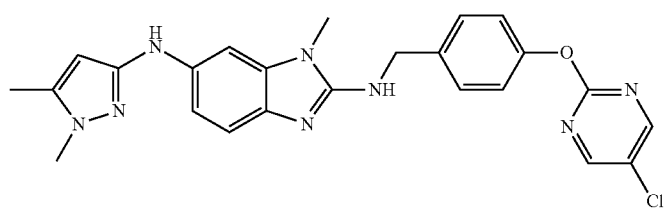 [SMILES: Cc1cc(Nc2ccc3nc(NCc4ccc(Oc5ncc(Cl)cn5)cc4)n(C)c3c2)nn1C] |
| 466 | 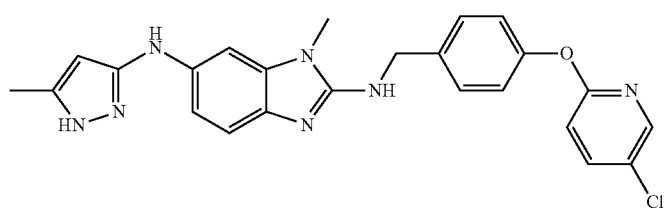 [SMILES: Cc1cc(Nc2ccc3nc(NCc4ccc(Oc5ccc(Cl)cn5)cc4)n(C)c3c2)n[nH]1] |
| 467 | 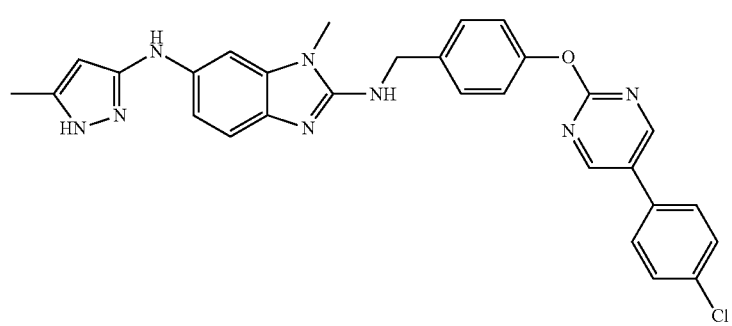 [SMILES: Cc1cc(Nc2ccc3nc(NCc4ccc(Oc5ncc(-c6ccc(Cl)cc6)cn5)cc4)n(C)c3c2)n[nH]1] |
| 468 | 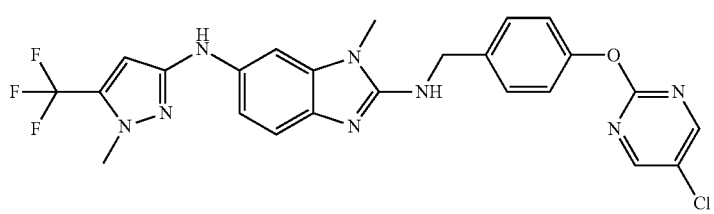 [SMILES: Cn1nc(Nc2ccc3nc(NCc4ccc(Oc5ncc(Cl)cn5)cc4)n(C)c3c2)cc1C(F)(F)F] |
| 469 | 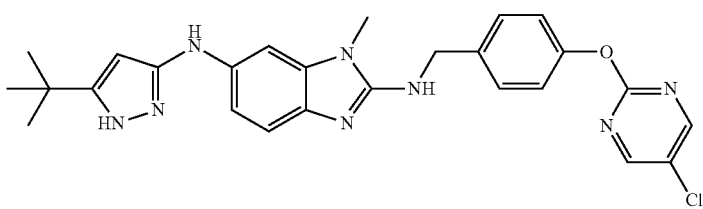 [SMILES: Cn1c(NCc2ccc(Oc3ncc(Cl)cn3)cc2)nc2ccc(Nc3cc(C(C)(C)C)[nH]n3)cc21] |

470 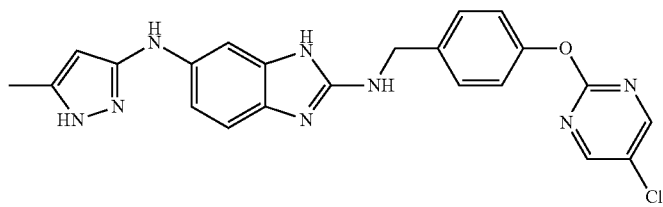 [SMILES: Cc1cc(Nc2ccc3nc(NCc4ccc(Oc5ncc(Cl)cn5)cc4)[nH]c3c2)n[nH]1]
471 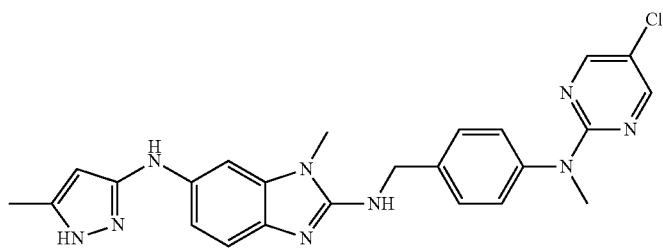 [SMILES: Cc1cc(Nc2ccc3nc(NCc4ccc(N(C)c5ncc(Cl)cn5)cc4)n(C)c3c2)n[nH]1]
472 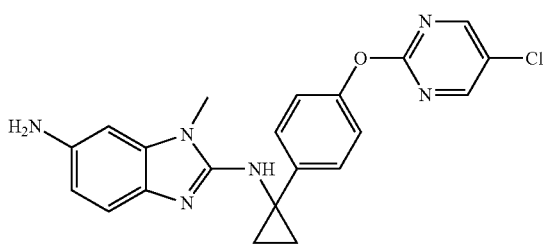 [SMILES: Cn1c(NC2(c3ccc(Oc4ncc(Cl)cn4)cc3)CC2)nc2ccc(N)cc21]
473 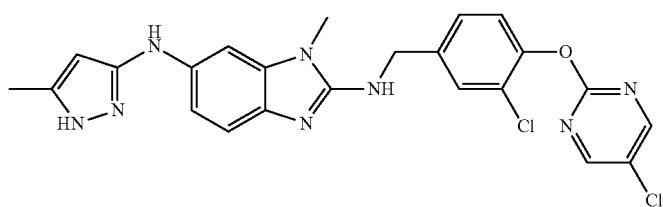 [SMILES: Cc1cc(Nc2ccc3nc(NCc4ccc(Oc5ncc(Cl)cn5)c(Cl)c4)n(C)c3c2)n[nH]1]
474 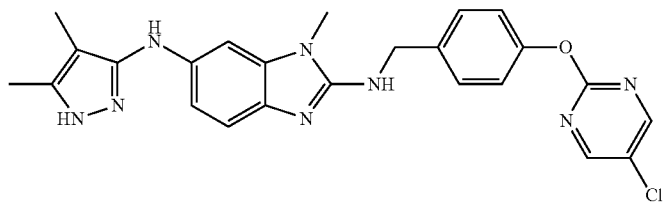 [SMILES: Cc1[nH]nc(Nc2ccc3nc(NCc4ccc(Oc5ncc(Cl)cn5)cc4)n(C)c3c2)c1C]
475 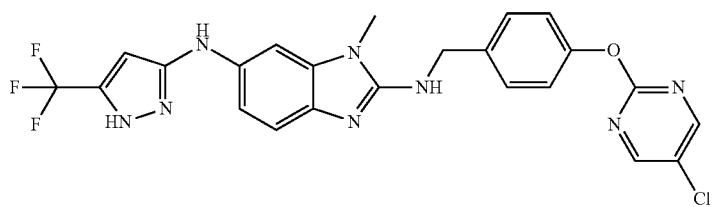 [SMILES: Cn1c(NCc2ccc(Oc3ncc(Cl)cn3)cc2)nc2ccc(Nc3cc(C(F)(F)F)[nH]n3)cc21]
476 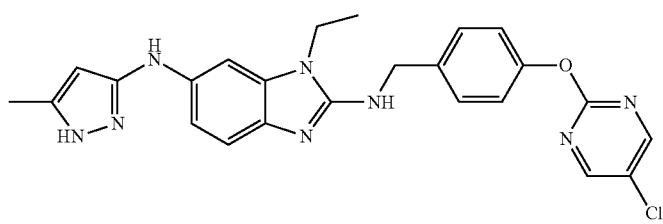 [SMILES: CCn1c(NCc2ccc(Oc3ncc(Cl)cn3)cc2)nc2ccc(Nc3cc(C)[nH]n3)cc21]

477 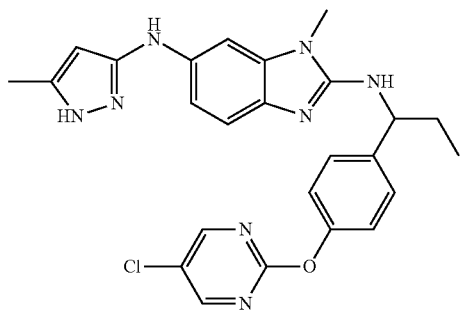 [SMILES: CCC(Nc1nc2ccc(Nc3cc(C)[nH]n3)cc2n1C)c1ccc(Oc2ncc(Cl)cn2)cc1]
478 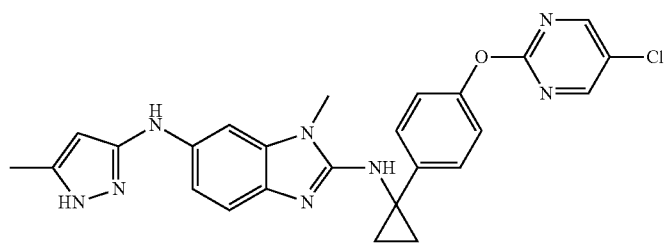 [SMILES: Cc1cc(Nc2ccc3nc(NC4(c5ccc(Oc6ncc(Cl)cn6)cc5)CC4)n(C)c3c2)n[nH]1]
479 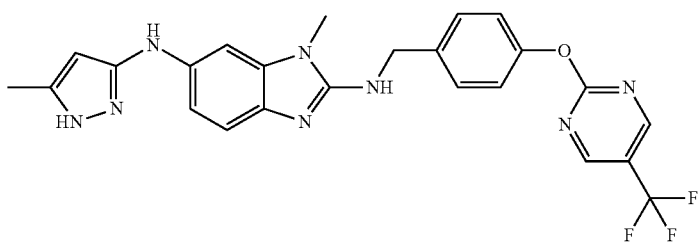
480 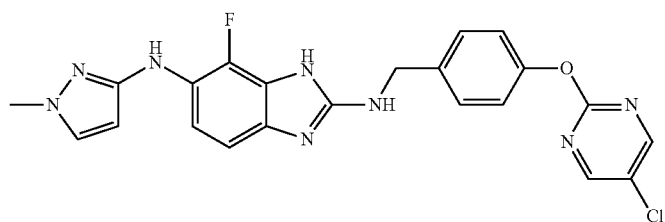 [SMILES: Cn1ccc(Nc2ccc3nc(NCc4ccc(Oc5ncc(Cl)cn5)cc4)[nH]c3c2F)n1]
481 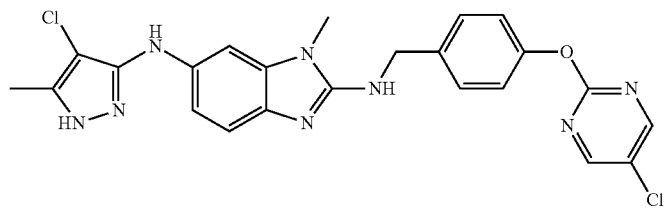
482 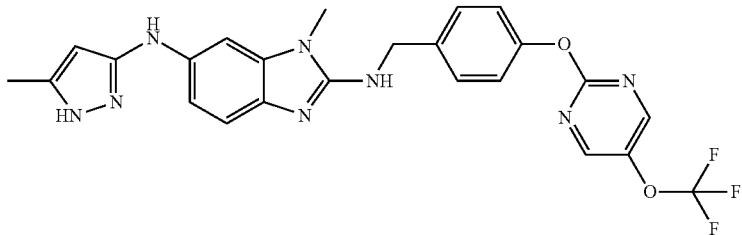

| | |
|---|---|
| 483 | 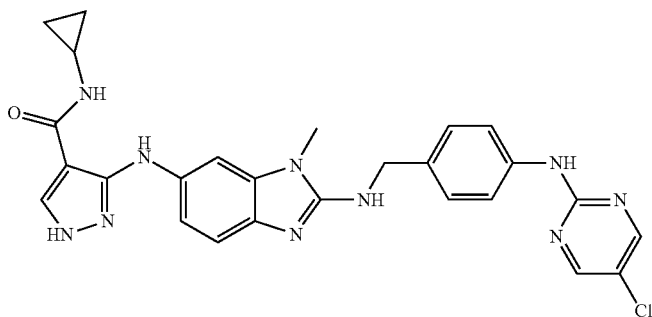 [SMILES: Cn1c(NCc2ccc(Nc3ncc(Cl)cn3)cc2)nc2ccc(Nc3n[nH]cc3C(=O)NC3CC3)cc21] |
| 484 | 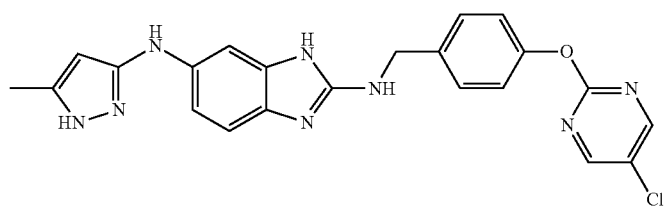 |
| 485 | 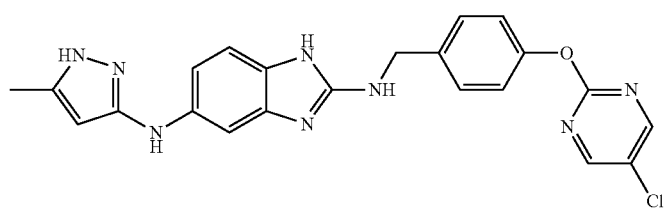 [SMILES: Cc1cc(Nc2ccc3[nH]c(NCc4ccc(Oc5ncc(Cl)cn5)cc4)nc3c2)n[nH]1] |
| 486 | 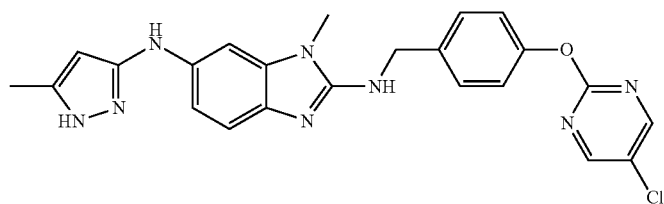 |
| 487 | 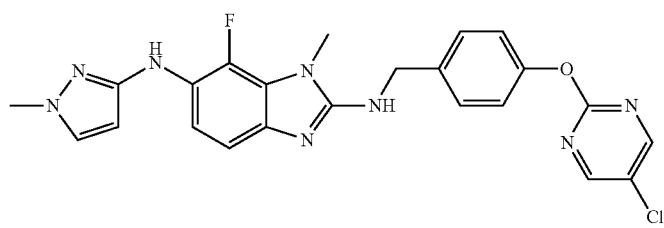 [SMILES: Cn1ccc(Nc2ccc3nc(NCc4ccc(Oc5ncc(Cl)cn5)cc4)n(C)c3c2F)n1] |
| 488 | 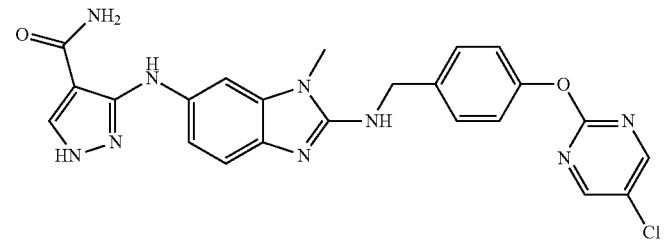 [SMILES: Cn1c(NCc2ccc(Oc3ncc(Cl)cn3)cc2)nc2ccc(Nc3n[nH]cc3C(N)=O)cc21] |
| 489 | 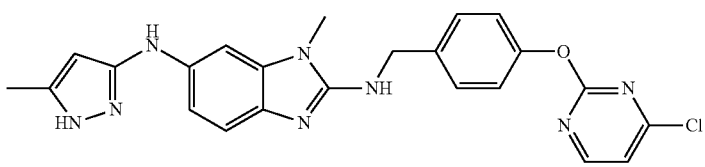 [SMILES: Cc1cc(Nc2ccc3nc(NCc4ccc(Oc5nccc(Cl)n5)cc4)n(C)c3c2)n[nH]1] |

490 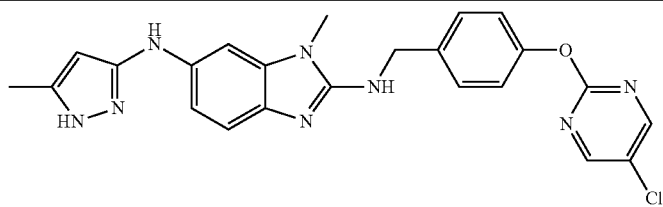
491 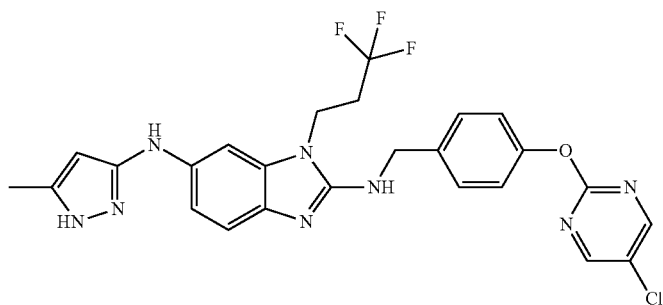 [SMILES: Cc1cc(Nc2ccc3nc(NCc4ccc(Oc5ncc(Cl)cn5)cc4)n(CCC(F)(F)F)c3c2)n[nH]1]
492 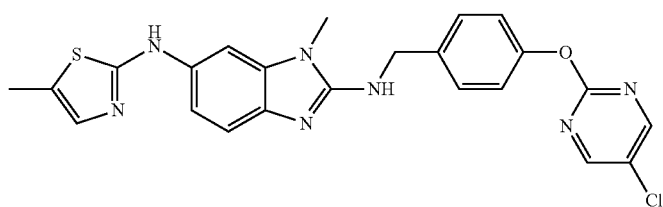 [SMILES: Cc1cnc(Nc2ccc3nc(NCc4ccc(Oc5ncc(Cl)cn5)cc4)n(C)c3c2)s1]
493 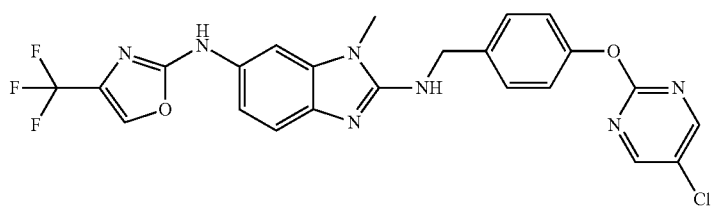 [SMILES: Cn1c(NCc2ccc(Oc3ncc(Cl)cn3)cc2)nc2ccc(Nc3nc(C(F)(F)F)co3)cc21]
494 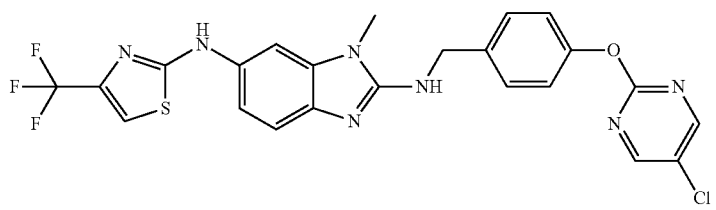 [SMILES: Cn1c(NCc2ccc(Oc3ncc(Cl)cn3)cc2)nc2ccc(Nc3nc(C(F)(F)F)cs3)cc21]
495 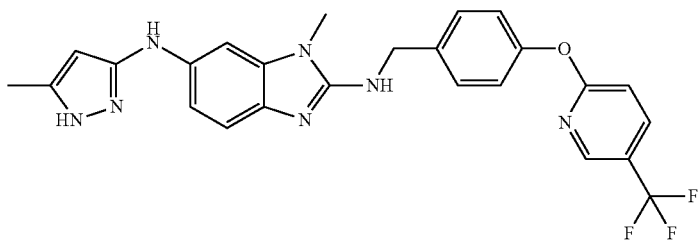 [SMILES: Cc1cc(Nc2ccc3nc(NCc4ccc(Oc5ccc(C(F)(F)F)cn5)cc4)n(C)c3c2)n[nH]1]
496 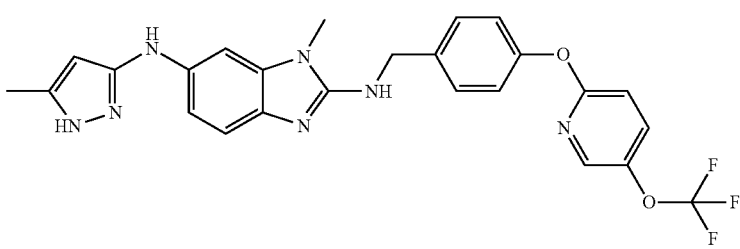 [SMILES: Cc1cc(Nc2ccc3nc(NCc4ccc(Oc5ccc(OC(F)(F)F)cn5)cc4)n(C)c3c2)n[nH]1]

497 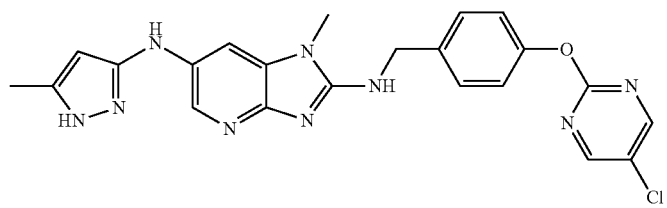 [SMILES: Cc1cc(Nc2cnc3nc(NCc4ccc(Oc5ncc(Cl)cn5)cc4)n(C)c3c2)n[nH]1]
498 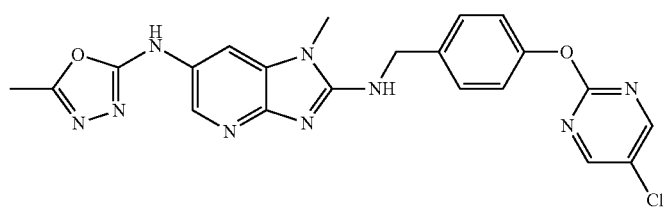 [SMILES: Cc1nnc(Nc2cnc3nc(NCc4ccc(Oc5ncc(Cl)cn5)cc4)n(C)c3c2)o1]
499 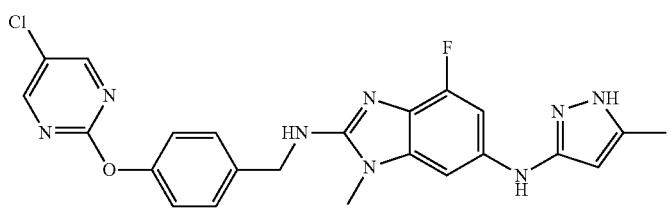 [SMILES: Cc1cc(Nc2cc(F)c3nc(NCc4ccc(Oc5ncc(Cl)cn5)cc4)n(C)c3c2)n[nH]1]
500 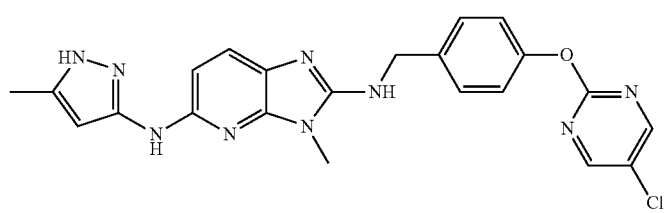 [SMILES: Cc1cc(Nc2ccc3nc(NCc4ccc(Oc5ncc(Cl)cn5)cc4)n(C)c3n2)n[nH]1]
501 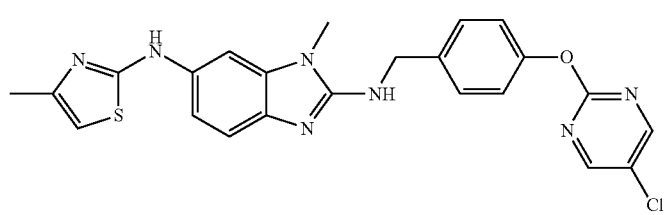 [SMILES: Cc1csc(Nc2ccc3nc(NCc4ccc(Oc5ncc(Cl)cn5)cc4)n(C)c3c2)n1]
502 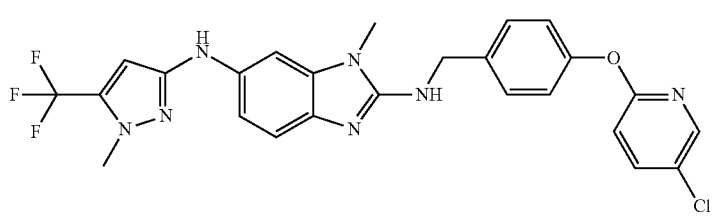
503 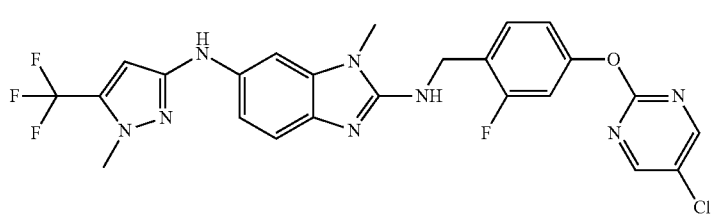 [SMILES: Cn1nc(Nc2ccc3nc(NCc4ccc(Oc5ncc(Cl)cn5)cc4F)n(C)c3c2)cc1C(F)(F)F]

504 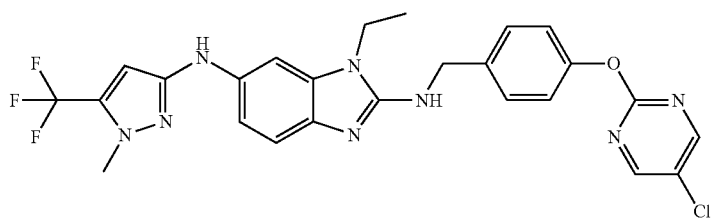
505 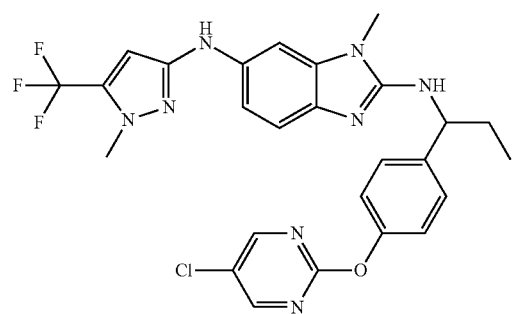
506 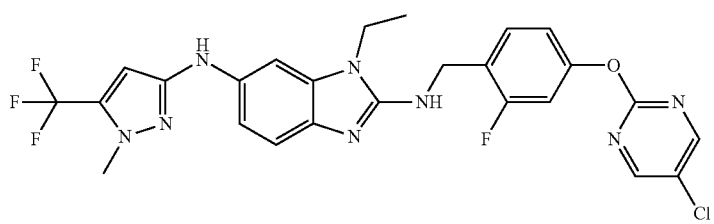 [SMILES: CCn1c(NCc2ccc(Oc3ncc(Cl)cn3)cc2)nc2ccc(Nc3cc(C(F)(F)F)n(C)n3)cc21]
507 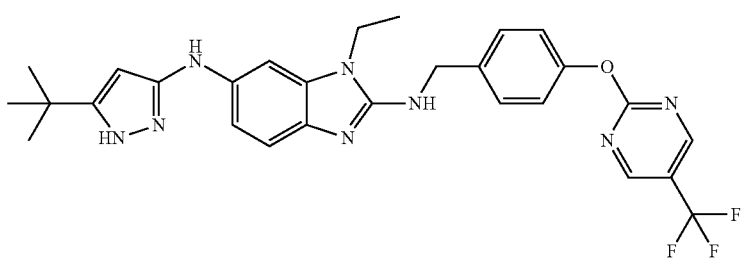 [SMILES: CCn1c(NCc2ccc(Oc3ncc(C(F)(F)F)cn3)cc2)nc2ccc(Nc3cc(C(C)(C)C)[nH]n3)cc21]
508 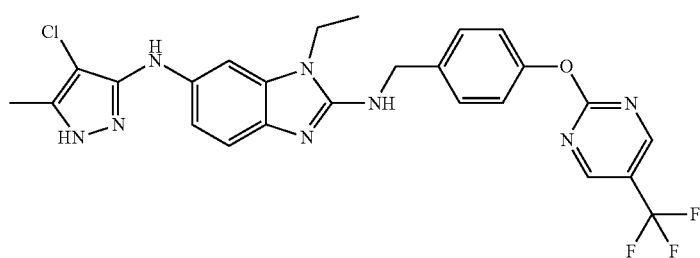 [SMILES: CCn1c(NCc2ccc(Oc3ncc(C(F)(F)F)cn3)cc2)nc2ccc(Nc3n[nH]c(C)c3Cl)cc21]
509 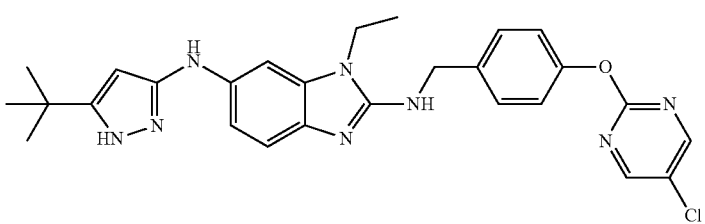 [SMILES: CCn1c(NCc2ccc(Oc3ncc(Cl)cn3)cc2)nc2ccc(Nc3cc(C(C)(C)C)[nH]n3)cc21]

-continued
510
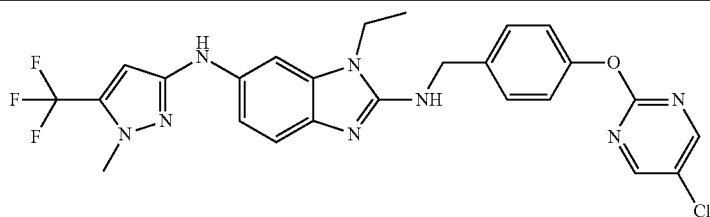
511
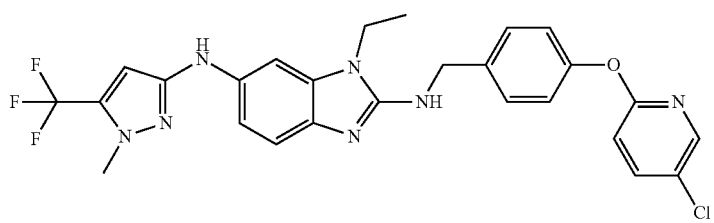
512
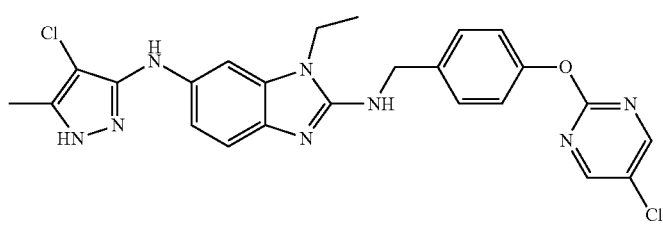 [SMILES: CCn1c(NCc2ccc(Oc3ncc(Cl)cn3)cc2)nc2ccc(Nc3n[nH]c(C)c3Cl)cc21]
513
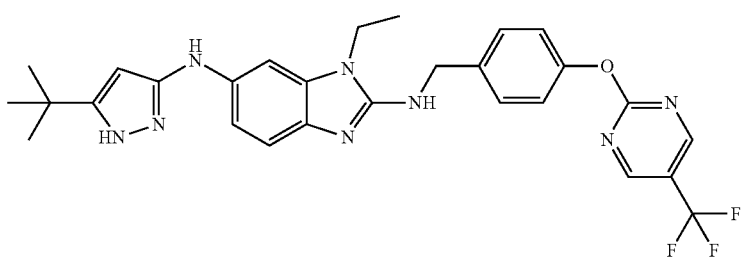 [SMILES: CCn1c(NCc2ccc(Oc3ncc(C(F)(F)F)cn3)cc2)nc2ccc(Nc3cc(C(C)(C)C)[nH]n3)cc21]
514
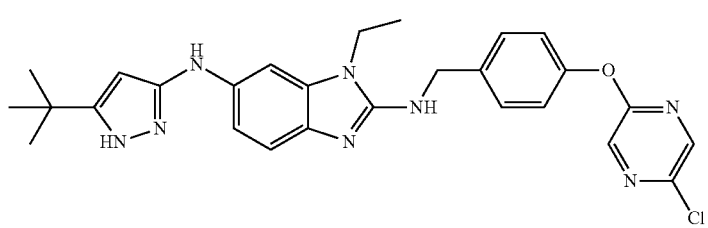 [SMILES: CCn1c(NCc2ccc(Oc3cnc(Cl)cn3)cc2)nc2ccc(Nc3cc(C(C)(C)C)[nH]n3)cc21]
515
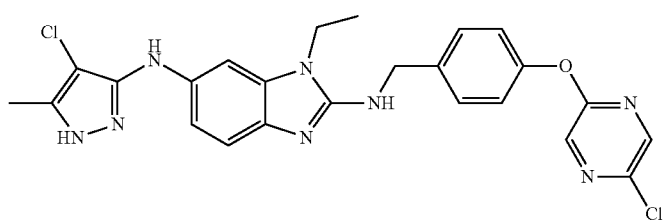 [SMILES: CCn1c(NCc2ccc(Oc3cnc(Cl)cn3)cc2)nc2ccc(Nc3n[nH]c(C)c3Cl)cc21]
516
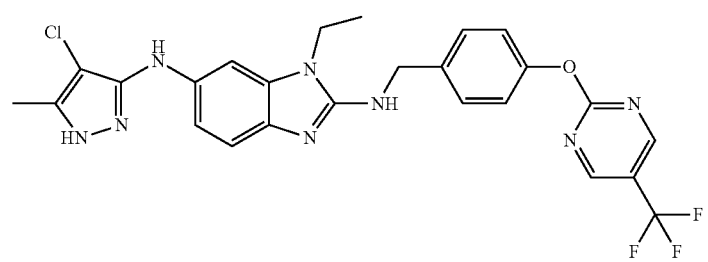 [SMILES: CCn1c(NCc2ccc(Oc3ncc(C(F)(F)F)cn3)cc2)nc2ccc(Nc3n[nH]c(C)c3Cl)cc21]

517
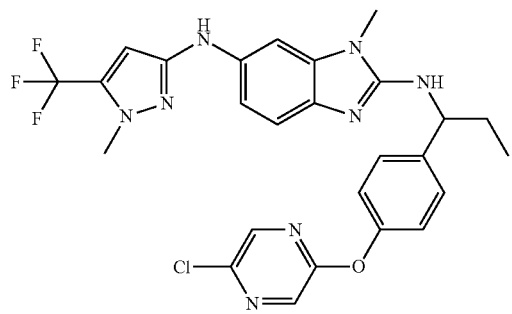 [SMILES: CCC(Nc1nc2ccc(Nc3cc(C(F)(F)F)n(C)n3)cc2n1C)c1ccc(Oc2cnc(Cl)cn2)cc1]
518
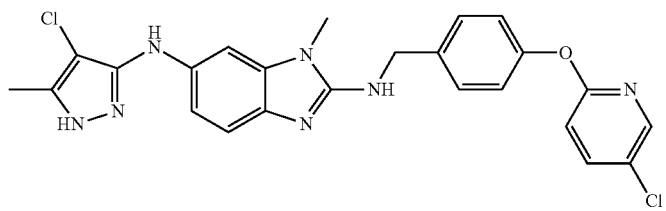 [SMILES: Cc1[nH]nc(Nc2ccc3nc(NCc4ccc(Oc5ccc(Cl)cn5)cc4)n(C)c3c2)c1Cl]
519
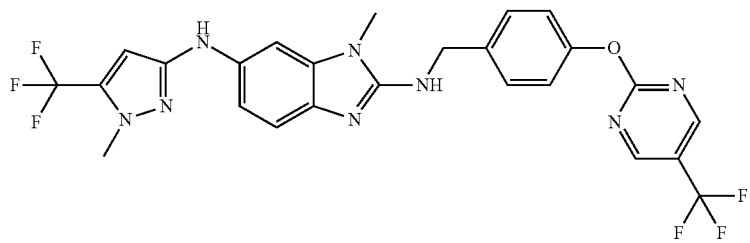 [SMILES: Cn1nc(Nc2ccc3nc(NCc4ccc(Oc5ncc(C(F)(F)F)cn5)cc4)n(C)c3c2)cc1C(F)(F)F]
520
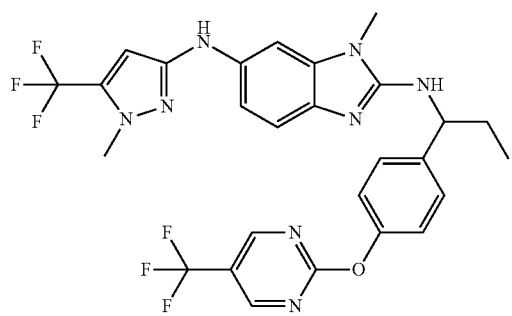 [SMILES: CCC(Nc1nc2ccc(Nc3cc(C(F)(F)F)n(C)n3)cc2n1C)c1ccc(Oc2ncc(C(F)(F)F)cn2)cc1]
521
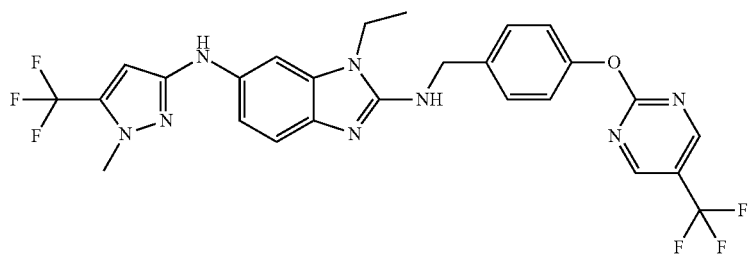 [SMILES: CCn1c(NCc2ccc(Oc3ncc(C(F)(F)F)cn3)cc2)nc2ccc(Nc3cc(C(F)(F)F)n(C)n3)cc21]

522 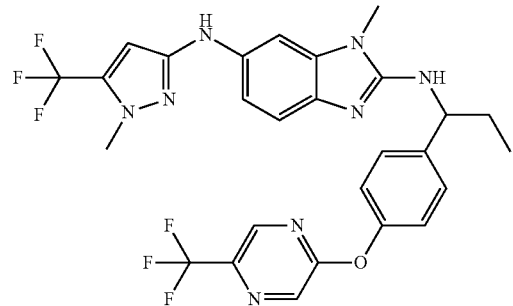 [SMILES: CCC(Nc1nc2ccc(Nc3cc(C(F)(F)F)n(C)n3)cc2n1C)c1ccc(Oc2cnc(C(F)(F)F)cn2)cc1]
523 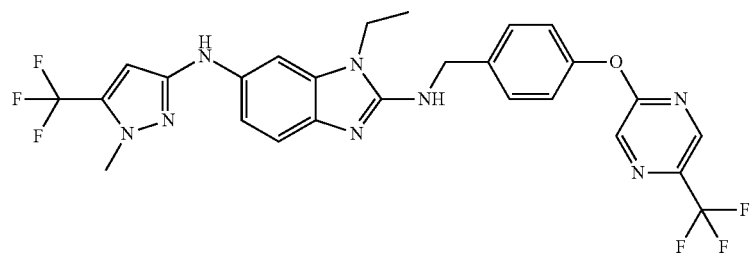 [SMILES: CCn1c(NCc2ccc(Oc3cnc(C(F)(F)F)cn3)cc2)nc2ccc(Nc3cc(C(F)(F)F)n(C)n3)cc21]
524 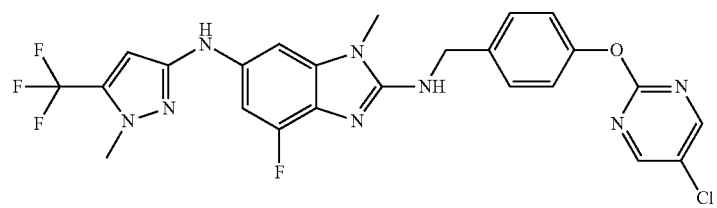 [SMILES: Cn1nc(Nc2cc(F)c3nc(NCc4ccc(Oc5ncc(Cl)cn5)cc4)n(C)c3c2)cc1C(F)(F)F]
525 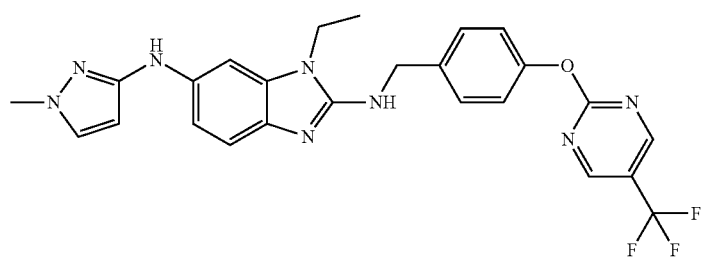 [SMILES: CCn1c(NCc2ccc(Oc3ncc(C(F)(F)F)cn3)cc2)nc2ccc(Nc3ccn(C)n3)cc21]
526 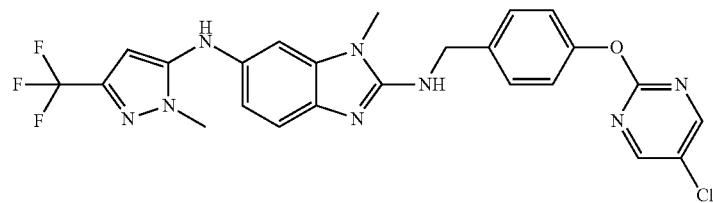 [SMILES: Cn1nc(C(F)(F)F)cc1Nc1ccc2nc(NCc3ccc(Oc4ncc(Cl)cn4)cc3)n(C)c2c1]
527 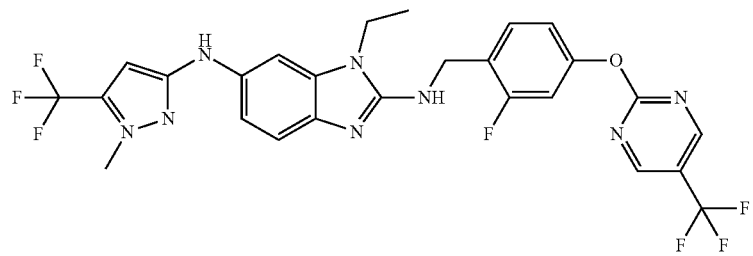

-continued
| | |
|---|---|
| 528 | 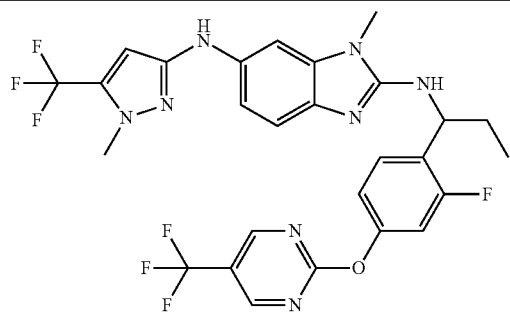 |
| 529 | 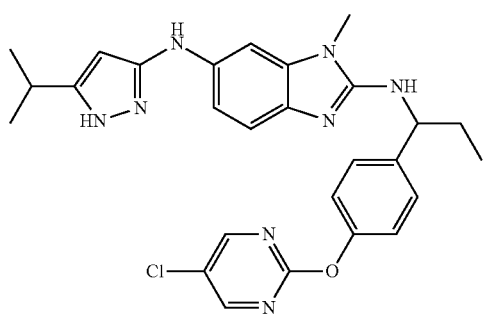 [SMILES: CCC(Nc1nc2ccc(Nc3cc(C(C)C)[nH]n3)cc2n1C)c1ccc(Oc2ncc(Cl)cn2)cc1] |
| 530 | 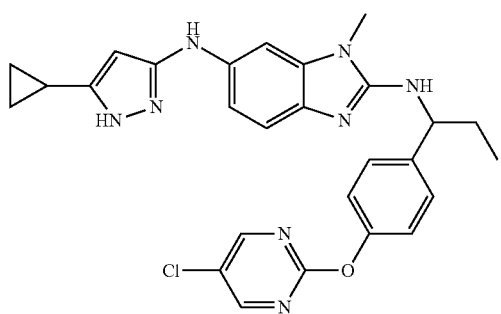 [SMILES: CCC(Nc1nc2ccc(Nc3cc(C4CC4)[nH]n3)cc2n1C)c1ccc(Oc2ncc(Cl)cn2)cc1] |
| 531 | 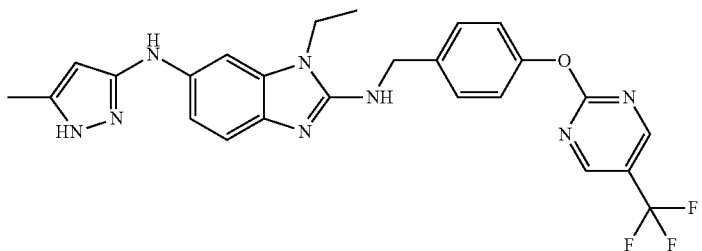 [SMILES: CCn1c(NCc2ccc(Oc3ncc(C(F)(F)F)cn3)cc2)nc2ccc(Nc3cc(C)[nH]n3)cc21] |
| 532 | 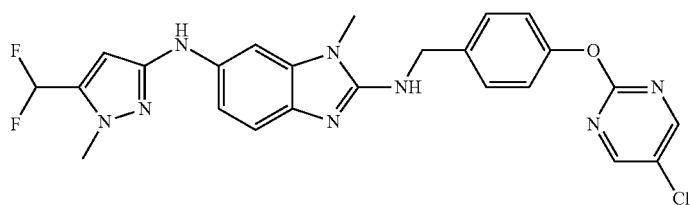 [SMILES: Cn1nc(Nc2ccc3nc(NCc4ccc(Oc5ncc(Cl)cn5)cc4)n(C)c3c2)cc1C(F)F] |
| 533 | 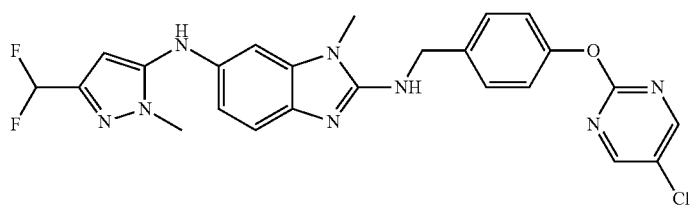 [SMILES: Cn1nc(C(F)F)cc1Nc1ccc2nc(NCc3ccc(Oc4ncc(Cl)cn4)cc3)n(C)c2c1] |

| | |
|---|---|
| 534 | 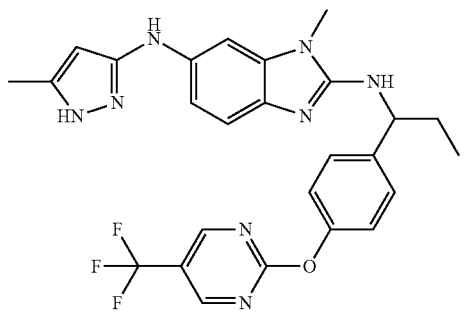 [SMILES: CCC(Nc1nc2ccc(Nc3cc(C)[nH]n3)cc2n1C)c1ccc(Oc2ncc(C(F)(F)F)cn2)cc1] |
| 535 | 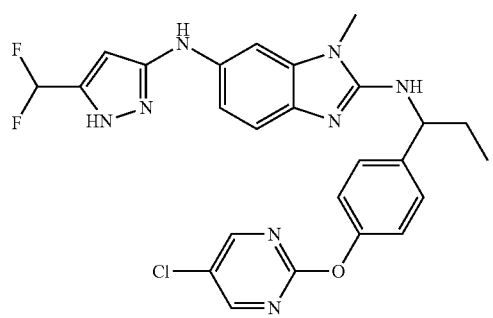 [SMILES: CCC(Nc1nc2ccc(Nc3cc(C(F)F)[nH]n3)cc2n1C)c1ccc(Oc2ncc(Cl)cn2)cc1] |
| 536 | 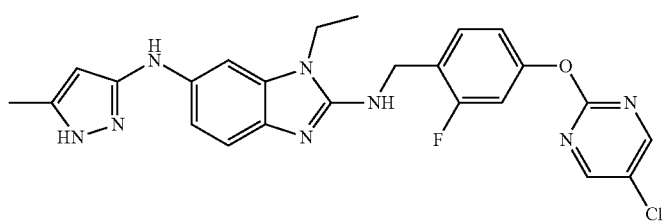 [SMILES: CCn1c(NCc2ccc(Oc3ncc(Cl)cn3)cc2F)nc2ccc(Nc3cc(C)[nH]n3)cc21] |
| 537 | 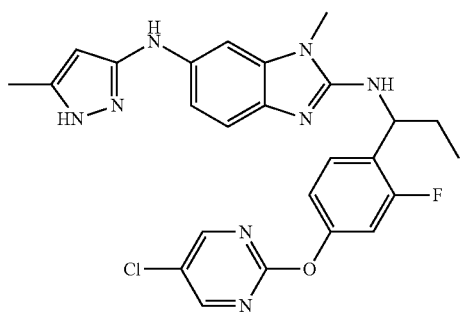 [SMILES: CCC(Nc1nc2ccc(Nc3cc(C)[nH]n3)cc2n1C)c1ccc(Oc2ncc(Cl)cn2)cc1F] |
| 538 | 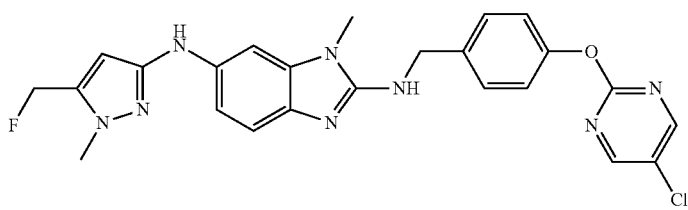 [SMILES: Cn1nc(Nc2ccc3nc(NCc4ccc(Oc5ncc(Cl)cn5)cc4)n(C)c3c2)cc1CF] |
| 539 | 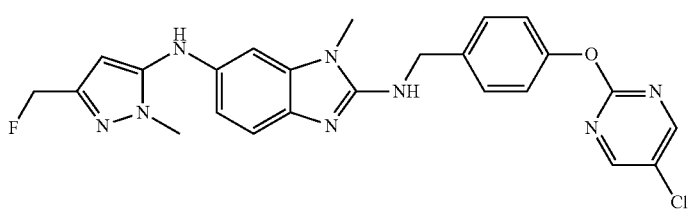 [SMILES: Cn1nc(CF)cc1Nc1ccc2nc(NCc3ccc(Oc4ncc(Cl)cn4)cc3)n(C)c2c1] |

-continued
540
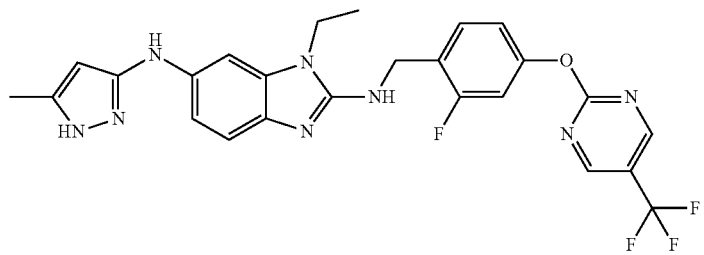 [SMILES: CCn1c(NCc2ccc(Oc3ncc(C(F)(F)F)cn3)cc2F)nc2ccc(Nc3cc(C)[nH]n3)cc21]
541
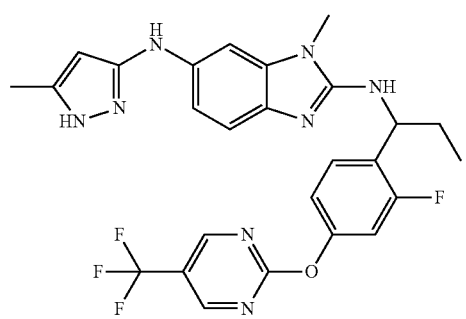 [SMILES: CCC(Nc1nc2ccc(Nc3cc(C)[nH]n3)cc2n1C)c1ccc(Oc2ncc(C(F)(F)F)cn2)cc1F]
542
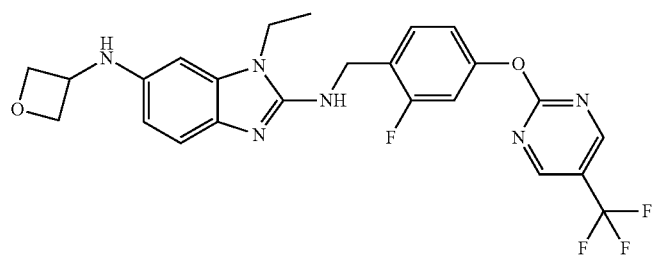
543
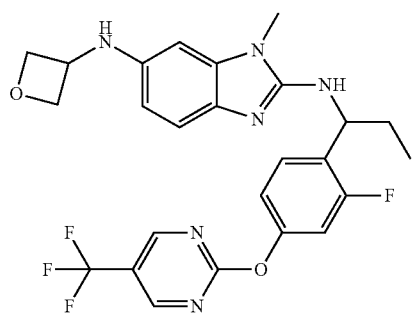 [SMILES: CCC(Nc1nc2ccc(NC3COC3)cc2n1C)c1ccc(Oc2ncc(C(F)(F)F)cn2)cc1F]
544
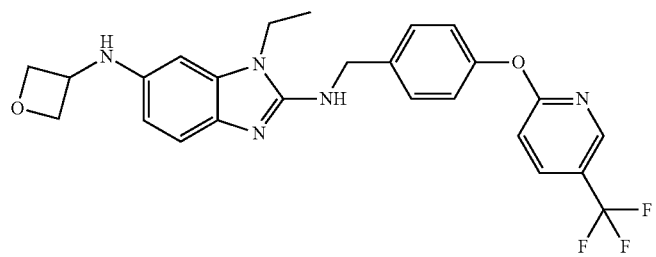

545 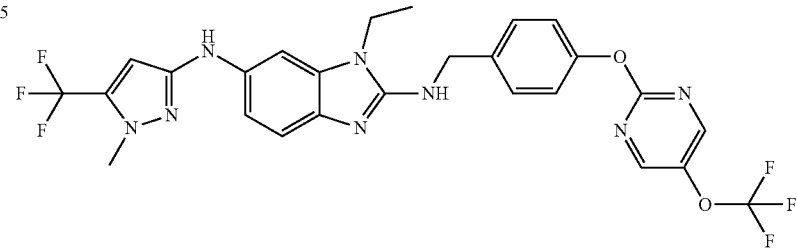
546 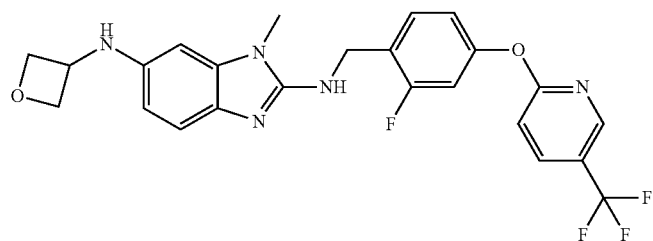 [SMILES: Cn1c(NCc2ccc(Oc3ccc(C(F)(F)F)cn3)cc2F)nc2ccc(NC3COC3)cc21]
547 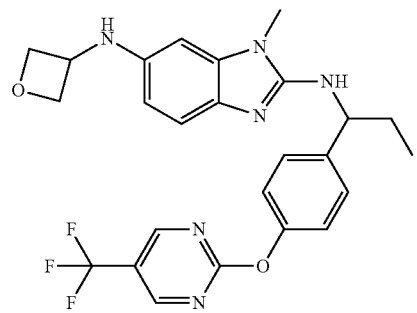 [SMILES: CCC(Nc1nc2ccc(NC3COC3)cc2n1C)c1ccc(Oc2ncc(C(F)(F)F)cn2)cc1]
548 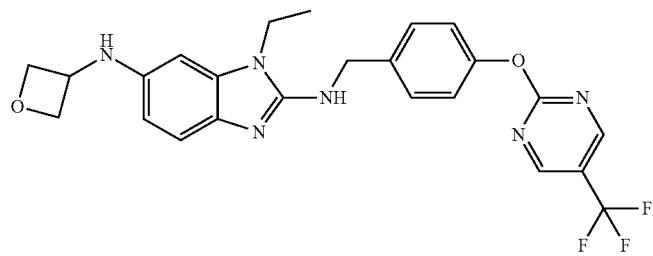 [SMILES: CCn1c(NCc2ccc(Oc3ncc(C(F)(F)F)cn3)cc2)nc2ccc(NC3COC3)cc21]
549 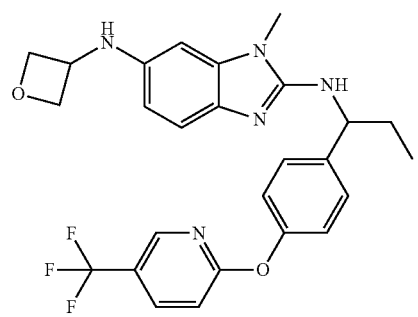 [SMILES: CCC(Nc1nc2ccc(NC3COC3)cc2n1C)c1ccc(Oc2ccc(C(F)(F)F)cn2)cc1]

| | |
|---|---|
| 550 | 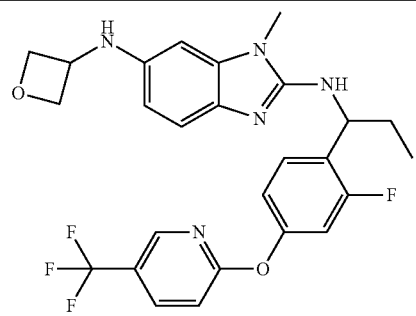 |
| 551 | 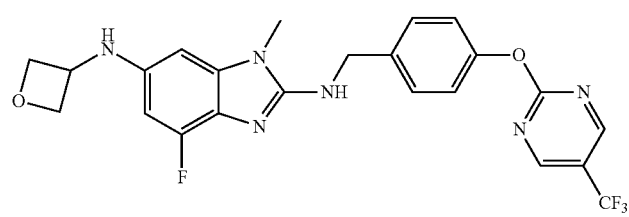 |
| 552 | 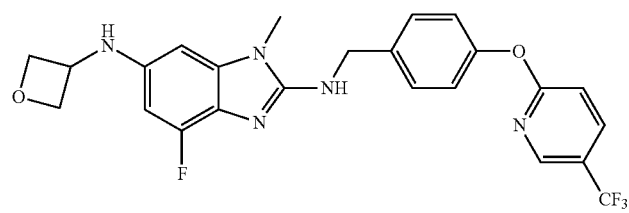 |
| 553 | 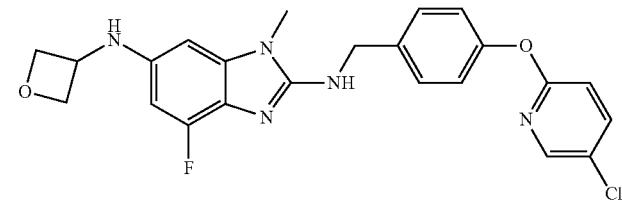 [SMILES: Cn1c(NCc2ccc(Oc3ccc(Cl)cn3)cc2)nc2c(F)cc(NC3COC3)cc21] |
| 554 | 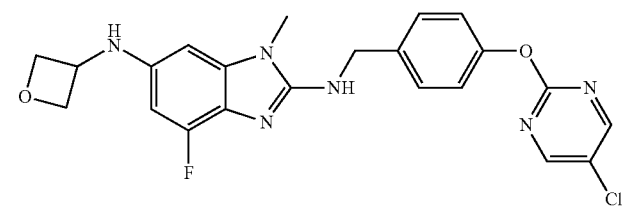 [SMILES: Cn1c(NCc2ccc(Oc3ncc(Cl)cn3)cc2)nc2c(F)cc(NC3COC3)cc21] |
| 555 | 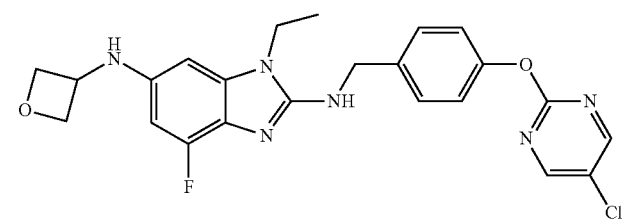 [SMILES: CCn1c(NCc2ccc(Oc3ncc(Cl)cn3)cc2)nc2c(F)cc(NC3COC3)cc21] |
| 556 | 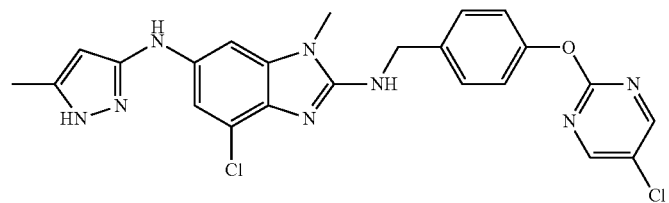 [SMILES: Cc1cc(Nc2cc(Cl)c3nc(NCc4ccc(Oc5ncc(Cl)cn5)cc4)n(C)c3c2)n[nH]1] |

| No. | NMR Characterization |
|---|---|
| 1 | Pale violet solid; 1H NMR (400 MHz, Acetone-d6); δ 9.77 (brs, 1H), 8.34-8.36 (m, 2H), 7.85 (s, 1H), 7.52-7.64 (m, 4H), 6.89 (s, 1H), 6.57 (s, 1H), 6.30-6.34 (m, 2H), 4.75 (s, 2H), 4.03 (brs, 2H); LCMS (electrospray) m/z 440 [M + H]+. |
| 2 | Green solid; 1H NMR (400 MHz, MeOH-d4); δ 7.22-7.27 (m, 4H), 6.90-6.99 (m, 5H), 6.69 (d, J = 1.6 Hz, 1H), 6.48 (dd, J = 8.0, 1.6 Hz, 1H), 4.43 (s, 2H), 3.43-3.50 (m, 3H), 3.03-3.09 (m, 2H), 2.06-2.10 (m, 2H), 1.81-1.87 (m, 2H); LCMS (electrospray) m/z 448 [M + H]+. |
| 3 | Pale brown solid; 1H NMR (400 MHz, MeOH-d4); δ 7.25 (d, J = 8., 2H), 7.22 (d, J = 8.4 Hz, 2H), 6.97-6.99 (m, 1H), 6.90-6.92 (m, 3H), 6.69 (m, 1H), 6.57 (d, J = 8.4 Hz, 2H), 6.50-6.52 (m, 1H), 4.58 (s, 2H, NH), 4.40 (s, 2H), 3.64-3.68 (m, 1H), 3.37-3.51 (m, 4H), 2.27-2.34 (m, 2H); LCMS (electrospray) m/z 434, 436 [M + H]+. |
| 4 | 1H NMR (400 MHz, Acetone-d6); δ 7.49 (dd, J = 8.4 2.4 Hz, 2H), 7.41 (dd, J = 8.4 2.4 Hz, 2H), 7.33 (t, J = 9.2 Hz, 2H), 7.08 (d, J = 8.0 Hz, 1H), 6.91 (t, J = 9.2 Hz, 2H), 6.60 (d, J = 34.0 Hz, 1H), 6.40 (dd, J = 34.0 8.0 Hz, 1H), 5.08 (d, J = 8.0 Hz, 2H), 4.56 (d, J = 8.8 Hz, 2H); LCMS (electrospray) m/z 378 [M + H]+. |
| 5 | Gray solid; 1H NMR (400 MHz, Methanol-d4); δ 7.27 (d, J = 8.8 Hz, 2H), 7.22-7.25 (m, 2H), 6.94-7.00 (m, 3H), 6.89-6.91 (m, 2H), 6.70 (d, J = 2.0 Hz, 1H), 6.52 (dd, J = 8.2, 2.2 Hz, 1H), 4.44 (s, 2H), 3.85 (d, J = 6.0 Hz, 2H), 3.69-3.72 (m, 2H), 3.60-3.62 (m, 1H), 2.68-2.74 (m, 2H), 1.92-1.95 (m, 2H), 1.50-1.54 (m, 2H); LCMS (electrospray) m/z 462 [M + H]+. |
| 6 | Pale yellow solid; 1H NMR (400 MHz, MeOH-d4); δ 7.33 (s, 4H), 7.25 (d, J = 8.8 Hz, 2H), 6.95-7.01 (m, 3H), 6.70 (d, J = 2.4 Hz, 1H), 6.54 (dd, J = 8.4, 2.4 Hz, 1H), 4.56 (s, 2H), 4.44 (s, 2H), 3.58-3.59 (m, 1H), 3.48-3.51 (m, 2H), 2.88-2.94 (m, 2H), 1.91-2.05 (m, 2H), 1.28-1.74 (m, 2H); LCMS (electrospray) m/z 461 [M + H]+. |
| 7 | 1H NMR (400 MHz, DMSO-d6); δ 7.22 (d, J = 8.8 Hz, 2H), 6.87 (d, J = 8.8 Hz, 2H), 6.77 (d, J = 8.0 Hz, 1H), 6.65 (brs, 1H, NH), 6.39 (d, J = 1.6 Hz, 1H), 6.18 (dd, J = 8.0 1.6 Hz, 1H), 4.32 (d, J = 2.0 Hz, 2H), 3.67-3.70 (m, 4H), 3.01-3.05 (m, 4H); LCMS (electrospray) m/z 323 [M + H]+. |
| 8 | Dark green solid; 1H NMR (400 MHz, Acetone-d6); δ 9.81 (s, 1H, NH), 7.44-7.50 (m, 3H), 7.37 (d, J = 6.8 Hz, 2H), 7.05 (s, 1H, NH), 6.91-7.00 (m, 5H), 6.83 (d, J = 8.4 Hz, 1H), 6.15-6.25 (m, 1H), 4.63 (s, 2H), 2.21 (s, 3H); LCMS (electrospray) m/z 445 [M + H]+. |
| 9 | Dark yellow solid; 1H NMR (400 MHz, Acetone-d6); δ 7.60 (d, J = 8.4 Hz, 2H), 7.40-7.43 (m, 2H), 7.02-7.07 (m, 3H), 6.94-6.96 (m, 1H), 6.91 (d, J = 8.4 Hz, 1H), 6.58-6.59 (m, 1H), 6.35-6.38 (m, 1H), 4.70 (s, 2H); LCMS (electrospray) m/z 400 [M + H]+. |
| 10 | Dark yellow solid; 1H NMR (400 MHz, Acetone-d6); δ 7.53-7.59 (m, 1H), 7.39-7.43 (m, 2H), 7.17 (s, 1H, NH), 7.03-7.07 (m, 2H), 6.90 (d, J = 8.4 Hz, 1H), 6.72-6.81 (m, 2H), 6.58 (d, J = 2.4 Hz, 1H), 6.35 (dd, J = 8.2, 2.4 Hz, 1H), 4.65 (s, 2H); LCMS (electrospray) m/z 383 [M + H]+. |
| 11 | Pale brown solid; 1H NMR (400 MHz, MeOH-d4); δ 7.25-7.29 (m, 4H), 7.00-7.08 (m, 2H), 6.80-6.90 (m, 4H), 6.68 (m, 1H), 6.58-6.60 (m, 2H), 3.60 (t, J = 6.0 Hz, 2H), 2.96 (t, J = 6.0 Hz, 2H); LCMS (electrospray) m/z 379, 381 [M + H]+. |
| 12 | Yellow solid; 1H NMR (400 MHz, DMSO-d6); δ 8.87 (s, 1H), 8.10 (s, 1H), 7.99-8.00 (m, 1H), 7.62 (s, 1H), 7.20-7.43 (m, 5H), 7.09-7.12 (m, 1H), 6.96-7.02 (m, 5H), 6.84-6.86 (m, 1H), 4.47 (d, J = 4.4 Hz, 2H), 2.71-2.76 (m, 1H), 0.66-0.70 (m, 2H), 0.47-0.51 (m, 2H); LCMS (electrospray) m/z 514 [M + H]+. |
| 13 | Pale yellow solid; 1H NMR (400 MHz, Acetone-d6); δ 8.07 (s, 1H), 7.98 (s, 1H), 7.75 (s, 1H), 7.44-7.48 (m, 2H), 7.33-7.37 (m, 2H), 7.08-7.10 (m, 2H), 6.93-7.01 (m, 4H), 6.60-6.78 (m, 2H), 4.65 (s, 2H), 4.26 (q, J = 7.2 Hz, 2H), 1.31 (t, J = 7.2 Hz, 3H); LCMS (electrospray) m/z 503 [M + H]+. |
| 14 | Pale yellow solid; 1H NMR (400 MHz, MeOH-d4); δ 8.27-8.28 (m, 1H), 7.45-7.48 (m, 1H), 7.40-7.42 (m, 2H), 7.35-7.39 (m, 1H), 7.03-7.04 (m, 1H), 7.01-7.02 (m, 1H), 6.98-7.00 (m, 1H), 6.70 (d, J = 2.0 Hz, 1H), 6.52 (dd, J = 8.4, 2.0 Hz, 1H), 4.65 (s, 2H); LCMS (electrospray) m/z 365 [M + H]+. |
| 15 | Pale yellow solid; 1H NMR (400 MHz, MeOH-d4); δ 7.31-7.33 (m, 1H), 7.28-7.29 (m, 1H), 7.12 (d, J = 8.4 Hz, 2H), 7.05-7.09 (m, 1H), 6.99-7.01 (m, 1H), 6.88-6.90 (m, 1H), 6.85-6.86 (m, 1H), 6.83-6.84 (m, 1H), 6.55-6.57 (m, 1H), 6.50-6.51 (m, 1H), 4.15 (t, J = 7.2 Hz, 2H), 3.02 (t, J = 7.2 Hz, 2H); LCMS (electrospray) m/z 378 [M + H]+. |
| 16 | Brown solid; 1H NMR (400 MHz, Acetone-d6); δ 8.27 (s, 1H), 7.90 (s, 1H), 7.46 (d, J = 7.6 Hz, 2H), 7.36 (d, J = 8.0 Hz, 2H), 7.23-7.28 (m, 2H), 7.07-7.14 (m, 3H), 6.97-6.99 (m, 4H), 6.78 (d, J = 8.0 Hz, 1H), 6.57 (brs, 1H), 4.66 (s, 2H); |

| | |
|---|---|
| 17 | 1H NMR (400 MHz, Acetone-d6); δ 9.21 (s, 1H, NH), 8.09 (s, 1H), 7.83 (s, 1H), 7.40 (s, 1H, NH), 7.15-7.24 (m, 4H), 7.05-7.09 (m, 2H), 6.41 (brs, 2H, NH2), 4.52 (t, J = 2.8 Hz, 2H), 4.42 (t, J = 2.8 Hz, 2H), 2.82-2.86 (m, 1H), 0.71-0.74 (m, 2H), 0.51-0.55 (m, 2H); LCMS (electrospray) m/z 502 [M + H]+. |
| 18 | 1H NMR (400 MHz, Acetone-d6); δ 9.16 (s, 1H, NH), 8.11 (s, 1H), 7.74 (s, 1H), 7.22 (d, J = 8.8 Hz, 2H), 7.06-7.16 (m, 4H), 5.55 (brs, 2H, NH2), .4.46 (t, J = 2.8 Hz, 2H), 4.39 (t, J = 2.8 Hz, 2H), 4.32-4.37 (m, 1H), 1.94-2.20 (m, 4H), 1.60-1.71 (m, 1H), 1.52-1.59 (m, 3H); LCMS (electrospray) m/z 530 [M + H]+. |
| 19 | Pale green solid; 1H NMR (400 MHz, Acetone-d6); δ 9.13 (s, 1H, NH), 8.10 (m, 1H); 7.84 (s, 1H, NH), 7.49 (d, J = 8.4 Hz, 2H), 7.37 (d, J = 8.4 Hz, 2H), 7.10-7.15 (m, 3H), 6.96-7.02 (m, 4H), 4.68 (s, 2H), 4.32-4.36 (m, 1H), 1.96-1.99 (m, 2H), 1.68-1.72 (m, 2H), 1.50-1.61 (m, 4H); LCMS (electrospray) m/z 542, 544 [M + H]+. |
| 20 | Dark beige solid; 1H NMR (400 MHz, Acetone-d6); δ 7.65 (s, 1H, NH), 7.56 (d, J = 8.4 Hz, 2H), 7.37 (d, J = 8.4 Hz, 2H), 6.97-7.02 (m, 4H), 6.88 (d, J = 8.4 Hz, 2H), 6.55 (s, 4H), 6.39 (d, J = 7.6 Hz, 1H), 1.82 (s, 6H); LCMS (electrospray) m/z 393 [M + H]+. |
| 21 | 1H NMR (400 MHz, DMSO-d6); δ 7.67 (d, J = 8.4 Hz, 2H), 7.62 (d, J = 8.4 Hz, 2H), 7.51 (d, J = 8.4 Hz, 2H), 7.24 (t, J = 8.4 Hz, 2H), 6.86 (d, J = 8.0 Hz, 1H), 6.29 (s, 1H), 6.27 (d, J = 8.0 Hz, 1H), 6.11 (s, 2H); LCMS (electrospray) m/z 348 [M + H]+. |
| 22 | 1H NMR (400 MHz, Acetone-d6); δ 8.15 (s, 1H), 8.02 (s, 1H), 7.78 (s, 1H, NH), 7.21 (d, J = 8.8 Hz, 2H), 7.12-7.17 (m, 2H), 7.06 (d, J = 8.8 Hz, 2H), 5.85 (brs, 2H, NH2), 4.74-4.48 (m, 2H), 4.38-4.30 (m, 2H), 4.28-4.35 (m, 2H), 1.32-1.37 (m, 3H); LCMS (electrospray) m/z 491 [M + H]+. |
| 23 | Pale green solid; 1H NMR (400 MHz, Acetone-d6); δ 10.00 (s, 1H, NH), 7.81 (s, 1H), 7.47-7.49 (m, 3H), 7.37 (d, J = 8.4 Hz, 2H), 7.14-7.18 (m, 1H), 7.11 (s, 1H, NH), 7.02-7.06 (m, 1H), 6.94-7.02 (m, 4H), 6.84 (d, J = 6.8 Hz, 1H), 6.76 (d, J = 6.8 Hz, 1H), 6.41 (s, 1H, NH), 4.66 (s, 2H); LCMS (electrospray) m/z 460 [M + H]+. |
| 24 | Pale green solid; 1H NMR (400 MHz, Acetone-d6); δ 7.45-7.50 (m, 3H), 7.37 (d, J = 7.2 Hz, 2H), 6.98-7.00 (m, 4H), 6.78 (s, 1H), 6.55 (d, J = 8.4 Hz, 1H), 6.30-6.35 (m, 2H), 4.63 (s, 2H); LCMS (electrospray) m/z 431 [M + H]+. |
| 25 | white solid; mp >220° C.; 1H NMR (DMSO-d6, 400 MHz); δ 12.74 (1H, brs), 8.30 (1H, s), 7.74 (1H, d, J = 3.6 Hz), 7.44 (0.6H, d, J = 8.8 Hz), 7.31 (0.4H, d, J = 8.4 Hz), 6.91-7.18 (6H, m), 3.20-3.30 (8H, m), 2.14 (3H, s); LCMS: 99.3%, MS (ESI); m/z 377.0 [M + H]+. |
| 26 | brown solid; 1H NMR (DMSO-d6, 400 MHz); δ 12.02 (1H, brs), 8.07-8.44 (2H, m), 7.28 (2H, t, J = 8.8 Hz), 7.09 (1H, d, J = 8.4 Hz), 6.63 (1H, d, J = 1.6 Hz), 6.57 (1H, dd, J = 8.4, 2.0 Hz); LCMS: 100%, MS (ESI); m/z 271.0 [M + H]+. |
| 27 | yellow amorphous; mp >142.9° C., decomposed; 1H NMR (DMSO-d6, 400 MHz); δ 4.06-4.22 (2H, m), 5.62-5.80 (1H, m), 6.57 (1H, dd, J = 8.4, 2.0 Hz), 6.83 (0.3H, s), 6.98 (0.7H, s), 7.13 (1H, d, J = 8.4 Hz), 7.28 (2H, t, J = 8.8 Hz), 7.50-7.62 (1H, m), 8.12-8.24 (2H, m), 12.02 (3H, brs); LCMS: 100%, MS (ESI); m/z 351.0 [M + H]+. |
| 28 | gray powder; 1H NMR (DMSO-d6, 400 MHz); δ 4.42 (2H, d, J = 5.6 Hz), 4.43 (2H, brs), 6.19 (1H, d, J = 8.0 Hz), 6.41 (1H, d, J = 1.6 Hz), 6.68-6.86 (2H, m), 7.08-7.20 (2H, m), 7.36-7.47 (2H, m), 10.38 (1H, brs); LCMS: 99.9%, MS (ESI); m/z 256.9 [M + H]+. |
| 29 | white amorphous; 1H NMR (DMSO-d6, 400 MHz); δ 4.07 (2H, s), 4.42 (2H, d, J = 6.0 Hz), 5.08 (1H, brs), 6.29 (1H, d, J = 7.2 Hz), 6.46 (1H, d, J = 1.6 Hz), 6.78-6.93 (3H, m), 7.08-7.17 (2H, m), 7.35-7.45 (2H, m), 7.54 (1H, s), 10.42 (1H, brs), 11.82 (1H, brs); LCMS: 98.4%, MS (ESI); m/z 337.0 [M + H]+. |
| 30 | white powder; 1H NMR (DMSO-d6, 400 MHz); δ 7.95 (1H, brs) 7.50-7.43 (2H, m), 7.28 (1H, dd, J = 8.4, 2.0 Hz), 6.93 (1H, d, J = 8.0 Hz), 6.52 (1H, s), 6.35 (1H, dd, J = 8.4, 2.0 Hz), 4.55 (2H, s); LCMS: 99.0%, MS (ESI); m/z 291.1 [M + H]+. |
| 31 | pale powder; 1H NMR (DMSO-d6, 400 MHz); δ 8.14 (1H, brs), 7.49-7.40 (2H, m), 7.29-7.25 (1H, m), 7.18-7.01 (2H, m), 6.90-6.75 (1H, m), 5.40 (1H, brs), 4.56 (2H, d, J = 4.8 Hz), 3.26 (2H, s, overlapped with water peak, confirmed after adding D2O), 1.19 (6H, s); LCMS: 96.5%, MS (ESI); m/z 363.2 [M + H]+. |
| 32 | white powder; hydroscopic; 1H NMR (DMSO-d6, 400 MHz); δ 8.45 (1H, brs), 7.35 (2H, dd, J = 8.0, 6.0 Hz), 7.13 (2H, t, J = 8.8 Hz), 7.01 (1H, d, J = 8.0 Hz), 6.57 (1H, s), 6.43 (1H, d, J = 7.6 Hz), 3.49 (2H, t, J = 7.2 Hz, overlapped with H2O peak), 2.85 (2H, t, J = 7.2 Hz); LCMS: 96.1%, MS (ESI); m/z 271.2 [M + H]+. |
| 33 | white powder; 1H NMR (DMSO-d6, 400 MHz); δ 7.32-7.25 (2H, m), 7.22-7.18 (2H, m), 6.88 (1H, d, J = 8.4 Hz), 6.39 (1H, brs), 6.27 (1H, d, J = 2.0 Hz), 6.14 (1H, dd, J = 8.4, 2.0 Hz), 5.71 (1H, d, J = 6.8 Hz), 4.81 (2H, t, J = 6.0 Hz), 4.50-4.40 (1H, m), 4.38 (2H, t, J = 6.0 Hz), 3.50-3.45 (2H, m), 2.85 (2H, t, J = 7.2 Hz); LCMS: 99.5%, MS (ESI); m/z 327.2 [M + H]+. |

| | |
|---|---|
| 34 | brown amorphous; mp = 193.3-205° C.; 1H NMR (DMSO-d6, 400 MHz); δ 7.17-7.07 (2H, m), 7.06-6.98 (2H, m), 6.92 (1H, d, J = 8.4 Hz), 6.51 (1H, s), 6.33 (1H, dd, J = 8.4, 1.6 Hz), 4.62-4.50 (1H, m), 3.86-3.70 (2H, m), 3.46-3.40 (2H, m), 2.08-1.95 (2H, m), 1.74-1.59 (2H, m); LCMS: 100%, MS (ESI); m/z 327.2 [M + H]+. |
| 35 | brown gum; 1H NMR (DMSO-d6, 400 MHz); δ 7.43 (1H, d, J = 8.8 Hz), 7.19-7.09 (2H, m), 7.09-6.96 (3H, m), 6.89 (1H, dd, J = 8.8, 1.6 Hz), 4.72-4.57 (1H, m), 3.75-3.65 (2H, m), 3.67 (3H, s), 3.49-3.40 (2H, m), 2.18-2.05 (2H, m), 1.90-1.77 (2H, m); LCMS: 100%, MS (ESI); m/z 341.2 [M + H]+. |
| 36 | off-white amorphous; 1H NMR (DMSO-d6, 400 MHz); δ 10.99 (1H, brs), 7.06-7.16 (2H, m), 6.98-7.05 (2H, m), 6.94 (1H, brs), 6.29 (1H, s), 6.20 (1H, d, J = 8.0 Hz), 5.78 (1H, brs), 4.82 (2H, t, J = 6.0 Hz), 4.54 (1H, brs), 4.43-4.50 (1H, m), 4.33-4.43 (2H, m), 3.79 (2H, d, m), 3.37-3.43 (2H, m), 1.98 (2H, m), 1.63 (2H, m); LCMS: 98.4%, MS (ESI); m/z 383.2 [M + H]+. |
| 37 | light green powder; 1H NMR (DMSO-d6, 400 MHz); δ 7.25 (1H, brs), 7.19-7.08 (2H, m), 7.08-6.92 (4H, m), 6.51-6.36 (2H, m), 5.44 (1H, brs), 4.60-4.52 (1H, m), 3.87-3.75 (2H, m), 3.43-3.41 (2H, m, overlapped with H2O peak), 2.10-2.00 (2H, m), 1.78-1.60 (2H, m), 1.35 (6H, s); LCMS: 100%, MS (ESI); m/z 412.1 [M + H]+. |
| 38 | brown powder; 1H NMR (DMSO-d6); δ 7.80 (1H, d, J = 8.4 Hz), 7.56 (1H, s), 7.41-7.25 (3H, m), 6.89 (2H, d, J = 8.8 Hz), 4.72 (2H, t, J = 4.8 Hz), 4.37 (2H, t, J = 4.8 Hz), 3.34 (6H, s); LCMS: 99.4%, MS (ESI); m/z 330.9 [M + H]+. |
| 39 | brown powder; 1H NMR (DMSO-d6); δ 7.34-7.24 (2H, m), 7.07 (1H, d, J = 8.0 Hz), 6.98-6.89 (2H, m), 6.66 (1H, d, J = 2.0 Hz), 6.41 (1H, dd, J = 8.0, 2.0 Hz), 4.80 (2H, brs), 4.30 (4H, s), 2.81 (6H, s); LCMS: 99.8%, MS (ESI); m/z 330.9 [M + H]+. |
| 40 | green powder; 1H NMR (DMSO-d6, 400 MHz); δ 7.39-7.25 (2H, m), 7.13 (1H, d, J = 8.4 Hz), 6.99-6.85 (2H, m), 6.46 (1H, d, J = 2.0 Hz), 6.37 (1H, dd, J = 8.4, 2.0 Hz), 6.08 (1H, d, J = 7.2 Hz), 4.84 (2H, t, J = 6.4 Hz), 4.62-4.47 (1H, m), 4.45-4.36 (2H, m), 4.35-4.25 (4H, m), 2.81 (6H, s); LCMS: 99.8%, MS (ESI); m/z 386.9 [M + H]+. |
| 41 | brown amorphous; 1H NMR (CDCl3, 400 MHz); δ 7.24-7.18 (2H, m), 7.14 (1H, d, J = 8.8 Hz), 6.80-6.72 (2H, m), 6.66 (1H, d, J = 2.4 Hz), 6.49 (1H, dd, J = 8.4 Hz, 2.0 Hz), 5.02 (2H, t, J = 6.4 Hz), 4.68-4.57 (1H, m), 4.53 (2H, d, J = 6.0 Hz), 4.42-4.32 (2H, m), 4.30-4.21 (2H, m), 4.06 (1H, brs), 2.98 (6H, s); LCMS: 99.6%, MS (ESI); m/z 387.0 [M + H]+. |
| 42 | white solid; mp = 178.2-179.6° C.; 1H NMR (DMSO-d6, 400 MHz); δ 8.95 (2H, brs), 7.44 (1H, d, J = 8.8 Hz), 7.39 (1H, s), 7.35-7.45 (2H, m), 7.10-7.25 (3H, m), 4.37 (2H, t, J = 7.2 Hz), 2.99 (2H, t, J = 7.2 Hz); LCMS: 99.2%, MS (ESI); m/z 271.0 [M + H]+. |
| 43 | white powder; mp = 60.8-61.6° C.; 1H NMR (DMSO-d6); δ 7.26 (2H, d, J = 8.4 Hz), 7.14 (1H, d, J = 8.4 Hz), 6.97 (2H, d, J = 9.2 Hz), 6.59 (1H, d, J = 1.6 Hz), 6.41 (1H, dd, J = 8.4, 2.0 Hz), 4.61 (2H, brs), 4.32 (4H, s), 2.85 (6H, s); LCMS: 99.6%, MS (ESI); m/z 380.9 [M + H]+. |
| 44 | white powder; mp >133° C.; 1H NMR (DMSO-d6); δ 7.27 (2H, d, J = 8.4 Hz), 7.14-6.94 (3H, m), 6.66 (1H, s), 6.41 (1H, d, J = 8.0 Hz), 4.77 (2H, brs), 4.25-4.35 (4H, m), 2.80 (6H, s); LCMS: 97.9%, MS (ESI); m/z 381.0 [M + H]+. |
| 45 | white powder; 1H NMR (DMSO-d6, 400 MHz); δ 8.23 (1H, s), 7.62 (1H, d, J = 2.0 Hz), 7.47 (1H, d, J = 2.0 Hz), 7.26 (2H, d, J = 8.8 Hz), 7.19 (1H, d, J = 8.4 Hz), 7.00-7.08 (2H, m), 6.97 (1H, dd, J = 8.4, 2.0 Hz), 5.76 (1H, d, J = 2.0 Hz), 4.37 (4H, dd, J = 8.0 Hz, 4.0 Hz), 3.68 (3H, s), 2.84 (6H, s); LCMS: 98.7%, MS (ESI); m/z 460.8 [M + H]+. |
| 46 | white powder; 1H NMR (DMSO-d6, 400 MHz); δ 8.11 (1H, s), 7.56 (1H, d, J = 2.0 Hz), 7.45 (1H, d, J = 2.0 Hz), 7.22-7.33 (3H, m), 6.91-7.03 (3H, m), 5.70 (1H, d, J = 2.0 Hz), 4.36 (4H, s), 3.72 (3H, s), 2.88 (6H, s); LCMS: 100%, MS (ESI); m/z 461.0 [M + H]+. |
| 47 | yellow gum; 1H NMR (CDCl3, 400 MHz); δ 7.10 (1H, s), 6.95-7.07 (5H, m), 6.63 (1H, dd, J = 8.4, 2.0 Hz), 4.18 (2H, t, J = 7.6 Hz), 3.25-3.40 (4H, m), 3.06 (2H, t, J = 7.6 Hz), 1.14 (6H, t, J = 7.2 Hz); LCMS: 95.7%, MS (ESI); m/z 327.2 [M + H]+. |
| 48 | white powder; 1H NMR (DMSO-d6, 400 MHz); δ 7.26 (2H, d, J = 8.8 Hz), 6.99 (2H, d, J = 8.8 Hz), 6.81 (1H, d, J = 8.4 Hz), 6.48 (1H, d, J = 1.6 Hz), 6.26 (1H, dd, J = 8.4, 2.0 Hz), 5.98 (2H, brs), 4.55 (2H, brs), 4.22-4.24 (2H, m), 4.18 (2H, t, J = 5.2 Hz); LCMS: 100%, MS (ESI); m/z 353.1 [M + H]+. |
| 49 | white powder; 1H NMR (DMSO-d6, 400 MHz); δ 7.26 (1H, d, J = 8.8 Hz), 6.96 (2H, d, J = 9.2 Hz), 6.86 (1H, d, J = 8.0 Hz), 6.41 (1H, d, J = 1.6 Hz), 6.21 (1H, dd, J = 8.4, 2.0 Hz), 6.17 (2H, brs), 4.39 (2H, brs), 4.22-4.29 (2H, m), 4.11-4.22 (2H, m); LCMS: 100%, MS (ESI); m/z 352.9 [M + H]+. |

| | | |
|---|---|---|
| 50 | yellow gum; 1H NMR (CDCl3, 400 MHz); δ 7.06 (2H, dd, J = 8.4, 4.2 Hz), 7.00 (2H, t, J = 7.2 Hz), 6.95-6.85 (2H, m), 6.49 (1H, dd, J = 8.4, 6.4 Hz), 4.19 (2H, t, J = 7.2 Hz), 3.52 (4H, t, J = 6.8 Hz), 3.00 (2H, t, J = 7.2 Hz), 1.95-2.05 (4H, m); LCMS: 97.4%, MS (ESI); m/z 324.9 [M + H]+. | |
| 51 | yellow powder; 1H NMR (CDCl3, 400 MHz); δ 7.31 (1H, d, J = 8.0 Hz), 7.13 (2H, d, J = 8.8 Hz), 6.83 (2H, dd, J = 6.8, 2.0 Hz), 6.60 (1H, d, J = 1.6 Hz), 6.57 (1H, d, J = 8.0 Hz), 4.39 (2H, t, J = 6.0 Hz), 4.25 (2H, t, J = 6.8 Hz), 3.59 (4H, t, J = 6.8 Hz), 1.99 (4H, m); LCMS: 98.3%, MS (ESI); m/z 407.1 [M + H]+. | |
| 52 | white powder; 1H NMR (DMSO-d6, 400 MHz); δ 7.28 (2H, d, J = 9.2 Hz), 7.08 (2H, d, J = 9.6 Hz), 6.89 (1H, d, J = 8.0 Hz), 6.58 (1H, t, J = 5.6 Hz), 6.35 (1H, d, J = 1.6 Hz), 6.27 (1H, dd, J = 8.4, 2.0 Hz), 4.55 (2H, brs), 4.19 (2H, t, J = 5.6 Hz), 3.52-3.68 (2H, m), 3.36 (3H, s); LCMS: 100%, MS (ESI); m/z 366.9 [M + H]+. | |
| 53 | white powder; 1H NMR (DMSO-d6, 400 MHz); δ 7.28 (2H, d, J = 8.8 Hz), 7.09 (2H, d, J = 9.2 Hz), 6.79 (1H, d, J = 8.4 Hz), 6.68 (1H, t, J = 5.6 Hz), 6.48 (1H, d, J = 1.6 Hz), 6.24 (1H, dd, J = 8.0, 1.6 Hz), 4.41 (2H, brs), 4.19 (2H, t, J = 5.6 Hz), 3.65-3.70 (2H, m), 3.38 (3H, s); LCMS: 100%, MS (ESI); m/z 367.1 [M + H]+. | |
| 54 | pale green powder; 1H NMR (DMSO-d6, 400 MHz); δ 10.72 (1H, brs), 7.30 (2H, d, J = 8.4 Hz), 7.06 (2H, d, J = 8.8 Hz), 6.82 (1H, d, J = 8.0 Hz), 6.45 (1H, s), 6.21 (1H, d, J = 8.0 Hz), 5.16 (1H, s), 4.50 (2H, brs), 3.65-3.85 (1H, m), 3.45-3.65 (3H, m), 2.23-2.40 (1H, m), 2.08-2.23 (1H, m); LCMS: 97.3%, MS (ESI); m/z 378.9 [M + H]+. | |
| 55 | yellow powder: 1H NMR (CDCl3, 400 MHz); δ 7.12 (2H, d, J = 8.4 Hz), 7.00 (1H, d, J = 8.0 Hz), 6.88 (1H, d, J = 2.0 Hz), 6.82 (2H, dd, J = 6.8, 2.4 Hz), 6.50 (1H, dd, J = 8.4, 2.0 Hz), 4.41 (2H, t, J = 6.0 Hz), 4.24 (2H, t, J = 6.4 Hz), 3.63 (4H, t, J = 6.8 Hz), 2.00 (4H, m); LCMS: 98.5%, MS (ESI); m/z 407.2 [M + H]+. | |
| 56 | white powder; 1H NMR (DMSO-d6, 400 MHz); δ 7.56 (1H, d, J = 2.8 Hz), 7.36-7.43 (1H, m), 7.30-7.36 (1H, m), 6.91 (1H, d, J = 8.4 Hz), 6.55 (1H, t, J = 5.6 Hz), 6.36 (1H, d, J = 1.6 Hz), 6.28 (1H, dd, J = 8.4, 2.0 Hz), 4.54 (2H, brs), 4.31 (2H, t, J = 6.0 Hz), 3.44-3.68 (2H, m), 3.36 (3H, s); LCMS: 100%, MS (ESI); m/z 400.9 [M + H]+. | |
| 57 | white powder; 1H NMR (DMSO-d6, 400 MHz); δ 7.56 (1H, d, J = 2.0 Hz), 7.39 (1H, d, J = 9.2 Hz), 7.29-7.36 (1H, m), 6.79 (1H, d, J = 8.4 Hz), 6.67 (1H, t, J = 5.6 Hz), 6.49 (1H, d, J = 2.0 Hz), 6.24 (1H, dd, J = 8.0, 1.6 Hz), 4.41 (2H, brs), 4.30 (2H, t, J = 6.0 Hz), 3.67-3.72 (2H, m), 3.38 (3H, s); LCMS: 100%, MS (ESI); m/z 401.0 [M + H]+. | |
| 58 | white powder; 1H NMR (DMSO-d6, 400 MHz); δ 7.47 (1H, d, J = 8.4 Hz), 7.41 (1H, d, J = 3.2 Hz), 7.08 (1H, dd, J = 8.8, 2.8 Hz), 6.91 (1H, d, J = 8.4 Hz), 6.57 (1H, t, J = 5.2 Hz), 6.36 (1H, d, J = 2.0 Hz), 6.28 (1H, dd, J = 8.4, 2.0 Hz), 4.54 (2H, brs), 4.24 (2H, t, J = 5.6 Hz), 3.60-3.66 (2H, m), 3.36 (3H, s); LCMS: 99.6%, MS (ESI); m/z 400.9 [M + H]+. | |
| 59 | white powder; 1H NMR (DMSO-d6, 400 MHz); δ 7.36-7.47 (2H, m) 7.05 (1H, dd, J = 9.2, 2.8 Hz), 6.77 (1H, d, J = 8.0 Hz), 6.66 (1H, t, J = 5.2 Hz), 6.48 (1H, d, J = 1.6 Hz), 6.22 (1H, dd, J = 8.0, 1.6 Hz), 4.43 (2H, brs), 4.21 (2H, t, J = 6.0 Hz), 3.62-3.69 (2H, m), 3.37 (3H, s); LCMS: 95.5%, MS (ESI); m/z 400.9 [M + H]+. | |
| 60 | white powder; 1H NMR (DMSO-d6, 400 MHz); δ 7.51 (1H, d, J = 9.2 Hz), 7.37 (1H, d, J = 2.8 Hz), 7.01 (1H, dd, J = 8.8, 2.8 Hz), 6.91 (1H, d, J = 8.4 Hz), 6.57 (1H, t, J = 5.2 Hz), 6.36 (1H, d, J = 2.0 Hz), 6.28 (1H, dd, J = 8.0, 1.6 Hz), 4.57 (2H, brs), 4.21 (2H, t, J = 6.0 Hz), 3.58-3.66 (2H, m), 3.36 (3H, s); LCMS: 99.7%, MS (ESI); m/z 350.9 [M + H]+. | |
| 61 | white powder; 1H NMR (DMSO-d6, 400 MHz); δ 7.48 (1H, d, J = 8.8 Hz), 7.39 (1H, d, J = 2.8 Hz), 7.01 (1H, dd, J = 8.8, 3.2 Hz), 6.79 (1H, d, J = 8.0 Hz), 6.69 (1H, t, J = 5.2 Hz), 6.50 (1H, d, J = 2.0 Hz), 6.24 (1H, dd, J = 8.0, 2.0 Hz), 4.46 (2H, brs), 4.21 (2H, t, J = 6.0 Hz), 3.63-3.68 (2H, m), 3.38 (3H, s); LCMS: 100%, MS (ESI); m/z 350.9 [M + H]+. | |
| 62 | white powder; 1H NMR (DMSO-d6, 400 MHz); δ 10.36 (1H, brs), 7.28 (1H, d, J = 8.8 Hz), 7.07 (1H, d, J = 9.2 Hz), 6.78-6.83 (1H, m), 6.40-6.44 (2H, m), 6.18-6.22 (1H, m.), 4.42 (2H, brs), 4.14 (2H, t, J = 5.6 Hz), 3.59-3.61 (2H, m); LCMS: 100%, MS (ESI); m/z 353.1 [M + H]+. | |
| 63 | dark powder; 1H NMR (DMSO-d6, 400 MHz); δ 12.17 (2H, brs), 8.23 (2H, brs), 7.30 (2H, d, J = 8.8 Hz), 7.17 (2H, d, J = 8.4 Hz), 7.06 (2H, d, J = 9.2 Hz), 6.45-6.55 (2H, m), 5.10-5.20 (1H, m), 3.55-3.75 (1H, m), 3.25-3.48 (3H, m), 2.28-2.49 (1H, m), 2.11-2.25 (1H, m); LCMS: 93.4%, MS (ESI); m/z 379.1 [M + H]+. | |
| 64 | white gum; 1H NMR (DMSO-d6, 400 MHz); δ 10.50 (1H, brs), 7.74 (1H, d, J = 8.8 Hz), 7.32 (2H, d, J = 8.8 Hz), 6.91 (2H, d, J = 8.4 Hz), 6.52 (1H, s), 6.30-6.34 (1H, m), 3.70-3.80 (1H, m), 3.50-3.70 (2H, m), 3.39-3.50 (2H, overlap with water peak), 2.20-2.33 (2H, m); LCMS: 99.7%, MS (ESI); m/z 406.1 [M + H]+. | |

| | |
|---|---|
| 65 | white powder; 1H NMR (DMSO-d6); δ 7.28 (2H, d, J = 8.8 Hz), 6.95-7.02 (2H, m), 6.92 (1H, d, J = 8.4 Hz), 6.49 (1H, d, J = 2.0 Hz), 6.29 (1H, dd, J = 8.0, 2.0 Hz), 5.51 (1H, brs), 4.67 (2H, brs), 4.27 (2H, t, J = 5.2 Hz), 4.18 (2H, t, J = 5.2 Hz), 1.42 (9H, s); LCMS: 99.8%, MS (ESI); m/z 409.2 [M + H]+. |
| 66 | off-white powder; 1H NMR (DMSO-d6); δ 7.27 (2H, d, J = 8.8 Hz), 6.95 (2H, d, J = 8.8 Hz), 6.88 (1H, d, J = 8.0 Hz), 6.50 (1H, d, J = 2.0 Hz), 6.24 (1H, dd, J = 8.0, 2.0 Hz), 5.58 (1H, brs), 4.40 (2H, brs), 4.28 (2H, t, J = 5.2 Hz), 4.16 (2H, t, J = 5.2 Hz), 1.43 (9H, s); LCMS: 99.5%, MS (ESI); m/z 409.3 [M + H]+. |
| 67 | off-white powder; 1H NMR (DMSO-d6); δ 10.57 (1H, brs), 7.73 (2H, d, J = 9.2 Hz), 7.34 (2H, d, J = 8.8 Hz), 6.93 (1H, d, J = 8.0 Hz), 6.22-6.33 (2H, m), 5.67-5.79 (1H, m), 4.74 (2H, s), 4.63 (2H, brs), 1.42 (9H, s); LCMS: 99.3%, MS (ESI); m/z 422.2 [M + H]+. |
| 68 | white powder; 1H NMR (DMSO-d6, 400 MHz); δ 7.28 (2H, d, J = 8.8 Hz), 7.02-7.06 (2H, m), 6.98 (1H, d, J = 8.4 Hz), 6.60 (1H, d, J = 2.0 Hz), 6.37 (1H, dd, J = 8.0, 2.0 Hz), 4.80 (2H, brs), 4.26 (2H, t, J = 4.8 Hz), 4.19 (2H, t, J = 5.2 Hz), 4.08 (4H, t, J = 7.2 Hz), 2.28-2.34 (2H, m); LCMS: 95.7%, MS (ESI); m/z 393.3 [M + H]+. |
| 69 | off-white powder; 1H NMR (DMSO-d6); δ 10.50 (1H, brs), 7.71 (2H, d, J = 8.8 Hz), 7.34 (2H, d, J = 8.8 Hz), 6.70 (1H, d, J = 8.0 Hz), 6.51 (1H, s), 6.19 (1H, d, J = 8.0 Hz), 5.84 (1H, s), 4.74 (2H, s), 4.42 (2H, brs), 1.43 (9H, s); LCMS: 92.7%, MS (ESI); m/z 422.0 [M + H]+. |
| 70 | white powder; 1H NMR (DMSO-d6, 400 MHz); δ 7.26 (2H, d, J = 8.4 Hz), 7.02 (1H, d, J = 8.4 Hz), 6.95-7.05 (2H, m), 6.52 (1H, d, J = 2.0 Hz), 6.32 (1H, dd, J = 8.0, 2.0 Hz), 4.53 (2H, brs), 4.25 (2H, t, J = 4.2 Hz), 4.20 (2H, t, J = 4.8 Hz), 4.10 (4H, t, J = 7.6 Hz), 2.28-2.33 (2H, m); LCMS: 95.9%, MS (ESI); m/z 393.2 [M + H]+. |
| 71 | white powder; 1H NMR (DMSO-d6, 400 MHz); δ 10.75 (1H, brs), 7.59 (2H, d, J = 2.4 Hz), 7.33-7.42 (2H, m), 6.77-6.83 (1H, m), 6.44 (1H, s), 6.17-6.24 (1H, m), 5.25-5.30 (1H, m), 4.45 (2H, brs), 3.70-3.82 (1H, m), 3.50-3.62 (3H, m), 2.28-2.38 (1H, m), 2.16-2.22 (1H, m); LCMS: 95.9%, MS (ESI); m/z 413.3 [M + H]+. |
| 72 | off-white powder; 1H NMR (DMSO-d6); δ 7.38 (1H, d, J = 2.4 Hz), 7.25 (2H, d, J = 8.8 Hz), 6.91-6.99 (2H, m), 6.80 (1H, d, J = 2.0 Hz), 4.67 (2H, brs), 4.48 (2H, t, J = 5.6 Hz), 4.32 (2H, t, J = 5.6 Hz), 3.51-3.63 (4H, m), 1.85-1.94 (4H, m); LCMS: 97.6%, MS (ESI); m/z 408.3 [M + H]+. |
| 73 | grey powder; 1H NMR (DMSO-d6, 400 MHz); δ 10.20 (1H, brs), 7.59 (1H, s), 7.30-7.40 (2H, m), 6.68-6.89 (1H, m), 6.10-6.48 (3H, m), 4.43 (2H, brs), 3.43-3.52 (2H, m), 2.99 (2H, t, J = 7.2 Hz); LCMS: 99.5%, MS (ESI); m/z 321.1 [M + H]+. |
| 74 | grey powder; 1H NMR (DMSO-d6, 400 MHz); δ 10.13-10.34 (1H, m), 7.49-7.61 (2H, m), 7.38 (1H, d, J = 8.4 Hz), 6.83-7.10 (1H, m), 6.80 (1H, dd, J = 8.4, 2.8 Hz), 6.31-6.43 (1H, m), 6.10-6.24 (1H, m), 5.08-5.25 (1H, m), 4.25-4.55 (2H, m), 1.40 (3H, d, J = 6.8 Hz); LCMS: 100%, MS (ESI); m/z 321.2 [M + H]+. |
| 75 | white powder; 1H NMR (DMSO-d6, 400 MHz); δ 10.27 (1H, brs.), 7.28 (2H, d, J = 8.4 Hz), 7.05 (2H, d, J = 9.2 Hz), 6.84 (1H, d, J = 8.0 Hz), 6.45 (1H, s), 6.27 (1H, d, J = 7.6 Hz), 5.77 (2H, brs.), 5.06 (1H, brs), 4.13 (2H, t, J = 5.6 Hz), 3.38 (2H, t, J = 5.6 Hz); LCMS: 100%, MS (ESI); m/z 353.3 [M + H]+. |
| 76 | yellow powder; 1H NMR (DMSO-d6, 400 MHz); δ 10.58 (1H, brs), 7.76 (2H, d, J = 8.8 Hz), 7.34 (2H, d, J = 8.4 Hz), 7.09 (1H, d, J = 8.4 Hz), 6.61 (1H, s), 6.54 (1H, d, J = 8.4 Hz), 3.78-3.95 (5H, m), 3.68 (3H, s), 2.27-2.40 (1H, m), 2.11-2.25 (1H, m); LCMS: 93.9%, MS (ESI); m/z 420.0 [M + H]+. |
| 77 | off-white powder; 1H NMR (DMSO-d6, 400 MHz); δ 12.5 (2H, brs), 9.23 (1H, brs), 7.29-7.49 (2H, m), 7.31 (2H, d, J = 8.8 Hz), 7.18-7.21 (3H, m), 7.08 (2H, d, J = 9.6 Hz), 6.50-6.52 (2H, m), 5.20-5.21 (1H, m), 4.60 (2H, d, J = 6.0 Hz), 3.67-3.72 (1H, m), 3.30-3.42 (3H, overlap with H2O peak), 2.33-2.38 (1H, m), 1.90-2.23 (1H, m); LCMS: 98.1%, MS (ESI); m/z 487.3 [M + H]+. |
| 78 | white powder; 1H NMR (DMSO-d6, 400 MHz); δ 8.56 (1H, d, J = 4.4 Hz), 7.98 (1H, d, J = 4.0 Hz), 7.30 (1H, d, J = 8.4 Hz), 7.24 (2H, d, J = 8.4 Hz), 6.85-6.95 (2H, m), 6.79 (1H, d, J = 2.0 Hz), 6.55-6.60 (1H, m), 5.17 (2H, brs), 4.68 (2H, t, J = 5.2 Hz), 4.30 (2H, t, J = 5.2 Hz); LCMS: 95.6%, MS (ESI); m/z 422.2 [M + H]+. |
| 79 | white powder; 1H NMR (DMSO-d6, 400 MHz); δ 7.46 (2H, d, J = 8.8 Hz), 7.29 (2H, d, J = 8.0 Hz), 6.88 (1H, brs), 6.77 (1H, d, J = 8.4 Hz), 6.40 (1H, d, J = 1.6 Hz), 6.17 (1H, dd, J = 8.4, 2.4 Hz), 4.45 (2H, d, J = 6.0 Hz); LCMS: 95.7%, MS (ESI); m/z 323.1 [M + H]+. |
| 80 | white powder; 1H NMR (DMSO-d6, 400 MHz); δ 9.72 (1H, t, J = 6.0 Hz), 7.49 (2H, d, J = 8.4 Hz), 7.35-7.45 (4H, m), 7.10-7.20 (2H, m), 6.95-7.09 (4H, m), 4.65 (2H, d, J = 6.0 Hz); LCMS: 100%, MS (ESI); m/z 331.2 [M + H]+. |

| | |
|---|---|
| 81 | white powder; 1H NMR (DMSO-d6, 400 MHz); δ 10.35 (1H, brs), 8.09-8.18 (1H, m), 7.90-7.99 (1H, m), 7.82 (1H, d, J = 8.0 Hz), 7.49-7.59 (3H, m), 7.46 (1H, t, J = 8.0 Hz), 6.66-6.91 (2H, m), 6.41 (1H, s), 6.10-6.20 (1H, m), 4.91 (2H, d, J = 4.4 Hz), 4.43 (2H, brs); LCMS: 96.0%, MS (ESI); m/z 289.1 [M + H]+. |
| 82 | white powder; 1H NMR (DMSO-d6, 400 MHz); δ 8.60 (1H, d, J = 4.8 Hz), 7.99 (1H, d, J = 4.4 Hz), 7.38 (1H, d, J = 8.4 Hz), 7.15-7.28 (2H, m), 6.80-6.93 (2H, m), 6.70-6.80 (1H, m), 6.63-6.75 (1H, m), 4.91 (2H, brs), 4.78 (2H, t, J = 5.2 Hz), 4.29 (2H, t, J = 5.2 Hz); LCMS: 99.1%, MS (ESI); m/z 422.2 [M + H]+. |
| 83 | off-white powder; 1H NMR (DMSO-d6, 400 MHz); δ 7.54 (1H, d, J = 2.4 Hz), 7.27 (2H, d, J = 8.4 Hz), 6.96-7.04 (3H, m), 4.78 (2H, brs), 4.38 (2H, t, J = 5.2 Hz), 4.26-4.34 (2H, m), 3.46-3.58 (4H, m), 1.85-1.95 (4H, m); LCMS: 97.7%, MS (ESI); m/z 408.0 [M + H]+. |
| 84 | white powder; 1H NMR (CDCl3, 400 MHz); δ 7.65 (1H, d, J = 8.4 Hz), 7.14 (2H, d, J = 8.8 Hz), 6.75-6.90 (2H, m), 6.39 (1H, d, J = 8.4 Hz), 6.21 (1H, s), 4.55-4.65 (2H, m), 4.29 (1H, t, J = 4.2 Hz), 3.95-4.05 (4H, m), 3.85-3.95 (4H, m), 2.35-2.45 (2H, m), 2.05-2.20 (4H, m); LCMS: 92%, MS (ESI); m/z 447.1 [M + H]+. |
| 85 | white powder; 1H NMR (CDCl3, 400 MHz); δ 7.12 (1H, d, J = 8.4 Hz), 7.08 (1H, d, J = 8.4 Hz), 6.81 (1H, d, J = 2.4 Hz), 6.75 (2H, d, J = 9.2 Hz), 6.31 (1H, dd, J = 8.8, 2.0 Hz), 4.55-4.65 (2H, m), 4.25-4.35 (2H, m), 3.90-4.00 (4H, m), 3.80-3.90 (4H, m), 2.35-2.45 (2H, m), 2.05-2.15 (4H, m); H NMR and NOE confirmed the structure; LCMS: 96.3%, MS (ESI); m/z 447.3 [M + H]+. |
| 86 | pale yellow powder; 1H NMR (DMSO-d6, 400 MHz); 7.40-7.45 (4H, m), 6.95-7.05 (4H, m), 6.90-6.98 (1H, brs), 6.81 (1H, d, J = 8.4 Hz), 6.43 (1H, s), 6.21 (1H, dd, J = 8.0, 2.0 Hz), 4.44 (2H, d, J = 4.8 Hz); LCMS: 99.5%, MS (ESI); m/z 365.1 [M + H]+. |
| 87 | pale yellow powder; hydroscopic; 1H NMR (DMSO-d6, 400 MHz); δ 12.60 (2H, brs), 9.24-9.38 (1H, m), 7.46 (2H, d, J = 8.8 Hz), 7.39 (2H, t, J = 7.6 Hz), 7.02 (2H, t, J = 8.4 Hz), 6.97-7.08 (4H, m), 6.74 (1H, s), 6.66 (1H, d, J = 8.4 Hz), 4.60 (2H, d, J = 6.4 Hz), 3.83-4.00 (2H, m), 3.71-3.82 (2H, m), 3.42-3.53 (1H, m); LCMS: 100%, MS (ESI); m/z 387.0 [M + H]+. |
| 88 | off-white powder; 1H NMR (DMSO-d6, 400 MHz); δ 7.42 (2H, d, J = 8.8 Hz), 7.37 (2H, d, J = 8.0 Hz), 7.00-7.10 (4H, m), 6.90-7.00 (1H, brs), 6.82 (1H, d, J = 8.0 Hz), 6.44 (1H, d, J = 2.0 Hz), 6.20-6.25 (1H m), 4.45 (2H, d, J = 5.2 Hz); LCMS: 99.5%, MS (ESI); m/z 415.0 [M + H]+. |
| 89 | white powder; 1H NMR (DMSO-d6, 400 MHz); δ 7.26 (2H, d, J = 8.8 Hz), 7.11 (1H, s), 6.90-7.00 (2H, m), 6.88 (1H, s), 4.61 (2H, t, J = 4.8 Hz), 4.35 (2H, t, J = 4.8 Hz), 3.74-3.76 (4H, m), 1.96-1.99 (4H, m); LCMS: 100%, MS (ESI); m/z 441.2 [M + H]+. |
| 90 | grey powder; mp >200° C.; 1H NMR (DMSO-d6, 400 MHz); δ 7.58-7.65 (4H, m), 7.41-7.48 (4H, m), 7.34 (1H, t, J = 7.6 Hz), 6.75-6.85 (2H, m), 6.41 (1H, d, J = 2.0 Hz), 6.18 (1H, d, J = 6.8 Hz), 4.30-4.65 (4H, m); LCMS: 99.1%, MS (ESI); m/z 315.1 [M + H]+ |
| 91 | white powder; mp >107.8° C.; 1H NMR (DMSO-d6, 400 MHz); δ 8.15 (1H, d, J = 7.6 Hz), 7.94 (1H, d, J = 2.4 Hz), 7.83 (1H, d, J = 8.0 Hz), 7.50-7.61 (3H, m), 7.44-7.48 (1H, m), 6.80 (1H, d, J = 8.0 Hz), 6.79 (1H, brs), 6.43 (1H, d, J = 2.0 Hz), 6.20 (1H, d, J = 6.8 Hz), 4.92 (2H, d, J = 5.6 Hz), 4.41 (2H, brs); LCMS: 99.3%, MS (ESI); m/z 289.1 [M + H]+. |
| 92 | pale yellow powder; 1H NMR (DMSO-d6, 400 MHz); δ 7.56 (1H, brs), 7.36-7.42 (6H, m), 7.24-7.26 (2H, m), 6.86 (1H, d, J = 8.4 Hz), 6.46 (1H, d, J = 2.0 Hz), 6.29 (1H, dd, J = 8.4, 2.0 Hz), 4.50 (2H, s); LCMS: 95.5%, MS (ESI); m/z 381.1 [M + H]+. |
| 93 | off-white powder; 1H NMR (DMSO-d6, 400 MHz); δ 7.26 (2H, d, J = 8.8 Hz), 6.92-7.01 (2H, m), 6.88 (1H, d, J = 8.4 Hz), 6.69 (1H, d, J = 2.0 Hz), 6.49 (1H, d, J = 8.0, 2.0 Hz), 6.12 (2H, brs), 4.29 (2H, t, J = 5.2 Hz), 4.17-4.25 (2H, m), 4.04 (1H, brs), 1.17 (9H, s); LCMS: 100%, MS (ESI); m/z 409.1 [M + H]+. |
| 94 | pale yellow powder; 1H NMR (DMSO-d6, 400 MHz); δ 7.37 (2H, d, J = 8.8 Hz), 7.16-7.24 (2H, m), 6.96-7.05 (2H, m), 6.94 (2H, d, J = 8.4 Hz), 6.70-6.79 (2H, m), 6.41 (1H, d, J = 2.0 Hz), 6.19 (1H, dd, J = 8.0, 1.6 Hz), 4.41 (2H, d, J = 6.0 Hz); LCMS: 99.2%, MS (ESI); m/z 349.2 [M + H]+. |
| 95 | mp >137.5° C.; 1H NMR (DMSO-d6, 400 MHz): δ 10.30-10.40 (1H, m), 7.35-7.45 (4H, m), 7.12 (1H, t, J = 7.6 Hz), 6.95-7.05 (4H, m), 6.70-6.90 (2H, m), 6.39 (1H, s), 6.20-6.30 (1H, m), 4.40-4.70 (3H, m), 3.45-3.50 (1H, m), 1.10 (6H, d, J = 6.4 Hz); LCMS: 99.4%, MS (ESI); m/z 373.2 [M + H]+. |
| 96 | white powder; 1H NMR (DMSO-d6, 400 MHz); δ 10.30-10.45 (1H, m), 7.35-7.45 (4H, m), 7.12 (1H, t, J = 7.2 Hz), 6.95-7.05 (4H, m), 6.60-6.90 (2H, m), 6.32 (1H, d, J = 2.0 Hz), 6.15-6.25 (1H, m), 5.16 (1H, brs), 4.42 (2H, d, J = 6.0 Hz), 3.65-3.80 (1H, m), 2.25-2.35 (2H, m), 1.65-1.85 (4H, m); LCMS: 98.8%, MS (ESI); m/z 385.3 [M + H]+. |

| | |
|---|---|
| 97 | white powder; 1H NMR (DMSO-d6, 400 MHz); δ 10.30-10.40 (1H, m), 7.30-7.40 (4H, m), 7.12 (1H, t, J = 7.6 Hz), 6.95-7.00 (4H, m), 6.60-6.95 (2H, m), 6.39 (1H, s), 6.15-6.30 (1H, m), 4.70-4.85 (1H, m), 4.40-4.50 (2H, m), 3.60-3.65 (1H, m), 1.75-1.95 (2H, m), 1.60-1.70 (2H, m), 1.45-1.55 (2H, m), 1.35-1.45 (2H, m); LCMS: 100%, MS (ESI); m/z 399.2 [M + H]+. |
| 98 | white solid; mp = 116.8-118.7° C.; 1H NMR (DMSO-d6, 400 MHz); δ 10.45 (1H, brs), 7.30-7.45 (4H, m), 7.12 (1H, t, J = 7.2 Hz), 6.75-7.05 (6H, m), 6.60 (1H, s), 6.40-6.50 (1H, m), 4.45 (2H, d, J = 6.0 Hz), 2.79 (6H, s); LCMS: 99.2%, MS (ESI); m/z 359.2 [M + H]+. |
| 99 | yellow powder; 1H NMR (DMSO-d6, 400 MHz); δ 10.70 (1H, brs), 7.29 (2H, d, J = 8.8 Hz), 7.00-7.08 (2H, m), 6.95-7.00 (1H, m), 6.42-6.48 (1H, m), 6.19-6.24 (1H, m), 5.12-51.9 (1H, m), 3.61-3.68 (1H, m), 3.30-3.40 (5H, m), 3.24-3.26 (2H, m), 2.32-2.35 (1H, m), 2.10-2.19 (1H, m), 1.90-1.95 (4H, m); LCMS: 95.2%, MS (ESI); m/z 433.2 [M + H]+. |
| 100 | yellow powder; 1H NMR (DMSO-d6, 400 MHz); δ 7.27 (2H, d, J = 4.2 Hz), 6.95-7.10 (3H, m), 6.66 (1H, d, J = 2.0 Hz), 6.35-6.45 (1H, m), 4.78 (2H, brs), 4.33 (4H, s), 3.83 (2H, t, J = 14.0 Hz), 3.64 (2H, J = 7.6 Hz), 2.40-2.55 (2H, M); LCMS: 95.3%, MS (ESI); m/z 443.2 [M + H]+. |
| 101 | grey powder; 1H NMR (DMSO-d6, 400 MHz); δ 7.30-7.40 (3H, m), 7.17 (1H, d, J = 7.6 Hz), 7.00-7.10 (2H, m), 6.92-7.01 (2H, m), 6.89 (1H, dd, J = 8.0, 2.0 Hz), 6.81 (1H, d, J = 8.0 Hz), 6.43 (1H, d, J = 1.6 Hz), 6.23 (1H, dd, J = 8.0, 2.0 Hz), 4.46 (2H, s); LCMS: 99.5% , MS (ESI); m/z 365.1 [M + H]+. |
| 102 | white powder; mp = 58.4-66.6° C.; 1H NMR (DMSO-d6, 400 MHz); δ 7.37-7.46 (3H, m), 7.22 (1H, dd, J = 6.4, 3.2 Hz), 6.96-7.03 (3H, m), 6.70-6.80 (2H, m), 6.41 (1H, d, J = 2.0 Hz), 6.19 (1H, d, J = 7.6 Hz), 4.30-4.55 (4H, m); LCMS: 95.7%, MS (ESI); m/z 383.1[M + H]+. |
| 103 | pale green powder; 1H NMR (DMSO-d6, 400 MHz); δ 7.30-7.40 (3H, m), 7.10-7.20 (2H, m), 7.04 (1H, s), 6.98 (2H, dd, J = 8.8, 1.2 Hz), 6.71-6.82 (3H, m), 6.41 (1H, J = 1.6 Hz), 6.20 (1H, d, J = 8.0 Hz), 4.44 (2H, d, J = 6.4 Hz); LCMS: 97.3%, MS (ESI); m/z 331.2 [M + H]+. |
| 104 | white powder; 1H NMR (DMSO-d6, 400 MHz); δ 10.44 (1H, brs), 7.30 (2H, d, J = 8.8 Hz), 7.06 (2H, d, J = 8.8 Hz), 6.90-6.99 (1H, m), 6.37-6.45 (1H, m), 6.07-6.28 (2H, m), 5.14-5.16 (1H, m), 3.62-3.67 (1H, m), 3.30-3.42 (3H, overlapped with H2O peak), 2.1 (3H, d, J = 4.0 Hz), 2.31-2.35 (1H, m), 2.14-2.17 (1H, m); LCMS: 96.2%, MS (ESI); m/z 393.1 [M + H]+. |
| 105 | white powder; 1H NMR (DMSO-d6, 400 MHz); δ 7.30 (2H, d, J = 8.8 Hz), 7.06 (2H, d, J = 9.2 Hz), 6.98 (1H, d, J = 8.4 Hz), 6.43 (1H, s) 6.25 (1H, d, J = 8.4 Hz), 5.14-5.17 (1H, m), 3.62-3.68 (1H, m), 3.30-3.42 (3H, overlap with H2O peak), 2.99 (6H, s), 2.32-2.38 (1H, m), 2.14-2.17 (1H, m); LCMS: 100%, MS (ESI); m/z 407.1 [M + H]+. |
| 106 | white powder; 1H NMR (DMSO-d6, 400 MHz); δ 10.35-10.49 (1H, brs), 7.64-7.73 (5H, m), 7.51-7.58 (4H, m), 6.78-7.01 (2H, m), 6.42 (1H, s), 6.18-6.22 (1H, m), 4.54-4.58 (2H, m), 4.42-4.45 (2H, m); LCMS: 99.1%, MS (ESI); m/z 343.1 [M + H]+. |
| 107 | white powder; mp >200.9° C.; 1H NMR (DMSO-d6, 400 MHz); δ 9.51 (1H, d, J = 8.8 Hz), 7.54-7.66 (2H, m), 7.33-7.51 (3H, m), 7.12-7.22 (1H, m), 4.15-4.29 (1H, m), 3.00-3.15 (2H, m), 1.29 (3H, d, J = 6.8 Hz); LCMS: 100%, MS (ESI); m/z 334.9 [M + H]+. |
| 108 | yellow solid; 1H NMR (DMSO-d6, 400 MHz); δ 7.41 (2H, d, J = 8.8 Hz), 7.29 (2H, d, J = 8.0 Hz), 7.23 (2H, d, J = 8.0 Hz), 6.94 (2H, d, J = 8.4 Hz), 6.80 (1H, d, J = 8.0 Hz), 6.64 (1H, brs), 6.42 (1H, d, J = 2.0 Hz), 6.19 (1H, d, J = 7.2 Hz), 4.34 (2H, d, J = 6.0 Hz), 4.04 (2H, d, J = 12.4 Hz), 2.68-2.75 (3H, m), 1.80-1.91 (2H, m), 1.65-1.80 (2H, m); LCMS: 98.0%, MS (ESI); m/z 482.1 [M + H]+. |
| 109 | white powder; mp >173° C.; 1H NMR (DMSO-d6, 400 MHz); δ 10.40 (1H, brs), 7.30-7.40 (4H, m), 7.18 (1H, s), 7.11 (1H, t, J = 7.2 Hz), 6.90-7.00 (5H, m), 6.70-6.85 (2H, m), 6.39 (1H, d, J = 2.0 Hz), 6.24 (1H, d, J = 7.6 Hz), 5.00 (1H, brs), 4.42 (2H, d, J = 6.0 Hz), 1.31 (6H, s); LCMS: 100%, MS (ESI); m/z 416.1 [M + H]+. |
| 110 | pale yellow powder; 1H NMR (DMSO-d6, 400 MHz); δ 10.03-10.31 (1H, m), 7.30-7.55 (4H, m), 6.91-7.07 (4H, m), 6.60-6.88 (2H, m), 6.39 (1H, brs), 6.05-6.15 (1H, m), 4.80-4.90 (1H, m), 4.40 (2H, brs), 1.44 (3H, d, J = 6.8 Hz); LCMS: 100%, MS (ESI); m/z 379.0 |
| 111 | white solid; mp = 156.4-158.5° C.; 1H NMR (DMSO-d6, 400 MHz); δ 7.40 (1H, d, J = 8.8 Hz), 7.21 (1H, d, J = 8.4 Hz), 6.95-7.04 (4H, m), 6.83 (1H, d, J = 8.4 Hz), 6.31 (1H, d, J = 2.0 Hz), 6.26 (1H, dd, J = 8.0, 2.0 Hz), 6.08 (2H, brs), 5.10 (2H, s), 4.47 (2H, brs); LCMS: 99.8%, MS (ESI); m/z 365.1 [M + H]+. |
| 112 | off-white powder; 1H NMR (DMSO-d6, 400 MHz); δ 7.60 (1H, d, J = 8.8 Hz), 7.44 (2H, d, J =8.4 Hz), 7.40 (1H, brs), 7.23 (1H, d, J = 3.2 Hz), 7.07 (2H, d, J = 8.8 Hz), 6.96 (1H, dd, J = 8.8, 2.8 Hz), 6.85 (1H, d, J = 8.4 Hz), 6.46 (1H, d, J = 2.0 Hz), 6.27 (1H, dd, J = 8.0, 2.0 Hz), 4.48 (2H, s); LCMS: 97.6%, MS (ESI); m/z 399.1 [M + H]+. |

| | |
|---|---|
| 113 | off-white powder; 1H NMR (DMSO-d6, 400 MHz); δ 7.65 (1H, brs), 7.32-7.50 (3H, m), 7.08-7.20 (1H, m), 7.02 (2H, d, J = 8.4 Hz), 6.88 (1H, d, J = 8.4 Hz), 6.74-6.84 (1H, m), 6.48 (1H, d, J = 2.0 Hz), 6.29 (1H, dd, J = 8.0, 2.0 Hz), 4.48 (2H, s); LCMS: 98.7%, MS (ESI); m/z 367.1 [M + H]+. |
| 114 | white powder; mp >220° C.; 1H NMR (DMSO-d6, 400 MHz); δ 10.30 (1H, brs), 7.15-7.35 (4H, m), 7.06 (2H, d, J = 9.6 Hz), 6.95 (1H, d, J = 8.8 Hz), 6.78 (1H, d, J = 7.2 Hz), 6.50-6.70 (1H, m), 6.41 (1H, s), 6.15-6.25 (1H, m), 4.25-4.55 (4H, m), 3.25-3.40 (4H, m), 3.15-3.25 (4H, m); LCMS: 98.8%, MS (ESI); m/z 483.2 [M + H]+. |
| 115 | white powder; mp >220° C.; 1H NMR (DMSO-d6, 400 MHz); δ 10.30 (1H, brs), 7.30-7.55 (4H, m), 7.22 (2H, d, J = 8.4 Hz), 6.92 (2H, d, J = 8.4 Hz), 6.79 (1H, d, J = 8.0 Hz), 6.50-6.75 (1H, m), 6.41 (1H, d, J = 2.0 Hz), 6.15-6.25 (1H, m), 4.25-4.50 (2H, brs), 4.33 (2H, J = 6.0 Hz) 3.60-3.80 (2H, m), 2.60-2.75 (3H, m), 1.80-1.95 (2H, m), 1.65-1.80 (2H, m); LCMS: 98.7%, MS (ESI); m/z 432.1 [M + H]+. |
| 116 | pale yellow; mp >130.8° C.; 1H NMR (DMSO-d6, 400 MHz); δ 7.34 (2H, d, J = 8.4 Hz), 7.28 (2H, d, J = 8.4 Hz), 7.02 (1H, brs), 6.75-6.85 (1H, m), 6.44 (1H, s), 6.22 (1H, d, J = 8.0 Hz), 4.43 (2H, s), 1.25 (9H, s); LCMS: 99.6%, MS (ESI); m/z 295.0 [M + H]+. |
| 117 | off-white powder; mp >207.2° C.; 1H NMR (DMSO-d6, 400 MHz); δ 9.78 (1H, t, J = 6.0 Hz), 7.42-7.49 (4H, m), 7.36-7.42 (2H, m), 7.19 (1H, dd, J = 8.4, 2.0 Hz), 7.00 (2H, d, J = 8.8 Hz), 6.88-6.96 (2H, m), 4.66 (2H, d, J = 6.0 Hz), 1.27 (9H, s); LCMS; LCMS: 98.5%, MS (ESI); m/z 387.1 [M + H]+. |
| 118 | pale green powder; mp >113.2° C.; 1H NMR (DMSO-d6, 400 MHz); δ 10.56 (0.4H, brs), 10.40 (0.4H, brs), 7.35-7.50 (4H, m), 7.19-7.25 (1H, m), 6.90-7.05 (5H, m), 6.75-6.95 (2H, m), 6.39 (1H, s), 6.15-6.35 (1H, m), 4.97 (0.5H, brs), 5.07 (0.5H, brs), 4.38-4.49 (2H, m), 1.31 (6H, d, J = 3.6 Hz); LCMS: 99.5%, MS (ESI); m/z 450.0 [M + H]+. |
| 119 | white powder; mp >54.3° C.; 1H NMR (DMSO-d6, 400 MHz); δ 10.35-10.65 (1H, m), 7.30-7.60 (5H, m), 7.10-7.20 (1H, m), 6.90-7.10 (4H, m), 6.75-6.90 (1H, m), 6.40 (1H, s), 6.15-6.30 (1H, m), 5.00-5.25 (1H, m), 4.40-4.60 (2H, m), 3.85-4.05 (2H, m), 3.75-3.85 (1H, m), 3.60-3.75 (1H, m), 3.45-3.60 (1H, m), 2.05-2.25 (1H, m), 1.65-1.80 (1H, m); LCMS: 97.3%, MS (ESI); m/z 401.1 [M + H]+. |
| 120 | white powder; mp = 200.7-201.3° C.; 1H NMR (DMSO-d6, 400 MHz); δ 7.27 (2H, d, J = 8.8 Hz), 6.92-7.05 (2H, m), 6.87 (1H, d, J = 8.0 Hz), 6.48 (1H, s), 6.26 (2H, dd, J = 8.4, 2.4 Hz), 6.01 (1H, d, J = 6.8 Hz), 4.53 (2H, brs), 4.20-4.30 (2H, m), 4.13-4.20 (2H, m), 4.05-4.13 (1H, m), 1.85-2.05 (2H, m), 1.60-1.75 (2H, m), 1.45-1.60 (4H, m); LCMS: 98.6%, MS (ESI); m/z 421.1 [M + H]+. |
| 121 | white powder; mp >59.7° C.; 1H NMR (DMSO-d6, 400 MHz); δ 7.26 (2H, d, J = 8.4 Hz), 6.90 (2H, d, J = 8.4 Hz), 6.79 (1, d, J = 8.4 Hz), 6.69 (1H, brs), 6.42 (1H, d, J = 2.0 Hz), 6.19 (1H, dd, J = 8.0, 2.0 Hz), 4.39 (2H, d, J = 6.0 Hz), 1.26 (9H, s); LCMS: 99.5%, MS (ESI); m/z 311.1 [M + H]+. |
| 122 | off-white powder; mp >160.8° C.; 1H NMR (DMSO-d6); δ 9.73 (1H, t, J = 6.4 Hz), 7.52 (2H, d, J = 8.4 Hz), 7.35-7.46 (3H, m), 7.19 (1H, dd, J = 8.0, 2.0 Hz), 7.14 (1H, d, J = 8.4 Hz), 7.10 (2H, d, J = 8.8 Hz), 7.02 (1H, t, J = 2.4 Hz), 6.95 (1H, dd, J = 8.4, 2.4 Hz), 4.67 (2H, d, J = 6.0 Hz); LCMS: 100%, MS (ESI); m/z 365.0 [M + H]+. |
| 123 | yellow powder (amorphous) 1H NMR (DMSO-d6, 400 MHz); δ 7.35-7.47 (4H, m), 6.95-7.05 (4H, m), 6.91 (1H, d, J = 8.0 Hz), 6.40 (1H, s), 6.34 (1H, d, J = 8.4 Hz), 5.79 (1H, brs), 4.22 (2H, s), 2.98 (6H, s); LCMS: 98.7%, MS (ESI); m/z 393.1 [M + H]+. |
| 124 | gray powder (amorphous) 1H NMR (DMSO-d6, 400 MHz); δ 10.14 (1H, brs), 7.30-7.40 (4H, m), 6.90-7.00 (4H, m), 6.55-6.87 (2H, m), 6.37 (1H, s), 6.14 (1H, d, J = 8.4 Hz), 4.20-4.70 (3H, m), 1.60-1.80 (2H, m), 0.87 (3H, t, J = 7.2 Hz); LCMS: 100%, MS (ESI); m/z 393.0 [M + H]+. |
| 125 | pale yellow powder (amorphous) 1H NMR (DMSO-d6, 400 MHz); δ 10.40 (1H, brs), 7.36-7.45 (4H, m), 6.95-7.06 (4H, m), 6.75-6.80 (2H, m), 6.26 (1H, s), 6.13 (1H, d, J = 7.6 Hz), 5.69 (1H, brs), 4.81 (2H, t, J = 6.0 Hz), 4.31-4.50 (5H, m); LCMS: 99.1%, MS (ESI); m/z 421.1 [M + H]+. |
| 126 | pale yellow powder; 1H NMR (DMSO-d6, 400 MHz); δ 13.14 (2H, brs), 7.78 (2H, d, J = 8.8 Hz), 7.39 (2H, d, J = 8.4 Hz), 7.30 (1H, d, J = 8.8 Hz), 6.90-7.10 (6H, m), 4.42 (2H, s), 3.21 (6H, s); LCMS: 100%, MS (ESI); m/z 443.1 [M + H]+. |
| 127 | pale yellow powder; 1H NMR (DMSO-d6, 400 MHz); δ 13.20 (2H, brs), 7.50 (2H, d, J = 8.8 Hz), 7.38 (2H, d, J = 8.4 Hz), 7.29 (1H, d, J = 8.8 Hz), 7.16 (1H, brs), 6.80-7.10 (5H, m), 4.71 (1H, d, J = 5.6 Hz), 3.20 (6H, s), 1.66 (3H, d, J = 6.0 Hz); LCMS: 100%, MS (ESI); m/z 457.1 [M + H]+. |

| | |
|---|---|
| 128 | pale green powder (amorphous) 1H NMR (DMSO-d6, 400 MHz); δ 12.66 (2H, brs), 7.36-7.47 (4H, m), 7.13 (1H, d, J = 7.6 Hz), 6.90-7.00 (4H, m), 6.60-6.85 (2H, m), 4.25-4.35 (1H, m), 3.15 (6H, s), 1.70-2.00 (2H, m), 0.87 (3H, t, J = 7.2 Hz); LCMS: 99.39%, MS (ESI); m/z 421.1 [M + H]+. |
| 129 | gray powder; 1H NMR (DMSO-d6, 400 MHz); δ 10.35-10.50 (1H, m), 7.80-7.98 (4H, m), 7.66 (2H, d, J = 8.8 Hz), 7.57 (2H, d, J = 8.4 Hz), 6.75-7.00 (1H, m), 6.70-6.80 (1H, m), 6.39 (1H, s), 6.10-6.25 (1H, m), 4.45-4.55 (2H, m), 4.25-4.45 (2H, m); LCMS: 98.0%, MS (ESI); m/z 413.0 [M + H]+. |
| 130 | white powder; 1H NMR (DMSO-d6); δ 9.92 (1H, t, J = 6.0 Hz), 7.69-7.83 (4H, m), 7.58-7.69 (4H, m), 7.39-7.51 (2H, m), 7.18 (1H, d, J = 8.8 Hz), 4.83 (2H, d, J = 6.0 Hz); LCMS: 100%, MS (ESI); m/z 377.0 [M + H]+. |
| 131 | pale green powder; 1H NMR (DMSO-d6, 400 MHz); δ 12.91 (2H, brs), 7.41-7.47 (4H, m), 7.22 (1H, d, J = 8.4 Hz), 6.86-6.99 (6H, m), 4.50-4.70 (1H, m), 3.17 (6H, s), 1.58 (3H, d, J = 5.2 Hz); LCMS: 99.7%, MS (ESI); m/z 407.0 [M + H]+. |
| 132 | pale green powder (amorphous) 1H NMR (DMSO-d6, 400 MHz); δ 12.76 (2H, brs), 7.43 (2H, d, J = 8.8 Hz), 7.38 (2H, d, J = 8.8 Hz), 7.16 (1H, d, J = 7.2 Hz), 7.02-7.08 (2H, m), 7.00 (2H, d, J = 8.8 Hz), 6.60-6.85 (2H, m), 4.30-4.40 (1H, m), 3.16 (6H, s), 1.75-2.10 (2H, m), 0.87 (3H, t, J = 7.2 Hz); LCMS: 99.6%, MS (ESI); m/z 471.1 [M + H]+. |
| 133 | pale yellow powder; 1H NMR (DMSO-d6, 400 MHz); δ 10.52 (1H, brs), 7.85-7.99 (4H, m), 7.61-7.70 (2H, m), 7.56 (2H, d, J = 8.4 Hz), 6.96 (1H, brs), 6.84 (1H, d, J = 8.0 Hz), 6.23 (1H, s), 6.12 (1H, dd, J = 8.4, 2.0 Hz), 5.70 (1H, brs), 4.80 (2H, t, J = 6.0 Hz), 4.52 (2H, d, J = 6.0 Hz), 4.38-4.45 (1H, m), 4.30-4.38 (2H, m); LCMS: 95.3%, MS (ESI); m/z 469.0 [M + H]+. |
| 134 | white amorphous; 1H NMR (DMSO-d6, 400 MHz); δ 10.24-10.59 (1H, m), 7.34-7.44 (4H, m), 6.94-7.09 (4H, m), 6.85-6.88 (2H, m), 6.42 (1H, d, J = 2.0 Hz), 6.20-6.25 (1H, m), 4.83 (1H, brs), 4.44 (2H, d, J = 6.4 Hz), 3.63-3.67 (1H, m), 2.51-2.53 (1H, m), 2.26-2.30 (1H, m), 1.21 (3H, d, J = 6.0 Hz); LCMS: 98.0%, MS (ESI); m/z 375.1 [M + H]+. |
| 135 | pale green powder; 1H NMR (DMSO-d6, 400 MHz); δ 7.76 (1H, d, J = 2.8 Hz), 7.30-7.45 (4H, m), 7.05 (1H, d, J = 8.8 Hz), 6.97 (2H, d, J = 8.4 Hz), 6.85 (1H, d, J = 8.4 Hz), 6.46 (1H, d, J = 2.0 Hz), 6.26 (1H, dd, J = 8.4, 2.0 Hz), 4.46 (2H, s); LCMS: 98.2%, MS (ESI); m/z 398.9 [M + H]+. |
| 136 | pale green powder; 1H NMR (DMSO-d6, 400 MHz); δ 8.19 (1H, d, J = 2.4 Hz), 7.41-7.52 (4H, m), 7.07 (2H, d, J = 8.8 Hz), 6.75-6.85 (2H, m), 6.42 (1H, d, J = 1.6 Hz), 6.20 (1H, dd, J = 8.4, 2.0 Hz), 4.45 (2H, d, J = 5.6 Hz); LCMS: 97.8%, MS (ESI); m/z 366.0 [M + H]+. |
| 137 | off-white amorphous; 1H NMR (DMSO-d6, 400 MHz); δ 10.47-10.63 (1H, m), 7.40 (4H, d, J = 8.8 Hz), 6.86-7.04 (6H, m), 6.40-6.45 (1H, m), 6.18-6.32 (1H, m), 5.91-6.08 (1H, m), 4.42-4.48 (2H, m), 2.59-2.72 (2H, m), 2.27-2.40 (2H, m), 1.98-2.15 (2H, m); LCMS: 92.6%, MS (ESI) m/z 444.2 [M + H]+. |
| 138 | white powder; 1H NMR (DMSO-d6); δ 9.78 (1H, t, J = 6.0 Hz), 8.17 (1H, d, J = 2.4 Hz), 7.96 (1H, dd, J = 8.8, 2.4 Hz), 7.51 (2H, d, J = 8.4 Hz), 7.37-7.45 (2H, m), 7.08-7.20 (4H, m), 4.69 (2H, d, J = 6.0 Hz); LCMS: 99.6%, MS (ESI); m/z 365.9 [M + H]+. |
| 139 | white powder; 1H NMR (DMSO-d6); δ 8.41 (1H, d, J = 4.8 Hz), 7.71-7.78 (1H, m), 7.53 (1H, d, J = 8.0 Hz), 7.29-7.35 (2H, m), 7.23-7.28 (2H, m), 7.16-7.22 (1H, m), 6.70-6.82 (2H, m), 6.40 (1H, s), 6.18 (1H, dd, J = 8.4, 2.0 Hz), 6.04 (1H, brs), 5.66 (1H, s), 4.38 (2H, d, J = 5.6 Hz); LCMS: 98.3%, MS (ESI); m/z 346.0 [M + H]+. |
| 140 | white amorphous; 1H NMR (DMSO-d6, 400 MHz); δ 7.52 (1H, d, J = 2.0 Hz), 7.33 (1H, d, J = 8.0 Hz), 7.20-7.30 (4H, m), 7.03 (2H, d, J = 6.8 Hz), 6.86 (1H, d, J = 8.8 Hz), 6.31 (1H, d, J = 8.4 Hz), 6.15-6.27 (2H, m), 5.00-5.20 (2H, m), 4.46 (2H, brs), 4.10-4.25 (1H, m), 2.87-3.08 (2H, m), 1.22 (3H, d, J = 6.4 Hz); LCMS: 100%, MS (ESI); m/z 425.1 [M + H]+. |
| 141 | pale yellow powder; 1H NMR (DMSO-d6); δ 8.70 (1H, d, J = 4.0 Hz), 8.01-8.10 (1H, m), 7.96 (1H, d, J = 8.0 Hz), 7.91 (2H, d, J = 8.4 Hz), 7.61-7.68 (1H, m), 7.50 (2H, d, J = 7.04 (brs)), 6.77-6.84 (1H, m), 6.43 (1H, d, J = 2.0 Hz), 6.21 (1H, dd, J = 8.0, 2.0 Hz), 4.55 (2H, s); LCMS: 89.4%, MS (ESI); m/z 344.1 [M + H]+. |
| 142 | white amorphous; hydroscopic; 1H NMR (DSMO-d6, 400 MHz); δ 12.52 (2H, brs), 10.73 (1H, brs), 8.87 (1H, t, J = 6.0 Hz), 7.29 (2H, d, J = 8.4 Hz), 7.11-7.22 (1H, m), 7.05 (2H, d, J = 9.2 Hz), 6.41-6.59 (2H, m), 5.10-5.22 (1H, m), 3.89-4.00 (2H, m), 3.71-3.81 (2H, m), 3.61-3.70 (3H, m), 3.50-3.60 (4H, m), 3.11-3.24 (4H, m), 2.92-3.10 (2H, m), 2.50-2.60 (2H, m), 2.11-2.21 (1H, m), 1.95-2.08 (1H, m); LCMS: 99.5%, MS (ESI); m/z 506.3 [M + H]+. |

| | |
|---|---|
| 143 | white powder; 1H NMR (DMSO-d6, 400 MHz); δ 10.30-10.43 (1H, m), 7.29 (2H, d, J = 8.8 Hz), 7.04 (2H, d, J = 9.2 Hz), 6.86-6.99 (1H, m), 6.34-6.45 (1H, m), 5.95-6.25 (2H, m), 5.10-5.20 (1H, m), 3.60-3.69 (1H, m), 3.47-3.58 (4H, m), 3.30-3.37 (2H, m), 3.20-3.29 (2H, m), 2.53-2.61 (2H, m), 2.43-2.49 (2H, m), 2.28-2.40 (5H, m), 2.05-2.17 (1H, m); LCMS: 100%, MS (ESI); m/z 492.1 [M + H]+. |
| 144 | pale-yellow amorphous; 1H NMR (DMSO-d6, 400 MHz); δ 7.53 (1H, d, J = 2.0 Hz), 7.33 (1H, d, J = 8.0 Hz), 7.15-7.28 (4H, m), 7.04 (2H, d, J = 7.6 Hz), 6.64 (1H, d, J = 8.0 Hz, 6.37-6.50 (2H, m), 6.05-6.15 (2H, m), 5.00-5.20 (2H, m), 4.40 (2H, brs), 4.15-4.29 (1H, m), 2.88-3.04 (2H, m), 1.23 (3H, d, J = 6.8 Hz); LCMS: 98.1%, MS (ESI); m/z 425.1 [M + H]+. |
| 145 | white powder; 1H NMR (DMSO-d6, 400 MHz); δ 10.62 (1H, brs), 7.35-7.45 (2H, m), 7.25 (1H, d, J = 8.8 Hz), 6.90-7.10 (4H, m), 6.78 (1H, d, J = 8.4 Hz), 6.40 (1H, s), 6.19 (1H, d, J = 6.4 Hz), 5.07 (1H, d, J = 8.0 Hz), 4.45 (2H, brs), 3.65-3.75 (1H, m), 3.40-3.55 (1H, m), 2.30-2.40 (1H, m), 1.75-2.00 (3H, m); LCMS: 97.0%, MS (ESI); m/z 405.1 [M + H]+. |
| 146 | gray powder; 1H NMR (DMSO-d6, 400 MHz); δ 10.20-10.40 (1H, m), 7.30-7.45 (4H, m), 6.90-7.10 (4H, m), 6.60-6.75 (2H, m), 6.45-6.55 (1H, m), 4.41 (2H, d, J = 6.0 Hz), 4.00-4.30 (2H, m), 3.70 (3H, s); LCMS: 99.5%, MS (ESI); m/z 394.9 [M + H]+. |
| 147 | off-white solid; mp = 191.4 C.-193.5 C.; 1H NMR (DMSO-d6, 400 MHz); δ 10.35-10.60 (1H, m), 7.35-7.45 (4H, m), 6.90-7.05 (6H, m), 6.63 (1H, s), 4.52-4.70 (2H, m), 4.40-4.45 (2H, m); LCMS: 100%, MS (ESI); m/z 399.0 [M + H]+. |
| 148 | white powder; 1H NMR (DMSO-d6, 400 MHz); δ 10.15-10.35 (1H, m), 7.28 (2H, d, J = 8.8 Hz), 7.04 (2H, d, J = 9.2 Hz), 6.86-6.98 (1H, m), 6.32-6.44 (1H, m), 6.12-6.26 (1H, m), 5.08-5.18 (1H, m), 3.60-3.70 (3H, m), 3.51-3.59 (2H, m), 3.36-3.41 (2H, m), 3.30-3.35 (1H, m), 3.21-3.29 (4H, m), 2.27-2.36 (1H, m), 2.05-2.18 (1H, m); LCMS: 100%, MS (ESI); m/z 437.2 [M + H]+. |
| 149 | pink amorphous; 1H NMR (DMSO-d6, 400 MHz); δ 10.29-10.47 (1H, m), 8.51 (1H, d, J = 4.0 Hz), 7.70 (1H, t, J = 8.0 Hz), 7.29-7.47 (5H, m), 7.22 (1H, t, J = 6.0 Hz), 6.92-7.06 (4H, m), 6.65-6.90 (2H, m), 6.34 (1H, s), 6.15-6.31 (1H, m), 5.60-5.86 (1H, m), 4.41 (2H, t, J = 6.8 Hz), 4.30 (2H, d, J = 5.6 Hz); LCMS: 99.5%, MS (ESI); m/z 456.1 [M + H]+. |
| 150 | pale-yellow amorphous; 1H NMR (DMSO-d6, 400 MHz); δ 10.60-10.85 (1H, m), 8.15 (1H, d, J = 2.0 Hz), 7.87 (1H, dd, J = 8.4, 2.4 Hz), 7.38 (2H, d, J = 8.4 Hz), 7.22 (2H, d, J = 9.2 Hz), 7.01 (1H, d, J = 8.8 Hz), 6.75-6.94 (1H, m), 6.18-6.40 (2H, m), 5.46-5.69 (1H, m), 4.41-4.55 (1H, m), 2.90-2.95 (6H, m), 1.42 (3H, d, J = 6.4 Hz); LCMS: 97.6%, MS (ESI); m/z 458.1 [M + H]+. |
| 151 | grey powder; mp >200° C.; 1H NMR (DMSO-d6, 400 MHz); δ 9.56 (1H, s), 6.83 (2H, d, J = 8.4 Hz), 6.61 (2H, d, J = 8.4 Hz), 6.39 (2H, d, J = 8.8 Hz), 6.21 (2H, d, J = 8.8 Hz), 5.97 (1H, brs), 5.90 (1H, d, J = 8.0 Hz), 5.53 (1H, d, J = 2.0 Hz), 5.32 (1H, d, J = 8.0 Hz), 3.62 (4H, d, J = 6.0 Hz); LCMS: 97.1%, MS (ESI); m/z 428.1 [M + H]+. |
| 152 | pale yellow amorphous; 1H NMR (DMSO-d6, 400 MHz); δ 10.60-10.85 (1H, m), 8.19 (1H, s), 7.93 (1H, dd, J = 8.8, 2.4 Hz), 7.42 (2H, d, J = 8.8 Hz), 7.00-7.10 (3H, m), 6.75-6.90 (1H, m), 6.19-6.36 (2H, m), 5.46-5.67 (1H, m), 4.36-4.50 (1H, m), 2.90-2.95 (6H, m), 1.42 (3H, d, J = 5.2 Hz); LCMS: 99.2%, MS (ESI); m/z 408.1 [M + H]+. |
| 153 | off-white powder; 1H NMR (DMSO-d6); δ 8.12-8.23 (1H, m), 7.79 (1H, s), 7.71-7.77 (1H, m), 7.64-7.71 (1H, m), 6.98 (1H, d, J = 8.8 Hz), 6.89 (1H, brs), 6.79 (1H, d, J = 8.0 Hz), 6.42 (1H, d, J = 2.0 Hz), 6.19 (1H, dd, J = 8.0 Hz), 4.59 (2H, d, J = 5.6 Hz), 3.96 (3H, s); LCMS: 93%, MS (ESI); m/z 319.9 [M + H]+. |
| 154 | grey amorphous; 1H NMR (DMSO-d6, 400 MHz); δ 10.33-10.54 (1H, m), 8.60 (1H, d, J = 4.8 Hz), 7.40 (2H, d, J = 8.4 Hz), 7.22 (1H, t, J = 4.8 Hz), 7.10 (2H, d, J = 8.4 Hz), 6.70-6.94 (2H, m), 6.36-6.45 (1H, m), 6.11-6.22 (1H, m), 4.27-4.50 (4H, m); LCMS: 100%, MS (ESI); m/z 333.1 [M + H]+. |
| 155 | white solid; mp = 203.8-204.6° C.; 1H NMR (DMSO-d6, 400 MHz); δ 7.37-7.44 (1H, m), 7.19 (1H, d, J = 8.4 Hz), 6.90-7.04 (4H, m), 6.88 (1H, d, J = 8.4 Hz), 6.53 (1H, t, J = 5.2 Hz), 6.30 (1H, d, J = 2.0 Hz), 6.26 (1H, dd, J = 8.0, 2.0 Hz), 5.10 (2H, s), 5.02 (1H, brs), 4.51 (2H, brs), 3.50-3.60 (2H, m), 3.34-3.38 (2H, m); LCMS: 100%, MS (ESI); m/z 490.0 [M + H]+. |
| 156 | off-white amorphous; 1H NMR (DMSO-d6, 400 MHz); δ 8.30 (1H, d, J = 8.8 Hz), 8.08 (1H, d, J = 2.0 Hz), 7.99 (1H, d, J = 9.2 Hz), 7.75 (1H, dd, J = 8.8, 2.4 Hz), 7.60 (1H, d, J = 8.4 Hz), 6.97 (1H, brs), 6.79 (1H, d, J = 8.0 Hz), 6.41 (1H, d, J = 2.0 Hz), 6.19 (1H, d, J = 6.4 Hz), 4.72 (2H, d, J = 5.6 Hz); LCMS: 93.1%, MS (ESI); m/z 323.9 [M + H]+. |

| | |
|---|---|
| 157 | white amorphous; 1H NMR (DMSO-d6, 400 MHz); δ 7.45 (2H, d, J = 8.4 Hz), 7.32 (2H, d, J = 8.0 Hz), 7.08 (1H, d, J = 8.4 Hz), 6.46 (1H, d, J = 2.0 Hz), 6.41 (1H, dd, J = 8.4, 2.0 Hz), 4.77 (2H, brs), 3.50-3.60 (2H, m), 3.48 (3H, s), 2.88-3.01 (2H, m), 2.73-2.85 (1H, m), 1.80-1.95 (4H, m); LCMS: 100%, MS (ESI); m/z 390.9 [M + H]+. |
| 158 | off-white powder; mp = 101.8-104.0° C.; 1H NMR (DMSO-d6, 400 MHz); δ 10.49 (1H, brs), 8.56 (1H, d, J = 2.0 Hz), 7.87 (1H, dd, J = 8.4, 2.4 Hz), 7.40 (1H, d, J = 8.0 Hz), 6.85 (1H, brs), 6.79 (1H, d, J = 8.4 Hz), 6.41 (1H, d, J = 1.6 Hz), 6.19 (1H, d, J = 7.2 Hz), 4.54 (2H, d, J = 6.0 Hz), 4.42 (2H, brs); LCMS: 99.2%, MS (ESI); m/z 273.9 [M + H]+. |
| 159 | green solid; 1H NMR (DMSO-d6, 400 MHz); δ 8.84-8.86 (1H, m), 8.33 (1H, d, J = 8.4 Hz), 7.91-8.00 (2H, m), 7.61-7.64 (1H, m), 7.49 (1H, dd, J = 8.0, 4.0 Hz), 7.13 (1H, brs), 6.81 (1H, d, J = 8.4 Hz), 6.43 (1H, d, J = 2.0 Hz), 6.21 (1H, dd, J = 8.0, 2.0 Hz), 4.68 (2H, d, J = 6.0 Hz); LCMS: 93.2%, MS (ESI); m/z 290.3 [M + H]+. |
| 160 | off-white amorphous; 1H NMR (DMSO-d6, 400 MHz); δ 10.64-10.85 (1H, m), 8.25 (1H, d, J = 2.4 Hz), 7.81 (1H, dd, J = 8.8, 2.4 Hz), 6.88 (1H, d, J = 8.4 Hz), 6.76-6.86 (1H, m), 6.44 (1H, d, J = 1.6 Hz), 6.14-6.28 (1H, m), 5.50-5.56 (1H, m), 4.30-4.57 (2H, m), 3.70-3.81 (1H, m), 3.49-3.67 (3H, m), 2.26-2.37 (1H, m), 2.10-2.24 (1H, m); LCMS: 96.8%, MS (ESI); m/z 329.9 [M + H]+. |
| 161 | white amorphous; 1H NMR (DMSO-d6, 400 MHz); δ 7.40 (2H, d, J = 8.8 Hz), 7.16 (2H, d, J = 8.8 Hz), 6.93-7.05 (4H, m), 6.89 (1H, d, J = 8.0 Hz), 6.22-6.30 (2H, m), 6.19 (1H, d, J = 6.8 Hz), 5.12 (2H, s), 4.47 (2H, brs), 4.06-4.19 (1H, m), 1.91-1.94 (2H, m), 1.48-1.56 (2H, m), 1.56-1.66 (4H, m); LCMS: 98.4%, MS (ESI); m/z 433.0 [M + H]+. |
| 162 | white powder; 1H NMR (DMSO-d6, 400 MHz); δ 6.71-6.81 (2H, m), 6.69 (1H, brs), 6.35-6.45 (3H, m), 6.20 (1H, d, J = 8.4 Hz), 5.58 (1H, brs), 4.25 (2H, d, J = 6.0 Hz), 3.09-3.18 (2H, m), 2.55-2.65 (2H, m), 1.65-1.80 (2H, m); LCMS: 96.9%, MS (ESI); m/z 293.9 [M + H]+. |
| 163 | white amorphous; 1H NMR (DMSO-d6, 400 MHz); δ 7.32 (2H, d, J = 8.8 Hz), 7.01 (1H, d, J = 8.4 Hz), 7.00 (2H, d, J = 8.8 Hz), 6.50 (1H, s), 6.40 (1H, d, J = 8.4 Hz), 4.73 (2H, brs), 3.90 (2H, d, J = 6.0 Hz), 3.40-3.50 (5H, m), 2.80-2.87 (2H, m), 1.94-2.00 (1H, m), 1.80-1.88 (2H, m), 1.46-1.55 (2H, m); LCMS 95%, MS (ESI); m/z 370.9 [M + H]+. |
| 164 | grey amorphous; 1H NMR (DMSO-d6, 400 MHz); δ 10.30-10.40 (1H, m), 8.68 (1H, d, J = 1.2 Hz), 8.02 (2H, d, J = 8.4 Hz), 7.98 (2H, d, J = 1.6 Hz), 7.47 (2H, d, J = 8.0 Hz), 6.70-6.91 (2H, m), 6.41 (1H, d, J = 2.0 Hz), 6.10-6.22 (1H, m), 4.49 (2H, d, J = 6.0 Hz), 4.30-4.45 (2H, m); LCMS: 100%, MS (ESI); m/z 349.9 [M + H]+. |
| 165 | pale yellow powder; 1H NMR (DMSO-d6, 400 MHz); δ 7.37-7.45 (2H, m), 7.20 (2H, d, J = 8.4 Hz), 6.94-7.04 (4H, m), 6.87 (1H, d, J = 8.3 Hz), 6.51 (1H, brs), 6.33 (1H, d, J = 2.0 Hz), 6.28 (1H, dd, J = 8.0, 2.0 Hz), 5.15 (2H, s), 3.27-3.30 (2H, m), 1.08 (6H, s); LCMS: 97.8%, MS (ESI); m/z 437.0 [M + H]+. |
| 166 | off-white amorphous; 1H NMR (DMSO-d6, 400 MHz); δ 10.30-10.50 (1H, m), 8.16 (1H, d, J = 2.4 Hz), 7.92 (1H, dd, J = 8.8, 2.4 Hz), 7.38 (2H, d, J = 8.4 Hz), 7.01-7.09 (3H, m), 6.75-6.95 (2H, m), 6.24 (1H, d, J = 4.8 Hz), 6.08-6.20 (1H, m), 5.60-5.78 (1H, m), 4.81 (2H, t, J = 6.4 Hz), 4.35-4.50 (5H, m); LCMS: 98.13%, MS (ESI); m/z 422.0 [M + H]+. |
| 167 | pale yellow powder; 1H NMR (DMSO-d6, 400 MHz); δ 7.36-7.44 (4H, m), 6.93-7.05 (4H, m), 6.86 (2H, d, J = 8.4 Hz), 6.36 (1H, d, J = 1.6 Hz), 6.27 (1H, dd, J = 8.4, 2.0 Hz), 4.57 (2H, brs), 4.50 (2H, d, J = 6.0 Hz), 3.40 (3H, s); LCMS: 97.8%, MS (ESI); m/z 378.9 [M + H]+. |
| 168 | off-white amorphous; 1H NMR (DMSO-d6, 400 MHz); δ 7.93 (1H, d, J = 8.4 Hz), 7.48 (1H, d, J = 8.4 Hz), 7.41 (1H, brs), 6.81 (1H, d, J = 8.4 Hz), 6.43 (1H, d, J = 2.0 Hz), 6.22 (1H, dd, J = 8.0, 2.0 Hz), 4.53 (2H, s), 3.73-3.84 (1H, m), 1.79-1.93 (2H, m), 1.65-1.77 (2H, m), 1.59 (4H, m); LCMS: 94%, MS (ESI); m/z 335.1 [M + H]+. |
| 169 | off-white powder; 1H NMR (DMSO-d6, 400 MHz); δ 7.44 (2H, d, J = 7.2 Hz), 7.38 (2H, t, J = 7.6 Hz), 7.25-7.34 (1H, m), 7.23 (2H, d, J = 8.8 Hz), 6.93 (2H, d, J = 8.8 Hz), 6.84 (1H, d, J = 8.0 Hz), 6.52 (1H, brs), 6.45 (1H, d, J = 2.0 Hz), 6.22 (1H, dd, J = 8.4, 2.0 Hz), 5.54 (1H, t, J = 6.0 Hz), 3.59-3.70 (2H, m); LCMS: 97.4%, MS (ESI); m/z 378.9 [M + H]+. |
| 170 | white amorphous; 1H NMR (DMSO-d6, 400 MHz); δ 7.38-7.45 (4H, m), 7.28 (1H, brs), 7.09 (1H, brs), 6.96-7.02 (4H, m), 6.88-6.96 (2H, m), 6.33 (1H, d, J = 2.0 Hz), 6.28 (1H, dd, J = 8.4, 2.0 Hz), 5.37 (1H, t, J = 6.0 Hz), 4.50 (2H, d, J = 5.6 Hz), 3.57 (2H, d, J = 5.6 Hz), 3.42 (3H, s); LCMS: 95.5%, MS (ESI): m/z 435.9 [M + H]+. |
| 171 | white powder; 1H NMR (DMSO-d6, 400 MHz); δ 7.37-7.46 (4H, m), 6.95-7.04 (6H, m), 6.58 (1H, d, J = 2.0 Hz), 6.41 (1H, dd, J = 8.4, 2.1 Hz), 5.74 (1H, t, J = 7.2 Hz), 4.52 (2H, d, J = 6.0 Hz), 4.21 (2H, d, J = 7.2 Hz), 3.47 (3H, s); LCMS: 96.6%, MS (ESI); m/z 418.0 [M + H]+. |

| | |
|---|---|
| 172 | grey powder (amorphous) 1H NMR (DMSO-d6, 400 MHz); δ 7.27 (2H, d, J = 8.4 Hz), 6.87 (2H, d, J = 8.4 Hz), 6.77 (1H, d, J = 8.4 Hz), 6.66 (1H, brs), 6.40 (1H, d, J = 1.6 Hz), 6.17 (1H, d, J = 8.4 Hz), 4.62-4.78 (1H, m), 4.34 (2H, d, J = 6.4 Hz), 2.56-2.74 (2H, m), 1.28 (3H, d, J = 6.0 Hz); LCMS: 99.4%, MS (ESI); m/z 364.9 [M + H]+. |
| 173 | pale-yellow powder; 1H NMR (DMSO-d6, 400 MHz); δ 10.32-10.50 (1H, m), 8.16 (2H, d, J = 8.4 Hz), 7.56 (1H, s), 7.47 (2H, d, J = 8.0 Hz), 7.17 (1H, s), 6.88-6.98 (0.5H, m), 6.70-6.84 (1.5H, m), 6.40 (1H, s), 6.10-6.23 (1H, m), 4.25-4.60 (4H, m), 3.97 (3H, s); LCMS: 90%, MS (ESI); m/z 347.1 [M + H]+. |
| 174 | off-white powder (amorphous) 1H NMR (DMSO-d6, 400 MHz); δ 7.11-7.39 (6H, m), 6.93 (1H, d, J = 7.6 Hz), 6.42 (1H, d, J = 1.6 Hz), 6.34 (1H, d, J = 8.4 Hz), 4.66-4.83 (3H, m), 3.72 (1H, t, J = 8.8 Hz), 3.36-3.43 (4H, m), 2.91 (2H, d, J = 6.4 Hz); LCMS: 97.0%, MS (ESI); m/z 352.0 [M + H]+. |
| 175 | off-white powder (amorphous) 1H NMR (DMSO-d6, 400 MHz); δ 8.03 (1H, s), 7.96 (2H, d, J = 8.4 Hz), 7.59 (2H, d, J = 8.4 Hz), 6.81 (1H, d, J = 8.0 Hz), 6.43 (1H, d, J = 1.6 Hz), 6.20 (1H, d, J = 7.6 Hz), 4.39 (2H, d, J = 5.6 Hz); LCMS: 100%, MS (ESI); m/z 340.1 [M + H]+. |
| 176 | grey powder (amorphous) 1H NMR (DMSO-d6, 400 MHz); δ 9.50-9.62 (1H, m), 7.34-7.42 (3H, m), 7.31 (1H, s), 7.07 (1H, d, J = 7.6 Hz), 6.97 (2H, J = 8.4 Hz), 4.56 (2H, d, J = 5.6 Hz), 4.18 (2H, t, J = 6.0 Hz), 2.67-2.85 (2H, m); LCMS: 100%, MS (ESI); m/z 351.1 [M + H]+. |
| 177 | off-white amorphous; 1H NMR (DMSO-d6, 400 MHz); δ 10.35-10.60 (1H, m), 8.16 (1H, d, J = 2.4 Hz), 7.92 (1H, dd, J = 8.8, 2.4 Hz), 7.39 (2H, d, J = 8.0 Hz), 7.14-7.25 (1H, m), 7.05-7.12 (3H, m), 6.77-6.97 (3H, m), 6.38 (1H, s), 6.15-6.33 (1H, m), 4.90-5.10 (1H, m), 4.40-4.70 (2H, m), 1.31 (6H, s); LCMS: 96.3%, MS (ESI); m/z 451.0 [M + H]+. |
| 178 | pale yellow powder; 1H NMR (DMSO-d6, 400 MHz); δ 8.17 (2H, d, J = 8.8 Hz), 7.54 (2H, d, J = 8.0 Hz), 6.83 (1H, d, J = 8.4 Hz), 6.44 (1H, d, J = 2.0 Hz), 6.22 (2H, dd, J = 8.0, 2.0 Hz), 4.28-4.35 (1H, m), 3.70-3.79 (1H, m), 3.57-3.68 (1H, m), 3.45-3.51 (2H, m), 2.25-2.35 (1H, m), 2.08-2.20 (1H, m); LCMS: 99.5%, MS (ESI); m/z 390.9 [M + H]+. |
| 179 | off-white amorphous; 1H NMR (DMSO-d6, 400 MHz); δ 10.60-10.89 (1H, m), 7.90 (2H, d, J = 8.0 Hz), 7.51 (2H, d, J = 8.0 Hz), 6.74-7.00 (1H, m), 6.14-6.45 (2H, m), 5.63-5.96 (1H, m), 4.31 (2H, d, J = 4.8 Hz), 3.83 (3H, s), 2.94 (3H, s), 2.93 (3H, s); LCMS: 99.3%, MS (ESI); m/z 394.9 [M + H]+. |
| 180 | off-white powder (amorphous) 1H NMR (DMSO-d6, 400 MHz); δ 10.29 (1H, brs), 7.42 (2H, d, J = 7.2 Hz), 7.36 (2H, t, J = 7.6 Hz), 7.28 (1H, t, J = 7.2 Hz), 7.18-7.24 (2H, m), 6.83-6.95 (3H, m), 6.58 (1H, brs), 6.27 (1H, d, J = 1.6 Hz), 6.13 (1H, d, J = 8.0 Hz), 5.71 (1H, brs), 5.52 (1H, t, J = 6.4 Hz), 4.81 (2H, t, J = 6.0 Hz), 4.31-4.49 (3H, m), 3.63 (2H, t, J = 6.0 Hz); LCMS: 99.1%, MS (ESI); m/z 435.0 [M + H]+. |
| 181 | off-white amorphous; 1H NMR (DMSO-d6, 400 MHz); δ 8.44 (1H, d, J = 4.0 Hz), 7.77 (1H, t, J = 7.2 Hz), 7.50 (1H, d, J = 8.0 Hz), 7.25-7.36 (4H, m), 7.16-7.25 (1H, m), 6.78 (1H, d, J = 8.4 Hz) 6.72 (1H, brs), 6.41 (1H, s), 6.19 (1H, d, J = 8.0 Hz), 5.32 (1H, s), 4.40 (2H, d, J = 4.4 Hz), 3.29 (3H, s); LCMS: 96.7%, MS (ESI); m/z 359.9 [M + H]+. |
| 182 | pale green powder; 1H NMR (DMSO-d6, 400 MHz); δ 9.12 (1H, brs), 7.40-7.55 (4H, m), 7.15 (1H, d, J = 8.4 Hz), 7.07 (2H, d, J = 8.4 Hz), 6.99-7.02 (2H, m), 6.65 (1H, s), 6.59 (1H, d, J = 8.8 Hz), 4.62 (2H, d, J = 5.6 Hz), 3.72-3.80 (2H, m), 3.60 (3H, s), 3.14-3.28 (2H, m), 1.95-2.06 (2H, m); LCMS 96.6%, MS (ESI); m/z 419.0 [M + H]+. |
| 183 | off-white powder; 1H NMR (DMSO-d6, 400 MHz); δ 7.27 (2H, d, J = 8.8 Hz), 7.00-7.12 (3H, m), 6.79 (1H, s), 6.95 (1H, d, J = 8.4 Hz), 4.49-4.61 (1H, m), 3.48-3.55 (1H, m), 3.19-3.24 (1H, m), 3.05 (6H, s), 2.73-2.89 (2H, m), 1.98-2.10 (1H, m), 1.80-1.90 (1H, m), 1.62-1.76 (1H, m), 1.45-1.58 (1H, m); LCMS: 100%, MS (ESI); m/z 421.0 [M + H]+. |
| 184 | white powder; 1H NMR (DMSO-d6, 400 MHz); δ 7.37-7.44 (4H, m), 6.86-7.04 (6H, m), 6.17-6.28 (2H, m), 5.82 (1H, d, J = 7.2 Hz), 4.84 (2H, t, J = 6.0 Hz), 4.46-4.56 (3H, m), 4.39 (2H, t, J = 6.0 Hz), 3.43 (3H, s); LCMS: 98.4%, MS (ESI); m/z 434.9 [M + H]+. |
| 185 | pale yellow powder (amorphous) 1H NMR (DMSO-d6, 400 MHz); δ 10.65-10.86 (1H, m), 7.26 (2H, d, J = 8.0 Hz), 7.05-7.18 (2H, m), 6.95-7.04 (2H, m), 6.81-6.95 (3H, m), 6.20-6.45 (2H, m), 5.45-5.66 (1H, m), 4.49 (2H, s), 4.04-4.21 (4H, m), 2.97 (3H, s), 2.94 (3H, s), 1.17 (3H, t, J = 7.2 Hz); Based on H NMR, it is a mixture of tautomers; LCMS: 99.3%, MS (ESI); m/z 462.1 [M + H]+. |
| 186 | off-white powder; 1H NMR (DMSO-d6, 400 MHz); δ 7.91 (1H, s), 7.38-7.40 (2H, m), 7.30-7.33 (2H, m), 6.89 (1H, d, J = 8.4 Hz), 6.48 (1H, d, J = 2.0 Hz), 6.30 (1H, dd, J = 8.4, 2.0 Hz), 4.34 (2H, s), 4.13 (2H, s); LCMS: 100%, MS (ESI); m/z 354.1 [M + H]+. |
| 187 | off-white powder; 1H NMR (DMSO-d6, 400 MHz); δ 7.39-7.43 (2H, m), 7.21 (2H, d, J = 8.4 Hz), 6.96-7.03 (5H, m), 6.36-6.40 (3H, m), 5.26 (2H, s), 3.53 (2H, s), 1.32 (6H, s); LCMS: 100%, MS (ESI); m/z 437.0 [M + H]+. |

| | |
|---|---|
| 188 | off-white amorphous; 1H NMR (DMSO-d6, 400 MHz); δ 10.16-10.45 (1H, m), 8.44 (1H, d, J = 4.4 Hz), 7.77 (1H, t, J = 7.6 Hz), 7.51 (1H, d, J = 7.6 Hz), 7.26-7.35 (4H, m), 7.17-7.25 (1H, m), 6.55-6.88 (2H, m), 6.39 (1H, d, J = 1.6 Hz), 6.17 (1H, brs), 5.42 (1H, s), 4.20-4.63 (4H, m), 3.40-3.49 (2H, q, J = 6.8 Hz), 1.17 (3H, t, J = 7.0 Hz); LCMS: 95.4%, MS (ESI); m/z 373.8 [M + H]+. |
| 189 | off-white powder; 1H NMR (DMSO-d6, 400 MHz); δ 10.29-10.48 (1H, m), 8.40-8.49 (1H, m), 7.72-7.82 (1H, m), 7.50 (1H, d, J = 7.6 Hz), 7.26-7.35 (4H, m), 7.19-7.26 (1H, m), 6.79-6.90 (2H, m), 6.24 (1H, d, J = 4.8 Hz), 6.06-6.17 (1H, m), 5.59-5.79 (1H, m), 5.32 (1H, s), 4.81 (2H, t, J = 6.0 Hz), 4.30-4.50 (5H, m), 3.29 (3H, s); LCMS: 95.7%, MS (ESI); m/z 416.0 [M + H]+. |
| 190 | off-white amorphous; 1H NMR (DMSO-d6, 400 MHz); δ 10.67-10.95 (1H, m), 8.18 (2H, d, J = 8.8 Hz), 7.53 (2H, d, J = 8.4 Hz), 6.88-7.07 (1H, m), 6.12-6.54 (2H, m), 4.23-4.40 (1H, m), 3.53 (1H, t, J = 8.8 Hz), 3.37-3.43 (1H, m, overlap with H2O signal), 3.20-3.30 (2H, m, overlap with H2O signal), 2.97 (6H, s), 2.25-2.34 (1H, m), 2.10-2.21 (1H, m); LCMS: 97.4%, MS (ESI, TOF); m/z 419.1985 [M + H]+. |
| 191 | off-white powder; 1H NMR (DMSO-d6, 400 MHz); δ 10.74-10.84 (1H, m), 7.32-7.42 (4H, m), 7.03 (2H, d, J = 9.2 Hz), 6.95 (2H, d, J = 8.4 Hz), 6.51-6.64 (1H, m), 6.05-6.18 (1H, m), 4.58-4.75 (1H, m), 4.43-4.50 (1H, m), 3.76-4.02 (1H, m), 2.96-2.98 (6H, m), 1.42-1.47 (3H, m); LCMS: 96.6%, MS (ESI); m/z 486.9 [M + H]+. |
| 192 | pale brown powder; 1H NMR (DMSO-d6, 400 MHz); δ 7.35-7.51 (4H, m), 6.91-7.06 (6H, m), 6.25 (1H, d, J = 2.0 Hz), 6.09 (1H, dd, J = 8.4, 2.0 Hz), 5.50 (1H, d, J = 6.8 Hz), 4.46-4.57 (3H, m), 3.90-4.05 (2H, m), 3.44 (3H, s), 3.30-3.45 (2H, m); LCMS: 96.0%, MS (ESI); m/z 435.0 [M + H]+. |
| 193 | pale yellow powder; 1H NMR (DMSO-d6, 400 MHz); δ 7.36-7.45 (4H, m), 7.01-7.09 (2H, m), 6.93-7.01 (4H, m), 6.43 (1H, d, J = 2.0 Hz), 6.21 (1H, dd, J = 8.4, 2.0 Hz), 4.51 (2H, d, J = 6.0 Hz), 4.17 (4H, t, J = 12.0 Hz), 3.46 (3H, s); LCMS: 100%, MS (ESI); m/z 455.0 [M + H]+. |
| 194 | brown powder; 1H NMR (DMSO-d6, 400 MHz); δ 7.92 (2H, d, J = 8.8 Hz), 7.08 (2H, d, J = 9.2 Hz), 6.95-7.05 (1H, m), 6.21-6.47 (2H, m), 5.20-5.30 (1H, m), 3.82 (3H, s), 3.60-3.70 (1H, m), 3.30-3.36 (3H, m), 2.97 (3H, s), 3.92 (3H, s), 2.37-2.40 (2H, m); LCMS: 95.3%, MS (ESI); m/z 308.8 [M + H]+. |
| 195 | off-white power; 1H NMR (DMSO-d6, 400 MHz); δ 8.15 (1H, d, J = 2.8 Hz), 7.92 (1H, dd, J = 8.8, 2.8 Hz), 7.19 (2H, d, J = 8.4 Hz), 7.03-7.12 (3H, m), 6.82 (1H, d, J = 8.4 Hz), 6.32 (1H, d, J = 1.6 Hz), 6.25 (1H, dd, J = 8.0, 2.0 Hz), 6.14 (2H, brs), 5.11 (2H, s), 4.49 (2H, brs); LCMS: 97.1%, MS (ESI); m/z 365.9 [M + H]+. |
| 196 | yellow powder; 1H NMR (DMSO-d6, 400 MHz); δ 7.40-7.60 (5H, m), 7.06 (1H, d, J = 8.4 Hz), 6.45-6.60 (2H, m), 6.32-6.37 (1H, m), 4.34 (2H, s), 3.83 (3H, s), 3.10 (6H, s); LCMS: 98.1%, MS (ESI); m/z 346.8 [M + H]+. |
| 197 | off-white amorphous; 1H NMR (DMSO-d6, 400 MHz); δ 10.74 (1H, brs), 8.68 (1H, s), 7.90-8.05 (4H, m), 7.49 (2H, d, J = 8.0 Hz), 6.87 (1H, d, J = 6.8 Hz), 6.37 (1H, s), 6.15-6.45 (1H, m), 5.78 (1H, brs), 4.29 (2H, d, J = 5.6 Hz), 2.93 (6H, s); LCMS: 100%, MS (ESI); m/z 377.9 [M + H]+. |
| 198 | white amorphous; 1H NMR (DMSO-d6, 400 MHz); δ 10.37 (1H, brs), 7.20-7.38 (4H, m), 6.52-6.95 (2H, m), 6.41 (1H, d, J = 2.0 Hz), 6.18 (1H, d, J = 6.4 Hz), 5.63 (1H, d, J = 4.0 Hz), 4.67 (1H, d, J = 4.0 Hz), 4.17-4.56 (4H, m), 1.06 (3H, s), 0.86 (3H, s); LCMS: 100%, MS (ESI); m/z 379.1 [M + H]+. |
| 199 | white powder; 1H NMR (DMSO-d6, 400 MHz); δ 8.14 (1H, d, J = 2.4 Hz), 7.92 (1H, dd, J = 8.4, 2.4 Hz), 7.21 (2H, d, J = 8.4 Hz), 7.01-7.02 (3H, m), 6.74 (1H, d, J = 8.4 Hz), 6.41 (1H, d, J = 1.2 Hz), 6.29 (2H, brs), 6.14 (1H, dd, J = 8.4, 2.0 Hz), 5.11 (2H, s), 4.39 (2H, brs); LCMS: 92.3%, MS (ESI); m/z 365.8 [M + H]+. |
| 200 | yellow powder; 1H NMR (DMSO-d6, 400 MHz); δ 10.25-10.60 (1H, m), 7.35-7.60 (5H, m), 6.65-7.00 (2H, m), 6.41 (1H, s), 6.35 (1H, d, J = 1.6 Hz), 6.10-6.25 (1H, m), 4.25-4.60 (4H, m), 3.82 (3H, s); LCMS: 100%, MS (ESI); m/z 318.9 [M + H]+. |
| 201 | white powder; 1H NMR (DMSO-d6, 400 MHz); δ 10.40-10.60 (1H, m), 7.40-7.50 (5H, m), 6.80-7.10 (2H, m), 6.35 (1H, d, J = 2.0 Hz), 6.26 (1H, s), 6.10-6.20 (1H, m), 5.60-5.80 (1H, m), 4.81 (1H, t, J = 6.0 Hz), 4.30-4.60 (5H, m), 3.83 (3H, s); LCMS: 99.8%, MS (ESI); m/z 374.9 [M + H]+. |
| 202 | red amorphous; 1H NMR (DMSO-d6, 400 MHz); δ 10.76-10.90 (1H, m), 8.38 (2H, d, J = 6.0 Hz), 6.90-7.03 (3H, m), 6.37-6.47 (1H, m), 6.17-6.30 (1H, m), 5.24-5.26 (1H, m), 3.64-3.71 (1H, m), 3.30-3.32 (3H, m), 2.99 (3H, s), 2.97 (3H, s), 2.37-2.45 (1H, m), 2.16-2.25 (1H, m); LCMS: 100%, MS (ESI); m/z 324.1 [M + H]+. |

| | |
|---|---|
| 203 | off-white amorphous; 1H NMR (DMSO-d6, 400 MHz); δ 8.18 (1H, d, J = 2.4 Hz), 7.94 (1H, dd, J = 8.8, 2.4 Hz), 7.42 (2H, d, J = 8.4 Hz), 7.05-7.10 (3H, m), 6.88 (1H, d, J = 8.0 Hz), 6.60 (1H, t, J = 6.0 Hz), 6.46 (1H, d, J = 2.0 Hz), 6.28 (1H, dd, J = 8.0, 2.0 Hz), 5.26 (1H, s), 4.40-4.60 (4H, m), 3.75 (2H, s), 1.19 (6H, s); LCMS: 100%, MS (ESI); m/z 438.0 [M + H]+. |
| 204 | white amorphous; 1H NMR (DMSO-d6, 400 MHz); δ 7.37-7.43 (2H, m), 7.24 (2H, d, J = 8.8 Hz), 6.92-7.03 (5H, m), 6.62 (1H, t, J = 5.2 Hz), 6.14-6.21 (2H, m), 5.82 (1H, d, J = 6.8 Hz), 5.14 (2H, s), 5.00 (1H, brs), 4.77 (2H, t, J = 6.4 Hz), 4.38-4.48 (1H, m), 4.29-4.37 (2H, m), 3.52-3.59 (2H, m), 3.30-3.45 (2H, m); LCMS: 99.4%, MS (ESI); m/z 465.0 [M + H]+. |
| 205 | off-white amorphous; 1H NMR (DMSO-d6, t = 80° C., 400 MHz); δ 10.15 (1H, brs), 7.60-7.67 (2H, m), 7.46-7.52 (2H, m), 6.83 (1H, d, J = 8.4 Hz), 6.40-6.60 (2H, m), 6.24 (1H, d, J = 7.6 Hz), 4.56 (2H, s), 4.17 (2H, brs), 1.49-1.56 (6H, m); LCMS: 98.9%, MS (ESI); m/z 377.0 [M + H]+. |
| 206 | white powder; 1H NMR (DSMO-d6, 400 MHz); δ 7.42 (2H, d, J = 8.8 Hz), 7.17 (2H, d, J = 8.4 Hz), 6.95-7.10 (5H, m), 6.38 (2H, d, J = 8.8 Hz), 6.32 (1H, s), 5.17-5.28 (2H, m), 4.99 (1H, brs), 4.25-4.35 (1H, m), 3.50-3.70 (2H, m), 3.10-3.22 (2H, m), 1.92-1.95 (1H, m), 1.70-1.80 (1H, m); LCMS: 97.8%, MS (ESI); m/z 434.9 [M + H]+. |
| 207 | off-white powder (amorphous) 1H NMR (DMSO-d6, 400 MHz); δ 7.38-7.43 (2H, m), 7.25 (2H, d, J = 8.4 Hz), 7.05 (1H, t, J = 6.4 Hz), 6.96-7.02 (4H, m), 6.89 (1H, d, J = 8.4 Hz), 6.32 (1H, d, J = 2.0 Hz), 6.27 (1H, dd, J = 8.4, 2.0 Hz), 5.14 (2H, s), 4.54 (2H, brs), 4.01 (2H, q, J = 7.2 Hz), 4.05 (2H, d, J = 6.0 Hz), 1.19 (3H, t, J = 7.2 Hz); LCMS: 98.5%, MS (ESI); m/z 451.0 [M + H]+. |
| 208 | off-white amorphous; 1H NMR (DMSO-d6, 400 MHz); δ 8.18 (1H, d, J = 2.4 Hz), 7.93 (1H, dd, J = 8.8, 2.8 Hz), 7.41 (2H, d, J = 8.4 Hz), 7.08 (3H, d, J = 8.8 Hz), 6.95 (1H, d, J = 8.4 Hz), 6.64 (1H, t, J = 6.0 Hz), 6.35 (1H, d, J = 1.6 Hz), 6.22 (1H, dd, J = 8.4, 2.0 Hz), 5.80 (1H, d, J = 7.6 Hz), 5.22 (1H, s), 4.83 (2H, t, J = 6.4 Hz), 4.47-4.59 (3H, m), 4.32-4.44 (2H, m), 3.80 (2H, s), 1.18 (6H, s); LCMS: 100%, MS (ESI); m/z 494.0 [M + H]+. |
| 209 | off-white amorphous; 1H NMR (DMSO-d6, 400 MHz); δ 7.36-7.46 (4H, m), 6.95-7.04 (4H, m), 6.88 (1H, d, J = 8.4 Hz), 6.55 (1H, t, J = 6.0 Hz), 6.45 (1H, d, J = 2.0 Hz), 6.27 (1H, dd, J = 8.4, 2.0 Hz), 5.23 (1H, brs), 4.45-4.50 (4H, m), 3.74 (2H, s), 1.18 (6H, s); LCMS: 100%, MS (ESI); m/z 437.0 [M + H]+. |
| 210 | white power; 1H NMR (DMSO-d6, 400 MHz); δ 8.18 (1H, d, J = 2.4 Hz), 7.94 (1H, dd, J = 8.8, 2.4 Hz), 7.44 (2H, d, J = 8.4 Hz), 7.04-7.13 (3H, m), 6.82-6.97 (2H, m), 6.37 (1H, d, J = 1.6 Hz), 6.28 (1H, dd, J = 8.0, 1.6 Hz), 4.42-4.65 (4H, m), 3.42 (3H, s); LCMS: 99.7%, MS (TOF, ESI); m/z 380.1267 [M + H]+. |
| 211 | off-white power; 1H NMR (DMSO-d6, 400 MHz); δ 8.17 (1H, d, J = 2.4 Hz), 7.95 (1H, dd, J = 2.4 Hz), 7.33-7.51 (3H, m), 7.05-7.18 (3H, m), 6.99 (1H, d, J = 8.8 Hz), 6.21-6.37 (2H, m), 5.99 (1H, d, J = 2.0 Hz), 4.86 (2H, t, J = 6.4 Hz), 4.48-4.61 (3H, m), 4.41 (2H, t, J = 6.0 Hz), 3.49 (3H, s); LCMS: 99.2%, MS (ESI); m/z 436.0 [M + H]+. |
| 212 | pale yellow powder; 1H NMR (DMSO-d6, 400 MHz); δ 10.54-10.91 (1H, m), 7.43 (1H, s), 7.23 (2H, d, J = 8.4 Hz), 6.95-7.19 (5H, m), 6.75-7.91 (3H, m), 6.37 (1H, s), 6.28 (1H, d, J = 7.6 Hz), 5.52 (1H, brs), 4.05-4.21 (4H, m), 2.93 (6H, s); LCMS: 99.0%, MS (ESI); m/z 432.9 [M + H]+. |
| 213 | pale-yellow powder (amorphous) 1H NMR (DMSO-d6, 400 MHz); δ 8.04 (1H, s), 7.25 (2H, d, J = 8.4 Hz), 7.06-7.18 (5H, m), 6.88-6.97 (3H, m), 6.42 (1H, d, J = 1.6 Hz), 6.38 (1H, d, J = 8.4 Hz), 5.78 (1H, brs, 5.01 (2H, s), 4.15 (2H, s), 3.01 (6H, s); LCMS: 97.6%, MS (ESI); m/z 457.0 [M + H]+. |
| 214 | white powder (amorphous) 1H NMR (DMSO-d6, 400 MHz); δ 10.64-10.86 (1H, m), 10.19 (1H, brs), 7.63 (2H, d, J = 9.2 Hz), 7.41 (1H, d, J = 10.4 Hz), 7.33 (2H, d, J = 8.8 Hz), 6.80-6.96 (1H, m), 6.45-6.55 (1H, m), 6.24-6.40 (1H, m), 5.15-5.43 (1H, m), 4.02 (2H, t, J = 5.2 Hz), 2.96 (3H, s), 2.93 (3H, s); LCMS: 100%, MS (ESI); m/z 382.9 [M + H]+. |
| 215 | white powder; 1H NMR (DMSO-d6, 400 MHz); δ 10.31-10.49 (1H, m), 7.29-7.46 (4H, m), 6.88-7.06 (4H, m), 6.65-6.88 (2H, m), 6.41 (1H, d, J = 6.4 Hz), 6.15-6.29 (1H, m), 4.50-4.81 (3H, m), 4.34-4.50 (2H, m), 3.55-3.71 (1H, m), 3.04-3.18 (1H, m), 2.70-2.91 (1H, m); LCMS: 100%, MS (ESI); m/z 439.0 [M + H]+. |
| 216 | white powder (amorphous) 1H NMR (DMSO-d6, 400 MHz); δ 11.86 (1H, brs), 10.60-10.82 (1H, m), 7.19-7.25 (2H, m), 7.02-7.18 (4H, m), 6.74-7.00 (5H, m), 6.35-6.38 (1H, m), 6.18-6.31 (1H, m), 5.39-5.65 (1H, m), 4.80 (2H, s), 4.10 (2H, s), 2.94 (3H, s), 2.92 (3H, s); LCMS: 99.1%, MS (ESI); m/z 456.0 [M + H]+. |

| | |
|---|---|
| 217 | white amorphous; 1H NMR DMSO-d6, 400 MHz); δ 7.41 (2H, d, J = 8.8 Hz), 7.33 (1H, brs), 7.25 (1H, d, J = 8.0 Hz), 6.94-7.06 (5H, m), 6.89 (1H, d, J = 8.0 Hz), 6.77 (1H, t, J = 6.0 Hz), 6.32 (1H, s), 6.27 (1H, d, J = 8.4 Hz), 5.13 (2H, s), 4.53 (2H, brs), 3.84 (2H, d, J = 5.6 Hz); LCMS: 99.4%, MS (ESI); m/z 422.0 [M + H]+. |
| 218 | white amorphous; 1H NMR (DMSO-d6, 400 MHz); δ 8.92 (1H, s), 7.98 (2H, d, J = 8.4 Hz), 7.55 (2H, d, J = 8.4 Hz), 7.09 (1H, d, J = 8.4 Hz), 6.49-6.59 (2H, m), 6.46 (1H, d, J = 2.0 Hz), 4.38 (2H, d, J = 5.2 Hz), 4.31 (2H, q, J = 7.2 Hz), 3.12 (6H, s), 1.30 (3H, t, J = 7.2 Hz); LCMS: 98.7%, MS (ESI); m/z 406.0 [M + H]+. |
| 219 | white amorphous; 1H NMR (DMSO-d6, 400 MHz); δ 7.36-7.44 (1H, m), 7.17 (1H, d, J = 8.4 Hz), 6.95-7.03 (4H, m), 6.90 (1H, d, J = 8.4 Hz), 6.42 (1H, q, J = 4.4 Hz), 6.31 (1H, d, J = 2.0 Hz), 6.26 (1H, dd, J = 8.0, 2.0 Hz), 5.07 (2H, s), 4.50 (2H, brs), 2.85 (3H, d, J = 4.4 Hz); LCMS: 97.7%, MS (ESI); m/z 378.9 [M + H]+. |
| 220 | off-white amorphous; 1H NMR (DMSO-d6, 400 MHz); δ 8.18 (1H, s), 7.92 (2H, d, J = 8.4 Hz), 7.52 (2H, d, J = 8.4 Hz), 7.35 (1H, s), 6.91 (1H, d, J = 8.0 Hz), 6.37 (1H, d, J = 2.0 Hz), 6.34 (1H, J = 8.0, 2.0 Hz), 5.92 (1H, brs), 4.31 (2H, s), 2.97 (6H, s); LCMS: 100%, MS (ESI); m/z 333.9 [M + H]+. |
| 221 | yellow powder; 1H NMR (DMSO-d6, 400 MHz); δ 11.56 (1H, brs), 10.68-10.79 (1H, m), 7.70 (2H, d, J = 6.8 Hz), 7.45-7.53 (3H, m), 6.82-6.89 (1H, m), 6.50-6.60 (1H, m), 6.26-6.35 (3H, m), 5.71-5.83 (1H, m), 4.25-4.35 (2H, m), 2.94 (3H, s), 2.93 (3H, s); LCMS: 98.9%, MS (ESI); m/z 359.9 [M + H]+. |
| 222 | white powder; 1H NMR (DMSO-d6, 400 MHz); δ 8.21 (1H, d, J = 2.4 Hz), 7.65 (1H, dd, J = 8.8, 2.4 Hz), 7.30 (2H, d, J = 8.4 Hz), 7.08 (2H, dd, J = 6.8, 2.4 Hz), 7.00 (1H, d, J = 8.4 Hz), 6.89 (1H, d, J = 8.8 Hz), 6.56 (1H, s), 6.43 (1H, d, J = 7.2 Hz), 4.42 (2H, d, J = 5.2 Hz), 4.20-4.30 (1H, m), 4.10-4.18 (2H, m), 3.95-4.05 (2H, m), 3.80-3.90 (1H, m), 3.55-3.65 (1H, m), 2.80-2.90 (1H, m), 2.65-2.75 (1H, m); LCMS: 98.1%, MS (ESI); m/z 515.0 [M + H]+. |
| 223 | pale-yellow amorphous; 1H NMR (DMSO-d6, 400 MHz); δ 8.54 (1H, d, J = 2.8 Hz), 7.88 (1H, d, J = 8.8 Hz), 7.45-7.52 (3H, m), 7.17 (2H, d, J = 8.8 Hz), 6.84-6.93 (2H, m), 6.37 (1H, d, J = 2.0 Hz), 6.27 (1H, dd, J = 8.4, 2.0 Hz), 4.50-4.58 (4H, m); 3.41 (3H, s); LCMS: 100%, MS (ESI); m/z 414.0 [M + H]+. |
| 224 | pale-yellow amorphous; 1H NMR (DMSO-d6, 400 MHz); δ 8.32-8.37 (2H, m), 7.35-7.46 (4H, m), 7.03 (2H, J = 8.8 Hz), 6.83-6.88 (2H, m), 6.36 (1H, d, J = 2.8 Hz), 6.24-6.28 (1H, m), 4.53 (2H, brs), 4.50 (2H, d, J = 6.0 Hz), 3.40 (3H, s); LCMS: 100%, MS (ESI); m/z 345.9 [M + H]+. |
| 225 | off-white powder; 1H NMR (DMSO-d6, 400 MHz); δ 9.68 (1H, brs), 7.35-7.48 (5H, m), 6.96-7.17 (6H, m), 5.49 (2H, brs), 4.29 (2H, d, J = 6.4 Hz); LCMS: 100%, MS (ESI) m/z 423.0 [M + H]+. |
| 226 | pale-yellow amorphous; 1H NMR (DMSO-d6, 400 MHz); δ 8.53 (1H, d, J = 2.8 Hz), 7.87 (1H, d, J = 8.8 Hz), 7.45-7.54 (3H, m), 7.16 (2H, d, J = 8.8 Hz), 6.91-6.99 (2H, m), 6.25 (1H, d, J = 2.0 Hz), 6.21 (1H, dd, J = 8.4, 2.4 Hz), 5.84 (1H, d, J = 6.8 Hz), 4.80-4.88 (2H, m), 4.48-4.56 (3H, m), 4.39 (2H, t, J = 6.8 Hz), 3.44 (3H, s); LCMS: 100%, MS (ESI); m/z 469.9 [M + H]+. |
| 227 | pale-yellow amorphous; 1H NMR (DMSO-d6, 400 MHz); δ 8.32-8.36 (2H, m), 7.35-7.46 (4H, m), 7.03 (2H, d, J = 8.8 Hz), 6.89-6.96 (2H, m), 6.18-6.26 (2H, m), 5.83 (1H, d, J = 7.2 Hz), 4.84 (2H, d, J = 6.4 Hz), 4.48-4.55 (3H, m), 4.39 (2H, t, J = 5.6 Hz), 3.43 (3H, s); LCMS: 100%, MS (ESI); m/z 402.2 [M + H]+. |
| 228 | off-white amorphous; 1H NMR (DMSO-d6, 400 MHz); δ 8.71 (1H, s), 7.94 (2H, d, J = 8.4 Hz), 7.54 (2H, d, J = 8.0 Hz), 6.91 (1H, d, J = 8.4 Hz), 6.27-6.43 (2H, m), 4.32 (2H, s), 2.97 (6H, s); LCMS: 97.9%, MS (ESI) m/z 377.9 [M + H]+. |
| 229 | white powder; 1H NMR (DMSO-d6, 400 MHz); δ 8.16 (1H, d, J = 2.4 Hz), 7.94 (1H, dd, J = 8.8, 2.8 Hz), 7.17 (2H, d, J = 8.4 Hz), 7.04-7.12 (3H, m), 6.91 (1H, d, J = 8.4 Hz), 6.44 (1H, brs), 6.33 (1H, d, J = 2.0 Hz), 6.26 (1H, dd, J = 8.0, 1.6 Hz), 5.10 (2H, s), 4.51 (2H, brs), 2.86 (3H, d, J = 4.4 Hz); LCMS: 100.0%, MS (ESI); m/z 379.9 [M + H]+. |
| 230 | pale yellow powder; 1H NMR (DSMO-d6 + D2O, 400 MHz); δ 8.72 (1H, s), 7.94-8.11 (2H, m), 7.03 (1H, d, J = 8.0 Hz), 6.47 (1H, s), 6.32 (1H, d, J = 7.6 Hz), 4.40-4.54 (1H, m), 3.44-3.45 (1H, m), 3.29-3.40 (1H, m), 3.14-3.29 (2H, m), 2.97 (6H, s), 2.04-2.21 (1H, m), 2.22-2.35 (1H, m); LCMS: 100%, MS (ESI); m/z 369.9 [M + H]+. |
| 231 | white powder (amorphous) 1H NMR (DMSO-d6, 400 MHz); δ 7.36-7.43 (1H, m), 7.25 (1H, d, J = 8.8 Hz), 6.94-7.04 (2H, m), 6.89 (1H, d, J = 8.4 Hz), 6.14-6.23 (4H, m), 5.78 (1H, d, J = 6.8 Hz), 5.13 (2H, s), 4.78 (2H, t, J = 6.4 Hz), 4.38-4.80 (1H, m), 4.29-4.37 (2H, t, J = 6.0 Hz); LCMS: 98.8%, MS (ESI) m/z 421.0 [M + H]+. |
| 232 | white powder (amorphous) 1H NMR (DMSO-d6, 400 MHz); δ 10.60-10.80 (1H, m), 7.40-7.50 (1H, m), 7.27 (2H, d, J = 8.0 Hz), 7.17 (2H, d, J = 7.2 Hz), 6.80-6.95 (2H, m), 6.15-6.45 (2H, m), 5.45-5.75 (1H, m), 4.17 (2H, s), 3.30 (2H, s), 2.93 (3H, s), 2.91 (3H, s); LCMS: 95.2%, MS (ESI); m/z 324.0 [M + H]+. |

| | |
|---|---|
| 233 | pale-yellow powder (amorphous) 1H NMR (DMSO-d6, 400 MHz); δ 10.60-10.80 (1H, m), 8.14 (1H, s), 7.28 (2H, d, J = 8.4 Hz), 7.24 (1H, s), 6.95 (2H, d, J = 6.8 Hz), 6.77-6.91 (1H, m), 6.17-6.40 (2H, m), 5.44-5.65 (1H, m), 5.17 (2H, s), 4.13 (2H, s), 2.94 (3H, s), 2.91 (3H, s); LCMS: 98.8%, MS (ESI): m/z 364.1 [M + H]+. |
| 234 | white powder; 1H NMR (DMSO-d6, 400 MHz); δ 8.16 (1H, d, J = 2.4 Hz), 7.94 (1H, dd, J = 8.8, 2.8 Hz), 7.26 (2H, d, J = 8.8 Hz), 7.05-7.13 (3H, m), 6.91 (1H, d, J = 8.4 Hz), 6.13-6.25 (4H, m), 5.79 (1H, d, J = 7.2 Hz), 5.16 (2H, s), 4.79 (2H, t, J = 6.4 Hz), 4.40-4.50 (1H, m), 4.35 (2H, t, J = 6.0 Hz); LCMS: 97.8%, MS (ESI); m/z 421.9 [M + H]+. |
| 235 | off-white powder (amorphous) 1H NMR (DMSO-d6, 400 MHz); δ 8.16 (1H, d, J = 2.4 Hz), 7.94 (1H, dd, J = 8.8, 2.8 Hz), 7.24 (2H, d, J = 8.4 Hz), 7.07-7.13 (3H, m), 7.03 (1H, d, J = 8.4 Hz), 6.45 (1H, d, J = 7.6 Hz), 6.33 (2H, brs), 6.23 (1H, dd, J = 8.4, 2.0 Hz), 5.22 (2H, s), 4.15 (4H, t, J = 12.0 Hz); LCMS: 100.0%, MS (ESI); m/z 442.1 [M + H]+. |
| 236 | pale-yellow powder; 1H NMR (DMSO-d6, 400 MHz); δ 10.86 (1H, brs), 7.84 (1H, d, J = 2.0 Hz), 7.76 (1H, d, J = 8.8 Hz), 7.43 (1H, dd, J = 8.4, 2.0 Hz), 6.99 (1H, d, J = 8.4 Hz), 6.46 (1H, s), 6.27 (1H, d, J = 6.4 Hz), 3.85-4.00 (1H, m), 3.63-3.72 (2H, m), 3.35-3.43 (2H, m), 2.98 (3H, s), 2.33-2.45 (2H, m); LCMS: 99.0%, MS (ESI): m/z 382.0 [M + H]+. |
| 237 | yellow powder; 1H NMR (DMSO-d6, 400 MHz); δ 10.72 (1H, brs), 7.25-7.40 (4H, m), 7.15 (1H, d, J = 6.8 Hz), 6.95 (1H, s), 6.87 (1H, d, J = 7.6 Hz), 6.37 (1H, s), 6.29 (1H, s), 5.63 (1H, brs), 4.19 (2H, d, J = 6.0 Hz), 3.68-3.79 (2H, m), 3.44-3.53 (2H, m), 2.94 (6H, s), 2.36-2.45 (2H, m), 1.71-1.83 (2H, m); LCMS: 97.1%, MS (ESI); m/z 394.1 [M + H]+. |
| 238 | white powder (amorphous) 1H NMR (DMSO-d6, 400 MHz); δ 8.20 (1H, s), 7.45-7.54 (2H, m), 7.23 (2H, d, J = 8.4 Hz), 7.08 (2H, d, J = 8.8 Hz), 6.31 (1H, s), 6.26 (1H, dd, J = 2.0, 8.0 Hz), 6.10 (2H, s), 5.11 (2H, s), 4.48 (2H, s); LCMS: 99.8%, MS (ESI); m/z 365.9 [M + H]+. |
| 239 | off-white powder; 1H NMR (DMSO-d6, 400 MHz); δ 8.37 (1H, d, J = 2.8 Hz), δ 7.43-7.47 (3H, m), 7.00-7.07 (2H, m), 7.01 (1H, d, J = 8.8 Hz), 6.84 (1H, d, J = 8.0 Hz), 6.25-6.28 (2H, m), 6.09 (2H, brs), 5.18 (2H, s), 4.49 (2H, brs); LCMS: 100%, MS (ESI); m/z 366.0 [M + H]+. |
| 240 | grey powder; 1H NMR (DMSO-d6, 400 MHz); δ 8.08 (1H, s), 7.64 (1H, d, J = 8.4 Hz), 7.44 (2H, d, J = 8.4 Hz), 7.14 (2H, d, J = 8.8 Hz), 7.04 (1H, d, J = 8.8 Hz), 6.82 (1H, d, J = 8.0 Hz), 6.37 (1H, s), 6.26 (1H, d, J = 8.4 Hz), 6.17 (2H, brs), 5.10 (2H, s), 4.49 (2H, brs); LCMS: 100%, MS (ESI); m/z 366.0 [M + H]+. |
| 241 | pale-yellow powder (amorphous) 1H NMR (DMSO-d6, 400 MHz); δ 7.41-7.52 (4H, m), 6.88 (2H, d, J = 8.4 Hz), 6.36 (1H, d, J = 1.6 Hz), 6.31 (1H, d, J = 8.4 Hz), 5.75 (1H, brs), 4.25 (2H, d, J = 4.4 Hz), 3.94-4.06 (2H, m), 3.60-3.71 (2H, m), 2.95 (6H, s), 1.96-2.13 (4H, m); LCMS: 97.5%, MS (ESI); m/z 376.1 [M + H]+. |
| 242 | pale white powder; 1H NMR (DMSO-d6, 400 MHz); δ 7.35-7.49 (4H, m), 7.13 (1H, d, J = 6.4 Hz), 6.95-7.09 (4H, m), 6.46 (1H, s), 6.32 (1H, d, J = 8.4 Hz), 4.53 (2H, d, J = 5.6 Hz), 4.22 (4H, t, J = 12.0 Hz); LCMS: 100%, MS (ESI); m/z 440.9 [M + H]+. |
| 243 | white powder; 1H NMR (DMSO-d6); δ 8.54 (1H, s), 8.21 (1H, dd, J = 8.8, 2.0 Hz), 7.19-7.28 (3H, m), 7.15 (2H, d, J = 8.4 Hz), 6.84 (1H, d, J = 8.4 Hz), 6.34 (1H, d, J = 2.0 Hz), 6.26 (1H, dd, J = 8.4, 2.0 Hz), 6.15 (2H, brs), 5.14 (2H, s), 4.50 (2H, brs); LCMS: 97.7%, MS (ESI); m/z 400.0 [M + H]+. |
| 244 | white amorphous; 1H NMR (DMSO-d6, 400 MHz); δ 9.10 (2H, brs), 8.19 (1H, d, J = 2.4 Hz), 7.95 (1H, dd, J = 8.4, 2.4 Hz), 7.65 (1H, s), 7.48 (1H, d, J = 8.4 Hz), 7.39 (2H, d, J = 8.4 Hz), 7.29 (1H, d, J = 8.0 Hz), 7.06 (2H, d, J = 8.4 Hz), 7.00 (1H, d, J = 8.8 Hz), 4.42 (2H, t, J = 7.4 Hz), 3.01 (2H, t, J = 7.4 Hz); LCMS: 100%, MS (ESI); m/z 379.9 [M + H]+. |
| 245 | white powder; 1H NMR (DSMO-d6, 400 MHz); δ 7.36 (2H, d, J = 8.8 Hz), 7.23 (2H, d, J = 8.8 Hz), 6.98-7.11 (4H, m), 6.84 (1H, d, J = 8.0 Hz), 6.23 (1H, d, J = 2.0 Hz), 6.26 (1H, dd, J = 8.0, 2.0 Hz), 6.12 (2H, brs), 5.11 (2H, s), 4.49 (2H, brs); LCMS: 100%, MS (ESI); m/z 415.0 [M + H]+ |
| 246 | white amorphous; 1H NMR (DMSO-d6, 400 MHz); δ 7.57-7.65 (1H, m), 7.42-7.54 (3H, m), 7.22-7.33 (4H, m), 6.86 (1H, d, J = 8.0 Hz), 6.33 (1H, d, J = 1.6 Hz), 6.28 (1H, dd, J = 8.0, 1.6 Hz), 6.18 (2H, brs), 5.18 (2H, s), 4.50 (2H, brs); LCMS: 99.7%, MS (ESI); m/z 372.0 [M + H]+. |
| 247 | yellow powder; 1H NMR (DMSO-d6, 400 MHz); δ 8.18 (1H, d, J = 2.4 Hz), δ 7.95 (1H, dd, J = 8.8, 2.8 Hz), 7.27 (2H, d, J = 8.8 Hz), 7.08-7.14 (3H, m), 6.82 (1H, d, J = 8.0 Hz), 6.19-6.24 (2H, m), 6.02 (2H, brs), 5.64 (1H, q, J = 7.2 Hz), 4.39 (2H, brs), 1.83 (3H, d, J = 7.2 Hz); LCMS: 99.8%, MS (ESI); m/z 380.0 [M + H]+. |

| | |
|---|---|
| 248 | purple powder; 1H NMR (DMSO-d6, 400 MHz); δ 8.15 (1H, d, J = 2.4 Hz), δ 7.97 (1H, dd, J = 8.8, 2.4 Hz), 7.31 (1H, t, J = 8.4 Hz), 7.20 (1H, d, J = 8.8 Hz), 7.14 (1H, d, J = 11.2 Hz), 7.01 (1H, d, J = 8.0 Hz), 6.87 (1H, d, J = 8.4 Hz), 6.43 (2H, brs), 6.38 (1H, s), 6.30 (1H, d, J = 7.2 Hz), 5.18 (2H, s); LCMS: 95.5%, MS (ESI); m/z 383.9 [M + H]+. |
| 249 | off-white amorphous; 1H NMR (DMSO-d6, 400 Mhz); δ 8.20 (1H, d, J = 2.4 Hz), 7.80 (1H, dd, J = 8.8, 2.8 Hz), 7.38 (2H, d, J = 8.0 Hz), 7.14 (2H, d, J = 8.0 Hz), 6.91 (1H, d, J = 8.8 Hz), 6.79-6.85 (1H, m), 6.24 (2H, dd, J = 4.4, 2.0 Hz), 6.08 (2H, brs), 5.27 (2H, s), 5.11 (2H, s), 4.45 (2H, brs); LCMS: 100%, MS (ESI); m/z 379.9 [M + H]+. |
| 250 | white powder; 1H NMR (DMSO-d6, 400 MHz); δ 8.16 (1H, d, J = 2.4 Hz), 7.94 (1H, dd, J = 8.8, 2.4 Hz), 7.19 (2H, d, J = 8.8 Hz), 7.04-7.13 (3H, m), 6.89 (1H, d, J = 8.0 Hz), 6.58 (1H, t, J = 5.6 Hz), 6.32 (1H, d, J = 2.0 Hz), 6.27 (1H, dd, J = 8.0, 2.0 Hz), 5.13 (2H, s), 5.05 (1H, brs), 4.52 (2H, brs), 3.53-3.64 (2H, m), 3.36-3.43 (2H, m); LCMS: 100%, MS (ESI); m/z 410.0 [M + H]+. |
| 251 | white powder; 1H NMR (DMSO-d6, 400 MHz); δ 8.15 (1H, d, J = 2.4 Hz), 7.94 (1H, dd, J = 8.8, 2.8 Hz), 7.23 (2H, d, J = 8.4 Hz), 7.03-7.15 (3H, m), 6.96 (1H, d, J = 8.4 Hz), 6.64 (1H, t, J = 5.6 Hz), 6.21 (1H, s), 6.17 (1H, d, J = 8.4 Hz), 5.83 (1H, d, J = 6.8 Hz), 5.16 (2H, s), 4.99 (1H, t, J = 5.2 Hz), 4.78 (2H, t, J = 6.0 Hz), 4.38-4.50 (1H, m), 4.33 (2H, d, J = 6.0 Hz), 3.54-3.63 (2H, m), 3.36-3.44 (2H, m); LCMS: 99.4%, MS (ESI); m/z 466.0 [M + H]+. |
| 252 | off-white powder; 1H NMR (DMSO-d6, 400 MHz); δ 7.36-7.43 (2H, m), 7.22 (1H, d, J = 8.8 Hz), 6.95-7.02 (5H, m), 6.93 (1H, d, J = 8.4 Hz), 6.33 (1H, d, J = 2.0 Hz), 6.28 (1H, dd, J = 8.0, 2.0 Hz), 5.11 (2H, s), 4.55 (2H, brs), 3.54 (2H, q, J = 6.0 Hz), 2.88 (2H, t, J = 6.8 Hz); LCMS: 100%, MS (ESI); m/z 418.0 [M + H]+. |
| 253 | white amorphous; 1H NMR (DMSO-d6, 400 MHz); δ 8.17 (1H, d, J = 2.4 Hz), 7.93 (1H, dd, J = 8.4, 2.4 Hz), 7.44 (2H, d, J = 8.4 Hz), 6.93-7.16 (5H, m), 6.60 (1H, d, J = 1.6 Hz), 6.46-6.49 (1H, m), 4.54 (2H, d, J = 5.6 Hz), 3.49 (3H, s), 2.83 (6H, s); LCMS: 99.9%, MS (ESI); m/z 407.9 [M + H]+. |
| 254 | white amorphous; 1H NMR (DMSO-d6); δ 8.61 (1H, d, J = 2.4 Hz), 7.95 (1H, dd, J = 8.4, 2.4 Hz), 7.52 (1H, d, J = 8.4 Hz), 7.12 (2H, d, J = 8.4 Hz), 6.97 (2H, d, J = 8.4 Hz), 6.82 (1H, d, J = 8.0 Hz), 6.29 (1H, d, J = 1.6 Hz), 6.24 (1H, dd, J = 8.0, 2.0 Hz), 6.08 (2H, brs), 5.14 (2H, s), 5.03 (2H, s), 4.45 (2H, s); LCMS: 100%, MS (ESI); m/z 379.9 [M + H]+. |
| 255 | pale yellow powder; 1H NMR (DMSO-d6, 400 MHz); δ 8.14 (1H, d, J = 2.4 Hz), 7.97 (1H, dd, J = 8.4, 2.4 Hz), 7.26-7.37 (2H, m), 7.10-7.22 (2H, m), 6.85 (1H, d, J = 8.4 Hz), 6.35 (1H, d, J = 2.0 Hz), 6.27 (1H, dd, J = 8.0, 1.6 Hz), 6.18 (2H, brs), 5.15 (2H, s), 4.53 (2H, brs); LCMS: 100%, MS (ESI); m/z 399.9 [M + H]+. |
| 256 | off-white powder; 1H NMR (DMSO-d6, 400 MHz); δ 8.17 (1H, d, J = 2.0 Hz), 7.93 (1H, dd, J = 8.8, 2.8 Hz), 7.46 (2H, d, J = 8.8 Hz), 7.02-7.10 (3H, m), 6.90 (1H, d, J = 8.4 Hz), 6.70 (1H, d, J = 8.0 Hz), 6.23 (1H, d, J = 2.0 Hz), 6.19 (1H, dd, J = 8.4, 2.0 Hz), 5.83 (1H, d, J = 7.2 Hz), 5.00-5.12 (1H, m), 4.83 (2H, t, J = 6.4 Hz), 4.45-4.55 (1H, m), 4.35-4.40 (2H, m), 3.46 (3H, s), 1.50 (3H, d, J = 6.8 Hz); LCMS: 99.6%, MS (ESI); m/z 450.1 [M + H]+. |
| 257 | white powder; 1H NMR (DMSO-d6, 400 MHz); δ 8.17 (1H, d, J = 2.8 Hz), 7.93 (1H, dd, J = 8.8, 2.8 Hz), 7.41 (2H, d, J = 8.4 Hz), 6.90-7.00 (3H, m), 6.93 (1H, d, J = 8.4 Hz), 6.79 (1H, t, J = 6.0 Hz), 6.31 (1H, d, J = 1.6 Hz), 6.20 (1H, dd, J = 8.4, 2.0 Hz), 5.82 (1H, d, J = 7.2 Hz), 5.03 (1H, brs), 4.83 (2H, t, J = 6.4 Hz), 4.45-4.56 (3H, m), 4.39 (2H, t, J = 6.0 Hz), 3.98 (2H, t, J = 5.2 Hz), 3.59-3.70 (2H, m); LCMS: 100%, MS (ESI); m/z 466.1 [M + H]+. |
| 258 | off-white solid; 1H NMR (CDCl3, 400 MHz); δ 8.11 (1H, d, J = 2.4 Hz), 7.66 (1H, dd, J = 8.8, J = 2.8 Hz), 7.46 (2H, d, J = 8.8 Hz), 7.31 (1H, d, J = 8.4 Hz), 7.11 (2H, d, J = 8.4 Hz), 6.91 (1H, d, J = 8.8 Hz), 6.66 (1H, d, J = 2.0 Hz), 6.54 (1H, dd, J = 8.4 Hz, J = 2.0 Hz), 4.67 (2H, d, J = 4.8 Hz), 4.29-4.38 (1H, m), 4.24 (1H, brs), 3.55 (2H, brs), 1.56 (6H, d, J = 6.8 Hz); LCMS: 99.6%, MS (ESI); m/z 408.1 [M + H]+. |
| 259 | white powder; 1H NMR (DMSO-d6, 400 MHz); δ 8.18 (1H, d, J = 2.8 Hz), 7.94 (1H, dd, J = 8.8, 2.8 Hz), 7.42 (2H, d, J = 8.4 Hz), 7.05-7.10 (3H, m), 6.87 (1H, d, J = 8.0 Hz), 6.75 (1H, t, J = 5.2 Hz), 6.41 (1H, d, J = 1.6 Hz), 6.27 (1H, dd, J = 8.0, 1.6 Hz), 5.06 (1H, t, J = 4.8 Hz), 4.57 (2H, brs), 4.50 (2H, d, J = 6.0 Hz), 3.95 (2H, t, J = 5.2 Hz), 3.64 (2H, q, J = 5.2 Hz); LCMS: 99.3%, MS (ESI); m/z 410.0 [M + H]+. |
| 260 | off-white powder; 1H NMR (DMSO-d6, 400 MHz); δ 8.19 (1H, d, J = 2.8 Hz), 7.94 (1H, dd, J = 8.8, 2.8 Hz), 7.47 (2H, d, J = 8.4 Hz), 7.05-7.10 (3H, m), 6.83 (1H, d, J = 8.4 Hz), 6.65 (1H, d, J = 8.0 Hz), 6.35 (1H, d, J = 1.6 Hz), 6.25 (1H, dd, J = 8.4, 2.0 Hz), 5.00-5.09 (1H, m), 4.55 (2H, brs), 3.44 (3H, s), 1.51 (3H, d, J = 7.2 Hz); LCMS: 98.2%, MS (ESI); m/z 394.0 [M + H]+. |

| | |
|---|---|
| 261 | white amorphous; 1H NMR (DMSO-d6, 400 MHz); δ 8.17 (1H, d, J = 2.8 Hz), 7.94 (1H, dd, J = 8.8, 2.4 Hz), 7.42 (2H, d, J = 8.4 Hz), 7.04-7.14 (3H, m), 7.01 (1H, d, J = 1.2 Hz), 6.95 (1H, d, J = 8.4 Hz), 6.76 (1H, t, J = 5.6 Hz), 6.35 (1H, dd, J = 8.8, 2.4 Hz), 5.53-5.65 (1H, m), 5.04-5.17 (2H, m), 4.90-5.03 (2H, m), 4.71 (2H, brs), 4.45 (2H, d, J = 5.6 Hz); LCMS: 98.3%, MS (ESI); m/z 422.1 [M + H]+. |
| 262 | white powder; 1H NMR (DSMO-d6, 400 MHz); δ 7.39 (2H, d, J = 8.8 Hz), 7.27 (2H, d, J = 8.8 Hz), 7.07 (1H, t, J = 5.6 Hz), 6.94-7.02 (5H, m), 6.17-6.24 (2H, m), 5.87 (1H, d, J = 6.8 Hz), 5.14 (2H, s), 4.78 (2H, t, J = 6.4 Hz), 4.39-4.48 (1H, m), 4.34 (2H, t, J = 6.0 Hz), 3.55 (2H, q, J = 6.0 Hz), 2.88 (2H, t, J = 6.4 Hz); LCMS: 98.6%, MS (ESI); m/z 474.2 [M + H]+. |
| 263 | yellow powder; 1H NMR (DMSO-d6, 400 MHz); δ 8.18 (1H, d, J = 2.8 Hz), 7.94 (1H, dd, J = 8.8, 2.8 Hz), 7.42 (2H, d, J = 8.8 Hz), 7.05-7.11 (3H, m), 6.86 (1H, d, J = 8.0 Hz), 6.78 (1H, t, J = 5.6 Hz), 6.41 (1H, d, J = 1.6 Hz), 6.26 (1H, dd, J = 8.0, 2.0 Hz), 4.49-4.51 (4H, m), 4.06 (2H, t, J = 5.6 Hz), 3.57 (2H, t, J = 4.8 Hz), 3.24 (3H, s); LCMS: 98.5%, MS (ESI); m/z 424.1 [M + H]+. |
| 264 | white powder; 1H NMR (DMSO-d6, 400 MHz); δ 7.37-7.44 (2H, m), 7.18 (2H, d, J = 8.8 Hz), 6.95-7.03 (4H, m), 6.93 (1H, d, J = 8.4 Hz), 6.75 (1H, t, J = 5.6 Hz), 6.31 (1H, d, J = 2.0 Hz), 6.27 (1H, dd, J = 8.4, 2.0 Hz), 5.08 (2H, s), 4.5 (2H, brs), 3.53 (2H, q, J = 6.4 Hz), 2.59-2.70 (2H, m); LCMS: 100%, MS (ESI); m/z 461.0 [M + H]+. |
| 265 | off-white powder; 1H NMR (DMSO-d6, 400 MHz); δ 8.17 (1H, d, J = 2.4 Hz), 7.93 (1H, dd, J = 8.8, 2.8 Hz), 7.41 (2H, d, J = 8.8 Hz), 7.05-7.10 (3H, m), 6.92 (1H, t, J = 6.0 Hz), 6.85 (1H, d, J = 8.4 Hz), 6.39 (1H, d, J = 1.6 Hz), 6.26 (1H, dd, J = 8.0, 2.0 Hz), 4.43-4.60 (4H, m), 3.93 (2H, q, J = 7.2 Hz), 1.20 (3H, t, J = 7.2 Hz); LCMS: 99.2%, MS (ESI); m/z 394.1 [M + H]+. |
| 266 | off-white powder; 1H NMR (DMSO-d6, 400 MHz); δ 8.16 (1H, d, J = 2.4 Hz), 7.93 (1H, dd, J = 8.8, 2.8 Hz), 7.42 (2H, d, J = 8.4 Hz), 7.01-7.16 (4H, m), 6.84-6.97 (2H, m), 6.26 (1H, dd, J = 8.4, 2.0 Hz), 6.05 (1H, d, J = 6.0 Hz), 5.51-5.68 (1H, m), 5.04-5.12 (2H, m), 4.96-5.04 (2H, m), 4.82 (2H, t, J = 6.0 Hz), 4.39-4.54 (5H, m); LCMS: 98.8%, MS (ESI); m/z 478.1 [M + H]+. |
| 267 | off-white powder; 1H NMR (DMSO-d6, 400 MHz); δ 8.16 (1H, d, J = 2.4 Hz), 7.97 (1H, dd, J = 8.8, 2.4 Hz), 7.36 (1H, d, J = 11.2 Hz), 7.24-7.30 (2H, m), 7.20 (1H, d, J = 8.8 Hz), 6.97 (1H, t, J = 6.0 Hz), 6.87 (1H, d, J = 8.4 Hz), 6.37 (1H, d, J = 1.6 Hz), 6.27 (1H, dd, J = 8.4, 2.0 Hz), 4.56 (2H, brs), 4.52 (2H, d, J = 5.6 Hz), 3.42 (3H, s); LCMS: 100%, MS (ESI); m/z 398.0 [M + H]+. |
| 268 | off-white powder; 1H NMR (DMSO-d6, 400 MHz); δ 8.16 (1H, d, J = 2.4 Hz), 7.98 (1H, dd, J = 8.8, 2.8 Hz), 7.36 (1H, d, J = 11.2 Hz), 7.23-7.31 (2H, m), 7.20 (1H, d, J = 8.8 Hz), 7.04 (1H, t, J = 6.0 Hz), 6.95 (1H, d, J = 8.0 Hz), 6.27 (1H, d, J = 2.0 Hz), 6.23 (1H, dd, J = 8.0, 2.0 Hz), 5.87 (1H, d, J = 7.2 Hz), 4.85 (2H, t, J = 6.4 Hz), 4.46-4.60 (3H, m), 4.40 (2H, t, J = 6.0 Hz), 3.46 (3H, s); LCMS: 100%, MS (ESI); m/z 454.1 [M + H]+. |
| 269 | pale yellow powder; 1H NMR (DMSO-d6, 400 MHz); δ 8.17 (1H, d, J = 2.4 Hz), 7.94 (1H, dd, J = 8.8, 2.8 Hz), 7.41 (2H, d, J = 8.0 Hz), 7.05-7.10 (3H, m), 6.93 (1H, d, J = 8.4 Hz) 6.84 (1H, t, J = 5.6 Hz), 6.31 (1H, s), 6.20 (1H, dd, J = 8.4, 2.0 Hz), 5.84 (1H, d, J = 7.2 Hz), 4.84 (2H, t, J = 6.4 Hz), 4.45-4.56 (3H, m), 4.39 (2H, t, J = 6.0 Hz), 4.10 (2H, t, J = 5.2 Hz), 3.58 (2H, t, J = 5.2 Hz), 3.25 (3H, s); LCMS: 100%, MS (ESI); m/z 480.2 [M + H]+. |
| 270 | off-white powder; 1H NMR (DMSO-d6, 400 MHz); δ 8.17 (1H, d, J = 2.8 Hz), 7.93 (1H, dd, J = 8.8, 2.8 Hz), 7.40 (2H, d, J = 8.8 Hz), 7.05-7.10 (3H, m), 6.99 (1H, t, J = 6.0 Hz), 6.93 (1H, d, J = 8.4 Hz), 6.28 (1H, d, J = 2.0 Hz), 6.19 (1H, dd, J = 8.4, 2.0 Hz), 5.83 (1H, d, J = 7.2 Hz), 4.84 (2H, t, J = 6.4 Hz), 4.47-4.56 (3H, m), 4.39 (2H, t, J = 6.0 Hz), 3.97 (2H, q, J = 6.8 Hz), 1.20 (2H, d, J = 7.2 Hz); LCMS: 100%, MS (ESI); m/z 450.0 [M + H]+. |
| 271 | brown powder; 1H NMR (DMSO-d6, 400 MHz); δ 8.16 (1H, d, J = 2.8 Hz), 7.93 (1H, dd, J = 8.8, 2.8 Hz), 7.40 (2H, d, J = 8.4 Hz), 7.05-7.10 (3H, m), 6.94 (1H, d, J = 8.4 Hz), 6.84 (1H, t, J = 5.6 Hz), 6.47 (1H, d, J = 1.6 Hz), 6.16 (1H, dd, J = 8.4, 2.0 Hz), 5.80 (1H, d, J = 7.2 Hz), 4.83 (2H, t, J = 6.8 Hz), 4.56-4.65 (1H, m), 4.45-4.55 (3H, m), 4.39 (2H, t, J = 6.0 Hz), 1.47 (2H, d, J = 6.8 Hz); LCMS: 98.8%, MS (ESI); m/z 464.1 [M + H]+. |
| 272 | off-white amorphous; 1H NMR (DMSO-d6, 400 MHz); δ 8.20 (1H, d, J = 2.4 Hz), 7.97 (1H, dd, J = 8.8, 2.8 Hz), 7.48 (1H, t, J = 8.8 Hz), 7.13 (1H, d, J = 9.2 Hz), 7.10 (1H, dd, J = 11.2, 2.4 Hz), 6.95 (1H, dd, J = 8.4, 2.4 Hz), 6.83-6.92 (2H, m), 6.37 (1H, d, J = 2.0 Hz), 6.27 (1H, dd, J = 8.4, 2.4 Hz), 4.56 (2H, brs), 4.53 (2H, d, J = 6.0 Hz), 3.42 (3H, s); LCMS: 99.6%, MS (ESI); m/z 398.0 [M + H]+. |

| 273 | off-white amorphous; 1H NMR (DMSO-d6, 400 MHz); δ 8.20 (1H, d, J = 2.4 Hz), 7.96 (1H, dd, J = 8.8, 2.4 Hz), 7.48 (1H, t, J = 8.4 Hz), 7.05-7.18 (2H, m), 6.89-7.02 (3H, m), 6.16-6.33 (2H, m), 5.87 (1H, d, J = 7.2 Hz), 4.85 (2H, t, J = 6.4 Hz), 4.46-4.62 (3H, m), 4.34-4.45 (2H, m), 3.46 (3H, s); LCMS: 98.6%, MS (ESI); m/z 454.1 [M + H]+. |
|---|---|
| 274 | white powder; 1H NMR (DMSO-d6, 400 MHz); δ 8.18 (1H, d, J = 2.8 Hz), 7.93 (1H, dd, J = 8.8, 2.8 Hz), 7.46 (2H, d, J = 8.4 Hz), 7.01-7.12 (3H, m), 6.81 (1H, d, J = 8.4 Hz), 6.61 (1H, d, J = 2.4 Hz), 6.33 (1H, d, J = 1.6 Hz), 6.23 (1H, dd, J = 8.0, 2.0 Hz), 4.75-4.86 (1H, m), 4.52 (1H, brs), 3.44 (3H, s), 1.84-1.95 (1H, m), 1.70-1.83 (1H, m), 0.93 (3H, t, J = 7.2 Hz); LCMS: 97.2%, MS (ESI); m/z 408.0 [M + H]+. |
| 275 | white powder; 1H NMR (DMSO-d6, 400 MHz); δ 8.18 (1H, d, J = 2.4 Hz), 7.93 (1H, dd, J = 8.8, 2.8 Hz), 7.46 (2H, d, J = 8.4 Hz), 7.02-7.12 (3H, m), 7.07 (1H, d, J = 8.4 Hz), 6.89 (1H, t, J = 8.4 Hz), 6.22 (1H, d, J = 2.0 Hz), 6.18 (1H, dd, J = 8.4, 2.0 Hz), 5.82 (1H, d, J = 7.2 Hz), 4.76-4.88 (3H, m), 4.45-4.51 (1H, m), 4.35-4.44 (2H, m), 3.48 (3H, s), 1.85-1.96 (1H, m), 1.73-1.84 (1H, m), 0.94 (3H, t, J = 7.2 Hz); LCMS: 95.9%, MS (ESI); m/z 464.2 [M + H]+. |
| 276 | white powder; 1H NMR (DMSO-d6, 400 MHz); δ 8.55 (1H, s), 8.22 (1H, dd, J = 8.8, 2.4 Hz), 7.46 (2H, d, J = 8.8 Hz), 7.23 (1H, d, J = 8.8 Hz), 7.14 (2H, d, J = 8.4 Hz), 6.93 (1H, t, J = 6.0 Hz), 6.86 (1H, d, J = 8.0 Hz), 6.34 (1H, d, J = 1.6 Hz), 6.27 (1H, dd, J = 8.4, 2.0 Hz), 4.55 (2H, brs), 4.52 (2H, d, J = 6.0 Hz), 3.42 (3H, s); LCMS: 100%, MS (ESI); m/z 414.1 [M + H]+. |
| 277 | white powder; 1H NMR (DMSO-d6, 400 MHz); δ 8.16 (1H, d, J = 2.4 Hz), 7.94 (1H, dd, J = 8.8, 2.8 Hz), 7.42 (2H, d, J = 8.8 Hz), 7.05-7.13 (4H, m), 7.02 (1H, d, J = 8.4 Hz), 6.59 (1H, d, J = 2.0 Hz), 6.40 (1H, dd, J = 8.4, 2.0 Hz), 4.69-4.75 (2H, m), 4.54 (2H, d, J = 6.0 Hz), 4.43-4.49 (2H, m), 4.34-4.41 (1H, m), 3.49 (3H, s), 2.70 (3H, s); LCMS: 98.7%, MS (ESI); m/z 450.0 [M + H]+. |
| 278 | white powder; 1H NMR (DMSO-d6, 400 MHz); δ 8.16 (1H, d, J = 2.0 Hz), 7.93 (1H, dd, J = 8.8, 2.8 Hz), 7.43 (2H, d, J = 8.8 Hz), 7.13 (1H, t, J = 6.0 Hz), 7.05-7.10 (3H, m), 7.03 (1H, d, J = 8.4 Hz), 6.61 (1H, d, J = 2.0 Hz), 6.44 (1H, dd, J = 8.0, 2.0 Hz), 4.68 (2H, t, J = 6.4 Hz), 4.55 (2H, d, J = 6.0 Hz), 4.44-4.52 (1H, m), 4.36 (2H, t, J = 6.4 Hz), 3.49 (3H, s), 3.12 (2H, q, J = 6.8 Hz) 0.83 (3H, t, J = 7.2 Hz); LCMS: 99.8%, MS (ESI); m/z 464.1 [M + H]+. |
| 279 | white powder; mp = 155.5-159.8° C.; 1H NMR (DMSO-d6, 400 MHz); δ 7.37-7.43 (2H, m), 7.23 (2H, d, J = 8.4 Hz), 6.95-7.03 (5H, m), 6.80-6.84 (1H, m), 6.16-6.23 (2H, m), 5.86 (1H, d, J = 6.8 Hz), 5.11 (2H, s), 4.78 (2H, t, J = 6.4 Hz), 4.41-4.48 (1H, m), 4.33 (2H, d, J = 6.0 Hz), 3.54 (2H, q, J = 6.8 Hz), 2.60-2.71 (2H, m); LCMS: 98.9%, MS (ESI); m/z 417.0 [M + H]+. |
| 280 | yellow powder; 1H NMR (DMSO-d6, 400 MHz); δ 8.19 (1H, d, J = 2.8 Hz), 7.41-7.52 (4H, m), 7.07 (2H, d, J = 8.8 Hz), 6.75-6.85 (2H, m), 6.37 (1H, d, J = 2.0 Hz), 6.27 (1H, dd, J = 8.4, 2.0 Hz), 4.55 (2H, brs), 4.51 (1H, d, J = 5.6 Hz), 3.41 (3H, s); LCMS: 98.7%, MS (ESI); m/z 380.0 [M + H]+. |
| 281 | off-white powder; 1H NMR (DMSO-d6, 400 MHz); δ 8.19 (1H, d, J = 2.4 Hz), 7.41-7.56 (4H, m), 7.07 (2H, d, J = 8.4 Hz), 6.90-6.95 (2H, m), 6.25 (1H, s), 6.21 (1H, dd, J = 8.4, 2.0 Hz), 5.85 (1H, d, J = 6.8 Hz), 4.85 (2H, t, J = 6.4 Hz), 4.46-4.57 (3H, m), 4.40 (2H, t, J = 6.0 Hz), 3.44 (3H, s); LCMS: 98.1%, MS (ESI); m/z 436.1 [M + H]+. |
| 282 | brown powder; 1H NMR (DMSO-d6, 400 MHz); δ 8.14 (1H, d, J = 2.4 Hz), 7.93 (1H, dd, J = 8.8, 2.8 Hz), 7.31 (1H, s), 7.25 (1H, d, J = 8.4 Hz), 7.07 (1H, d, J = 8.8 Hz), 7.00 (1H, d, J = 8.0 Hz), 6.83-6.90 (2H, m), 6.36 (1H, d, J = 1.6 Hz), 6.26 (1H, d, J = 8.0, 2.0 Hz), 4.54 (2H, brs), 4.48 (2H, d, J = 5.6 Hz), 3.41 (3H, s), 2.04 (3H, s); LCMS: 100%, MS (ESI); m/z 394.0 [M + H]+. |
| 283 | off-white powder; 1H NMR (DMSO-d6, 400 MHz); δ 8.14 (1H, d, J = 2.8 Hz), 7.92 (1H, dd, J = 8.8, 2.8 Hz), 7.30 (1H, s), 7.25 (1H, d, J = 8.0 Hz), 7.07 (1H, d, J = 8.8 Hz), 7.00 (1H, d, J = 8.0 Hz), 6.89-6.96 (2H, m), 6.25 (1H, d, J = 1.6 Hz), 6.21 (1H, dd, J = 8.4, 2.0 Hz), 5.85 (1H, d, J = 7.2 Hz), 4.84 (2H, t, J = 6.0 Hz), 4.46-4.56 (3H, m), 4.39 (2H, t, J = 6.0 Hz), 3.45 (3H, s), 2.03 (3H, s); LCMS: 99.8%, MS (ESI); m/z 450.1 [M + H]+. |
| 284 | grey powder; 1H NMR (DMSO-d6, 400 MHz); δ 8.54 (1H, s), 8.21 (1H, dd, J = 8.8, 2.4 Hz), 7.45 (2H, d, J = 8.0 Hz), 7.22 (1H, d, J = 8.4 Hz), 7.13 (2H, d, J = 8.4 Hz), 6.98 (1H, t, J = 5.6 Hz), 6.93 (1H, d, J = 8.4 Hz), 6.25 (1H, s), 6.21 (1H, dd, J = 8.0, 2.0 Hz), 5.84 (1H, d, J = 6.8 Hz), 4.79-4.88 (2H, m), 4.45-4.57 (3H, m), 4.35-4.44 (2H, m), 3.45 (3H, s); LCMS: 99.6%, MS (ESI); m/z 470.0 [M + H]+. |
| 285 | off-white amorphous; 1H NMR (DMSO-d6, 400 MHz); δ 8.20 (1H, d, J = 2.4 Hz), 7.97 (1H, dd, J = 8.8, 2.8 Hz), 7.46 (1H, d, J = 8.8 Hz), 7.33 (1H, d, J = 2.4 Hz), 7.14 (1H, d, J = 8.8 Hz), 7.10 (1H, dd, J = 8.8, 2.4 Hz), 6.97 (1H, t, J = 6.0 Hz), 6.85 (1H, d, J = 8.4 Hz), 6.38 (1H, d, J = 2.0 Hz), 6.27 (1H, dd, J = 8.0, 2.0 Hz), 4.51-4.61 (4H, m), 3.45 (3H, s); LCMS: 100%, MS (ESI); m/z 414.0 [M + H]+. |

| | |
|---|---|
| 286 | off-white powder; 1H NMR (DMSO-d6, 400 MHz); δ 8.17 (1H, d, J = 2.8 Hz), 7.94 (1H, dd, J = 8.8, 2.8 Hz), 7.42 (2H, d, J = 8.0 Hz), 7.13 (1H, t, J = 5.6 Hz), 7.06-7.10 (3H, m), 6.86 (1H, d, J = 8.4 Hz), 6.39 (1H, d, J = 1.6 Hz), 6.26 (1H, dd, J = 8.4, 2.0 Hz), 4.55 (2H, brs), 4.50 (2H, d, J = 5.6 Hz), 3.95 (2H, t, J = 6.8 Hz), 2.47-2.49 (2H, m), 2.20 (6H, s); LCMS: 100%, MS (ESI); m/z 437.0 [M + H]+. |
| 287 | white amorphous; 1H NMR (CDCl3, 400 MHz); δ 8.20 (1H, s), 7.83 (1H, dd, J = 8.4, 2.0 Hz), 7.35 (2H, d, J = 8.8 Hz), 7.26-7.29 (1H, m), 7.07 (2H, d, J = 8.4 Hz), 6.91 (1H, d, J = 8.4 Hz), 6.54 (1H, dd, J = 8.0, 2.0 Hz), 6.45 (1H, d, J = 1.6 Hz), 4.65 (2H, d, J = 5.6 Hz), 4.21 (1H, t, J = 5.2 Hz), 3.58 (2H, brs), 3.41 (3H, s); LCMS: 100%, MS (ESI); m/z 380.0 [M + H]+. |
| 288 | pale yellow powder; 1H NMR (DMSO-d6, 400 MHz); δ 8.73 (2H, s), 7.44 (2H, d, J = 8.4 Hz), 7.15 (2H, d, J = 8.4 Hz), 6.92 (1H, t, J = 6.0 Hz), 6.86 (1H, d, J = 8.0 Hz), 6.36 (1H, d, J = 2.0 Hz), 6.26 (1H, dd, J = 8.4, 2.0 Hz), 4.58 (2H, brs), 4.51 (2H, d, J = 5.6 Hz), 3.41 (3H, s); LCMS: 99.7%, MS (ESI); m/z 381.0 [M + H]+. |
| 289 | pale yellow powder; 1H NMR (DSMO-d6, 400 MHz); δ 8.73 (2H, s), 8.32 (1H, s), 7.44 (2H, d, J = 8.4 Hz), 7.15 (2H, d, J = 8.4 Hz), 6.89-7.01 (2H, m), 6.25 (1H, s), 6.21 (1H, dd, J = 2.4, 8.4 Hz), 5.84 (1H, d, J = 7.2 Hz), 4.84 (2H, t, J = 6.4 Hz), 4.45-4.57 (3H, m), 4.39 (2H, t, J = 6.0 Hz), 3.45 (3H, s); LCMS: 100%, MS (ESI); m/z 437.1 [M + H]+. |
| 290 | off-white amorphous; 1H NMR (DMSO-d6, 400 MHz); δ 8.18 (1H, d, J = 2.4 Hz), 7.93 (1H, dd, J = 8.8, 2.8 Hz), 7.35 (1H, d, J = 8.4 Hz), 7.06 (1H, d, J = 8.8 Hz), 6.96 (1H, s), 6.91 (1H, d, J = 8.0 Hz), 6.86 (1H, d, J = 8.4 Hz), 6.73 (1H, t, J = 5.6 Hz), 6.37 (1H, s), 6.26 (1H, dd, J = 8.0, 1.2 Hz), 4.64 (2H, brs), 4.46 (2H, d, J = 5.2 Hz), 3.42 (3H, s), 2.34 (3H, s); LCMS: 98.8%, MS (ESI); m/z 394.1 [M + H]+. |
| 291 | off-white amorphous; 1H NMR (DMSO-d6, 400 MHz); δ 8.17 (1H, d, J = 2.8 Hz), 7.92 (1H, dd, J = 8.8, 2.4 Hz), 7.34 (1H, d, J = 8.4 Hz), 7.05 (1H, d, J = 8.8 Hz), 6.85-7.00 (3H, m), 6.81 (1H, t, J = 5.6 Hz), 6.26 (1H, d, J = 1.2 Hz), 6.22 (1H, d, J = 8.4 Hz), 5.84 (1H, d, J = 7.2 Hz), 4.85 (2H, t, J = 6.0 Hz), 4.44-4.56 (3H, m), 4.40 (2H, t, J = 6.0 Hz), 3.46 (3H, s), 2.34 (3H, s); LCMS: 99.6%, MS (ESI); m/z 450.0 [M + H]+. |
| 292 | white powder; 1H NMR (DMSO-d6, 400 MHz); δ 7.44 (2H, d, J = 8.4 Hz), 7.37 (2H, d, J = 8.4 Hz), 7.01-7.12 (4H, m), 6.82-6.93 (2H, m), 6.37 (1H, d, J = 1.6 Hz), 6.27 (1H, dd, J = 8.4, 2.0 Hz), 4.55 (2H, s), 4.50 (2H, d, J = 6.0 Hz), 3.41 (3H, s); LCMS: 98.5%, MS (ESI); m/z 429.1 [M + H]+. |
| 293 | white powder; 1H NMR (DMSO-d6, 400 MHz); δ 7.44 (2H, d, J = 8.4 Hz), 7.37 (2H, d, J = 8.4 Hz), 6.98-7.10 (4H, m), 6.89-6.98 (2H, m), 6.26 (1H, d, J = 2.0 Hz), 6.22 (1H, dd, J = 8.4, 2.0 Hz), 5.85 (1H, d, J = 7.2 Hz), 4.85 (2H, t, J = 6.4 Hz), 4.45-4.37 (3H, m), 4.40 (2H, t, J = 6.0 Hz), 3.44 (3H, s); LCMS: 97.4%, MS (ESI); m/z 485.2 [M + H]+. |
| 294 | white amorphous; 1H NMR (DMSO-d6, 400 MHz); δ 8.19 (1H, d, J = 2.8 Hz), 7.96 (1H, dd, J = 8.8, 2.8 Hz), 7.45 (1H, d, J = 8.4 Hz), 7.32 (1H, d, J = 2.4 Hz), 7.13 (1H, d, J = 8.8 Hz), 7.09 (1H, dd, J = 8.4, 2.4 Hz), 7.01 (1H, t, J = 5.6 Hz), 6.93 (1H, d, J = 8.4 Hz), 6.27 (1H, d, J = 1.6 Hz), 6.22 (1H, dd, J = 8.4, 2.0 Hz), 5.86 (1H, d, J = 6.8 Hz), 4.85 (2H, t, J = 6.4 Hz), 4.57 (2H, d, J = 5.6 Hz), 4.45-4.55 (1H, m), 4.40 (2H, t, J = 6.0 Hz), 3.49 (3H, s); LCMS: 99.4%, MS (ESI); m/z 470.1 [M + H]+. |
| 295 | pale yellow powder; 1H NMR (DMSO-d6, 400 MHz); δ 8.41 (1H, d, J = 1.2 Hz), 8.32 (1H, s), 7.45 (2H, d, J = 8.4 Hz), 7.16 (2H, d, J = 8.4 Hz), 6.90 (1H, t, J = 6.0 Hz), 6.86 (1H, d, J = 8.0 Hz), 6.36 (1H, d, J = 1.6 Hz), 6.26 (1H, dd, J = 8.0, 2.0 Hz), 4.54 (2H, brs), 4.51 (2H, d, J = 6.0 Hz), 3.41 (3H, s); LCMS: 98.7%, MS (ESI); m/z 381.0 [M + H]+. |
| 296 | pale yellow powder; 1H NMR (DMSO-d6, 400 MHz); δ 8.41 (1H, s), 8.32 (1H, s), 7.44 (2H, d, J = 8.4 Hz), 7.16 (2H, d, J = 8.4 Hz), 6.89-7.02 (2H, m), 6.24 (1H, s), 6.21 (1H, d, J = 8.0 Hz), 5.85 (1H, d, J = 6.8 Hz), 4.84 (2H, t, J = 6.4 Hz), 4.46-4.58 (3H, m), 4.39 (2H, t, J = 6.0 Hz), 3.44 (3H, s); LCMS: 97.5%, MS (ESI); m/z 437.0 [M + H]+. |
| 297 | white poder; 1H NMR (DMSO-d6, 400 MHz); δ 8.35 (1H, s), 7.43-7.46 (4H, m), 7.01-7.07 (3H, m), 6.84 (1H, d, J = 8.0 Hz), 6.37 (1H, s), 6.26 (1H, dd, J = 8.0, 2.0 Hz), 4.59 (2H, d, J = 6.0 Hz), 4.56 (2H, brs), 3.44 (3H, s); LCMS: 99.5%, MS (ESI); m/z 380.0 [M + H]+. |
| 298 | white power; 1H NMR (DMSO-d6, 400 MHz); δ 8.34 (1H, s), 7.41-7.45 (4H, m), 7.03-7.07 (3H, m), 6.92 (1H, d, J = 8.8 Hz), 6.25 (1H, s), 6.21 (1H, d, J = 8.4 Hz), 5.84 (1H, d, J = 6.8 Hz), 4.84 (2H, t, J = 6.0 Hz), 4.59 (2H, d, J = 5.6 Hz), 4.48-4.51 (1H, m), 4.39 (2H, t, J = 6.0 Hz), 3.46 (3H, s); LCMS: 100%, MS (ESI); m/z 436.0 [M + H]+. |
| 299 | off-white powder; 1H NMR (DMSO-d6, 400 MHz); δ 8.39 (1H, d, J = 2.4 Hz), 8.18 (1H, d, J = 2.8 Hz), 7.98 (1H, dd, J = 8.8, 2.8 Hz), 7.58 (1H, dd, J = 8.8, 2.8 Hz), 7.46 (1H, d, J = 8.8 Hz), 7.20 (1H, d, J = 8.8 Hz), 7.04 (1H, t, J = 6.0 Hz), 6.85 (1H, d, J = 8.0 Hz), 6.38 (1H, d, J = 2.0 Hz), 6.27 (1H, dd, J = 8.0, 2.0 Hz), 4.60 (2H, d, J = 6.0 Hz), 4.55 (2H, brs), 3.45 (3H, s); LCMS: 99.3%, MS (ESI); m/z 381.0 [M + H]+. |

| | |
|---|---|
| 300 | off-white powder; 1H NMR (DMSO-d6, 400 MHz); δ 8.39 (1H, d, J = 2.4 Hz), 8.17 (1H, d, J = 2.4 Hz), 7.98 (1H, dd, J = 8.8, 2.8 Hz), 7.58 (1H, dd, J = 8.4, 2.8 Hz), 7.45 (1H, d, J = 8.4 Hz), 7.19 (1H, d, J = 8.8 Hz), 7.09 (1H, t, J = 5.6 Hz), 6.92 (1H, d, J = 8.0 Hz), 6.26 (1H, d, J = 2.0 Hz), 6.21 (1H, dd, J = 8.4, 2.0 Hz), 5.85 (1H, d, J = 7.2 Hz), 4.84 (1H, t, J = 6.0 Hz), 4.61 (1H, d, J = 6.0 Hz), 4.45-4.57 (1H, m), 4.39 (1H, t, J = 6.0 Hz), 3.48 (3H, s); LCMS: 99.0%, MS (ESI); m/z 437.0 [M + H]+. |
| 301 | pale yellow solid; mp = 121.4-124.6° C.; 1H NMR (DMSO-d6, 400 MHz); δ 8.12 (1H, d, J = 3.2 Hz), 7.74-7.85 (1H, m), 7.42 (2H, d, J = 8.4 Hz), 7.02-7.12 (3H, m), 6.82-6.92 (2H, m), 6.36 (1H, d, J = 2.0 Hz), 6.26 (1H, dd, J = 8.4, 2.0 Hz), 4.54 (2H, brs), 4.50 (2H, d, J = 5.6 Hz), 3.41 (3H, s); LCMS: 98.8%, MS (ESI); m/z 364.0 [M + H]+. |
| 302 | pale yellow powder; 1H NMR (DMSO-d6, 400 MHz); δ 8.11 (1H, d, J = 3.2 Hz), 7.76-7.85 (1H, m), 7.41 (2H, d, J = 8.4 Hz), 7.01-7.12 (3H, m), 6.90-6.97 (2H, m), 6.24 (1H, s), 6.21 (1H, dd, J = 8.4, 2.0 Hz), 5.84 (1H, d, J = 7.2 Hz), 4.84 (2H, t, J = 6.0 Hz), 4.45-4.57 (3H, m), 4.39 (2H, t, J = 6.0 Hz), 3.44 (3H, s); LCMS: 98.4%, MS (ESI); m/z 420.1 [M + H]+. |
| 303 | white power; 1H NMR (DSMO-d6, 400 MHz); δ 10.92 (1H, brs), 8.42 (1H, d, J = 2.4 Hz), 8.22 (1H, d, J = 8.8 Hz), 7.92-7.98 (3H, m), 7.48 (2H, d, J = 8.4 Hz), 7.04 (1H, t, J = 6.0 Hz), 6.91 (1H, d, J = 8.0 Hz), 6.25 (1H, s), 6.20 (1H, d, J = 8.4 Hz), 5.83 (1H, d, J = 7.2 Hz), 4.84 (2H, t, J = 6.0 Hz), 4.58 (2H, d, J = 6.0 Hz), 4.45-4.55 (1H, m), 4.39 (2H, t, J = 6.0 Hz), 3.46 (3H, s); LCMS: 100%, MS (ESI); m/z 463.2 [M + H]+. |
| 304 | white amorphous; 1H NMR (DMSO-d6, 400 MHz); δ 8.21 (1H, d, J = 2.4 Hz), 7.80 (1H, dd, J = 8.8, 2.4 Hz), 7.33-7.42 (4H, m), 6.91 (1H, d, J = 8.4 Hz), 6.81-6.89 (2H, m), 6.36 (1H, d, J = 2.0 Hz), 6.27 (1H, dd, J = 8.4, 2.0 Hz), 5.29 (2H, s), 4.54 (2H, brs), 4.50 (2H, d, J = 6.0 Hz), 3.40 (3H, s); LCMS: 98.1%, MS (ESI); m/z 394.1 [M + H]+. |
| 305 | white amorphous; 1H NMR (DMSO-d6, 400 MHz); δ 8.21 (1H, d, J = 2.4 Hz), 7.80 (1H, dd, J = 8.8, 2.8 Hz), 7.31-7.42 (4H, m), 6.97-6.85 (3H, m), 6.24 (1H, d, J = 2.0 Hz), 6.20 (1H, dd, J = 8.0, 2.0 Hz), 5.83 (1H, d, J = 6.8 Hz), 5.29 (2H, s), 4.84 (2H, t, J = 6.4 Hz), 4.44-4.58 (3H, m), 4.33-4.43 (2H, m), 3.43 (3H, s); LCMS: 99.1%, MS (ESI); m/z 450.0 [M + H]+. |
| 306 | white amorphous; 1H NMR (DMSO-d6, 400 MHz); δ 8.17 (1H, d, J = 2.8 Hz), 7.93 (1H, dd, J = 8.8, 2.8 Hz), 7.42 (2H, d, J = 8.4 Hz), 7.21-7.23 (1H, m), 7.05-7.09 (3H, m), 6.96-7.02 (2H, m), 6.93 (1H, d, J = 8.4 Hz), 6.33 (1H, d, J = 1.6 Hz), 6.29 (1H, dd, J = 8.4, 2.0 Hz), 5.14 (1H, brs), 4.52 (2H, d, J = 6.0 Hz), 3.40 (3H, s), 1.33 (6H, s); LCMS: 99.1%, MS (ESI); m/z 465.1 [M + H]+. |
| 307 | white amorphous; 1H NMR (DMSO-d6, 400 MHz); δ 8.16 (1H, d, J = 2.4 Hz), 7.90 (1H, dd, J = 8.0, 2.4 Hz), 7.40-7.46 (2H, m), 7.09-7.16 (2H, m), 7.02 (1H, d, J = 8.0 Hz), 6.89-6.96 (2H, m), 6.24 (1H, d, J = 2.4 Hz), 6.21 (1H, dd, J = 8.4, 2.4 Hz), 5.85 (1H, d, J = 6.8 Hz), 4.82-4.86 (2H, m), 4.43-4.55 (3H, m), 4.38 (2H, t, J = 6.0 Hz), 3.41 (3H, s); LCMS: 99.0%, MS (ESI); m/z 436.1 [M + H]+. |
| 308 | white powder; 1H NMR (DMSO-d6, 400 MHz); δ 8.25-8.30 (2H, m), 7.99 (1H, dd, J = 8.4, 2.8 Hz), 7.94 (1H, dd, J = 8.0, 2.4 Hz), 7.18 (1H, d, J = 8.8 Hz), 7.11 (1H, d, J = 8.0 Hz), 6.92 (1H, d, J = 6.0 Hz), 6.87 (1H, d, J = 8.0 Hz), 6.36 (1H, d, J = 1.6 Hz), 6.27 (1H, dd, J = 8.0, 2.0 Hz), 4.55 (2H, brs), 4.50 (2H, t, J = 5.6 Hz), 3.39 (3H, s); LCMS: 99.0%, MS (ESI); m/z 381.0 [M + H]+. |
| 309 | white powder; 1H NMR (DMSO-d6, 400 MHz); δ 8.25-8.35 (2H, m), 7.99 (1H, dd, J = 8.8, 2.8 Hz), 7.93 (1H, dd, J = 8.4, 2.4 Hz), 7.18 (1H, d, J = 8.8 Hz), 7.12 (1H, d, J = 8.4 Hz), 6.98 (1H, t, J = 5.6 Hz), 6.95 (1H, d, J = 8.0 Hz), 6.25 (1H, d, J = 1.6 Hz), 6.22 (1H, dd, J = 8.4, 2.4 Hz), 5.86 (1H, d, J = 6.8 Hz), 4.85 (2H, t, J = 6.4 Hz), 4.45-4.60 (3H, m), 4.39 (2H, t, J = 6.0 Hz), 3.39 (3H, s); LCMS: 98.4%, MS (ESI); m/z 437.0 [M + H]+. |
| 310 | white powder; 1H NMR (DMSO-d6, 400 MHz); δ 10.94 (1H, brs), 8.43 (1H, d, J = 2.4 Hz), 8.23 (1H, d, J = 8.8 Hz), 7.94-7.98 (3H, m), 7.49 (2H, d, J = 8.4 Hz), 6.99 (1H, t, J = 6.0 Hz), 6.84 (1H, d, J = 8.0 Hz), 6.36 (1H, d, J = 1.6 Hz), 6.25 (1H, dd, J = 8.0, 2.0 Hz), 4.58 (2H, d, J = 6.0 Hz), 4.55 (2H, brs), 3.43 (3H, s); LCMS: 98.6%, MS (ESI); m/z 407.0 [M + H]+. |
| 311 | pale yellow powder; 1H NMR (DMSO-d6, 400 MHz); δ 7.62 (1H, d, J = 8.8 Hz), 7.45 (2H, d, J = 8.4 Hz), 7.32 (1H, d, J = 8.8 Hz), 7.12 (2H, d, J = 8.4 Hz), 6.82-6.92 (2H, m), 6.36 (1H, d, J = 1.6 Hz), 6.26 (1H, dd, J = 8.0, 2.0 Hz), 4.46-4.55 (4H, m), 3.41 (3H, s), 2.54 (3H, s); LCMS: 97.7%, MS (ESI); m/z 361.1 [M + H]+. |
| 312 | pale yellow powder; 1H NMR (DMSO-d6, 400 MHz); δ 7.61 (1H, d, J = 9.2 Hz), 7.44 (2H, d, J = 8.4 Hz), 7.32 (1H, d, J = 8.8 Hz), 7.12 (2H, d, J = 8.8 Hz), 6.94 (2H, d, J = 8.0 Hz), 6.25 (1H, d, J = 2.0 Hz), 6.21 (1H, dd, J = 8.4, 2.4 Hz), 5.84 (1H, d, J = 7.2 Hz), 4.84 (2H, t, J = 6.4 Hz), 4.45-4.57 (3H, m), 4.39 (2H, t, J = 5.6 Hz), 3.44 (3H, s), 2.53 (3H, s); LCMS: 96.4%, MS (ESI); m/z 417.1 [M + H]+. |

| | |
|---|---|
| 313 | white amorphous; 1H NMR (DMSO-d6, 400 MHz); δ 8.17 (1H, d, J = 2.0 Hz), 7.94 (1H, dd, J = 8.4, 2.4 Hz), 7.43 (2H, d, J = 8.8 Hz), 7.06-7.10 (3H, m), 6.88-6.73 (2H, m), 6.39 (1H, d, J = 2.0 Hz), 6.31 (1H, dd, J = 8.0, 2.0 Hz), 4.90 (1H, brs), 4.66 (1H, t, J = 5.6 Hz), 4.51 (2H, d, J = 5.6 Hz), 3.57 (2H, q, J = 6.0 Hz), 3.45 (3H, s), 3.00-3.10 (2H, m); LCMS: 99.0%, MS (ESI); m/z 424.0 [M + H]+. |
| 314 | white solid; m.p = 96.6-100.9° C.; 1H NMR (DMSO-d6, 400 MHz); δ 8.62 (1H, d, J = 2.4 Hz), 7.95 (1H, dd, J = 8.4, 2.4 Hz), 7.53 (1H, d, J = 8.4 Hz), 7.31 (2H, d, J = 8.8 Hz), 6.96 (2H, d, J = 8.4 Hz), 6.85 (1H, d, J = 8.0 Hz), 6.75 (1H, t, J = 6.0 Hz), 6.35 (1H, d, J = 1.6 Hz), 6.26 (1H, dd, J = 8.0, 2.0 Hz), 5.16 (2H, s), 4.55 (2H, brs), 4.42 (2H, d, J = 5.6 Hz), 3.38 (3H, s); LCMS: 97.0%, MS (ESI); m/z 394.1 [M + H]+. |
| 315 | white amorphous; 1H NMR (DMSO-d6, 400 MHz); δ 8.62 (1H, d, J = 2.4 Hz), 7.95 (1H, dd, J = 8.8, 2.8 Hz), 7.53 (1H, d, J = 8.4 Hz), 7.31 (2H, d, J = 8.8 Hz), 6.88-7.01 (3H, m), 6.81 (1H, t, J = 6.0 Hz), 6.23 (1H, d, J = 2.0 Hz), 6.20 (1H, dd, J = 8.4, 2.0 Hz), 5.83 (1H, d, J = 6.8 Hz), 5.15 (2H, s), 4.84 (2H, t, J = 6.4 Hz), 4.46-4.56 (1H, m), 4.34-4.45 (4H, m), 3.41 (3H, s); LCMS: 100%, MS (ESI); m/z 450.1 [M + H]+. |
| 316 | white amorphous; 1H NMR (DMSO-d6, 400 MHz); δ 8.17 (1H, d, J = 2.8 Hz), 7.93 (1H, dd, J = 8.8, 2.8 Hz), 7.43 (2H, d, J = 8.4 Hz), 7.00-7.13 (3H, m), 6.83-6.98 (2H, m), 6.42 (1H, d, J = 2.0 Hz), 6.32 (1H, dd, J = 8.0, 2.0 Hz), 4.94 (1H, t, J = 6.0 Hz), 4.52 (2H, d, J = 6.0 Hz), 3.50 (2H, t, J = 5.6 Hz), 3.45 (3H, s), 3.28 (3H, s), 3.18 (2H, q, J = 5.8 Hz); LCMS: 98.0%, MS (ESI); m/z 438.1 [M + H]+. |
| 317 | off-white powder; 1H NMR (DMSO-d6, 400 MHz); δ 8.19 (1H, d, J = 2.8 Hz), 7.94 (1H, dd, J = 8.8, 2.8 Hz), 7.40 (2H, d, J = 8.8 Hz), 6.99-7.15 (4H, m), 6.45 (1H, d, J = 1.6 Hz), 6.40 (1H, dd, J = 8.4, 2.4 Hz), 4.90 (1H, t, J = 5.6 Hz), 4.77 (2H, brs), 4.44 (2H, s), 3.59 (2H, q, J = 5.6 Hz), 3.52 (3H, s), 3.24 (1H, t, J = 6.0 Hz); LCMS: 100%, MS (ESI); m/z 424.0 [M + H]+. |
| 318 | off-white powder; 1H NMR (DMSO-d6, 400 MHz); δ 8.19 (1H, d, J = 2.8 Hz), 7.94 (1H, dd, J = 8.8, 2.4 Hz), 7.40 (2H, d, J = 8.8 Hz), 7.12 (1H, d, J = 8.4 Hz), 7.04-7.10 (3H, m), 6.38 (1H, dd, J = 8.4, 2.0 Hz), 6.30 (1H, d, J = 2.0 Hz), 6.08 (1H, d, J = 6.8 Hz), 4.87 (1H, t, J = 6.4 Hz), 4.50-4.62 (1H, m), 4.45 (2H, brs), 4.40 (1H, t, J = 6.0 Hz), 3.53-3.62 (5H, m), 3.24 (2H, t, J = 6.0 Hz); LCMS: 100%, MS (ESI); m/z 480.1 [M + H]+. |
| 319 | white power; 1H NMR (DMSO-d6, 400 MHz); δ 8.41 (1H, d, J = 2.4 Hz), 7.80 (1H, dd, J = 8.8, 2.8 Hz), 7.19-7.33 (5H, m), 6.89 (1H, d, J = 8.4 Hz), 6.43 (1H, s), 6.33 (1H, d, J = 7.6 Hz), 4.53 (2H, d, J = 5.2 Hz), 3.44 (6H, s); LCMS: 100%, MS (ESI); m/z 421.1 [M + H]+. |
| 320 | white power; 1H NMR (DMSO-d6, 400 MHz); δ 8.41 (1H, d, J = 2.4 Hz), 7.99 (1H, dd, J = 8.8, 2.4 Hz), 7.18-7.30 (5H, m), 6.89-6.94 (2H, m), 6.24 (1H, s), 6.20 (1H, d, J = 8.4 Hz), 5.83 (1H, d, J = 7.2 Hz), 4.84 (2H, t, J = 6.4 Hz), 4.48-4.53 (3H, m), 4.38 (2H, t, J = 6.4 Hz), 3.42 (6H, s); LCMS: 100%, MS (ESI); m/z 477.1 [M + H]+. |
| 321 | white power; 1H NMR (DMSO-d6, 400 MHz); δ 8.33 (1H, d, J = 2.0 Hz), 8.13 (1H, d, J = 2.4 Hz), 7.44 (2H, d, J = 8.4 Hz), 7.11 (2H, d, J = 8.8 Hz), 6.91 (1H, t, J = 6.0 Hz), 6.85 (1H, d, J = 8.0 Hz), 6.36 (1H, d, J = 2.0 Hz), 6.26 (1H, dd, J = 8.0, 2.0 Hz); LCMS: 100%, MS (ESI); m/z 414.0 [M + H]+. |
| 322 | white power; 1H NMR (DMSO-d6, 400 MHz); δ 8.32 (1H, d, J = 2.0 Hz), 8.12 (1H, d, J = 2.4 Hz), 7.43 (2H, d, J = 8.8 Hz), 7.11 (2H, d, J = 8.4 Hz), 6.89-7.00 (2H, m), 6.25 (1H, d, J = 2.0 Hz), 6.21 (1H, dd, J = 8.4, 2.0 Hz), 5.84 (1H, d, J = 6.8 Hz), 4.84 (2H, t, J = 6.4 Hz), 4.45-4.57 (3H, m), 4.39 (2H, t, J = 6.0 Hz), 3.44 (3H, s); LCMS: 99.7%, MS (ESI); m/z 470.0 [M + H]+. |
| 323 | white power; 1H NMR (DMSO-d6, 400 MHz); δ 8.20 (1H, dd, J = 10.0, 2.4 Hz), 8.02 (1H, d, J = 2.0 Hz), 7.44 (2H, d, J = 8.4 Hz), 7.14 (2H, d, J = 8.8 Hz), 6.93 (1H, t, J = 6.0 Hz), 6.86 (1H, d, J = 8.0 Hz), 6.37 (1H, d, J = 1.6 Hz), 6.27 (1H, dd, J = 8.0, 2.0 Hz), 4.57 (2H, brs), 4.51 (2H, d, J = 6.0 Hz), 3.41 (3H, s); LCMS: 100%, MS (ESI); m/z 398.0 [M + H]+. |
| 324 | white power; 1H NMR (DMSO-d6, 400 MHz); δ 8.20 (1H, dd, J = 10.0, 2.0 Hz), 8.01 (1H, d, J = 2.0 Hz), 7.43 (2H, d, J = 8.4 Hz), 7.13 (2H, d, J = 8.8 Hz), 6.89-7.00 (2H, m), 6.25 (1H, d, J = 2.0 Hz), 6.21 (1H, dd, J = 8.4, 2.4 Hz), 5.84 (1H, d, J = 6.8 Hz), 4.84 (2H, t, J = 6.8 Hz), 4.45-4.57 (3H, m), 4.39 (2H, t, J = 6.0 Hz), 3.44 (3H, s); LCMS: 98.6%, MS (ESI); m/z 454.1 [M + H]+. |
| 325 | off-white powder; 1H NMR (DMSO-d6, 400 MHz); δ 8.17 (1H, d, J = 2.8 Hz), 7.93 (1H, dd, J = 8.8, 2.8 Hz), 7.43 (2H, d, J = 8.4 Hz), 7.02-7.11 (4H, m), 6.94 (1H, d, J = 8.4 Hz), 6.62 (1H, d, J = 2.0 Hz), 6.49 (1H, d, J = 8.4, 2.0 Hz), 4.75 (1H, t, J = 5.2 Hz), 4.54 (2H, d, J = 5.6 Hz), 3.46 (3H, s), 3.27 (2H, d, J = 5.6 Hz), 1.10 (6H, s); LCMS: 98.9%, MS (ESI); m/z 452.0 [M + H]+. |

| | |
|---|---|
| 326 | off-white solid; 1H NMR (DMSO-d6, 400 MHz); δ 8.17 (1H, d, J = 2.4 Hz), 7.94 (1H, dd, J = 8.8, 2.8 Hz), 7.42 (2H, d, J = 8.4 Hz), 7.05-7.10 (3H, m), 7.02 (1H, t, J = 4.8 Hz), 6.92 (1H, d, J = 8.4 Hz), 6.36 (1H, d, J = 2.0 Hz), 6.31 (1H, dd, J = 8.4, 2.0 Hz), 4.52 (2H, d, J = 5.2 Hz), 3.41 (3H, s), 1.40 (6H, s); LCMS: 93.1%, MS (ESI); m/z 466.1 [M + H]+. |
| 327 | yellow powder; 1H NMR (Methanol-d4, 400 MHz); δ 8.16 (1H, d, J = 2.8 Hz), 7.93 (1H, dd, J = 8.8, 2.8 Hz), 7.55-7.62 (2H, m), 7.45 (1H, d, J = 8.4 Hz), 7.39 (1H, dd, J = 8.4, 2.0 Hz), 7.04 (1H, d, J = 8.8 Hz), 6.90 (1H, d, J = 2.0 Hz), 6.75 (1H, dd, J = 8.4, 2.4 Hz), 4.73 (2H, s), 3.84 (3H, s), 3.76 (3H, s); LCMS: 100%, MS (ESI); m/z 410.0 [M + H]+. |
| 328 | off-white powder; 1H NMR (DMSO-d6, 400 MHz); δ 8.19 (1H, d, J = 2.4 Hz), 7.93 (1H, dd, J = 8.8, 2.8 Hz), 7.27 (1H, d, J = 8.4 Hz), 7.06 (1H, d, J = 8.4 Hz), 6.91 (1H, d, J = 8.0 Hz), 6.81 (1H, d, J = 2.0 Hz), 6.76 (1H, t, J = 6.0 Hz), 6.64 (1H, dd, J = 8.4, 2.4 Hz), 6.25 (1H, d, J = 1.6 Hz), 6.20 (1H, dd, J = 8.4, 2.0 Hz), 5.84 (1H, d, J = 6.8 Hz), 4.84 (1H, t, J = 6.4 Hz), 4.49-4.57 (1H, m), 4.47 (2H, d, J = 6.0 Hz), 4.39 (1H, t, J = 6.0 Hz), 3.80 (3H, s), 3.47 (3H, s); LCMS: 98.9%, MS (ESI); m/z 466.0 [M + H]+. |
| 329 | white amorphous; 1H NMR (DMSO-d6, 400 MHz); δ 8.51 (1H, dd, J = 4.8, 0.8 Hz), 8.17 (1H, d, J = 2.4 Hz), 7.93 (1H, dd, J = 8.8, 2.8 Hz), 7.70 (1H, dt, J = 8.0, 2.0 Hz), 7.43 (2H, d, J = 8.8 Hz), 7.32 (1H, d, J = 7.6 Hz), 7.18-7.25 (1H, m), 7.03-7.14 (3H, m), 6.87-6.97 (2H, m), 6.40 (1H, d, J = 2.0 Hz), 6.32 (1H, dd, J = 8.4, 2.4 Hz), 5.15 (1H, t, J = 6.0 Hz), 4.51 (2H, d, J = 6.0 Hz), 3.45 (3H, s), 3.35-3.40 (2H, m), 3.00 (2H, t, J = 7.2 Hz); LCMS: 96.1%, MS (ESI); m/z 485.1 [M + H]+. |
| 330 | white powder (amorphous); (note: HNMR showed 10% of methyl isomer); 1H NMR (DMSO-d6, 400 MHz); δ 7.84 (1H, d, J = 3.2 Hz), 7.48 (1H, dd, J = 8.8, 3.2 Hz), 7.39 (2H, d, J = 8.8 Hz), 6.93-7.05 (3H, m), 6.80-6.90 (2H, m), 6.36 (1H, d, J = 1.6 Hz), 6.26 (1H, dd, J = 8.0, 2.0 Hz), 4.54 (2H, brs), 4.48 (2H, d, J = 6.0 Hz), 3.78 (3H, s), 3.40 (3H, s); LCMS: 98.8%, MS (ESI); m/z 376.1 [M + H]+. |
| 331 | white powder (amorphous); (Note: HNMR showed 10% of methyl isomer); 1H NMR (DMSO-d6, 400 MHz); δ 7.84 (1H, d, J = 2.8 Hz), 7.48 (1H, dd, J = 8.8, 3.2 Hz), 7.38 (2H, d, J = 8.8 Hz), 6.89-7.02 (5H, m), 6.24 (1H, d, J = 2.0 Hz), 6.20 (1H, dd, J = 8.4, 2.0 Hz), 5.84 (1H, d, J = 7.2 Hz), 4.84 (2H, t, J = 6.4 Hz), 4.45-4.57 (3H, m), 4.39 (2H, t, J = 6.0 Hz), 3.78 (3H, s), 3.44 (3H, s); LCMS: 100%, MS (ESI); m/z 432.1 [M + H]+. |
| 332 | white powder (amorphous); 1H NMR (DMSO-d6, 400 MHz); δ 8.17 (1H, d, J = 2.4 Hz), 7.94 (1H, dd, J = 8.8, 2.8 Hz), 7.40 (2H, d, J = 8.4 Hz), 7.21 (1H, t, J = 6.0 Hz), 7.06-7.10 (3H, m), 6.93 (1H, d, J = 8.4 Hz), 6.27 (1H, d, J = 1.6 Hz), 6.19 (1H, dd, J = 8.4, 2.0 Hz), 5.85 (1H, d, J = 6.8 Hz), 4.80-4.86 (2H, m), 4.47-4.55 (3H, m), 4.36-4.42 (2H, m), 3.99 (2H, t, J = 6.8 Hz), 2.51-2.54 (2H, m, overlapped with DMSO peak), 2.20 (6H, s); LCMS: 96.1%, MS (ESI) m/z 493.1 [M + H]+. |
| 333 | white powder (amorphous); 1H NMR (CDCl3, 400 MHz); δ 8.12 (1H, d, J = 2.8 Hz), 7.66 (1H, dd, J = 8.8, 2.4 Hz), 7.48 (2H, d, J = 8.4 Hz), 7.34 (1H, d, J = 8.4 Hz), 7.12 (2H, d, J = 8.4 Hz), 6.92 (1H, d, J = 8.8 Hz), 6.53 (1H, dd, J = 8.4, 2.0 Hz), 6.40 (1H, d, J = 1.6 Hz), 4.70 (2H, d, J = 5.6 Hz), 4.14 (1H, t, J = 5.4 Hz), 3.45 (3H, s), 3.21 (2H, t, J = 5.6 Hz), 2.68 (2H, t, J = 5.8 Hz), 2.30-2.65 (8H, m), 2.31 (3H, s); LCMS: 100%, MS (ESI); m/z 506.2 [M + H]+. |
| 334 | white amorphous; 1H NMR (DMSO-d6, 400 MHz); δ 8.20 (1H, d, J = 2.0 Hz), 7.94 (1H, dd, J = 8.8, 2.4 Hz), 7.07 (1H, d, J = 8.8 Hz), 6.93 (1H, d, J = 8.4 Hz), 6.84 (2H, s), 6.36 (1H, s), 6.29 (1H, d, J = 8.0 Hz), 6.22 (1H, brs), 4.59 (2H, brs), 4.43 (2H, d, J = 4.0 Hz), 3.36 (3H, s), 2.38 (6H, s); LCMS: 100%, MS (ESI); m/z 408.1 [M + H]+. |
| 335 | white amorphous; 1H NMR (DMSO-d6, 400 MHz); δ 8.20 (1H, d, J = 2.8 Hz), 7.94 (1H, dd, J = 8.8, 2.8 Hz), 7.07 (1H, d, J = 8.8 Hz), 7.01 (1H, d, J = 9.2 Hz), 6.84 (2H, s), 6.18-6.32 (3H, m), 5.86 (1H, d, J = 6.8 Hz), 4.85 (2H, t, J = 6.4 Hz), 4.48-4.58 (1H, m), 4.45 (2H, d, J = 4.4 Hz), 4.40 (2H, t, J = 6.0 Hz), 3.39 (3H, s), 2.37 (6H, s); LCMS: 99.4%, MS (ESI); m/z 464.1 [M + H]+. |
| 336 | pale yellow powder (amorphous); 1H NMR (DMSO-d6, 400 MHz); δ 8.71 (2H, s), 7.44 (2H, d, J = 8.4 Hz), 7.13 (2H, d, J = 8.8 Hz), 6.91 (1H, t, J = 6.0 Hz), 6.86 (1H, d, J = 8.4 Hz), 6.36 (1H, d, J = 1.2 Hz), 6.26 (1H, dd, J = 8.0, 1.6 Hz), 4.55 (2H, brs), 4.51 (2H, d, J = 6.0 Hz), 3.41 (3H, s); LCMS: 100%, MS (ESI); m/z 365.0 [M + H]+. |
| 337 | pale yellow amorphous; 1H NMR (DMSO-d6, 400 MHz); δ 8.71 (2H, s), 7.43 (2H, d, J = 8.0 Hz), 7.13 (2H, d, J = 8.4 Hz), 6.97 (1H, brs), 6.93 (1H, d, J = 8.0 Hz), 6.25 (1H, d, J = 1.6 Hz), 6.21 (1H, dd, J = 8.4, 2.0 Hz), 5.85 (1H, d, J = 7.2 Hz), 4.82-4.86 (2H, m), 4.47-4.55 (3H, m), 4.36-4.42 (2H, m), 3.45 (3H, s); LCMS: 99.5%, MS (ESI); m/z 421.1 [M + H]+. |

| | |
|---|---|
| 338 | off-white powder; 1H NMR (DMSO-d6, 400 MHz); δ 8.18 (1H, d, J = 2.8 Hz), 7.94 (1H, dd, J = 8.8, 2.8 Hz), 7.38 (1H, d, J = 8.8 Hz), 7.01-7.12 (4H, m), 6.45 (1H, d, J = 1.6 Hz), 6.40 (1H, dd, J = 8.8, 2.0 Hz), 4.78 (2H, brs), 4.43 (2H, s), 3.53-3.47 (5H, m), 3.29-3.34 (2H, m), 3.21 (3H, s); LCMS: 99.6%, MS (ESI); m/z 438.1 [M + H]+. |
| 339 | off-white powder; 1H NMR (DMSO-d6, 400 MHz); δ 8.18 (1H, d, J = 2.4 Hz), 7.94 (1H, dd, J = 8.4, 2.4 Hz), 7.37 (2H, d, J = 8.8 Hz), 7.13 (1H, d, J = 8.4 Hz), 7.00-7.10 (3H, m), 6.38 (1H, dd, J = 8.8, 2.4 Hz), 6.30 (1H, d, J = 2.0 Hz), 6.09 (1H, d, J = 6.4 Hz), 4.86 (2H, t, J = 6.4 Hz), 4.51-4.58 (1H, m), 4.44 (2H, s), 4.40 (2H, t, J = 6.0 Hz), 3.55 (3H, s), 3.49 (2H, t, J = 5.6 Hz), 3.28-3.33 (2H, m), 3.21 (3H, s); LCMS: 99.6%, MS (ESI); m/z 494.1 [M + H]+. |
| 340 | pale yellow powder (amorphous); 1H NMR (DMSO-d6, 400 MHz); δ 8.58 (2H, s), 7.46 (2H, d, J = 8.8 Hz), 7.15 (2H, d, J = 8.4 Hz), 6.81-6.92 (2H, m), 6.36 (1H, d, J = 2.0 Hz), 6.26 (1H, dd, J = 8.4, 2.0 Hz), 4.55 (2H, brs), 4.51 (2H, d, J = 5.6 Hz), 3.40 (3H, s); LCMS: 100%, MS (ESI); m/z 381 [M + H]+. |
| 341 | pale yellow amorphous; 1H NMR (DMSO-d6, 400 MHz); δ 8.57 (2H, s), 7.45 (2H, d, J = 8.4 Hz), 7.15 (2H, d, J = 8.4 Hz), 6.92-6.95 (2H, m), 6.14-6.28 (2H, m), 5.85 (1H, d, J = 6.4 Hz), 4.84 (2H, t, J = 6.4 Hz), 4.35-4.45 (3H, m), 4.39 (2H, t, J = 5.6 Hz), 3.44 (3H, s); LCMS: 100%, MS (ESI); m/z 436.9 [M + H]+. |
| 342 | grey powder (amorphous); 1H NMR (DMSO-d6, 400 MHz); δ 8.15 (1H, s), 7.32 (2H, d, J = 8.4 Hz), 7.26 (1H, s), 6.97 (2H, d, J = 8.4 Hz), 6.85 (1H, d, J = 8.4 Hz), 6.77 (1H, brs), 6.35 (1H, s), 6.26 (1H, dd, J = 8.0, 2.4 Hz), 5.19 (2H, s), 4.55 (2H, brs), 4.42 (2H, d, J = 6.0 Hz), 3.38 (3H, s); LCMS: 100%, MS (ESI); m/z 350.2 [M + H]+. |
| 343 | white powder (amorphous); 1H NMR (DMSO-d6, 400 MHz); δ 8.15 (1H, s), 7.31 (2H, d, J = 8.4 Hz), 7.25 (1H, s), 6.90-7.02 (3H, m), 6.82 (1H, t, J = 6.0 Hz), 6.15-6.25 (2H, m), 5.83 (1H, d, J = 6.8 Hz), 5.19 (2H, s), 4.77-4.89 (2H, m), 4.34-4.55 (5H, m), 3.41 (3H, s); LCMS: 100%, MS (ESI); m/z 406.0 [M + H]+. |
| 344 | pale-yellow power; 1H NMR (DMSO-d6, 400 MHz); δ 8.61 (2H, d, J = 4.8 Hz), 7.45 (2H, d, J = 8.4 Hz), 7.25 (1H, t, J = 4.8 Hz), 7.14 (2H, d, J = 8.4 Hz), 6.92 (1H, d, J = 8.4 Hz), 6.43 (1H, s), 6.33 (1H, d, J = 8.0 Hz), 4.54 (2H, d, J = 5.6 Hz), 3.46 (3H, s); LCMS: 98.4%, MS (ESI); m/z 347.0 [M + H]+. |
| 345 | pale-yellow power; 1H NMR (DMSO-d6, 400 MHz); δ 8.61 (2H, d, J = 4.4 Hz), 7.43 (2H, d, J = 8.4 Hz), 7.24 (2H, t, J = 4.8 Hz), 7.11 (2H, d, J = 8.4 Hz), 6.93-6.98 (2H, m), 6.25 (1H, s), 6.21 (1H, d, J = 8.4 Hz), 5.83 (1H, d, J = 6.8 Hz), 4.84 (2H, t, J = 6.4 Hz), 4.49-4.53 (3H, m), 4.39 (2H, t, J = 5.6 Hz), 3.45 (3H, s); LCMS: 99.5%, MS (ESI); m/z 403.0 [M + H]+. |
| 346 | off-white powder; 1H NMR (DMSO-d6, 400 MHz); δ 8.12 (1H, dd, J = 4.8, 1.2 Hz), 7.77-7.89 (1H, m), 7.43 (2H, d, J = 8.0 Hz), 7.04-7.12 (3H, m), 7.00 (1H, d, J = 8.4 Hz), 6.92 (1H, t, J = 5.2 Hz), 6.88 (1H, d, J = 8.0 Hz), 6.37 (1H, d, J = 1.6 Hz), 6.28 (1H, dd, J = 8.0, 1.6 Hz), 4.36-4.83 (4H, m), 3.42 (3H, s); LCMS: 100%, MS (ESI); m/z 346.0 [M + H]+. |
| 347 | off-white powder; 1H NMR (DMSO-d6, 400 MHz); δ 8.11 (1H, dd, J = 4.8, 1.6 Hz), 7.78-7.88 (1H, m), 7.41 (2H, d, J = 8.4 Hz), 7.03-7.13 (3H, m), 7.00 (1H, d, J = 8.8 Hz), 6.90-7.02 (2H, m), 6.25 (1H, d, J = 2.0 Hz), 6.21 (1H, dd, J = 8.0, 2.0 Hz), 5.84 (1H, d, J = 7.2 Hz), 4.84 (2H, t, J = 6.4 Hz), 4.45-4.62 (3H, m), 4.39 (2H, t, J = 6.0 Hz), 3.44 (3H, s); LCMS: 100%, MS (ESI); m/z 402.0 [M + H]+. |
| 348 | off-white powder; 1H NMR (DMSO-d6, 400 MHz); δ 8.45 (2H, s), 7.45 (2H, d, J = 8.4 Hz), 7.13 (2H, d, J = 8.4 Hz), 6.96 (1H, d, J = 8.4 Hz), 6.47 (1H, s), 6.38 (1H, d, J = 8.4 Hz), 4.56 (2H, d, J = 5.2 Hz), 3.48 (3H, s), 2.20 (3H, s); LCMS: 97.8%, MS (ESI); m/z 361.0 [M + H]+. |
| 349 | off-white powder; 1H NMR (DMSO-d6, 400 MHz); δ 8.44 (2H, s), 7.41 (2H, d, J = 8.0 Hz), 7.08 (2H, d, J = 8.4 Hz), 6.92-6.96 (2H, m), 6.25 (1H, s), 6.21 (1H, d, J = 8.4 Hz), 5.83 (1H, d, J = 7.2 Hz), 4.84 (2H, t, J = 6.4 Hz), 4.47-4.52 (3H, m), 4.39 (2H, t, J = 6.0 Hz), 3.44 (3H, s), 2.19 (3H, s); LCMS: 98.5%, MS (ESI); m/z 417.1 [M + H]+. |
| 350 | off white powder; 1H NMR (DMSO-d6, 400 MHz); δ 8.62 (1H, d, J = 2.0 Hz), 8.30 (1H, dd, J = 8.8, 2.4 Hz), 7.47 (2H, d, J = 8.0 Hz), 7.23 (1H, d, J = 8.8 Hz), 7.14 (2H, d, J = 8.4 Hz), 6.85-6.94 (2H, m), 6.37 (1H, d, J = 2.0 Hz), 6.27 (1H, dd, J = 8.0, 2.0 Hz), 4.45-4.61 (4H, m), 3.42 (3H, s); LCMS: 99.8%, MS (ESI); m/z 371.1 [M + H]+. |
| 351 | pale yellow powder; 1H NMR (DMSO-d6, 400 MHz); δ 8.62 (1H, d, J = 2.0 Hz), 8.30 (1H, dd, J = 8.8, 2.4 Hz), 7.46 (2H, d, J = 8.8 Hz), 7.23 (1H, d, J = 8.8 Hz), 7.14 (2H, d, J = 8.4 Hz), 6.90-7.01 (2H, m), 6.26 (1H, s), 6.22 (1H, dd, J = 8.4, 2.0 Hz), 5.85 (1H, d, J = 7.2 Hz), 4.85 (2H, t, J = 6.4 Hz), 4.48-4.59 (3H, m), 4.40 (2H, t, J = 6.0 Hz), 3.45 (3H, s); LCMS: 98.3%, MS (ESI); m/z 427.1 [M + H]+. |
| 352 | white powder; 1H NMR (DMSO-d6, 400 MHz); δ 7.95 (1H, d, J = 2.4 Hz), 7.65 (1H, dd, J = 8.4, 2.4 Hz), 7.41 (2H, d, J = 8.4 Hz), 7.03 (2H, d, J = 8.4 Hz), 6.95-6.83 (3H, m), 6.37 (1H, d, J = 1.6 Hz), 6.27 (1H, dd, J = 8.0, 2.0 Hz), 4.54 (2H, s), 4.50 (2H, d, J = 6.0 Hz), 3.41 (3H, s), 2.23 (3H, s); LCMS: 98.3%, MS (ESI); m/z 360.0 [M + H]+. |

| | |
|---|---|
| 353 | a white powder; 1H NMR (DMSO-d6, 400 MHz); δ 7.95 (1H, s), 7.65 (1H, dd, J = 8.4, 2.4 Hz), 7.40 (2H, d, J = 8.4 Hz), 7.02 (2H, d, J = 8.4 Hz), 6.86-6.98 (3H, m), 6.16-6.31 (2H, m), 5.84 (1H, d, J = 7.2 Hz), 4.85 (2H, t, J = 6.4 Hz), 4.46-4.57 (3H, m), 4.40 (2H, t, J = 6.0 Hz), 3.44 (3H, s), 2.23 (3H, s); LCMS: 98.0%, MS (ESI); m/z 416.2 [M + H]+. |
| 354 | pale yellow powder (amorphous); 1H NMR (DMSO-d6, 400 MHz); δ 8.77 (2H, s), 8.46 (1H, d, J = 2.8 Hz), 7.66 (1H, dd, J = 8.4, 2.8 Hz), 7.48 (1H, d, J = 8.8 Hz), 7.05 (1H, t, J = 6.0 Hz), 6.84 (1H, d, J = 8.0 Hz), 6.38 (1H, d, J = 1.6 Hz), 6.26 (1H, dd, J = 8.4, 2.0 Hz), 4.61 (2H, d, J = 6.0 Hz), 4.55 (2H, s), 3.45 (3H, s); LCMS: 99.5%, MS (ESI); m/z 382.0 [M + H]+. |
| 355 | pale yellow amorphous; 1H NMR (DMSO-d6, 400 MHz); δ 8.76 (2H, s), 8.46 (1H, d, J = 2.4 Hz), 7.66 (1H, dd, J = 8.4, 2.8 Hz), 7.47 (1H, d, J = 8.8 Hz), 7.10 (1H, t, J = 6.0 Hz), 6.92 (1H, d, J = 8.0 Hz), 6.26 (1H, d, J = 1.6 Hz), 6.21 (1H, dd, J = 8.4, 2.0 Hz), 5.85 (1H, d, J = 7.2 Hz), 4.84 (2H, t, J = 6.0 Hz), 4.62 (2H, d, J = 6.0 Hz), 4.547-4.55 (1H, m), 4.39 (2H, t, J = 6.0 Hz), 3.48 (3H, s); LCMS: 100%, MS (ESI); m/z 438.1 [M + H]+. |
| 356 | white amorphous; 1H NMR (DMSO-d6, 400 MHz); δ 7.40-7.53 (3H, m), 7.25-7.40 (3H, m), 7.05-7.20 (2H, m), 6.82-6.96 (2H, m), 6.37 (1H, d, J = 1.2 Hz), 6.27 (1H, dd, J = 8.0, 2.0 Hz), 4.40-4.65 (4H, m), 3.71 (3H, s), 3.42 (3H, s); LCMS: 100%, MS (ESI); m/z 399.1 [M + H]+. |
| 357 | white amorphous; 1H NMR (DMSO-d6, 400 MHz); δ 7.40-7.52 (3H, m), 7.27-7.39 (3H, m), 7.06-7.19 (2H, m), 6.91-7.02 (2H, m), 6.26 (1H, d, J = 2.0 Hz), 6.22 (1H, dd, J = 8.0, 2.0 Hz), 5.83 (1H, d, J = 7.6 Hz), 4.84 (2H, t, J = 6.4 Hz), 4.45-4.62 (3H, m), 4.39 (2H, t, J = 6.0 Hz), 3.70 (3H, s), 3.45 (3H, s); LCMS: 100%, MS (ESI); m/z 455.2 [M + H]+. |
| 358 | pale-yellow powder (amorphous); 1H NMR (DMSO-d6, 400 MHz); δ 8.73 (2H, s), 7.44 (2H, d, J = 8.4 Hz), 7.22 (1H, brs), 7.14 (2H, d, J = 8.4 Hz), 6.96-7.05 (2H, m), 6.92 (1H, d, J = 8.4 Hz), 6.33 (1H, d, J = 1.6 Hz), 6.30 (1H, dd, J = 8.4, 2.0 Hz), 5.15 (1H, brs), 4.52 (2H, d, J = 6.4 Hz), 3.40 (3H, s), 1.32 (6H, s); LCMS: 99.1%, MS (ESI); m/z 466.1 [M + H]+. |
| 359 | yellow powder (amorphous); 1H NMR (DMSO-d6, 400 MHz); δ 8.73 (2H, s), 7.44 (2H, d, J = 8.8 Hz), 7.14 (2H, d, J = 8.0 Hz), 7.05 (1H, s), 6.87-7.00 (2H, m), 6.79 (1H, s), 6.57 (1H, s), 6.42 (1H, d, J = 8.4 Hz), 5.46 (1H, brs), 4.51 (2H, d, J = 5.6 Hz), 4.24 (2H, d, J = 4.8 Hz), 3.64 (3H, s), 3.44 (3H, s); LCMS: 99.53%, MS (ESI); m/z 475.1 [M + H]+. |
| 360 | white powder (amorphous); 1H NMR (DMSO-d6, 400 MHz); δ 8.11 (2H, s), 7.35 (1H, d, J = 8.4 Hz), 6.89 (2H, d, J = 8.8 Hz), 6.75-6.88 (2H, m), 6.62 (2H, brs), 6.35 (1H, d, J = 1.2 Hz), 6.25 (1H, dd, J = 8.0, 1.6 Hz), 4.53 (2H, brs), 4.44 (2H, d, J = 5.6 Hz), 3.38 (3H, s); LCMS: 97.1%, MS (ESI); m/z 362.1 [M + H]+. |
| 361 | pale-yellow powder; 1H NMR (DMSO-d6, 400 MHz); δ 8.78 (2H, s), 7.44 (2H, d, J = 8.4 Hz), 7.16 (2H, d, J = 8.4 Hz), 7.02 (1H, brs), 6.86 (1H, d, J = 8.0 Hz), 6.37 (1H, s), 6.27 (1H, dd, J = 8.4, 1.6 Hz), 4.77 (2H, brs), 4.51 (2H, d, J = 5.6 Hz), 3.42 (3H, s); LCMS: 98.8%, MS (ESI); m/z 425.0 [M + H]+. |
| 362 | pale-yellow powder; 1H NMR (DMSO-d6, 400 MHz); δ 8.77 (2H, s), 7.43 (2H, d, J = 8.0 Hz), 7.14 (2H, t, J = 8.4 Hz), 6.90-6.98 (2H, m), 6.25 (1H, s), 6.21 (1H, d, J = 8.4 Hz), 5.83 (1H, d, J = 6.8 Hz), 4.84 (2H, t, J = 6.4 Hz), 4.47-4.52 (3H, m), 4.39 (2H, t, J = 5.6 Hz), 3.45 (3H, s); LCMS: 100%, MS (ESI); m/z 482.9 [M + 3]+. |
| 363 | pale-yellow powder; 1H NMR (DMSO-d6, 400 MHz); δ 8.95 (1H, d, J = 4.8 Hz), 7.76 (1H, d, J = 5.2 Hz), 7.47 (2H, d, J = 8.4 Hz), 7.22 (2H, d, J = 8.8 Hz), 6.90 (1H, d, J = 8.0 Hz), 6.41 (1H, s), 6.31 (1H, d, J = 8.4 Hz), 4.55 (2H, d, J = 5.6 Hz), 3.45 (3H, s); LCMS: 97.7%, MS (ESI); m/z 415.1 [M + H]+. |
| 364 | pale-yellow powder; 1H NMR (DMSO-d6, 400 MHz); δ 8.96 (1H, d, J = 4.4 Hz), 7.75 (1H, d, J = 4.8 Hz), 7.46 (2H, d, J = 8.4 Hz), 7.20 (2H, d, J = 8.4 Hz), 6.93-6.99 (2H, m), 6.25 (1H, s), 6.21 (1H, d, J = 8.8 Hz), 5.83 (1H, d, J = 6.8 Hz), 4.84 (2H, t, J = 6.0 Hz), 4.47-4.55 (3H, m), 4.39 (2H, t, J = 6.0 Hz), 3.45 (3H, s); LCMS: 100%, MS (ESI); m/z 471.1 [M + H]+. |
| 365 | yellow powder; 1H NMR (DMSO-d6, 400 MHz); δ 8.79 (2H, d, J = 5.2 Hz), 8.72 (2H, s), 7.44 (2H, d, J = 8.4 Hz), 7.39 (1H, t, J = 4.8 Hz), 7.12-7.17 (2H, m), 6.95 (1H, t, J = 6.0 Hz), 6.91 (1H, d, J = 8.4 Hz), 6.50 (1H, d, J = 2.0 Hz), 6.39 (1H, dd, J = 8.4, 2.0 Hz), 5.63 (1H, t, J = 6.0 Hz), 4.52 (2H, d, J = 5.6 Hz), 4.45 (2H, d, J = 5.6 Hz), 3.43 (3H, s); LCMS: 96.7%, MS (ESI); m/z 473.1 [M + H]+. |
| 366 | pale-yellow power; 1H NMR (DMSO-d6, 400 MHz); δ 8.72 (2H, s), 7.43 (2H, d, J = 8.8 Hz), 7.14 (2H, d, J = 8.4 Hz), 6.96 (1H, t, J = 6.0 Hz), 6.91 (1H, d, J = 8.4 Hz), 6.42 (1H, s), 6.27 (1H, dd, J = 8.8, 1.6 Hz), 5.76 (1H, d, J = 9.6 Hz), 4.70-4.78 (1H, m), 4.51 (2H, t, J = 6.0 Hz), 3.46 (3H, s), 3.30-3.35 (2H, m, after exchange with D2O), 3.25 (2H, t, J = 8.4 Hz); LCMS: 98.5%, MS (ESI); m/z 453.0 [M + H]+. |

| | |
|---|---|
| 367 | pale yellow powder; 1H NMR (DMSO-d6, 400 MHz); δ 9.12 (2H, s), 7.47 (2H, d, J = 8.0 Hz), 7.19 (2H, d, J = 8.0 Hz), 6.93 (1H, t, J = 6.0 Hz), 6.86 (1H, d, J = 8.4 Hz), 6.37 (1H, d, J = 1.6 Hz), 6.27 (1H, dd, J = 8.0, 2.0 Hz), 4.52 (2H, d, J = 6.0 Hz), 3.41 (3H, s); LCMS: 99.3%, MS (ESI); m/z 372.1 [M + H]+. |
| 368 | pale yellow amorphous; 1H NMR (DMSO-d6, 400 MHz); δ 9.12 (2H, s), 7.46 (2H, d, J = 8.4 Hz), 7.19 (2H, d, J = 8.4 Hz), 6.98 (1H, t, J = 6.0 Hz), 6.93 (1H, d, J = 8.4 Hz), 6.25 (1H, d, J = 2.0 Hz), 6.21 (1H, dd, J = 8.0, 2.0 Hz), 5.84 (1H, d, J = 7.2 Hz), 4.84 (2H, t, J = 6.0 Hz), 4.47-4.56 (3H, m), 4.39 (2H, t, J = 6.0 Hz), (2H, m), 3.45 (3H, s); LCMS: 100%, MS (ESI); m/z 428.0 [M + H]+. |
| 369 | white powder; 1H NMR (DMSO-d6, 400 MHz); δ 8.12 (2H, s), 7.35 (1H, d, J = 8.4 Hz), 6.80-7.00 (4H, m), 6.63 (1H, s), 6.75-6.88 (2H, m), 6.63 (2H, s), 6.24 (1H, d, J = 1.6 Hz), 6.21 (1H, dd, J = 8.8, 2.0 Hz), 5.83 (1H, d, J = 7.2 Hz), 4.84 (2H, t, J = 6.8 Hz), 4.50-4.60 (1H, m), 4.46 (2H, d, J = 6.0 Hz), 4.39 (2H, t, J = 6.0 Hz), 3.46 (3H, s); LCMS: 100%, MS (ESI); m/z 418.1 [M + H]+. |
| 370 | white powder; 1H NMR (DMSO-d6, 400 MHz); δ 8.74 (1H, s), 8.67 (1H, d, J = 5.6 Hz), 7.48 (2H, d, J = 8.8 Hz), 7.09-7.21 (3H, m), 6.92 (1H, t, J = 6.0 Hz), 6.87 (1H, d, J = 8.4 Hz), 6.37 (1H, d, J = 2.0 Hz), 6.27 (1H, dd, J = 8.0, 2.0 Hz), 4.49-4.61 (4H, m), 3.43 (3H, s); LCMS: 99.0%, MS (ESI); m/z 347.1 [M + H]+. |
| 371 | white powder; 1H NMR (DMSO-d6, 400 MHz); δ 8.74 (1H, s), 8.67 (1H, d, J = 2.0 Hz), 7.47 (2H, d, J = 8.8 Hz), 7.09-7.26 (3H, m), 6.98 (1H, t, J = 5.6 Hz), 6.95 (1H, d, J = 8.0 Hz), 6.26 (1H, d, J = 1.6 Hz), 6.22 (1H, dd, J = 8.0, 1.6 Hz), 5.85 (1H, d, J = 6.8 Hz), 4.85 (2H, t, J = 6.4 Hz), 4.44-4.69 (3H, m), 4.40 (2H, t, J = 6.0 Hz), 3.46 (3H, s); LCMS: 100%, MS (ESI); m/z 403.2 [M + H]+. |
| 372 | yellow amorphous; 1H NMR (DMSO-d6, 400 MHz); δ 8.73 (2H, s), 7.40-7.48 (4H, m), 7.10-7.20 (4H, m), 6.87-6.95 (2H, m), 6.41 (1H, s), 6.34 (1H, d, J = 8.4 Hz), 5.51 (1H, brs), 4.92-4.97 (1H, m), 4.74-4.80 (1H, m), 4.51 (2H, d, J = 6.0 Hz), 3.44 (3H, s), 3.17-3.25 (1H, m), 3.02-3.17 (1H, m); LCMS: 99.77%, MS (ESI); m/z 519.1 [M + H]+. |
| 373 | white powder; 1H NMR (DMSO-d6, 400 MHz); δ 9.09 (2H, s), 7.47 (2H, d, J = 7.6 Hz), 7.20 (2H, d, J = 7.6 Hz), 6.90-6.99 (1H, m), 6.86 (1H, d, J = 8.0 Hz), 6.37 (1H, s), 6.26 (1H, d, J = 8.4 Hz), 4.45-4.65 (4H, m), 3.41 (3H, s); LCMS: 99.7%, MS (ESI); m/z 415.1 [M + H]+. |
| 374 | pale yellow powder; 1H NMR (DMSO-d6, 400 MHz); δ 9.09 (2H, s), 7.46 (2H, d, J = 8.4 Hz), 7.20 (2H, d, J = 8.4 Hz), 6.99 (1H, d, J = 6.0 Hz), 6.93 (1H, d, J = 8.4 Hz), 6.17-6.28 (2H, m), 5.85 (1H, d, J = 6.8 Hz), 4.84 (2H, t, J = 6.4 Hz), 4.46-4.60 (3H, m), 4.39 (2H, t, J = 6.0 Hz), 3.45 (3H, s); LCMS: 98.2%, MS (ESI); m/z 471.1 [M + H]+. |
| 375 | off-white powder; 1H NMR (DMSO-d6, 400 MHz); δ 8.71 (1H, d, J = 5.6 Hz), 8.33 (1H, d, J = 8.8 Hz), 8.09 (1H, d, J = 2.0 Hz), 7.68 (1H, dd, J = 9.2, 2.4 Hz), 7.55 (2H, d, J = 8.4 Hz), 7.26 (2H, d, J = 8.4 Hz), 6.95 (1H, t, J = 6.0 Hz), 6.88 (1H, d, J = 8.4 Hz), 6.60 (1H, d, J = 5.6 Hz), 6.37 (1H, d, J = 2.0 Hz), 6.27 (1H, dd, J = 8.0, 2.0 Hz), 4.45-4.69 (4H, m), 3.43 (3H, s); LCMS: 99.3%, MS (ESI); m/z 430.0 [M + H]+. |
| 376 | grey powder; 1H NMR (DMSO-d6, 400 MHz); δ 7.95 (2H, s), 7.38 (2H, d, J = 8.0 Hz), 7.00 (2H, d, J = 8.4 Hz), 6.82-6.90 (2H, m), 6.36 (1H, d, J = 1.6 Hz), 6.26 (1H, dd, J = 8.4, 2.0 Hz), 5.21 (2H, s), 4.55 (2H, brs), 4.48 (2H, d, J = 5.6 Hz), 3.40 (3H, s); LCMS: 94.7%, MS (ESI); m/z 362.0 [M + H]+. |
| 377 | white powder; 1H NMR (DMSO-d6, 400 MHz); δ 8.24 (1H, d, J = 2.8 Hz), 7.95 (1H, dd, J = 8.8, 2.0 Hz), 7.45 (2H, d, J = 8.4 Hz), 7.16 (1H, d, J = 9.2 Hz), 7.12 (2H, d, J = 8.4 Hz), 6.83-6.95 (2H, m), 6.37 (1H, d, J = 1.6 Hz), 6.27 (1H, dd, J = 8.0, 2.0 Hz), 4.56 (2H, brs), 4.52 (2H, d, J = 6.0 Hz), 3.42 (3H, s); LCMS: 99.9%, MS (ESI); m/z 430.1 [M + H]+. |
| 378 | white powder; 1H NMR (DMSO-d6, 400 MHz); δ 8.23 (1H, d, J = 2.8 Hz), 7.95 (1H, dd, J = 8.8, 2.4 Hz), 7.44 (2H, d, J = 8.4 Hz), 7.16 (1H, d, J = 8.8 Hz), 7.12 (2H, d, J = 8.4 Hz), 6.90-7.01 (2H, m), 6.26 (1H, d, J = 1.6 Hz), 6.22 (2H, dd, J = 8.4, 2.0 Hz), 5.85 (1H, d, J = 6.8 Hz), 4.85 (2H, t, J = 6.0 Hz), 4.46-4.58 (3H, m), 4.40 (2H, t, J = 6.0 Hz), 3.45 (3H, s); LCMS: 97.9%, MS (ESI); m/z 486.1 [M + H]+. |
| 379 | off-white powder; 1H NMR (DSMO-d6, 400 MHz); δ 8.73 (2H, s), 7.45 (2H, d, J = 8.4 Hz), 7.15 (2H, d, J = 8.4 Hz), 6.85-6.98 (2H, m), 6.42 (1H, d, J = 2.0 Hz), 6.31 (1H, dd, J = 8.4, 2.0 Hz), 4.82 (1H, t, J = 5.6 Hz), 4.52 (2H, d, J = 5.6 Hz), 3.59 (4H, t, J = 4.6 Hz), 3.45 (3H, s), 3.12 (2H, q, J = 6.0 Hz), 2.51-2.54 (2H, m), 2.35-2.46 (4H, m); LCMS: 99.5%, MS (ESI); m/z 494.1 [M + H]+. |
| 380 | grey powder; 1H NMR (DMSO-d6, 400 MHz); δ 8.76 (2H, s), 7.50 (1H, t, J = 8.8 Hz), 7.21 (1H, dd, J = 10.8, 2.0 Hz), 7.03 (1H, dd, J = 8.4, 2.0 Hz), 6.84-6.93 (2H, m), 6.37 (1H, d, J = 2.0 Hz), 6.27 (1H, dd, J = 8.0, 2.0 Hz), 4.48-4.62 (4H, m), 3.42 (3H, s); LCMS: 100%, MS (ESI); m/z 399.0 [M + H]+. |

| | |
|---|---|
| 381 | pale yellow powder; 1H NMR (DMSO-d6, 400 MHz); δ 8.76 (2H, s), 7.50 (1H, t, J = 8.8 Hz), 7.21 (1H, dd, J = 11.2, 2.4 Hz), 7.03 (1H, dd, J = 8.4, 2.0 Hz), 6.92-7.00 (2H, m), 6.18-6.31 (2H, m), 5.86 (1H, d, J = 7.2 Hz), 4.85 (2H, t, J = 6.4 Hz), 4.46-4.61 (3H, m), 4.40 (2H, t, J = 6.0 Hz), 3.46 (3H, s); LCMS: 100%, MS (ESI); m/z 455.1 [M + H]+. |
| 382 | off-white powder; 1H NMR (DMSO-d6, 400 MHz); δ 8.38 (1H, d, J = 8.8 Hz), 7.76 (1H, dd, J = 9.2, 2.8 Hz), 7.68 (1H, dd, J = 9.2, 5.2 Hz), 7.53 (1H, td, J = 8.8, 3.2 Hz), 7.43-7.48 (2H, m), 7.31 (1H, d, J = 9.2 Hz), 7.15-7.21 (2H, m), 6.94 (1H, t, J = 5.8 Hz), 6.88 (1H, d, J = 8.0 Hz), 6.37 (1H, d, J = 2.0 Hz), 6.27 (1H, dd, J = 8.4, 2.0 Hz), 4.46-4.65 (4H, m), 3.43 (3H, s); LCMS: 100%, MS (ESI); m/z 414.1 [M + H]+. |
| 383 | white powder; 1H NMR (DMSO-d6, 400 MHz); δ 8.38 (1H, d, J = 8.8 Hz), 7.76 (1H, dd, J = 9.2, 2.8 Hz), 7.68 (1H, dd, J = 8.8, 5.2 Hz), 7.52 (1H, td, J = 8.8, 2.8 Hz), 7.46 (2H, d, J = 8.4 Hz), 7.30 (1H, d, J = 8.8 Hz), 7.18 (2H, d, J = 8.4 Hz), 6.92-7.02 (2H, m), 6.26 (1H, d, J = 2.0 Hz), 6.22 (1H, dd, J = 8.0, 2.0 Hz), 5.84 (1H, d, J = 7.2 Hz), 4.85 (2H, t, J = 6.0 Hz), 4.56 (2H, d, J = 5.6 Hz), 4.47-4.55 (1H, m), 4.40 (2H, t, J = 6.0 Hz), 3.46 (3H, s); LCMS: 100%, MS (ESI); m/z 470.1 [M + H]+. |
| 384 | off-white powder; 1H NMR (DMSO-d6, 400 MHz); δ 8.70 (1H, d, J = 5.2 Hz), 8.32 (1H, d, J = 8.8 Hz), 8.08 (1H, d, J = 2.0 Hz), 7.68 (1H, dd, J = 9.2, 2.4 Hz), 7.54 (2H, d, J = 8.0 Hz), 7.26 (2H, d, J = 8.4 Hz), 7.02 (1H, t, J = 6.0 Hz), 6.95 (1H, d, J = 8.4 Hz), 6.59 (1H, d, J = 5.2 Hz), 6.26 (1H, d, J = 1.6 Hz), 6.22 (1H, dd, J = 8.0, 2.0 Hz), 5.85 (1H, d, J = 6.8 Hz), 4.85 (2H, t, J = 6.4 Hz), 4.58 (2H, d, J = 6.0 Hz), 4.45-4.55 (1H, m), 4.40 (2H, t, J = 6.0 Hz), 3.46 (3H, s); LCMS: 97.1%, MS (ESI); m/z 481.2 [M + H]+. |
| 385 | pale yellow powder; 1H-NMR (DMSO-d6, 400 MHz): δ 8.75 (2H, s), 6.86-6.97 (3H, m), 6.36 (1H, s), 6.29 (1H, d, J = 8.0 Hz), 6.22 (1H, t, J = 4.8 Hz), 4.56 (2H, brs), 4.44 (2H, d, J = 4.8 Hz), 3.36 (3H, s), 2.39 (6H, s); LCMS: 100%, MS (ESI); m/z 409.2 [M + H]+. |
| 386 | pale yellow powder; 1H NMR (DMSO-d6, 400 MHz); δ 8.73 (2H, s), 7.44 (2H, d, J = 8.4 Hz), 7.15 (2H, t, J = 8.4 Hz), 7.01 (1H, brs), 6.96 (1H, d, J = 8.4 Hz), 6.30 (1H, s), 6.23 (1H, d, J = 8.4 Hz), 5.73 (1H, d, J = 4.8 Hz), 4.61-4.63 (1H, m), 4.53 (2H, d, J = 5.6 Hz), 3.44-3.52 (7H, m); LCMS: 98.9%, MS (ESI); m/z 469.2 [M + H]+. |
| 387 | white powder; 1H NMR (DMSO-d6, 400 MHz); δ 8.78 (1H, d, J = 5.2 Hz), 8.30 (1H, d, J = 8.4 Hz), 8.02 (1H, d, J = 6.4 Hz), 7.63 (1H, t, J = 8.0 Hz), 7.55 (2H, d, J = 8.8 Hz), 7.27 (2H, d, J = 8.0 Hz), 6.94 (1H, t, J = 6.0 Hz), 6.87 (1H, d, J = 8.0 Hz), 6.69 (1H, d, J = 4.8 Hz), 6.37 (1H, s), 6.27 (1H, dd, J = 8.0, 2.0 Hz), 4.48-4.65 (4H, m), 3.43 (3H, s); LCMS: 98.7%, MS (ESI); m/z 430.1 [M + H]+. |
| 388 | pale yellow powder; 1H NMR (DMSO-d6, 400 MHz); δ 8.78 (1H, d, J = 5.2 Hz), 8.30-8.35 (1H, m), 8.02 (1H, dd, J = 7.6, 1.6 Hz), 7.62 (1H, t, J = 8.4 Hz), 7.55 (2H, d, J = 8.4 Hz), 7.26 (2H, d, J = 8.4 Hz), 7.01 (1H, t, J = 6.0 Hz), 6.95 (1H, d, J = 8.4 Hz), 6.68 (1H, d, J = 5.2 Hz), 6.26 (1H, d, J = 2.0 Hz), 6.22 (1H, dd, J = 8.4, 2.0 Hz), 5.85 (1H, d, J = 6.8 Hz), 4.84 (2H, t, J = 6.4 Hz), 4.58 (2H, d, J = 6.0 Hz), 4.45-4.56 (1H, m), 4.40 (2H, t, J = 6.0 Hz), 3.46 (3H, s); LCMS: 97.1%, MS (ESI); m/z 486.1 [M + H]+. |
| 389 | pale yellow powder; 1H NMR (DMSO-d6, 400 MHz); δ 8.38 (1H, d, J = 9.2 Hz), 8.07 (1H, d, J = 1.6 Hz), 7.60-7.67 (2H, m), 7.47 (2H, d, J = 8.4 Hz), 7.32 (1H, d, J = 8.8 Hz), 7.19 (2H, d, J = 8.4 Hz), 6.92 (1H, t, J = 6.0 Hz), 6.88 (1H, d, J = 8.4 Hz), 6.37 (1H, d, J = 2.0 Hz), 6.27 (1H, dd, J = 8.4, 2.0 Hz), 4.50-4.60 (4H, m), 3.43 (3H, s); LCMS: 99.4%, MS (ESI); m/z 430.1 [M + H]+. |
| 390 | pale yellow amorphous; 1H NMR (DMSO-d6, 400 MHz); δ 8.38 (1H, d, J = 9.2 Hz), 8.07 (1H, s), 7.60-7.66 (2H, m), 7.46 (2H, d, J = 8.4 Hz), 7.31 (1H, d, J = 9.2 Hz), 7.19 (2H, d, J = 8.4 Hz), 6.93-7.00 (2H, m), 6.26 (1H, d, J = 2.0 Hz), 6.22 (1H, dd, J = 8.4, 2.0 Hz), 5.83 (1H, d, J = 7.2 Hz), 4.85 (2H, t, J = 6.4 Hz), 4.47-4.60 (3H, m), 4.40 (2H, t, J = 6.0 Hz), 3.46 (3H, s); LCMS: 100%, MS (ESI); m/z 486.1 [M + H]+. |
| 391 | pale yellow amorphous; 1H NMR (DMSO-d6, 400 MHz); δ 8.77 (2H, s), 7.59 (1H, d, J = 1.6 Hz), 7.43 (1H, dd, J = 8.4, 2.0 Hz), 7.35 (1H, d, J = 8.4 Hz), 6.99 (1H, t, J = 6.0 Hz), 6.86 (1H, d, J = 8.4 Hz), 6.37 (1H, d, J = 2.0 Hz), 6.27 (1H, d, J = 8.4, 2.0 Hz), 4.56 (2H, brs), 4.52 (2H, d, J = 6.0 Hz), 3.42 (3H, s); LCMS: 100%, MS (ESI); m/z 415.0 [M + H]+. |
| 392 | pale yellow amorphous; 1H NMR (DMSO-d6, 400 MHz); δ 8.77 (2H, s), 7.58 (1H, d, J = 2.0 Hz), 7.43 (1H, dd, J = 8.4, 2.0 Hz), 7.35 (1H, d, J = 2.4 Hz), 7.05 (1H, t, J = 6.0 Hz), 6.94 (1H, d, J = 8.4 Hz), 6.26 (1H, d, J = 1.6 Hz), 6.22 (1H, dd, J = 8.4, 2.0 Hz), 5.86 (1H, d, J = 6.8 Hz), 4.84 (2H, t, J = 6.4 Hz) 4.47-4.56 (3H, m), 4.39 (2H, t, J = 6.0 Hz) 3.46 (3H, s); LCMS: 100%, MS (ESI); m/z 471.0 [M + H]+. |
| 393 | pale yellow powder; 1H NMR (DMSO-d6, 400 MHz); δ 8.61 (1H, s), 7.46 (2H, d, J = 8.4 Hz), 7.37 (1H, s), 7.16 (2H, d, J = 8.8 Hz), 6.91 (1H, t, J = 5.6 Hz), 6.85 (1H, d, J = 8.0 Hz), 6.35 (1H, d, J = 2.0 Hz), 6.25 (1H, dd, J = 8.0, 2.0 Hz), 4.46-4.57 (4H, m), 3.40 (3H, s); LCMS: 100%, MS (ESI); m/z 381.00 [M + H]+. |

| | |
|---|---|
| 394 | yellow powder; 1H NMR (DMSO-d6, 400 MHz); δ 8.63 (1H, s), 7.47 (2H, d, J = 8.8 Hz), 7.38 (1H, s), 7.18 (2H, d, J = 8.4 Hz), 6.98 (1H, t, J = 6.0 Hz), 6.94 (1H, d, J = 8.0 Hz), 6.26 (1H, d, J = 1.6 Hz), 6.22 (1H, dd, J = 8.0, 2.0 Hz), 5.85 (1H, d, J = 7.2 Hz), 4.85 (2H, t, J = 6.4 Hz), 4.45-4.61 (3H, m), 4.40 (2H, t, J = 5.6 Hz), 3.45 (3H, s); LCMS: 99.3%, MS (ESI); m/z 437.0 [M + H]+. |
| 395 | pale yellow powder; 1H NMR (DMSO-d6, 400 MHz); δ 8.73 (2H, s), 7.44 (1H, d, J = 1.6 Hz), 7.26 (1H, dd, J = 8.4, 1.6 Hz), 7.02-7.05 (2H, m), 6.87 (1H, d, J = 8.0 Hz), 6.38 (1H, d, J = 1.6 Hz), 6.28 (1H, dd, J = 8.4, 1.6 Hz), 4.51 (2H, d, J = 6.0 Hz), 3.43 (3H, s), 2.89-2.97 (1H, m), 1.11 (6H, d, J = 6.8 Hz); LCMS: 99.2%, MS (ESI); m/z 423.1 [M + H]+. |
| 396 | pale yellow powder; 1H NMR (DMSO-d6, 400 MHz); δ 8.72 (2H, s), 7.43 (1H, d, J = 1.6 Hz), 7.25 (1H, dd, J = 8.0, 1.6 Hz), 7.02 (1H, d, J = 8.4 Hz), 6.92-6.95 (2H, m), 6.25 (1H, d, J = 1.6 Hz), 6.21 (1H, dd, J = 8.4, 2.0 Hz), 5.84 (2H, d, J = 6.8 Hz), 4.84 (2H, t, J = 6.0 Hz), 4.49-4.54 (3H, m), 4.39 (2H, t, J = 6.0 Hz), 3.45 (3H, s), 2.89-2.96 (1H, m), 1.10 (6H, d, J = 6.8 Hz); LCMS: 99.3%, MS (ESI); m/z 479.2 [M + H]+. |
| 397 | white powder; 1H NMR (CDCl3, 400 MHz); δ 8.28 (1H, s), 7.48 (2H, d, J = 8.4 Hz), 7.32 (2H, d, J = 8.4 Hz), 7.15 (1H, d, J = 8.4 Hz), 6.56 (1H, d, J = 8.0 Hz), 6.48 (1H, s), 4.71 (2H, d, J = 3.6 Hz), 4.24 (1H, brs), 3.45 (3H, s), 2.41-2.52 (1H, m), 1.12-1.30 (4H, m); LCMS: 99.8%, MS (ESI); m/z 421.1 [M + H]+. |
| 398 | white powder; 1H NMR (DMSO-d6, 400 MHz); δ 8.51 (1H, s), 7.42 (2H, d, J = 8.4 Hz), 7.12 (2H, d, J = 8.4 Hz), 6.91-7.00 (2H, m), 6.25 (1H, d, J = 1.6 Hz), 6.22 (1H, dd, J = 8.4, 1.6 Hz), 5.85 (1H, d, J = 7.2 Hz), 4.85 (2H, t, J = 6.4 Hz), 4.47-4.59 (3H, m), 4.40 (2H, t, J = 6.0 Hz), 3.45 (3H, s), 2.38-2.46 (1H, m), 1.01-2.01 (2H, m), 0.80-1.05 (2H, m); LCMS: 99.7%, MS (ESI); m/z 447.1 [M + H]+. |
| 399 | off-white powder; 1H NMR (DMSO-d6, 400 MHz); δ 8.45 (1H, d, J = 8.0 Hz), 8.14 (1H, d, J = 8.4 Hz), 8.07 (1H, s), 8.03 (1H, t, J = 7.6 Hz), 7.86 (1H, t, J = 7.8 Hz), 7.48 (2H, d, J = 8.0 Hz), 7.22 (2H, d, J = 8.4 Hz), 7.01 (1H, brs), 6.88 (1H, d, J = 8.4 Hz), 6.38 (1H, d, J = 1.2 Hz), 6.28 (1H, dd, J = 8.0, 2.0 Hz), 4.55 (2H, d, J = 5.6 Hz), 3.43 (3H, s); LCMS: 99.8%, MS (ESI); m/z 430.1 [M + H]+. |
| 400 | white powder; 1H NMR (DMSO-d6, 400 MHz); δ 8.45 (1H, d, J = 8.4 Hz), 8.14 (1H, d, J = 8.4 Hz), 8.07 (1H, s), 7.99-8.06 (1H, m), 7.86 (1H, t, J = 7.4 Hz), 7.47 (2H, d, J = 8.4 Hz), 7.21 (2H, d, J = 8.4 Hz), 6.99 (1H, t, J = 6.2 Hz), 6.95 (1H, d, J = 8.4 Hz), 6.26 (1H, d, J = 2.0 Hz), 6.22 (1H, dd, J = 8.0, 2.0 Hz), 5.84 (1H, d, J = 6.8 Hz), 4.85 (2H, t, J = 6.4 Hz), 4.47-4.60 (3H, m), 4.40 (2H, t, J = 6.0 Hz), 3.46 (3H, s); LCMS: 100%, MS (ESI); m/z 486.1 [M + H]+. |
| 401 | white powder; 1H NMR (CDCl3, 400 MHz); δ 8.11 (1H, d, J = 2.4 Hz), 7.65 (1H, dd, J = 8.8, 2.8 Hz), 7.46 (2H, d, J = 8.4 Hz), 7.32 (1H, d, J = 8.4 Hz), 7.11 (2H, d, J = 8.4 Hz), 6.91 (1H, d, J = 8.4 Hz), 6.42 (1H, d, J = 8.4, 1.6 Hz), 6.28 (1H, d, J = 2.0 Hz), 4.67 (2H, d, J = 4.0 Hz), 4.35-4.47 (1H, m), 4.25 (1H, brs), 3.97 (2H, t, J = 7.2 Hz), 3.54 (2H, t, J = 7.0 Hz), 3.43 (3H, s); LCMS: 98.6%, MS (ESI); m/z 435.1 [M + H]+. |
| 402 | white powder; 1H NMR (CDCl3, 400 MHz); δ 7.52 (2H, d, J = 8.4 Hz), 7.45 (1H, d, J = 2.0 Hz), 7.33-7.40 (3H, m), 7.29 (1H, s), 7.22 (1H, dd, J = 8.4, 2.0 Hz), 6.55 (1H, dd, J = 8.4, 2.0 Hz), 6.47 (1H, d, J = 2.0 Hz), 4.61-4.82 (3H, m), 3.46 (3H, s); LCMS: 98.4%, MS (ESI); m/z 420 [M + H]+. |
| 403 | white powder; 1H NMR (DMSO-d6, 400 MHz); δ 7.66 (1H, d, J = 8.4 Hz), 7.62 (1H, d, J = 2.0 Hz), 7.51 (2H, d, J = 8.8 Hz), 7.44 (2H, d, J = 8.4 Hz), 7.32 (1H, dd, J = 8.8, 2.4 Hz), 7.00 (1H, t, J = 6.0 Hz), 6.94 (1H, d, J = 8.4 Hz), 6.26 (1H, d, J = 2.0 Hz), 6.22 (1H, dd, J = 8.4, 2.0 Hz), 5.84 (1H, d, J = 7.2 Hz), 4.84 (2H, t, J = 6.4 Hz), 4.47-4.60 (3H, m), 4.40 (2H, t, J = 6.0 Hz), 3.46 (3H, s); LCMS: 99.2%, MS (ESI); m/z 476.2 [M + H]+. |
| 404 | white powder; 1H NMR (DSMO-d6, 400 MHz); δ 8.17 (1H, d, J = 2.4 Hz), 7.93 (1H, dd, J = 8.8, 2.8 Hz), 7.43 (2H, d, J = 8.8 Hz), 7.03-7.11 (3H, m), 6.91-7.00 (2H, m), 6.29 (1H, d, J = 2.0 Hz), 6.24 (1H, dd, J = 8.4, 2.0 Hz), 5.75-5.84 (2H, m), 5.73 (1H, d, J = 4.8 Hz), 4.52 (2H, d, J = 5.6 Hz), 4.10-4.30 (3H, m), 3.56 (2H, d, J = 4.0 Hz), 3.45 (3H, s); LCMS: 99.7%, MS (ESI); m/z 478.2 [M + H]+. |
| 405 | yellow powder; 1H NMR (DMSO-d6, 400 MHz); δ 9.52 (1H, s), 8.26 (1H, d, J = 2.4 Hz), 7.91 (1H, dd, J = 9.2, 2.4 Hz), 7.75 (1H, d, J = 9.2 Hz), 7.47 (2H, d, J = 8.4 Hz), 7.22 (2H, d, J = 8.4 Hz), 6.92 (1H, t, J = 6.0 Hz), 6.88 (1H, d, J = 8.0 Hz), 6.37 (1H, d, J = 2.0 Hz), 6.27 (1H, dd, J = 8.4, 2.0 Hz), 4.48-4.64 (4H, m), 3.43 (3H, s); LCMS: 99.4%, MS (ESI); m/z 431.1 [M + H]+. |
| 406 | pale yellow powder; 1H NMR (DMSO-d6, 400 MHz); δ 9.51 (1H, s), 8.26 (1H, d, J = 2.4 Hz), 7.91 (1H, dd, J = 9.2, 2.4 Hz), 7.74 (1H, d, J = 9.2 Hz), 7.46 (2H, d, J = 8.4 Hz), 7.21 (2H, d, J = 8.4 Hz), 6.93-7.04 (2H, m), 6.26 (1H, s), 6.22 (1H, dd, J = 8.0, 2.0 Hz), 5.83 (1H, d, J = 7.2 Hz), 4.84 (2H, t, J = 6.4 Hz), 4.46-4.60 (3H, m), 4.39 (2H, t, J = 6.0 Hz), 3.46 (3H, s); LCMS: 97.3%, MS (ESI); m/z 487.2 [M + H]+. |

| | |
|---|---|
| 407 | off-white powder; 1H NMR (CDCl3, 400 MHz); δ 8.50 (2H, s), 7.51 (2H, d, J = 8.4 Hz), 7.32 (1H, d, J = 8.4 Hz), 7.18 (2H, d, J = 8.4 Hz), 6.43 (1H, dd, J = 8.4, 1.6 Hz), 6.28 (1H, s), 4.71 (2H, d, J = 3.2 Hz), 4.34-4.46 (1H, m), 4.21 (1H, brs), 3.97 (2H, t, J = 7.2 Hz), 3.54 (2H, t, J = 7.2 Hz), 3.44 (3H, s); LCMS: 98.5%, MS (ESI); m/z 436.1 [M + H]+. |
| 408 | white powder; 1H NMR (CDCl3, 400 MHz); δ 8.50 (2H, s), 7.51 (1H, d, J = 8.4 Hz), 7.35 (1H, d, J = 8.4 Hz), 7.18 (2H, d, J = 8.8 Hz), 6.41 (1H, dd, J = 8.4, 2.0 Hz), 6.28 (1H, d, J = 2.0 Hz), 4.72 (2H, d, J = 5.6 Hz), 4.29-4.43 (5H, m), 4.26 (1H, t, J = 5.0 Hz), 3.93 (1H, brs), 3.76-3.86 (2H, m), 3.45 (3H, s); LCMS: 97.7%, MS (ESI); m/z 479.2 [M + H]+. |
| 409 | white powder; 1H NMR (DMSO-d6, 400 MHz); δ 7.43 (2H, d, J = 8.4 Hz), 7.27 (2H, d, J = 8.8 Hz), 7.03 (1H, d, J = 8.4 Hz), 6.90-6.98 (2H, m), 6.52 (1H, s), 6.42 (1H, d, J = 8.4 Hz), 6.25 (1H, s), 6.21 (1H, d, J = 8.4 Hz), 5.82 (1H, d, J = 6.8 Hz), 4.77-4.91 (4H, m), 4.47-4.57 (3H, m), 4.39 (2H, t, J = 6.0 Hz), 3.54 (3H, s), 3.44 (3H, s); LCMS: 98.5%, MS (ESI); m/z 470.3 [M + H]+. |
| 410 | yellow powder; 1H NMR (CDCl3, 400 MHz); δ 8.50 (2H, s), 7.53 (2H, d, J = 8.4 Hz), 7.31 (1H, d, J = 8.4 Hz), 7.20 (2H, d, J = 8.4 Hz), 6.55 (1H, dd, J = 8.0, 2.0 Hz), 6.47 (1H, d, J = 1.6 Hz), 4.72 (2H, d, J = 4.8 Hz), 4.18 (1H, brs), 3.43 (3H, s); LCMS: 96.9%, MS (ESI); m/z 431.1 [M + H]+. |
| 411 | pale yellow powder; 1H NMR (DMSO-d6, 400 MHz); δ 8.73 (2H, s), 7.15 (1H, s), 6.81-6.90 (2H, m), 6.37 (1H, d, J = 1.6 Hz), 6.27 (1H, dd, J = 8.0, 2.0 Hz), 4.55 (2H, brs), 4.45 (2H, d, J = 6.0 Hz), 3.42 (3H, s), 2.02 (6H, s); LCMS: 100%, MS (ESI); m/z 409.1 [M + H]+. |
| 412 | yellow powder; 1H NMR (CDCl3, 400 MHz); δ 8.50 (2H, s), 7.52 (2H, d, J = 8.8 Hz), 7.34 (1H, d, J = 8.4 Hz), 7.19 (2H, d, J = 8.4), 6.40 (1H, dd, J = 8.4, 2.0 Hz), 6.24 (1H, d, J = 2.0 Hz), 5.03 (2H, t, J = 6.4 Hz), 4.73 (2H, d, J = 4.4 Hz), 4.63-4.70 (1H, m), 4.56 (2H, t, J = 6.0 Hz), 4.36 (1H, brs), 3.46 (3H, s); LCMS: 100%, MS (ESI); m/z 487.3 [M + H]+. |
| 413 | 1H NMR (DMSO-d6, 400 MHz); δ 8.17 (1H, d, J = 2.8 Hz), 8.02 (1H, s), 7.93 (1H, dd, J = 8.8, 2.8 Hz), 7.45-7.42 (3H, m), 7.23 (1H, d, J = 2.4 Hz), 7.09-7.06 (3H, m), 7.05-6.98 (m, 2H) 6.85 (1H, dd, J = 8.8, 2.8 Hz), 5.73 (1H, d, J = 2.4 Hz), 4.53 (2H, d, J = 6.0 Hz), 3.71 (3H, s), 3.46 (3H, s); LCMS: 100%, MS (ESI); m/z 460.3 [M + H]+. |
| 414 | pale yellow solid; 1H NMR (DMSO-d6, 400 MHz); δ 8.74 (2H, s), 8.03 (1H, s), 7.48-7.45 (m, 3H), 7.23 (1H, d, J = 1.6 Hz), 7.17 (2H, d, J = 8.4 Hz), 7.04-6.99 (2H, m), 6.86 (1H, dd, J = 8.8, 2.8 Hz), 5.74 (1H, d, J = 1.6 Hz), 4.56 (2H, d, J = 5.6 Hz) 3.73 (3H, s), 3.48 (3H, s); LCMS: 99.4%, MS (ESI); m/z 461.2 [M + H]+. |
| 415 | yellow powder; 1H NMR (DMSO-d6, 400 MHz); δ 11.48 (1H, s), 8.73 (2H, s), 7.92-7.91 (1H, m), 7.46 (2H, d, J = 8.4 Hz), 7.33 (1H, s), 7.16 (2H, d, J = 8.4 Hz), 7.02-6.07 (2H, m), 6.78-6.75 (1H, m), 5.55 (1H, s), 4.54 (2H, d, J = 5.2 Hz), 3.46 (s, 3H), 2.16 (s, 3H); LCMS: 95.5%, MS (ESI); m/z 461.2 [M + H]+. |
| 416 | pale yellow powder (amorphous); 1H-NMR (DMSO-d6, 400 MHz): δ 8.75 (2H, s), 6.86-6.97 (3H, m), 6.36 (1H, s), 6.29 (1H, d, J = 8.0 Hz), 6.22 (1H, t, J = 4.8 Hz), 4.56 (2H, brs), 4.44 (2H, d, J = 4.8 Hz), 3.36 (3H, s), 2.39 (6H, s); LCMS: 100%, MS (ESI); m/z 409.2 [M + H]+. |
| 417 | off-white powder (amorphous); 1H-NMR (DMSO-d6, 400 MHz): δ 8.74 (2H, s), 7.00 (1H, d, J = 8.8 Hz), 6.90 (2H, s), 6.29 (1H, t, J = 4.8 Hz), 6.19-6.25 (2H, m), 5.85 (1H, d, J = 7.2 Hz), 4.84 (2H, t, J = 6.4 Hz), 4.47-4.56 (1H, m), 4.44 (1H, d, J = 4.8 Hz), 4.39 (1H, t, J = 6.0 Hz), 3.37 (3H, s, D2O) added), 2.38 (6H, s); LCMS: 100%, MS (ESI): m/z 465.2 [M + H]+. |
| 418 | a white powder; 1H-NMR (DMSO-d6, 400 MHz): δ 8.73 (2H, s), 8.14 (2H, s), 6.94 (1H, d, J = 8.4 Hz), 6.90 (1H, t, J = 5.6 Hz), 6.25 (1H, d, J = 2.0 Hz), 6.22 (1H, dd, J = 8.4, 2.0 Hz), 5.84 (1H, d, J = 7.2 Hz), 4.85 (2H, t, J = 6.0 Hz), 4.49-4.54 (1H, m), 4.46 (1H, d, J = 6.0 Hz), 4.40 (2H, t, J = 6.0 Hz), 3.45 (3H, s), 2.01 (6H, s); LCMS: 96.9%, MS (ESI): m/z 465.2 [M + H]+. |
| 419 | white powder; 1H-NMR (DMSO-d6, 400 MHz): δ 8.43 (1H, d, J = 9.2 Hz), 7.98 (1H, d, J = 8.4 Hz), 7.68 (1H, d, J = 2.4 Hz), 7.51 (1H, dd, J = 8.4, 2.0 Hz), 7.47 (2H, d, J = 8.4 Hz), 7.28 (1H, d, J = 8.8 Hz), 7.20 (2H, d, J = 8.8 Hz), 6.93 (1H, t, J = 6.0 Hz), 6.88 (1H, d, J = 8.0 Hz), 6.38 (1H, d, J = 2.0 Hz), 6.27 (1H, d, J = 8.4, 2.0 Hz), 4.50-4.55 (4H, m), 3.43 (3H, s); LCMS: 100%, MS (ESI): m/z 430.1 [M + H]+. |
| 420 | white powder; 1H-NMR (DMSO-d6, 400 MHz): δ 8.43 (1H, d, J = 8.8 Hz), 7.98 (1H, d, J = 8.4 Hz), 7.67 (1H, d, J = 2.0 Hz), 7.51 (1H, dd, J = 8.4, 2.0 Hz), 7.46 (2H, d, J = 8.8 Hz), 7.28 (1H, d, J = 8.8 Hz), 7.19 (2H, d, J = 8.4 Hz), 6.93-7.02 (2H, m), 6.26 (1H, d, J = 2.0 Hz), 6.22 (1H, dd, J = 8.4, 2.0 Hz), 5.84 (1H, d, J = 7.2 Hz), 4.85 (2H, t, J = 6.4 Hz), 4.56 (2H, d, J = 6.0 Hz), 4.46-4.54 (1H, m), 4.40 (2H, t, J = 5.8 Hz), 3.46 (3H, s); LCMS: 99.8%, MS (ESI): m/z 486.2 [M + H]+. |

-continued

| | |
|---|---|
| 421 | white amorphous; 1H-NMR (DMSO-d6, 400 MHz): δ 8.47 (1H, d, J = 9.2 Hz), 7.94 (1H, dd, J = 8.0, 1.2 Hz), 7.85 (1H, dd, J = 8.0, 1.2 Hz), 7.43-7.50 (3H, m), 7.29-7.33 (3H, m), 6.93 (1H, brs) 6.88 (1H, d, J = 8.0 Hz), 6.37 (1H, d, J = 2.0 Hz), 6.27 (1H, dd, J = 8.0, 2.0 Hz), 4.50-4.65 (4H, m), 3.43 (3H, s); LCMS: 100%, MS (ESI): m/z 430.1 [M + H]+. |
| 422 | white amorphous; 1H-NMR (DMSO-d6, 400 MHz): δ 8.47 (1H, d, J = 9.2 Hz), 7.94 (1H, dd, J = 8.0, 1.2 Hz), 7.85 (1H, dd, J = 7.6, 1.2 Hz), 7.42-7.51 (3H, m), 7.27-7.34 (3H, m), 6.91-7.00 (2H, m), 6.26 (1H, d, J = 2.0 Hz), 6.22 (1H, dd, J = 8.0, 2.0 Hz), 5.83 (1H, d, J = 7.6 Hz), 4.84 (2H, t, J = 6.0 Hz), 4.57 (2H, d, J = 5.6 Hz), 4.47-4.55 (1H, m), 4.40 (2H, t, J = 6.0 Hz), 3.46 (3H, s); LCMS: 100%, MS (ESI): m/z 486.2 [M + H]+. |
| 423 | white solid; mp 138.9-140.8° C.; 1H-NMR (DMSO-d6, 400 MHz): δ 7.61 (1H, d, J = 2.0 Hz), 7.47 (2H, d, J = 8.8 Hz), 7.29-7.40 (3H, m), 7.12 (1H, dd, J = 8.8, 2.0 Hz), 6.90-7.02 (2H, m), 6.25 (1H, d, J = 2.0 Hz), 6.21 (1H, dd, J = 8.4, 2.4 Hz), 5.84 (1H, d, J = 7.2 Hz), 4.84 (2H, t, J = 6.4 Hz), 4.46-4.59 (3H, m), 4.40 (2H, t, J = 6.0 Hz), 3.71 (3H, s), 3.45 (3H, s); LCMS: 98.5%, MS (ESI): m/z 489.2 [M + H]+. |
| 424 | off-white powder; 1H-NMR (DMSO-d6, 400 MHz): δ 8.58 (1H, d, J = 8.8 Hz), 7.58-7.67 (3H, m), 7.48 (2H, d, J = 8.4 Hz), 7.40 (1H, d, J = 8.8 Hz), 7.21 (2H, d, J = 8.4 Hz), 6.93 (1H, t, J = 6.0 Hz), 6.88 (1H, d, J = 8.0 Hz), 6.38 (1H, d, J = 1.6 Hz), 6.28 (1H, dd, J = 8.0, 2.0 Hz), 4.49-4.60 (4H, m), 3.43 (3H, s); LCMS: 95.9%, MS (ESI): m/z 430.1 [M + H]+. |
| 425 | white solid; mp: 102.3-107.3° C.; 1H-NMR (DMSO-d6, 400 MHz): δ 8.43 (1H, d, J = 8.8 Hz), 7.98 (1H, d, J = 8.4 Hz), 7.67 (1H, d, J = 2.0 Hz), 7.51 (1H, dd, J = 8.4, 2.0 Hz), 7.46 (2H, d, J = 8.8 Hz), 7.28 (1H, d, J = 8.8 Hz), 7.19 (2H, d, J = 8.4 Hz), 6.93-7.02 (2H, m), 6.26 (1H, d, J = 2.0 Hz), 6.22 (1H, dd, J = 8.4, 2.0 Hz), 5.84 (1H, d, J = 7.2 Hz), 4.85 (2H, t, J = 6.4 Hz), 4.56 (2H, d, J = 6.0 Hz), 4.46-4.54 (1H, m), 4.40 (2H, t, J = 6.0 Hz), 3.46 (3H, s); LCMS: 99.8%, MS (ESI): m/z 486.2 [M + H]+. |
| 426 | white powder; 1H-NMR (DMSO-d6, 400 MHz): δ 8.90 (1H, s), 8.15 (1H, s), 7.74-7.77 (2H, m), 7.49 (2H, d, J = 8.8 Hz), 7.27 (2H, dd, J = 6.8, 2.0 Hz), 6.95 (3H, t, J = 5.6 Hz), 6.87 (1H, d, J = 8.0 Hz), 6.37 (1H, d, J = 1.6 Hz), 6.27 (1H, dd, J = 8.4, 2.0 Hz), 4.45-4.70 (4H, m), 3.43 (3H, s); LCMS: 100%, MS (ESI): m/z 431.1 [M + H]+. |
| 427 | pale yellow powder; 1H-NMR (DMSO-d6, 400 MHz): δ 8.90 (1H, s), 8.15 (1H, s), 7.74 (2H, s), 7.49 (2H, d, J = 8.4 Hz), 7.27 (2H, dd, J = 8.8 Hz), 6.99 (1H, t, J = 6.4 Hz), 6.95 (1H, d, J = 8.4 Hz), 6.26 (1H, d, J = 2.0 Hz), 6.22 (1H, dd, J = 8.4, 2.0 Hz), 5.83 (1H, d, J = 7.2 Hz), 4.84 (2H, t, J = 6.4 Hz), 4.45-4.70 (3H, m), 4.40 (2H, t, J = 6.0 Hz), 3.46 (3H, s); LCMS: 100%, MS (ESI): m/z 487.2 [M + H]+. |
| 428 | white powder; 1H-NMR (DMSO-d6, 400 MHz): δ 7.61 (1H, d, J = 2.0 Hz), 7.48 (2H, d, J = 8.4 Hz), 7.30-7.40 (3H, m), 7.12 (1H, dd, J = 8.0, 2.0 Hz), 6.93 (1H, t, J = 6.0 Hz), 6.88 (1H, d, J = 8.0 Hz), 6.37 (1H, d, J = 1.6 Hz), 6.27 (1H, dd, J = 8.4, 2.4 Hz), 4.56 (1H, brs), 4.53 (2H, d, J = 5.6 Hz), 3.71 (3H, s), 3.42 (3H, s); LCMS: 100%, MS (ESI): m/z 433.2 [M + H]+ |
| 429 | white powder; 1H-NMR (DMSO-d6, 400 MHz): δ 13.10 (1H, brs), 9.39 (1H, t, J = 5.2 Hz), 8.88 (1H, s), 8.74 (2H, s), 7.78 (1H, d, J = 2.0 Hz), 7.53 (2H, d, J = 8.4 Hz), 7.21-7.31 (3H, m), 7.08 (1H, d, J = 8.4 Hz), 5.94 (2H, brs), 4.70 (2H, d, J = 6.0 Hz), 3.63 (3H, s); LCMS: 100%, MS (ESI): m/z 424.2 [M + H]+. |
| 430 | pale yellow powder; 1H-NMR (DMSO-d6, 400 MHz): δ 8.80 (2H, s), 7.12-7.21 (2H, m), 6.91 (1H, d, J = 8.0 Hz), 6.64 (1H, t, J = 5.2 Hz), 6.36 (1H, d, J = 2.0 Hz), 6.29 (1H, dd, J = 8.4, 2.0 Hz), 4.57 (2H, brs), 4.51 (2H, d, J = 4.8 Hz); LCMS: 97.4%, MS (ESI): m/z 417.1 [M + H]+. |
| 431 | white powder; 1H-NMR (DMSO-d6, 400 MHz): δ 8.80 (2H, s), 7.17 (2H, d, J = 8.4 Hz), 6.99 (1H, d, J = 8.8 Hz), 6.70 (1H, t, J = 5.6 Hz), 6.20-6.25 (2H, m), 5.86 (1H, d, J = 7.2 Hz), 4.84 (2H, t, J = 6.4 Hz), 4.48-4.55 (3H, m), 4.40 (2H, t, J = 6.0 Hz), 3.39 (3H, s); LCMS: 100%, MS (ESI): m/z 473.1 [M + H]+. |
| 432 | white powder; 1H-NMR (DMSO-d6, 400 MHz): δ 8.80 (2H, s), 7.70 (1H, s), 7.59 (1H, s), 7.02 (1H, t, J = 6.0 Hz), 6.86 (1H, d, J = 8.0 Hz), 6.39 (1H, d, J = 2.0 Hz), 6.28 (1H, dd, J = 8.0, 2.0 Hz), 4.50-4.66 (4H, m), 3.46 (3H, s); LCMS: 97.1%, MS (ESI): m/z 449.0 [M + H]+. |
| 433 | white powder; 1H-NMR (DMSO-d6, 400 MHz): δ 8.80 (2H, s), 7.70 (1H, s), 7.58 (1H, s), 7.08 (1H, t, J = 6.0 Hz), 6.94 (1H, d, J = 8.4 Hz), 6.28 (1H, d, J = 2.0 Hz), 6.23 (1H, dd, J = 8.0, 2.0 Hz), 5.88 (1H, d, J = 6.8 Hz), 4.85 (2H, t, J = 6.4 Hz), 4.57 (2H, d, J = 6.0 Hz), 4.46-4.54 (1H, m), 4.40 (2H, t, J = 6.0 Hz), 3.50 (3H, s); LCMS: 100%, MS (ESI): m/z 507.0 [M + H]+. |
| 434 | off-white powder; 1H-NMR (CDCl3, 400 MHz): δ 9.67 (1H, s), 7.71-7.80 (2H, m), 7.49-7.58 (3H, m), 7.29-7.33 (2H, m), 6.57 (1H, dd, J = 8.4, 2.0 Hz), 6.49 (1H, d, J = 2.0 Hz), 4.76 (2H, s), 4.63 (1H, brs), 3.48 (3H, s); LCMS: 97.5%, MS (ESI): m/z 431.2 [M + H] |

| | |
|---|---|
| 435 | yellow powder; 1H-NMR (DMSO-d6, 400 MHz): δ 9.68 (1H, s), 7.88 (1H, t, J = 8.0 Hz), 7.65-7.72 (2H, m), 7.47 (2H, d, J = 8.4 Hz), 7.22 (2H, d, J = 8.4 Hz), 6.98 (1H, brs), 6.95 (1H, d, J = 8.4 Hz), 6.25 (1H, s), 6.20 (1H, dd, J = 8.4, 2.0 Hz), 5.84 (1H, d, J = 6.8 Hz), 4.84 (2H, t, J = 6.4 Hz), 4.46-4.58 (3H, m), 4.39 (2H, t, J = 6.0 Hz), 3.44 (3H, s); LCMS: 99.1%, MS (ESI): m/z 487.2 [M + H]+. |
| 436 | yellow powder; 1H-NMR (DMSO-d6, 400 MHz): δ 9.58 (1H, s), 8.08-8.17 (2H, m), 7.59 (1H, t, J = 8.0 Hz), 7.47 (2H, d, J = 8.4 Hz), 7.27 (2H, d, J = 8.8 Hz), 6.90 (1H, t, J = 6.0 Hz), 6.88 (1H, d, J = 8.0 Hz), 6.37 (1H, d, J = 1.6 Hz), 6.26 (1H, dd, J = 8.0, 2.0 Hz), 4.47-4.61 (4H, m), 3.43 (3H, s); LCMS: 99.1%, MS (ESI): m/z 431.1 [M + H]+. |
| 437 | yellow powder; 1H-NMR (DMSO-d6, 400 MHz): δ 9.57 (1H, s), 8.06-8.19 (2H, m), 7.59 (1H, t, J = 8.0 Hz), 7.47 (2H, d, J = 8.4 Hz), 7.27 (2H, d, J = 8.4 Hz), 7.02-7.23 (1H, brs), 6.97 (1H, d, J = 8.0 Hz), 6.28 (1H, s), 6.24 (1H, d, J = 8.4 Hz), 5.89 (1H, d, J = 6.8 Hz), 4.85 (2H, t, J = 6.4 Hz), 4.46-4.62 (3H, m), 4.40 (2H, t, J = 6.0 Hz), 3.47 (3H, s); LCMS: 97.8%, MS (ESI): m/z 487.2 [M + H]+. |
| 438 | pale green powder; 1H-NMR (DMSO-d6, 400 MHz): δ 8.38 (1H, d, J = 8.8 Hz), 8.14 (1H, d, J = 2.0 Hz), 7.96 (1H, d, J = 6.0 Hz), 7.74 (1H, d, J = 9.2, 2.0 Hz), 7.40-7.55 (3H, m), 7.21 (2H, d, J = 8.4 Hz), 6.94 (1H, brs), 6.89 (1H, d, J = 8.0 Hz), 6.38 (1H, d, J = 2.0 Hz), 6.28 (1H, d, J = 8.4, 2.0 Hz), 4.42-4.69 (4H, m), 3.45 (3H, s); LCMS: 100%, MS (ESI): m/z 430.1 [M + H]+. |
| 439 | off-white powder; 1H-NMR (DMSO-d6, 400 MHz): δ 8.36 (1H, d, J = 8.8 Hz), 8.12 (1H, d, J = 2.0 Hz), 7.93 (1H, d, J = 5.6 Hz), 7.71 (1H, dd, J = 8.8, 2.0 Hz), 7.47 (1H, d, J = 6.0 Hz), 7.45 (2H, d, J = 8.4 Hz), 7.18 (2H, d, J = 8.4 Hz), 6.96 (1H, brs), 6.94 (1H, d, J = 8.0 Hz), 6.24 (1H, d, J = 1.6 Hz), 6.20 (1H, dd, J = 8.0, 2.0 Hz), 5.82 (1H, d, J = 7.6 Hz), 4.83 (2H, t, J = 6.4 Hz), 4.43-4.56 (3H, m), 4.38 (2H, t, J = 6.0 Hz), 3.44 (3H, s); LCMS: 99.1%, MS (ESI): m/z 486.2 [M + H]+. |
| 440 | off-white powder; 1H-NMR (DMSO-d6, 400 MHz): δ 9.55 (1H, s), 8.16 (1H, d, J = 8.4 Hz), 7.83 (1H, s), 7.63 (1H, dd, J = 8.8, 2.0 Hz), 7.47 (2H, d, J = 8.0 Hz), 7.22 (2H, d, J = 8.4 Hz), 6.98 (1H, brs), 6.89 (1H, d, J = 8.0 Hz), 6.38 (1H, d, J = 1.6 Hz), 6.28 (1H, dd, J = 8.0, 1.6 Hz), 4.67 (2H, brs), 4.55 (2H, d, J = 5.6 Hz), 3.43 (3H, s); LCMS: 98.1%, MS (ESI): m/z 431.2 [M + H]+. |
| 441 | white powder; 1H-NMR (DMSO-d6, 400 MHz): δ 13.90 (1H, brs), 10.08 (1H, s), 9.80 (1H, brs), 8.74 (2H, s), 7.40-7.65 (8H, m), 7.24 (2H, d, J = 8.8 Hz), 7.09-7.18 (1H, m), 4.79 (2H, d, J = 6.0 Hz), 3.73 (3H, s); LCMS: 100%, MS (ESI): m/z 423.2 [M + H]+. |
| 442 | off-white powder; 1H-NMR (CDCl3, 400 MHz): δ 8.48 (1H, d, J = 7.6 Hz), 7.95 (1H, s), 7.49 (2H, d, J = 8.8 Hz), 7.14 (2H, d, J = 8.8 Hz), 7.02 (1H, brs), 6.89 (1H, d, J = 8.0 Hz), 6.84 (1H, dd, J = 7.6, 2.4 Hz), 6.74 (1H, d, J = 2.0 Hz), 6.39 (1H, d, J = 1.6 Hz), 6.29 (1H, dd, J = 8.0, 1.6 Hz), 4.54 (2H, d, J = 5.6 Hz), 3.43 (3H, s); LCMS: 98.7%, MS (ESI): m/z 419.1 [M + H]+. |
| 443 | white powder (hydroscopic); 1H-NMR (DMSO-d6, 400 MHz): δ 13.11 (1H, s), 9.40 (1H, t, J = 6.0 Hz), 8.74 (2H, s), 7.54 (2H, d, J = 8.4 Hz), 7.33-7.48 (4H, m), 7.12-7.28 (4H, m), 6.61 (1H, s), 6.54 (1H, d, J = 8.4 Hz), 4.70 (2H, d, J = 6.0 Hz), 4.40-4.50 (2H, m), 4.28-4.39 (1H, m), 3.77-3.86 (2H, m), 3.63 (3H, s); LCMS: 99.4%, MS (ESI): m/z 478.3 [M + H]+. |
| 444 | yellow powder; 1H NMR (DMSO-d6, 400 MHz): δ 9.55 (1H, s), 8.16 (1H, d, J = 8.8 Hz), 7.82 (1H, d, J = 1.6 Hz), 7.63 (1H, dd, J = 8.4, 2.0 Hz), 7.46 (2H, d, J = 8.4 Hz), 7.21 (2H, d, J = 8.4 Hz), 7.04 (1H, brs), 6.96 (1H, d, J = 8.0 Hz), 6.26 (1H, d, J = 1.6 Hz), 6.20-6.25 (1H, dd, J = 8.0, 2.0 Hz), 5.86 (1H, d, J = 6.8 Hz), 4.85 (2H, t, J = 6.0 Hz), 4.56 (2H, d, J = 6.0 Hz), 4.47-4.54 (1H, m), 4.40 (2H, d, J = 6.0 Hz), 3.46 (3H, s); LCMS: 96.9%, MS (ESI): m/z 487.2 [M + H]+. |
| 445 | white powder; 1H-NMR (DMSO-d6, 400 MHz): δ 8.29 (1H, d, J = 2.4 Hz), 8.21 (1H, d, J = 2.4 Hz), 7.99 (1H, d, J = 3.6 Hz), 7.76 (2H, d, J = 8.4 Hz), 7.55 (2H, d, J = 8.8 Hz), 6.94 (1H, t, J = 6.0 Hz), 6.86 (1H, d, J = 8.0 Hz), 6.71 (1H, d, J = 8.0 Hz), 6.37 (1H, d, J = 1.6 Hz), 6.26 (1H, d, J = 8.4, 2.0 Hz), 4.40-4.60 (4H, m), 3.43 (3H, s); LCMS: 99.3%, MS (ESI): m/z 430.1 [M + H]+. |
| 446 | white powder; 1H-NMR (DMSO-d6, 400 MHz): δ 8.28 (1H, d, J = 2.4 Hz), 8.21 (1H, d, J = 2.4 Hz), 7.99 (1H, d, J = 4.0 Hz), 7.76 (2H, d, J = 8.4 Hz), 7.55 (2H, d, J = 8.4 Hz), 7.00 (1H, t, J = 6.0 Hz), 6.94 (1H, d, J = 8.4 Hz), 6.70 (1H, d, J = 3.6 Hz), 6.26 (1H, d, J = 2.0 Hz), 6.21 (1H, dd, J = 8.4, 2.0 Hz), 5.84 (1H, d, J = 7.2 Hz), 4.84 (2H, t, J = 6.8 Hz), 4.57 (2H, d, J = 6.0 Hz), 4.55-4.60 (1H, m), 4.39 (2H, d, J = 6.0 Hz), 3.46 (3H, s); LCMS: 98.3%, MS (ESI): m/z 459.3 [M + H]+. |
| 447 | pale yellow solid; 1H-NMR (DMSO-d6, 400 MHz): δ 8.72 (2H, s), 8.68 (1H, brs), 8.07 (1H, dd, J = 4.8, 1.2 Hz), 7.54 (1H, d, J = 2.0 Hz), 7.40-7.49 (3H, m), 7.11-7.20 (3H, m), 7.07 (1H, d, J = 8.0 Hz), 7.00 (1H, dd, J = 8.4, 2.0 Hz), 6.72 (1H, d, J = 8.4 Hz), 6.61 (1H, dd, J = 6.8, 6.0 Hz), 4.56 (2H, d, J = 6.0 Hz), 3.50 (3H, s); LCMS: 100%, MS (ESI): m/z 458.2 [M + H]+. |

| | |
|---|---|
| 448 | white powder; 1H-NMR (DMSO-d6, 400 MHz): δ 8.69 (1H, s), 8.17 (1H, d, J = 2.8 Hz), 8.08 (1H, dd, J = 4.8, 2.0 Hz), 7.94 (1H, dd, J = 8.8, 2.8 Hz), 7.55 (1H, d, J = 2.0 Hz), 7.42-7.49 (3H, m), 7.15 (1H, t, J = 6.0 Hz), 7.06-7.11 (4H, m), 7.01 (1H, dd, J = 8.1, 2.0 Hz), 6.73 (1H, d, J = 8.4 Hz), 6.62 (1H, dd, J = 6.4, 5.2 Hz), 4.57 (2H, d, J = 6.0 Hz), 3.51 (3H, s); LCMS: 99.3%, MS (ESI): m/z 457.2 [M + H]+. |
| 449 | white powder; 1H-NMR (DMSO-d6, 400 MHz): δ 11.80 (1H, brs), 8.17 (1H, d, J = 2.8 Hz), 8.02 (1H, brs), 7.93 (1H, dd, J = 8.8, 2.8 Hz), 7.50 (1H, d, J = 2.4 Hz), 7.44 (2H, d, J = 8.4 Hz), 7.33 (1H, s), 7.06-7.10 (3H, m), 6.97-7.03 (2H, m), 6.78 (1H, dd, J = 8.4, 2.0 Hz), 5.78 (1H, d, J = 2.4 Hz), 4.54 (2H, d, J = 5.6 Hz), 3.46 (3H, s); LCMS: 97.2%, MS (ESI): m/z 446.1 [M + H]+. |
| 450 | pale yellow solid; 1H-NMR (DMSO-d6, 400 MHz): δ 11.81 (1H, brs), 8.72 (2H, s), 8.02 (1H, s), 7.48 (1H, s), 7.45 (2H, d, J = 8.4 Hz), 7.33 (1H, s), 7.14 (2H, d, J = 8.4 Hz), 7.01 (1H, t, J = 6.0 Hz), 6.98 (1H, d, J = 8.4 Hz), 6.77 (1H, d, J = 8.8 Hz), 5.77 (1H, d, J = 2.0 Hz), 4.53 (2H, d, J = 6.0 Hz), 3.45 (3H, s); LCMS: 100%, MS (ESI): m/z 447.2 [M + H]+. |
| 451 | off-white solid; 1H-NMR (CDCl3, 400 MHz): δ 8.61 (1H, d, J = 2.8 Hz), 8.34 (1H, d, J = 8.8 Hz), 8.09 (1H, dd, J = 8.8, 2.4 Hz), 8.02 (1H, d, J = 3.2 Hz), 7.83 (1H, d, J = 8.8 Hz), 7.34 (1H, d, J = 8.4 Hz), 6.85-6.95 (2H, m), 6.76 (1H, d, J = 3.6 Hz), 6.38 (1H, d, J = 1.6 Hz), 6.28 (1H, dd, J = 8.4, 2.0 Hz), 4.41-4.72 (4H, m), 3.43 (3H, s); LCMS: 99.6%, MS (ESI): m/z 403.2 [M + H]+. |
| 452 | pale yellow powder; 1H-NMR (DMSO-d6, 400 MHz): δ 8.71 (2H, s), 7.46 (2H, d, J = 8.4 Hz), 7.12 (2H, d, J = 8.4 Hz), 6.80 (1H, d, J = 8.0 Hz), 6.60 (1H, d, J = 8.4 Hz), 6.32 (1H, d, J = 1.6 Hz), 6.22 (1H, dd, J = 8.4, 2.0 Hz), 4.79 (1H, q, J = 8.0 Hz), 4.50 (2H, brs), 3.43 (3H, s), 1.65-1.96 (2H, m), 0.93 (3H, t, J = 7.2 Hz); LCMS: 100%, MS (ESI): m/z 409.2 [M + H]+. |
| 453 | pale yellow powder; 1H-NMR (DMSO-d6, 400 MHz): δ 8.73 (2H, s), 7.49 (2H, d, J = 8.8 Hz), 7.15 (2H, d, J = 8.4 Hz), 6.91 (1H, d, J = 8.4 Hz), 6.74 (1H, brs), 6.24 (1H, d, J = 1.6 Hz), 6.20 (1H, dd, J = 8.4, 2.0 Hz), 5.85 (1H, d, J = 6.8 Hz), 4.75-4.91 (3H, m), 4.45-4.61 (1H, m), 4.39 (2H, td, J = 6.0, 2.4 Hz), 3.49 (3H, s), 1.69-2.01 (2H, m), 0.95 (3H, t, J = 7.2 Hz); LCMS: 98.7%, MS (ESI): m/z 465.3 [M + H]+. |
| 454 | white powder; 1H-NMR (DMSO-d6, 400 MHz): δ 8.39 (1H, s), 7.44 (2H, d, J = 8.4 Hz), 7.16 (2H, d, J = 8.8 Hz), 6.87-6.94 (1H, m), 6.85 (1H, d, J = 8.0 Hz), 6.36 (1H, d, J = 2.0 Hz), 6.26 (1H, dd, J = 8.4, 2.0 Hz), 4.55 (2H, brs), 4.51 (2H, d, J = 5.6 Hz), 3.97 (3H, s), 3.41 (3H, s); LCMS: 100%, MS (ESI): m/z 411.1 [M + H]+. |
| 455 | off-white powder; 1H-NMR (DMSO-d6, 400 MHz): δ 8.48 (1H, d, J = 7.6 Hz), 7.95 (1H, s), 7.48 (2H, d, J = 8.4 Hz), 7.12 (2H, d, J = 8.4 Hz), 6.91-6.98 (2H, m), 6.83 (1H, dd, J = 7.6, 2.4 Hz), 6.73 (1H, d, J = 2.4 Hz), 6.20-6.30 (2H, m), 5.83 (1H, d, J = 6.8 Hz), 4.85 (2H, t, J = 6.4 Hz), 4.40 (2H, t, J = 6.0 Hz), 4.49-4.60 (3H, m), 3.45 (3H, s); LCMS: 97.2%, MS (ESI): m/z 475.0 [M + H]+. |
| 456 | white powder; 1H-NMR (DMSO-d6, 400 MHz): δ 8.72 (2H, s), 7.45 (2H, d, J = 8.8 Hz), 7.17 (2H, d, J = 8.8 Hz), 6.90 (1H, t, J = 6.0 Hz), 6.86 (1H, d, J = 8.0 Hz), 6.36 (1 H, d, J = 2.0 Hz), 6.26 (1 H, dd, J = 8.4, 2.0 Hz), 4.50-4.53 (4H, m), 3.41 (3H, s), 2.98 (6H, s); LCMS: 100%, MS (ESI): m/z 418.3 [M + H]+. |
| 457 | off-white powder; 1H-NMR (DMSO-d6, 400 MHz): δ 8.61 (1H, d, J = 2.4 Hz), 8.33 (1H, dd, J = 8.8 Hz), 8.08 (1H, dd, J = 8.8, 2.4 Hz), 8.01 (1H, d, J = 3.2 Hz), 7.82 (1H, d, J = 8.8 Hz), 7.64 (1H, s), 7.33 (1H, d, J = 8.4 Hz), 6.83-6.97 (2H, m), 6.75 (1H, d, J = 3.2 Hz), 6.25 (1H, s), 6.21 (1H, d, J = 8.4 Hz), 5.82 (1H, d, J = 7.6 Hz), 4.85 (2H, t, J = 6.4 Hz), 4.62 (2H, d, J = 6.0 Hz), 4.46-4.57 (1H, m), 4.40 (2H, t, J = 6.0 Hz), 3.45 (3H, s); LCMS: 97.8%, MS (ESI): m/z 459.1 [M + H]+. |
| 458 | off-white powder; 1H-NMR (DMSO-d6, 400 MHz): δ 9.80 (1H, s), 8.51 (2H, s), 7.61 (2H, d, J = 8.4 Hz), 7.31 (2H, d, J = 8.4 Hz), 6.86 (1H, d, J = 8.0 Hz), 6.77 (1H, t, J = 5.8 Hz), 6.36 (1H, d, J = 1.6 Hz), 6.26 (1H, dd, J = 8.4, 2.0 Hz), 4.56 (2H, brs), 4.44 (2H, d, J = 6.0 Hz), 3.40 (3H, s); LCMS: 98.5%, MS (ESI): 380.1 [M + H]+. |
| 459 | white powder; 1H-NMR (DMSO-d6, 400 MHz): δ 8.39 (1H, s), 7.43 (2H, d, J = 8.4 Hz), 7.15 (2H, d, J = 8.4 Hz), 6.90-6.97 (2H, m), 6.25 (1H, d, J = 2.0 Hz), 6.21 (1H, dd, J = 8.4, 2.0 Hz), 5.82 (1H, d, J = 7.2 Hz), 4.84 (2H, t, J = 6.4 Hz), 4.45-4.56 (3H, m), 4.39 (2H, t, J = 6.0 Hz), 3.97 (3H, s), 3.44 (3H, s); LCMS: 99.5%, MS (ESI): m/z 467.1 [M + H]+. |
| 460 | off-white powder; 1H-NMR (DMSO-d6, 400 MHz): δ 8.95 (2H, s), 7.74-7.77 (2H, m), 7.54-7.59 (2H, m), 7.46 (2H, d, J = 8.8 Hz), 7.17 (2H, d, J = 8.8 Hz), 6.90 (1H, t, J = 5.8 Hz), 6.87 (1H, d, J = 8.0 Hz), 6.37 (1H, d, J = 2.0 Hz), 6.27 (1H, dd, J = 8.4, 2.0 Hz), 4.47-4.58 (4H, m), 3.42 (3H, s); LCMS: 100%, MS (ESI): m/z 457.1 [M + H]+. |

| | |
|---|---|
| 461 | yellow powder; 1H-NMR (DMSO-d6, 400 MHz): δ 9.80 (1H, brs), 8.51 (2H, s), 7.61 (2H, d, J = 8.8 Hz), 7.30 (2H, d, J = 8.8 Hz), 6.93 (1H, d, J = 8.4 Hz), 6.81 (1H, t, J = 5.8 Hz), 6.24 (1H, d, J = 1.6 Hz), 6.20 (1H, dd, J = 8.4, 1.6 Hz), 5.82 (1H, d, J = 7.2 Hz), 4.84 (2H, t, J = 6.4 Hz), 4.48-4.56 (1H, m), 4.45 (2H, d, J = 6.0 Hz), 4.36-4.42 (1H, t, J = 5.8 Hz), 3.43 (3H, s); LCMS: 99.7%, MS (ESI): m/z 436.1 [M + H]+. |
| 462 | pale yellow powder; 1H-NMR (DMSO-d6, 400 MHz): δ 8.96 (1H, s), 8.65 (1H, brs), 7.47 (2H, d, J = 8.4 Hz), 7.18 (2H, d, J = 8.8 Hz), 6.92 (1H, brs), 6.88 (1H, d, J = 8.4 Hz), 6.37 (1H, d, J = 2.0 Hz), 6.27 (1H, dd, J = 8.0, 2.0 Hz), 4.50-4.70 (4H, m), 3.43 (3H, s), 2.80 (3H, d, J = 4.8 Hz); LCMS: 99.3%, MS (ESI): m/z 404.2 [M + H]+. |
| 463 | brown powder; 1H-NMR (DMSO-d6, 400 MHz): δ 8.40 (2H, s), 7.40 (2H, d, J = 8.4 Hz), 7.26 (2H, d, J = 8.4 Hz), 6.90 (1H, t, J = 5.8 Hz), 6.86 (1H, d, J = 8.4 Hz), 6.36 (1H, d, J = 1.6 Hz), 6.26 (1H, dd, J = 8.4, 1.6 Hz), 4.59 (2H, brs), 4.50 (2H, d, J = 5.6 Hz), 3.41 (6H, s); LCMS: 100%, MS (ESI): m/z 394.2 [M + H]+. |
| 464 | yellow powder; 1H-NMR (DMSO-d6, 400 MHz): δ 8.72 (2H, s), 7.90 (1H, d, J = 3.6 Hz), 7.59 (1H, s), 7.49 (1H, d, J = 1.6 Hz), 7.46 (2H, d, J = 8.8 Hz), 7.34 (1H, d, J = 6.8 Hz), 7.10-7.19 (4H, m), 7.05 (1H, d, J = 8.8 Hz), 6.57-6.62 (1H, m), 4.57 (2H, d, J = 5.6 Hz), 3.49 (3H, s), 2.22 (3H, s); LCMS: 96.4%, MS (ESI): m/z 472.2 [M + H]+. |
| 465 | pale yellow solid; 1H-NMR (DMSO-d6, 400 MHz): δ 8.74 (2H, s), 7.91 (1H, brs), 7.47 (2H, d, J = 8.4 Hz), 7.22 (1H, d, J = 2.0 Hz), 7.16 (2H, d, J = 8.8 Hz), 7.04 (1H, t, J = 6.0 Hz), 6.99 (1H, d, J = 8.4 Hz), 6.84 (1H, dd, J = 8.4, 2.0 Hz), 5.58 (1H, s), 4.55 (2H, d, J = 5.6 Hz), 3.60 (3H, s), 3.48 (3H, s), 2.19 (3H, s); LCMS: 98.3%, MS (ESI): m/z 475.3 [M + H]+. |
| 466 | off-white powder; 1H-NMR (DMSO-d6, 400 MHz): δ 11.48 (1H, brs), 8.17 (1H, d, J = 2.0 Hz), 7.90-7.95 (2H, m), 7.44 (2H, d, J = 8.8 Hz), 7.32-7.35 (1H, m), 7.04-7.15 (3H, m), 6.92-7.04 (2H, m), 6.77 (1H, d, J = 8.0 Hz), 5.55 (1H, s), 4.54 (2H, d, J = 6.0 Hz), 3.46 (3H, s), 2.16 (3H, s); LCMS: 100%, MS (ESI): m/z 460.3 [M + H]+. |
| 467 | off-white powder; 1H-NMR (DMSO-d6, 400 MHz): δ 11.48 (1H, s), 8.95 (2H, s), 7.92 (1H, s), 7.75 (2H, d, J = 8.4 Hz), 7.56 (2H, d, J = 8.4 Hz), 7.47 (2H, d, J = 8.4 Hz), 7.34 (1H, s), 7.17 (2H, d, J = 8.0 Hz), 7.01 (1H, t, J = 5.6 Hz), 6.98 (1H, d, J = 8.4 Hz), 6.77 (1H, d, J = 7.2 Hz), 5.55 (1H, s), 4.55 (2H, d, J = 5.6 Hz), 3.47 (3H, s), 2.16 (3H, s); LCMS: 100%, MS (ESI): m/z 537.1 [M + H]+. |
| 468 | pale yellow powder; 1H-NMR (DMSO-d6, 400 MHz): δ 8.74 (2H, s), 8.38 (1H, brs), 7.47 (2H, d, J = 8.8 Hz), 7.24 (1H, d, J = 2.0 Hz), 7.17 (2H, d, J = 8.4 Hz), 7.12 (1H, brs), 7.05 (2H, d, J = 8.4 Hz), 6.89 (1H, dd, J = 8.4, 2.0 Hz), 6.27 (1H, s), 4.57 (2H, d, J = 5.6 Hz), 3.85 (3H, s), 3.51 (3H, s); LCMS: 100%, MS (ESI): m/z 529.4 [M + H]+. |
| 469 | off-white powder; 1H-NMR (DMSO-d6, 400 MHz): δ 11.57 (1H, brs), 8.74 (2H, s), 7.94 (1H, brs), 7.35-7.51 (3H, m), 7.17 (2H, d, J = 8.4 Hz), 7.01 (1H, brs), 6.99 (1H, d, J = 8.4 Hz), 6.77 (1H, d, J = 8.8 Hz), 5.53 (1H, s), 4.56 (2H, d, J = 5.6 Hz), 3.46 (3H, s), 1.26 (9H, s); LCMS: 97.9%, MS (ESI): m/z 503.2 [M + H]+. |
| 470 | yellow solid; 1H-NMR (DMSO-d6, 400 MHz): δ 11.52 (1H, brs), 8.72 (2H, s), 8.06 (1H, brs), 7.93 (1H, brs), 7.40-7.53 (3H, m), 7.18 (2H, d, J = 8.4 Hz), 7.01 (1H, d, J = 8.4 Hz), 6.84 (1H, d, J = 8.0), 5.53 (1H, s), 4.51 (2H, d, J = 3.6 Hz), 2.15 (3H, s); LCMS: 95.9%, MS (ESI): m/z 447.2 [M + H]+. |
| 471 | yellow powder; 1H-NMR (DMSO-d6, 400 MHz): δ 11.48 (1H, brs), 8.40 (2H, s), 7.91 (1H, brs), 7.41 (2H, d, J = 8.4 Hz), 7.33 (1H, s), 7.26 (2H, d, J = 8.0 Hz), 6.93-7.05 (2H, m), 6.77 (1H, d, J = 7.2 Hz), 5.55 (1H, s), 4.53 (2H, d, J = 5.2 Hz), 3.46 (3H, s), 3.42 (3H, s), 2.16 (3H, s); LCMS: 97.7%, MS (ESI): m/z 474.2 [M + H]+. |
| 472 | off-white solid; 1H-NMR (DMSO-d6, 400 MHz): δ 8.72 (2H, s), 7.21-7.39 (3H, m), 7.08 (2H, d, J = 8.4 Hz), 6.84 (1H, d, J = 8.0 Hz), 6.37 (1H, brs), 6.26 (1H, d, J = 7.6 Hz), 4.55 (2H, brs), 3.43 (3H, s), 1.20-1.38 (4H, m); LCMS: 99.8%, MS (ESI): m/z 407.1 [M + H]+. |
| 473 | yellow powder; 1H-NMR (DMSO-d6, 400 MHz): δ 11.49 (1H, brs), 8.77 (2H, s), 7.95 (1H, brs), 7.60 (1H, d, J = 1.6 Hz), 7.46 (1H, dd, J = 8.4, 2.0 Hz), 7.32-7.42 (2H, m), 7.10 (1H, brs), 6.99 (1H, d, J = 8.4 Hz), 6.75-6.80 (1H, m), 5.55 (1H, s), 4.55 (2H, d, J = 4.8 Hz), 3.47 (3H, s), 2.16 (3H, s); LCMS: 100%, MS (ESI): m/z 495.2 [M + H]+. |
| 474 | off-white powder; 1H-NMR (DMSO-d6, 400 MHz): δ 11.42 (1H, brs), 8.72 (2H, s), 7.44 (2H, d, J = 8.8 Hz), 7.21-7.34 (2H, m), 7.14 (2H, d, J = 8.8 Hz), 7.02 (1H, brs), 6.95 (1H, d, J = 8.4 Hz), 6.76-6.88 (1H, m), 4.53 (2H, d, J = 5.6 Hz), 3.43 (3H, s), 2.08 (3H, s), 1.82 (3H, s); LCMS: 100%, MS (ESI): m/z 475.2 [M + H]+. |
| 475 | brown powder; 1H NMR (DMSO-d6): δ 12.78 (1H, brs), 8.73 (2H, s), 8.27 (1H, brs), 7.45 (2H, d, J = 8.4 Hz), 7.11-7.23 (3H, m), 7.07 (1H, d, J = 8.0 Hz), 6.85 (1H, brs), 6.66 (1H, d, J = 8.0 Hz), 6.08 (1H, s), 4.56 (2H, d, J = 6.0 Hz), 3.50 (3H, s); LCMS: 100%, MS (ESI): m/z 515.1 [M + H]+. |

| | |
|---|---|
| 476 | pale yellow powder; 1H-NMR (DMSO-d6, 400 MHz): δ 11.49 (1H, brs), 8.72 (2H, s), 7.91 (1H, brs), 7.43 (2H, d, J = 8.8 Hz), 7.37 (1H, s), 7.14 (2H, d, J = 8.4 Hz), 7.04 (1H, brs), 6.96 (1H, d, J = 8.4 Hz), 6.75 (1H, d, J = 8.0 Hz), 5.53 (1H, s), 4.54 (2H, d, J = 6.0 Hz), 3.96 (2H, q, J = 7.2 Hz), 2.14 (3H, s), 1.22 (3H, t, J = 6.8 Hz); LCMS: 100%, MS (ESI): m/z 475.2 [M + H]+. |
| 477 | off-white powder; 1H-NMR (DMSO-d6, 400 MHz): δ 11.46 (1H, brs), 8.72 (2H, s), 7.89 (1H, s), 7.48 (2H, d, J = 8.4 Hz), 7.29 (1H, s), 7.13 (2H, d, J = 8.4 Hz), 6.92 (1H, d, J = 8.4 Hz), 6.70-6.74 (2H, m), 5.54 (1H, s), 4.80-4.87 (1H, m), 3.48 (3H, s), 2.15 (3H, s), 1.76-1.94 (2H, m), 0.94 (3H, t, J = 7.2 Hz); LCMS: 100%, MS (ESI): m/z 489.2 [M + H]+. |
| 478 | red powder; 1H-NMR (DMSO-d6, 400 MHz): δ 11.49 (1H, brs), 8.72 (2H, s), 7.91 (1H, brs), 7.40 (1H, brs), 7.21-7.38 (3H, m), 7.08 (2H, d, J = 8.8 Hz), 6.95 (1H, d, J = 8.4 Hz), 6.75 (1H, d, J = 8.0 Hz), 5.55 (1H, s), 3.48 (3H, s), 2.16 (3H, s), 1.20-1.39 (4H, m); LCMS: 89.0%, MS (ESI): m/z 487.2 [M + H]+. |
| 479 | off-white powder; 1H-NMR (DMSO-d6): δ 11.48 (1H, brs), 9.09 (2H, s), 7.91 (1H, brs), 7.48 (2H, d, J = 8.8 Hz), 7.34 (1H, s), 7.21 (2H, d, J = 8.4 Hz), 7.03 (1H, t, J = 6.0 Hz), 6.97 (1H, d, J = 8.0 Hz), 6.77 (1H, d, J = 8.0 Hz), 5.55 (1H, s), 4.56 (2H, d, J = 6.0 Hz), 3.46 (3H, s), 2.16 (3H, s); LCMS: 100%, MS (ESI): m/z 495.2 [M + H]+. |
| 480 | off-white powder; 1H NMR (DMSO-d6): δ 8.74 (2H, s), 7.79 (1H, brs), 7.59 (1H, brs), 7.42-7.50 (3H, m), 7.21 (3H, d, J = 8.4 Hz), 6.94 (1H, d, J = 9.2 Hz), 5.76 (1H, d, J = 2.0 Hz), 4.59 (2H, d, J = 6.0 Hz), 3.70 (3H, s); LCMS: 99.0%, MS (ESI): m/z 465.1 [M + H]+. |
| 481 | white powder; 1H-NMR (DMSO-d6, 400 MHz): δ 12.02 (1H, brs), 8.76 (2H, s), 7.52 (1H, brs), 7.47 (2H, d, J = 8.8 Hz), 7.30 (1H, s), 7.17 (2H, d, J = 8.0 Hz), 7.07 (1H, brs), 7.00 (1H, d, J = 8.8 Hz), 6.94 (1H, d, J = 8.0 Hz), 4.56 (2H, d, J = 6.0 Hz), 3.46 (3H, s), 2.18 (3H, s); LCMS: 95.4%, MS (ESI): m/z 475.2 [M + H]+. From LCMS, the product contains 4.6% impurity of de-Cl of compound 1. |
| 482 | off-white powder; 1H-NMR (CDCl3, 400 MHz): δ 8.50 (2H, s), 7.52 (2H, d, J = 8.4 Hz), 7.37 (1H, d, J = 8.4 Hz), 7.20 (2H, d, J = 8.4 Hz), 7.07 (1H, s), 6.83 (1H, dd, J = 8.4, 1.6 Hz), 6.05 (1H, brs), 5.75 (1H, s), 4.73 (2H, s), 4.33 (1H, brs), 3.41 (3H, s), 2.28 (3H, s); LCMS: 98.0%, MS (ESI): m/z 511.1 [M + H]+. |
| 483 | white powder; 1H-NMR (DMSO-d6, 400 MHz): δ 12.25 (1H, brs), 8.95 (1H, s), 8.72 (2H, s), 8.11 (1H, s), 8.02 (1H, s), 7.55 (1H, s), 7.45 (2H, d, J = 8.4 Hz), 7.15 (2H, d, J = 8.8 Hz), 7.10 (1H, brs), 7.04 (1H, d, J = 8.8 Hz), 6.94 (1H, d, J = 8.4 Hz), 4.55 (2H, d, J = 5.6 Hz), 3.49 (3H, s), 2.64-2.81 (1H, m), 0.60-0.76 (2H, m), 0.41-0.53 (2H, m); LCMS: 100%, MS (ESI): m/z 530.4 [M + H]+. |
| 484 | off-white powder; 1H-NMR (DMSO-d6, 400 MHz): δ 11.43 (1H, brs), 10.60 (0.6H, brs), 10.48 (0.4H, brs), 8.74 (2H, s), 7.83 (0.6H, brs), 7.70 (0.4H, brs), 7.31-7.48 (2.6H, m), 7.10-7.26 (2.4H, m), 6.83-7.01 (2H, m), 6.62-6.80 (1H, m), 5.53 (1H, s), 4.41-4.55 (2H, m), 2.16 (3H, s); LCMS: 99.6%, MS (ESI): m/z 447.1 [M + H]+. |
| 485 | off-white powder; 1H-NMR (DMSO-d6, 400 MHz): δ 11.44 (1H, brs), 10.33-10.78 (1H, m), 8.74 (2H, s), 7.65-7.90 (1H, m), 7.44 (2H, d, J = 8.4 Hz), 7.21-7.40 (1H, m), 7.16 (2H, d, J = 8.8 Hz), 6.81-7.00 (1H, m), 6.73 (1H, d, J = 7.2 Hz), 5.53 (1H, s), 4.48 (2H, d, J = 5.6 Hz), 2.16 (3H, s); LCMS: 99.3%, MS (ESI): m/z 447.2 [M + H]+. |
| 486 | off-white powder; 1H NMR (DMSO-d6): δ 11.48 (1H, brs), 9.80 (1H, brs), 8.51 (2H, s), 7.91 (1H, brs), 7.62 (2H, d, J = 8.8 Hz), 7.25-7.39 (3H, m), 6.98 (1H, d, J = 8.4 Hz), 6.90 (1H, brs), 6.76 (1H, d, J = 7.2 Hz), 5.55 (1H, s), 4.47 (2H, d, J = 5.6 Hz), 3.44 (3H, s), 2.16 (3H, s); LCMS: 95.9%, MS (ESI): m/z 460.2 [M + H]+. |
| 487 | off-white powder; 1H NMR (DMSO-d6): δ 8.73 (2H, s), 7.56 (1H, brs), 7.46 (2H, d, J = 8.4 Hz), 7.37-7.43 (2H, m), 7.23 (1H, t, J = 6.0 Hz), 7.17 (2H, d, J = 8.4 Hz), 6.86 (1H, d, J = 8.8 Hz), 5.71 (1H, d, J = 2.4 Hz), 4.55 (2H, d, J = 6.0 Hz), 3.69 (3H, s), 3.68 (3H, s); LCMS: 98.6%, MS (ESI): m/z 479.2 [M + H]+. |
| 488 | pale yellow powder; 1H-NMR (DMSO-d6, 400 MHz): δ 12.27 (1H, brs), 8.91 (1H, s), 8.72 (2H, s), 8.14 (1H, s), 7.53 (2H, brs), 7.45 (2H, d, J = 8.8 Hz), 7.10-7.21 (3H, m), 6.82-7.09 (3H, m), 4.55 (2H, d, J = 5.6 Hz), 3.49 (3H, s); LCMS: 100%, MS (ESI): m/z 489.9 [M + H]+. |
| 489 | yellow powder; 1H-NMR (DMSO-d6, 400 MHz): δ 11.49 (1H, brs), 8.54 (1H, s), 8.49 (1H, s), 7.95 (1H, brs), 7.47 (2H, d, J = 8.4 Hz), 7.35 (1H, s), 7.20 (2H, d, J = 8.4 Hz), 6.99 (1H, d, J = 8.8 Hz), 6.70-6.80 (1H, m), 5.56 (1H, s), 4.56 (2H, d, J = 6.0 Hz), 3.47 (3H, s), 2.16 (3H, s); LCMS: 99%, MS (ESI): m/z 461.2 [M + H]+. |
| 490 | light yellow powder; 1H NMR (DMSO-d6): δ 11.48 (1H, brs), 8.41 (1H, s), 8.32 (1H, s), 7.92 (1H, brs), 7.46 (2H, d, J = 8.4 Hz), 7.34 (1H, s), 7.17 (2H, d, J = 8.4 Hz), 7.03 (1H, brs), 6.98 (1H, d, J = 8.4 Hz), 6.77 (1H, d, J = 7.6 Hz), 5.55 (1H, s), 4.54 (2H, d, J = 5.6 Hz), 3.46 (3H, s), 2.16 (3H, s); LCMS: 100%, MS (ESI): m/z 462.1 [M + H]+. |

| | |
|---|---|
| 491 | yellow powder; 1H-NMR (DMSO-d6, 400 MHz): δ 11.51 (1H, brs), 8.74 (2H, s), 7.97 (1H, brs), 7.47 (2H, d, J = 8.4 Hz), 7.31 (1H, s), 7.09-7.22 (3H, m), 7.01 (1H, d, J = 8.4 Hz), 6.86 (1H, d, J = 7.6 Hz), 5.57 (1H, s), 4.56 (2H, d, J = 5.2 Hz), 4.24 (2H, t, J = 7.2 Hz), 2.61-2.80 (2H, m), 2.17 (3H, s); LCMS: 98.6%, MS (ESI): m/z 543.3 [M + H]+. |
| 492 | white powder; 1H-NMR (DMSO-d6, 400 MHz): δ 9.75 (1H, brs), 8.73 (2H, s), 7.62 (1H, s), 7.47 (1H, d, J = 8.8 Hz), 7.17 (1H, d, J = 8.8 Hz), 7.11 (1H, d, J = 8.0 Hz), 6.99 (1H, d, J = 8.0 Hz), 6.86 (1H, s), 4.58 (1H, d, J = 5.6 Hz), 3.52 (3H, s), 2.27 (3H, s). LCMS: 96.4%, MS (ESI): m/z 478.0 [M + H]+. |
| 493 | off-white powder; 1H NMR (DMSO-d6, 400 MHz): δ 10.24 (1H, brs), 8.73 (2H, s), 8.28-8.35 (1H, m), 7.46 (2H, d, J = 8.8 Hz), 7.38 (1H, d, J = 1.6 Hz), 7.27 (1H, t, J = 6.0 Hz), 7.16 (2H, d, J = 8.8 Hz), 7.13 (1H, s), 7.08-7.12 (1H, dd, J = 8.4, 2.0 Hz), 4.57 (2H, d, J = 6.0 Hz), 3.51 (3H, s); LCMS: 100%, MS (ESI): m/z 516.1 [M + H]+. |
| 494 | white powder; 1H-NMR (DMSO-d6, 400 MHz): δ 10.29 (1H, brs), 8.73 (2H, s), 7.45-7.60 (3H, m), 7.30-7.45 (2H, m), 7.10-7.25 (3H, m), 7.04 (1H, d, J = 8.8 Hz), 4.58 (1H, d, J = 6.0 Hz), 3.52 (3H, s); LCMS: 100%, MS (ESI): m/z 532.0 [M + H]+. |
| 495 | white powder; 1H-NMR (DMSO-d6, 400 MHz): δ 11.49 (1H, brs), 8.55 (1H, s), 8.20 (1H, dd, J = 8.8, 2.4 Hz), 7.93 (1H, brs), 7.47 (2H, d, J = 8.0 Hz), 7.33 (1H, s), 7.23 (1H, d, J = 8.4 Hz), 7.15 (2H, d, J = 8.4 Hz), 7.05 (1H, t, J = 5.6 Hz), 6.98 (1H, d, J = 8.4 Hz), 6.77 (1H, d, J = 8.0 Hz), 5.56 (1H, s), 4.50 (2H, d, J = 6.0 Hz), 3.47 (3H, s), 2.16 (3H, s); LCMS: 100%, MS (ESI): m/z 494.2 [M + H]+. |
| 496 | off-white powder; 1H NMR (DMSO-d6, 400 MHz): δ 11.48 (1H, brs), 8.23 (1H, d, J = 2.4 Hz), 7.86-8.01 (2H, m), 7.45 (2H, d, J = 8.4 Hz), 7.34 (1H, s), 7.16 (1H, d, J = 9.2 Hz), 7.11 (2H, d, J = 8.8 Hz), 7.01 (1H, t, J = 5.6 Hz), 6.98 (1H, d, J = 8.4 Hz), 6.77 (1H, d, J = 7.2 Hz), 5.55 (1H, s), 4.54 (2H, d, J = 5.6 Hz), 3.46 (3H, s), 2.16 (3H, s); LCMS: 100%, MS (ESI): m/z 510.1 [M + H]+. |
| 497 | yellow powder; 1H-NMR (DMSO-d6, 400 MHz): δ 11.60 (1H, brs), 8.75 (2H, s), 8.22 (1H, brs), 7.95 (1H, s), 7.75 (1H, s), 7.61 (1H, brs), 7.48 (2H, d, J = 8.4 Hz), 7.19 (2H, d, J = 8.0 Hz), 5.57 (1H, s), 4.61 (2H, d, J = 4.4 Hz), 3.52 (3H, s), 2.19 (3H, s); LCMS: 96.4%, MS (ESI): m/z 462.0 [M + H]+. |
| 498 | off-white powder; 1H NMR (DMSO-d6, 400 MHz): δ 10.04 (1H, s), 8.73 (2H, s), 7.50 (1H, d, J = 2.0 Hz), 7.46 (2H, d, J = 8.8 Hz), 7.25 (1H, t, J = 6.0 Hz), 7.17 (2H, d, J = 8.4 Hz), 7.11 (1H, d, J = 8.4 Hz), 6.99 (1H, dd, J = 8.4, 2.0 Hz), 4.57 (2H, d, J = 6.0 Hz), 3.52 (3H, s), 2.38 (3H, s); LCMS: 99.2%, MS (ESI): m/z 463.0 [M + H]+. |
| 499 | off-white powder; 1H-NMR (DMSO-d6, 400 MHz): δ 11.56 (1H, brs), 8.73 (2H, s), 8.15 (1H, brs), 7.46 (2H, d, J = 8.4 Hz), 7.10-7.20 (3H, m), 7.05 (1H, s), 6.79 (1H, d, J = 13.6 Hz), 5.56 (1H, s), 4.56 (2H, d, J = 5.6 Hz), 3.46 (3H, s), 2.17 (3H, s); LCMS: 99.0%, MS (ESI): m/z 479.0 [M + H]+. |
| 500 | white powder; 1H-NMR (DMSO-d6, 400 MHz): δ 11.75 (1H, s), 8.68 (2H, s), 8.63 (1H, s), 7.81 (1H, t, J = 6.0 Hz), 7.50 (1H, d, J = 8.0 Hz), 7.41 (2H, d, J = 8.8 Hz), 7.07 (2H, d, J = 8.8 Hz), 7.01 (1H, d, J = 8.0 Hz), 5.57 (1H, s), 4.61 (2H, d, J = 6.0 Hz), 3.54 (3H, s), 2.17 (3H, s); LCMS: 93.0%, MS (ESI): m/z 462.1 [M + H]+. |
| 501 | white powder; 1H-NMR (DMSO-d6, 400 MHz): δ 9.83 (1H, brs), 8.73 (2H, s), 7.35-7.70 (4H, m), 7.00-7.25 (5H, m), 6.32 (1H, s), 4.58 (2H, d, J = 6.0 Hz), 3.52 (3H, s), 2.20 (3H, s); LCMS: 98.7%, MS (ESI): m/z 478.1 [M + H]+. |
| 502 | white powder; 1H-NMR (DMSO-d6, 400 MHz): δ 8.37 (1H, s), 8.18 (1H, d, J = 2.4 Hz), 7.94 (1H, dd, J = 8.8, 2.8 Hz), 7.45 (2H, d, J = 8.4 Hz), 7.23 (1H, d, J = 2.0 Hz), 7.01-7.16 (5H, m), 6.88 (1H, dd, J = 8.0, 2.0 Hz), 6.26 (1H, s), 4.55 (2H, d, J = 6.0 Hz), 3.84 (3H, s), 3.50 (3H, s); LCMS: 100%, MS (ESI): m/z 528.2 [M + H]+. |
| 503 | white powder; 1H-NMR (DSMO-d6, 400 MHz): δ 8.76 (2H, s), 8.39 (1H, brs), 7.52 (1H, t, J = 8.4 Hz), 7.20-7.25 (2H, m), 7.11 (1H, brs), 7.05 (2H, d, J = 8.0 Hz), 6.88 (1H, dd, J = 8.4, 2.0 Hz), 6.26 (1H, s), 4.58 (2H, d, J = 5.6 Hz), 3.83 (3H, s), 3.51 (3H, s); LCMS: 97.3%, MS (ESI): m/z 547.1 [M + H]+. |
| 504 | yellow powder; 1H-NMR (DMSO-d6, 400 MHz): δ 8.74 (2H, s), 8.38 (1H, brs), 7.46 (2H, d, J = 8.4 Hz), 7.24-7.35 (2H, m), 7.18 (2H, d, J = 8.4 Hz), 7.06 (1H, d, J = 8.0 Hz), 6.92 (1H, d, J = 8.4 Hz), 6.26 (1H, s), 4.58 (2H, d, J = 5.6 Hz), 4.03 (2H, q, J = 6.8 Hz), 3.84 (3H, s), 1.26 (3H, t, J = 6.8 Hz); LCMS: 98.4%, MS (ESI): m/z 543.0 [M + H]+. |
| 505 | yellow powder; 1H-NMR (DMSO-d6, 400 MHz): δ 8.72 (2H, s), 8.34 (1H, brs), 7.50 (2H, d, J = 8.4 Hz), 7.20 (1H, d, J = 1.6 Hz), 7.15 (2H, d, J = 8.8 Hz), 7.00 (1H, d, J = 8.4 Hz), 6.86 (1H, dd, J = 2.4, 0.4 Hz), 6.81 (1H, d, J = 8.4 Hz), 6.24 (1H, s), 4.82-4.88 (1H, m), 3.83 (3H, s), 3.52 (3H, s), 1.76-1.94 (2H, m), 0.95 (3H, t, J = 7.2 Hz); LCMS: 99.8%, MS (ESI): m/z 557.1 [M + H]+. |

| | |
|---|---|
| 506 | off-white solid; 1H-NMR (DMSO-d6, 400 MHz): δ 8.78 (2H, s), 8.56 (1H, brs), 7.51 (1H, t, J = 8.4 Hz), 7.35 (1H, brs), 7.27 (1H, d, J = 9.2 Hz), 7.09-7.20 (2H, m), 6.95-7.06 (1H, m), 6.28 (1H, s), 4.63 (2H, d, J = 5.2 Hz), 4.00-4.10 (2H, m), 3.85 (3H, s), 1.28 (3H, t, J = 6.8 Hz); LCMS: 99.8%, MS (ESI): m/z 561.0 [M + H]+. |
| 507 | off-white powder; 1H NMR (DMSO-d6, 400 MHz): δ 11.59 (1H, brs), 8.73 (1H, s), 8.70 (1H, s), 7.95 (1H, brs), 7.40-7.57 (3H, m), 7.22 (2H, d, J = 8.4 Hz), 7.07 (1H, t, J = 6.0 Hz), 6.98 (1H, d, J = 8.4 Hz), 6.74 (1H, d, J = 8.4 Hz), 5.51 (1H, s), 4.57 (2H, d, J = 6.0 Hz), 3.97 (2H, q, J = 6.8 Hz), 1.21-1.28 (12H, m); LCMS: 98.9%, MS (ESI): m/z 551.0 [M + H]+. |
| 508 | off-white solid; 1H-NMR (DMSO-d6, 400 MHz): δ 12.09 (1H, brs), 8.74 (1H, s), 8.70 (1H, s), 7.60 (1H, brs), 7.49 (2H, d, J = 8.4 Hz), 7.43 (1H, s), 7.24 (2H, d, J = 8.4 Hz), 6.91-7.10 (2H, m), 4.59 (2H, d, J = 6.0 Hz), 4.00 (2H, q, J = 6.8 Hz), 2.18 (3H, s), 1.25 (3H, t, J = 6.8 Hz); LCMS: 100%, MS (ESI): m/z 543.0 [M + H]+. |
| 509 | yellow powder; 1H-NMR (DMSO-d6, 400 MHz): δ 11.59 (1H, brs), 8.72 (2H, s), 7.94 (1H, brs), 7.50 (1H, s), 7.43 (2H, d, J = 8.8 Hz), 7.14 (2H, d, J = 8.4 Hz), 7.04 (1H, brs), 6.96 (1H, d, J = 8.0 Hz), 6.72 (1H, d, J = 8.4 Hz), 5.49 (1H, s), 4.54 (2H, d, J = 5.6 Hz), 3.95-4.00 (2H, m), 1.20-1.25 (12H, m); LCMS: 98.7%, MS (ESI): m/z 517.1 [M + H]+. |
| 510 | off-white powder; 1H NMR (DMSO-d6): δ 8.41 (1H, d, J = 1.2 Hz), 8.35 (1H, s), 8.32 (1H, d, J = 1.6 Hz), 7.45 (2H, d, J = 8.8 Hz), 7.22 (1H, d, J = 1.6 Hz), 7.17 (2H, d, J = 8.4 Hz), 7.13 (1H, t, J = 5.6 Hz), 7.03 (1H, d, J = 8.4 Hz), 6.90 (1H, dd, J = 8.4, 2.0 Hz), 6.24 (1H, s), 4.56 (2H, d, J = 5.6 Hz), 4.01 (2H, q, J = 6.8 Hz), 3.82 (3H, s), 1.24 (3H, t, J = 6.8 Hz); LCMS: 100%, MS (ESI): m/z 543.1 [M + H]+. |
| 511 | white powder; 1H-NMR (CDCl3, 400 MHz): δ 8.35 (1H, s), 8.17 (1H, d, J = 2.8 Hz), 7.94 (1H, dd, J = 8.8, 2.8 Hz), 7.42 (2H, d, J = 8.4 Hz), 7.22 (1H, d, J = 1.6 Hz), 7.06-7.16 (4H, m), 7.04 (1H, d, J = 8.8 Hz), 6.90 (1H, dd, J = 8.0, 2.0 Hz), 6.24 (1H, s), 4.55 (2H, d, J = 6.0 Hz), 4.01 (2H, q, J = 6.8 Hz), 3.83 (3H, s), 1.24 (3H, t, J = 7.2 Hz); LCMS: 99.0%, MS (ESI): m/z 542.0 [M + H]+. |
| 512 | off-white powder; 1H-NMR (DMSO-d6, 400 MHz): δ 12.05 (1H, brs), 8.74 (2H, s), 7.51 (1H, brs), 7.44 (2H, d, J = 8.4 Hz), 7.39 (1H, s), 7.16 (2H, d, J = 8.4 Hz), 7.10 (1H, s), 6.93-7.05 (2H, m), 4.60 (2H, d, J = 6.4 Hz), 3.97 (2H, q, J = 6.8 Hz), 2.17 (3H, s), 1.24 (3H, t, J = 7.2 Hz); LCMS: 97.6%, MS (ESI): m/z 508.9 [M + H]+. |
| 513 | off-white powder; 1H NMR (DMSO-d6, 400 MHz): δ 11.60 (1H, brs), 9.09 (2H, s), 7.96 (1H, brs), 7.51 (1H, s), 7.47 (2H, d, J = 8.0 Hz), 7.21 (2H, d, J = 8.4 Hz), 7.08 (1H, t, J = 6.0 Hz), 6.98 (1H, d, J = 8.4 Hz), 6.74 (1H, d, J = 8.4 Hz), 5.51 (1H, s), 4.57 (2H, d, J = 6.0 Hz), 3.98 (2H, q, J = 6.8 Hz), 1.20-1.28 (12H, m); LCMS: 94.2%, MS (ESI): m/z 551.1 [M + H]+. |
| 514 | white powder; 1H NMR (DMSO-d6, 400 MHz): δ 11.59 (1H, brs), 8.41 (1H, s), 8.32 (1H, s), 7.95 (1H, brs), 7.50 (1H, s), 7.45 (2H, d, J = 8.4 Hz), 7.17 (2H, d, J = 8.8 Hz), 7.06 (1H, brs), 6.98 (1H, d, J = 8.0 Hz), 6.74 (1H, d, J = 8.4 Hz), 5.51 (1H, s), 4.55 (2H, d, J = 5.6 Hz), 3.97 (2H, q, J = 6.8 Hz), 1.21-1.26 (12H, m); LCMS: 99.4%, MS (ESI): m/z 517.0 [M + H]+. |
| 515 | off-white solid; 1H-NMR (DMSO-d6, 400 MHz): δ 12.07 (1H, brs), 8.43 (1H, s), 8.34 (1H, s), 7.55 (1H, brs), 7.46 (2H, d, J = 8.4 Hz), 7.40 (1H, s), 7.11-7.27 (3H, m), 6.95-7.04 (2H, m), 4.57 (2H, d, J = 5.6 Hz), 3.90-4.00 (2H, m), 2.18 (3H, s), 1.25 (3H, t, J = 6.8 Hz); LCMS: 100%, MS (ESI): m/z 508.9 [M + H]+. |
| 516 | yellow solid; 1H-NMR (DMSO-d6, 400 MHz): δ 12.06 (1H, brs), 9.10 (2H, s), 7.44-7.59 (3H, m), 7.39 (1H, s), 7.22 (2H, d, J = 8.4 Hz), 7.12 (1H, brs), 6.97-7.06 (2H, m), 4.58 (2H, d, J = 6.0 Hz), 3.98 (2H, q, J = 6.8 Hz), 2.18 (3H, s), 1.25 (3H, t, J = 6.8 Hz); LCMS: 100%, MS (ESI): m/z 543.0 [M + H]+. |
| 517 | yellow powder; 1H-NMR (DMSO-d6, 400 MHz): δ 8.41 (1H, d, J = 1.2 Hz), 8.36 (1H, brs), 8.32 (1H, d, J = 1.2 Hz), 7.50 (2H, d, J = 8.4 Hz), 7.20 (1H, s), 7.15 (2H, d, J = 8.8 Hz), 6.99 (1H, d, J = 8.4 Hz), 6.80-6.85 (2H, m), 6.24 (1H, s), 4.80-4.90 (1H, m), 3.83 (3H, s), 3.52 (3H, s), 1.74-1.97 (2H, m), 0.94 (3H, t, J = 8.8 Hz); LCMS: 100%, MS (ESI): m/z 557.0 [M + H]+. |
| 518 | yellow powder; 1H-NMR (DMSO-d6, 400 MHz): δ 12.02 (1H, brs), 8.17 (1H, d, J = 2.4 Hz), 7.94 (1H, dd, J = 8.8, 2.8 Hz), 7.49 (1H, s), 7.44 (2H, d, J = 8.8 Hz), 7.35 (1H, s), 7.01-7.11 (4H, m), 6.94-7.01 (2H, m), 4.54 (2H, d, J = 6.0 Hz), 3.45 (3H, s), 2.17 (3H, s); LCMS: 99.1%, MS (ESI): m/z 493.9 [M + H]+. |
| 519 | yellow powder; 1H-NMR (DSMO-d6, 400 MHz): δ 9.10 (2H, s), 8.39 (1H, brs), 7.50 (2H, d, J = 8.4 Hz), 7.25 (1H, d, J = 2.0 Hz), 7.22 (2H, d, J = 8.8 Hz), 7.14 (1H, brs), 7.05 (1H, d, J = 8.0 Hz), 6.89 (1H, dd, J = 8.4, 2.0 Hz), 6.27 (1H, s), 4.58 (2H, d, J = 6.0 Hz), 3.84 (3H, s), 3.51 (3H, s); LCMS: 100%, MS (ESI): m/z 563.0 [M + H]+. |

| | |
|---|---|
| 520 | yellow powder; 1H-NMR (DMSO-d6, 400 MHz): δ 9.09 (2H, s), 8.35 (1H, brs), 7.52 (2H, d, J = 8.4 Hz), 7.15-7.24 (3H, m), 6.99 (1H, d, J = 8.8 Hz), 6.78-6.89 (2H, m), 6.24 (1H, s), 4.79-4.95 (1H, m), 3.83 (3H, s), 3.53 (3H, s), 1.72-2.00 (2H, m), 0.96 (3H, t, J = 7.2 Hz); LCMS: 100%, MS (ESI): m/z 591.0 [M + H]+. |
| 521 | pale yellow powder; 1H-NMR (DMSO-d6, 400 MHz): δ 9.10 (2H, s), 8.36 (1H, brs), 7.48 (2H, d, J = 8.8 Hz), 7.21-7.27 (3H, m), 7.17 (1H, brs), 7.05 (1H, d, J = 8.4 Hz), 6.91 (1H, dd, J = 8.4, 2.0 Hz), 6.25 (1H, s), 4.59 (2H, d, J = 5.6 Hz), 4.03 (2H, q, J = 7.2 Hz), 3.84 (3H, s), 1.26 (3H, t, J = 7.2 Hz); LCMS: 100%, MS (ESI): m/z 577.0 [M + H]+. |
| 522 | yellow powder; 1H-NMR (DMSO-d6, 400 MHz): δ 8.72 (1H, s), 8.69 (1H, s), 8.36 (1H, brs), 7.53 (2H, d, J = 8.4 Hz), 7.19-7.24 (3H, m), 7.00 (1H, d, J = 8.0 Hz), 6.77-6.90 (2H, m), 6.24 (1H, s), 4.82-4.91 (1H, m), 3.83 (3H, s), 3.53 (3H, s), 1.73-1.99 (2H, m), 0.95 (3H, t, J = 7.2 Hz); LCMS: 100%, MS (ESI): m/z 590.9 [M + H]+. |
| 523 | white powder; 1H-NMR (DMSO-d6, 400 MHz): δ 8.73 (1H, s), 8.70 (1H, s), 8.35 (1H, brs), 7.48 (2H, d, J = 8.4 Hz), 7.20-7.30 (3H, m), 7.15 (1H, t, J = 6.0 Hz), 7.03 (1H, d, J = 8.4 Hz), 6.89 (1H, dd, J = 8.4, 2.4 Hz), 6.24 (1H, s), 4.57 (1H, d, J = 6.0 Hz), 4.02 (2H, q, J = 6.8 Hz), 3.83 (3H, s), 1.24 (3H, t, J = 7.2 Hz); LCMS: 100%, MS (ESI): m/z 577.1 [M + H]+. |
| 524 | a white powder; 1H NMR (DMSO-d6, 400 MHz): δ 8.73 (2H, s), 8.60 (1H, brs), 7.46 (2H, d, J = 8.4 Hz), 7.25 (1H, t, J = 6.0 Hz), 7.17 (2H, d, J = 8.4 Hz), 6.99 (1H, s), 6.87 (1H, d, J = 13.2 Hz), 6.29 (1H, s), 4.57 (2H, d, J = 6.0 Hz), 3.85 (3H, s), 3.50 (3H, s); LCMS: 100%, MS (ESI): m/z 546.9 [M + H]+. |
| 525 | off-white solid; 1H-NMR (DMSO-d6, 400 MHz): δ 9.10 (2H, s), 8.01 (1H, brs), 7.42-7.51 (3H, m), 7.20-7.31 (3H, m), 7.11 (1H, brs), 7.00 (1H, d, J = 8.4 Hz), 6.88 (1H, d, J = 8.4 Hz), 5.73 (1H, d, J = 2.0 Hz), 4.57 (2H, d, J = 5.6 Hz), 4.00 (2H, q, J = 6.8 Hz), 3.72 (3H, s), 1.25 (3H, t, J = 7.2 Hz); LCMS: 99.2%, MS (ESI): m/z 509.0 [M + H]+. |
| 526 | yellow powder; 1H-NMR (DMSO-d6, 400 MHz): δ 8.74 (2H, s), 8.02 (1H, brs), 7.46 (2H, d, J = 8.4 Hz), 7.23 (1H, brs), 7.17 (2H, d, J = 8.4 Hz), 7.10 (1H, d, J = 8.0 Hz), 6.83 (1H, d, J = 1.6 Hz), 6.69 (1H, dd, J = 8.4, 2.0 Hz), 6.14 (1H, s), 4.57 (2H, d, J = 6.0 Hz), 3.74 (3H, s), 3.50 (3H, s); LCMS: 98.4%, MS (ESI): m/z 529.1 [M + H]+. |
| 527 | yellow powder; 1H-NMR (DMSO-d6, 400 MHz): δ 9.13 (2H, s), 8.38 (1H, brs), 7.52 (1H, t, J = 8.8 Hz), 7.29 (1H, dd, J = 10.8, 2.4 Hz), 7.25 (1H, d, J = 2.0 Hz), 7.16 (1H, brs), 7.11 (1H, dd, J = 8.4, 1.6 Hz), 7.06 (1H, d, J = 8.4 Hz), 6.91 (1H, dd, J = 8.0, 2.0 Hz), 6.26 (1H, s), 4.61 (2H, d, J = 6.0 Hz), 4.04 (2H, q, J = 2.8 Hz), 3.84 (3H, s), 1.26 (3H, t, J = 6.8 Hz); LCMS: 100%, MS (ESI): m/z 595.1 [M + H]+. |
| 528 | white solid; 1H NMR (DMSO-d6, 400 MHz): δ 9.12 (2H, s), 8.38 (1H, brs), 7.60 (1H, t, J = 8.8 Hz), 7.19-7.28 (2H, m), 7.06-7.13 (1H, m), 7.01 (1H, d, J = 8.4 Hz), 6.80-6.94 (2H, m), 6.25 (1H, s), 5.10-5.20 (1H, m), 3.83 (3H, s), 3.55 (3H, s), 1.74-1.98 (2H, m), 0.99 (3H, t, J = 7.2 Hz); LCMS: 99.2%, MS (ESI): m/z 609.0 [M + H]+. |
| 529 | yellow powder; 1H-NMR (DMSO-d6, 400 MHz): δ 11.53 (1H, brs), 8.71 (2H, s), 7.90 (1H, brs), 7.48 (2H, d, J = 8.4 Hz), 7.31 (1H, s), 7.13 (2H, d, J = 8.4 Hz), 6.92 (1H, d, J = 8.4 Hz), 6.60-6.81 (2H, m), 5.51 (1H, s), 4.83 (1H, q, J = 8.0 Hz), 3.47 (3H, s), 2.75-2.91 (1H, m), 1.70-2.01 (2H, m), 1.18 (6H, d, J = 7.2 Hz), 0.94 (3H, t, J = 7.2 Hz); LCMS: 98.0%, MS (ESI): m/z 517.1 [M + H]+. |
| 530 | pale yellow powder; 1H-NMR (DMSO-d6, 400 MHz): δ 11.51 (1H, brs), 8.69 (2H, s), 7.85 (1H, brs), 7.45 (2H, d, J = 8.8 Hz), 7.23 (1H, s), 7.11 (2H, d, J = 8.4 Hz), 6.89 (1H, d, J = 8.4 Hz), 6.61-6.82 (2H, m), 5.41 (1H, s), 4.70-4.85 (1H, m), 3.66 (3H, s), 1.65-1.96 (3H, m), 0.76-0.99 (5H, m), 0.55-0.64 (2H, m); LCMS: 96.3%, MS (ESI): m/z 537.0 [M + Na]+. |
| 531 | white powder; 1H NMR (DMSO-d6, 400 MHz): δ 11.50 (1H, brs), 9.09 (2H, s), 7.95 (1H, brs), 7.47 (2H, d, J = 8.4 Hz), 7.38 (1H, s), 7.21 (2H, d, J = 8.4 Hz), 7.14 (1H, brs), 6.98 (1H, d, J = 8.4 Hz), 6.77 (1H, d, J = 8.0 Hz), 5.54 (1H, s), 4.57 (2H, d, J = 5.6 Hz), 3.95-4.00 (2H, m), 2.16 (3H, s), 1.24 (3H, t, J = 6.8 Hz); LCMS: 100%, MS (ESI): m/z 509.0 [M + H]+. |
| 532 | light-yellow powder; 1H NMR (DMSO-d6, 400 MHz): δ 8.73 (2H, s), 8.23 (1H, brs), 7.46 (2H, d, J = 8.0 Hz), 7.07-7.35 (1H, m), 7.22 (1H, s), 7.16 (2H, d, J = 8.4 Hz), 7.08 (1H, brs), 7.02 (1H, d, J = 8.4 Hz), 6.84-6.89 (1H, m), 6.06 (1H, s), 4.54 (2H, d, J = 5.6 Hz), 3.78 (3H, s), 3.48 (3H, s); LCMS: 99.3%, MS (ESI): m/z 510.9 [M + H]+. |
| 533 | light-yellow powder; 1H NMR (DMSO-d6, 400 MHz): δ 8.73 (2H, s), 7.88 (1H, s), 7.45 (2H, d, J = 8.4 Hz), 7.12-7.40 (3H, m), 7.07 (1H, d, J = 8.0 Hz), 6.80 (1H, t, J = 55.2 Hz), 6.78 (1H, s), 6.62-6.68 (1H, m), 5.98 (1H, s), 4.56 (1H, d, J = 5.6 Hz), 3.69 (3H, s), 3.49 (3H, s); LCMS: 97.7%, MS (ESI): m/z 511.0 [M + H]+. |

| | |
|---|---|
| 534 | pale yellow powder; 1H-NMR (DMSO-d6, 400 MHz): δ 11.45 (1H, brs), 9.07 (2H, s), 7.89 (1H, brs), 7.50 (2H, d, J = 8.4 Hz), 7.29 (1H, s), 7.18 (2H, d, J = 8.4 Hz), 6.91 (1H, d, J = 8.4 Hz), 6.60-6.81 (2H, m), 5.53 (1H, s), 4.80-4.90 (1H, m), 3.48 (3H, s), 2.14 (3H, s), 1.65-1.96 (2H, m), 0.94 (3H, t, J = 6.8 Hz); LCMS: 96.7%, MS (ESI): 523.0 m/z [M + H]+. |
| 535 | pale yellow powder; 1H-NMR (CDCl3, 400 MHz): δ 8.43 (2H, s), 7.41 (2H, d, J = 8.4 Hz), 7.01-7.20 (3H, m), 6.41-6.85 (3H, m), 6.16 (1H, brs), 6.01 (1H, s), 4.90-5.06 (1H, m), 4.44 (1H, brs), 3.30 (3H, s), 1.76-2.11 (2H, m), 0.93 (3H, t, J = 7.2 Hz); LCMS: 96.1%, MS (ESI): 525.0 m/z [M + H]+. |
| 536 | pale yellow powder; 1H-NMR (DMSO-d6, 400 MHz): δ 11.51 (1H, brs), 8.76 (2H, s), 7.94 (1H, brs), 7.45-7.55 (1H, m), 7.40 (1H, s), 7.21 (1H, d, J = 10.8 Hz), 6.90-7.12 (3H, m), 6.71-6.82 (1H, m), 5.54 (1H, s), 4.58 (2H, d, J = 5.2 Hz), 3.95-4.00 (2H, m), 2.16 (3H, s), 1.24 (3H, t, J = 6.8 Hz); LCMS: 100%, MS (ESI): 492.9 m/z [M + H]+. |
| 537 | white powder; 1H-NMR (DMSO-d6, 400 MHz): δ 11.48 (1H, brs), 8.76 (2H, s), 7.93 (1H, brs), 7.57 (1H, t, J = 8.8 Hz), 7.32 (1H, s), 7.17 (1H, d, J = 10.8 Hz), 7.05 (1H, d, J = 8.4 Hz), 6.94 (1H, d, J = 8.4 Hz), 6.50-6.85 (2H, m), 5.55 (1H, s), 5.08-5.20 (1H, m), 3.51 (3H, s), 2.16 (3H, s), 1.60-1.95 (2H, m), 0.98 (3H, t, J = 7.2 Hz); LCMS: 98.6%, MS (ESI): m/z 507.0 [M + H]+. |
| 538 | white powder; 1H NMR (DMSO-d6, 400 MHz): δ 8.73 (2H, s), 8.11 (1H, brs), 7.46 (2H, d, J = 8.0 Hz), 7.21 (1H, s), 7.16 (2H, d, J = 8.4 Hz), 7.07 (1H, brs), 7.02 (1H, d, J = 8.4 Hz), 6.85 (1H, d, J = 7.2 Hz), 5.96 (1H, d, J = 2.8 Hz), 5.43 (2H, d, J = 48.4 Hz), 4.55 (2H, d, J = 5.2 Hz), 3.73 (3H, s), 3.48 (3H, s); LCMS: 89.5%, MS (ESI): m/z 493.1 [M + H]+. |
| 539 | white powder; 1H NMR (DMSO-d6, 400 MHz): δ 8.73 (2H, s), 7.76 (1H, brs), 7.46 (2H, d, J = 8.4 Hz), 7.15-7.17 (3H, m), 7.05 (1H, d, J = 8.0 Hz), 6.74 (1H, s), 6.62 (1H, dd, J = 8.4, 1.6 Hz), 5.96 (1H, s), 5.19 (2H, d, J = 48.8 Hz), 4.56 (2H, d, J = 6.0 Hz), 3.65 (3H, s), 3.48 (3H, s); LCMS: 95.3%, MS (ESI): m/z 493.1 [M + H]+. |
| 540 | white powder; 1H NMR (DMSO-d6, 400 MHz): δ 9.12 (2H, s), 7.95 (1H, brs), 7.51 (1H, t, J = 8.4 Hz), 7.37 (1H, s), 7.28 (1H, dd, J = 10.8, 2.0 Hz), 7.03-7.14 (2H, m), 6.98 (1H, d, J = 8.4 Hz), 6.77 (1H, dd, J = 8.4, 1.6 Hz), 5.54 (1H, s), 4.59 (2H, d, J = 5.2 Hz), 3.94-4.03 (2H, m), 2.16 (3H, q, 6.8 Hz), 1.24 (3H, t, J = 6.8 Hz); LCMS: 100%, MS (ESI): m/z 527.0 [M + H]+. |
| 541 | white powder; 1H NMR (DMSO-d6, 400 MHz): δ 11.48 (1 H, brs), 9.12 (2 H, s), 7.95 (1 H, brs), 7.58-7.62 (1 H, m), 7.32 (1 H, s), 7.24 (1 H, d, J = 10.8 Hz), 7.10 (1 H, d, J = 8.0 Hz), 6.95 (1 H, d, J = 8.0 Hz), 6.80-6.90 (1 H, brs), 6.76 (1 H, d, J = 7.6 Hz), 5.55 (1 H, s), 5.12-5.13 (1 H, m), 3.52 (3 H, s), 2.33 (3 H, s), 1.80-1.92 (2 H, m), 0.97 (3 H, t, J = 7.2 Hz); LCMS: 95.9%, MS (ESI): m/z 541.0 [M + H]+. |
| 542 | white solid; 1H-NMR (DMSO-d6, 400 MHz): δ 9.11 (2H, s), 7.47 (1H, t, J = 8.4 Hz), 7.26 (1H, d, J = 10.8 Hz), 7.07 (1H, d, J = 8.4 Hz), 6.95-7.05 (1H, m), 6.93 (1H, d, J = 8.4 Hz), 6.28 (1H, s), 6.19 (1H, d, J = 8.4 Hz), 5.84 (1H, d, J = 7.2 Hz), 4.83 (2H, t, J = 6.4 Hz), 4.45-4.65 (3H, m), 4.38 (2H, t, J = 6.0 Hz), 3.90-4.10 (2H, m), 1.20 (3H, t, J = 6.8 Hz); LCMS: 100%, MS (ESI): m/z 503.0 [M + H]+. |
| 543 | white powder; 1H-NMR (DMSO-d6, 400 MHz): δ 9.12 (2H, s), 7.58 (1H, t, J = 8.4 Hz), 7.23 (1H, d, J = 11.2 Hz), 7.09 (1H, d, J = 6.8 Hz), 6.90 (1H, d, J = 8.0 Hz), 6.76 (1H, brs), 6.15-6.25 (2H, m), 5.85 (1H, d, J = 5.2 Hz), 5.05-5.15 (1H, m), 4.70-4.90 (2H, m), 4.45-4.55 (1H, m), 4.30-4.40 (2H, m), 3.50 (3H, s), 1.60-2.00 (2H, m), 0.97 (3H, t, J = 7.2 Hz); LCMS: 98.15%, MS (ESI): m/z 517.0 [M + H]+. |
| 544 | white powder; 1H NMR (DMSO-d6, 400 MHz): δ 8.54 (1H, s), 8.21 (1H, dd, J = 8.8, 2.0 Hz), 7.45 (2H, d, J = 8.4 Hz), 7.22 (1H, d, J = 8.8 Hz), 7.14 (2H, d, J = 8.4 Hz), 6.95-7.00 (1H, m), 6.94 (1H, d, J = 8.0 Hz), 6.25 (1H, s), 6.22 (1H, d, J = 8.4 Hz), 5.85 (1H, d, J = 6.8 Hz), 4.84 (2H, t, J = 6.4 Hz), 4.45-4.58 (3H, m), 4.39 (2H, t, J = 6.0 Hz), 3.45 (3H, s); LCMS: 100%, MS (ESI): m/z 470.0 [M + H]+. |
| 545 | white powder; 1H-NMR (DMSO-d6, 400 MHz): δ 8.83 (2H, s), 8.37 (1H, brs), 7.45 (2H, d, J = 8.4 Hz), 7.16-7.26 (3H, m), 7.05 (1H, d, J = 8.4 Hz), 6.91 (1H, d, J = 8.4 Hz), 6.25 (1H, s), 4.57 (2H, d, J = 4.8 Hz), 4.02-4.04 (2H, m), 3.83 (3H, s), 1.25 (3H, t, J = 6.8 Hz); LCMS: 100%, MS (ESI): m/z 593.0 [M + H]+. |
| 546 | white powder; 1H-NMR (DMSO-d6, 400 MHz): δ 8.57 (1H, s), 8.24 (1H, dd, J = 8.8, 2.4 Hz), 7.50 (1H, t, J = 8.4 Hz), 7.28 (1H, d, J = 8.4 Hz), 7.18 (1H, dd, J = 10.8, 2.4 Hz), 7.01 (2H, dd, J = 8.4, 2.0 Hz), 6.95 (1H, d, J = 8.4 Hz), 6.26 (1H, d, J = 1.2 Hz), 6.23 (1H, d, J = 8.0, 1.2 Hz), 5.87 (1H, J = 6.8 Hz), 4.84 (2H, t, J = 6.4 Hz), 4.46-4.61 (3H, m), 4.34-4.44 (2H, m), 3.46 (3H, s); LCMS: 100%, MS (ESI): m/z 487.9 [M + H]+. |

| | |
|---|---|
| 547 | pale yellow powder; 1H-NMR (DMSO-d6, 400 MHz): δ 9.05 (2H, s), 7.47 (2H, d, J = 8.4 Hz), 7.15 (2H, d, J = 8.8 Hz), 6.86 (1H, dd, J = 8.0 Hz), 6.65 (1H, d, J = 8.4 Hz), 6.19 (1H, d, J = 1.6 Hz), 6.15 (1H, dd, J = 8.4, 2.0 Hz), 5.78 (1H, d, J = 7.2 Hz), 4.74-4.88 (3H, m), 4.35-4.50 (1H, m), 4.20-4.38 (2H, m), 3.44 (3H, s), 1.71-1.95 (2H, m), 0.91 (3H, t, J = 7.2 Hz); LCMS: 100%, MS (ESI): m/z 499.0 [M + H]+. |
| 548 | white powder; 1H-NMR (DMSO-d6, 400 MHz): δ 9.09 (2H, s), 7.45 (2H, d, J = 8.4 Hz), 7.20 (2H, d, J = 8.4 Hz), 7.04 (1H, brs), 6.93 (1H, d, J = 8.4 Hz), 6.29 (1H, d, J = 1.6 Hz), 6.19 (1H, dd, J = 8.0, 1.6 Hz), 5.84 (1H, d, J = 7.2 Hz), 4.84 (2H, t, J = 6.0 Hz), 4.47-4.57 (3H, m), 4.36-4.42 (2H, m), 3.98 (2H, q, J = 6.8 Hz), 1.20 (3H, t, J = 7.2 Hz); LCMS: 99.5%, MS (ESI): m/z 485.0 [M + H]+. |
| 549 | white powder; 1H-NMR (DSMO-d6, 400 MHz): δ 8.53 (1H, s), 8.18 (1H, dd, J = 8.8, 2.4 Hz), 7.46 (2H, d, J = 8.8 Hz), 7.19 (1H, d, J = 8.8 Hz), 7.10 (2H, d, J = 8.8 Hz), 6.87 (1H, d, J = 8.0 Hz), 6.66 (1H, d, J = 8.4 Hz), 6.20 (1H, s), 6.16 (1H, dd, J = 8.4, 2.0 Hz), 5.80 (1H, d, J = 6.8 Hz), 4.72-4.85 (3H, m), 4.40-4.50 (1H, m), 4.33-4.41 (2H, m), 3.45 (3H, s), 1.69-1.96 (2H, m), 0.92 (3H, t, J = 7.6 Hz); LCMS: 100%, MS (ESI): m/z 498.1 [M + H]+. |
| 550 | white powder; 1H NMR (DMSO-d6, 400 MHz): δ 8.58 (1H, s.), 8.23 (1H, d, J = 8.8 Hz), 7.56 (1H, t, J = 8.4 Hz), 7.26 (1H, d, J = 8.8 Hz), 7.13 (1H, d, J = 10.8 Hz), 7.01 (1H, d, J = 8.0 Hz), 6.90 (1H, d, J = 8.0 Hz), 6.73 (1H, d, J = 8.0 Hz), 6.13-6.25 (2H, m), 5.83 (1H, d, J = 6.8 Hz), 5.06-5.15 (1H, m), 4.83 (2H, t, J = 6.4 Hz), 4.44-4.55 (1H, m), 4.33-4.41 (2H, m), 3.50 (3H, s), 1.68-1.96 (2H, m), 0.97 (3H, t, J = 7.2 Hz); LCMS: 99.3%, MS (ESI): m/z 516.0 [M + H]+. |
| 551 | white powder; 1H-NMR (DMSO-d6, 400 MHz): δ 9.08 (2H, s), 7.45 (2H, d, J = 8.4 Hz), 7.19 (2H, d, J = 8.4 Hz), 7.11 (1H, t, J = 6.0 Hz), 6.00-6.15 (3H, m), 4.83 (2H, t, J = 6.4 Hz), 4.46-4.57 (3H, m), 4.36 (2H, t, J = 6.0 Hz), 3.44 (3H, s); LCMS: 100%, MS (ESI): m/z 489.0 [M + H]+. |
| 552 | white powder; 1H-NMR (DMSO-d6, 400 MHz): δ 8.51 (1H, s), 8.18 (1H, dd, J = 8.4, 2.0 Hz), 7.42 (2H, d, J = 8.8 Hz), 7.19 (1H, d, J = 8.8 Hz), 7.02-7.16 (3H, m), 5.95-6.12 (3H, m), 4.81 (2H, t, J = 6.4 Hz), 4.42-4.56 (3H, m), 4.34 (2H, t, J = 6.4 Hz), 3.42 (3H, s); LCMS: 100.0%, MS (ESI): m/z 488.0 [M + H]+. |
| 553 | yellow powder; 1H-NMR (DMSO-d6, 400 MHz): δ 8.14 (1H, d, J = 2.4 Hz), 7.91 (1H, dd, J = 8.4, 2.4 Hz), 7.40 (2H, d, J = 8.0 Hz), 6.97-7.12 (3H, m), 5.95-6.27 (3H, m), 4.82 (2H, t, J = 6.4 Hz), 4.41-4.60 (3H, m), 4.35 (2H, t, J = 5.6 Hz), 3.44 (3H, s); LCMS: 86.5%, MS (ESI): m/z 476.0 [M + Na]+. |
| 554 | pale yellow powder; 1H-NMR (DMSO-d6, 400 MHz): δ 8.70 (2H, s), 7.41 (2H, d, J = 8.0 Hz), 7.12 (2H, d, J = 8.0 Hz), 7.07 (1H, t, J = 6.0 Hz), 5.95-6.10 (3H, m), 4.81 (2H, t, J = 6.0 Hz), 4.45-4.55 (3H, m), 4.34 (2H, t, J = 6.0 Hz), 3.42 (3H, s); LCMS: 99.3%, MS (ESI): m/z 455.0 [M + H]+. |
| 555 | white powder; ¹H-NMR (DMSO-d6, 400 MHz): δ 8.73 (2H, s), 7.42 (2H, d, J = 8.0 Hz), 7.16 (3H, d, J = 8.0 Hz), 5.98-6.17 (3H, m), 4.84 (2H, t, J = 6.4 Hz), 4.47-4.60 (3H, m), 4.34-4.42 (2H, m), 3.98 (2H, q, J = 6.8 Hz), 1.19 (3H, t, J = 6.8 Hz); LCMS: 100%, MS (ESI): m/z 469.0 [M + H]+. |
| 556 | pink powder; ¹H-NMR (DMSO-d6, 400 MHz): δ 11.57 (1H, brs), 8.74 (2H, s), 8.14 (1H, s), 7.47 (2H, d, J = 8.0 Hz), 7.15-7.25 (4H, m), 7.03 (1H, s), 5.55 (1H, s), 4.59 (2H, d, J = 5.6 Hz), 3.47 (3H, s), 2.17 (3H, s); LCMS: 100%, MS (ESI): m/z = 517.0 [M + Na]+. |

The invention claimed is:

1. A compound having general formula I:

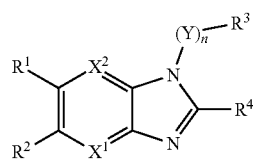

Formula I wherein n is 0 or 1;

$X^1$ and $X^2$ are independently, at each occurrence, $CR^5$ or N;

Y is $C_1$-$C_6$ alkylene, wherein alkylene is optionally substituted with one to two $C_1$-$C_3$ alkyl groups;

$R^1$ is —$NHR^6$;

$R^2$ is selected from the group consisting of $C_2$-$C_6$alkyl, —$NH_2$, —$NHR^6$, —$NR^7R^8$ and —NH—$(R^9)n$, —$R^{10}$, n being 0 or 1;

$R^3$ is selected from the group consisting of hydroxyl, $OR^{11}$, —$NR^7R^8$, $C_1$-$C_6$ alkoxy, $C_1$-$C_6$ alkyl, $C_3$-$C_{10}$cycloalkyl, $C_1$-$C_3$ haloalkyl, —$C(O)NHR^{11}$, aryl, heteroaryl, wherein each of said cycloalkyl, aryl, and heteroaryl is optionally and independently substituted with one to four $R^a$ groups;

$R^4$ is selected from the group consisting of —$N(R^{12})(V)_p$ $R^{13}$, —$NH(V)_p$—$OR^{14}$, and groups of formula Ia shown below, Formula Ia

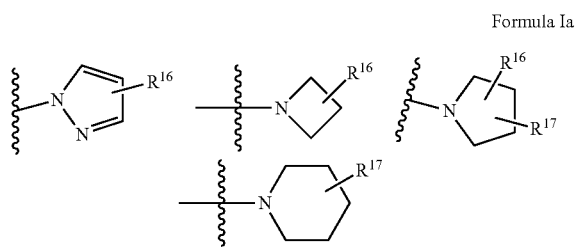

wherein,
p is 0,
V is $C_1$-$C_6$ alkylene, wherein alkylene is optionally substituted with one to three $C_1$-$C_3$ alkyl, $C_3$-$C_6$ cycloalkyl or phenyl groups, or wherein a carbon atom of said alkylene forms part of a $C_3$-$C_6$ cycloalkyl group;
$R^5$ is selected from the group consisting of hydrogen, halogen, $C_1$-$C_6$ alkyl, $C_1$-$C_6$ haloalkyl and $C_1$-$C_6$ alkoxy;
$R^6$ is selected from the group consisting of heteroaryl and heterocyclyl, wherein each of said heteroaryl and heterocyclyl is optionally and independently substituted with one to four $R^a$ groups;
$R^7$ and $R^8$ are independently, at each occurrence, heterocyclyl; or
$R^7$ and $R^8$ are connected to each other to make a four, five or six membered heterocyclyl or heteroaryl group, wherein each of said heterocyclyl and heteroaryl is optionally and independently substituted with one to four $R^a$ groups;
$R^9$ is $C_1$-$C_4$ alkylene, wherein said alkylene is optionally substituted with one to three $C_1$-$C_3$ alkyl groups;
$R^{10}$ is selected from the group consisting of hydroxyl, —$OR^{11}$, —CN, —C(O)$OR^{18}$, —C(O)$NH_2$, —C(NH)$NH_2$, aryl, heteroaryl and heterocyclyl wherein each of said aryl, heteroaryl and heterocyclyl is optionally and independently substituted with one to four $R^a$ groups;
$R^{11}$ is independently, at each occurrence, selected from the group consisting of aryl heteroaryl and heterocyclyl wherein each of said aryl, heteroaryl and heterocyclyl is optionally and independently substituted with one to four $R^a$ groups;
$R^{12}$ is selected from the group consisting of hydrogen, $C_2$-$C_6$ alkyl, $C_1$-$C_4$ alkyl-hydroxyl and $C_1$-$C_4$ alkyl-alkoxy;
$R^{13}$ is selected from the group consisting of $C_2$, $C_5$-$C_6$ alkyl, $C_3$-$C_5$, $C_7$-$C_{10}$ cycloalkyl, $C_1$-$C_4$ alkyl-hydroxyl, —OH, —C(O)$NH_2$, —C(O)$OR^{18}$, —CN, $C_1$-$C_3$ haloalkyl, and groups of formula Ib shown below, Formula Ib

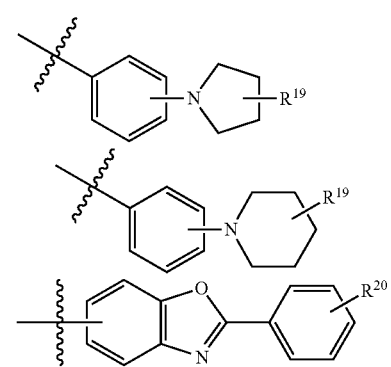

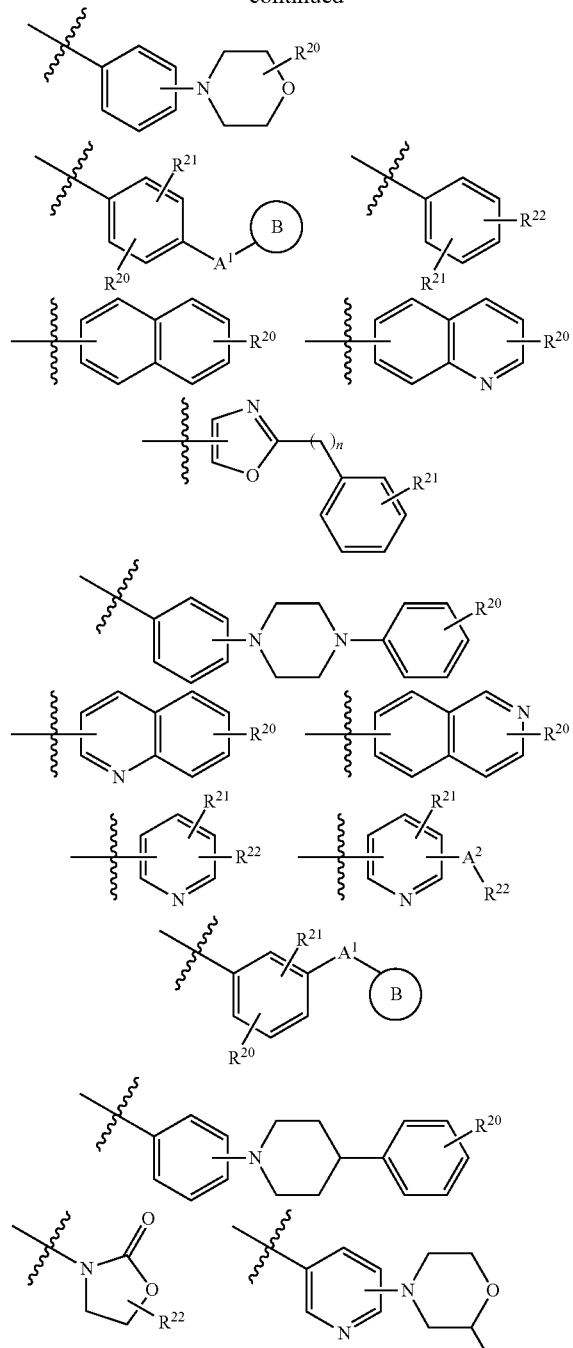

wherein,
n is 0 or 1;
$A^1$ is —O—, —$CH_2$O—, —$OCH_2$—, —S—, —$SO_2$—, —$SO_2NH$—, —C(O)—, —C(O)NH—, —C(O)N ($R^7$)—, —CH(OH)—, —CH(O$R^7$)—, —NH—, —N(CH$_3$)— or —N(CH$_2$COO$R^7$)—;

A$^2$ is —O— or NH—;

B is selected from the group consisting of aryl, heteroaryl and heterocyclyl wherein each of said aryl, heteroaryl and heterocyclyl is optionally and independently substituted with one to four R$^a$ groups;

R$^{14}$ is selected from the group consisting of hydrogen, C$_1$-C$_6$ alkyl and aryl, wherein each of said alkyl and aryl is optionally and independently substituted with one to four halogen or C$_1$-C$_3$ haloalkoxy groups;

R$^{16}$ is selected from the group consisting of hydrogen, halogen, C$_1$-C$_6$ alkyl and hydroxyl;

R$^{17}$ is selected from the group consisting of hydrogen, halogen, C$_1$-C$_6$ alkyl, —C(O)R$^{11}$, —C(O)NHR$^{11}$, —OR$^{11}$ and aryl, wherein each of said alkyl and aryl is optionally and independently substituted with one to four R$^a$ groups;

R$^{18}$ is hydrogen or C$_2$-C$_6$ alkyl;

R$^{19}$ is selected from the group consisting of hydrogen, —OR$^{22}$ and —CH$_2$OR$^{22}$;

R$^{20}$ is selected from the group consisting of hydrogen, halogen, C$_1$-C$_6$ alkyl, C$_1$-C$_6$ alkoxy, —C(O)R$^a$ and C$_1$-C$_6$ haloalkoxy;

R$^{21}$1 is selected from the group consisting of hydrogen, halogen and C$_1$-C$_6$ alkyl;

R$^{22}$ is selected from the group consisting of C$_1$-C$_6$ haloalkyl, aryl, and heteroaryl, wherein each of said haloalkyl, aryl and heteroaryl is optionally and independently substituted with one to four R$^a$ groups;

R$^a$ is independently, at each occurrence, selected from the group consisting of hydrogen, halogen, C$_1$-C$_3$ alkyl, C$_3$-C$_{10}$ cycloalkyl, C$_1$-C$_4$ alkoxy, C$_1$-C$_4$ haloalkyl, C$_1$-C$_6$ haloalkoxy, hydroxyl, C$_1$-C$_3$ alkylhydroxyl, —CH$_2$OH, —OCH$_3$, —NR$^b$H, —C(O)NR$^b$H, —C(O)H, —CH$_2$OR$^c$, —OCH$_2$R$^c$, —OR$^c$, —CN, NO$_2$, —NR$^b$R$^c$, —C(O)NR$^b$R$^c$, —C(NH)NH$_2$, —C(O)R$^c$, —C(O)OR$^c$, sulfonyl, sulfoxide, heterocyclyl, heteroaryl and aryl, wherein each of said alkyl, haloalkyl, haloalkoxy, alkoxy, cycloalkyl, aryl, heteroaryl and heterocyclyl is optionally and independently substituted with one to four C$_1$-C$_3$ alkyl, C$_1$-C$_4$ alkoxy, halogen, C$_1$-C$_3$ haloalkyl, —CN, —C(O)NH$_2$, —CO$_2$Et or heteroaryl;

R$^b$ is independently, at each occurrence, selected from the group consisting of hydrogen, C$_1$-C$_{10}$ alkyl, C$_3$-C$_{10}$ cycloalkyl, C$_1$-C$_6$ alkyl-O-alkyl, C$_2$-C$_{10}$ alkenyl, C$_1$-C$_4$ alkoxy, C$_1$-C$_3$ alkylhydroxyl, C$_3$-C$_{10}$ cycloalkenyl, C$_2$-C$_{10}$ alkynyl, C$_1$-C$_6$ haloalkyl, aryl, heteroaryl, and heterocyclyl wherein each of said alkyl, cycloalkyl, alkyl-O-alkyl, alkenyl, alkoxy, cycloalkenyl, alkynyl, haloalkyl, aryl, heteroaryl and heterocyclyl is optionally and independently substituted with one to four C$_1$-C$_3$ alkyl, C$_1$-C$_4$ alkoxy, halogen, C$_1$-C$_6$ haloalkyl, C$_1$-C$_6$ haloalkoxy, hydroxyl, —C(O)NH$_2$, —COOH, —COOMe, —COOEt, —CN, —NO$_2$, or —NH$_2$;

R$^c$ is independently, at each occurrence, selected from the group consisting of C$_1$-C$_{10}$ alkyl, C$_3$-C$_{10}$ cycloalkyl, C$_1$-C$_6$ alkyl-O-alkyl, C$_2$-C$_{10}$alkenyl, C$_1$-C$_4$ alkoxy, C$_1$-C$_3$ alkylhydroxyl, C$_3$-C$_{10}$cycloalkenyl, C$_2$-C$_{10}$ alkynyl, C$_1$-C$_6$ haloalkyl, aryl, heteroaryl, and heterocyclyl wherein each of said alkyl, cycloalkyl, alkyl-O-alkyl, alkenyl, alkoxy, cycloalkenyl, alkynyl, haloalkyl, aryl, heteroaryl and heterocyclyl is optionally and independently substituted with one to four C$_1$-C$_3$ alkyl, C$_1$-C$_4$ alkoxy, halogen, C$_1$-C$_6$ haloalkyl, C$_1$-C$_6$ haloalkoxy, hydroxyl, —C(O)NH$_2$, —COOH, —COOMe, —COOEt, —CN, —NO$_2$, or —NH$_2$; or R$^b$ and R$^c$ are connected to each other to make a four, five or six membered saturated or unsaturated cyclic or heterocyclic ring;

or a pharmaceutically acceptable salts thereof.

2. A compound having general formula II:

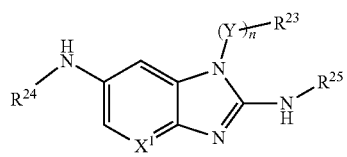

Formula II wherein n is 0 or 1;

X$^1$ is CR$^5$ or N;

Y is C$_1$-C$_6$ alkylene, wherein alkylene is optionally substituted with one to two C$_1$-C$_3$ alkyl groups;

R$^5$ is selected from the group consisting of hydrogen, halogen, C$_1$-C$_6$ alkyl, C$_1$-C$_6$ haloalkyl and C$_1$-C$_6$ alkoxy;

R$^{23}$ is selected from the group consisting of C$_1$-C$_6$ alkyl, C$_1$-C$_3$ haloalkyl, aryl, heteroaryl and heterocyclyl, wherein each of said aryl, heteroaryl and heterocyclyl is optionally and independently substituted with one to four R$^a$ groups;

R$^{24}$ is selected from the group consisting of C$_3$-C$_{10}$ cycloalkyl, aryl, heteroaryl and heterocyclyl, wherein each of said cycloalkyl, aryl, heteroaryl and heterocyclyl is optionally and independently substituted with one to four R$^a$ groups;

R$^{25}$ is selected from the group consisting of —(V)$_p$R$^{26}$ and —(V)$_p$—OR$^{14}$;

wherein, p is 0,

V is C$_1$-C$_6$ alkylene, wherein alkylene is optionally substituted with one to three C$_1$-C$_3$ alkyl or phenyl groups, or wherein a carbon atom of said alkylene forms part of a C$_3$-C$_6$ cycloalkyl group;

R$^{14}$ is selected from the group consisting of hydrogen, C$_1$-C$_6$ alkyl and aryl, wherein each of said alkyl and aryl is optionally and independently substituted with one to four halogen or C$_1$-C$_3$ haloalkoxy groups;

R$^{26}$ is selected from the group consisting of C$_1$-C$_6$ alkyl, —CN and C$_1$-C$_3$ haloalkyl, and groups of formula IIa shown below,

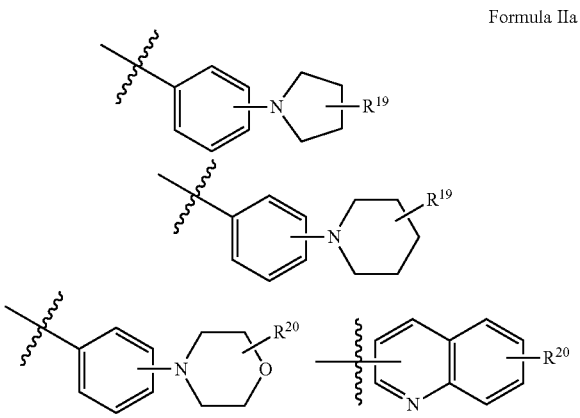

Formula IIa

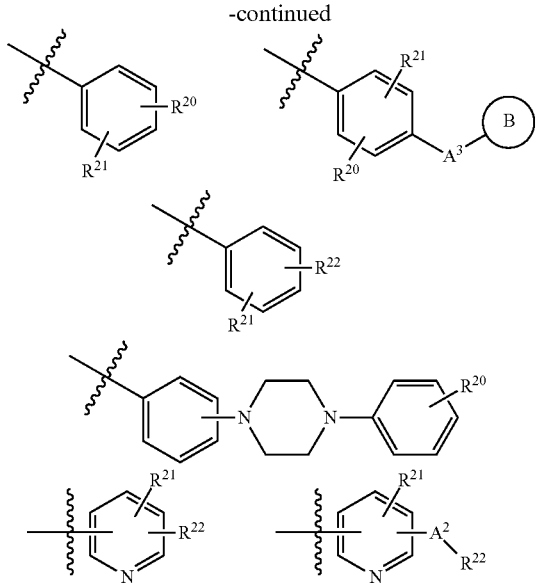

wherein,
A² is —O— or NH—;
A³ is —O—, —CH₂O—, —OCH₂-, or —NH—;
B is selected from the group consisting of aryl, heteroaryl and heterocyclyl wherein each of said aryl, heteroaryl and heterocyclyl is optionally and independently substituted with one to four R$^a$ groups;
R$^{19}$ is selected from the group consisting of hydrogen, —OR$^{22}$ and —CH₂OR$^{22}$;
R$^{20}$ is selected from the group consisting of hydrogen, halogen, $C_1$-$C_6$ alkyl, $C_1$-$C_6$ alkoxy and $C_1$-$C_6$ haloalkoxy;
R$^{21}$ is selected from the group consisting of hydrogen, halogen and $C_1$-$C_6$ alkyl;
R$^{22}$ is selected from the group consisting of aryl, and heteroaryl, wherein each of said aryl and heteroaryl is optionally and independently substituted with one to four R$^a$ groups;
R$^a$ is independently, at each occurrence, selected from the group consisting of hydrogen, halogen, $C_1$-$C_3$ alkyl, $C_3$-$C_{10}$ cycloalkyl, $C_1$-$C_4$ alkoxy, $C_1$-$C_4$ haloalkyl, $C_1$-$C_6$ haloalkoxy, hydroxyl, $C_1$-$C_3$ alkylhydroxyl, —CH₂OR$^c$, —OCH₂R$^c$, —OR$^c$, —CN, NO₂, —NR$^b$R$^c$, —C(O)NR$^b$R$^c$, —C(NH)NH₂, —C(O)R$^c$, —C(O)OR$^c$, sulfonyl, sulfoxide, heterocyclyl, heteroaryl and aryl, wherein each of said alkyl, haloalkyl, haloalkoxy, alkoxy, cycloalkyl, aryl, heteroaryl and heterocyclyl is optionally and independently substituted with one to four $C_1$-$C_3$ alkyl, $C_1$-$C_4$ alkoxy, halogen, $C_1$-$C_3$ haloalkyl, —CN, —C(O)NH₂, —COOH, —CO₂Et and heteroaryl;
R$^b$ and R$^c$ are independently, at each occurence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_6$ haloalkyl, aryl, heteroaryl, and heterocyclyl wherein each of said alkyl, alkyl-O-alkyl, alkenyl, alkoxy, cycloalkenyl, alkynyl, haloalkyl, cycloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH₂, —COOH, —COOMe, —COOEt, —CN, —NO₂, —NH₂; or R$^b$ and R$^c$ are connected to each other to make a four, five or six membered saturated or unsaturated cyclic or heterocyclic ring;

or a pharmaceutically acceptable salts thereof.

3. A compound having general formula III:

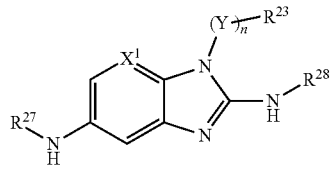

Formula III wherein
n is 0 or 1;
X¹ is CR$^5$ or N;
Y is $C_1$-$C_6$ alkylene, wherein alkylene is optionally substituted with one to two $C_1$-$C_3$ alkyl groups;
R$^5$ is selected from the group consisting of hydrogen, halogen, $C_1$-$C_6$ alkyl, $C_1$-$C_6$ haloalkyl and $C_1$-$C_6$ alkoxy;
R$^{23}$ is selected from the group consisting of $C_1$-$C_6$ alkyl, aryl, heteroaryl and heterocyclyl, wherein each of said aryl, heteroaryl and heterocyclyl is optionally and independently substituted with one to four R$^a$ groups;
R$^{27}$ is selected from the group consisting of hydrogen, —R$^6$, and —R$^9$—R$^{10}$;
wherein,
R$^6$ is selected from the group consisting of $C_1$-$C_6$ alkyl, $C_3$-$C_{10}$ cycloalkyl, $C_1$-$C_6$ haloalkyl, aryl, heteroaryl and heterocyclyl, wherein said alkyl, cycloalkyl, haloalkyl, aryl, heteroaryl and heterocyclyl is optionally and independently substituted with one to four R$^a$ groups;
R$^9$ is $C_1$-$C_4$ alkylene, wherein said alkylene is optionally substituted with one to three $C_1$-$C_3$ alkyl groups;
R$^{10}$ is selected from the group consisting of hydroxyl, —OR$^{11}$, —C(O)OR$^{18}$, —C(O)NH₂, aryl, heteroaryl and heterocyclyl wherein each of said aryl, heteroaryl and heterocyclyl is optionally and independently substituted with one to four R$^a$ groups;
R$^{11}$ is independently, at each occurrence selected from the group consisting of aryl, heteroaryl and heterocyclyl group wherein said aryl, heteroaryl and heterocyclyl is optionally and independently substituted with one to four R$^a$ groups;
R$^{18}$ is hydrogen or $C_1$-$C_6$ alkyl;
R$^{28}$ is selected from the group consisting of —(V)$_p$R$^{29}$ and —(V)$_p$—OR$^{14}$;
wherein,
p is 0,
V is $C_1$-$C_6$ alkylene, wherein alkylene is optionally substituted with one to three $C_1$-$C_6$ alkyl or phenyl groups;
R14 is selected from the group consisting of hydrogen, $C_1$-$C_6$ alkyl and aryl, wherein each of said alkyl and aryl is optionally and independently substituted with one to four halogen or $C_1$-$C_3$ haloalkoxy groups;
R$^{29}$ is selected from the group consisting of $C_2$, $C_5$-$C_6$ alkyl and $C_1$-$C_3$ haloalkyl, and groups of formula IIIa shown below,

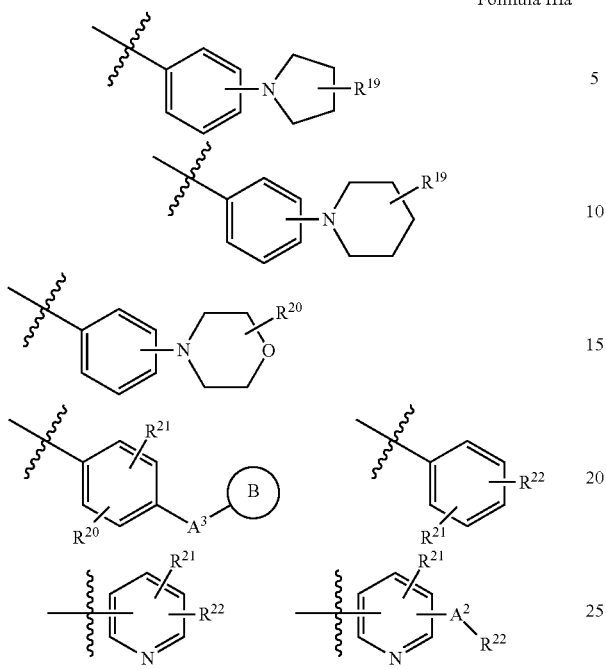

Formula IIIa wherein,
A² is —O— or NH—;
A³ is —O—, —CH₂O—, —OCH₂—, or —NH—;
B is selected from the group consisting of aryl, heteroaryl and heterocyclyl wherein each of said aryl, heteroaryl and heterocyclyl is optionally and independently substituted with one to four $R^a$ groups;
$R^{19}$ is selected from the group consisting of hydrogen, —OR²² and —CH₂OR²²;
$R^{20}$ is selected from the group consisting of hydrogen, halogen, $C_1$-$C_6$ alkyl, $C_1$-$C_6$ alkoxy and $C_1$-$C_6$ haloalkoxy;
$R^{21}$ is selected from the group consisting of hydrogen, halogen and $C_1$-$C_6$ alkyl;
$R^{22}$ is selected from the group consisting of aryl, and heteroaryl, wherein said aryl and heteroaryl is optionally and independently substituted with one to four $R^a$ groups;
$R^a$ is independently, at each occurrence, selected from the group consisting of hydrogen, halogen, $C_1$-$C_3$ alkyl, $C_3$-$C_{10}$ cycloalkyl, $C_1$-$C_4$ alkoxy, $C_1$-$C_4$ haloalkyl, $C_1$-$C_6$ haloalkoxy, hydroxyl, $C_1$-$C_3$ alkylhydroxyl, —CH₂OH, —OCH₃, —NR$^b$H, —C(O)NR$^b$H, C(O)H, —CH₂OR$^c$, —OCH₂R$^c$, —OR$^c$, —CN, NO₂, —NR$^b$R$^b$, —C(O)NR$^b$R$^c$, —C(NH)NH₂, —C(O)R$^c$, —C(O)OR$^c$, sulfonyl, sulfoxide, heterocyclyl, heteroaryl and aryl, wherein each of said alkyl, haloalkyl, haloalkoxy, alkoxy, cycloalkyl, aryl, heteroaryl and heterocyclyl is optionally and independently substituted with one to four $C_1$-$C_3$ alkyl, $C_1$-$C_4$ alkoxy, halogen, $C_1$-$C_3$ haloalkyl, —CN, —C(O)NH₂, —CO₂Et and heteroaryl;
$R^b$ is independently, at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$cycloalkenyl, $C_2$-$C_{10}$ alkynyl, $C_1$-$C_6$ haloalkyl, alkyl-O-alkyl, alkenyl, alkoxy, cycloalkenyl, alkynyl, haloalkyl, aryl, heteroaryl, and heterocyclyl wherein each of said alkyl, cycloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH₂, —COOH, —COOMe, —COOEt, —CN, —NO₂, —NH₂;
$R^c$ is independently, at each occurrence, selected from the group consisting of $C_1$-$C_{10}$ alkyl, $C_3$-$C_{10}$ cycloalkyl, $C_1$-$C_6$ alkyl-O-alkyl, $C_2$-$C_{10}$alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_6$ haloalkyl, alkyl-O-alkyl, alkenyl, alkoxy, cycloalkenyl, alkynyl, haloalkyl, aryl, heteroaryl, and heterocyclyl wherein each of said alkyl, cycloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH₂, —COOH, —COOMe, —COOEt, —CN, —NO₂, —NH₂; or
$R^b$ and $R^c$ are connected to each other to make a four, five or six membered saturated or unsaturated cyclic or heterocyclic ring;
or a pharmaceutically acceptable salts thereof.

4. A compound having general formula I:

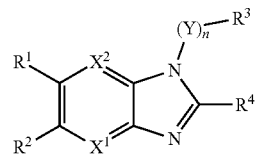

Formula I wherein
n is 0 or 1;
$X^1$ and $X^2$ are independently, at each occurrence, CR⁵ or N;
Y is $C_1$-$C_6$ alkylene, wherein alkylene is optionally substituted with one to two $C_1$-$C_3$ alkyl groups;
$R^1$ is selected from the group consisting of hydrogen, halogen, $C_1$-$C_6$ alkoxy, —NHR⁶, —NR⁷R⁸ and —NH—(R⁹)$_n$—R¹⁰, n being 0 or 1;
$R^2$ is selected from the group consisting of $C_1$-$C_6$ alkyl, —NH₂, —NHR⁶, —NR⁷R⁸ and —NH—(R⁹)$_n$—R¹⁰, n being 0 or 1;
$R^3$ is selected from the group consisting of hydroxyl, OR¹¹, —NR⁷R⁸, $C_1$-$C_6$ alkoxy, $C_1$-$C_6$ alkyl, $C_3$-$C_{10}$cycloalkyl, $C_1$-$C_3$ haloalkyl, —C(O)NHR¹¹, aryl, heteroaryl, wherein each of said cycloalkyl, aryl, and heteroaryl is optionally and independently substituted with one to four $R^a$ groups;
$R^4$ is —N(R¹²)(V)$_p$R¹³, R¹² is H, V is $C_1$-alkylene, p is 1, R¹³ is

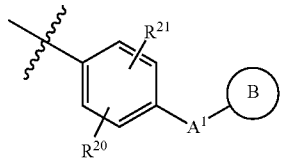

wherein A¹ is —O—, —CH₂O—, —OCH₂⁻, —S—, —SO₂⁻, —SO₂NH—, —C(O)—, —C(O)NH—, —C(O)N(R⁷)—, —CH(OH)—, —CH(OR⁷)—, —NH—, —N(CH₃)— or —N(CH₂COOR⁷)—; and B is heteroaryl which is optionally substituted with one to four $R^a$ groups;

R⁵ is selected from the group consisting of hydrogen, halogen, $C_1$-$C_6$ alkyl, $C_1$-$C_6$ haloalkyl and $C_1$-$C_6$ alkoxy;

R⁶ is selected from the group consisting of $C_1$-$C_6$ alkyl, $C_3$-$C_{10}$cycloalkyl, $C_1$-$C_6$ haloalkyl, aryl, heteroaryl and heterocyclyl, wherein each of said alkyl, cycloalkyl, haloalkyl, aryl, heteroaryl and heterocyclyl is optionally and independently substituted with one to four $R^a$ groups;

R⁷ and R⁸ are independently, at each occurrence, heterocyclyl; or

R⁷ and R⁸ are connected to each other to make a four, five or six membered heterocyclyl or heteroaryl group, wherein each of said heterocyclyl and heteroaryl is optionally and independently substituted with one to four $R^a$ groups;

R⁹ is $C_1$-$C_4$ alkylene, wherein said alkylene is optionally substituted with one to three $C_1$-$C_3$ alkyl groups;

R¹⁰ is selected from the group consisting of hydroxyl, —OR¹¹, —CN, —C(O)OR¹⁸, —C(O)NH₂, —C(NH)NH₂, aryl, heteroaryl and heterocyclyl wherein each of said aryl, heteroaryl and heterocyclyl is optionally and independently substituted with one to four $R^a$ groups;

R¹¹ is independently, at each occurrence, selected from the group consisting of aryl heteroaryl and heterocyclyl wherein each of said aryl, heteroaryl and heterocyclyl is optionally and independently substituted with one to four $R^a$ groups;

R¹⁸ is hydrogen or $C_1$-$C_6$ alkyl;

R²⁰ is selected from the group consisting of hydrogen, halogen, $C_1$-$C_6$ alkyl, $C_1$-$C_6$ alkoxy, —C(O)$R^a$ and $C_1$-$C_6$ haloalkoxy;

R²¹ is selected from the group consisting of hydrogen, halogen and $C_1$-$C_6$ alkyl;

$R^a$ is independently, at each occurrence, selected from the group consisting of hydrogen, halogen, $C_1$-$C_3$ alkyl, $C_3$-$C_{10}$ cycloalkyl, $C_1$-$C_4$ alkoxy, $C_1$-$C_4$ haloalkyl, $C_1$-$C_6$ haloalkoxy, hydroxyl, $C_1$-$C_3$ alkylhydroxyl, —CH₂OH, —OCH₃, —NR$^b$H, —C(O)NR$^b$H, —C(O)H, —CH₂OR$^c$, —OCH₂R$^c$, —OR$^c$, —CN, NO₂, —NR$^b$R$^c$, —C(O)NR$^b$R$^c$, —C(NH)NH₂, —C(O)R$^c$, —C(O)OR$^c$, sulfonyl, sulfoxide, heterocyclyl, heteroaryl and aryl, wherein each of said alkyl, haloalkyl, haloalkoxy, alkoxy, cycloalkyl, aryl, heteroaryl and heterocyclyl is optionally and independently substituted with one to four $C_1$-$C_3$ alkyl, $C_1$-$C_4$ alkoxy, halogen, $C_1$-$C_3$ haloalkyl, —CN, —C(O)NH₂, —CO₂Et or heteroaryl;

$R^b$ is independently, at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_6$ haloalkyl, aryl, heteroaryl, and heterocyclyl wherein each of said alkyl, cycloalkyl, alkyl-O-alkyl, alkenyl, alkoxy, cycloalkenyl, alkynyl, haloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH₂, —COOH, —COOMe, —COOEt, —CN, —NO₂, or —NH₂;

$R^c$ is independently, at each occurrence, selected from the group consisting of $C_1$-$C_{10}$alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$cycloalkenyl, $C_2$-$C_{10}$alkynyl, $C_1$-$C_6$ haloalkyl, aryl, heteroaryl, and heterocyclyl wherein each of said alkyl, cycloalkyl, alkyl-O-alkyl, alkenyl, alkoxy, cycloalkenyl, alkynyl, haloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH₂, —COOH, —COOMe, —COOEt, —CN, —NO₂, or —NH₂; or $R^b$ and $R^c$ are connected to each other to make a four, five or six membered saturated or unsaturated cyclic or heterocyclic ring;

or a pharmaceutically acceptable salts thereof.

5. A method of inhibiting the activity on an enzyme involved in an inflammatory pathway or several inflammatory pathways, using a compound according to claim 1 at a concentration between 0.001-50 μM, wherein the enzyme is selected from arachidonate 5-lipoxygenase, LTA4-synthase, LTA4-hydrolase, LTC4-synthase, glutamyltranspeptidase, cysteinylglycinase, 5-hydroxy-6,8,11,14-eicosatetraenoic acid dehydrogenase, cyclooxygenase-2, and prostaglandin E synthase.

6. A composition comprising a compound or a pharmaceutically acceptable salt thereof, as defined in claim 1, and a pharmaceutically acceptable carrier.

7. A method of treatment of a disease associated with the 5-LOX-pathway and/or the prostaglandin E synthase (PGES) pathway, said disease being selected from inflammatory diseases, cancer and Alzheimer's disease, said method comprising the administration of a suitable amount of a compound as defined in claim 1 to a patient in need thereof, suffering from a disease associated with the 5-LOX-pathway and/or the prostaglandin E synthase (PGES) pathway.

8. The method of treatment according to claim 7, wherein said inflammatory disease is selected from asthma, allergic rhinitis, dermatitis, chronic obstructive pulmonary disease (COPD), inflammation post infection, arthritis, atherosclerosis, an allergy, an autoimmune disease, an inflammatory bowel disease, celiac disease, acne, and pain.

9. The method, according to claim 5, wherein said compound has an IC₅₀ on arachidonate 5-lipoxygenase of less than 1 μM and/or an EC₅₀ of less than 10 μM on the production of leukotriene B4 (LTB4) in rat basophilic leucocyte cells (RBL) and/or rat whole blood (RWB), and/or has a 40-70% inhibitory activity, or a >70% inhibitory activity, on the production of prostaglandin E2 in HeLaS3 cells, stimulated with TNF-α, at a concentration of 10 μM of said compound.

10. The method, according to claim 8, wherein the inflammatory disease is hay fever, lupus erythematosus, Crohn's disease, inflammatory pain or neuropathic pain.

11. A compound having general formula II:

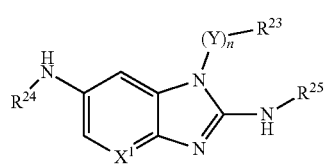

Formula II wherein
n is 0 or 1;
X1 is CR⁵ or N;
Y is $C_1$-$C_6$ alkylene, wherein alkylene is optionally substituted with one to two $C_1$-$C_3$ alkyl groups;
R⁵ is selected from the group consisting of hydrogen, halogen, $C_1$-$C_6$ alkyl, $C_1$-$C_6$ haloalkyl and $C_1$-$C_6$alkoxy;

R²³ is selected from the group consisting of C₁-C₆ alkyl, C₁-C₃ haloalkyl, aryl, heteroaryl and heterocyclyl, wherein each of said aryl, heteroaryl and heterocyclyl is optionally and independently substituted with one to four Rᵃ groups;

R²⁴ is selected from the group consisting of C₃-C₁₀ cycloalkyl, aryl, heteroaryl and heterocyclyl, wherein each of said cycloalkyl, aryl, heteroaryl and heterocyclyl is optionally and independently substituted with one to four Rᵃ groups;

R²⁵ is selected from the group consisting of —(V)ₚR²⁶ and —(V)ₚ—OR¹⁴;

wherein, p is 1,

V is C₁-C₆ alkylene, wherein alkylene is optionally substituted with one to three C₁-C₃ alkyl or phenyl groups, or wherein a carbon atom of said alkylene forms part of a C₃-C₆ cycloalkyl group;

R¹⁴ is selected from the group consisting of hydrogen, C₁-C₆ alkyl and aryl, wherein each of said alkyl and aryl is optionally and independently substituted with one to four halogen or C₁-C₃ haloalkoxy groups;

R²⁶ is selected from the group consisting of hydrogen, C₁-C₆ alkyl, —CN and C₁-C₃ haloalkyl, and groups of formula IIa shown below,

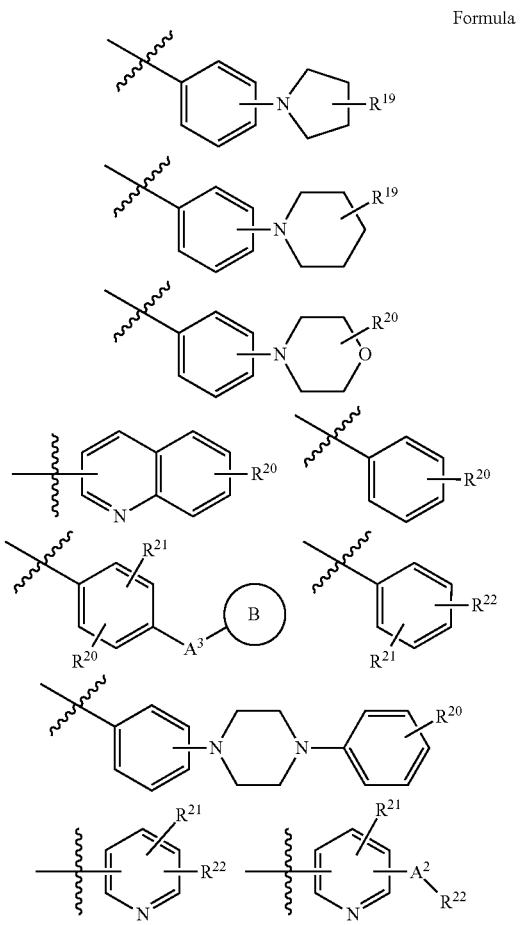

Formula IIa wherein,

A² is —O— or NH—;

A³ is —O—, —CH₂O—, —OCH₂⁻, or —NH—;

B is selected from the group consisting of aryl, heteroaryl and heterocyclyl wherein each of said aryl, heteroaryl and heterocyclyl is optionally and independently substituted with one to four Rᵃ groups;

R¹⁹ is selected from the group consisting of hydrogen, —OR²² and —CH₂OR²²;

R²⁰ is selected from the group consisting of hydrogen, halogen, C₁-C₆ alkyl, C₁-C₆ alkoxy and C₁-C₆ haloalkoxy;

R²¹ is selected from the group consisting of hydrogen, halogen and C₁-C₆ alkyl;

R²² is selected from the group consisting of aryl, and heteroaryl, wherein each of said aryl and heteroaryl is optionally and independently substituted with one to four Rᵃ groups;

Rᵃ is independently, at each occurrence, selected from the group consisting of hydrogen, halogen, C₁-C₃ alkyl, C₃-C₁₀ cycloalkyl, C₁-C₄ alkoxy, C₁-C₄ haloalkyl, C₁-C₆ haloalkoxy, hydroxyl, C₁-C₃ alkylhydroxyl, —CH₂ORᶜ, —OCH₂Rᶜ, —ORᶜ, —CN, NO₂, —NRᵇRᶜ, —C(O)NRᵇRᶜ, —C(NH)NH₂, —C(O)Rᶜ, —C(O)ORᶜ, sulfonyl, sulfoxide, heterocyclyl, heteroaryl and aryl, wherein each of said alkyl, haloalkyl, haloalkoxy, alkoxy, cycloalkyl, aryl, heteroaryl and heterocyclyl is optionally and independently substituted with one to four C₁-C₃ alkyl, C₁-C₄ alkoxy, halogen, C₁-C₃ haloalkyl, —CN, —C(O)NH₂, —COOH, —CO₂Et and heteroaryl;

Rᵇ and Rᶜ are independently, at each occurence, selected from the group consisting of hydrogen, C₁-C₁₀ alkyl, C₃-C₁₀ cycloalkyl, C₁-C₆ alkyl-O-alkyl, C₂-C₁₀ alkenyl, C₁-C₄ alkoxy, C₁-C₃ alkylhydroxyl, C₃-C₁₀ cycloalkenyl, C₂-C₁₀ alkynyl, C₁-C₆ haloalkyl, aryl, heteroaryl, and heterocyclyl wherein each of said alkyl, alkyl-O-alkyl, alkenyl, alkoxy, cycloalkenyl, alkynyl, haloalkyl, cycloalkyl, aryl, heteroaryl and heterocyclyl is optionally and independently substituted with one to four C₁-C₃ alkyl, C₁-C₄ alkoxy, halogen, C₁-C₆ haloalkyl, C₁-C₆ haloalkoxy, hydroxyl, —C(O)NH₂, —COOH, —COOMe, —COOEt, —CN, —NO₂, —NH₂; or Rᵇ and Rᶜ are connected to each other to make a four, five or six membered saturated or unsaturated cyclic or heterocyclic ring;

or a pharmaceutically acceptable salts thereof.

12. A compound having general formula III:

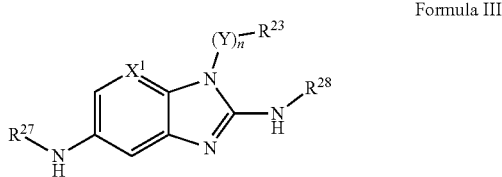

Formula III wherein n is 0 or 1;

X¹ is CR⁵ or N;

Y is C₁-C₆ alkylene, wherein alkylene is optionally substituted with one to two C₁-C₃ alkyl groups;

R⁵ is selected from the group consisting of hydrogen, halogen, C₁-C₆ alkyl, C₁-C₆ haloalkyl and C₁-C₆ alkoxy;

R²³ is selected from the group consisting of C₁-C₆ alkyl, aryl, heteroaryl and heterocyclyl, wherein each of said aryl, heteroaryl and heterocyclyl is optionally and independently substituted with one to four $R^a$ groups;

$R^{27}$ is selected from the group consisting of hydrogen, —$R^6$, and —$R^9$—$R^{10}$;

wherein, $R^6$ is selected from the group consisting of $C_1$-$C_6$ alkyl, $C_3$-$C_{10}$ cycloalkyl, $C_1$-$C_6$ haloalkyl, aryl, heteroaryl and heterocyclyl, wherein said alkyl, cycloalkyl, haloalkyl, aryl, heteroaryl and heterocyclyl is optionally and independently substituted with one to four $R^a$ groups;

$R^9$ is $C_1$-$C_4$ alkylene, wherein said alkylene is optionally substituted with one to three $C_1$-$C_3$ alkyl groups;

$R^{10}$ is selected from the group consisting of hydroxyl, —$OR^{11}$, —$C(O)OR^{18}$, —$C(O)NH_2$, aryl, heteroaryl and heterocyclyl wherein each of said aryl, heteroaryl and heterocyclyl is optionally and independently substituted with one to four $R^a$ groups;

$R^{11}$ is independently, at each occurrence selected from the group consisting of aryl, heteroaryl and heterocyclyl group wherein said aryl, heteroaryl and heterocyclyl is optionally and independently substituted with one to four $R^a$ groups;

$R^{18}$ is hydrogen or $C_1$-$C_6$ alkyl;

$R^{28}$ is selected from the group consisting of —$(V)_p R^{29}$ and —$(V)_p$—$OR^{14}$;

wherein, p is 1,

V is $C_1$-$C_6$ alkylene, wherein alkylene is optionally substituted with one to three $C_1$-$C_6$ alkyl or phenyl groups;

$R^{14}$ is selected from the group consisting of hydrogen, $C_1$-$C_6$ alkyl and aryl, wherein each of said alkyl and aryl is optionally and independently substituted with one to four halogen or $C_1$-$C_3$ haloalkoxy groups;

$R^{29}$ is selected from the group consisting of $C_4$-$C_6$ alkyl and $C_1$-$C_3$ haloalkyl, and groups of formula IIIa shown below,

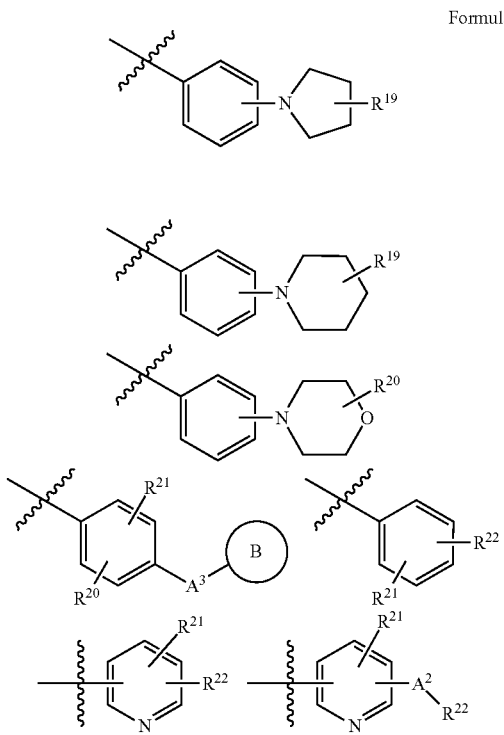

Formula IIIa wherein, $A^2$ is —O— or NH—;

$A^3$ is —O—, —$CH_2O$—, —$OCH_2$—, or —NH—;

B is selected from the group consisting of aryl, heteroaryl and heterocyclyl wherein each of said aryl, heteroaryl and heterocyclyl is optionally and independently substituted with one to four $R^a$ groups;

$R^{19}$ is selected from the group consisting of hydrogen, —$OR^{22}$ and —$CH_2OR^{22}$;

$R^{20}$ is selected from the group consisting of hydrogen, halogen, $C_1$-$C_6$ alkyl, $C_1$-$C_6$ alkoxy and $C_1$-$C_6$ haloalkoxy;

$R^{21}$ is selected from the group consisting of hydrogen, halogen and $C_1$-$C_6$ alkyl;

$R^{22}$ is selected from the group consisting of aryl, and heteroaryl, wherein said aryl and heteroaryl is optionally and independently substituted with one to four $R^a$ groups;

$R^a$ is independently, at each occurrence, selected from the group consisting of hydrogen, halogen, $C_1$-$C_3$ alkyl, $C_3$-$C_{10}$ cycloalkyl, $C_1$-$C_4$ alkoxy, $C_1$-$C_4$ haloalkyl, $C_1$-$C_6$ haloalkoxy, hydroxyl, $C_1$-$C_3$ alkylhydroxyl, —$CH_2OH$, —$OCH_3$, —$NR^bH$, —$C(O)NR^bH$, —$C(O)H$, —$CH_2OR^c$, —$OCH_2R^c$, —$OR^c$, —CN, $NO_2$, —$NR^bR^c$, —$C(O)NR^bR^c$, —$C(NH)NH_2$, —$C(O)R^c$, —$C(O)OR^c$, sulfonyl, sulfoxide, heterocyclyl, heteroaryl and aryl, wherein each of said alkyl, haloalkyl, haloalkoxy, alkoxy, cycloalkyl, aryl, heteroaryl and heterocyclyl is optionally and independently substituted with one to four $C_1$-$C_3$ alkyl, $C_1$-$C_4$ alkoxy, halogen, $C_1$-$C_3$ haloalkyl, —CN, —$C(O)NH_2$, —$CO_2Et$ and heteroaryl;

$R^b$ is independently, at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$cycloalkenyl, $C_2$-$C_{10}$ alkynyl, $C_1$-$C_6$haloalkyl, alkyl-O-alkyl, alkenyl, alkoxy, cycloalkenyl, alkynyl, haloalkyl, aryl, heteroaryl, and heterocyclyl wherein each of said alkyl, cycloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —$C(O)NH_2$, —COOH, —COOMe, —COOEt, —CN, —$N_2$, —$NH_2$;

$R^c$ is independently, at each occurrence, selected from the group consisting of $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$cycloalkenyl, $C_2$-$C_{10}$ alkynyl, $C_1$-$C_6$haloalkyl, alkyl-O-alkyl, alkenyl, alkoxy, cycloalkenyl, alkynyl, haloalkyl, aryl, heteroaryl, and heterocyclyl wherein each of said alkyl, cycloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —$C(O)NH_2$, —COOH, —COOMe, —COOEt, —CN, —$NO_2$, —$NH_2$, or $R^b$ and $R^c$ are connected to each other to make a four, five or six membered saturated or unsaturated cyclic or heterocyclic ring;

or a pharmaceutically acceptable salts thereof.

13. A compound having one of the following formulae:
| No. | Structure |
|---|---|
| 35 | 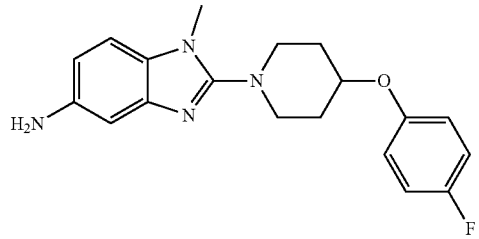 [SMILES: Cn1c(N2CCC(Oc3ccc(F)cc3)CC2)nc2cc(N)ccc21] |
| 47 | 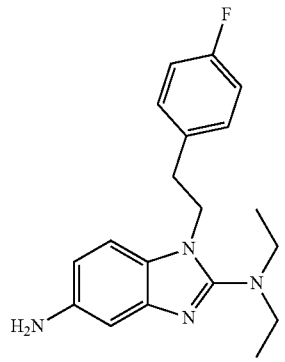 [SMILES: CCN(CC)c1nc2cc(N)ccc2n1CCc1ccc(F)cc1] |
| 50 | 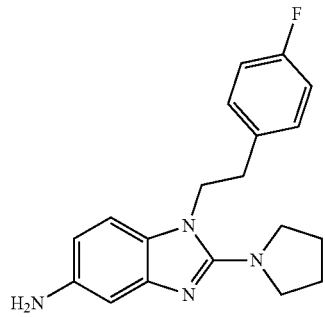 [SMILES: Nc1ccc2c(c1)nc(N1CCCC1)n2CCc1ccc(F)cc1] |
| 53 | 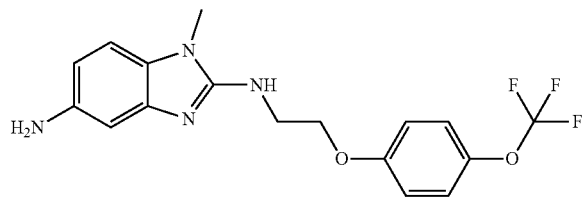 |
| 55 | 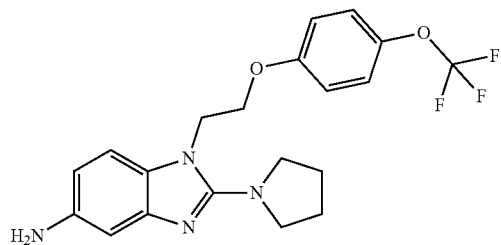 [SMILES: Nc1ccc2c(c1)nc(N1CCCC1)n2CCOc1ccc(OC(F)(F)F)cc1] |

| No. | Structure |
|---|---|
| 57 | 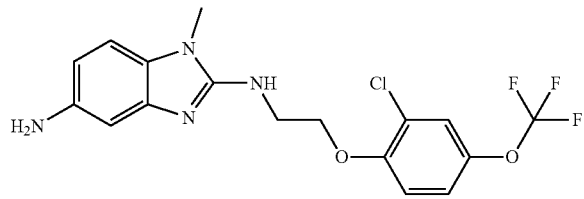 |
| 59 | 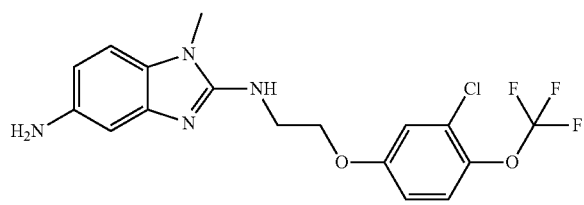 [SMILES: Cn1c(NCCOc2ccc(OC(F)(F)F)c(Cl)c2)nc2cc(N)ccc21] |
| 61 | 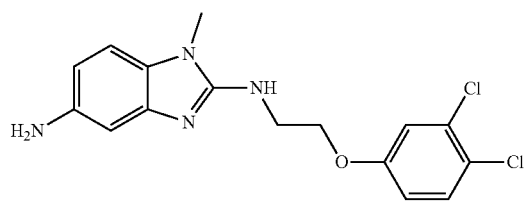 [SMILES: Cn1c(NCCOc2ccc(Cl)c(Cl)c2)nc2cc(N)ccc21] |
| 70 | 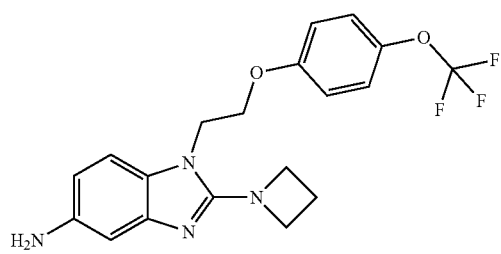 [SMILES: Nc1ccc2c(c1)nc(N1CCC1)n2CCOc1ccc(OC(F)(F)F)cc1] |
| 72 | 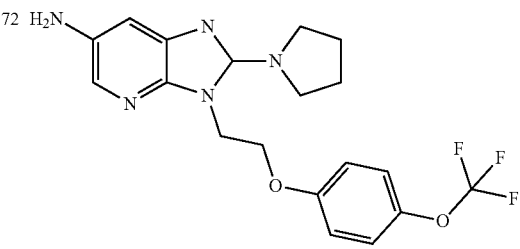 |
| 82 | 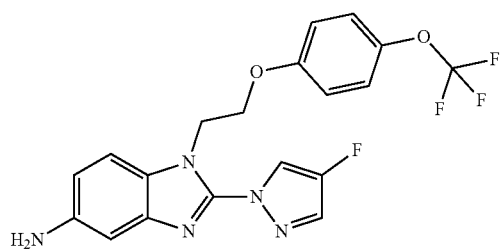 [SMILES: Nc1ccc2c(c1)nc(-n1cc(F)cn1)n2CCOc1ccc(OC(F)(F)F)cc1] |

-continued
| No. | Structure |
|---|---|
| 84 | 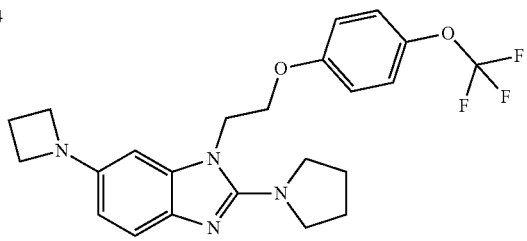 |
| 85 | 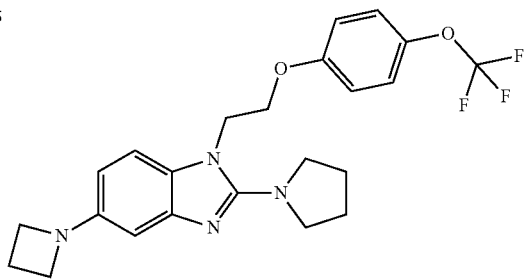 |
| 170 | 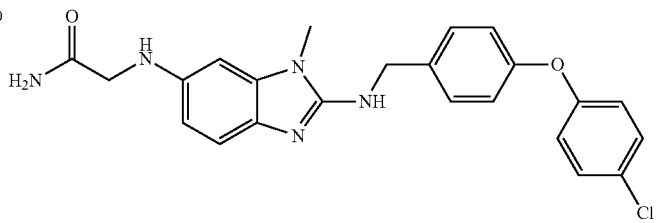 |
| 171 | 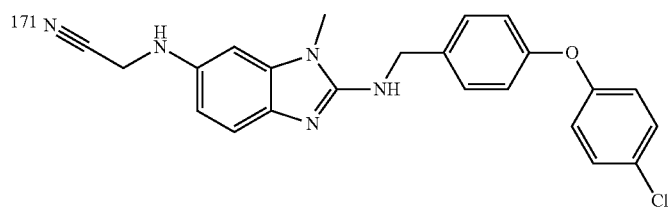 |
| 182 | 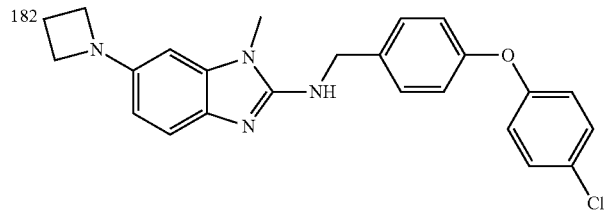 |
| 184 | 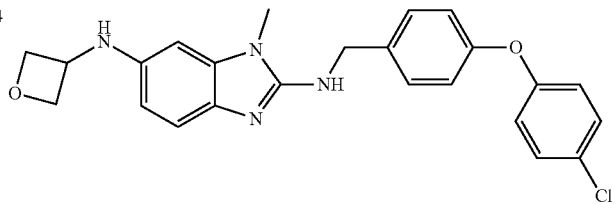 |

| No. | Structure |
|---|---|
| 192 | 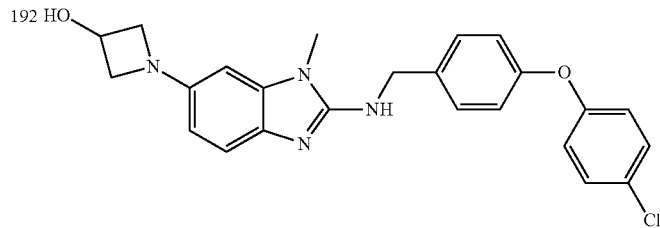 |
| 193 | 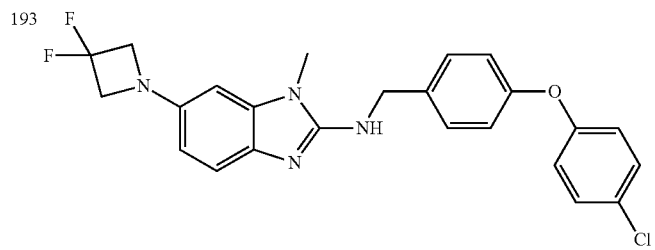 |
| 204 | 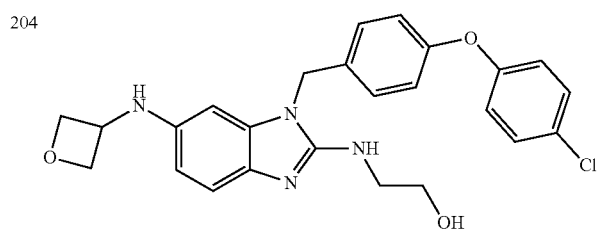 |
| 208 | 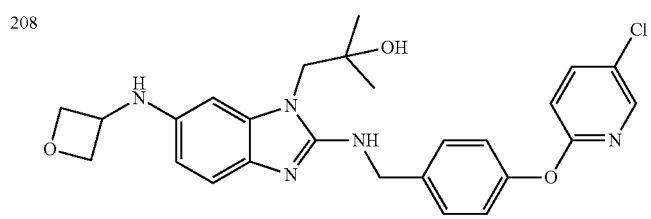 |
| 211 | 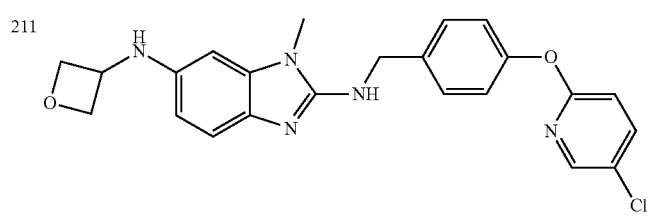 |
| 226 | 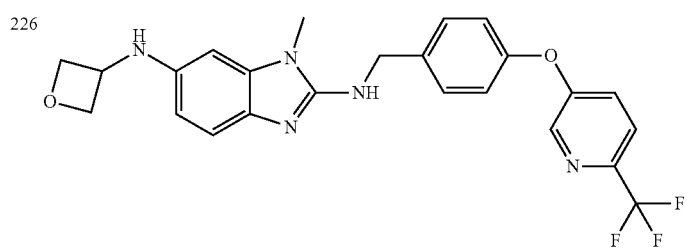 |
| 227 | 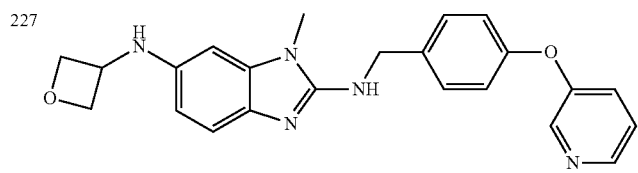 |

| No. | Structure |
|---|---|
| 251 | 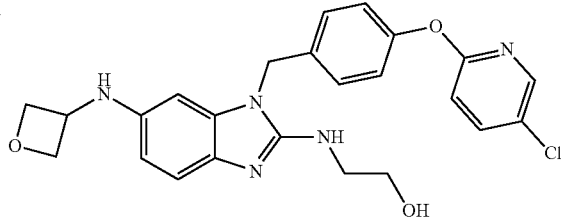 [SMILES: OCCNc1nc2ccc(NC3COC3)cc2n1Cc1ccc(Oc2ccc(Cl)cn2)cc1] |
| 256 | 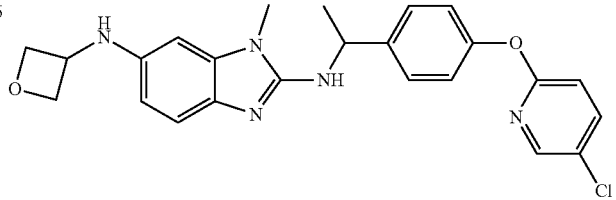 |
| 257 | 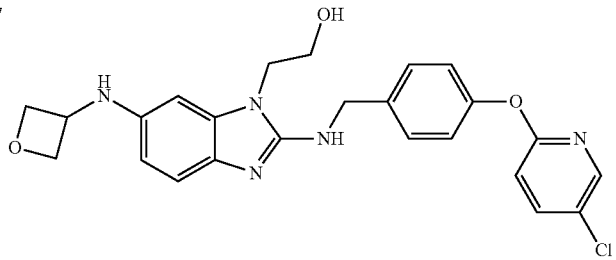 |
| 262 | 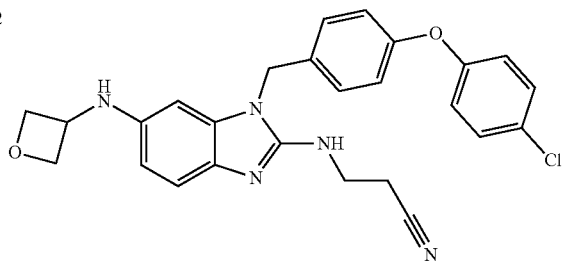 |
| 268 | 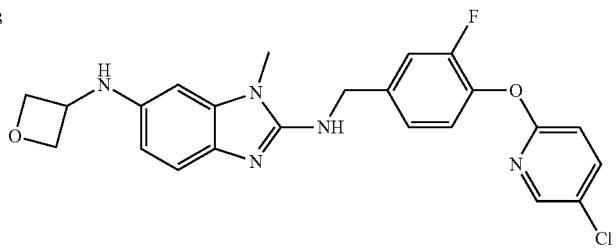 |
| 269 | 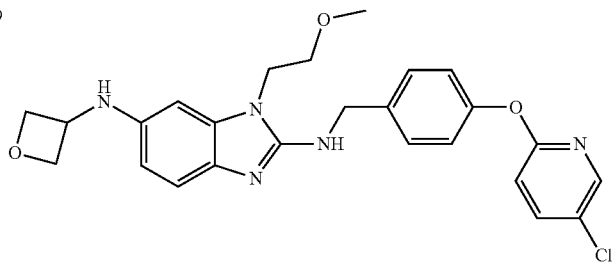 |

| No. | Structure |
|---|---|
| 270 | 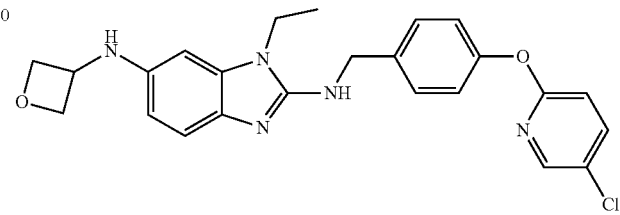 |
| 271 | 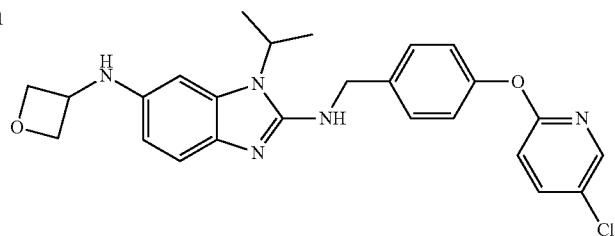 |
| 273 | 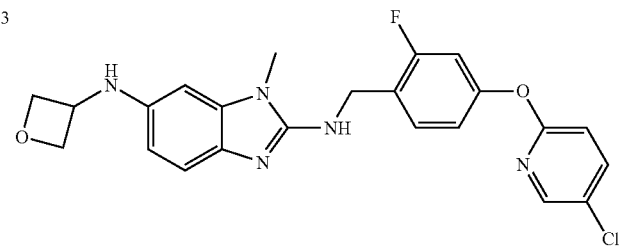 |
| 275 | 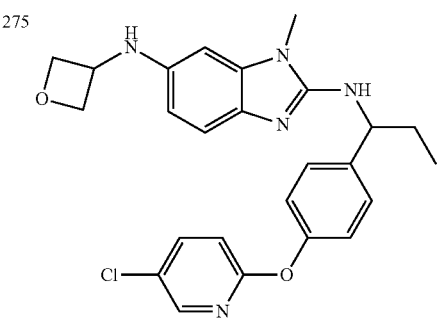 |
| 279 | 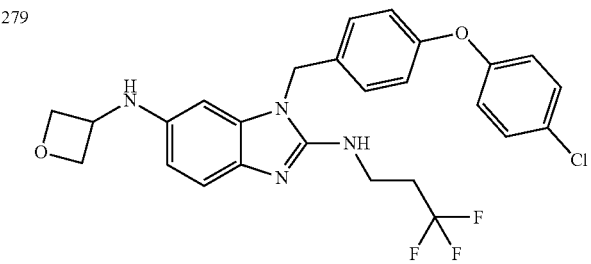 |
| 281 | 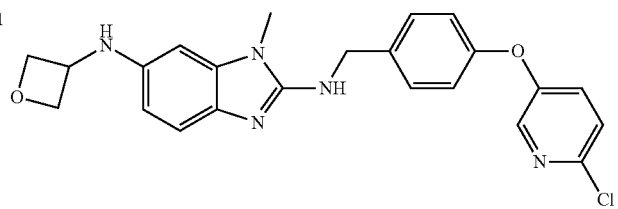 |

| No. | Structure |
|---|---|
| 283 | 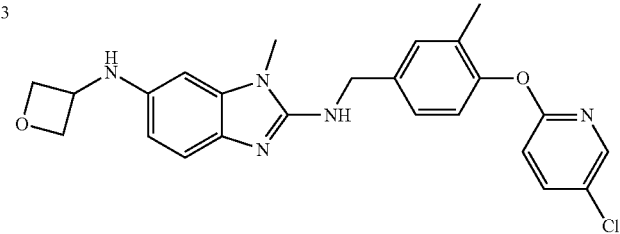 |
| 284 | 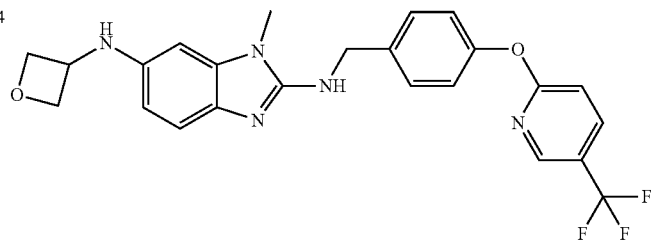 |
| 289 | 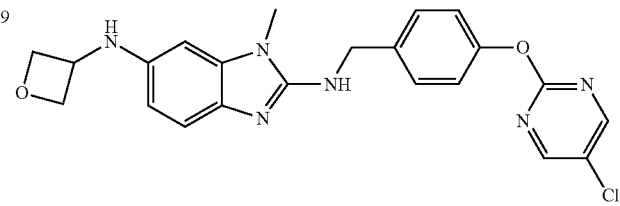 |
| 291 | 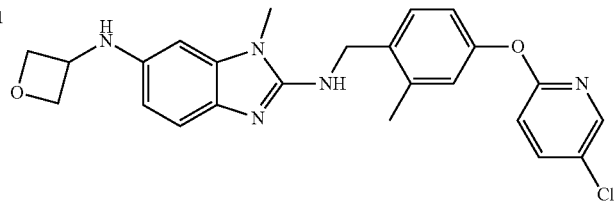 |
| 293 | 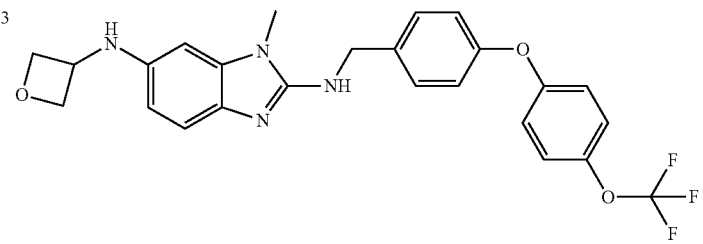 |
| 294 | 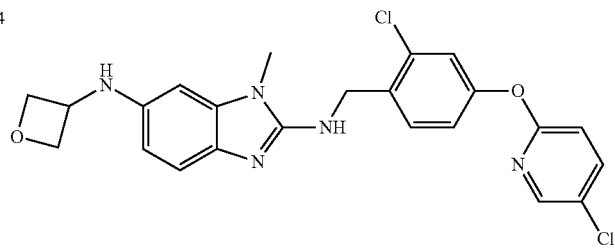 |

| No. | Structure |
|---|---|
| 296 | 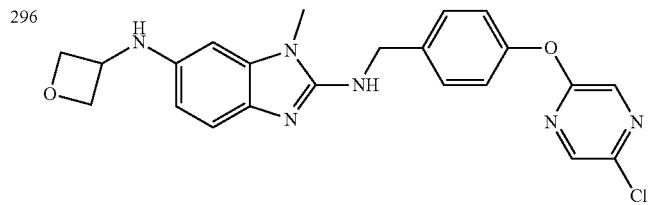 |
| 298 | 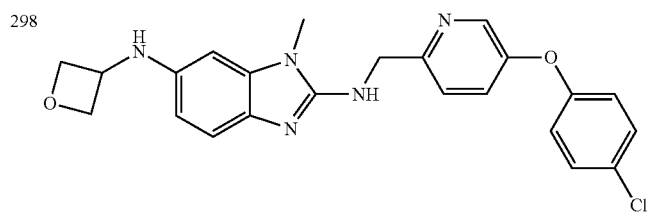 |
| 300 | 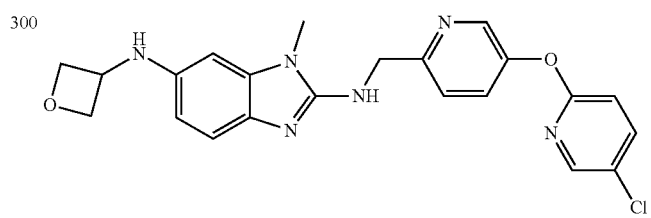 |
| 302 | 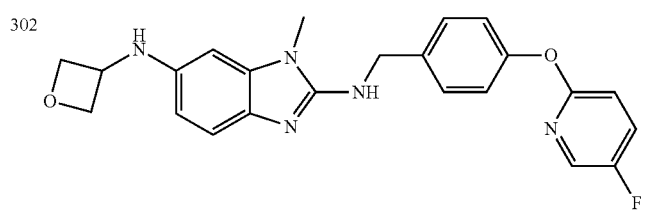 |
| 303 | 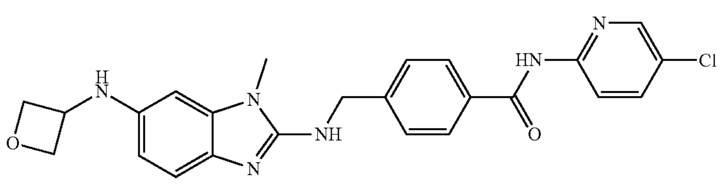 [SMILES: Cn1c(NCc2ccc(C(=O)Nc3ccc(Cl)cn3)cc2)nc2ccc(NC3COC3)cc21] |
| 305 | 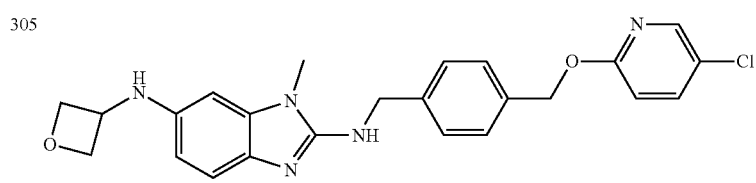 |
| 306 | 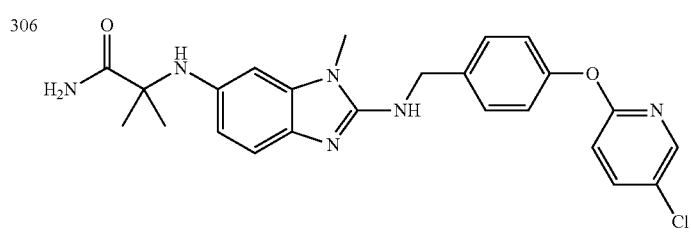 |

| No. | Structure |
|---|---|
| 307 | 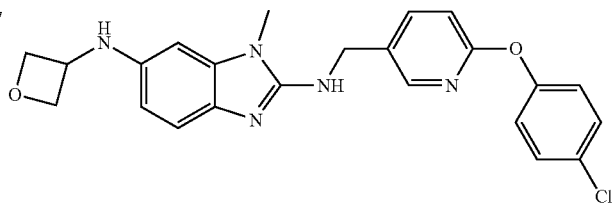 |
| 309 | 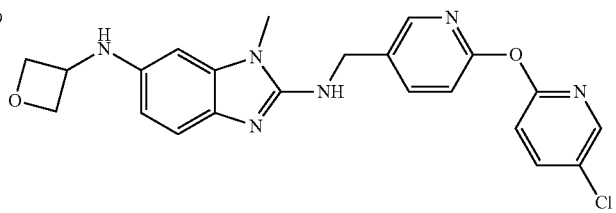 |
| 312 | 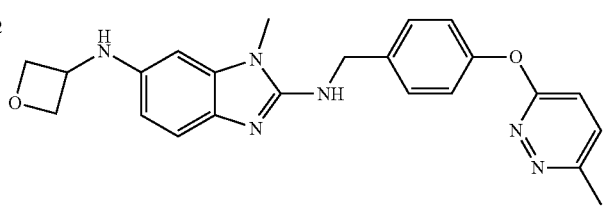 |
| 313 | 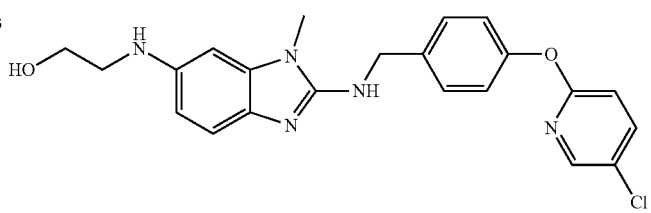 |
| 315 | 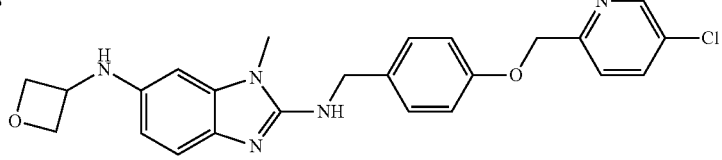 |
| 316 | 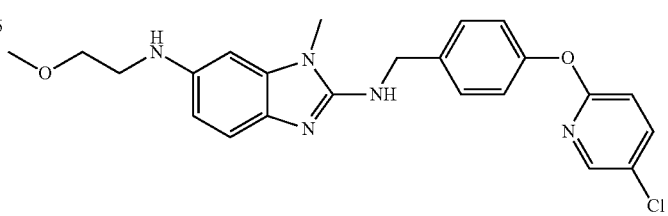 |
| 318 | 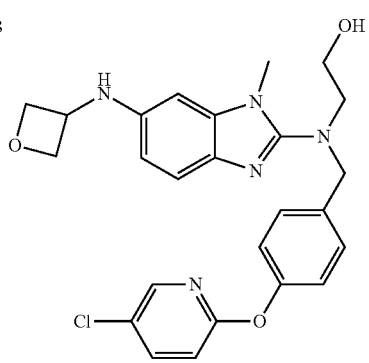 |

| No. | Structure |
|---|---|
| 320 | 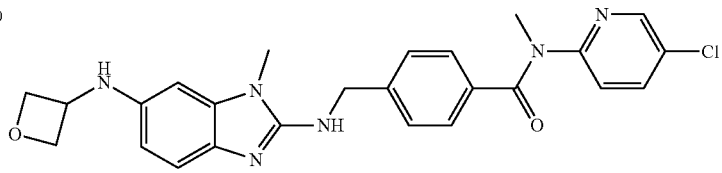 |
| 322 | 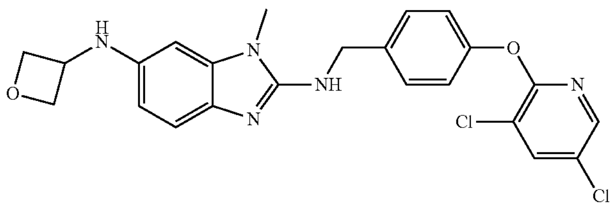 |
| 324 | 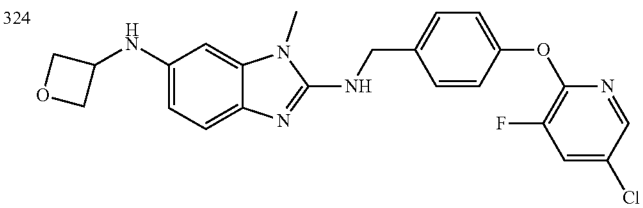 |
| 325 | 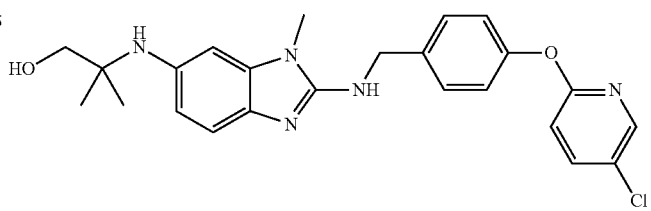 |
| 326 | 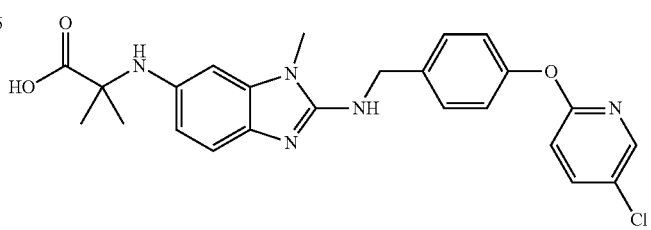 [SMILES: Cn1c(NCc2ccc(Oc3ccc(Cl)cn3)cc2)nc2ccc(NC(C)(C)C(N)=O)cc21] |
| 328 | 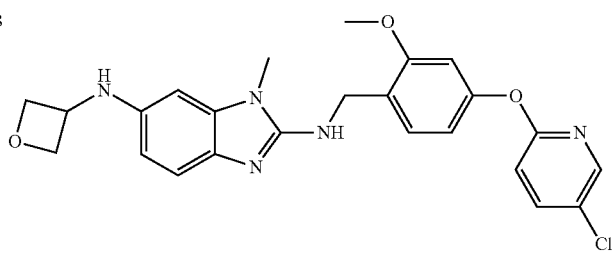 |
| 329 | 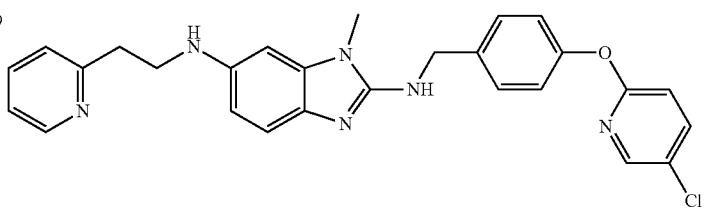 |

| No. | Structure |
|---|---|
| 331 | 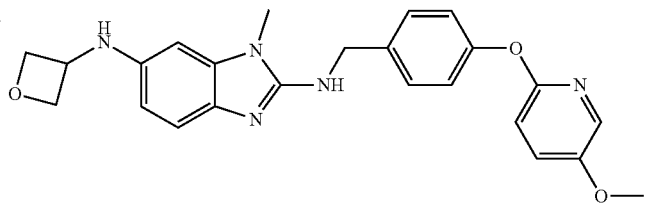 [SMILES: COc1ccc(Oc2ccc(CNc3nc4ccc(NC5COC5)cc4n3C)cc2)nc1] |
| 333 | 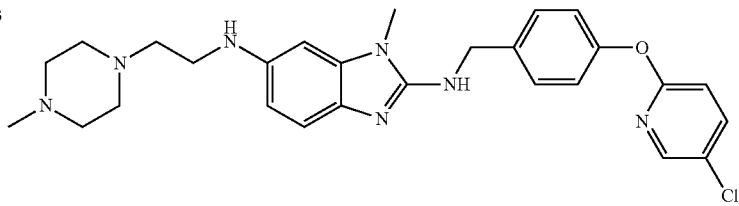 |
| 335 | 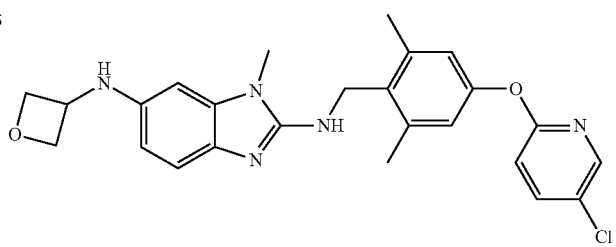 |
| 337 | 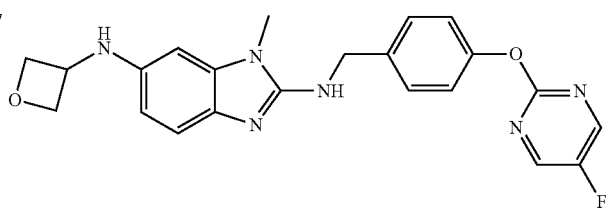 |
| 339 | 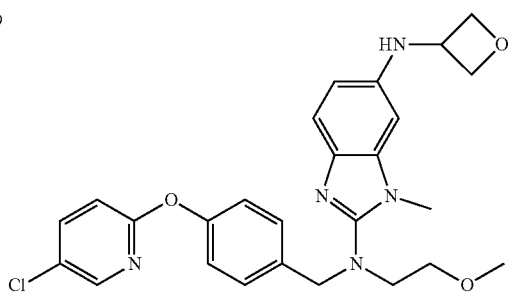 |
| 341 | 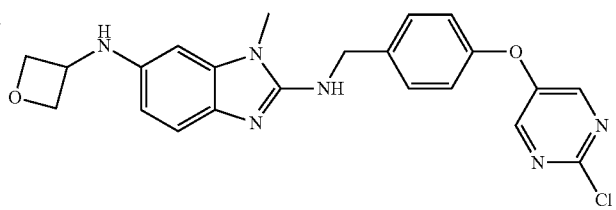 [SMILES: Cn1c(NCc2ccc(Oc3cnc(Cl)nc3)cc2)nc2ccc(NC3COC3)cc21] |
| 343 | 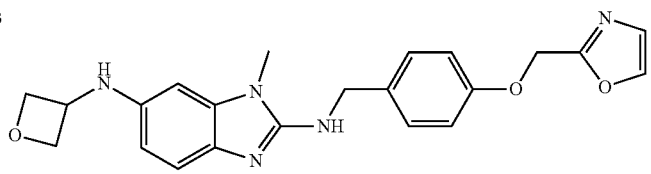 |

-continued
| No. | Structure |
|---|---|
| 345 | 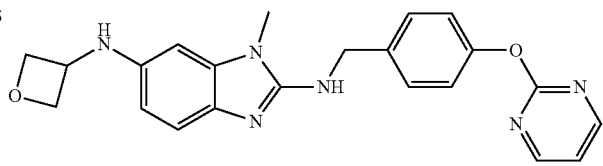 |
| 347 | 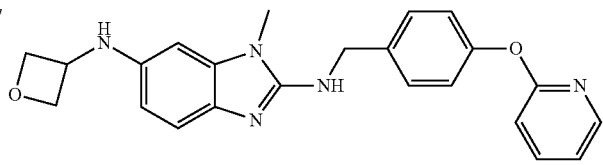 |
| 349 | 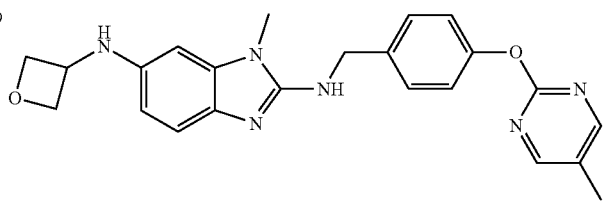 |
| 351 | 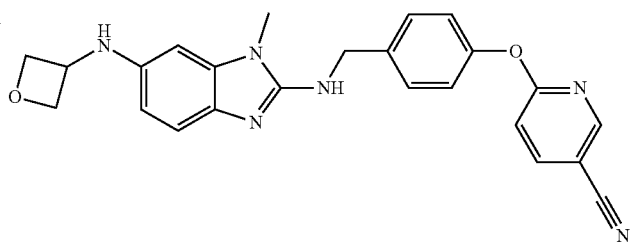 [SMILES: Cn1c(NCc2ccc(Oc3ccc(C#N)cn3)cc2)nc2ccc(NC3COC3)cc21] |
| 353 | 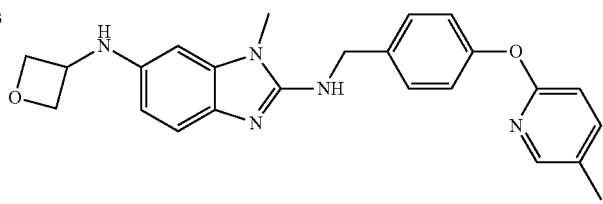 |
| 355 | 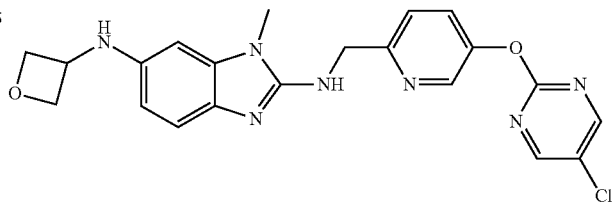 |
| 357 | 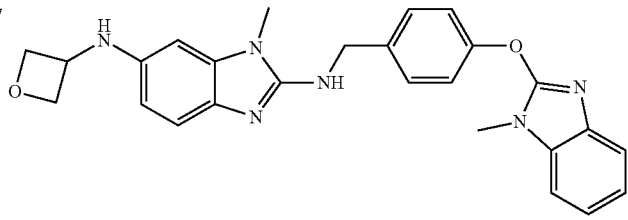 |

| No. | Structure |
|---|---|
| 358 | 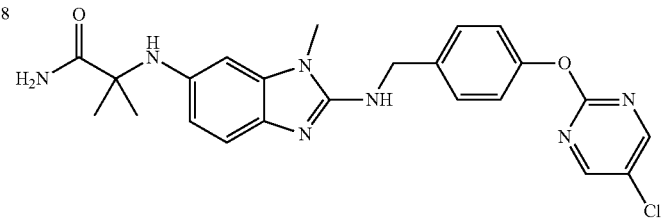 |
| 359 | 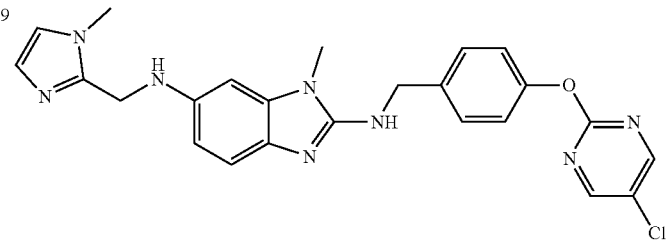 |
| 362 | 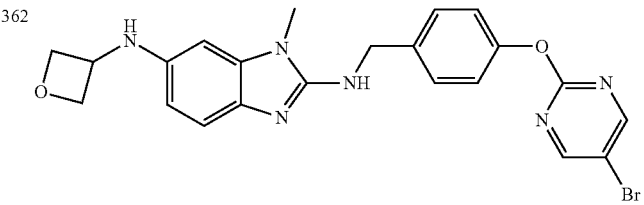 |
| 364 | 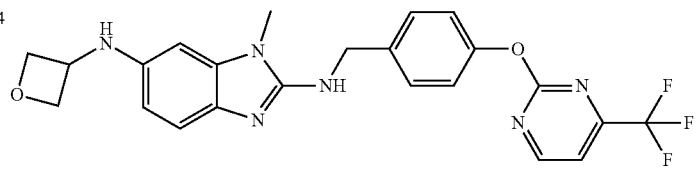 |
| 365 | 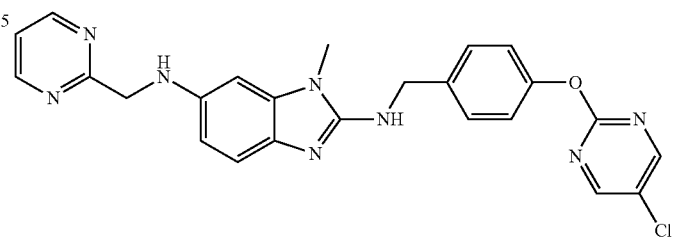 |
| 366 | 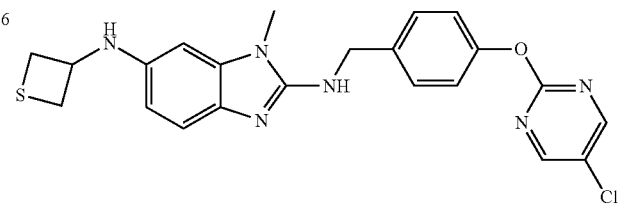 |
| 368 | 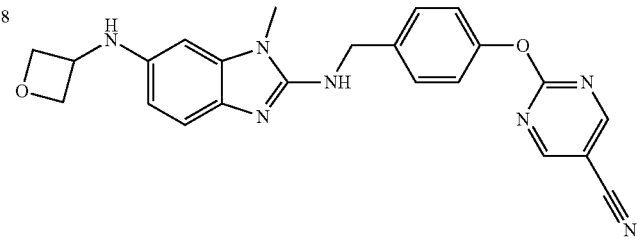 |

| No. | Structure |
|---|---|
| 369 | 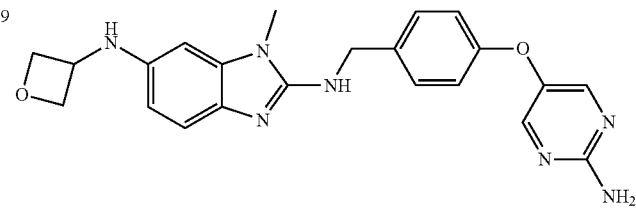 |
| 371 | 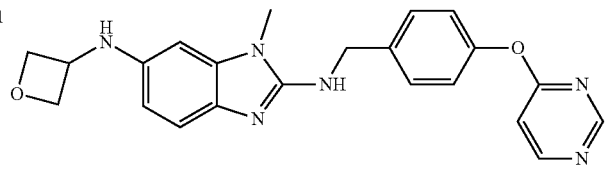 |
| 372 | 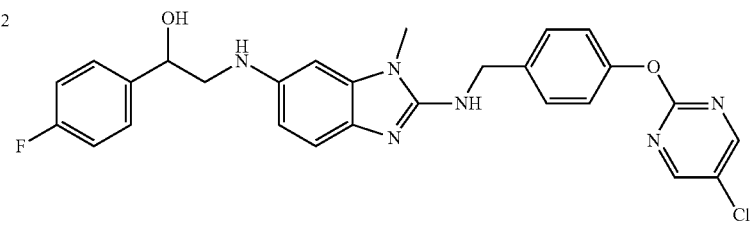 |
| 374 | 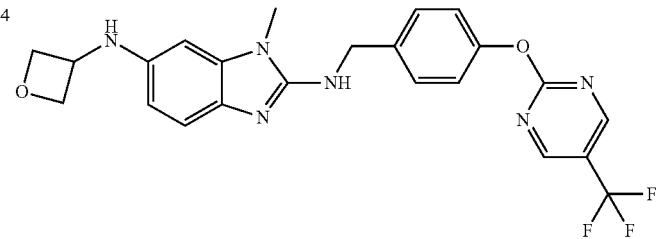 |
| 378 | 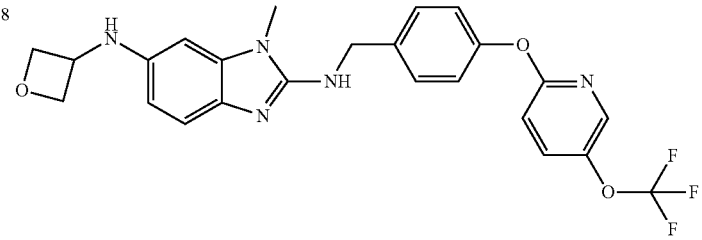 |
| 379 | 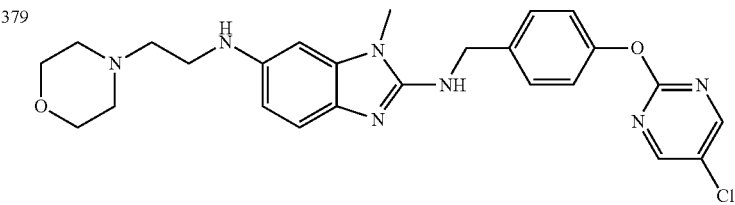 |
| 381 | 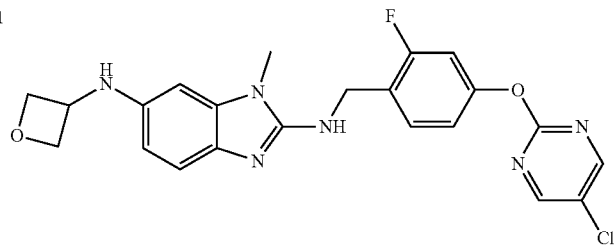 |

| No. | Structure |
|---|---|
| 383 | 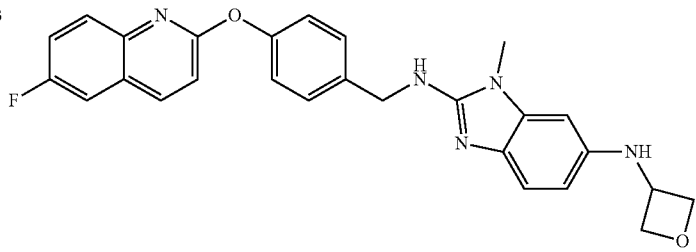 [SMILES: Cn1c(NCc2ccc(Oc3ncc4cc(Cl)ccc4n3)cc2)nc2ccc(NC3COC3)cc21] |
| 384 | 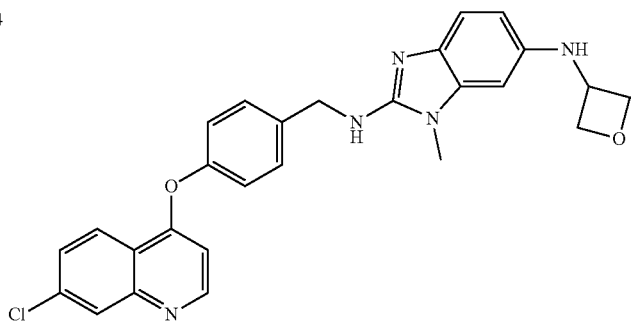 |
| 386 | 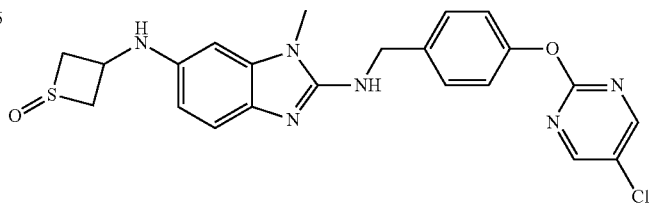 |
| 388 | 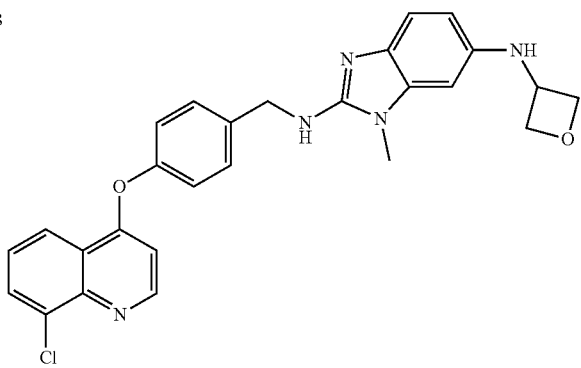 |
| 390 | 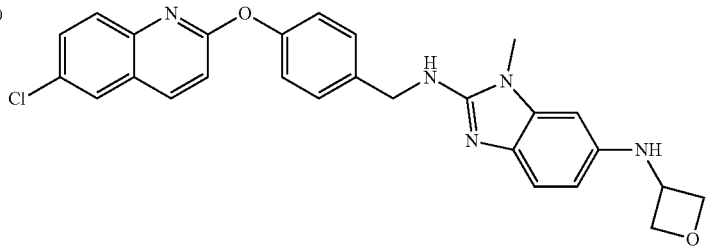 |

| No. | Structure |
|---|---|
| 392 | 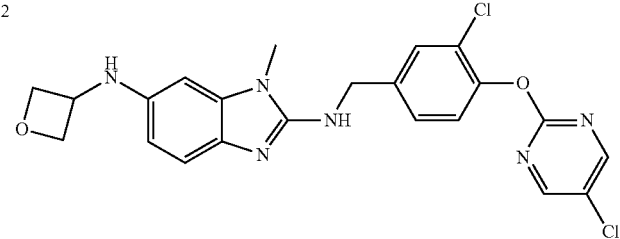 |
| 394 | 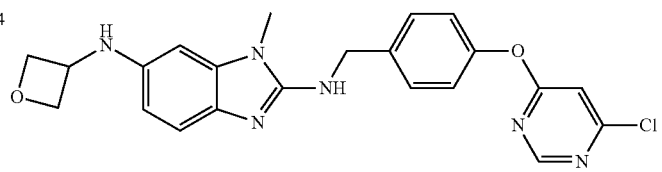 |
| 396 | 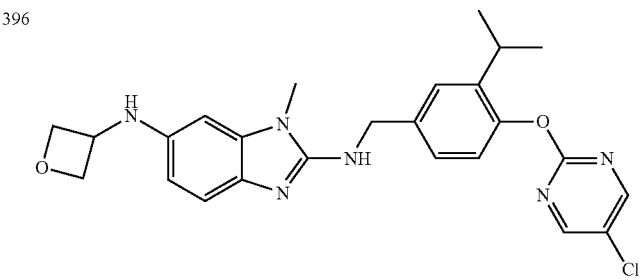 |
| 398 | 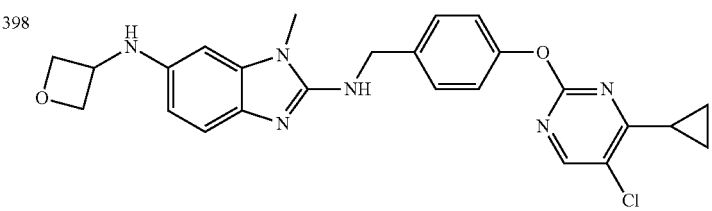 |
| 400 | 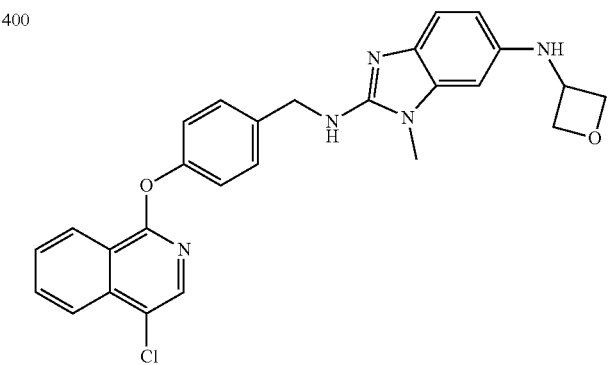 |
| 401 | 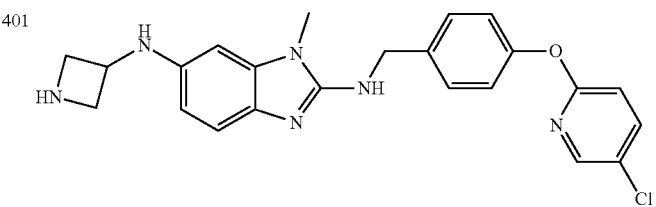 |

-continued
| No. | Structure |
|---|---|
| 403 | 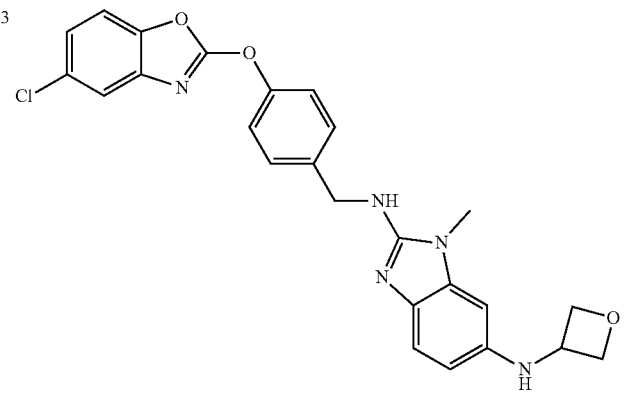 |
| 404 | 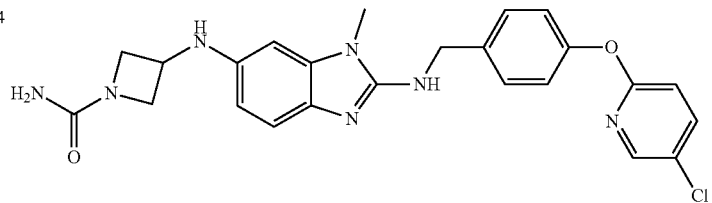 |
| 406 | 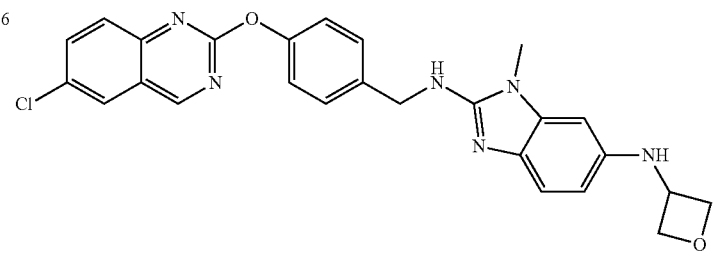 |
| 407 | 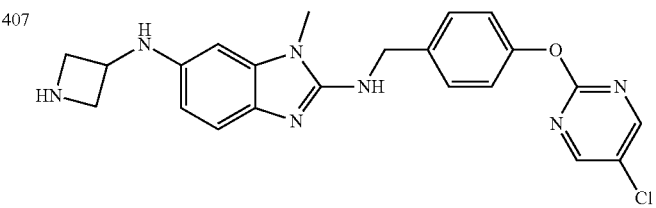 |
| 408 | 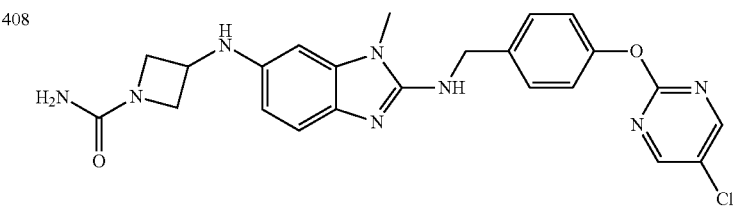 |
| 409 | 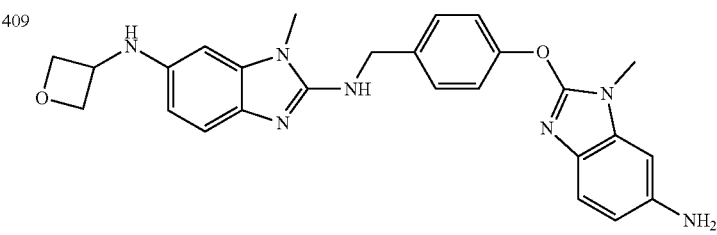 |

| No. | Structure |
|---|---|
| 412 | 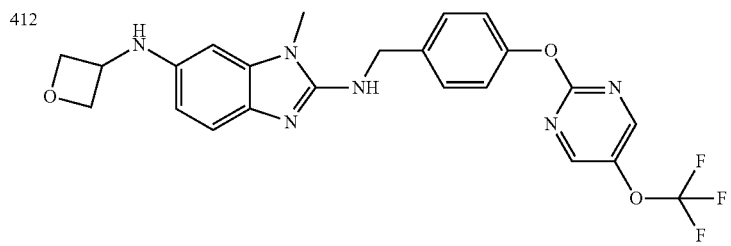 |
| 413 | 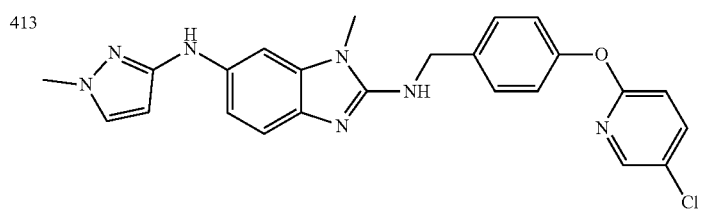 |
| 414 | 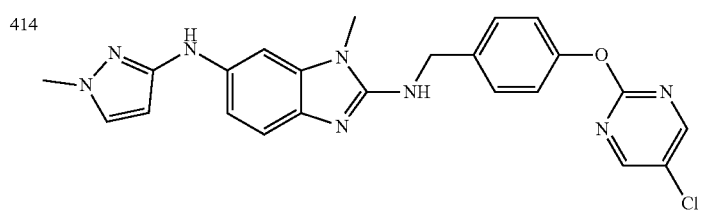 |
| 415 | 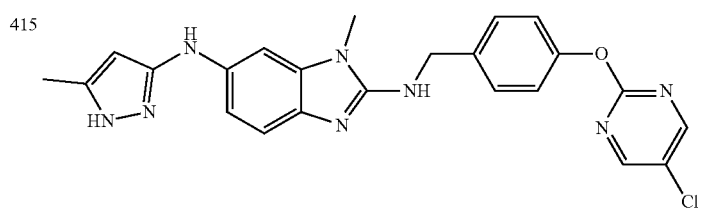 |
| 417 | 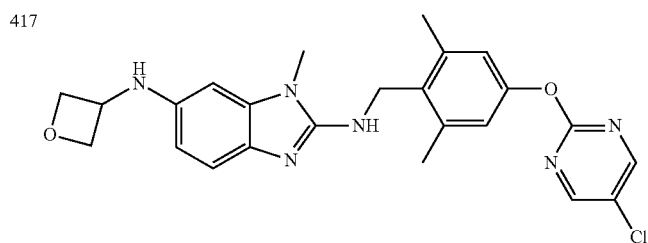 |
| 418 | 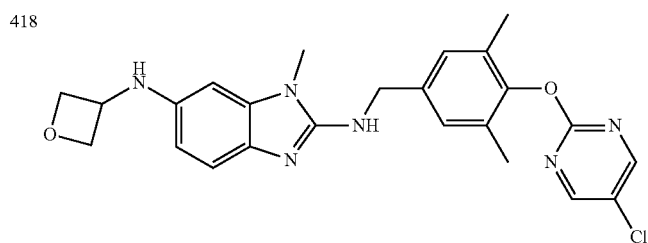 |

| No. | Structure |
|---|---|
| 420 | 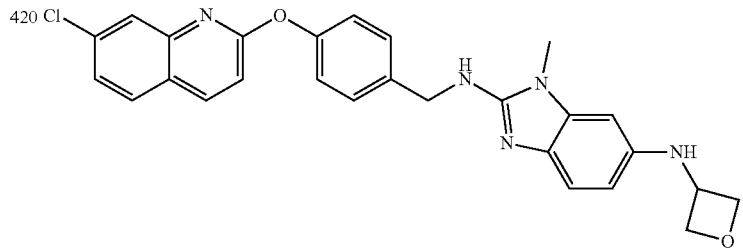 |
| 422 | 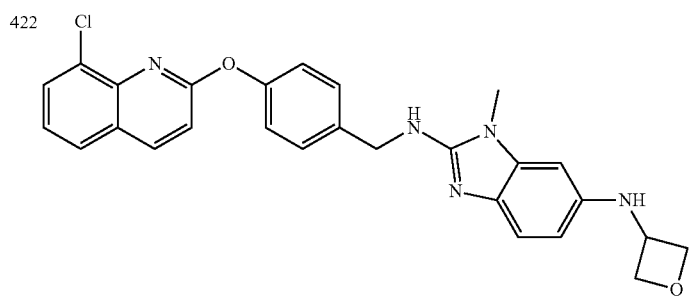 |
| 423 | 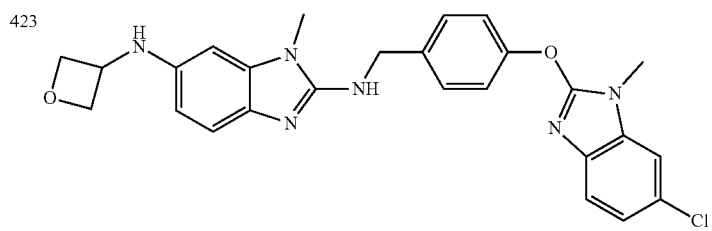 |
| 425 | 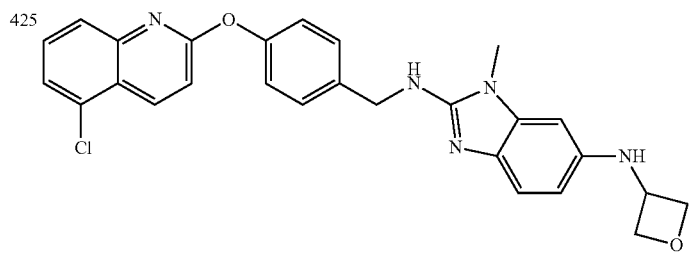 |
| 427 | 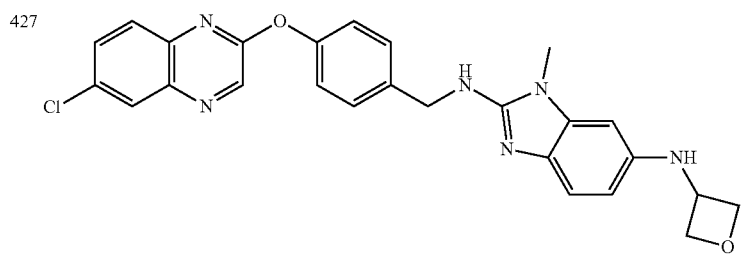 |
| 429 | 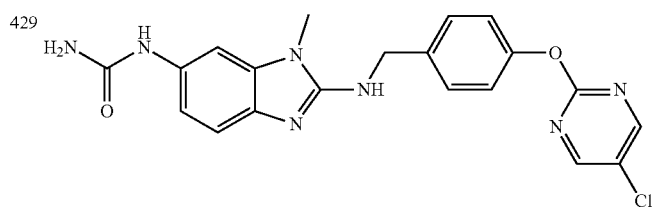 |

| No. | Structure |
|---|---|
| 431 | 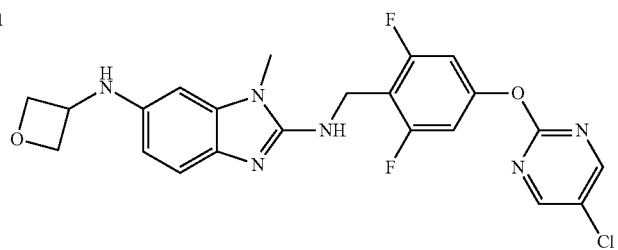 |
| 433 | 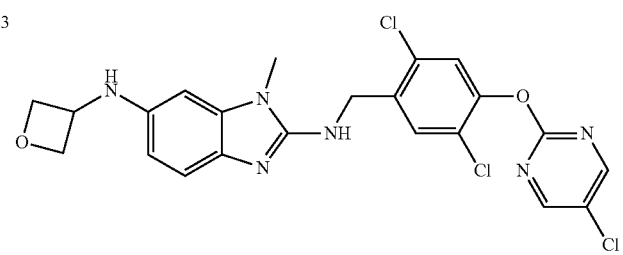 |
| 435 | 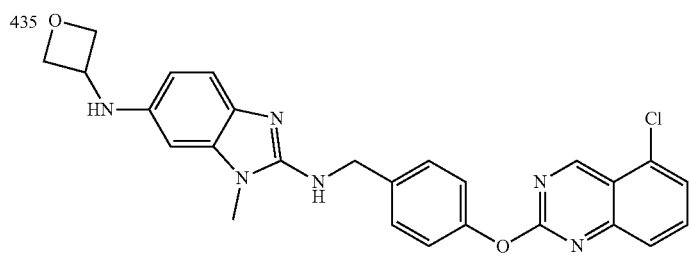 |
| 437 | 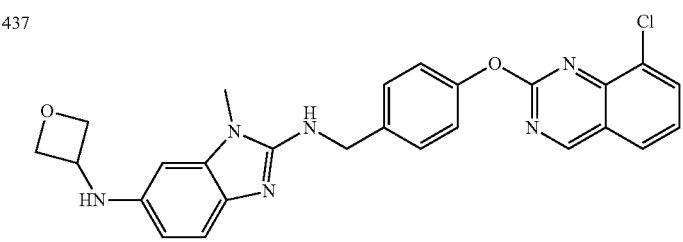 |
| 439 | 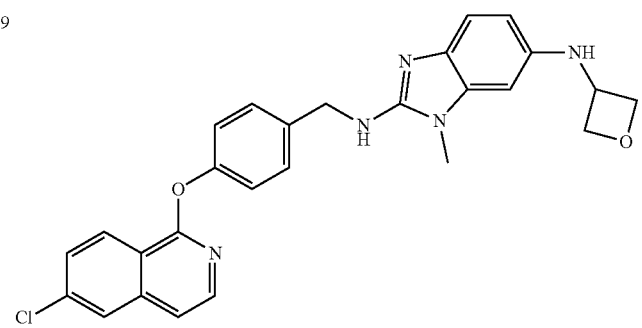 |
| 441 | 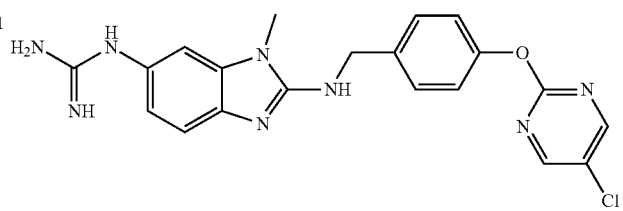 |

| No. | Structure |
|---|---|
| 443 | 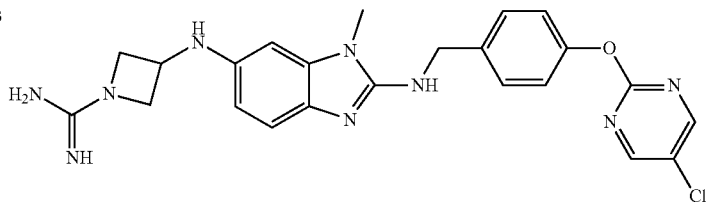 |
| 444 | 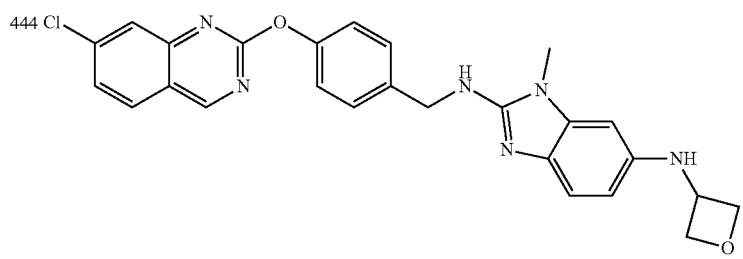 |
| 447 | 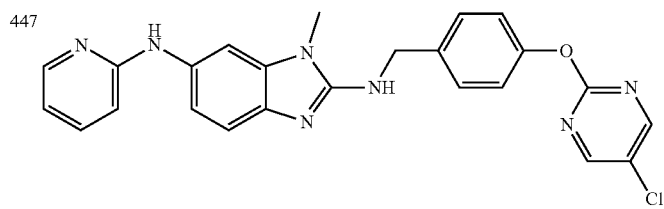 |
| 448 | 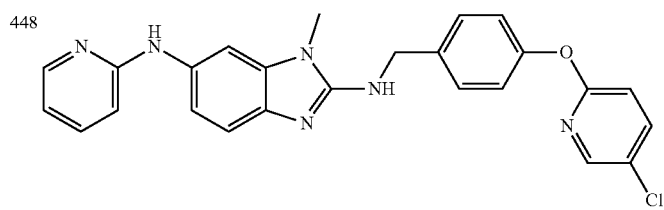 |
| 449 | 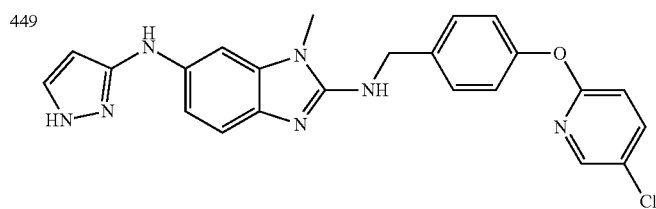 |
| 450 | 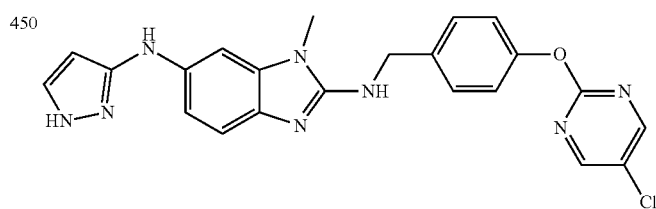 |

| No. | Structure |
|---|---|
| 453 | 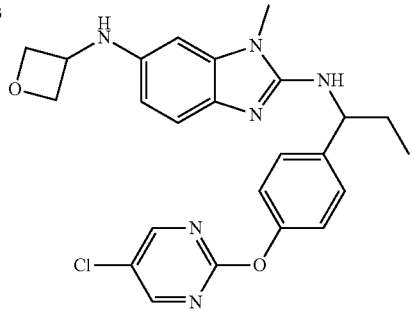 |
| 455 | 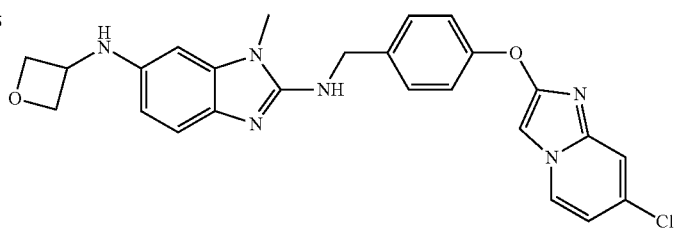 |
| 457 | 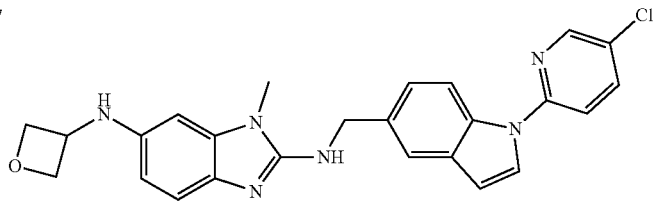 |
| 459 | 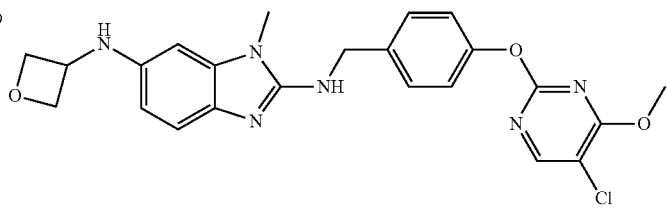 |
| 461 | 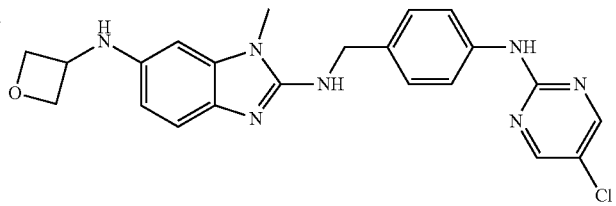 [SMILES: Cn1c(NCc2ccc(Nc3ncc(Cl)cn3)cc2)nc2ccc(NC3COC3)cc21] |
| 464 | 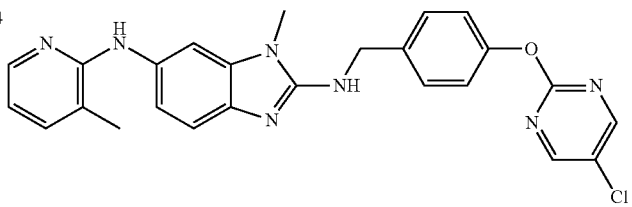 |
| 465 | 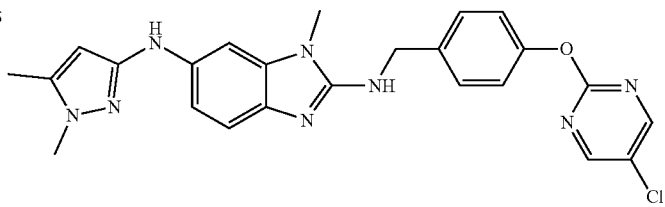 |

| No. | Structure |
|---|---|
| 466 | 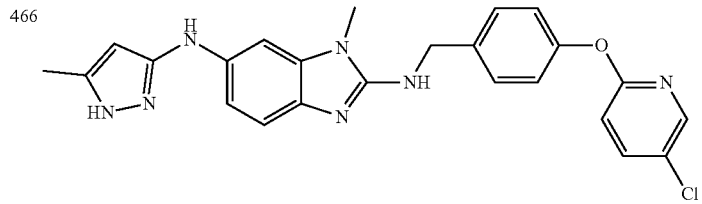 |
| 467 | 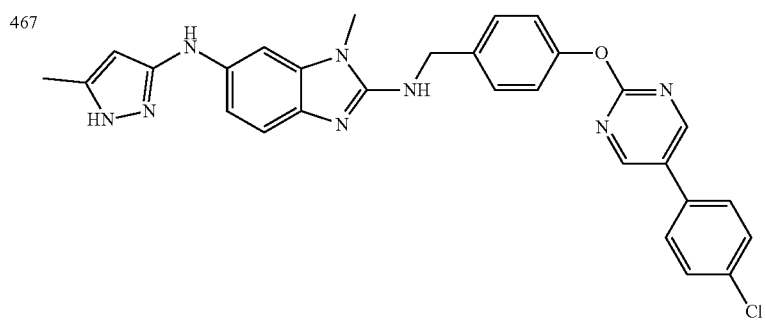 |
| 468 | 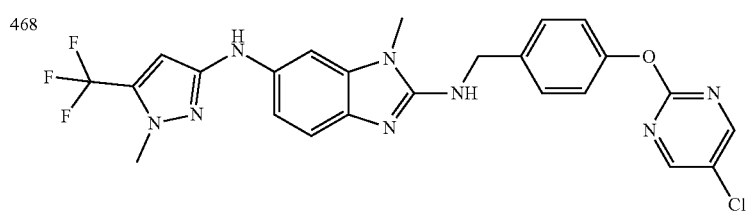 |
| 469 | 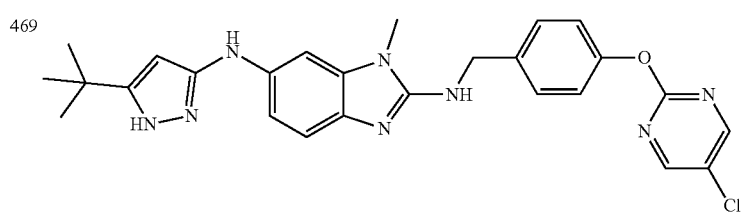 |
| 471 | 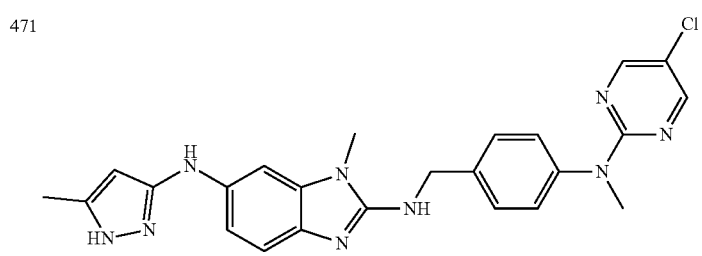 |
| 473 | 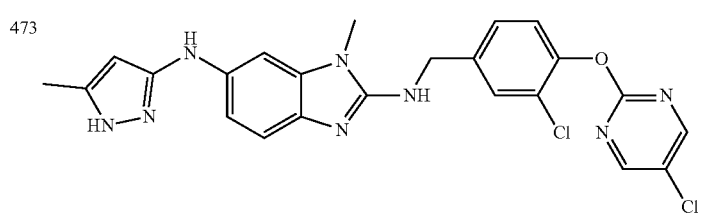 |

| No. | Structure |
|---|---|
| 474 | 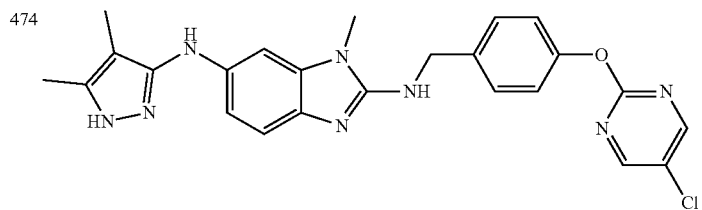 |
| 475 | 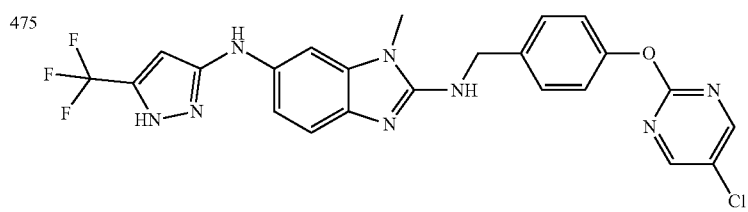 |
| 476 | 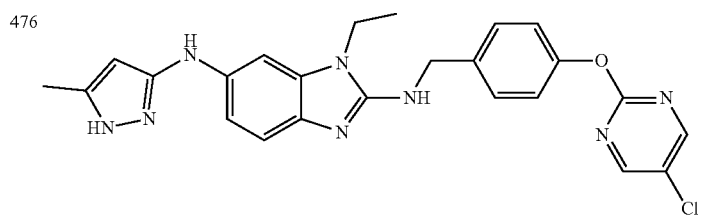 |
| 477 | 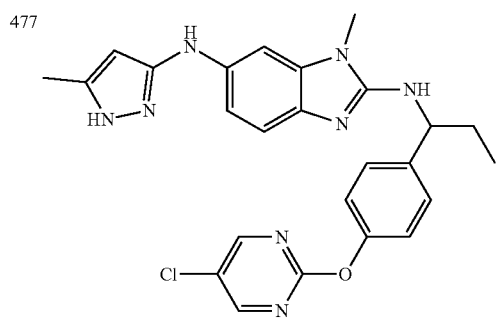 |
| 478 | 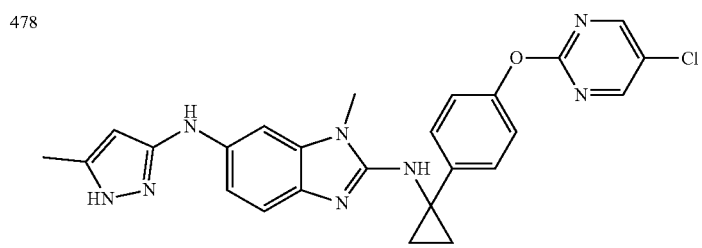 |
| 479 | 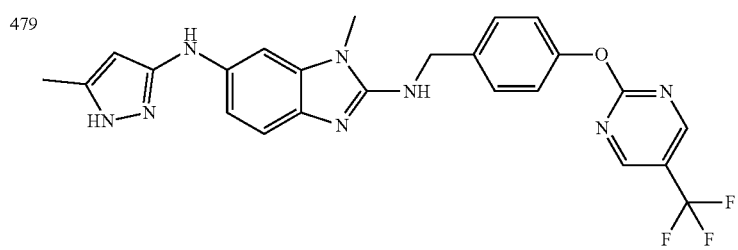 |

| No. | Structure |
|---|---|
| 481 | 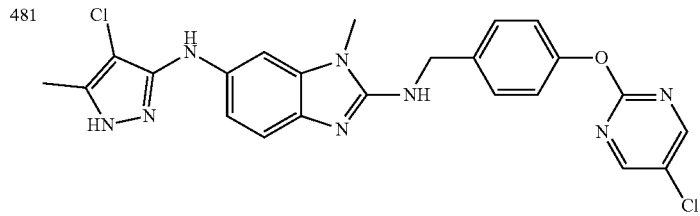 |
| 482 | 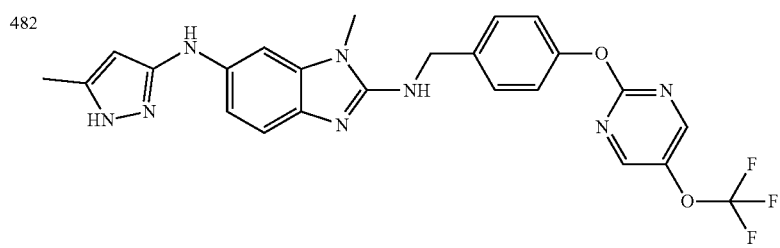 |
| 483 | 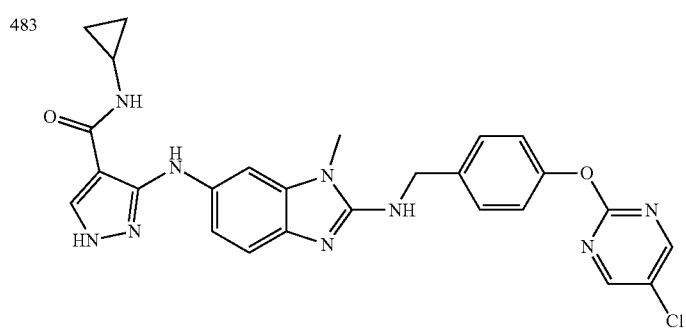 |
| 486 | 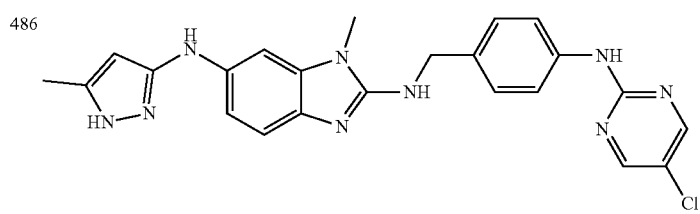 |
| 487 | 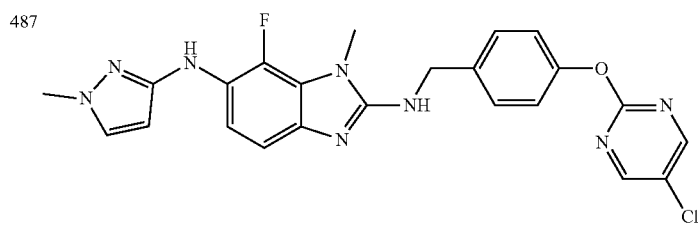 |
| 488 | 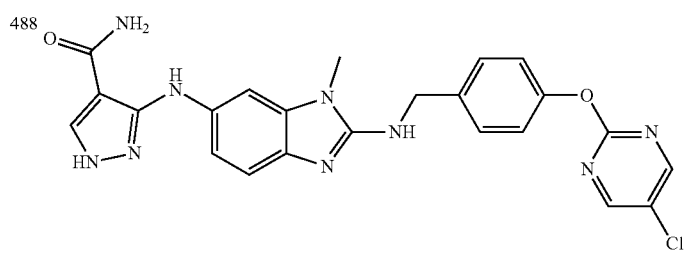 |

| No. | Structure |
|---|---|
| 489 | 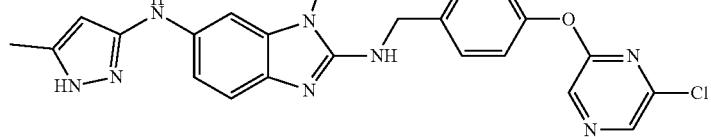 |
| 490 | 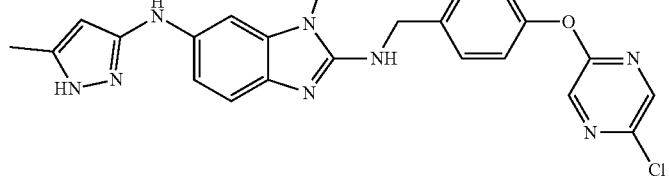 |
| 491 | 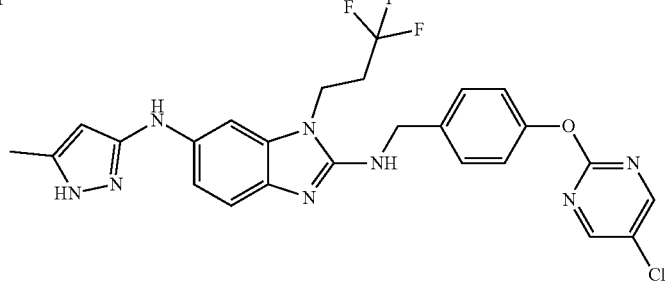 |
| 492 | 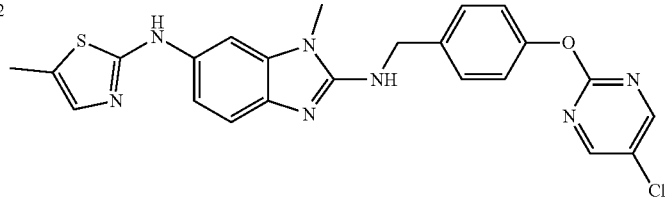 |
| 493 | 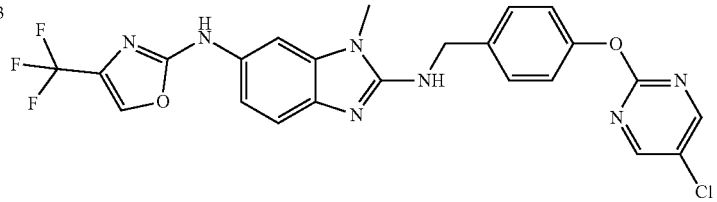 |
| 494 | 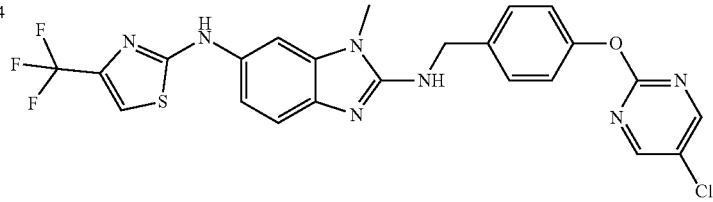 |
| 495 | 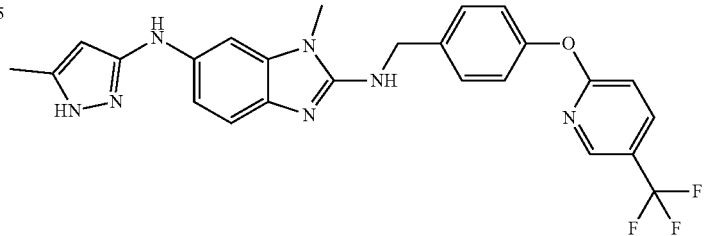 |

| No. | Structure |
|---|---|
| 496 | 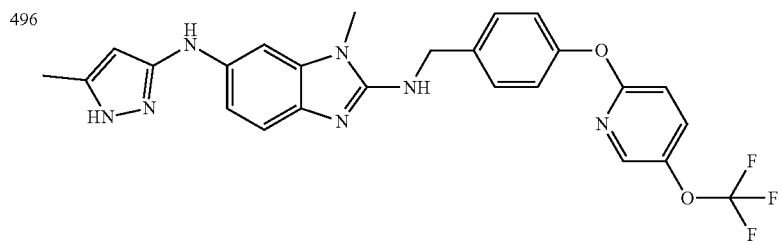 |
| 497 | 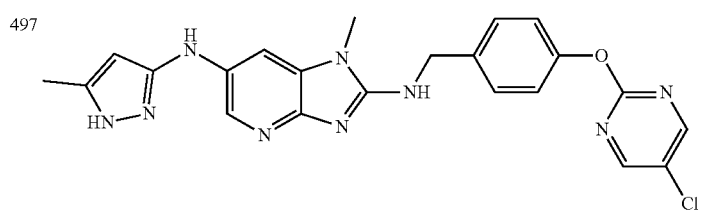 |
| 498 | 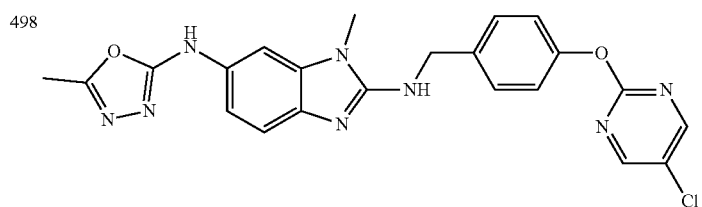 |
| 499 | 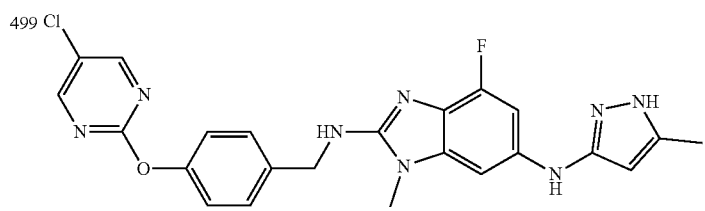 |
| 500 | 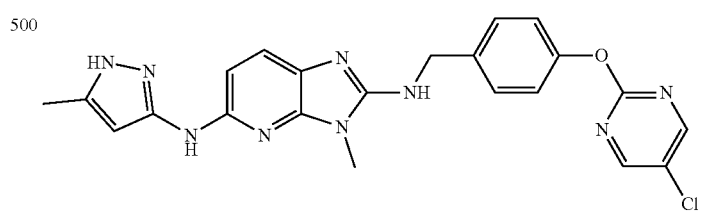 |
| 501 | 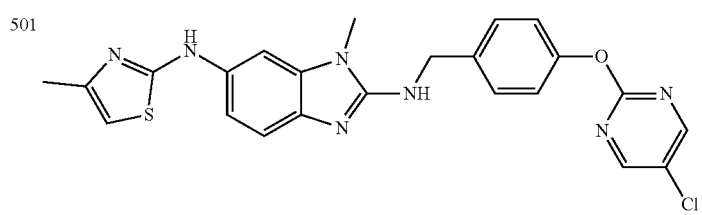 |
| 502 | 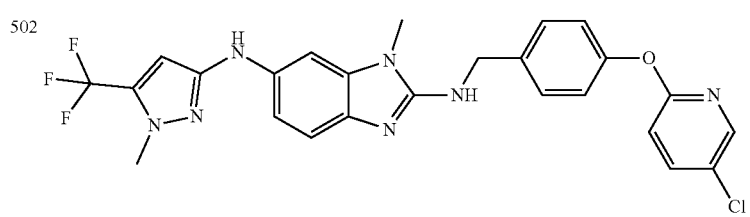 |

-continued
| No. | Structure |
|---|---|
| 503 | 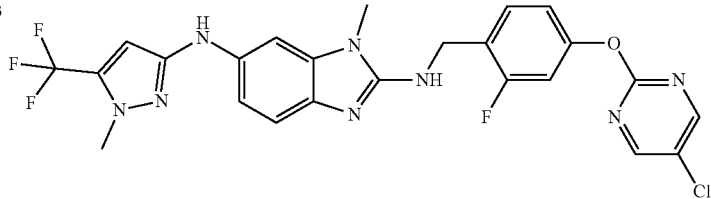 |
| 504 | 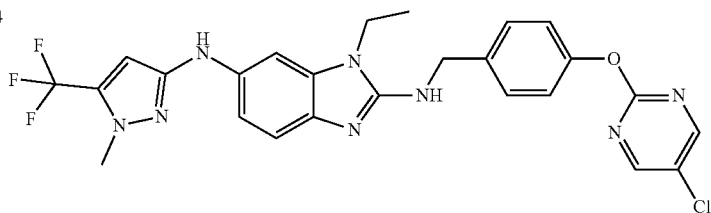 |
| 505 | 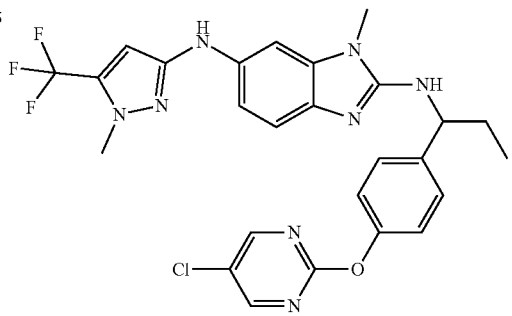 |
| 506 | 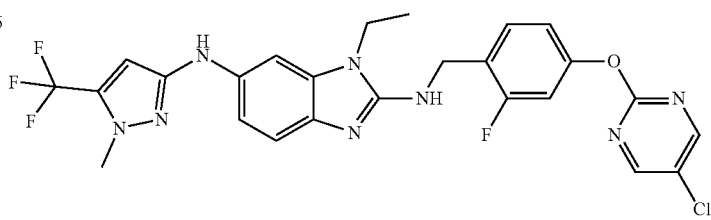 |
| 507 | 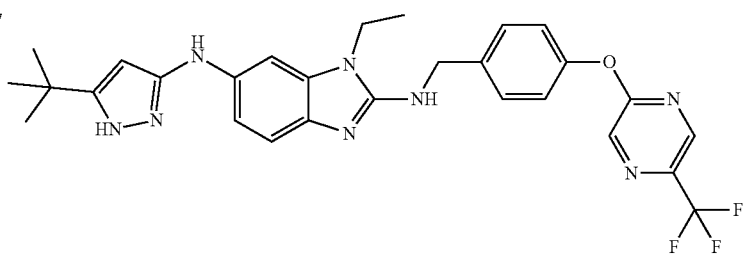 [SMILES: CCn1c(NCc2ccc(Oc3cnc(C(F)(F)F)cn3)cc2)nc2ccc(Nc3cc(C(F)(F)F)n(C)n3)cc21] |
| 508 | 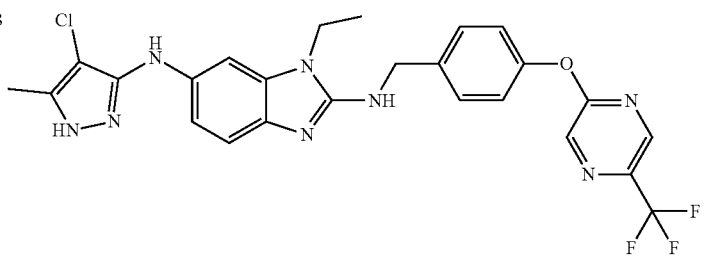 |

| No. | Structure |
|---|---|
| 509 | 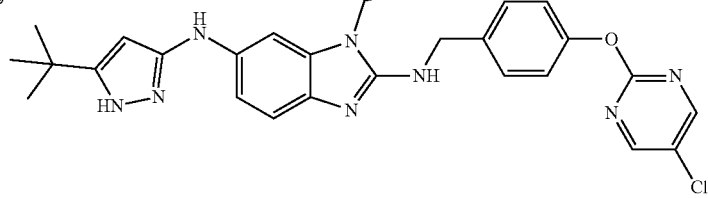 |
| 510 | 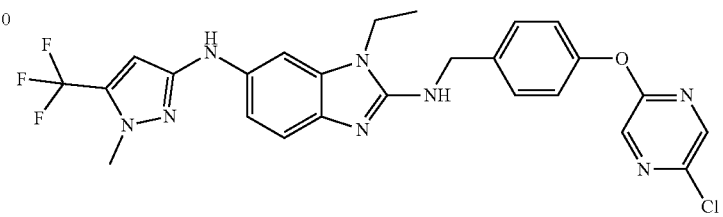 |
| 511 | 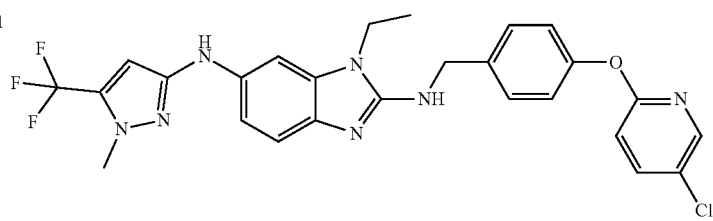 |
| 512 | 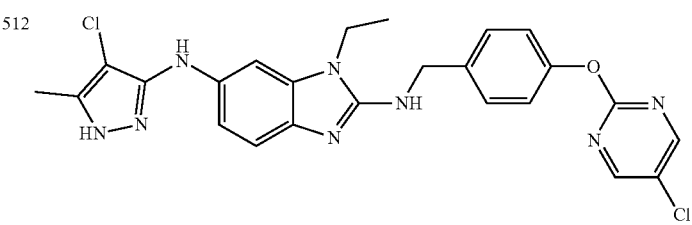 |
| 513 | 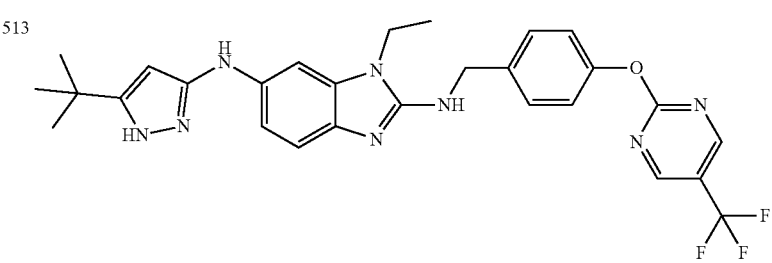 |
| 514 | 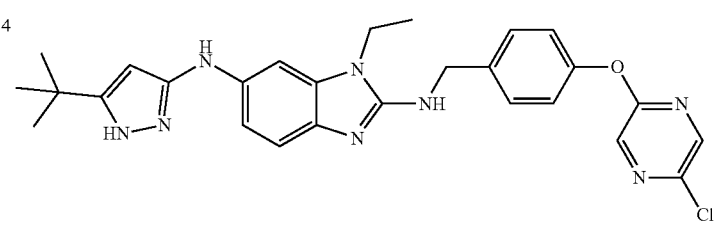 |
| 515 | 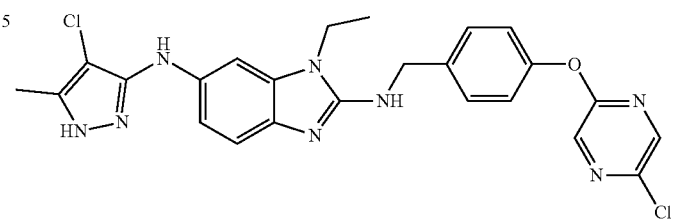 |

| No. | Structure |
|---|---|
| 516 | 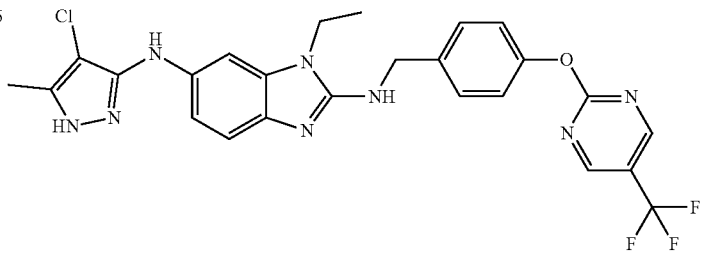 |
| 517 | 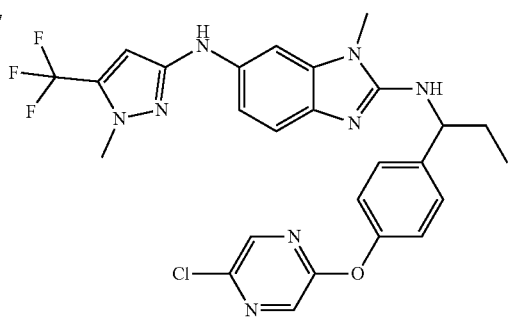 |
| 518 | 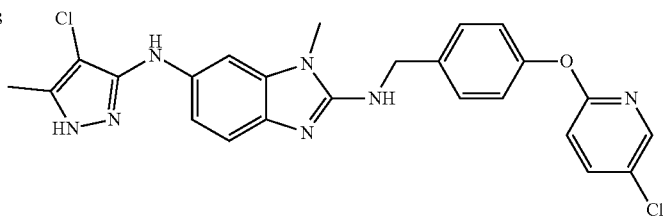 |
| 519 | 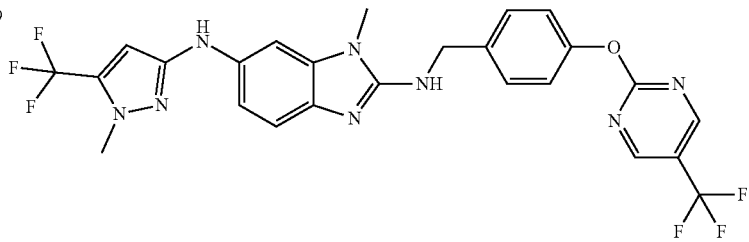 |
| 520 | 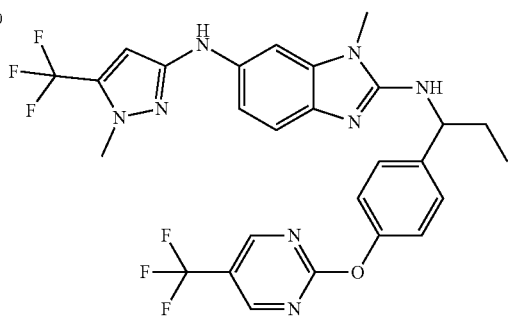 |

| No. | Structure |
|---|---|
| 521 | 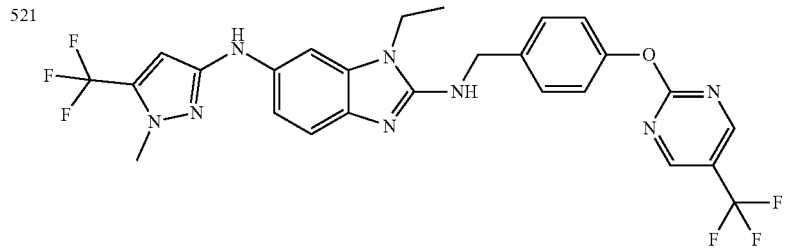 |
| 522 | 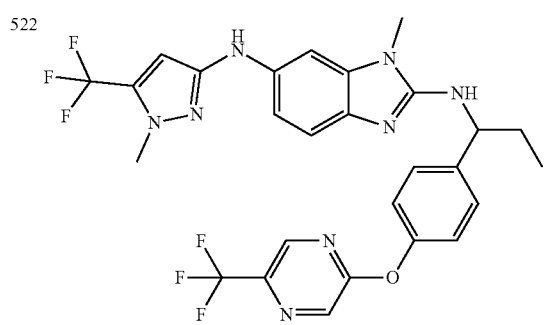 |
| 523 | 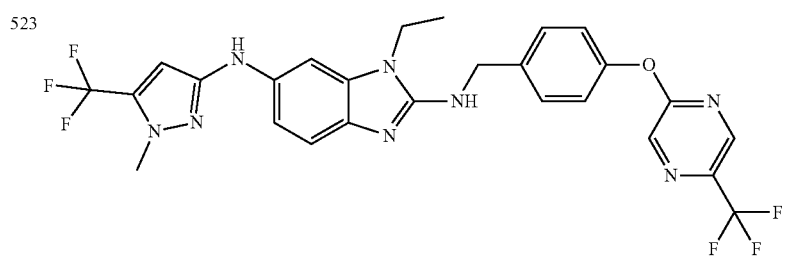 |
| 524 | 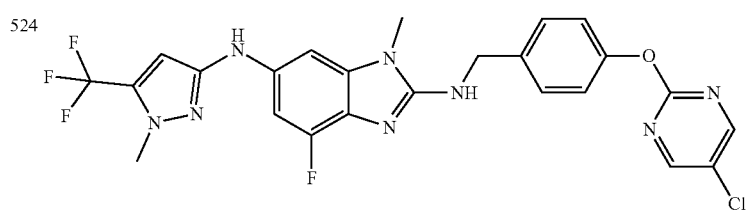 |
| 525 | 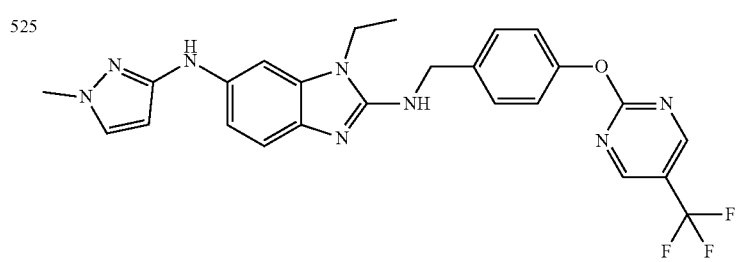 |
| 526 | 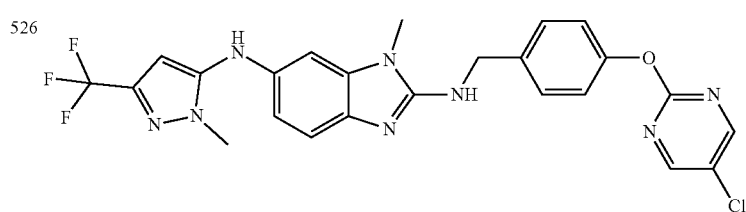 |

| No. | Structure |
|---|---|
| 527 | 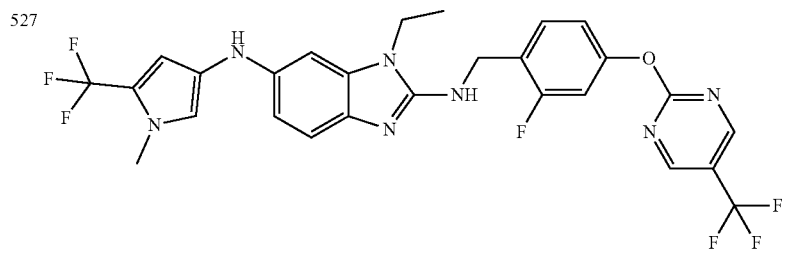 |
| 528 | 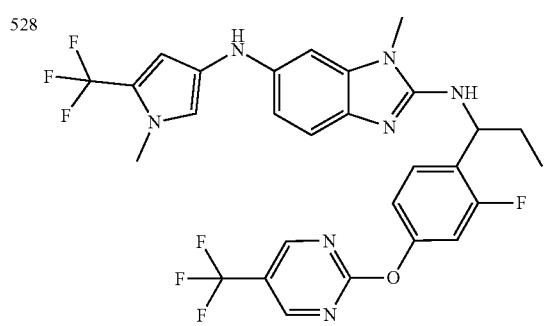 |
| 529 | 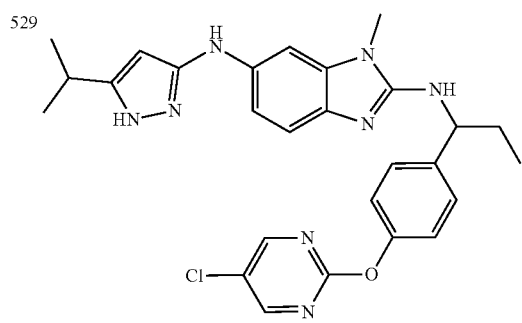 |
| 530 | 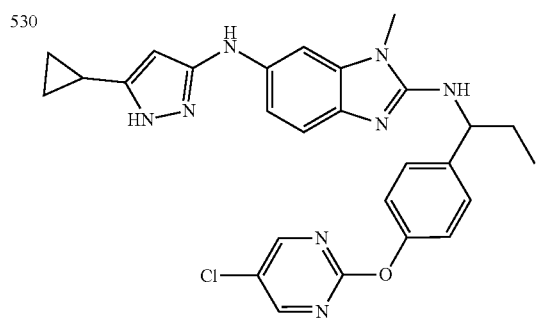 |
| 531 | 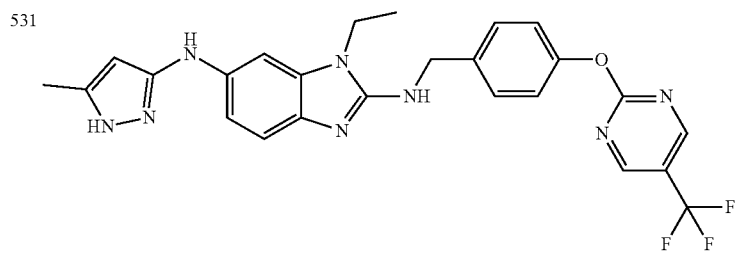 |

| No. | Structure |
|---|---|
| 532 | 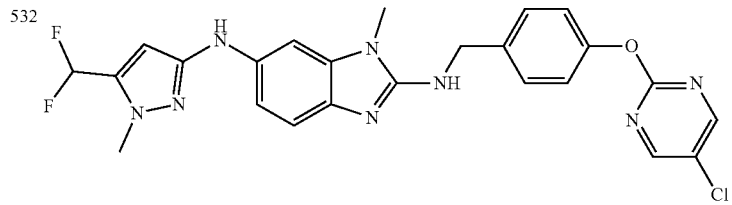 |
| 533 | 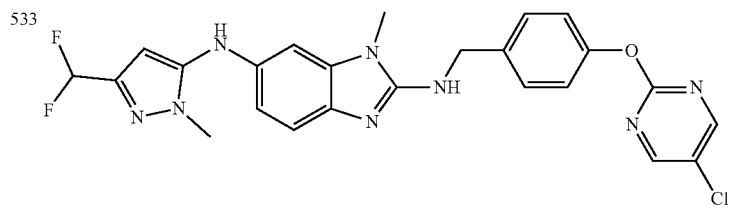 |
| 534 | 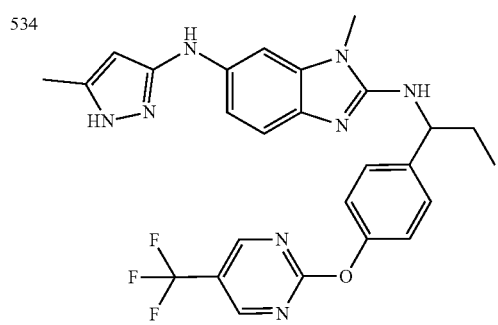 |
| 535 | 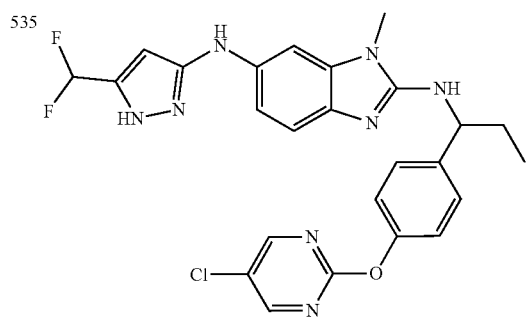 |
| 536 | 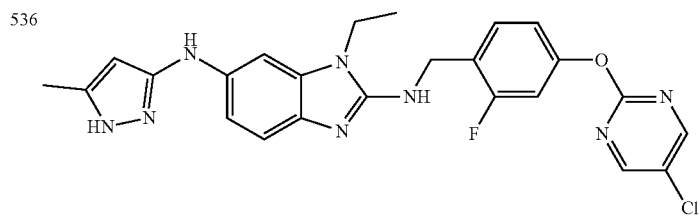 |
| 537 | 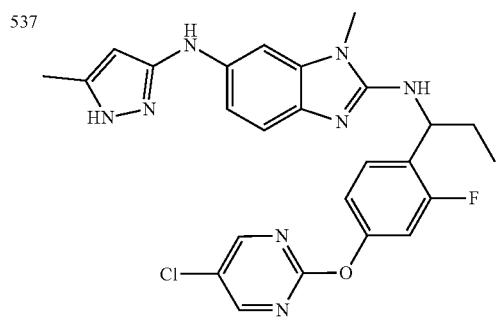 |

| No. | Structure |
|---|---|
| 538 | 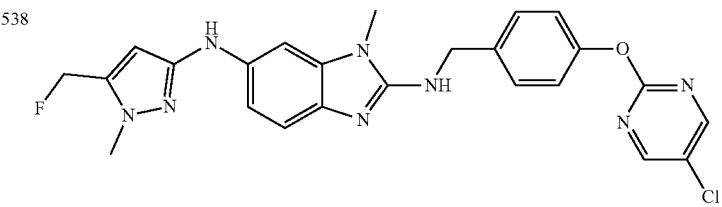 |
| 539 | 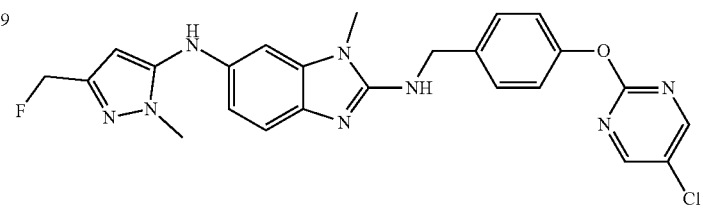 |
| 540 | 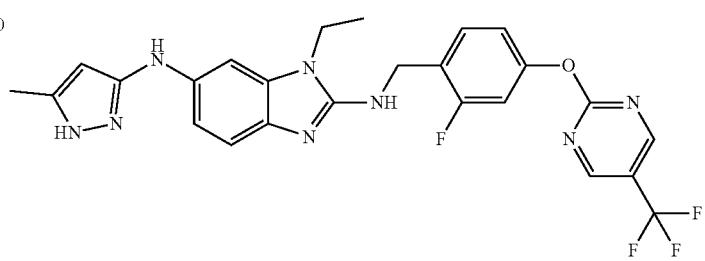 |
| 541 | 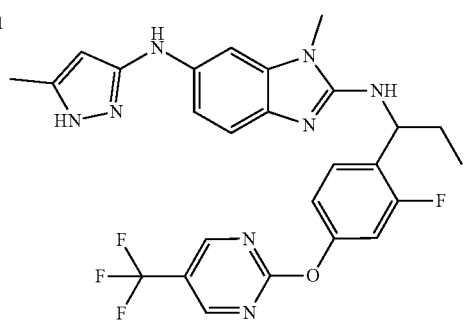 |
| 542 | 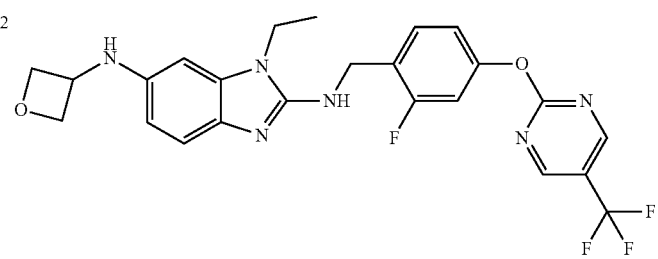 |
| 543 | 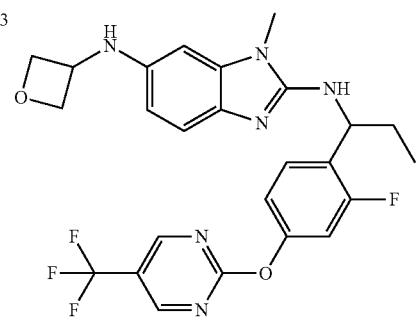 |

| No. | Structure |
|---|---|
| 544 | 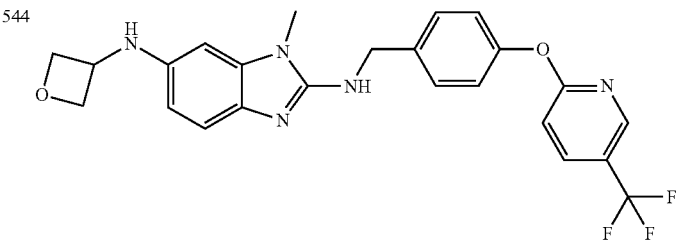 |
| 545 | 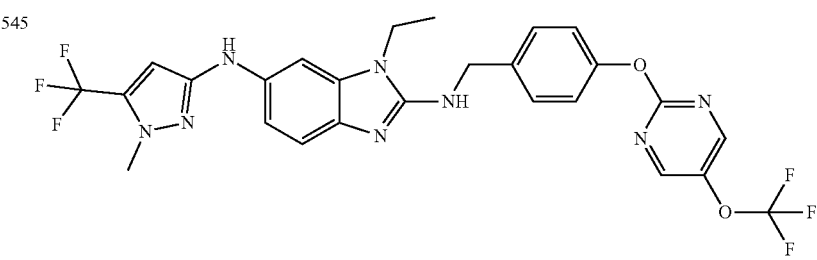 |
| 546 | 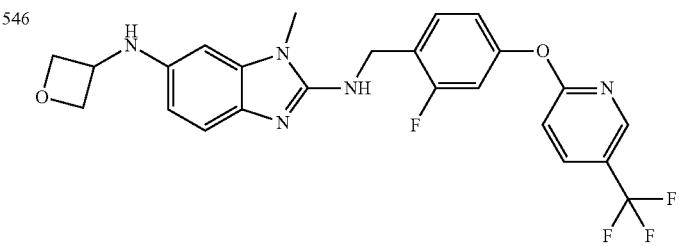 |
| 547 | 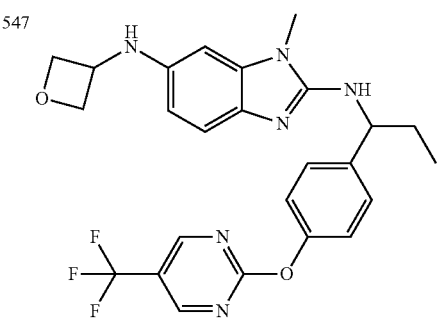 |
| 548 | 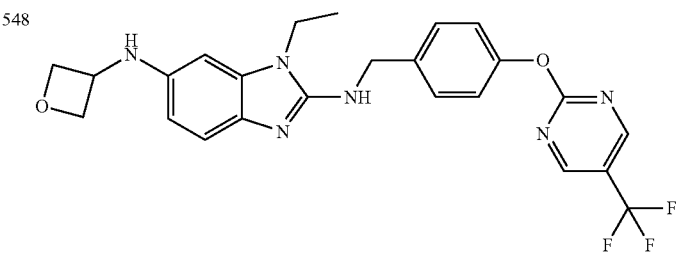 |

-continued
| No. | Structure |
|---|---|
| 549 | 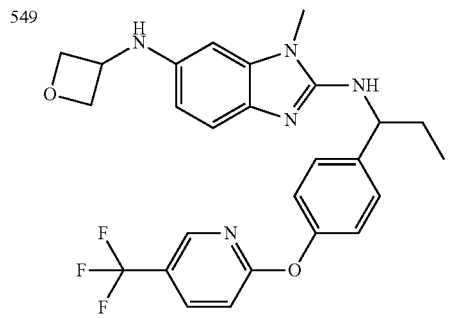 |
| 550 | 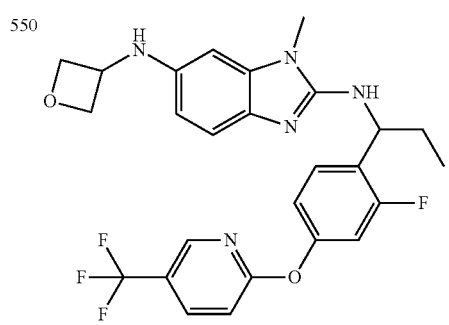 |
| 551 | 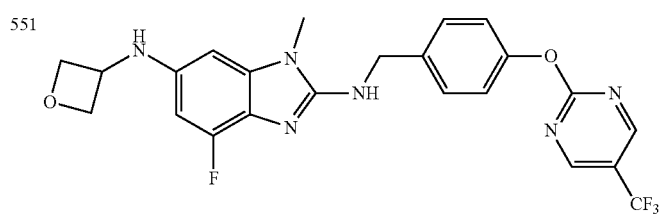 |
| 552 | 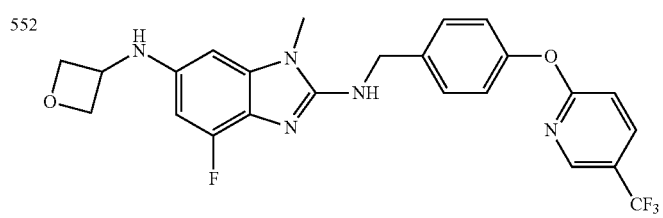 |
| 553 | 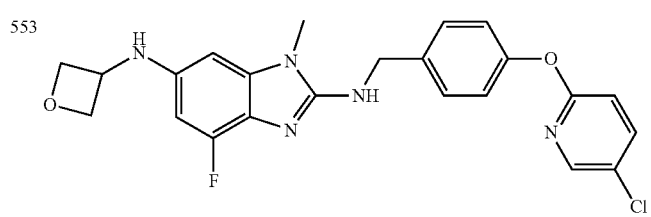 |
| 554 | 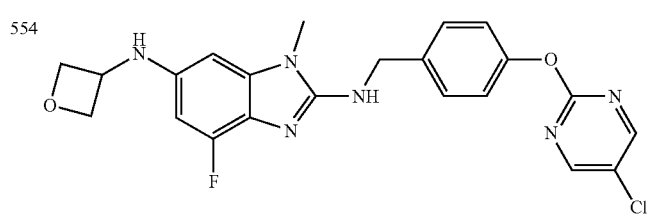 |

| No. | Structure |
|---|---|
| 555 | 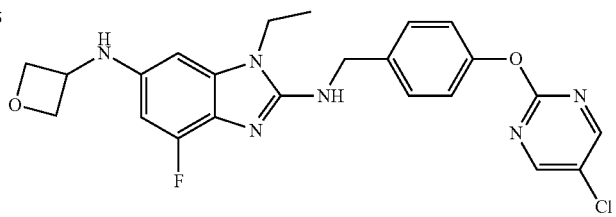 |
| 556 | 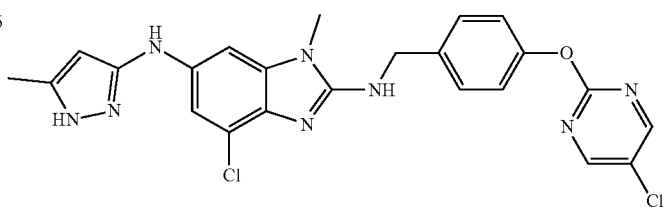 | or a pharmaceutically acceptable salt thereof.

14. A compound having general formula I:

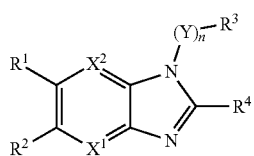

Formula I wherein n is 0 or 1;

$X^1$ and $X^2$ are independently, at each occurrence, $CR^5$ or N;

Y is $C_1$-$C_6$ alkylene, wherein alkylene is optionally substituted with one to two $C_1$-$C_3$ alkyl groups;

$R^1$ is selected from the group consisting of $C_1$-$C_6$ alkoxy, —$NHR^6$, —$NR^7R^8$ and —NH—$(R^9)_n$—$R^{10}$, n being 0 or 1;

$R^2$ is selected from the group consisting of hydrogen, $C_1$-$C_6$ alkyl, —$NH_2$, —$NHR^6$, —$NR^7R^8$ and —NH—$(R^9)_n$—$R^{10}$, n being 0 or 1;

$R^3$ is selected from the group consisting of hydroxyl, $OR^{11}$, —$NR^7R^8$, $C_1$-$C_6$ alkoxy, $C_1$-$C_6$ alkyl, $C_3$-$C_5$, $C_7$-$C_{10}$cycloalkyl, $C_1$-$C_3$ haloalkyl, —$C(O)NHR^{11}$, aryl, heteroaryl, wherein each of said cycloalkyl, aryl, and heteroaryl is optionally and independently substituted with one to four $R^a$ groups;

$R^4$ is selected from the group consisting of —$N(R^{12})(V)_p$ $R^{13}$, —$NH(V)_p$—$OR^{14}$, —$NHC(O)R^{15}$, and groups of formula Ia shown below, Formula Ia

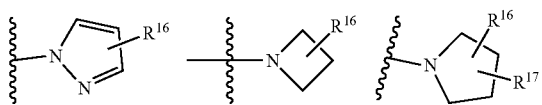

wherein, p is 0,

V is $C_1$-$C_6$ alkylene, wherein alkylene is optionally substituted with one to three $C_1$-$C_3$ alkyl, $C_3$-$C_6$ cycloalkyl or phenyl groups, or wherein a carbon atom of said alkylene forms part of a $C_3$-$C_6$ cycloalkyl group;

$R^5$ is selected from the group consisting of hydrogen, halogen, $C_1$-$C_6$ alkyl, $C_1$-$C_6$ haloalkyl and $C_1$-$C_6$ alkoxy;

$R^6$ is selected from the group consisting of $C_1$-$C_6$ alkyl, $C_3$-$C_{10}$cycloalkyl, $C_1$-$C_6$haloalkyl, aryl, heteroaryl and heterocyclyl, wherein each of said alkyl, cycloalkyl, haloalkyl, aryl, heteroaryl and heterocyclyl is optionally and independently substituted with one to four $R^a$ groups;

$R^7$ and $R^8$ are independently, at each occurrence, heterocyclyl; or $R^7$ and $R^8$ are connected to each other to make a four, five or six membered heterocyclyl or heteroaryl group, wherein each of said heterocyclyl and heteroaryl is optionally and independently substituted with one to four $R^a$ groups;

$R^9$ is $C_1$-$C_4$ alkylene, wherein said alkylene is optionally substituted with one to three $C_1$-$C_3$ alkyl groups;

$R^{10}$ is selected from the group consisting of hydroxyl, —$OR^{11}$, —CN, —$C(O)OR^{18}$, —$C(O)NH_2$, —C(NH) $NH_2$, aryl, heteroaryl and heterocyclyl wherein each of said aryl, heteroaryl and heterocyclyl is optionally and independently substituted with one to four $R^a$ groups;

$R^{11}$ is independently, at each occurrence, selected from the group consisting of aryl heteroaryl and heterocyclyl wherein each of said aryl, heteroaryl and heterocyclyl is optionally and independently substituted with one to four $R^a$ groups;

$R^{12}$ is selected from the group consisting of hydrogen, $C_2$-$C_6$ alkyl, $C_1$-$C_4$ alkyl-hydroxyl and $C_1$-$C_4$ alkyl-alkoxy;

$R^{13}$ is selected from the group consisting of $C_2$, $C_5$ $C_6$ alkyl, $C_3$-$C_{10}$ cycloalkyl, $C_1$-$C_4$ alkyl-hydroxyl, —OH, —$C(O)NH_2$, —$C(O)OR^{18}$, —CN, $C_1$-$C_3$ haloalkyl, and groups of formula 1b shown below, Formula Ib

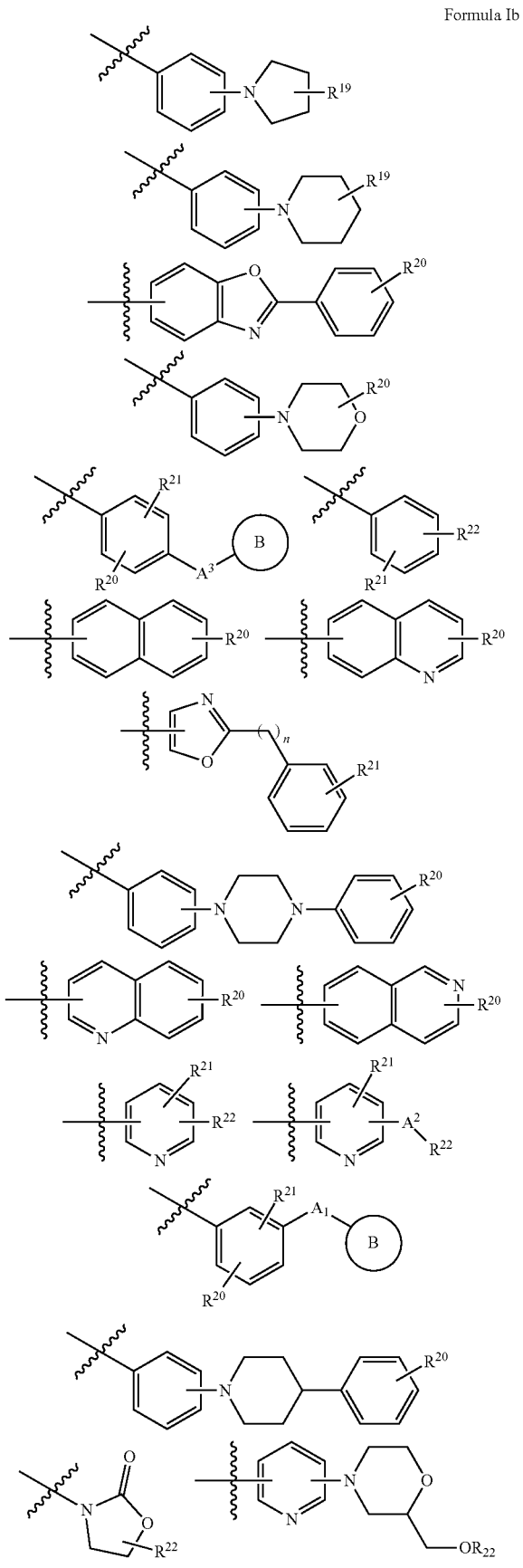
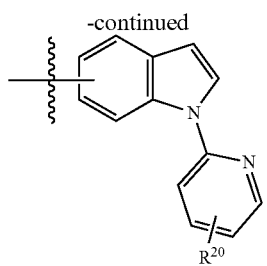

wherein, n is 0 or 1;

$A^1$ is —O—, —CH$_2$O—, —OCH$_2$-, —S—, —SO$_2$-, —SO$_2$NH—, —C(O)—, —C(O)NH—, —C(O)N(R$^7$)—, —CH(OH)—, —CH(OR$^7$)—, —NH—, —N(CH$_3$)— or —N(CH$_2$COOR$^7$)—;

$A^2$ is —O— or NH—;

B is selected from the group consisting of aryl, heteroaryl and heterocyclyl wherein each of said aryl, heteroaryl and heterocyclyl is optionally and independently substituted with one to four $R^a$ groups;

$R^{14}$ is selected from the group consisting of hydrogen, $C_1$-$C_6$ alkyl and aryl, wherein each of said alkyl and aryl is optionally and independently substituted with one to four halogen or $C_1$-$C_3$ haloalkoxy groups;

$R^{15}$ is aryl, wherein aryl is substituted with one to four halogen groups;

$R^{16}$ selected from the group consisting of hydrogen, halogen, $C_1$-$C_6$ alkyl and hydroxyl;

$R^{17}$ is selected from the group consisting of hydrogen, halogen, $C_1$-$C_6$ alkyl, —C(O)R$^{11}$, —C(O)NHR$^{11}$, —OR$^{11}$ and aryl, wherein each of said alkyl and aryl is optionally and independently substituted with one to four $R^a$ groups;

$R^{18}$ is hydrogen or $C_1$-$C_6$ alkyl;

$R^{19}$ is selected from the group consisting of hydrogen, —OR$^{22}$ and —CH$_2$OR$^{22}$;

$R^{20}$ is selected from the group consisting of hydrogen, halogen, $C_1$-$C_6$ alkyl, $C_1$-$C_6$ alkoxy, —C(O)R$^a$ and $C_1$-$C_6$ haloalkoxy;

$R^{21}$ is selected from the group consisting of hydrogen, halogen and $C_1$-$C_6$ alkyl;

$R^{22}$ is selected from the group consisting of $C_1$-$C_6$ haloalkyl, aryl, and heteroaryl, wherein each of said haloalkyl, aryl and heteroaryl is optionally and independently substituted with one to four $R^a$ groups;

$R^a$ is independently, at each occurrence, selected from the group consisting of hydrogen, halogen, $C_1$-$C_3$ alkyl, $C_3$-$C_{10}$ cycloalkyl, $C_1$-$C_4$ alkoxy, $C_1$-$C_4$ haloalkyl, $C_1$-$C_6$ haloalkoxy, hydroxyl, $C_1$-$C_3$ alkylhydroxyl, —CH$_2$OH, —OCH$_3$, —NR$^b$H, —C(O)NR$^b$H, —C(O)H, —CH$_2$OR$^c$, —OCH$_2$R$^c$, —OR$^c$, —CN, NO$_2$, —NR$^b$R$^c$, —C(O)NR$^b$R$^c$, —C(NH)NH$_2$, —C(O)R$^c$, —C(O)OR$^c$, sulfonyl, sulfoxide, heterocyclyl, heteroaryl and aryl, wherein each of said alkyl, haloalkyl, haloalkoxy, alkoxy, cycloalkyl, aryl, heteroaryl and heterocyclyl is optionally and independently substituted with one to four $C_1$-$C_3$ alkyl, $C_1$-$C_4$ alkoxy, halogen, $C_1$-$C_3$ haloalkyl, —CN, —C(O)NH$_2$, —CO$_2$Et or heteroaryl;

$R^b$ is independently, at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$alkenyl, $C_1$-$C_4$ alkoxy, $C_1$-$C_3$ alkylhydroxyl, $C_3$-$C_1$ cycloalkenyl, $C_2$-$C_{10}$ alkynyl, $C_1$-$C_6$ haloalkyl, aryl, heteroaryl, and heterocyclyl wherein each of said alkyl, cycloalkyl, alkyl-O-alkyl, alkenyl, alkoxy, cycloalkenyl, alkynyl, haloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH$_2$, —COOH, —COOMe, —COOEt, —CN, —NO$_2$, or —NH$_2$;

$R^c$ is independently, at each occurrence, selected from the group consisting of $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$cycloalkenyl, $C_2$-$C_{10}$ alkynyl, $C_1$-$C_6$ haloalkyl, aryl, heteroaryl, and heterocyclyl wherein each of said alkyl, cycloalkyl, alkyl-O-alkyl, alkenyl, alkoxy, cycloalkenyl, alkynyl, haloalkyl, aryl, heteroaryl and heterocyclyl is optionally and independently substituted with one to four $C_1$-$C_3$ alkyl, $C_1$-$C_4$ alkoxy, halogen, $C_1$-$C_6$ haloalkyl, $C_1$-$C_6$ haloalkoxy, hydroxyl, —C(O)NH$_2$, —COOH, —COOMe, —COOEt, —CN, —NO$_2$, or —NH$_2$; or $R^b$ and $R^c$ are connected to each other to make a four, five or six membered saturated or unsaturated cyclic or heterocyclic ring;

or a pharmaceutically acceptable salts thereof.

15. The compound, according to claim 13, one of the following formulae:

| No. | Structure |
| --- | --- |
| 53 | 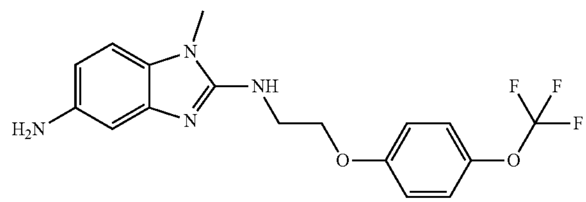 [SMILES: Cn1c(NCCOc2ccc(OC(F)(F)F)cc2)nc2cc(N)ccc21] |
| 57 | 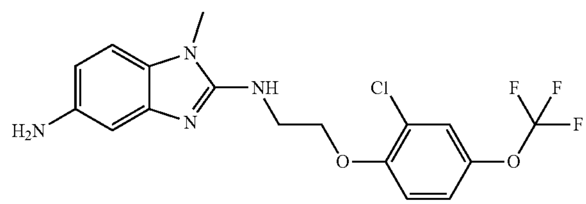 [SMILES: Cn1c(NCCOc2ccc(OC(F)(F)F)cc2Cl)nc2cc(N)ccc21] |
| 59 | 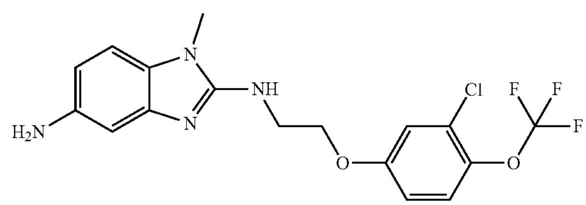 [SMILES: Cn1c(NCCOc2ccc(OC(F)(F)F)c(Cl)c2)nc2cc(N)ccc21] |
| 61 | 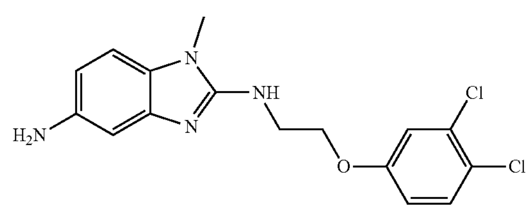 [SMILES: Cn1c(NCCOc2ccc(Cl)c(Cl)c2)nc2cc(N)ccc21] |
| 70 | 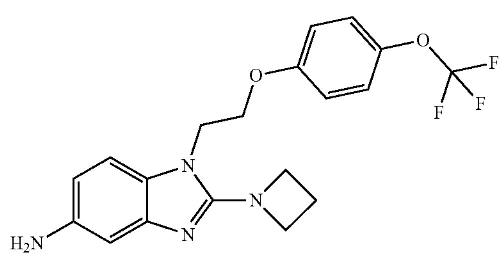 [SMILES: Nc1ccc2c(c1)nc(N1CCC1)n2CCOc1ccc(OC(F)(F)F)cc1] |

-continued

| No. | Structure |
|---|---|
| 72 | 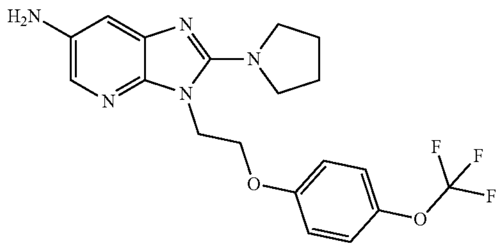 [SMILES: Nc1cnc2c(c1)nc(N1CCCC1)n2CCOc1ccc(OC(F)(F)F)cc1] |
| 84 | 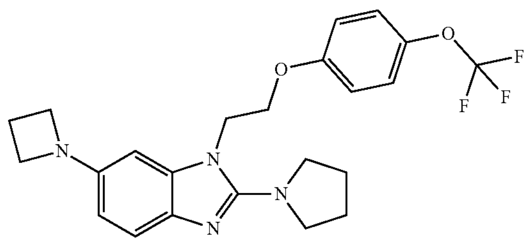 [SMILES: FC(F)(F)Oc1ccc(OCCn2c(N3CCCC3)nc3ccc(N4CCC4)cc32)cc1] |
| 144 | 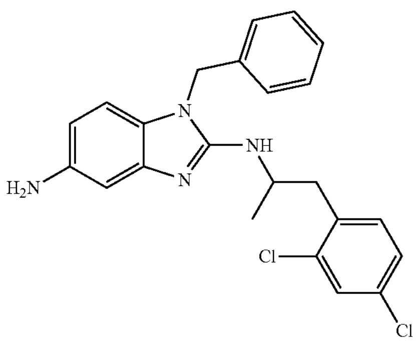 [SMILES: CC(Cc1ccc(Cl)cc1Cl)Nc1nc2cc(N)ccc2n1Cc1ccccc1] |
| 170 | 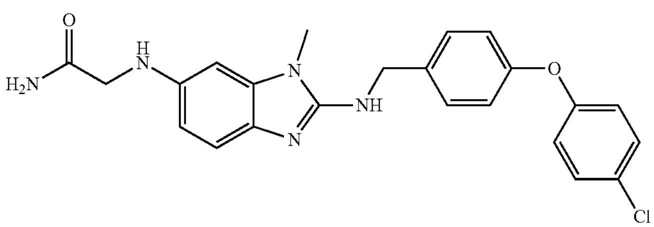 [SMILES: Cn1c(NCc2ccc(Oc3ccc(Cl)cc3)cc2)nc2ccc(NCC(N)=O)cc21] |
| 171 | 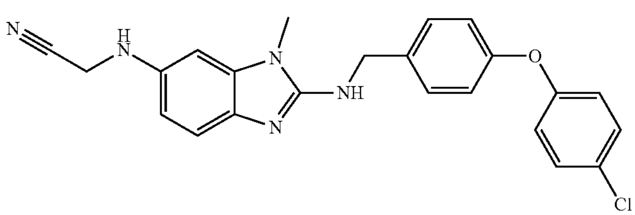 [SMILES: Cn1c(NCc2ccc(Oc3ccc(Cl)cc3)cc2)nc2ccc(NCC#N)cc21] |
| 182 | 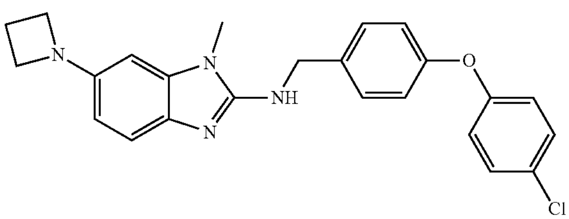 [SMILES: Cn1c(NCc2ccc(Oc3ccc(Cl)cc3)cc2)nc2ccc(N3CCC3)cc21] |

US 11,447,486 B2
425
426
-continued
| No. | Structure |
|---|---|
| 184 | 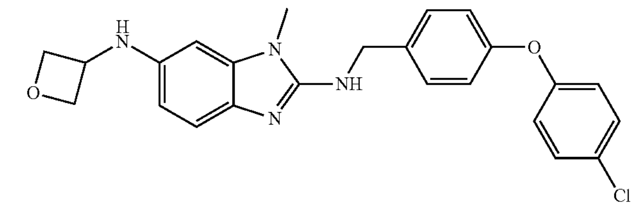 |
| 192 | 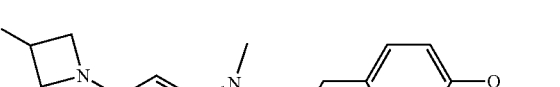 |
| 204 | 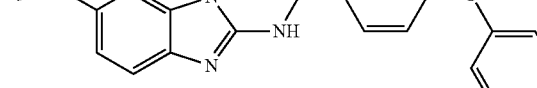 |
| 208 | 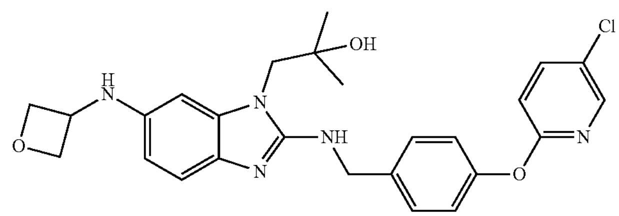 [SMILES: CC(C)(O)Cn1c(NCc2ccc(Oc3ccc(Cl)cn3)cc2)nc2ccc(NC3COC3)cc21] |
| 211 | 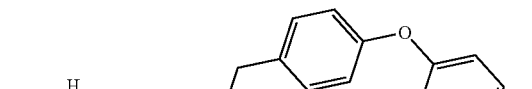 |
| 226 | 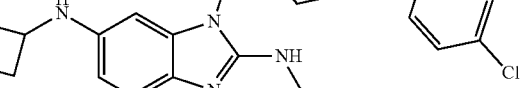 |
| 227 | 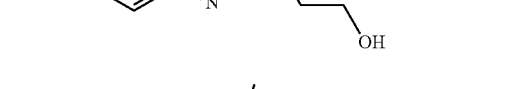 |

| No. | Structure |
|---|---|
| 251 | 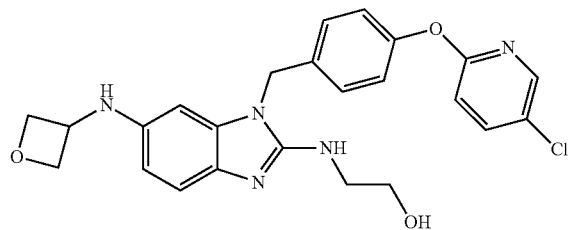 [SMILES: OCCNc1nc2ccc(NC3COC3)cc2n1Cc1ccc(Oc2ccc(Cl)cn2)cc1] |
| 256 | 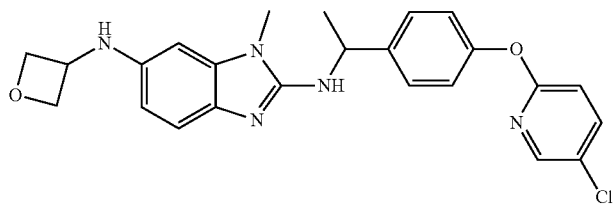 [SMILES: CC(Nc1nc2ccc(NC3COC3)cc2n1C)c1ccc(Oc2ccc(Cl)cn2)cc1] |
| 257 | 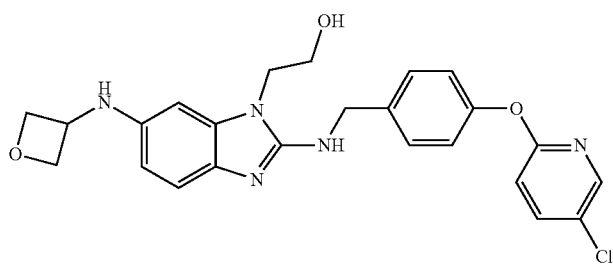 [SMILES: OCCn1c(NCc2ccc(Oc3ccc(Cl)cn3)cc2)nc2ccc(NC3COC3)cc21] |
| 268 | 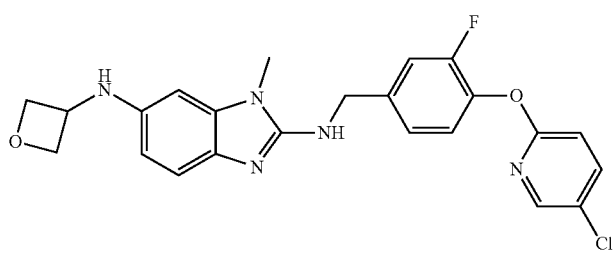 |
| 269 | 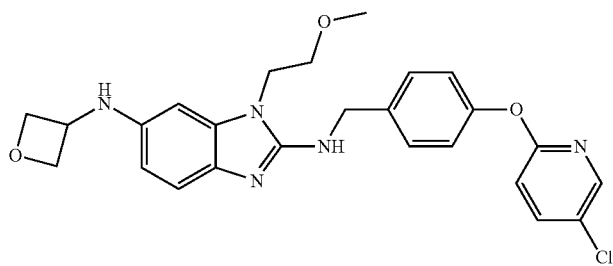 [SMILES: COCCn1c(NCc2ccc(Oc3ccc(Cl)cn3)cc2)nc2ccc(NC3COC3)cc21] |
| 270 | 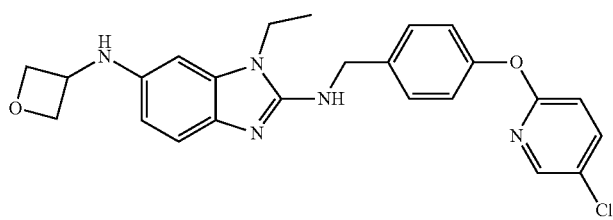 [SMILES: CCn1c(NCc2ccc(Oc3ccc(Cl)cn3)cc2)nc2ccc(NC3COC3)cc21] |

| No. | Structure |
|---|---|
| 271 | 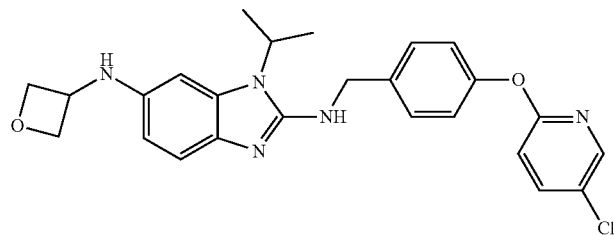 [SMILES: CC(C)n1c(NCc2ccc(Oc3ccc(Cl)cn3)cc2)nc2ccc(NC3COC3)cc21] |
| 273 | 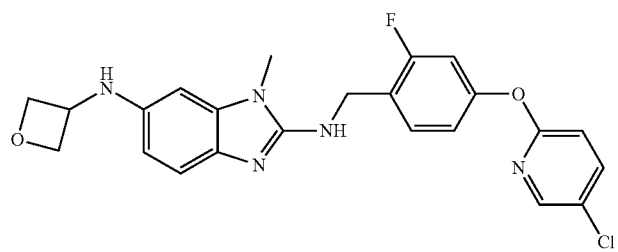 [SMILES: Cn1c(NCc2ccc(Oc3ccc(Cl)cn3)cc2F)nc2ccc(NC3COC3)cc21] |
| 275 | 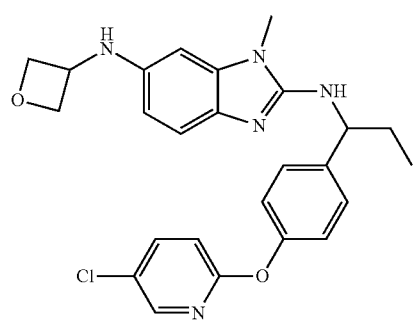 |
| 281 | 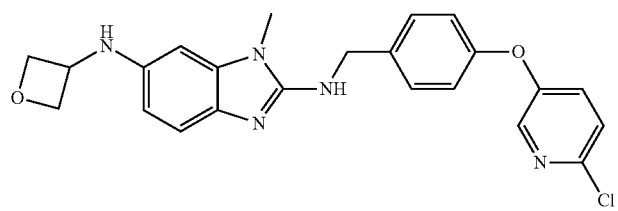 [SMILES: Cn1c(NCc2ccc(Oc3ccc(Cl)nc3)cc2)nc2ccc(NC3COC3)cc21] |
| 283 | 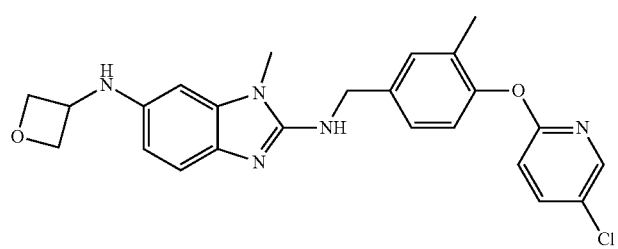 [SMILES: Cc1cc(CNc2nc3ccc(NC4COC4)cc3n2C)ccc1Oc1ccc(Cl)cn1] |
| 284 | 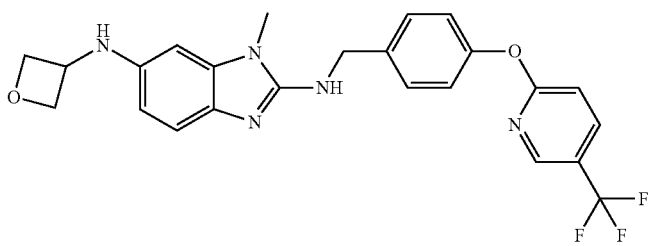 [SMILES: Cn1c(NCc2ccc(Oc3ccc(C(F)(F)F)cn3)cc2)nc2ccc(NC3COC3)cc21] |

| No. | Structure |
|---|---|
| 289 | 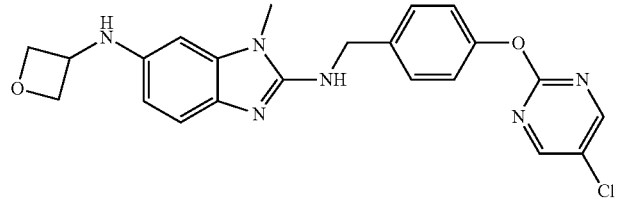 [SMILES: Cn1c(NCc2ccc(Oc3ncc(Cl)cn3)cc2)nc2ccc(NC3COC3)cc21] |
| 291 | 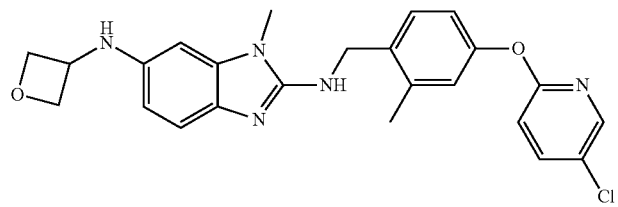 [SMILES: Cc1cc(Oc2ccc(Cl)cn2)ccc1CNc1nc2ccc(NC3COC3)cc2n1C] |
| 293 | 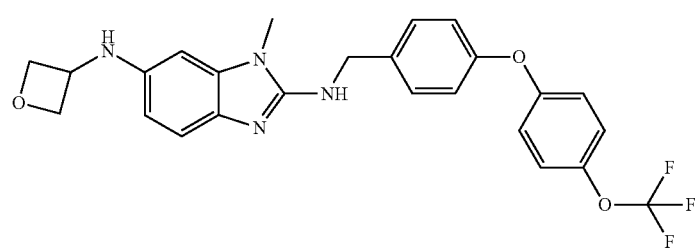 |
| 294 | 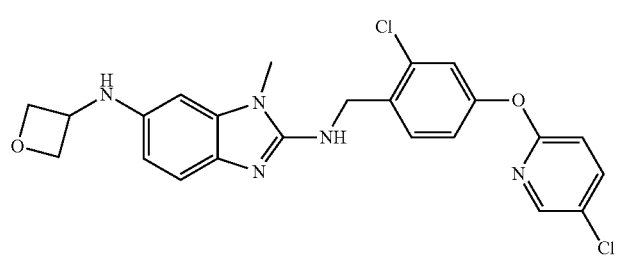 |
| 296 | 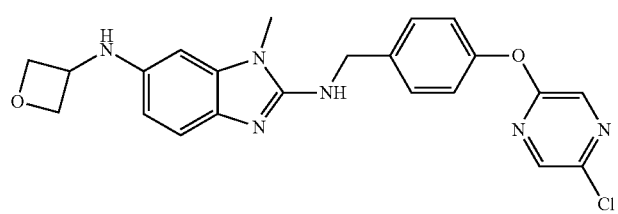 [SMILES: Cn1c(NCc2ccc(Oc3cnc(Cl)cn3)cc2)nc2ccc(NC3COC3)cc21] |
| 298 | 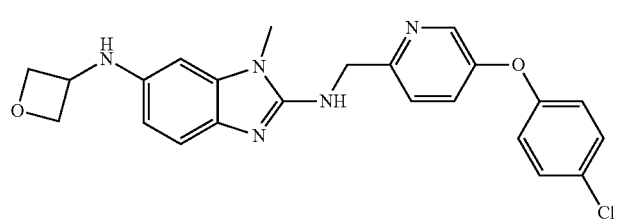 |
| 300 | 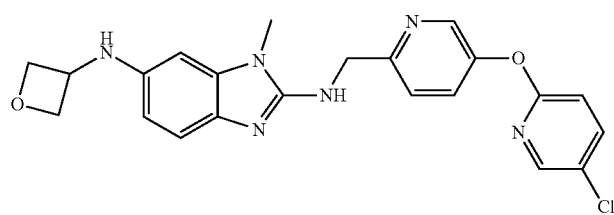 |

-continued

| No. | Structure |
|---|---|
| 302 | 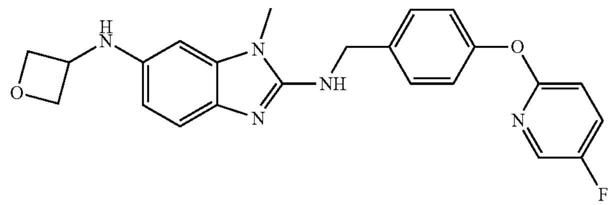 [SMILES: Cn1c(NCc2ccc(Oc3ccc(F)cn3)cc2)nc2ccc(NC3COC3)cc21] |
| 303 | 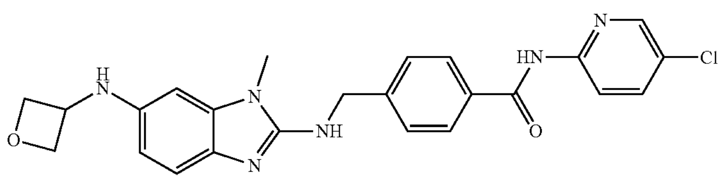 [SMILES: Cn1c(NCc2ccc(C(=O)Nc3ccc(Cl)cn3)cc2)nc2ccc(NC3COC3)cc21] |
| 305 | 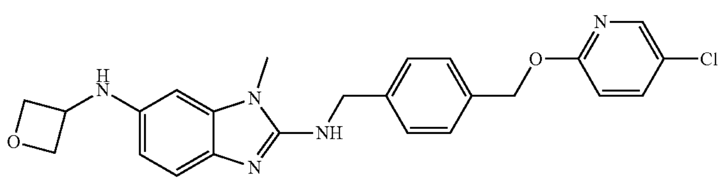 |
| 306 | 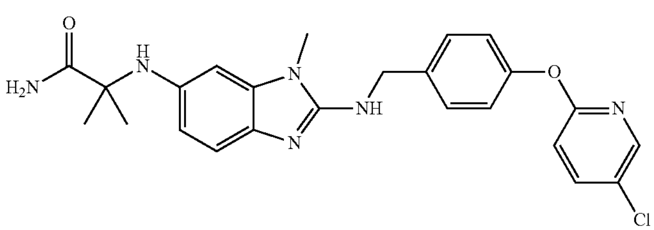 |
| 307 | 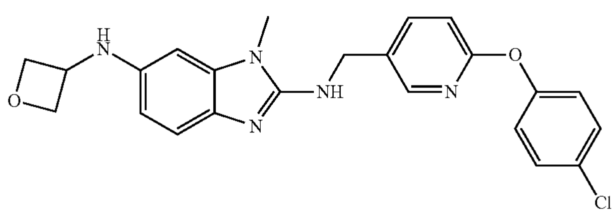 |
| 309 | 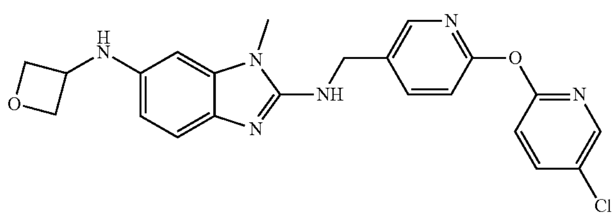 [SMILES: Cn1c(NCc2ccc(Oc3ccc(Cl)cn3)nc2)nc2ccc(NC3COC3)cc21] |
| 312 | 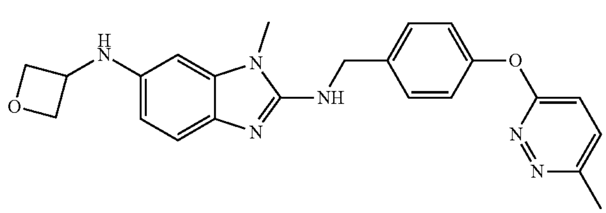 [SMILES: Cc1ccc(Oc2ccc(CNc3nc4ccc(NC5COC5)cc4n3C)cc2)nn1] |

-continued
| No. | Structure |
|---|---|
| 313 | 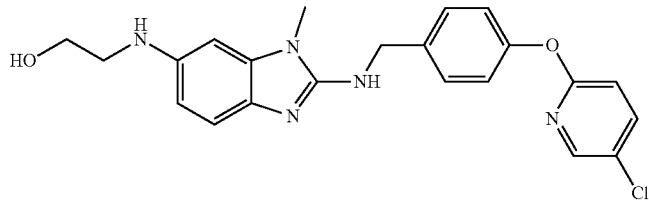 [SMILES: Cn1c(NCc2ccc(Oc3ccc(Cl)cn3)cc2)nc2ccc(NCCO)cc21] |
| 315 | 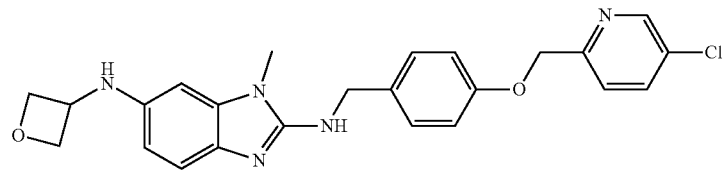 |
| 316 | 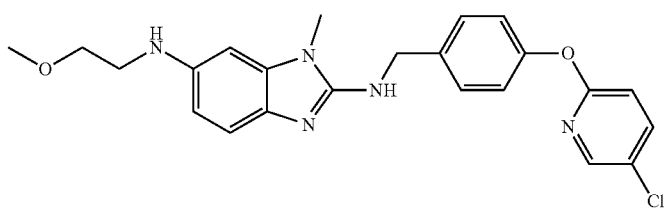 |
| 318 | 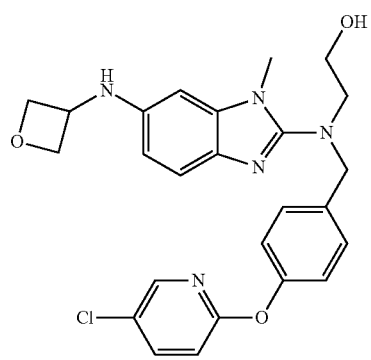 [SMILES: Cn1c(N(CCO)Cc2ccc(Oc3ccc(Cl)cn3)cc2)nc2ccc(NC3COC3)cc21] |
| 320 | 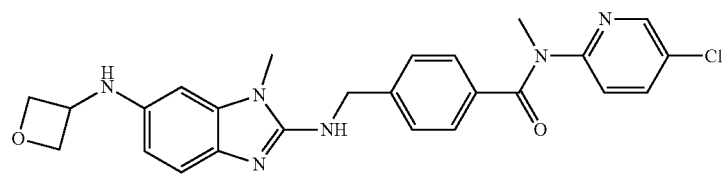 [SMILES: CN(C(=O)c1ccc(CNc2nc3ccc(NC4COC4)cc3n2C)cc1)c1ccc(Cl)cn1] |
| 324 | 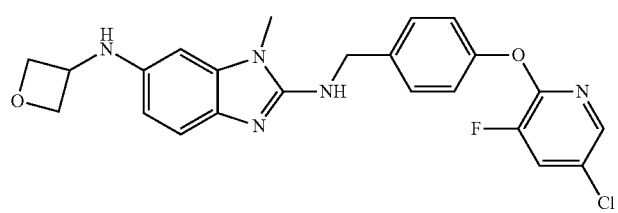 [SMILES: Cn1c(NCc2ccc(Oc3ncc(Cl)cc3F)cc2)nc2ccc(NC3COC3)cc21] |
| 325 | 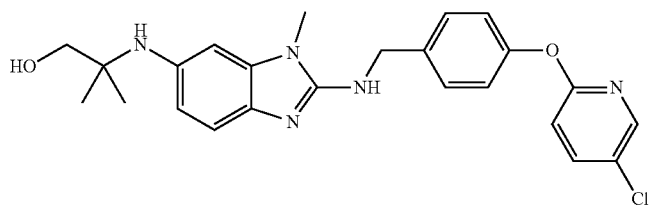 [SMILES: Cn1c(NCc2ccc(Oc3ccc(Cl)cn3)cc2)nc2ccc(NC(C)(C)CO)cc21] |

-continued
| No. | Structure |
|---|---|
| 326 | 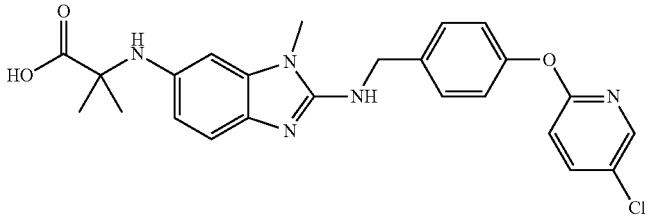 [SMILES: Cn1c(NCc2ccc(Oc3ccc(Cl)cn3)cc2)nc2ccc(NC(C)(C)C(=O)O)cc21] |
| 328 | 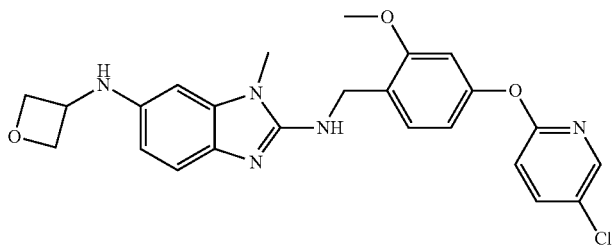 [SMILES: COc1cc(Oc2ccc(Cl)cn2)ccc1CNc1nc2ccc(NC3COC3)cc2n1C] |
| 329 | 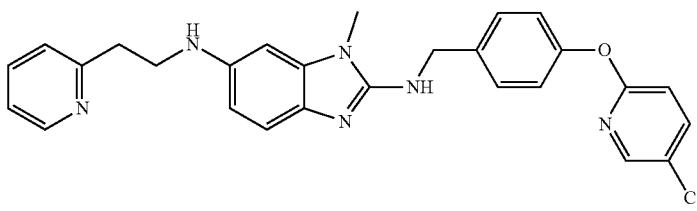 |
| 331 | 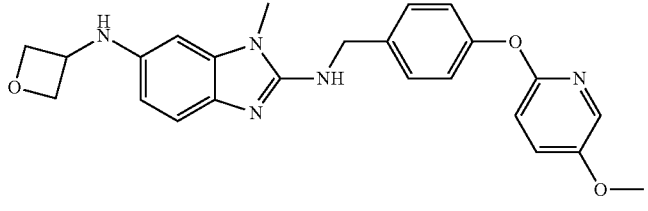 [SMILES: COc1ccc(Oc2ccc(CNc3nc4ccc(NC5COC5)cc4n3C)cc2)nc1] |
| 333 | 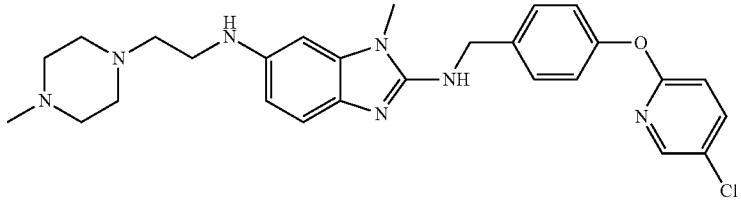 [SMILES: CN1CCN(CCNc2ccc3nc(NCc4ccc(Oc5ccc(Cl)cn5)cc4)n(C)c3c2)CC1] |
| 335 | 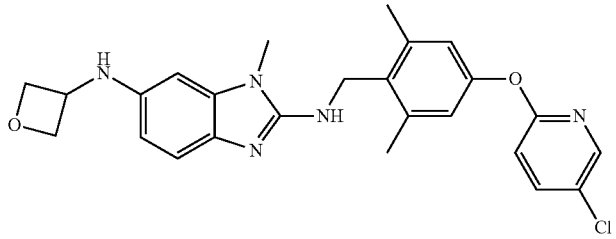 |
| 337 | 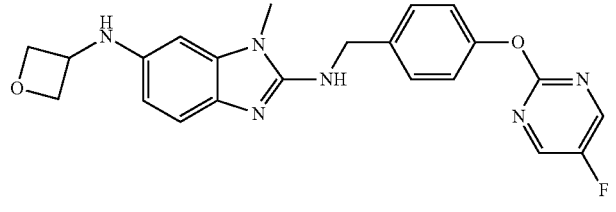 [SMILES: Cn1c(NCc2ccc(Oc3ncc(F)cn3)cc2)nc2ccc(NC3COC3)cc21] |

| No. | Structure |
|---|---|
| 339 | 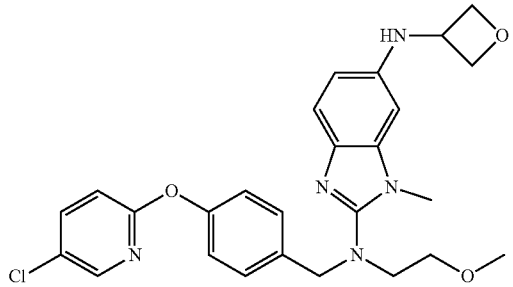 [SMILES: COCCN(Cc1ccc(Oc2ccc(Cl)cn2)cc1)c1nc2ccc(NC3COC3)cc2n1C] |
| 341 | 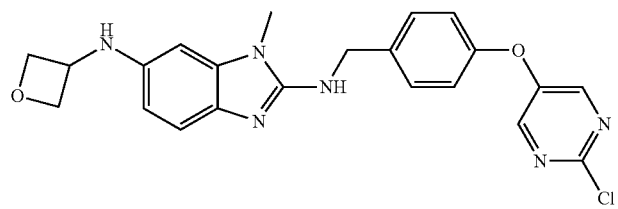 [SMILES: Cn1c(NCc2ccc(Oc3cnc(Cl)nc3)cc2)nc2ccc(NC3COC3)cc21] |
| 343 | 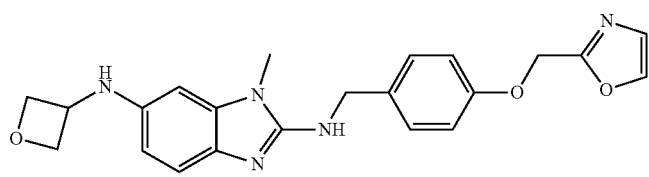 [SMILES: Cn1c(NCc2ccc(OCc3ncco3)cc2)nc2ccc(NC3COC3)cc21] |
| 345 | 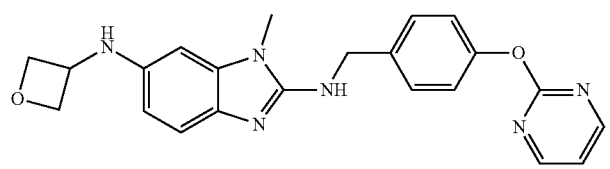 [SMILES: Cn1c(NCc2ccc(Oc3ncccn3)cc2)nc2ccc(NC3COC3)cc21] |
| 347 | 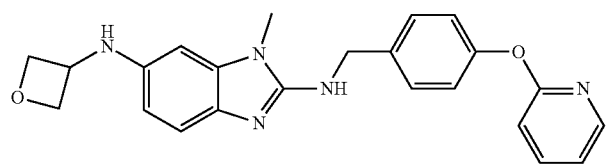 [SMILES: Cn1c(NCc2ccc(Oc3ccccn3)cc2)nc2ccc(NC3COC3)cc21] |
| 349 | 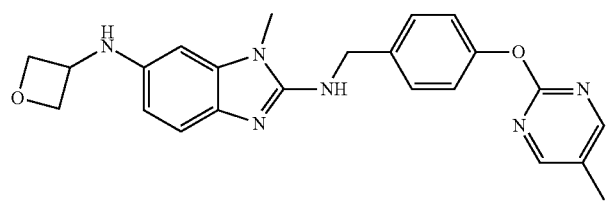 [SMILES: Cc1cnc(Oc2ccc(CNc3nc4ccc(NC5COC5)cc4n3C)cc2)nc1] |
| 351 | 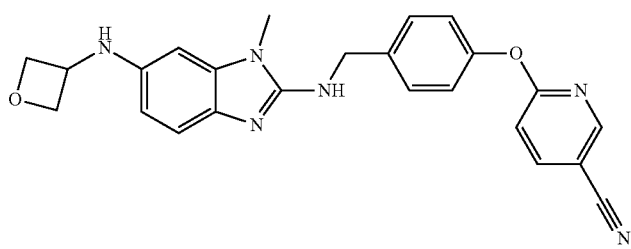 |

-continued

| No. | Structure |
|---|---|
| 353 | 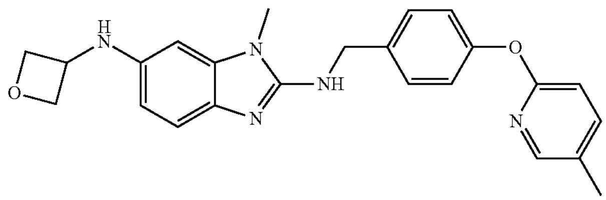 |
| 357 | 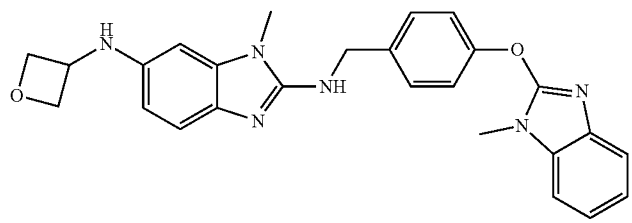 [SMILES: Cn1c(NCc2ccc(Oc3nc4ccccc4n3C)cc2)nc2ccc(NC3COC3)cc21] |
| 358 | 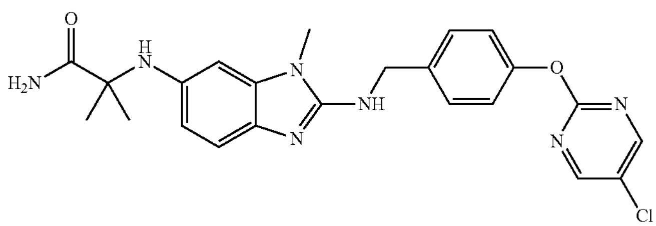 |
| 359 | 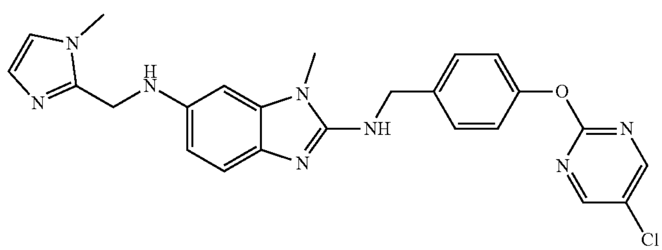 [SMILES: Cn1ccnc1CNc1ccc2nc(NCc3ccc(Oc4ncc(Cl)cn4)cc3)n(C)c2c1] |
| 362 | 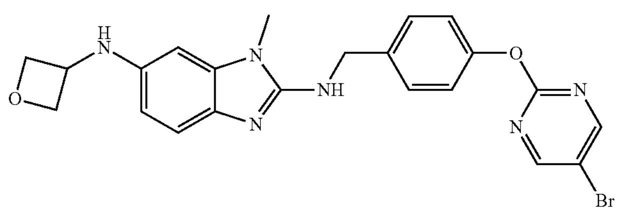 [SMILES: Cn1c(NCc2ccc(Oc3ncc(Br)cn3)cc2)nc2ccc(NC3COC3)cc21] |
| 364 | 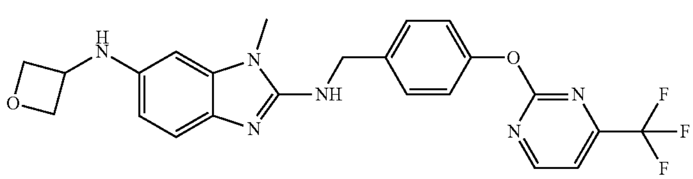 [SMILES: Cn1c(NCc2ccc(Oc3nccc(C(F)(F)F)n3)cc2)nc2ccc(NC3COC3)cc21] |
| 365 | 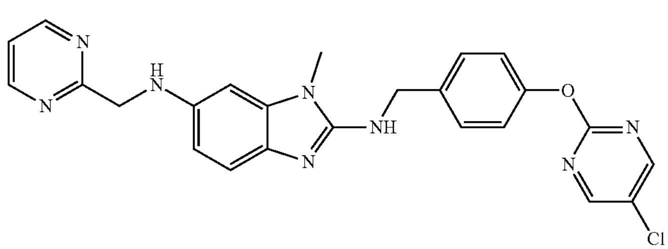 [SMILES: Cn1c(NCc2ccc(Oc3ncc(Cl)cn3)cc2)nc2ccc(NCc3ncccn3)cc21] |

-continued
| No. | Structure |
|---|---|
| 366 | 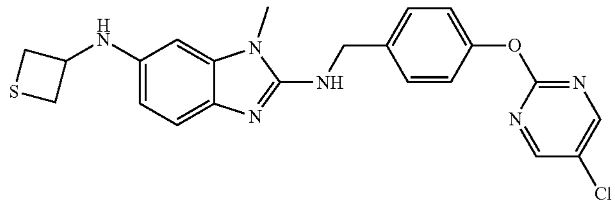 [SMILES: Cn1c(NCc2ccc(Oc3ncc(Cl)cn3)cc2)nc2ccc(NC3CSC3)cc21] |
| 368 | 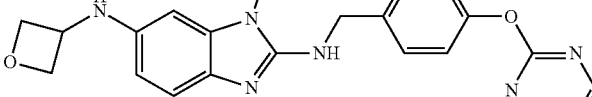 |
| 369 | 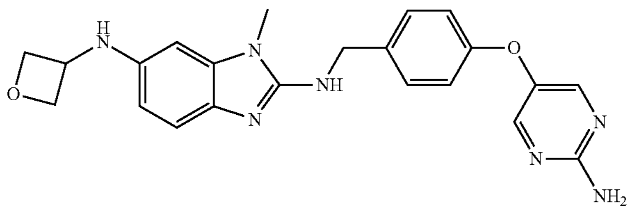 [SMILES: Cn1c(NCc2ccc(Oc3cnc(N)nc3)cc2)nc2ccc(NC3COC3)cc21] |
| 371 | 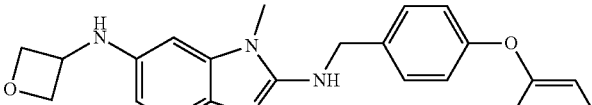 |
| 372 | 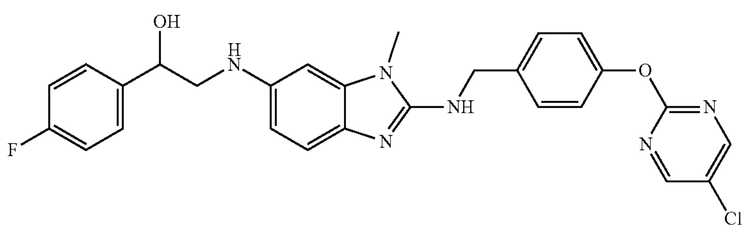 [SMILES: Cn1c(NCc2ccc(Oc3ncc(Cl)cn3)cc2)nc2ccc(NCC(O)c3ccc(F)cc3)cc21] |
| 374 | 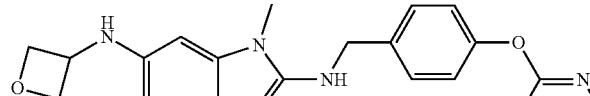 |
| 378 | 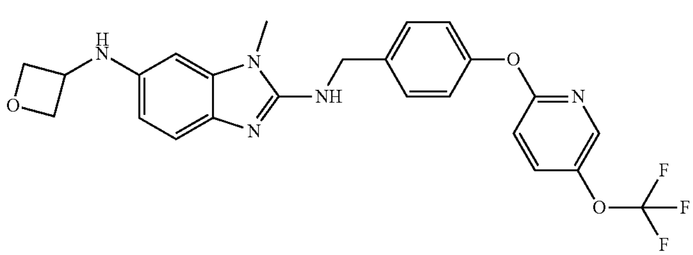 [SMILES: Cn1c(NCc2ccc(Oc3ccc(OC(F)(F)F)cn3)cc2)nc2ccc(NC3COC3)cc21] |

| No. | Structure |
|---|---|
| 379 | 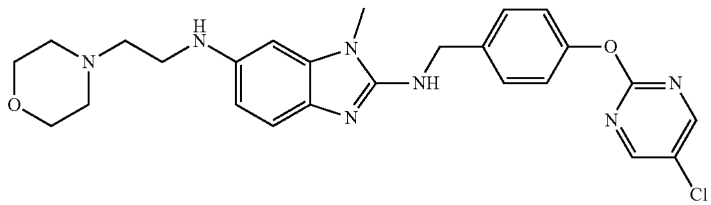 [SMILES: Cn1c(NCc2ccc(Oc3ncc(Cl)cn3)cc2)nc2ccc(NCCN3CCOCC3)cc21] |
| 381 | 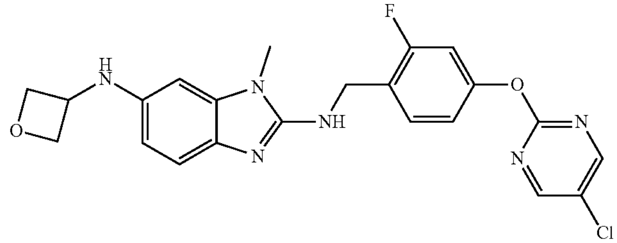 [SMILES: Cn1c(NCc2ccc(Oc3ncc(Cl)cn3)cc2F)nc2ccc(NC3COC3)cc21] |
| 383 | 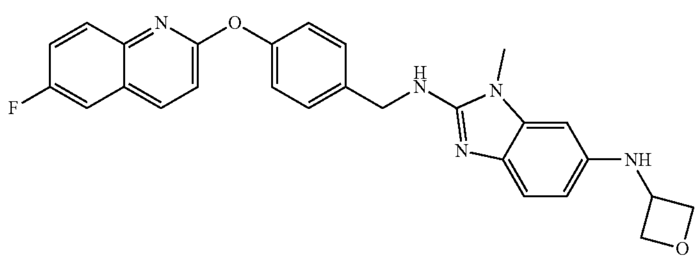 [SMILES: Cn1c(NCc2ccc(Oc3ccc4cc(F)ccc4n3)cc2)nc2ccc(NC3COC3)cc21] |
| 384 | 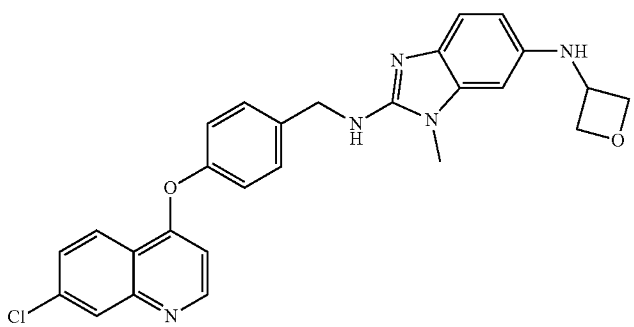 [SMILES: Cn1c(NCc2ccc(Oc3ccnc4cc(Cl)ccc34)cc2)nc2ccc(NC3COC3)cc21] |
| 388 | 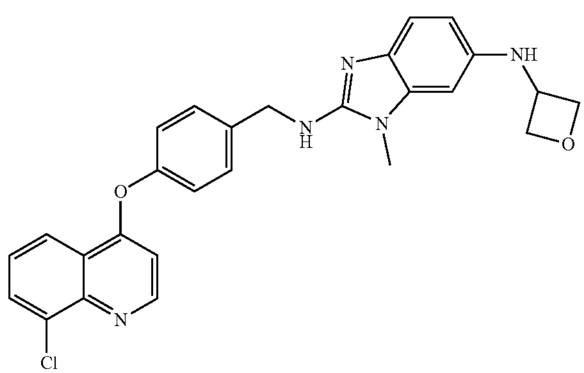 [SMILES: Cn1c(NCc2ccc(Oc3ccnc4c(Cl)cccc34)cc2)nc2ccc(NC3COC3)cc21] |

-continued
| No. | Structure |
|---|---|
| 390 | 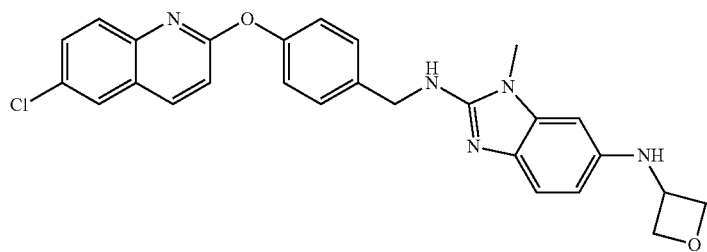 [SMILES: Cn1c(NCc2ccc(Oc3ccc4cc(Cl)ccc4n3)cc2)nc2ccc(NC3COC3)cc21] |
| 392 | 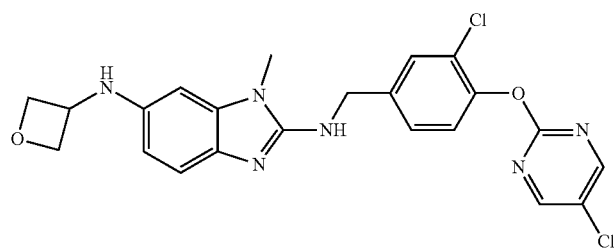 |
| 394 | 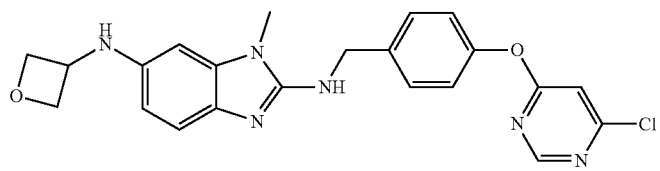 [SMILES: Cn1c(NCc2ccc(Oc3cc(Cl)ncn3)cc2)nc2ccc(NC3COC3)cc21] |
| 396 | 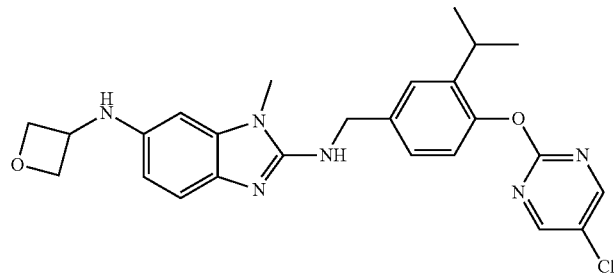 [SMILES: CC(C)c1cc(CNc2nc3ccc(NC4COC4)cc3n2C)ccc1Oc1ncc(Cl)cn1] |
| 398 | 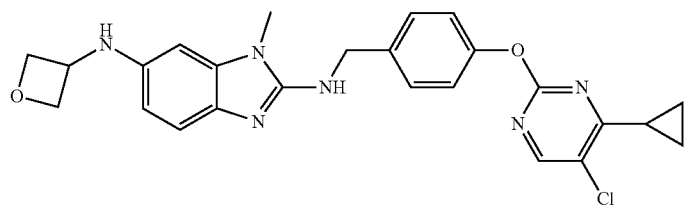 [SMILES: Cn1c(NCc2ccc(Oc3ncc(Cl)c(C4CC4)n3)cc2)nc2ccc(NC3COC3)cc21] |
| 400 | 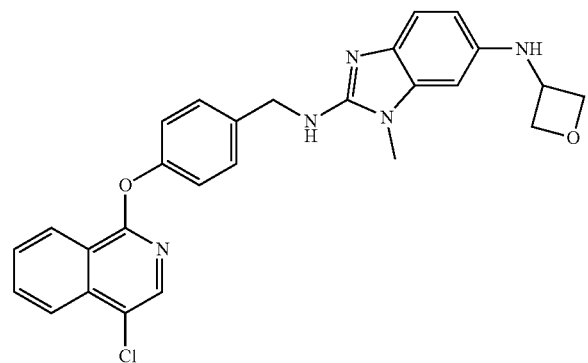 [SMILES: Cn1c(NCc2ccc(Oc3ncc(Cl)c4ccccc34)cc2)nc2ccc(NC3COC3)cc21] |

-continued
| No. | Structure |
|---|---|
| 401 | 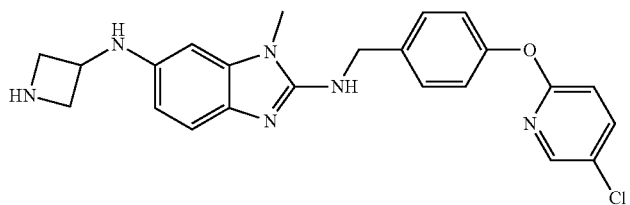 |
| 403 | 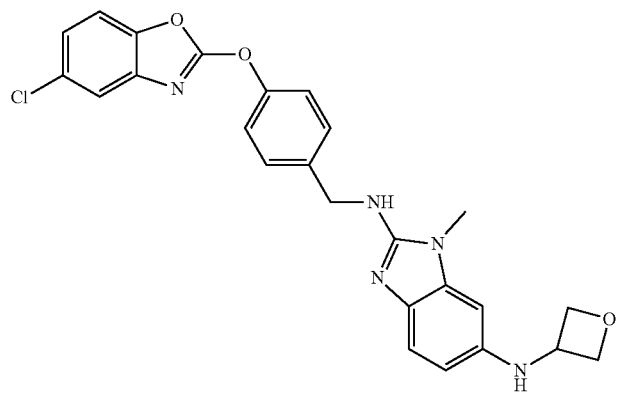 [SMILES: Cn1c(NCc2ccc(Oc3nc4cc(Cl)ccc4o3)cc2)nc2ccc(NC3COC3)cc21] |
| 404 | 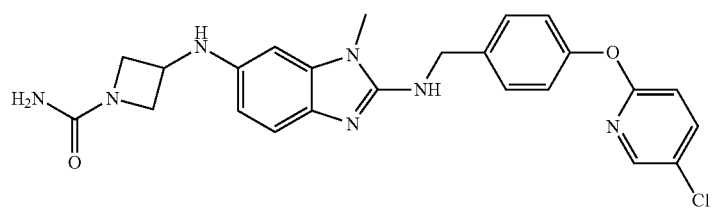 [SMILES: Cn1c(NCc2ccc(Oc3ccc(Cl)cn3)cc2)nc2ccc(NC3CN(C(N)=O)C3)cc21] |
| 406 | 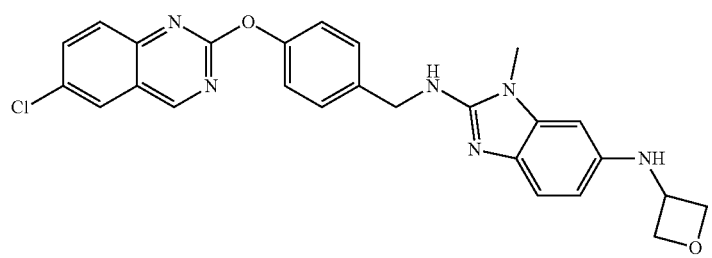 [SMILES: Cn1c(NCc2ccc(Oc3ncc4cc(Cl)ccc4n3)cc2)nc2ccc(NC3COC3)cc21] |
| 407 | 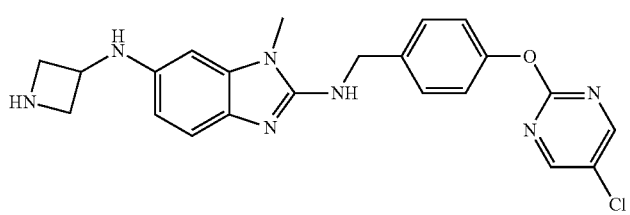 [SMILES: Cn1c(NCc2ccc(Oc3ncc(Cl)cn3)cc2)nc2ccc(NC3CNC3)cc21] |
| 408 | 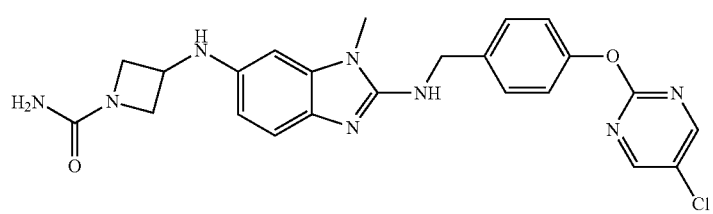 |

-continued
| No. | Structure |
|---|---|
| 409 | 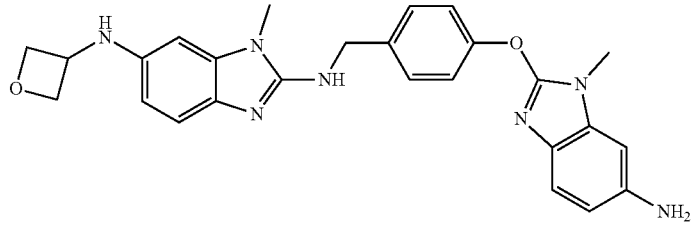 [SMILES: Cn1c(NCc2ccc(Oc3nc4ccc(N)cc4n3C)cc2)nc2ccc(NC3COC3)cc21] |
| 412 | 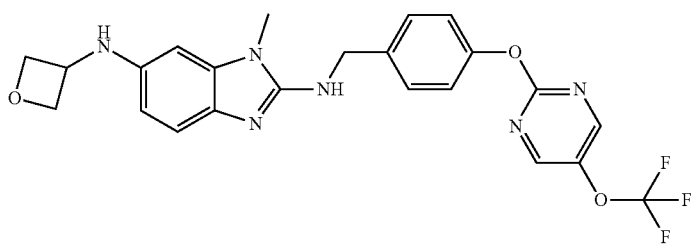 [SMILES: Cn1c(NCc2ccc(Oc3ncc(OC(F)(F)F)cn3)cc2)nc2ccc(NC3COC3)cc21] |
| 413 | 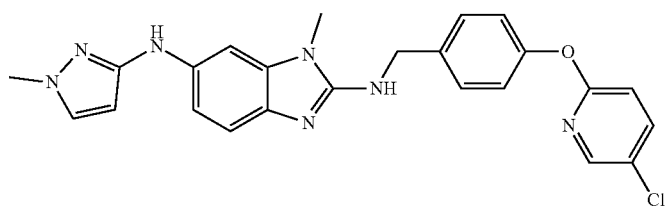 |
| 414 | 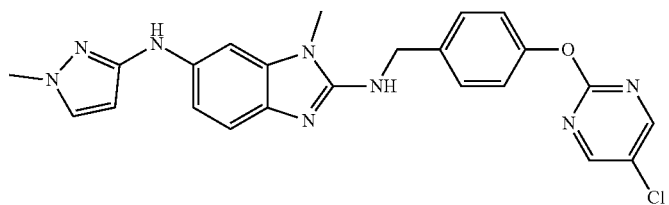 |
| 415 | 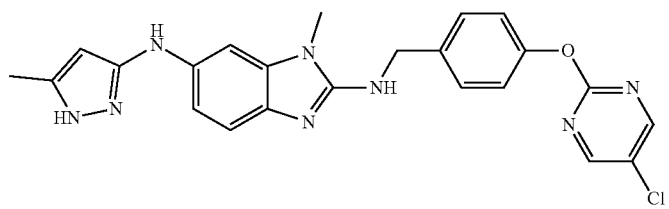 [SMILES: Cc1cc(Nc2ccc3nc(NCc4ccc(Oc5ncc(Cl)cn5)cc4)n(C)c3c2)n[nH]1] |
| 417 | 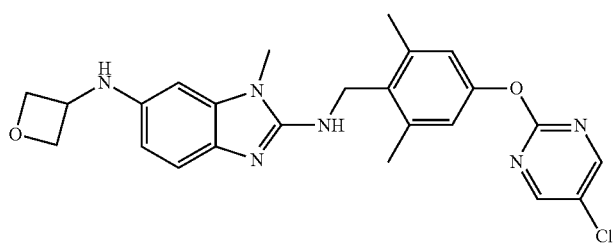 |

| No. | Structure |
|---|---|
| 418 | 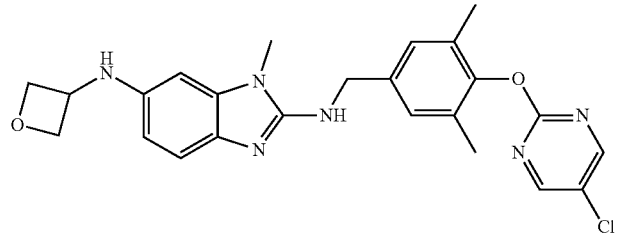 [SMILES: Cc1cc(CNc2nc3ccc(NC4COC4)cc3n2C)cc(C)c1Oc1ncc(Cl)cn1] |
| 420 | 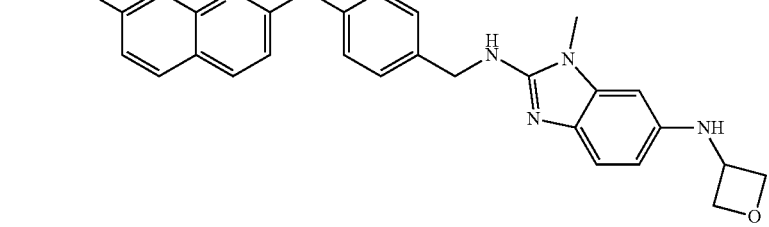 |
| 422 | 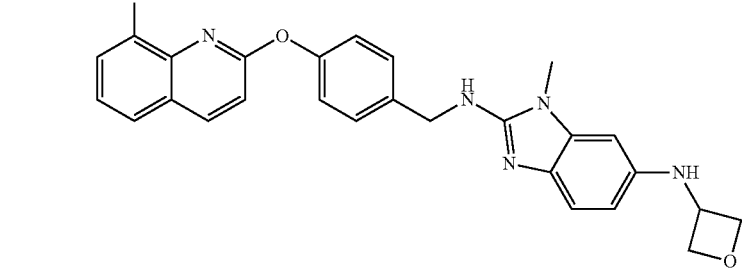 |
| 423 | 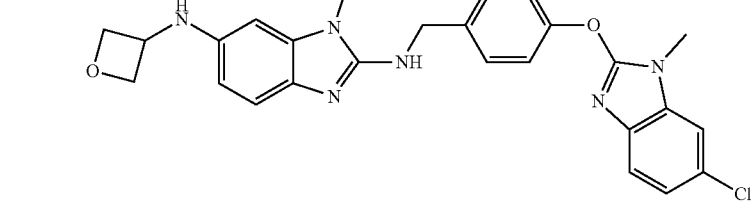 |
| 425 | 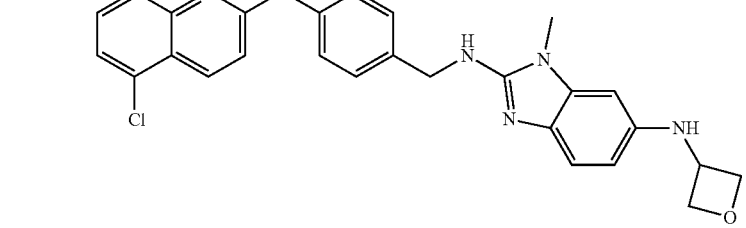 |
| 427 | 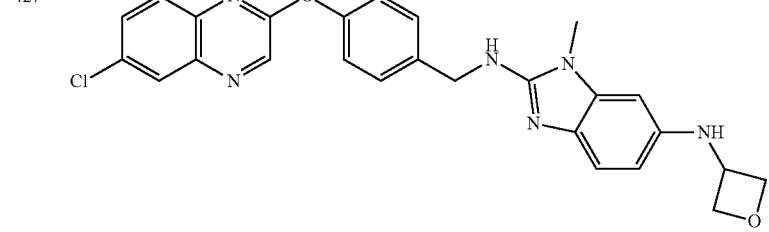 |

| No. | Structure |
|---|---|
| 429 | 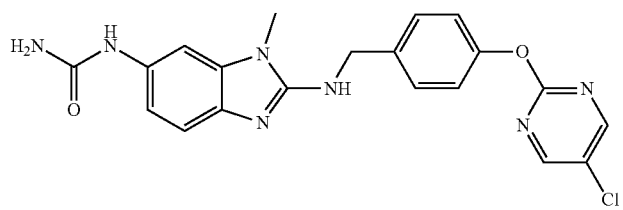 [SMILES: Cn1c(NCc2ccc(Oc3ncc(Cl)cn3)cc2)nc2ccc(NC(N)=O)cc21] |
| 431 | 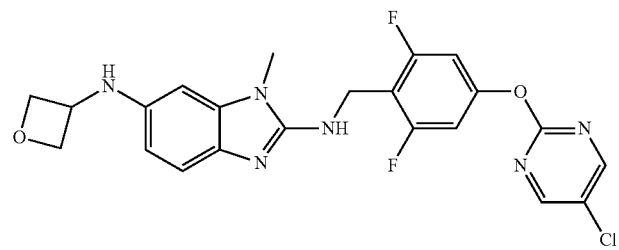 [SMILES: Cn1c(NCc2c(F)cc(Oc3ncc(Cl)cn3)cc2F)nc2ccc(NC3COC3)cc21] |
| 433 | 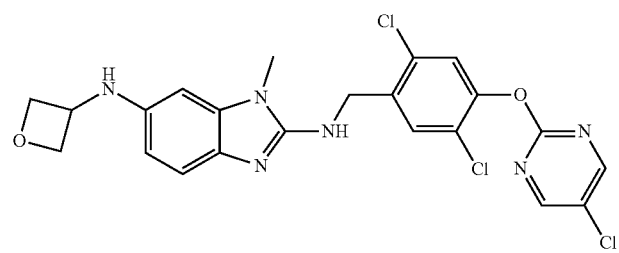 [SMILES: Cn1c(NCc2cc(Cl)c(Oc3ncc(Cl)cn3)cc2Cl)nc2ccc(NC3COC3)cc21] |
| 435 | 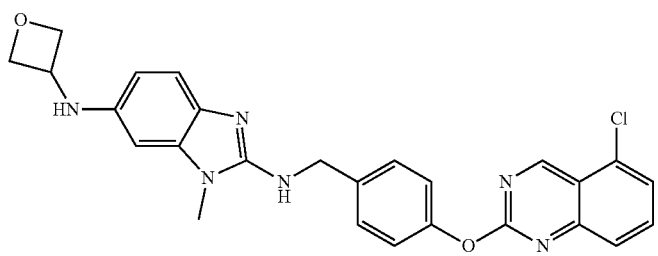 [SMILES: Cn1c(NCc2ccc(Oc3ncc4c(Cl)cccc4n3)cc2)nc2ccc(NC3COC3)cc21] |
| 437 | 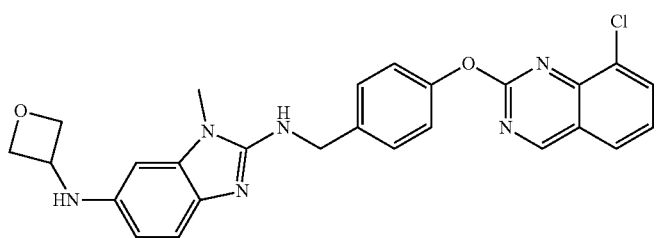 [SMILES: Cn1c(NCc2ccc(Oc3ncc4cccc(Cl)c4n3)cc2)nc2ccc(NC3COC3)cc21] |
| 439 | 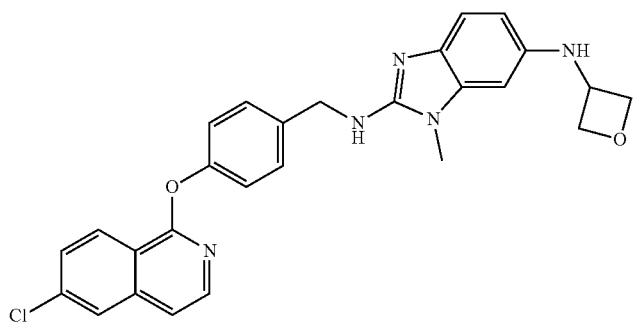 [SMILES: Cn1c(NCc2ccc(Oc3nccc4cc(Cl)ccc34)cc2)nc2ccc(NC3COC3)cc21] |

-continued
| No. | Structure |
|---|---|
| 443 | 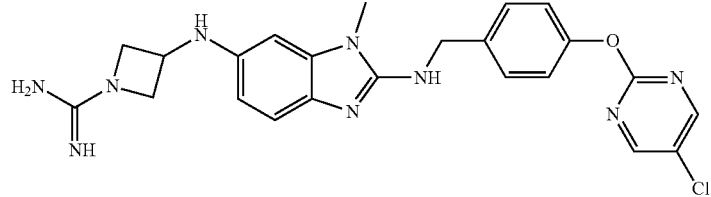 [SMILES: Cn1c(NCc2ccc(Oc3ncc(Cl)cn3)cc2)nc2ccc(NC3CN(C(=N)N)C3)cc21] |
| 444 | 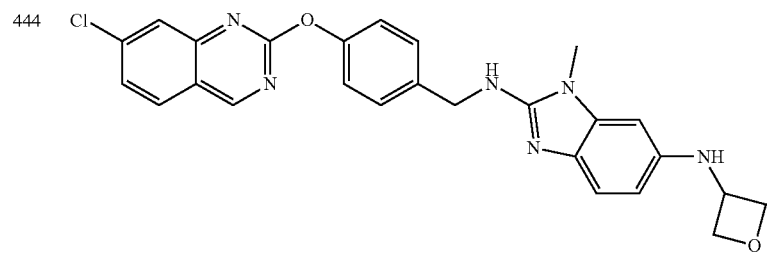 |
| 449 | 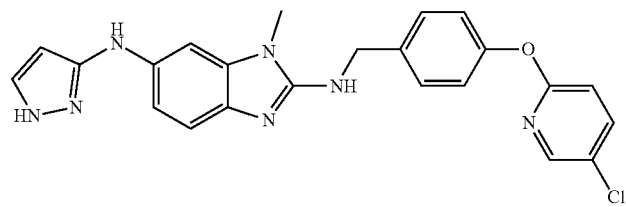 [SMILES: Cn1c(NCc2ccc(Oc3ccc(Cl)cn3)cc2)nc2ccc(Nc3cc[nH]n3)cc21] |
| 450 | 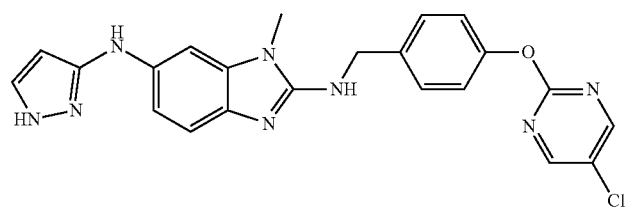 [SMILES: Cn1c(NCc2ccc(Oc3ncc(Cl)cn3)cc2)nc2ccc(Nc3cc[nH]n3)cc21] |
| 453 | 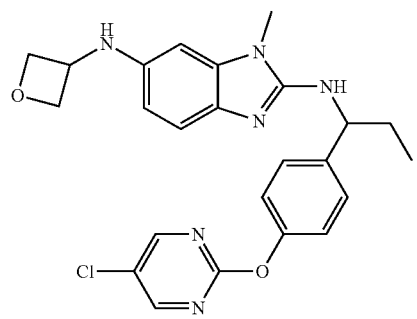 [SMILES: CCC(Nc1nc2ccc(NC3COC3)cc2n1C)c1ccc(Oc2ncc(Cl)cn2)cc1] |
| 455 | 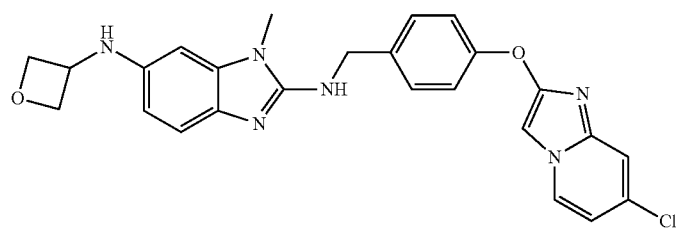 [SMILES: Cn1c(NCc2ccc(Oc3cn4ccc(Cl)cc4n3)cc2)nc2ccc(NC3COC3)cc21] |

| No. | Structure |
|---|---|
| 457 | 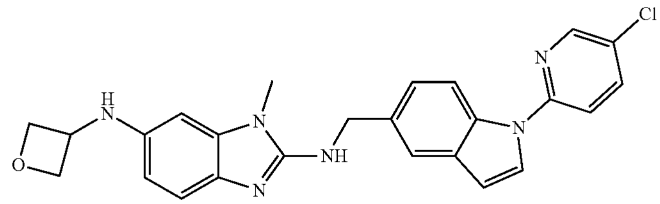 [SMILES: Cn1c(NCc2ccc3c(ccn3-c3ccc(Cl)cn3)c2)nc2ccc(NC3COC3)cc21] |
| 459 | 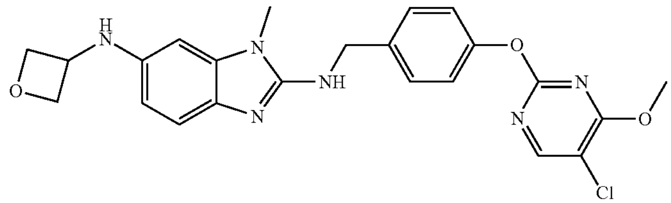 [SMILES: COc1nc(Oc2ccc(CNc3nc4ccc(NC5COC5)cc4n3C)cc2)ncc1Cl] |
| 461 | 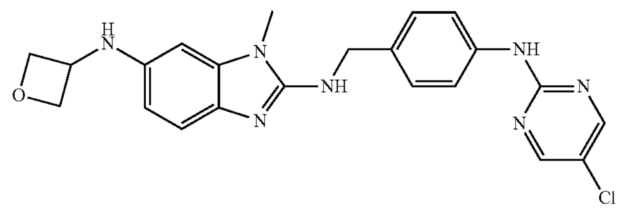 |
| 465 | 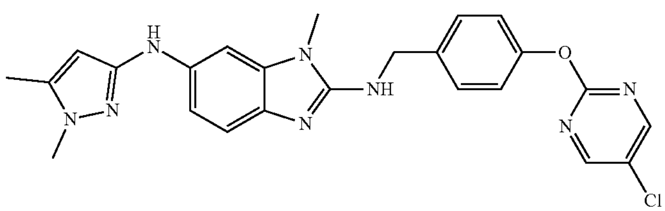 [SMILES: Cc1cc(Nc2ccc3nc(NCc4ccc(Oc5ncc(Cl)cn5)cc4)n(C)c3c2)nn1C] |
| 466 | 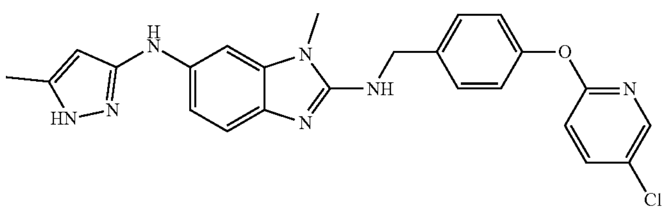 [SMILES: Cc1cc(Nc2ccc3nc(NCc4ccc(Oc5ccc(Cl)cn5)cc4)n(C)c3c2)n[nH]1] |
| 467 | 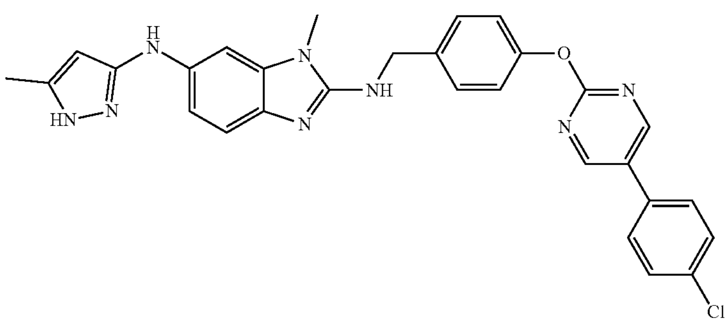 [SMILES: Cc1cc(Nc2ccc3nc(NCc4ccc(Oc5ncc(-c6ccc(Cl)cc6)cn5)cc4)n(C)c3c2)n[nH]1] |
| 468 | 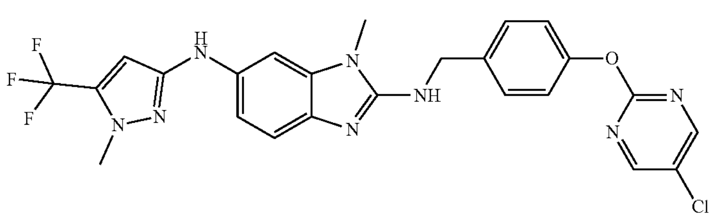 |

| No. | Structure |
|---|---|
| 469 | 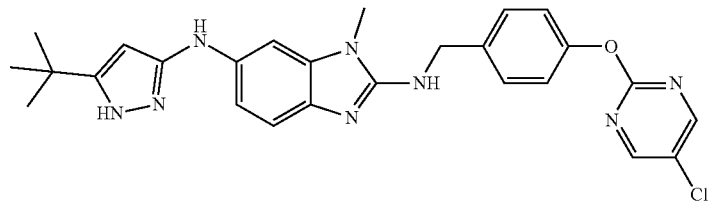 [SMILES: Cn1c(NCc2ccc(Oc3ncc(Cl)cn3)cc2)nc2ccc(Nc3cc(C(C)(C)C)[nH]n3)cc21] |
| 471 | 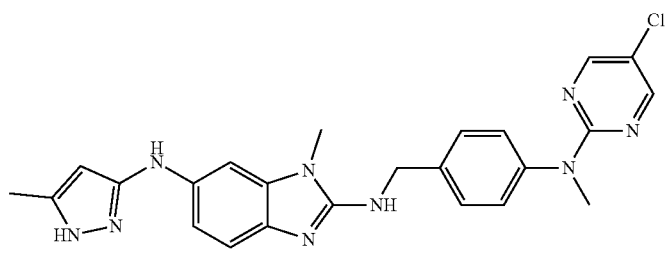 [SMILES: Cc1cc(Nc2ccc3nc(NCc4ccc(N(C)c5ncc(Cl)cn5)cc4)n(C)c3c2)n[nH]1] |
| 473 | 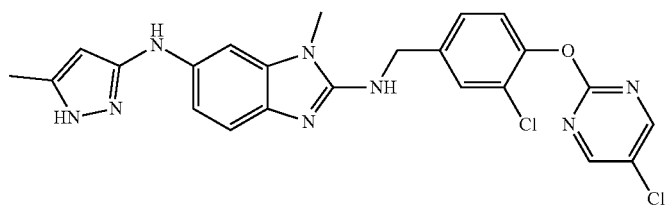 [SMILES: Cc1cc(Nc2ccc3nc(NCc4ccc(Oc5ncc(Cl)cn5)c(Cl)c4)n(C)c3c2)n[nH]1] |
| 474 | 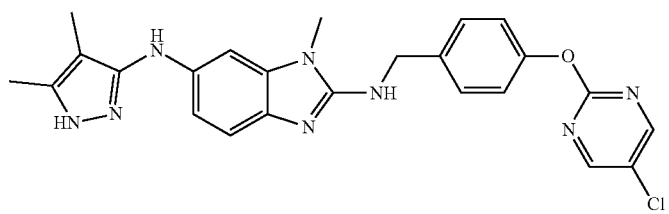 [SMILES: Cc1[nH]nc(Nc2ccc3nc(NCc4ccc(Oc5ncc(Cl)cn5)cc4)n(C)c3c2)c1C] |
| 475 | 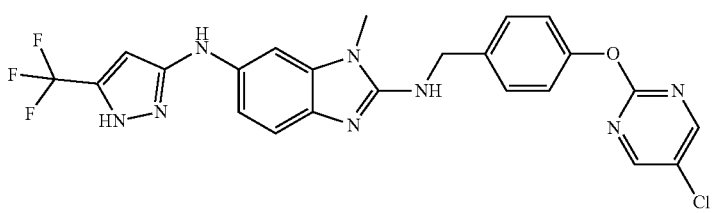 [SMILES: Cn1c(NCc2ccc(Oc3ncc(Cl)cn3)cc2)nc2ccc(Nc3cc(C(F)(F)F)[nH]n3)cc21] |
| 476 | 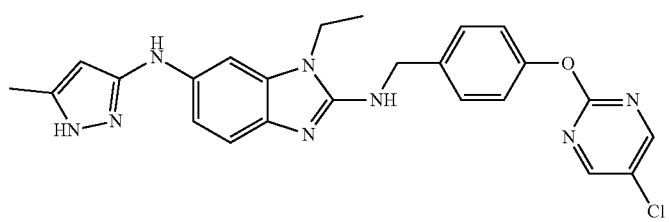 [SMILES: CCn1c(NCc2ccc(Oc3ncc(Cl)cn3)cc2)nc2ccc(Nc3cc(C)[nH]n3)cc21] |

-continued
| No. | Structure |
|---|---|
| 477 | 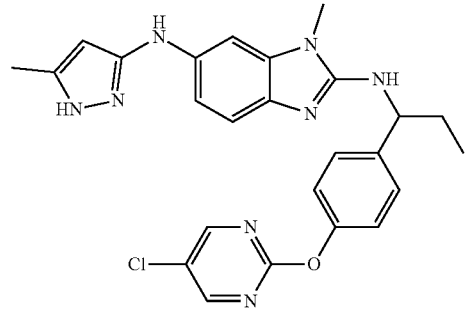 [SMILES: CCC(Nc1nc2ccc(Nc3cc(C)[nH]n3)cc2n1C)c1ccc(Oc2ncc(Cl)cn2)cc1] |
| 478 | 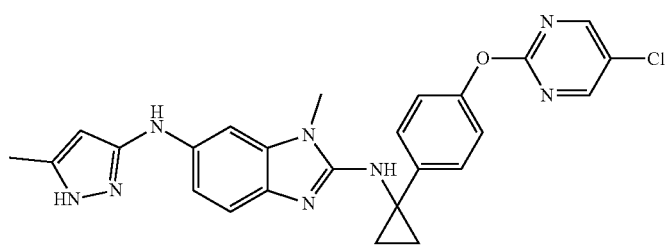 [SMILES: Cc1cc(Nc2ccc3nc(NC4(c5ccc(Oc6ncc(Cl)cn6)cc5)CC4)n(C)c3c2)n[nH]1] |
| 479 | 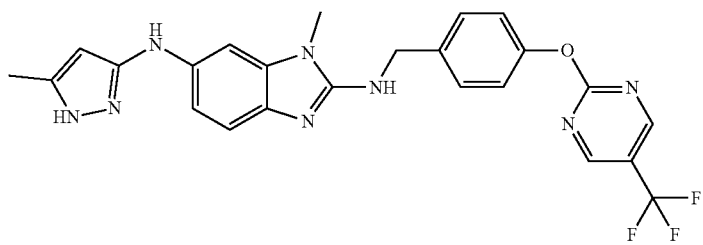 [SMILES: Cc1cc(Nc2ccc3nc(NCc4ccc(Oc5ncc(C(F)(F)F)cn5)cc4)n(C)c3c2)n[nH]1] |
| 481 | 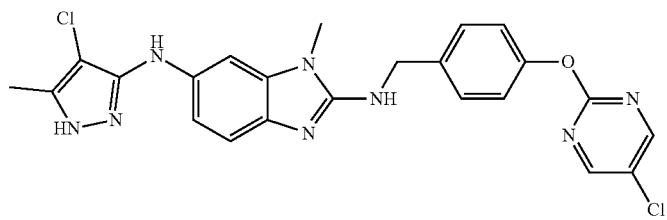 |
| 482 | 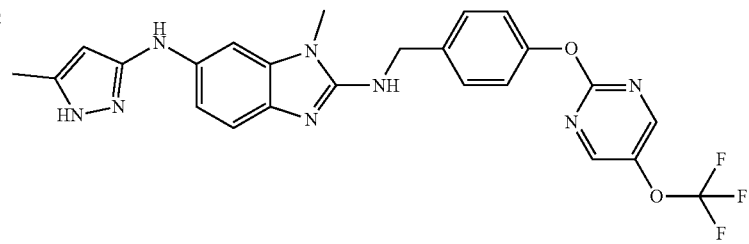 |
| 483 | 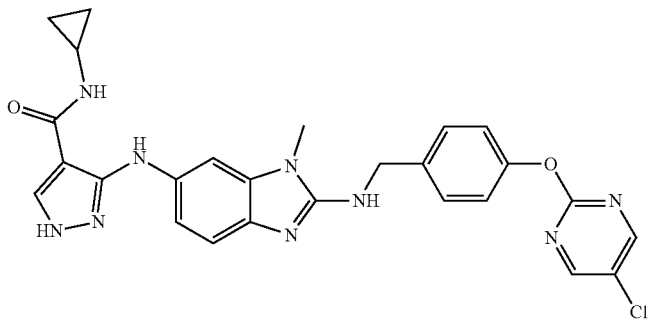 [SMILES: Cn1c(NCc2ccc(Oc3ncc(Cl)cn3)cc2)nc2ccc(Nc3n[nH]cc3C(=O)NC3CC3)cc21] |

-continued
| No. | Structure |
|---|---|
| 486 | 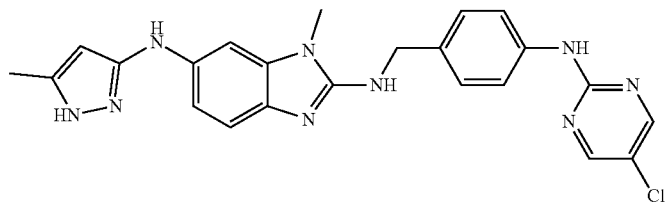 |
| 487 | 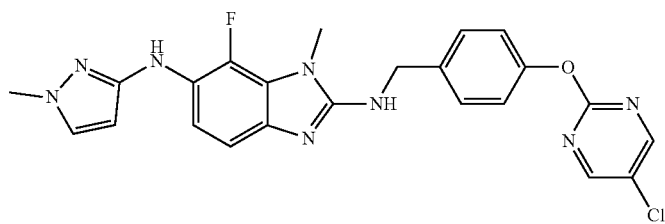 [SMILES: Cn1ccc(Nc2ccc3nc(NCc4ccc(Oc5ncc(Cl)cn5)cc4)n(C)c3c2F)n1] |
| 489 | 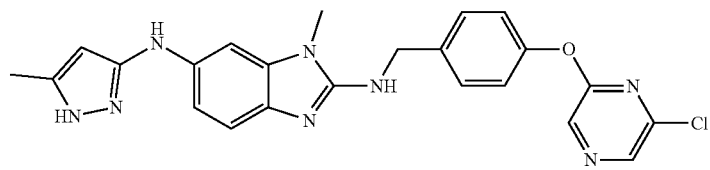 [SMILES: Cc1cc(Nc2ccc3nc(NCc4ccc(Oc5cncc(Cl)n5)cc4)n(C)c3c2)n[nH]1] |
| 490 | 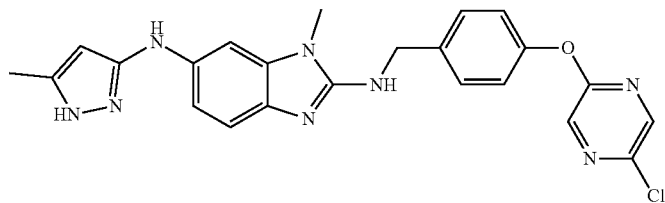 [SMILES: Cc1cc(Nc2ccc3nc(NCc4ccc(Oc5cnc(Cl)cn5)cc4)n(C)c3c2)n[nH]1] |
| 491 | 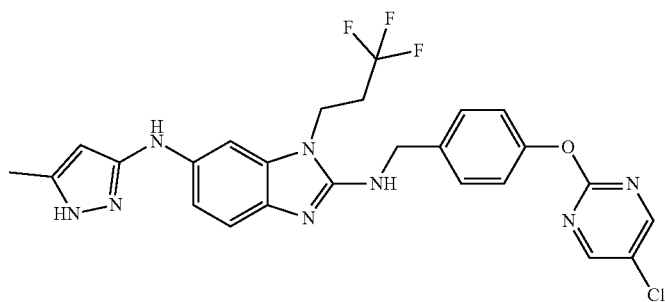 [SMILES: Cc1cc(Nc2ccc3nc(NCc4ccc(Oc5ncc(Cl)cn5)cc4)n(CCC(F)(F)F)c3c2)n[nH]1] |
| 492 | 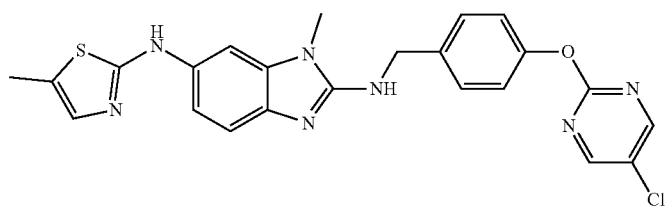 |

-continued
| No. | Structure |
|---|---|
| 495 | 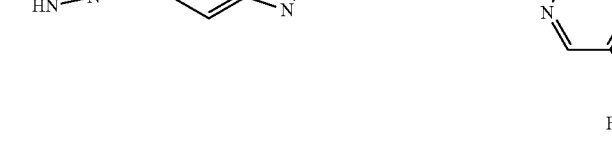 |
| 496 | 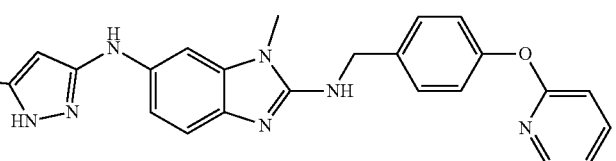 |
| 499 | 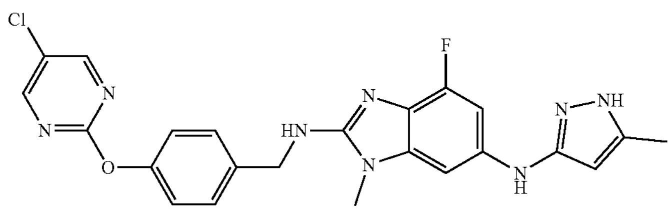 [SMILES: Cc1cc(Nc2cc(F)c3nc(NCc4ccc(Oc5ncc(Cl)cn5)cc4)n(C)c3c2)n[nH]1] |
| 501 | 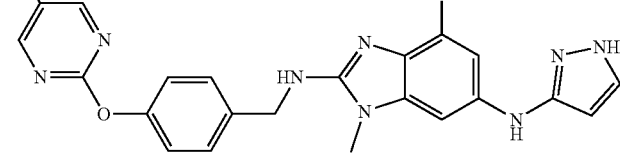 |
| 503 | 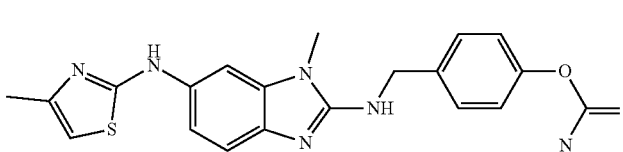 |
| 505 | 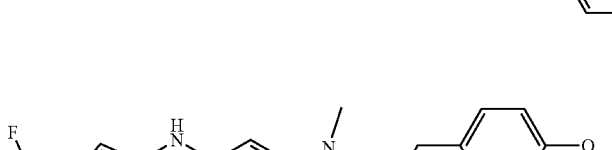 |

| No. | Structure |
|---|---|
| 507 | 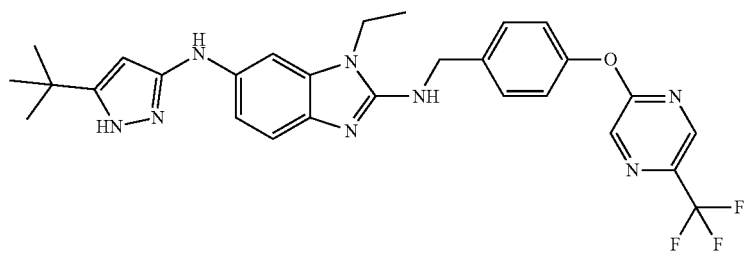 [SMILES: CCn1c(NCc2ccc(Oc3cnc(C(F)(F)F)cn3)cc2)nc2ccc(Nc3cc(C(C)(C)C)[nH]n3)cc21] |
| 509 | 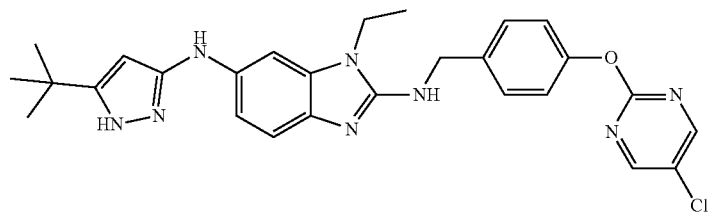 [SMILES: CCn1c(NCc2ccc(Oc3ncc(Cl)cn3)cc2)nc2ccc(Nc3cc(C(C)(C)C)[nH]n3)cc21] |
| 512 | 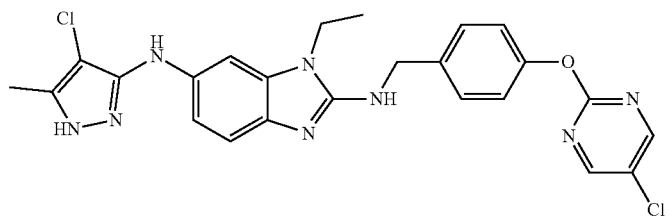 [SMILES: CCn1c(NCc2ccc(Oc3ncc(Cl)cn3)cc2)nc2ccc(Nc3n[nH]c(C)c3Cl)cc21] |
| 513 | 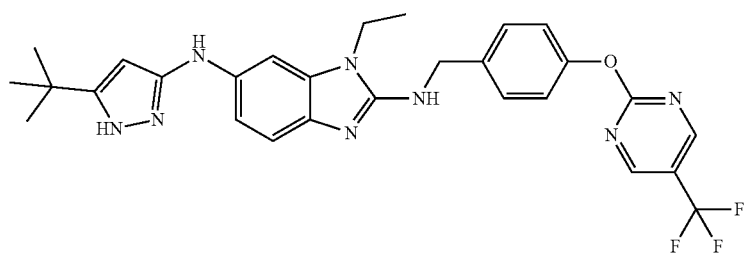 [SMILES: CCn1c(NCc2ccc(Oc3ncc(C(F)(F)F)cn3)cc2)nc2ccc(Nc3cc(C(C)(C)C)[nH]n3)cc21] |
| 514 | 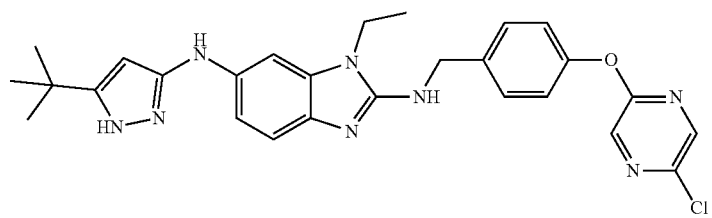 |
| 525 | 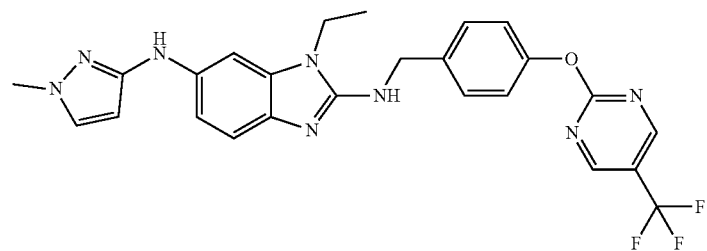 [SMILES: CCn1c(NCc2ccc(Oc3ncc(C(F)(F)F)cn3)cc2)nc2ccc(Nc3ccn(C)n3)cc21] |

-continued
| No. | Structure |
|---|---|
| 529 | 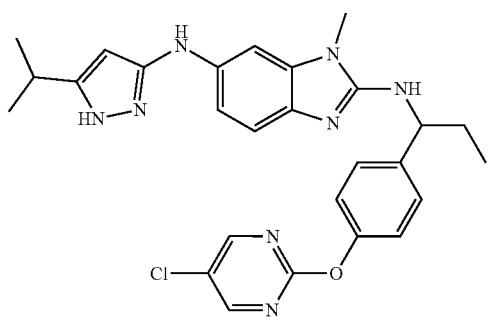 [SMILES: CCC(Nc1nc2ccc(Nc3cc(C(C)C)[nH]n3)cc2n1C)c1ccc(Oc2ncc(Cl)cn2)cc1] |
| 530 | 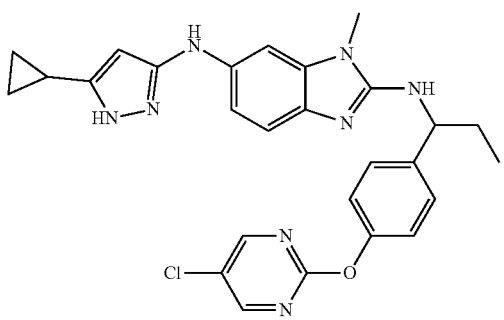 [SMILES: CCC(Nc1nc2ccc(Nc3cc(C4CC4)[nH]n3)cc2n1C)c1ccc(Oc2ncc(Cl)cn2)cc1] |
| 531 | 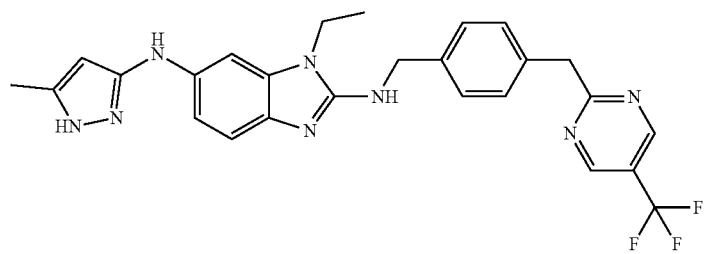 [SMILES: CCn1c(NCc2ccc(Cc3ncc(C(F)(F)F)cn3)cc2)nc2ccc(Nc3cc(C)[nH]n3)cc21] |
| 532 | 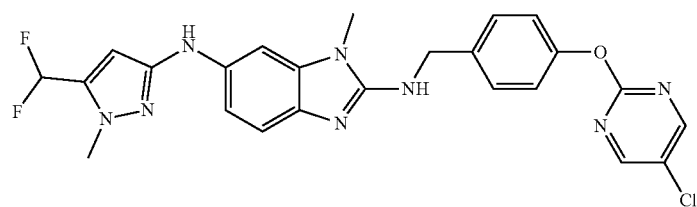 [SMILES: Cn1nc(Nc2ccc3nc(NCc4ccc(Oc5ncc(Cl)cn5)cc4)n(C)c3c2)cc1C(F)F] |
| 533 | 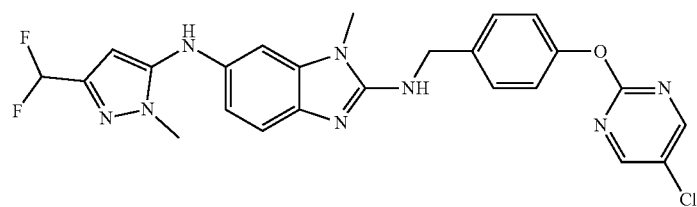 [SMILES: Cn1nc(C(F)F)cc1Nc1ccc2nc(NCc3ccc(Oc4ncc(Cl)cn4)cc3)n(C)c2c1] |

-continued
| No. | Structure |
|---|---|
| 534 | 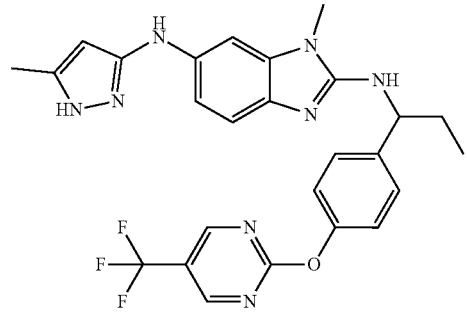 [SMILES: CCC(Nc1nc2ccc(Nc3cc(C)[nH]n3)cc2n1C)c1ccc(Oc2ncc(C(F)(F)F)cn2)cc1] |
| 535 | 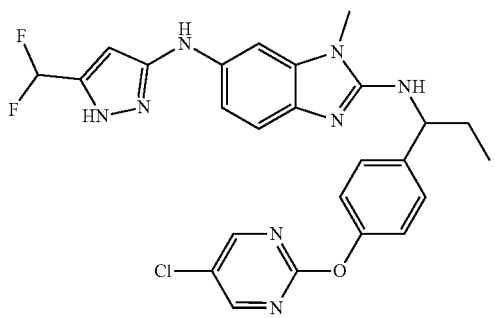 [SMILES: CCC(Nc1nc2ccc(Nc3cc(C(F)F)[nH]n3)cc2n1C)c1ccc(Oc2ncc(Cl)cn2)cc1] |
| 536 | 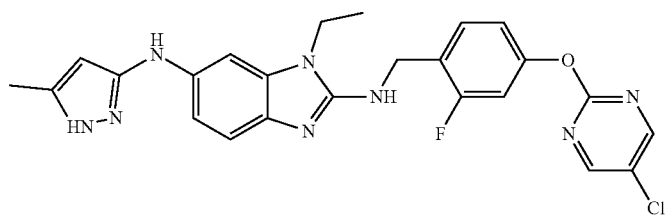 [SMILES: CCn1c(NCc2ccc(Oc3ncc(Cl)cn3)cc2F)nc2ccc(Nc3cc(C)[nH]n3)cc21] |
| 537 | 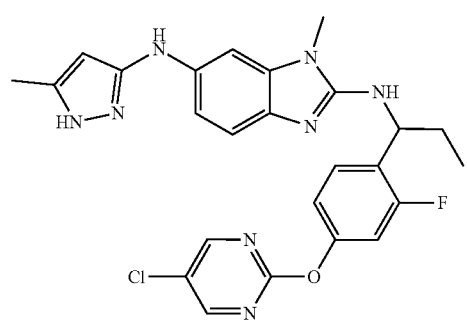 [SMILES: CCC(Nc1nc2ccc(Nc3cc(C)[nH]n3)cc2n1C)c1ccc(Oc2ncc(Cl)cn2)cc1F] |
| 538 | 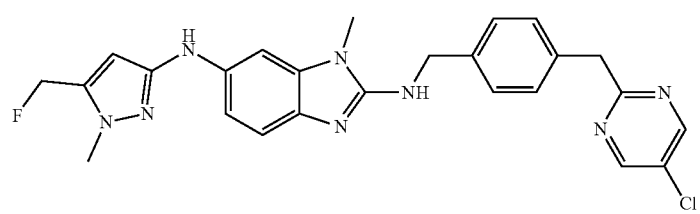 [SMILES: Cn1nc(Nc2ccc3nc(NCc4ccc(Cc5ncc(Cl)cn5)cc4)n(C)c3c2)cc1CF] |
| 539 | 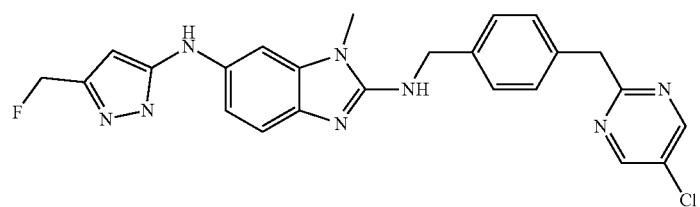 |

| No. | Structure |
|---|---|
| 540 | 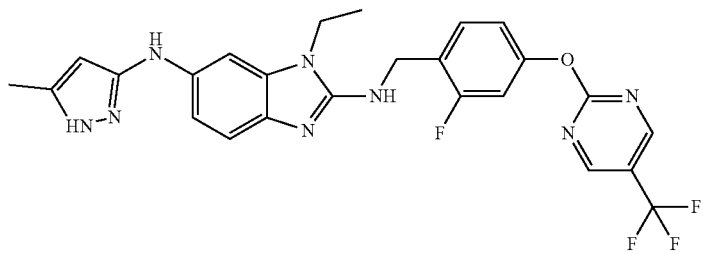 [SMILES: CCn1c(NCc2ccc(Oc3ncc(C(F)(F)F)cn3)cc2F)nc2ccc(Nc3cc(C)[nH]n3)cc21] |
| 541 | 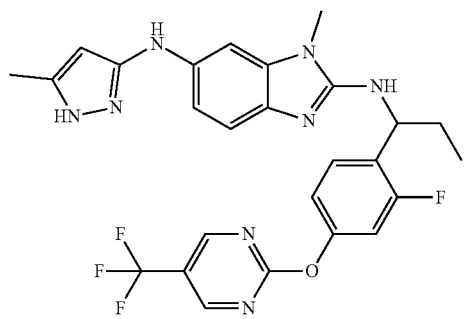 [SMILES: CCC(Nc1nc2ccc(Nc3cc(C)[nH]n3)cc2n1C)c1ccc(Oc2ncc(C(F)(F)F)cn2)cc1F] |
| 542 | 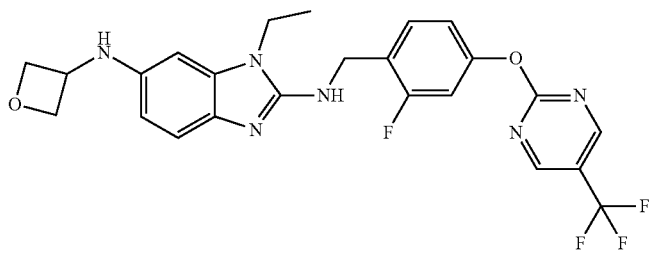 [SMILES: CCn1c(NCc2ccc(Oc3ncc(C(F)(F)F)cn3)cc2F)nc2ccc(NC3COC3)cc21] |
| 543 | 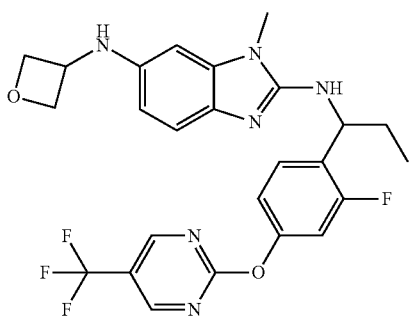 |
| 544 | 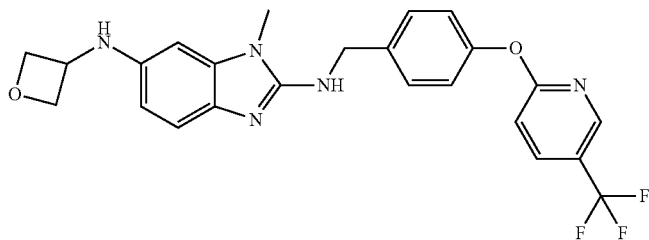 [SMILES: Cn1c(NCc2ccc(Oc3ccc(C(F)(F)F)cn3)cc2)nc2ccc(NC3COC3)cc21] |

-continued
| No. | Structure |
|---|---|
| 546 | 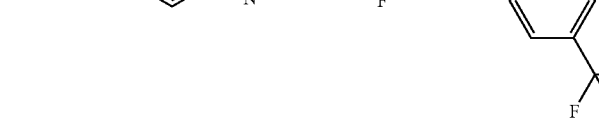 |
| 547 | 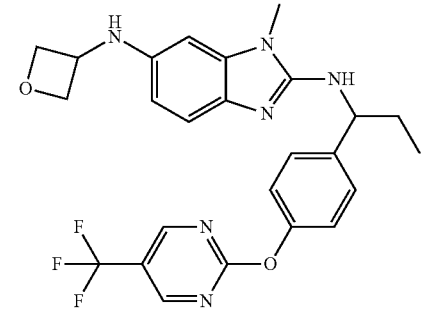 [SMILES: CCC(Nc1nc2ccc(NC3COC3)cc2n1C)c1ccc(Oc2ncc(C(F)(F)F)cn2)cc1] |
| 548 | 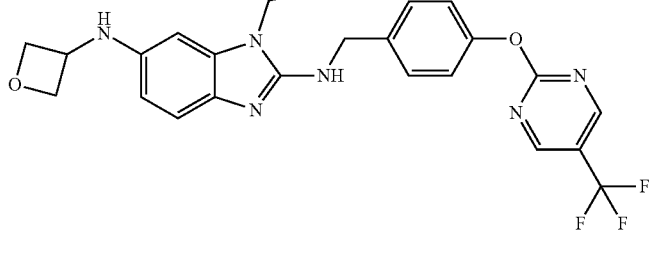 |
| 549 | 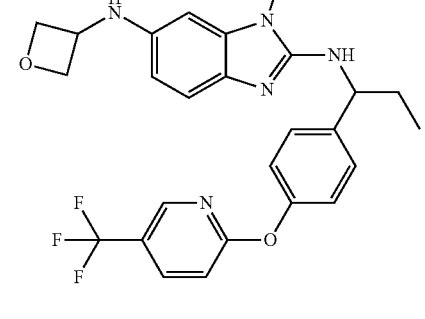 |
| 550 | 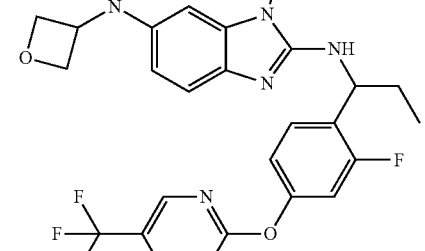 |

| No. | Structure |
|---|---|
| 551 | 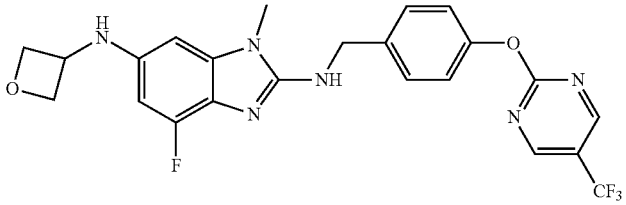 |
| 552 | 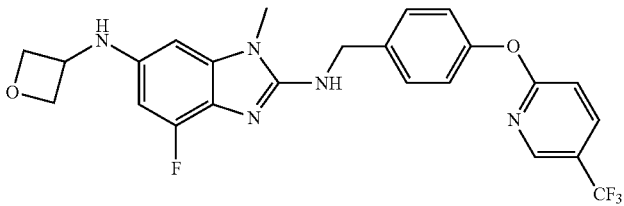 [SMILES: Cn1c(NCc2ccc(Oc3ccc(C(F)(F)F)cn3)cc2)nc2c(F)cc(NC3COC3)cc21] |
| 553 | 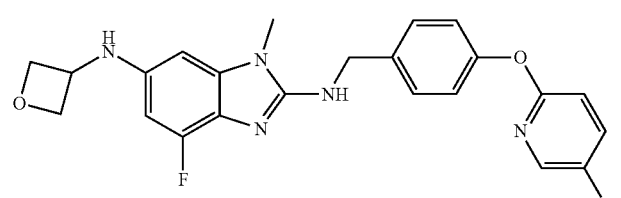 |
| 554 | 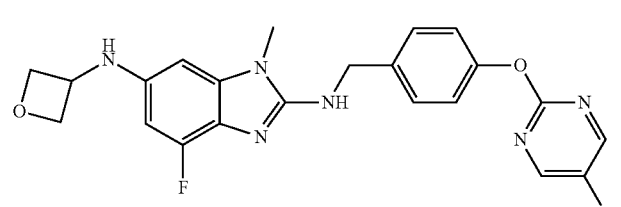 |
| 555 | 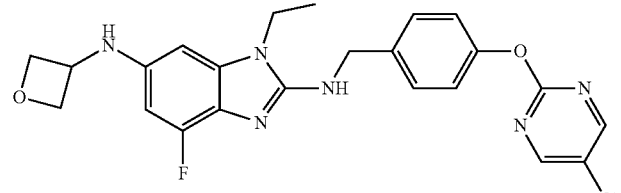 |
| 556 | 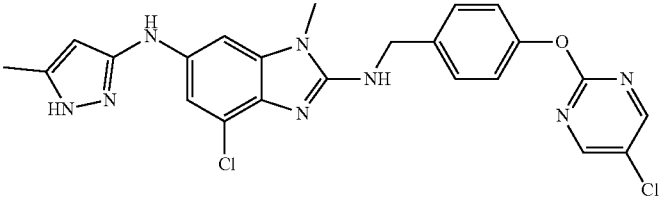 [SMILES: Cc1cc(Nc2cc(Cl)c3nc(NCc4ccc(Oc5ncc(Cl)cn5)cc4)n(C)c3c2)n[nH]1] |
or a pharmaceutically acceptable salt thereof.
16. The compound, according to claim 13, having the following formula:

| NO. | Structure |
|---|---|
| 211 | [chemical structure: oxetan-3-ylamino-substituted N-methyl benzimidazole with NH-CH2-phenyl-O-(5-chloropyridin-2-yl)] | or a pharmaceutically acceptable salt thereof.

17. The compound, according to claim 13, having one of the following formulae:

| | Structure |
|---|---|
| 53 | [chemical structure: 5-amino-1-methyl-benzimidazol-2-yl-NH-CH2CH2-O-phenyl-O-CF3] |
| 226 | [chemical structure: oxetan-3-ylamino-substituted N-methyl benzimidazole with NH-CH2-phenyl-O-(6-trifluoromethylpyridin-3-yl)] | or a pharmaceutically acceptable salt thereof.

18. The compound, according to claim 13, having one of the following formulae:

| No. | Structure |
|---|---|
| 53 | [chemical structure: 5-amino-1-methyl-benzimidazol-2-yl-NH-CH2CH2-O-phenyl-O-CF3] |
| 55 | [chemical structure: 5-amino-benzimidazole with N-CH2CH2-O-phenyl-O-CF3 and 2-pyrrolidinyl] |

| No. | Structure |
|---|---|
| 57 | 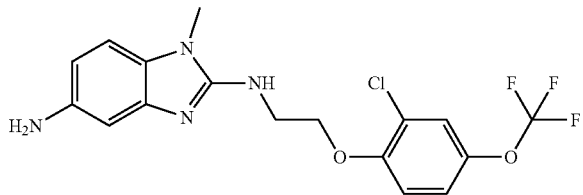 [SMILES: Cn1c(NCCOc2ccc(OC(F)(F)F)cc2)nc2cc(N)ccc21] |
| 59 | 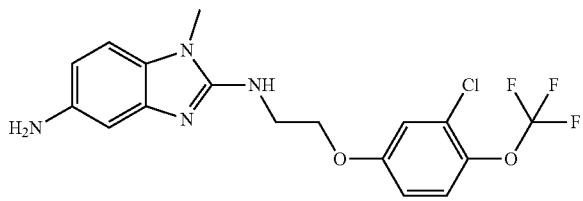 |
| 70 | 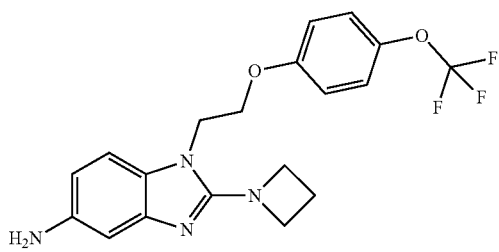 |
| 84 | 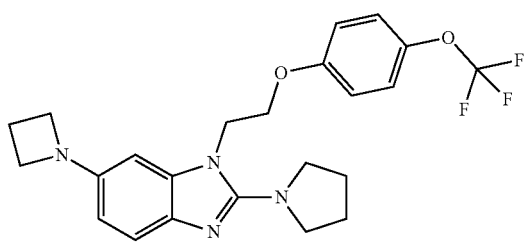 [SMILES: FC(F)(F)Oc1ccc(OCCn2c(N3CCCC3)nc3ccc(N4CCC4)cc32)cc1] |
| 184 | 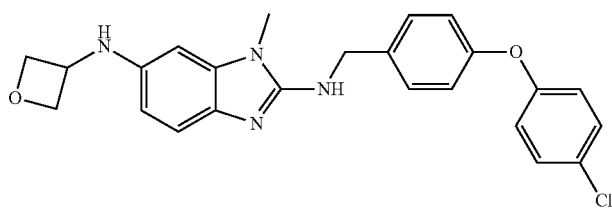 [SMILES: Cn1c(NCc2ccc(Oc3ccc(Cl)cc3)cc2)nc2ccc(NC3COC3)cc21] |
| 192 | 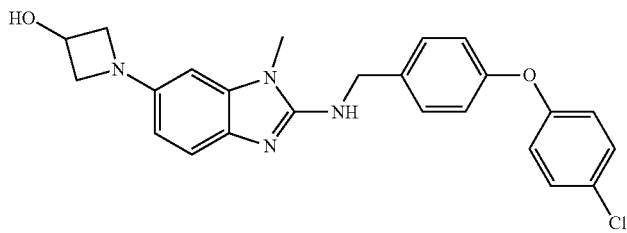 [SMILES: Cn1c(NCc2ccc(Oc3ccc(Cl)cc3)cc2)nc2ccc(N3CC(O)C3)cc21] |

| No. | Structure |
|---|---|
| 193 | 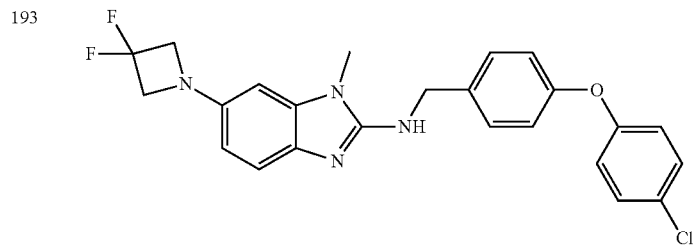 |
| 204 | 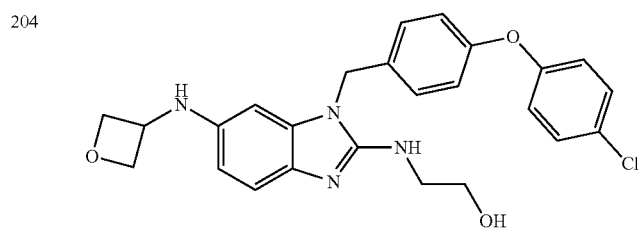 |
| 208 | 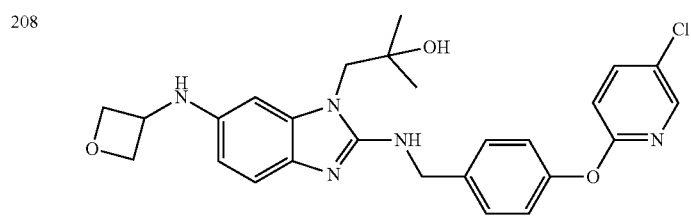 |
| 211 | 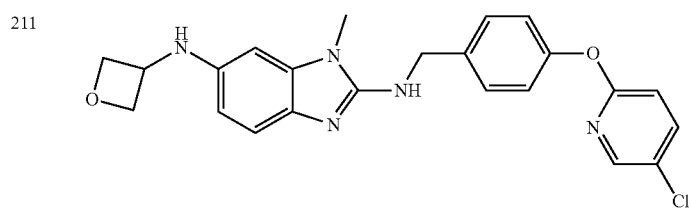 |
| 226 | 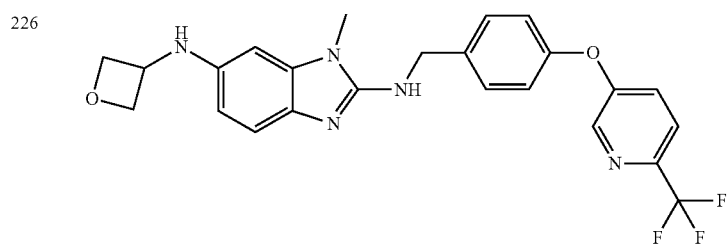 |
| 227 | 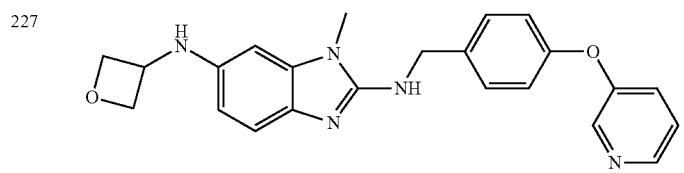 |
| 251 | 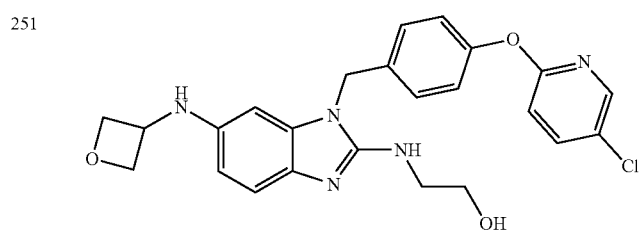 |

| No. | Structure |
|---|---|
| 257 | 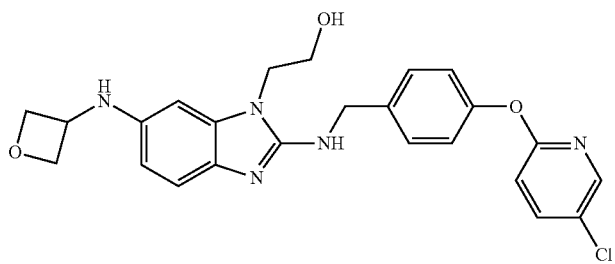 [SMILES: OCCn1c(NCc2ccc(Oc3ccc(Cl)cn3)cc2)nc2ccc(NC3COC3)cc21] |
| 262 | 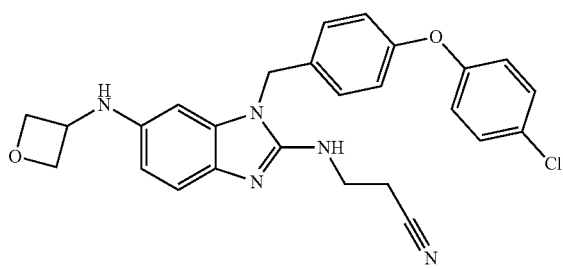 [SMILES: N#CCCNc1nc2ccc(NC3COC3)cc2n1Cc1ccc(Oc2ccc(Cl)cc2)cc1] |
| 268 | 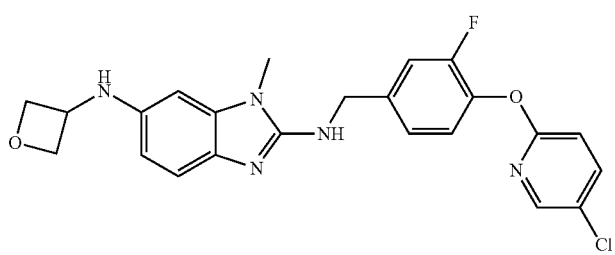 |
| 269 | 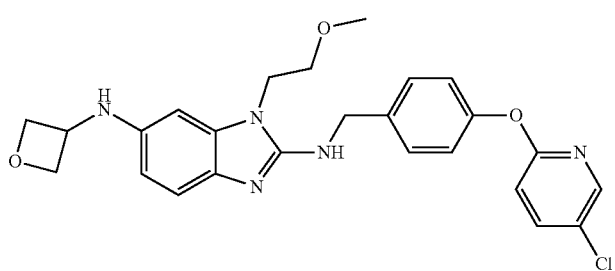 [SMILES: COCCn1c(NCc2ccc(Oc3ccc(Cl)cn3)cc2)nc2ccc(NC3COC3)cc21] |
| 270 | 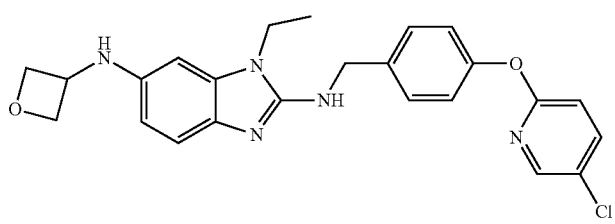 [SMILES: CCn1c(NCc2ccc(Oc3ccc(Cl)cn3)cc2)nc2ccc(NC3COC3)cc21] |
| 271 | 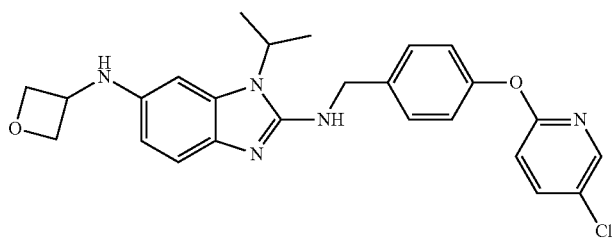 [SMILES: CC(C)n1c(NCc2ccc(Oc3ccc(Cl)cn3)cc2)nc2ccc(NC3COC3)cc21] |

-continued
| No. | Structure |
|---|---|
| 273 | 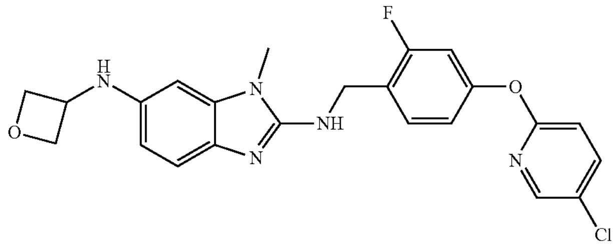 [SMILES: Cn1c(NCc2ccc(Oc3ccc(Cl)cn3)cc2F)nc2ccc(NC3COC3)cc21] |
| 275 | 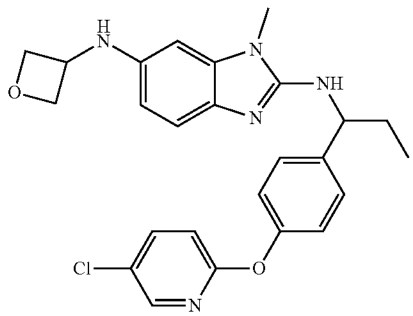 [SMILES: CCC(Nc1nc2ccc(NC3COC3)cc2n1C)c1ccc(Oc2ccc(Cl)cn2)cc1] |
| 279 | 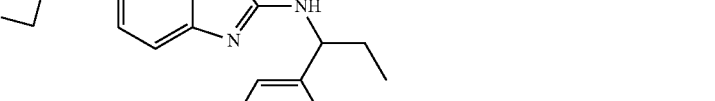 |
| 281 | 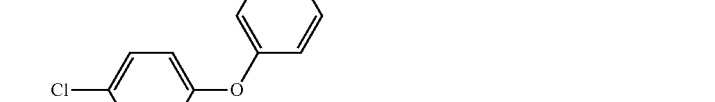 |
| 283 | 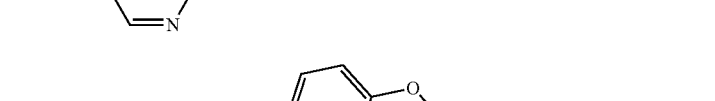 |
| 284 | 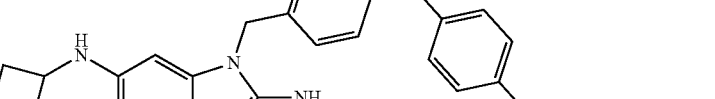 |

-continued
| No. | Structure |
|---|---|
| 289 | 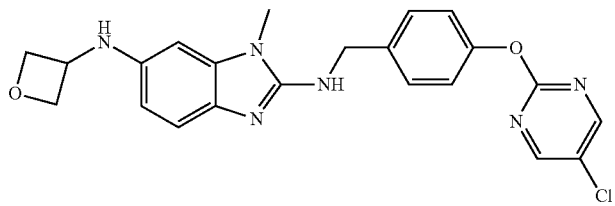 |
| 291 | 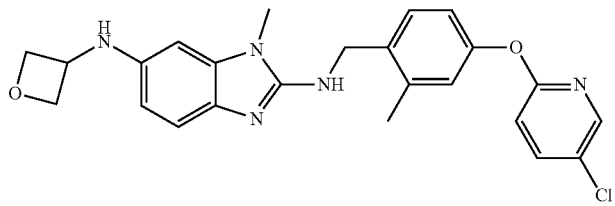 [SMILES: Cc1cc(Oc2ccc(Cl)cn2)ccc1CNc1nc2ccc(NC3COC3)cc2n1C] |
| 293 | 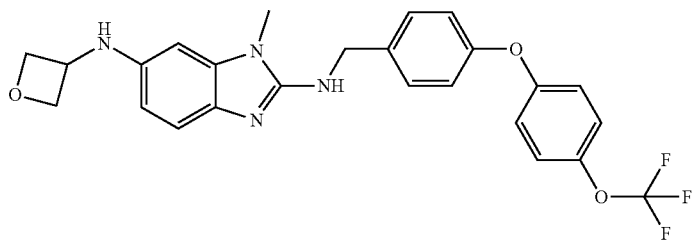 [SMILES: Cn1c(NCc2ccc(Oc3ccc(OC(F)(F)F)cc3)cc2)nc2ccc(NC3COC3)cc21] |
| 294 | 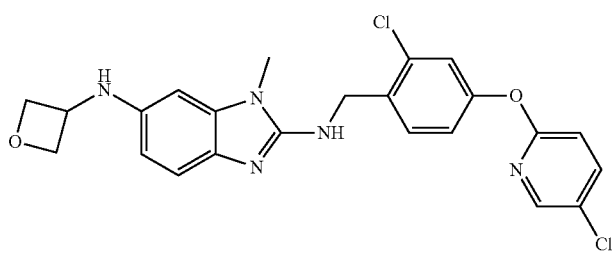 |
| 296 | 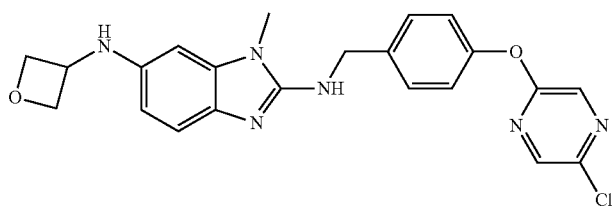 [SMILES: Cn1c(NCc2ccc(Oc3cnc(Cl)cn3)cc2)nc2ccc(NC3COC3)cc21] |
| 298 | 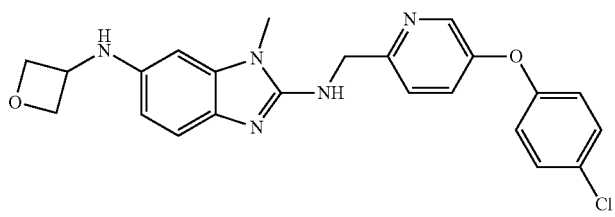 [SMILES: Cn1c(NCc2ccc(Oc3ccc(Cl)cc3)cn2)nc2ccc(NC3COC3)cc21] |
| 300 | 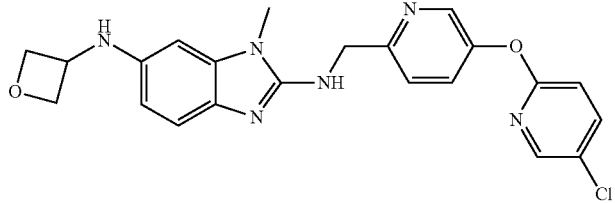 |

| No. | Structure |
|---|---|
| 302 | 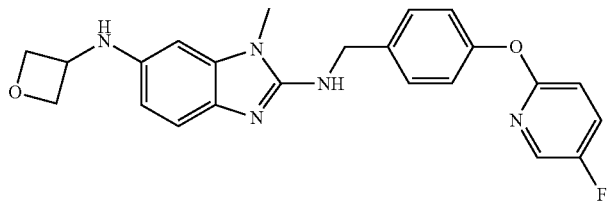 [SMILES: Cn1c(NCc2ccc(Oc3ccc(F)cn3)cc2)nc2ccc(NC3COC3)cc21] |
| 305 | 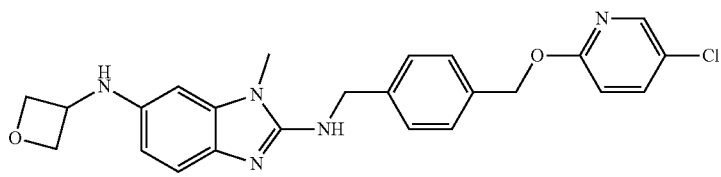 |
| 306 | 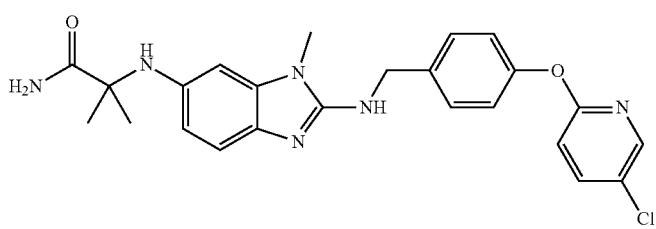 [SMILES: Cn1c(NCc2ccc(Oc3ccc(Cl)cn3)cc2)nc2ccc(NC(C)(C)C(N)=O)cc21] |
| 313 | 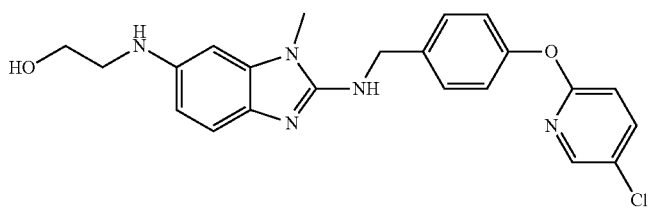 [SMILES: Cn1c(NCc2ccc(Oc3ccc(Cl)cn3)cc2)nc2ccc(NCCO)cc21] |
| 316 | 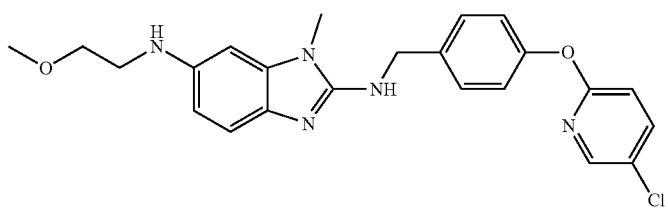 [SMILES: COCCNc1ccc2nc(NCc3ccc(Oc4ccc(Cl)cn4)cc3)n(C)c2c1] |
| 322 | 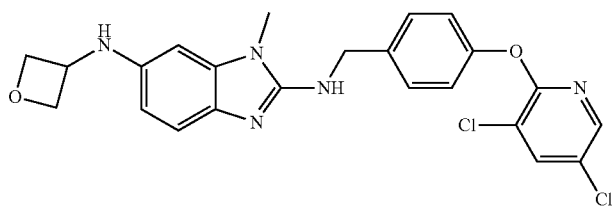 |
| 324 | 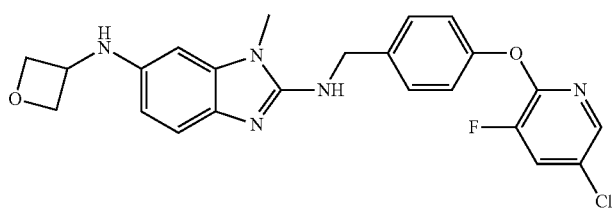 [SMILES: Cn1c(NCc2ccc(Oc3ncc(Cl)cc3F)cc2)nc2ccc(NC3COC3)cc21] |

| No. | Structure |
|---|---|
| 325 | 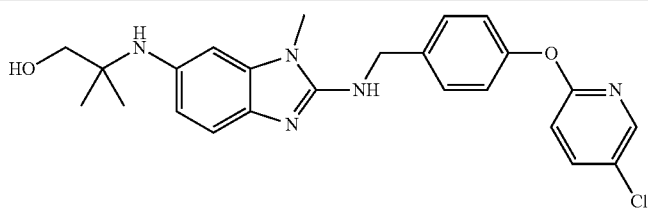 [SMILES: Cn1c(NCc2ccc(Oc3ccc(Cl)cn3)cc2)nc2ccc(NC(C)(C)CO)cc21] |
| 328 | 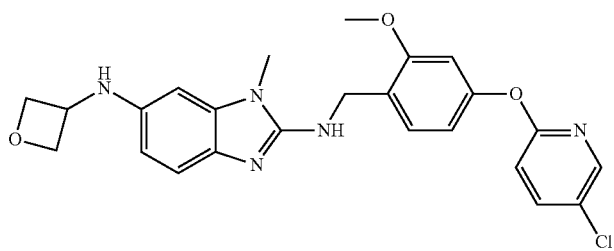 [SMILES: COc1cc(Oc2ccc(Cl)cn2)ccc1CNc1nc2ccc(NC3COC3)cc2n1C] |
| 329 | 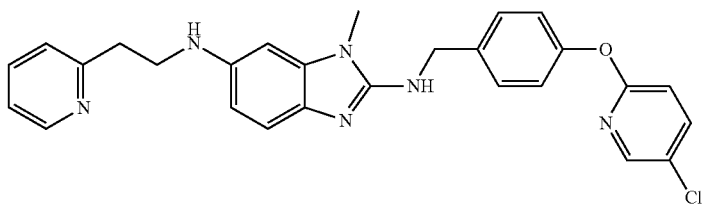 [SMILES: Cn1c(NCc2ccc(Oc3ccc(Cl)cn3)cc2)nc2ccc(NCCc3ccccn3)cc21] |
| 331 | 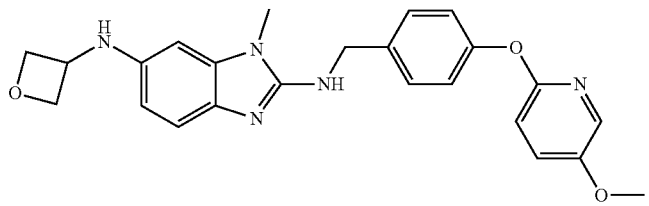 [SMILES: COc1ccc(Oc2ccc(CNc3nc4ccc(NC5COC5)cc4n3C)cc2)nc1] |
| 333 | 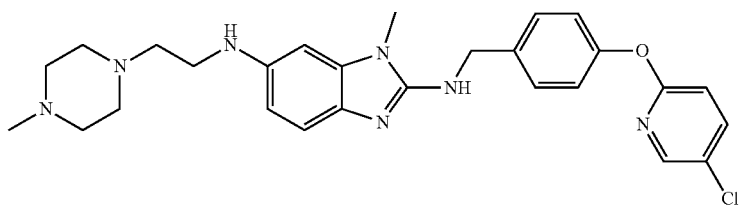 [SMILES: CN1CCN(CCNc2ccc3nc(NCc4ccc(Oc5ccc(Cl)cn5)cc4)n(C)c3c2)CC1] |
| 335 | 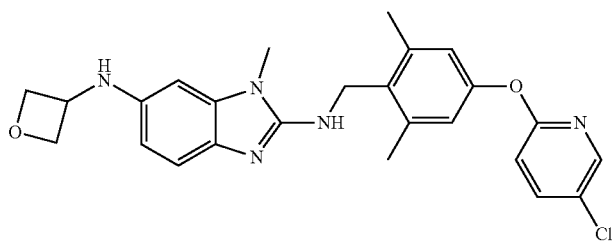 [SMILES: Cc1cc(Oc2ccc(Cl)cn2)cc(C)c1CNc1nc2ccc(NC3COC3)cc2n1C] |
| 347 | 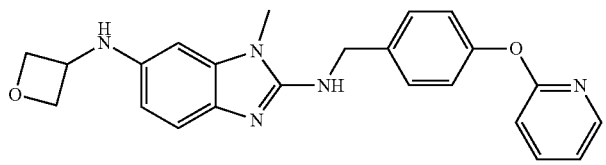 |

-continued

| No. | Structure |
|---|---|
| 349 | (structure) |
| 353 | (structure) |
| 357 | (structure) |
| 358 | (structure) |
| 359 | (structure) |
| 365 | (structure) |
| 366 | (structure) |

| No. | Structure |
|---|---|
| 368 | 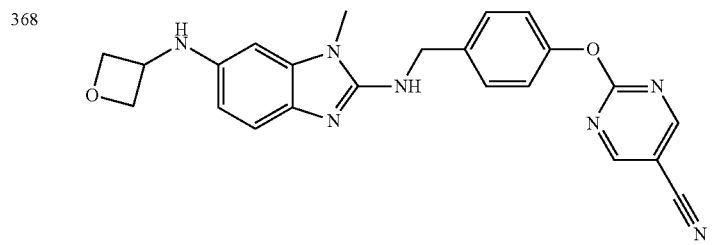 |
| 369 | 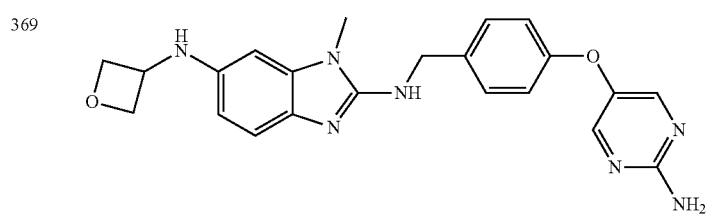 |
| 372 | 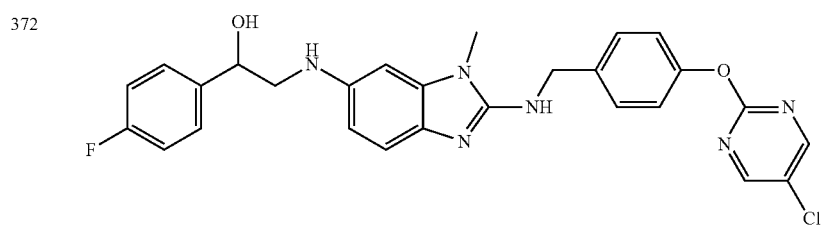 |
| 374 | 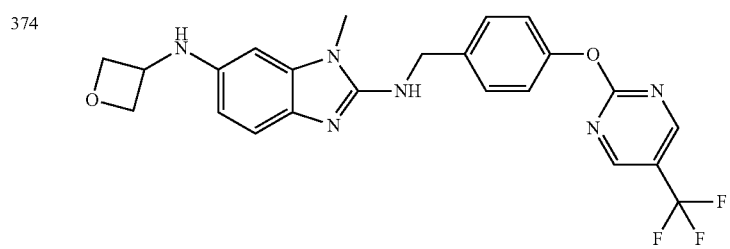 |
| 378 | 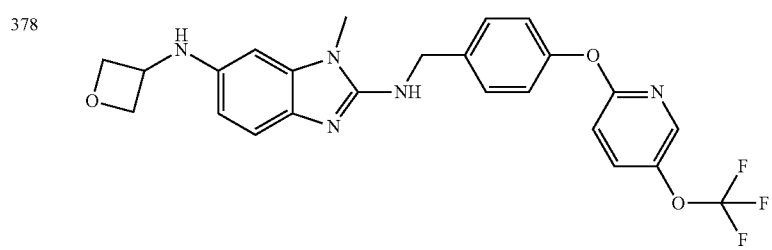 |
| 379 | 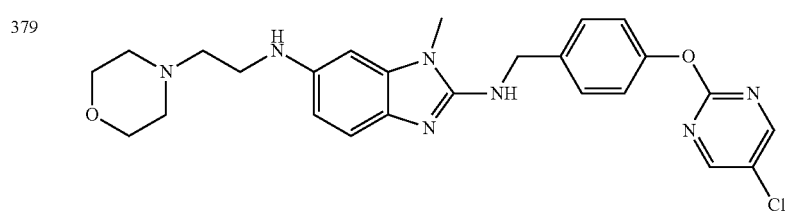 |

| No. | Structure |
|---|---|
| 383 | 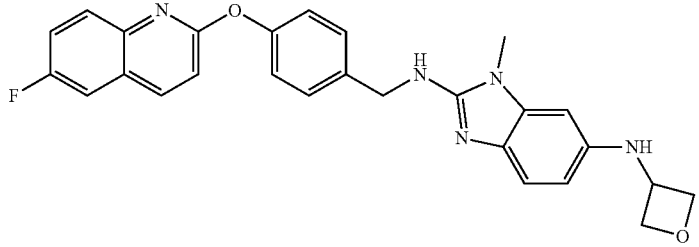 [SMILES: Cn1c(NCc2ccc(Oc3ccc4cc(F)ccc4n3)cc2)nc2ccc(NC3COC3)cc21] |
| 384 | 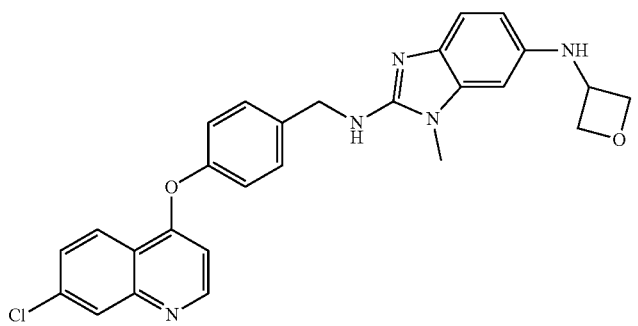 [SMILES: Cn1c(NCc2ccc(Oc3ccnc4cc(Cl)ccc34)cc2)nc2ccc(NC3COC3)cc21] |
| 390 | 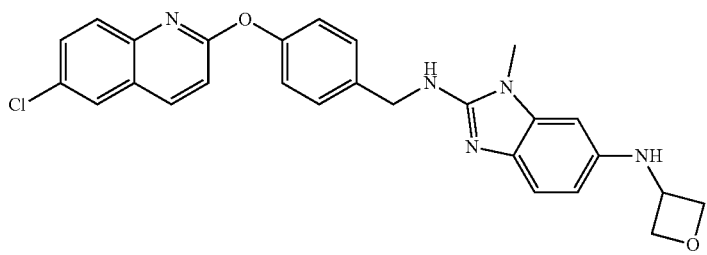 [SMILES: Cn1c(NCc2ccc(Oc3ccc4cc(Cl)ccc4n3)cc2)nc2ccc(NC3COC3)cc21] |
| 392 | 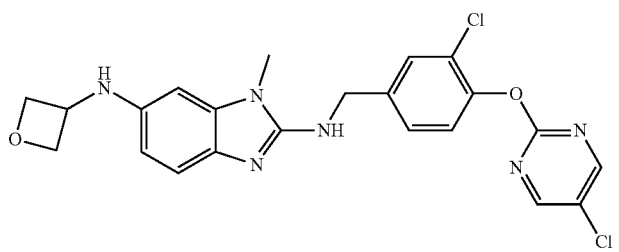 |
| 396 | 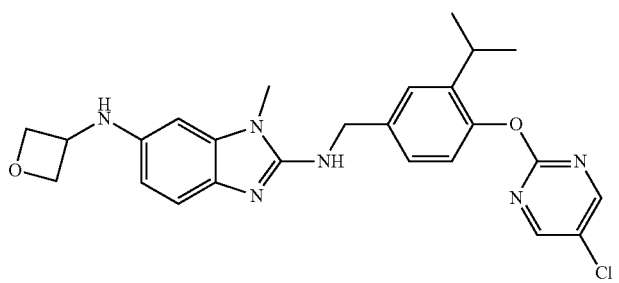 [SMILES: CC(C)c1cc(CNc2nc3ccc(NC4COC4)cc3n2C)ccc1Oc1ncc(Cl)cn1] |
| 398 | 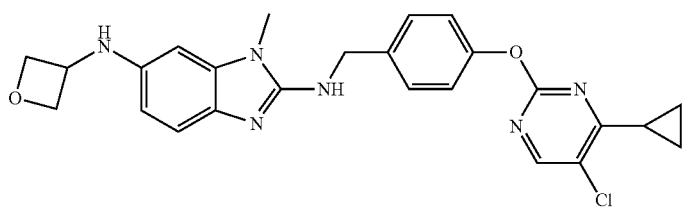 [SMILES: Cn1c(NCc2ccc(Oc3ncc(Cl)c(C4CC4)n3)cc2)nc2ccc(NC3COC3)cc21] |

| No. | Structure |
|---|---|
| 400 | 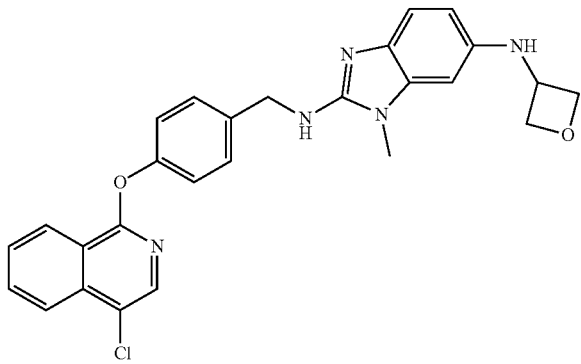 [SMILES: Cn1c(NCc2ccc(Oc3ncc(Cl)c4ccccc34)cc2)nc2ccc(NC3COC3)cc21] |
| 401 | 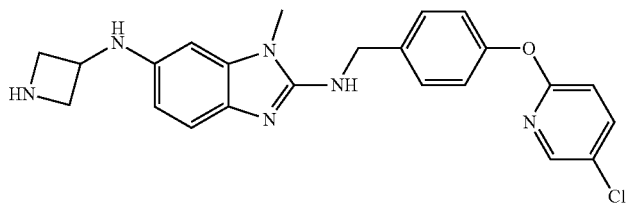 |
| 403 | 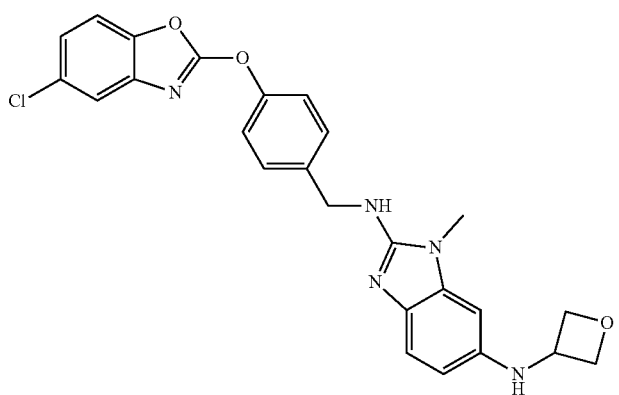 [SMILES: Cn1c(NCc2ccc(Oc3nc4cc(Cl)ccc4o3)cc2)nc2ccc(NC3COC3)cc21] |
| 406 | 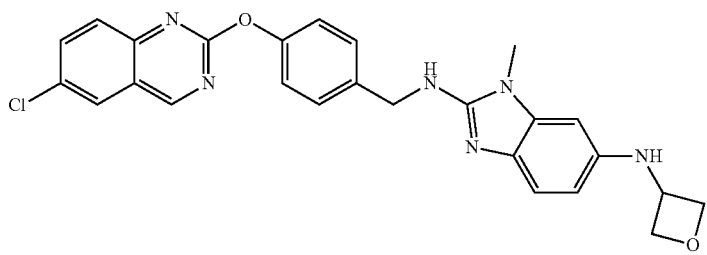 [SMILES: Cn1c(NCc2ccc(Oc3ncc4cc(Cl)ccc4n3)cc2)nc2ccc(NC3COC3)cc21] |
| 407 | 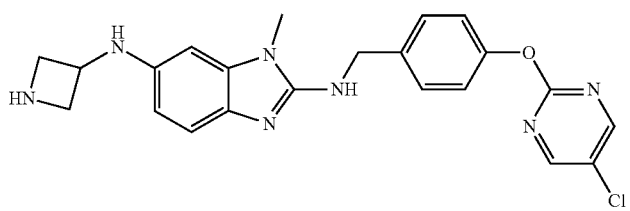 |

| No. | Structure |
|---|---|
| 412 | 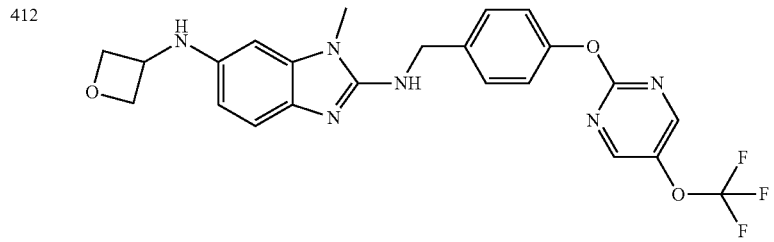 |
| 413 | 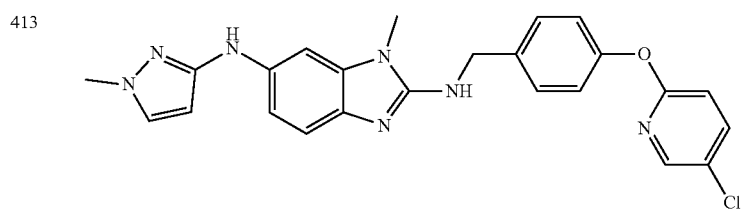 |
| 414 | 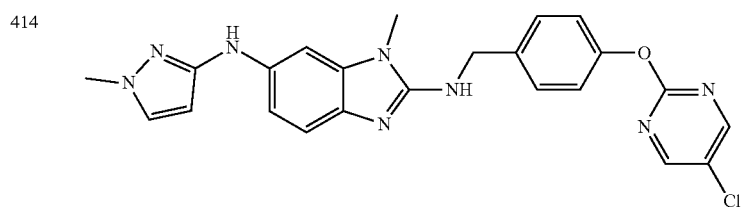 |
| 415 | 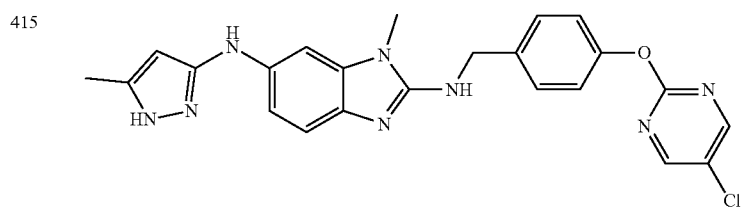 |
| 420 | 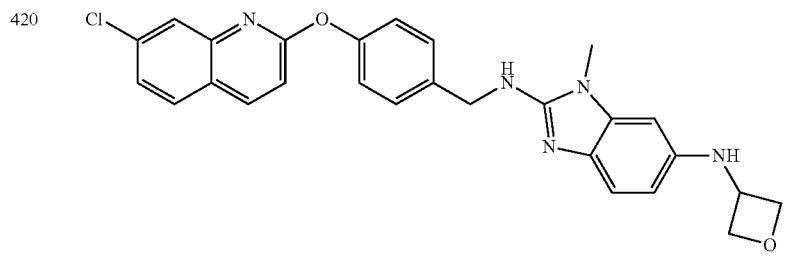 |
| 422 | 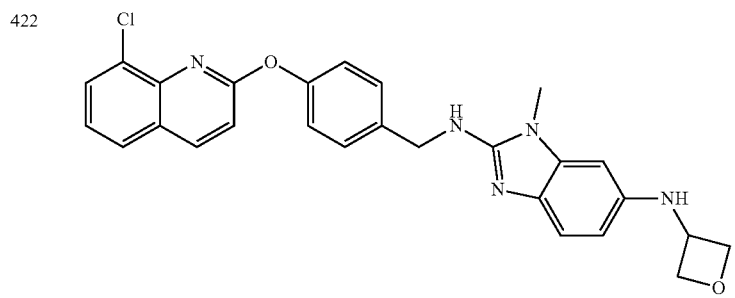 |

| No. | Structure |
|---|---|
| 423 | 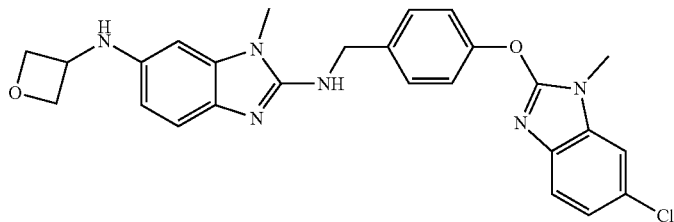 [SMILES: Cn1c(NCc2ccc(Oc3nc4ccc(Cl)cc4n3C)cc2)nc2ccc(NC3COC3)cc21] |
| 425 | 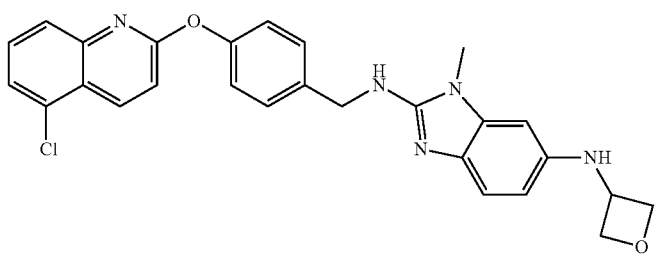 [SMILES: Cn1c(NCc2ccc(Oc3ccc4c(Cl)cccc4n3)cc2)nc2ccc(NC3COC3)cc21] |
| 427 | 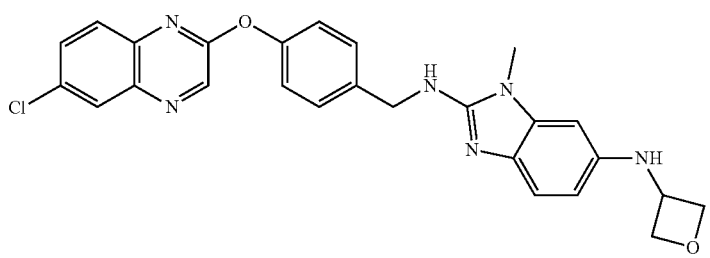 [SMILES: Cn1c(NCc2ccc(Oc3cnc4cc(Cl)ccc4n3)cc2)nc2ccc(NC3COC3)cc21] |
| 431 | 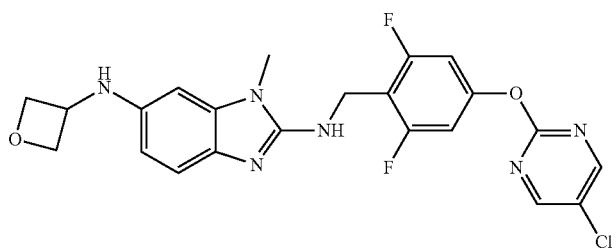 |
| 435 | 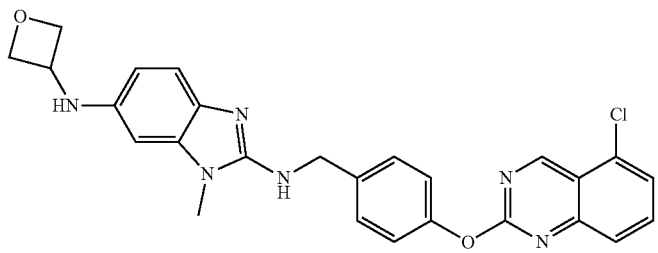 [SMILES: Cn1c(NCc2ccc(Oc3ncc4c(Cl)cccc4n3)cc2)nc2ccc(NC3COC3)cc21] |
| 437 | 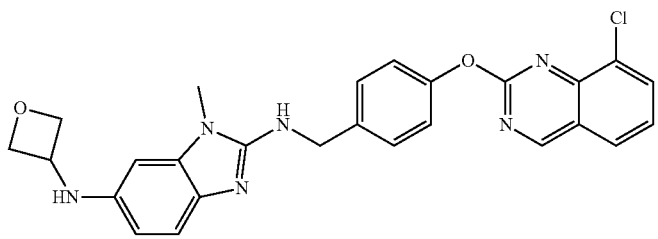 [SMILES: Cn1c(NCc2ccc(Oc3ncc4cccc(Cl)c4n3)cc2)nc2ccc(NC3COC3)cc21] |

| No. | Structure |
|---|---|
| 447 | 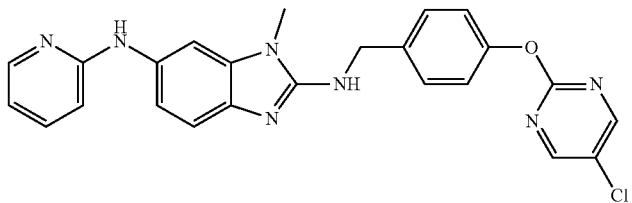 [SMILES: Cn1c(NCc2ccc(Oc3ncc(Cl)cn3)cc2)nc2ccc(Nc3ccccn3)cc21] |
| 448 | 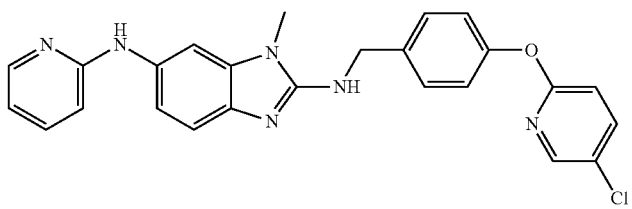 [SMILES: Cn1c(NCc2ccc(Oc3ccc(Cl)cn3)cc2)nc2ccc(Nc3ccccn3)cc21] |
| 449 | 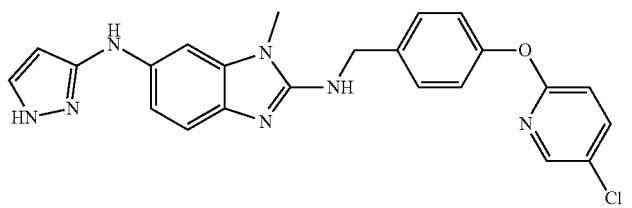 |
| 450 | 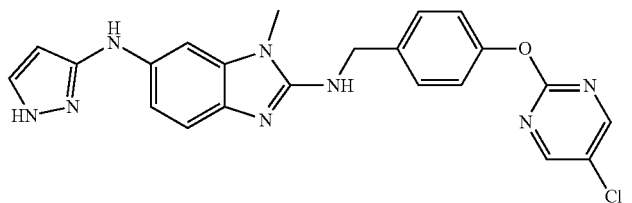 |
| 453 | 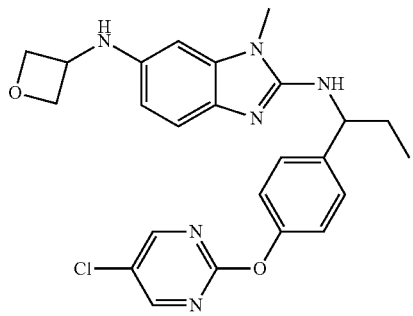 [SMILES: CCC(Nc1nc2ccc(NC3COC3)cc2n1C)c1ccc(Oc2ncc(Cl)cn2)cc1] |
| 455 | 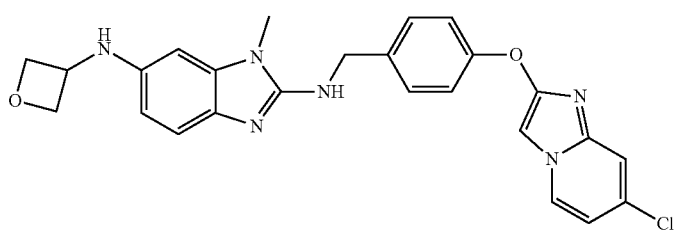 [SMILES: Cn1c(NCc2ccc(Oc3cn4ccc(Cl)cc4n3)cc2)nc2ccc(NC3COC3)cc21] |

-continued
| No. | Structure |
|---|---|
| 457 | 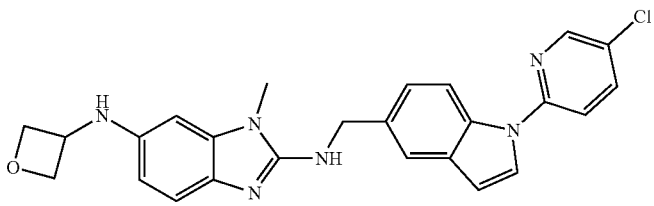 [SMILES: Cn1c(NCc2ccc3c(ccn3-c3ccc(Cl)cn3)c2)nc2ccc(NC3COC3)cc21] |
| 461 | 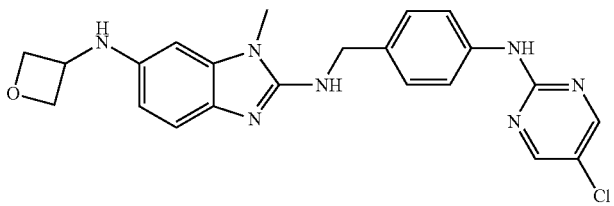 [SMILES: Cn1c(NCc2ccc(Nc3ncc(Cl)cn3)cc2)nc2ccc(NC3COC3)cc21] |
| 464 | 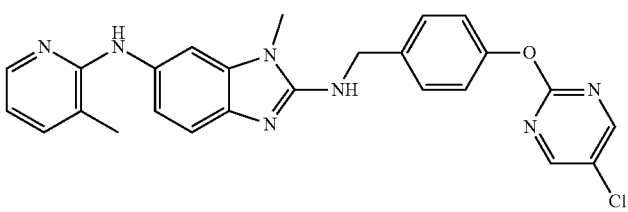 [SMILES: Cc1cccnc1Nc1ccc2nc(NCc3ccc(Oc4ncc(Cl)cn4)cc3)n(C)c2c1] |
| 465 | 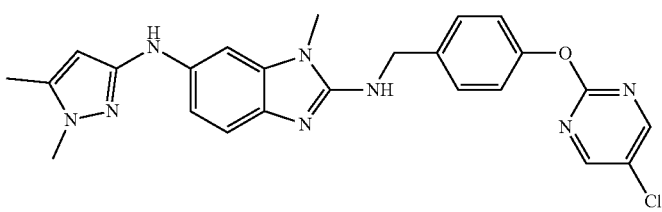 |
| 466 | 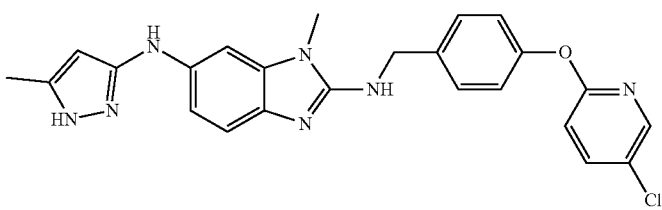 |
| 467 | 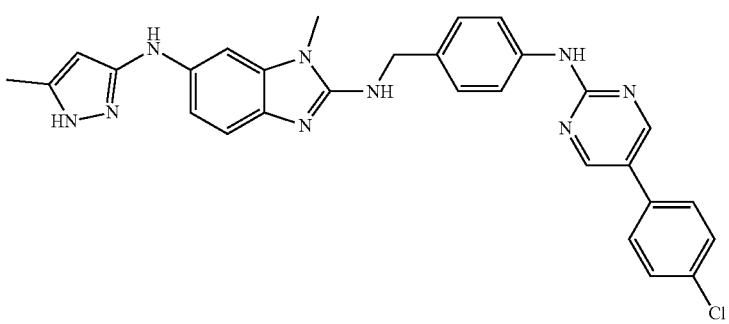 |
| 468 | 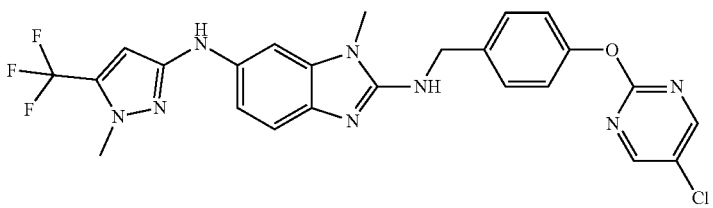 |

| No. | Structure |
|---|---|
| 469 | 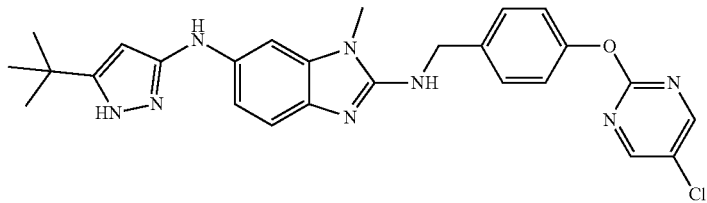 [SMILES: Cn1c(NCc2ccc(Oc3ncc(Cl)cn3)cc2)nc2ccc(Nc3cc(C(C)(C)C)[nH]n3)cc21] |
| 471 | 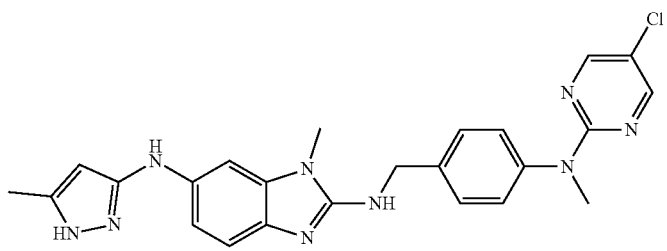 [SMILES: Cc1cc(Nc2ccc3nc(NCc4ccc(N(C)c5ncc(Cl)cn5)cc4)n(C)c3c2)n[nH]1] |
| 473 | 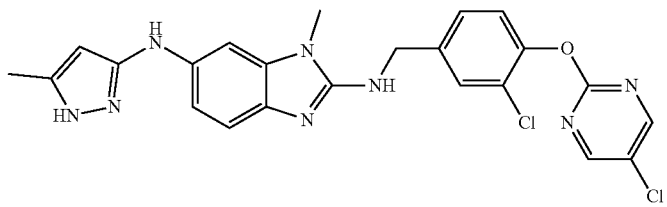 [SMILES: Cc1cc(Nc2ccc3nc(NCc4ccc(Oc5ncc(Cl)cn5)c(Cl)c4)n(C)c3c2)n[nH]1] |
| 474 | 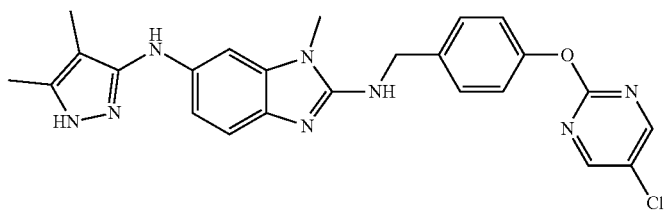 [SMILES: Cc1[nH]nc(Nc2ccc3nc(NCc4ccc(Oc5ncc(Cl)cn5)cc4)n(C)c3c2)c1C] |
| 475 | 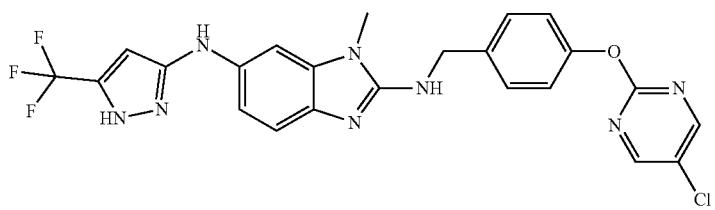 [SMILES: Cn1c(NCc2ccc(Oc3ncc(Cl)cn3)cc2)nc2ccc(Nc3cc(C(F)(F)F)[nH]n3)cc21] |
| 476 | 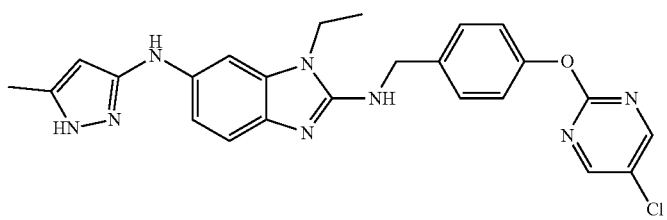 [SMILES: CCn1c(NCc2ccc(Oc3ncc(Cl)cn3)cc2)nc2ccc(Nc3cc(C)[nH]n3)cc21] |

| No. | Structure |
|---|---|
| 477 | 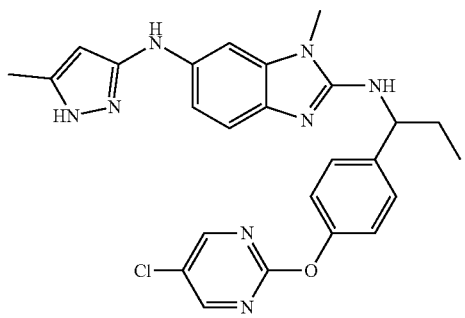 [SMILES: CCC(Nc1nc2ccc(Nc3cc(C)[nH]n3)cc2n1C)c1ccc(Oc2ncc(Cl)cn2)cc1] |
| 478 | 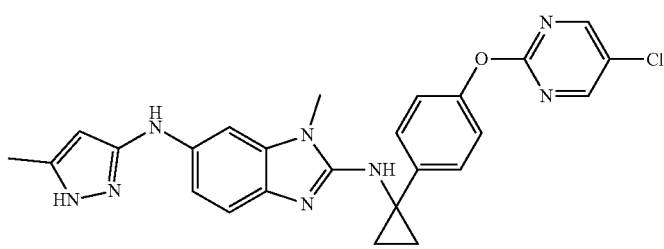 [SMILES: Cc1cc(Nc2ccc3nc(NC4(c5ccc(Oc6ncc(Cl)cn6)cc5)CC4)n(C)c3c2)n[nH]1] |
| 479 | 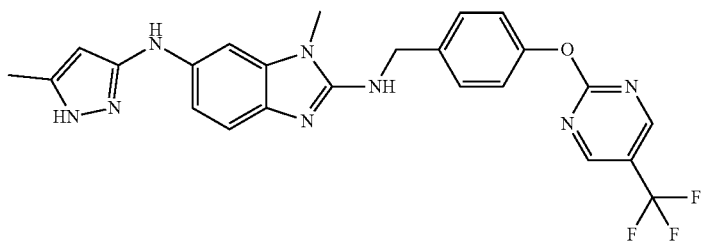 [SMILES: Cc1cc(Nc2ccc3nc(NCc4ccc(Oc5ncc(C(F)(F)F)cn5)cc4)n(C)c3c2)n[nH]1] |
| 481 | 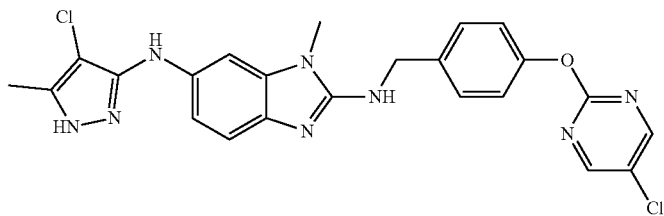 |
| 482 | 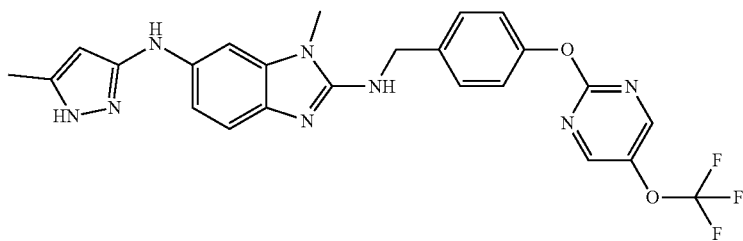 [SMILES: Cc1cc(Nc2ccc3nc(NCc4ccc(Oc5ncc(OC(F)(F)F)cn5)cc4)n(C)c3c2)n[nH]1] |
| 486 | 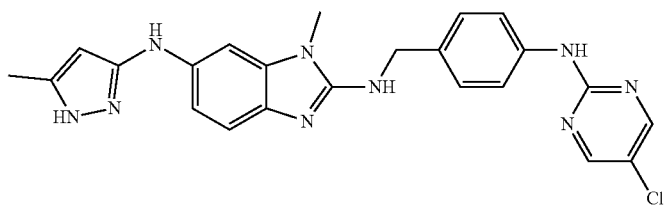 |

| No. | Structure |
|---|---|
| 487 | 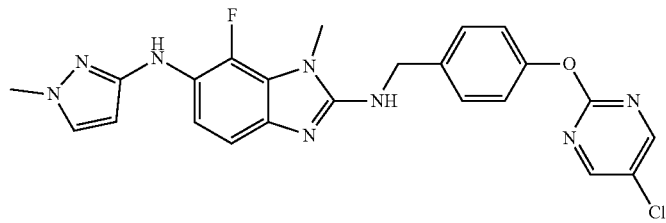 [SMILES: Cn1ccc(Nc2ccc3nc(NCc4ccc(Oc5ncc(Cl)cn5)cc4)n(C)c3c2F)n1] |
| 489 | 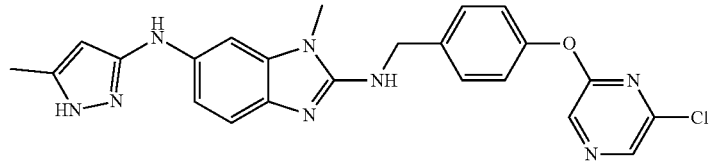 [SMILES: Cc1cc(Nc2ccc3nc(NCc4ccc(Oc5cncc(Cl)n5)cc4)n(C)c3c2)n[nH]1] |
| 490 | 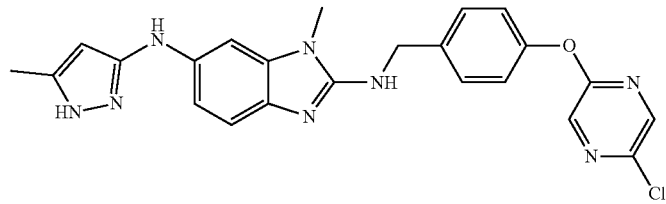 |
| 491 | 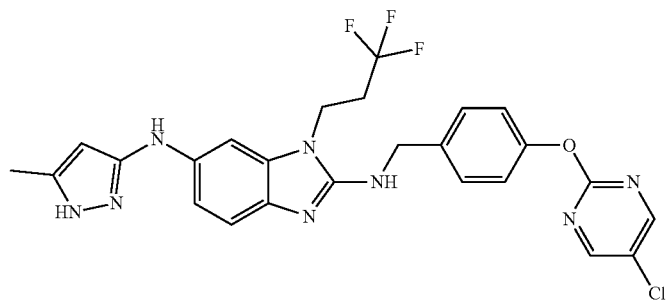 [SMILES: Cc1cc(Nc2ccc3nc(NCc4ccc(Oc5ncc(Cl)cn5)cc4)n(CCC(F)(F)F)c3c2)n[nH]1] |
| 492 | 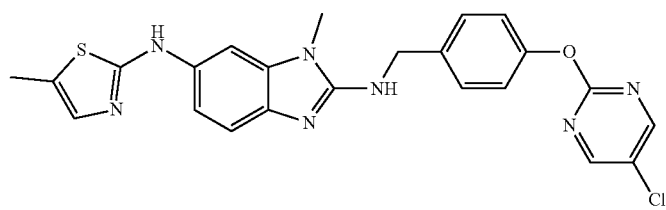 [SMILES: Cc1cnc(Nc2ccc3nc(NCc4ccc(Oc5ncc(Cl)cn5)cc4)n(C)c3c2)s1] |
| 493 | 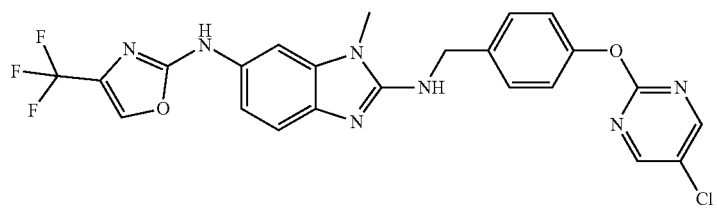 |
| 494 | 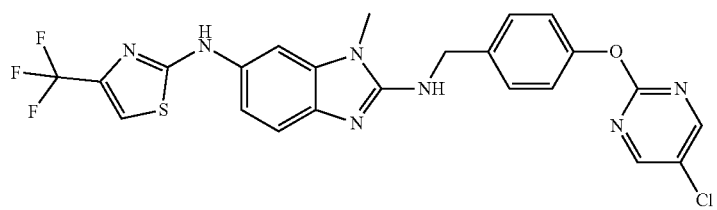 |

| No. | Structure |
|---|---|
| 495 | 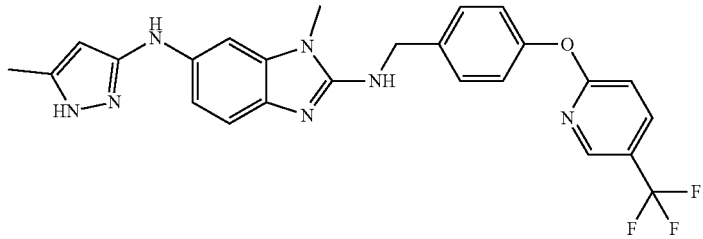 [SMILES: Cc1cc(Nc2ccc3nc(NCc4ccc(Oc5ccc(C(F)(F)F)cn5)cc4)n(C)c3c2)n[nH]1] |
| 496 | 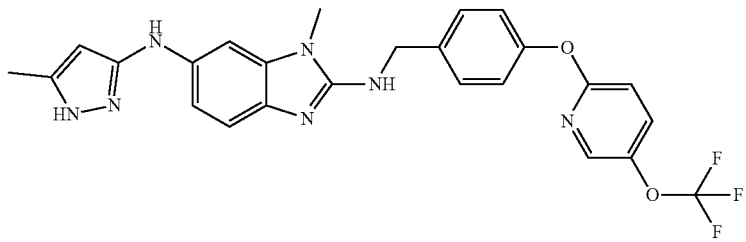 [SMILES: Cc1cc(Nc2ccc3nc(NCc4ccc(Oc5ccc(OC(F)(F)F)cn5)cc4)n(C)c3c2)n[nH]1] |
| 499 | 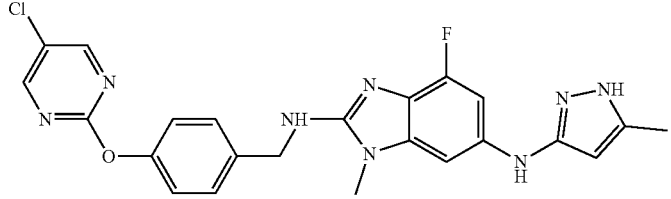 [SMILES: Cc1cc(Nc2cc(F)c3nc(NCc4ccc(Oc5ncc(Cl)cn5)cc4)n(C)c3c2)n[nH]1] |
| 501 | 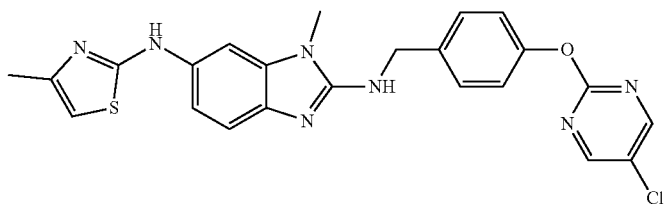 [SMILES: Cc1csc(Nc2ccc3nc(NCc4ccc(Oc5ncc(Cl)cn5)cc4)n(C)c3c2)n1] |
| 502 | 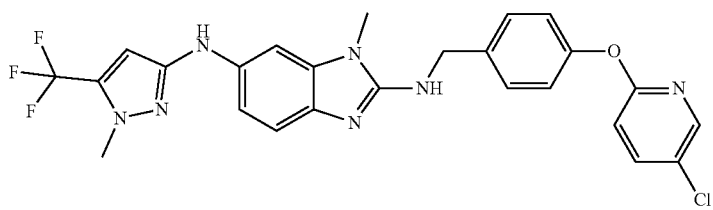 [SMILES: Cn1nc(Nc2ccc3nc(NCc4ccc(Oc5ccc(Cl)cn5)cc4)n(C)c3c2)cc1C(F)(F)F] |
| 503 | 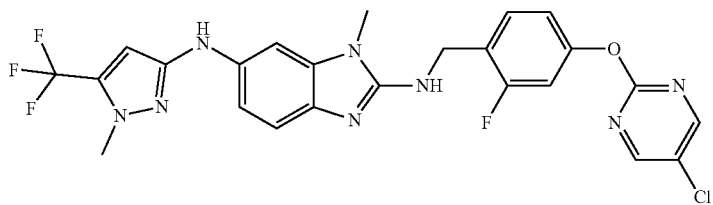 |
| 504 | 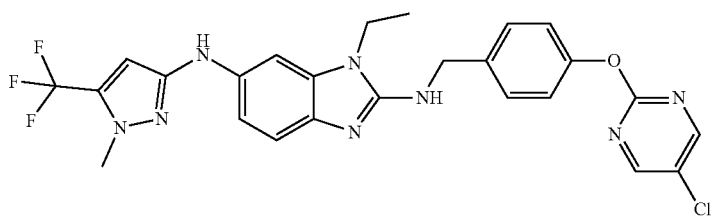 |

| No. | Structure |
|-----|-----------|
| 505 | 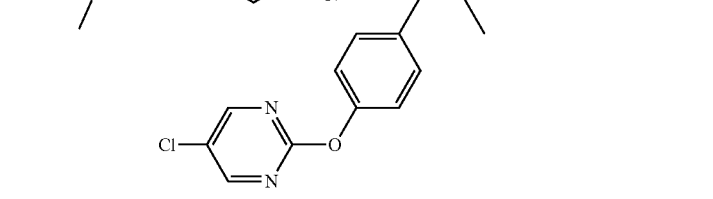 |
| 506 | 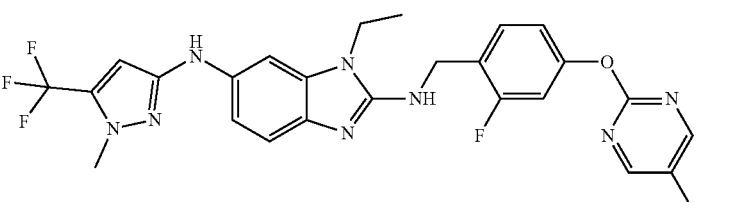 |
| 507 | 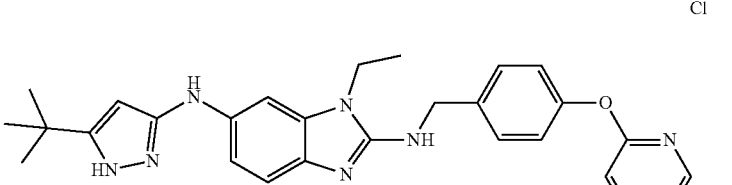 |
| 508 | 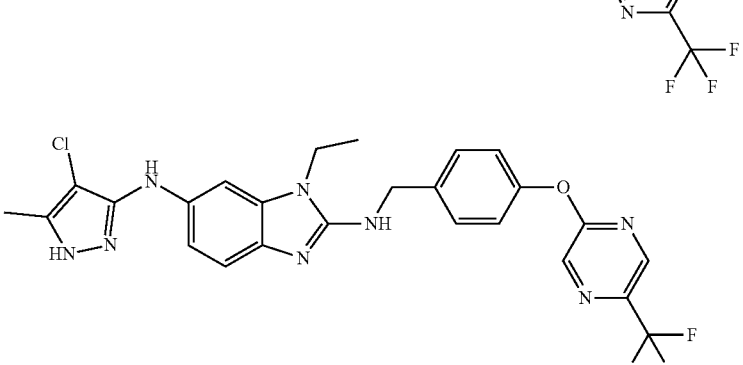 |
| 509 | 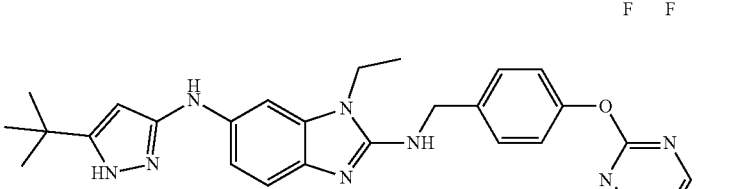 |
| 510 | 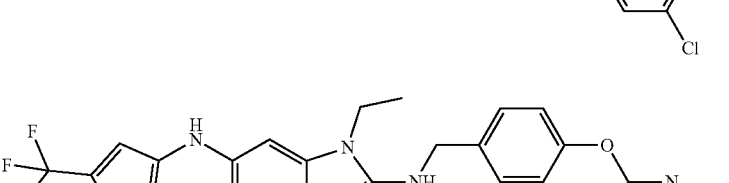 |

| No. | Structure |
|---|---|
| 511 | 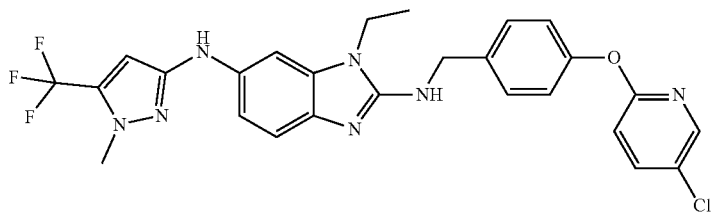 |
| 512 | 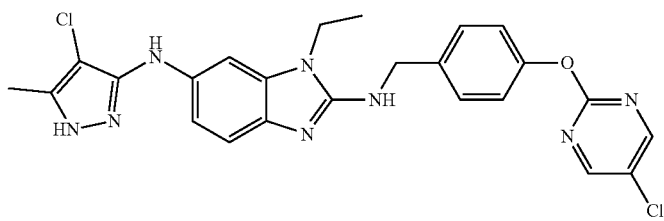 [SMILES: CCn1c(NCc2ccc(Oc3ncc(Cl)cn3)cc2)nc2ccc(Nc3n[nH]c(C)c3Cl)cc21] |
| 513 | 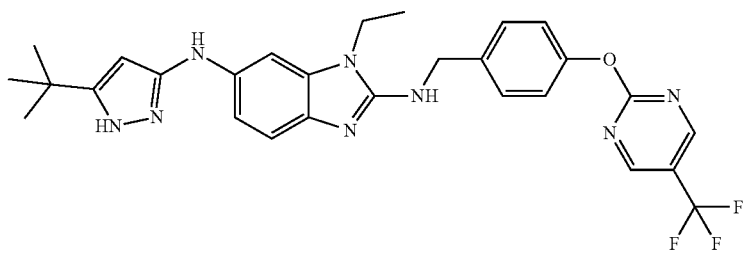 [SMILES: CCn1c(NCc2ccc(Oc3ncc(C(F)(F)F)cn3)cc2)nc2ccc(Nc3cc(C(C)(C)C)[nH]n3)cc21] |
| 514 | 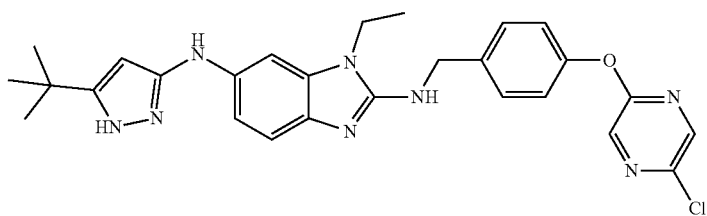 [SMILES: CCn1c(NCc2ccc(Oc3cnc(Cl)cn3)cc2)nc2ccc(Nc3cc(C(C)(C)C)[nH]n3)cc21] |
| 515 | 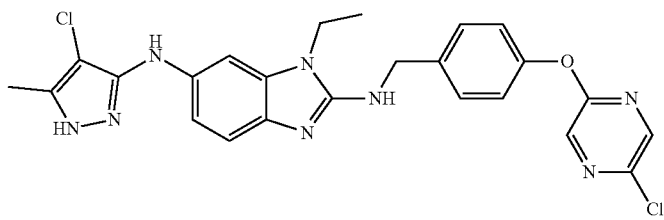 |
| 516 | 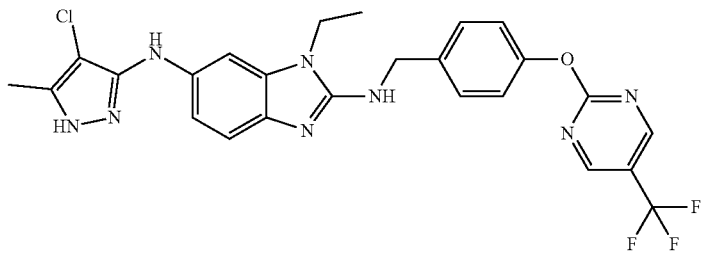 [SMILES: CCn1c(NCc2ccc(Oc3ncc(C(F)(F)F)cn3)cc2)nc2ccc(Nc3n[nH]c(C)c3Cl)cc21] |

| No. | Structure |
|-----|-----------|
| 517 | 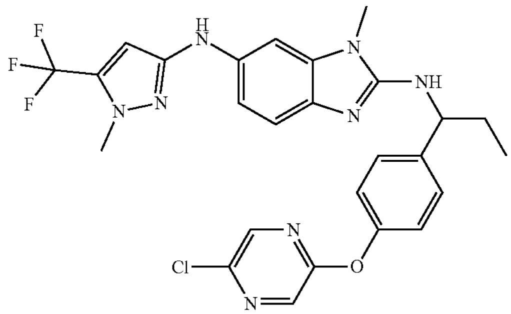 [SMILES: CCC(Nc1nc2ccc(Nc3cc(C(F)(F)F)n(C)n3)cc2n1C)c1ccc(Oc2cnc(Cl)cn2)cc1] |
| 518 | 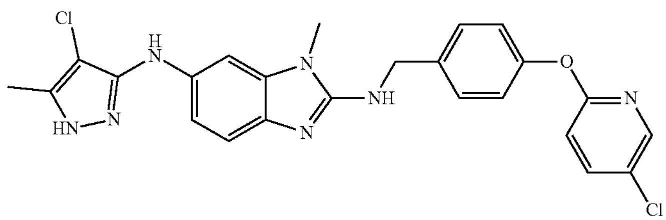 [SMILES: Cc1[nH]nc(Nc2ccc3nc(NCc4ccc(Oc5ccc(Cl)cn5)cc4)n(C)c3c2)c1Cl] |
| 519 | 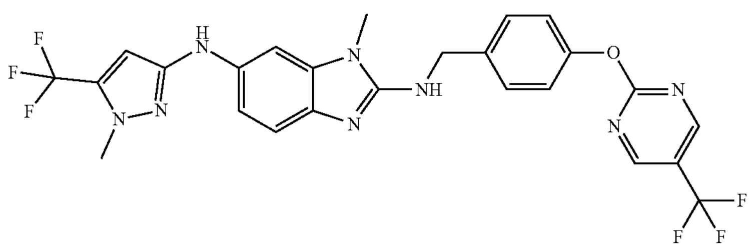 [SMILES: Cn1nc(Nc2ccc3nc(NCc4ccc(Oc5ncc(C(F)(F)F)cn5)cc4)n(C)c3c2)cc1C(F)(F)F] |
| 520 | 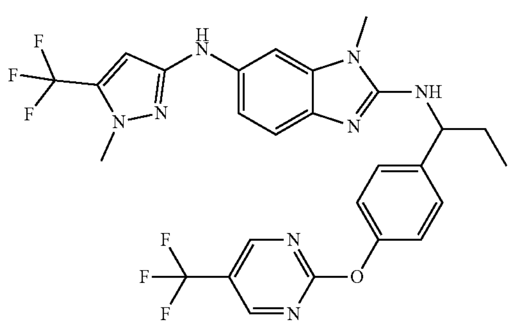 |
| 521 | 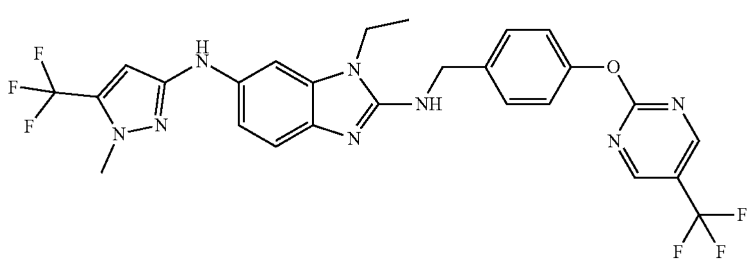 |

| No. | Structure |
|---|---|
| 522 | 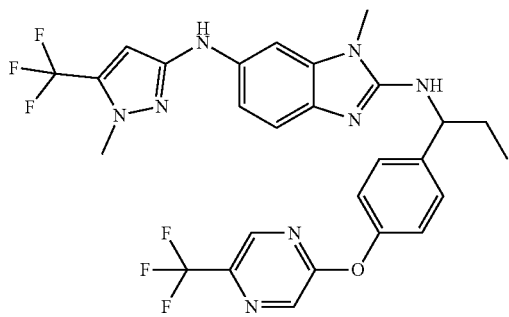 [SMILES: CCC(Nc1nc2ccc(Nc3cc(C(F)(F)F)n(C)n3)cc2n1C)c1ccc(Oc2cnc(C(F)(F)F)cn2)cc1] |
| 523 | 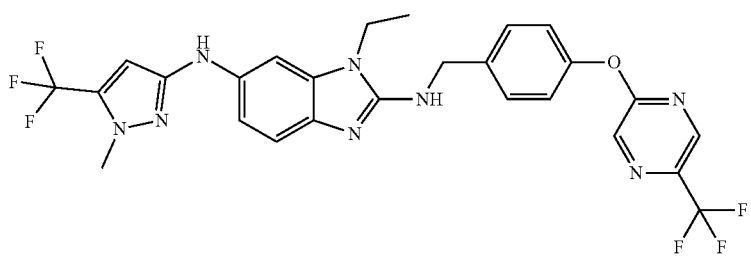 |
| 524 | 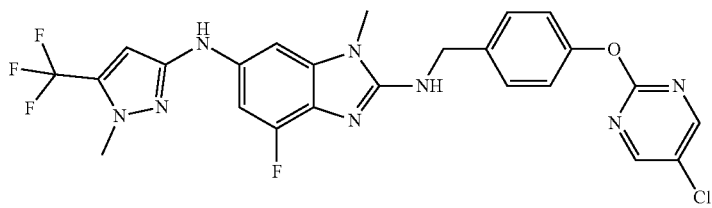 |
| 525 | 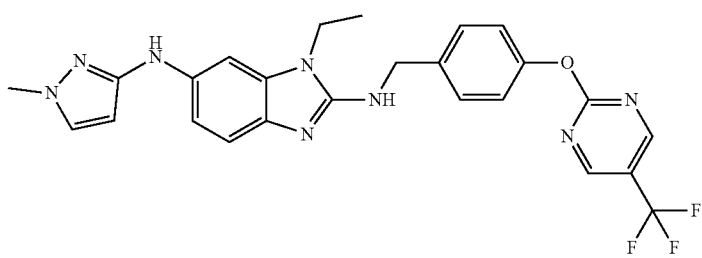 [SMILES: CCn1c(NCc2ccc(Oc3ncc(C(F)(F)F)cn3)cc2)nc2ccc(Nc3ccn(C)n3)cc21] |
| 526 | 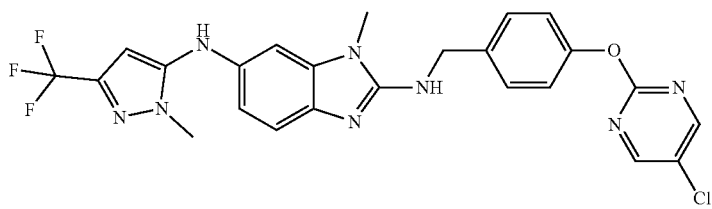 [SMILES: Cn1nc(C(F)(F)F)cc1Nc1ccc2nc(NCc3ccc(Oc4ncc(Cl)cn4)cc3)n(C)c2c1] |
| 527 | 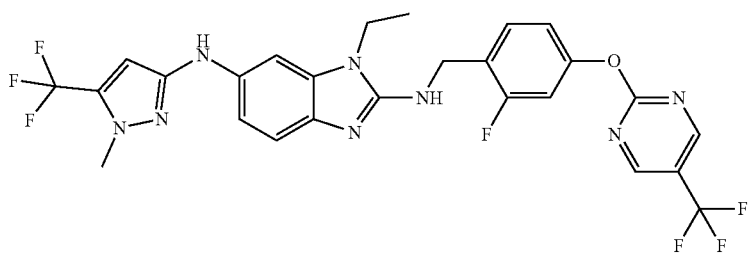 |

| No. | Structure |
|---|---|
| 528 | (chemical structure) |
| 529 | (chemical structure) |
| 530 | (chemical structure) |
| 531 | (chemical structure) |
| 532 | (chemical structure) |

| No. | Structure |
|---|---|
| 533 | 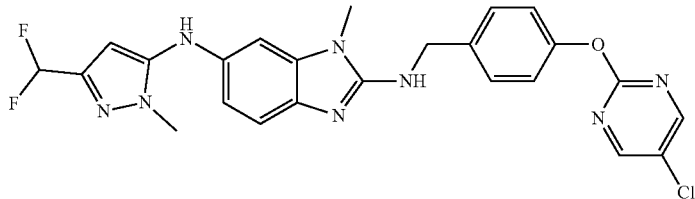 |
| 534 | 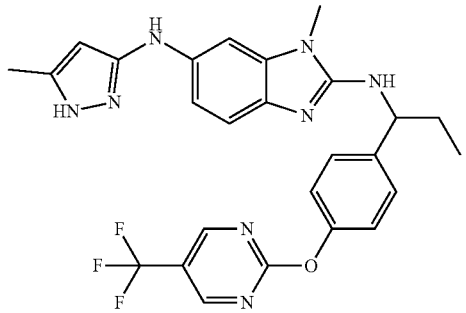 [SMILES: CCC(Nc1nc2ccc(Nc3cc(C)[nH]n3)cc2n1C)c1ccc(Oc2ncc(C(F)(F)F)cn2)cc1] |
| 535 | 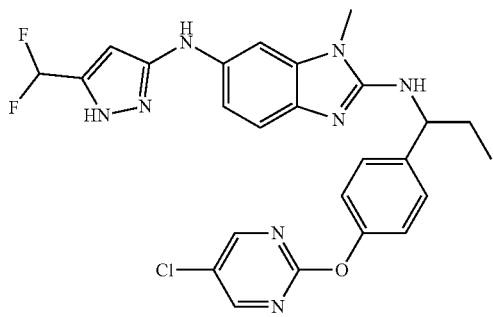 [SMILES: CCC(Nc1nc2ccc(Nc3cc(C(F)F)[nH]n3)cc2n1C)c1ccc(Oc2ncc(Cl)cn2)cc1] |
| 536 | 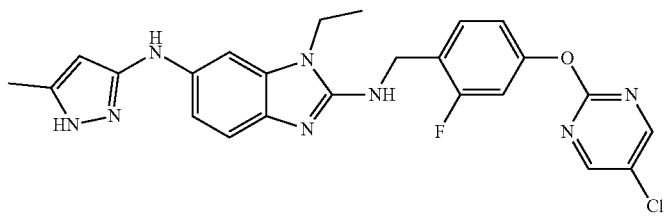 [SMILES: CCn1c(NCc2ccc(Oc3ncc(Cl)cn3)cc2F)nc2ccc(Nc3cc(C)[nH]n3)cc21] |
| 537 | 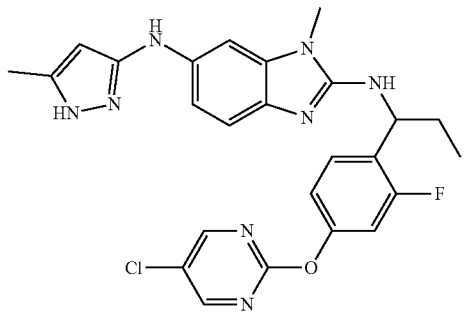 [SMILES: CCC(Nc1nc2ccc(Nc3cc(C)[nH]n3)cc2n1C)c1ccc(Oc2ncc(Cl)cn2)cc1F] |
| 538 | 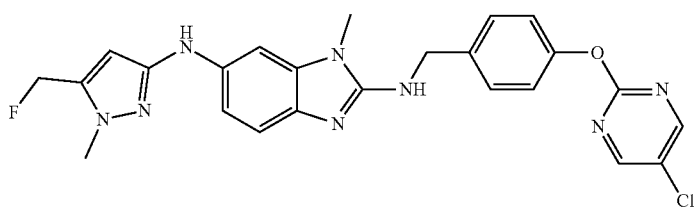 [SMILES: Cn1nc(Nc2ccc3nc(NCc4ccc(Oc5ncc(Cl)cn5)cc4)n(C)c3c2)cc1CF] |

| No. | Structure |
|---|---|
| 539 | 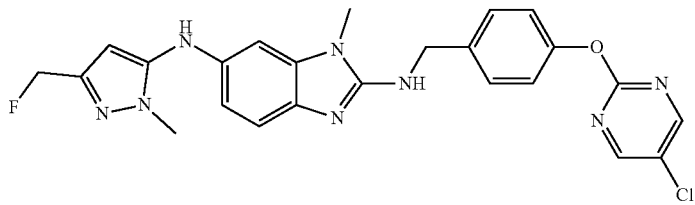 [SMILES: Cn1nc(CF)cc1Nc1ccc2nc(NCc3ccc(Oc4ncc(Cl)cn4)cc3)n(C)c2c1] |
| 540 | 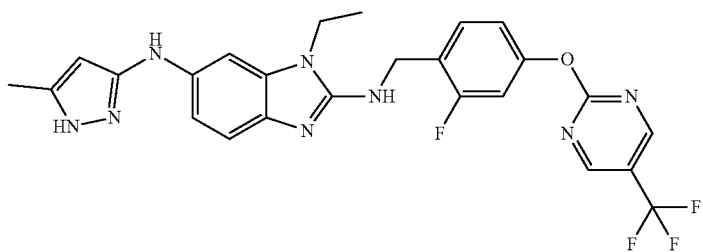 |
| 541 | 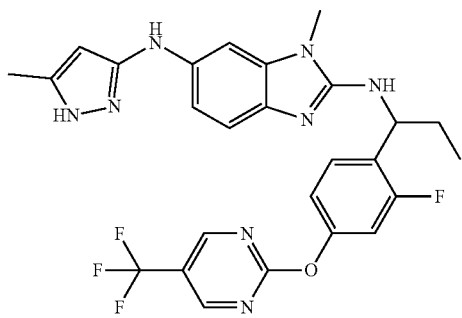 [SMILES: CCC(Nc1nc2ccc(Nc3cc(C)[nH]n3)cc2n1C)c1ccc(Oc2ncc(C(F)(F)F)cn2)cc1F] |
| 542 | 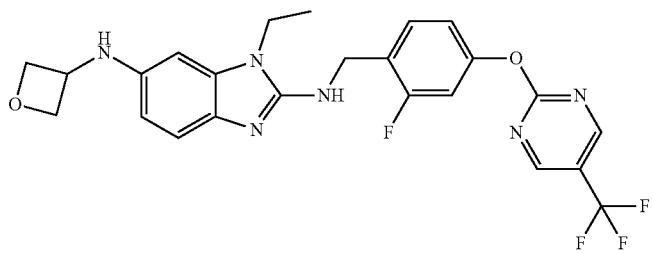 [SMILES: CCn1c(NCc2ccc(Oc3ncc(C(F)(F)F)cn3)cc2F)nc2ccc(NC3COC3)cc21] |
| 543 | 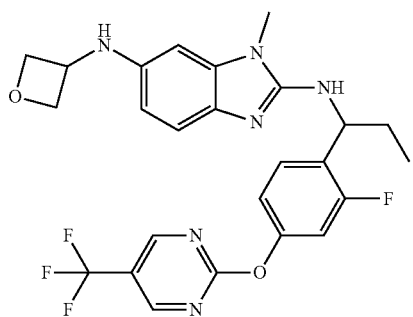 |

| No. | Structure |
|---|---|
| 544 | 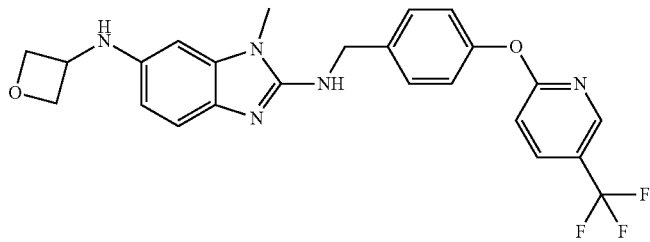 [SMILES: Cn1c(NCc2ccc(Oc3ccc(C(F)(F)F)cn3)cc2)nc2ccc(NC3COC3)cc21] |
| 545 | 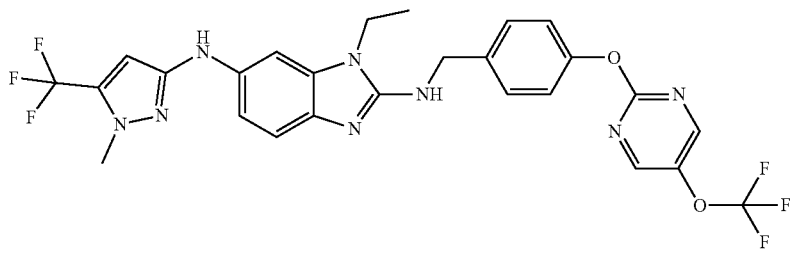 [SMILES: CCn1c(NCc2ccc(Oc3ncc(OC(F)(F)F)cn3)cc2)nc2ccc(Nc3cc(C(F)(F)F)n(C)n3)cc21] |
| 546 | 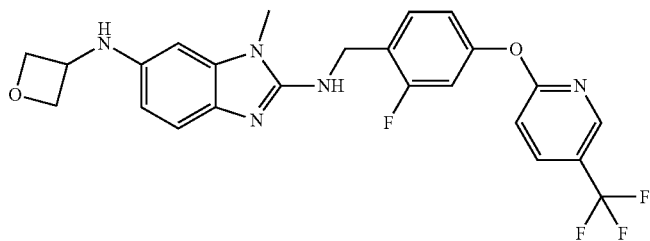 |
| 547 | 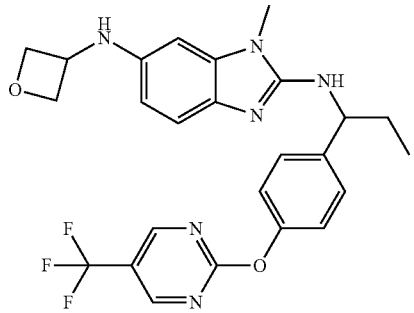 |
| 548 | 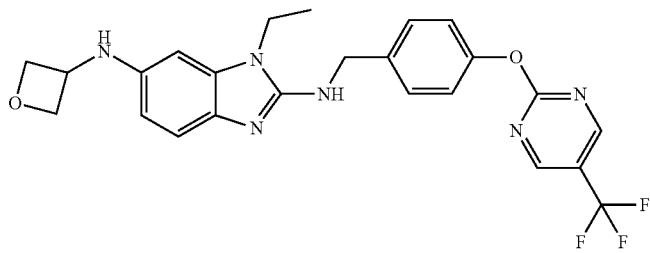 [SMILES: CCn1c(NCc2ccc(Oc3ncc(C(F)(F)F)cn3)cc2)nc2ccc(NC3COC3)cc21] |

| No. | Structure |
|---|---|
| 549 | [chemical structure: 1-methyl-6-(oxetan-3-ylamino)-benzimidazol-2-yl amine linked via CH(Et) to phenyl-O-(5-trifluoromethylpyridin-2-yl)] |
| 550 | [chemical structure: 1-methyl-6-(oxetan-3-ylamino)-benzimidazol-2-yl amine linked via CH(Et) to 2-fluoro-4-((5-trifluoromethylpyridin-2-yl)oxy)phenyl] |
| 551 | [chemical structure: 4-fluoro-1-methyl-6-(oxetan-3-ylamino)-benzimidazol-2-yl-NH-CH2-phenyl-O-(5-trifluoromethylpyrimidin-2-yl)] |
| 552 | [chemical structure: 4-fluoro-1-methyl-6-(oxetan-3-ylamino)-benzimidazol-2-yl-NH-CH2-phenyl-O-(5-trifluoromethylpyridin-2-yl)] |
| 553 | [chemical structure: 4-fluoro-1-methyl-6-(oxetan-3-ylamino)-benzimidazol-2-yl-NH-CH2-phenyl-O-(5-chloropyridin-2-yl)] |
| 556 | [chemical structure: 4-chloro-1-methyl-6-((5-methyl-1H-pyrazol-3-yl)amino)-benzimidazol-2-yl-NH-CH2-phenyl-O-(5-chloropyrimidin-2-yl)] | or a pharmaceutically acceptable salt thereof.

19. The compound, according to claim 13, having one of the following formulae:

| No. | Structure |
|---|---|
| 53 | 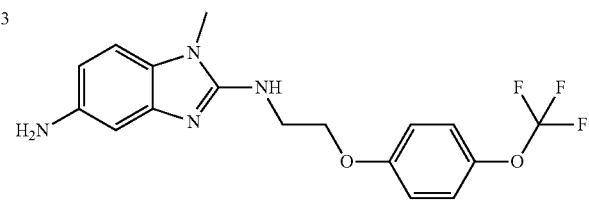 |
| 184 | 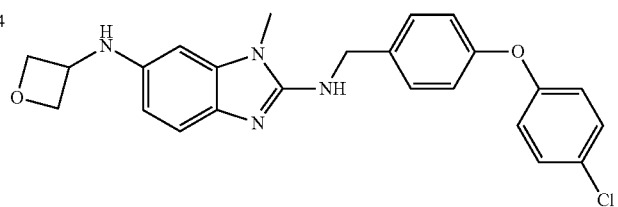 |
| 193 | 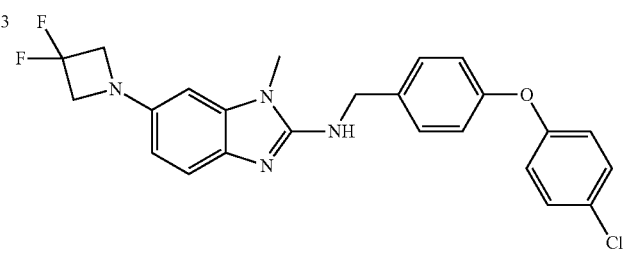 |
| 204 | 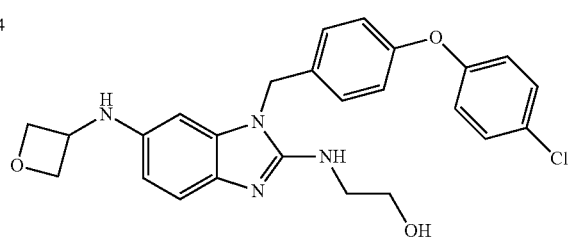 |
| 211 | 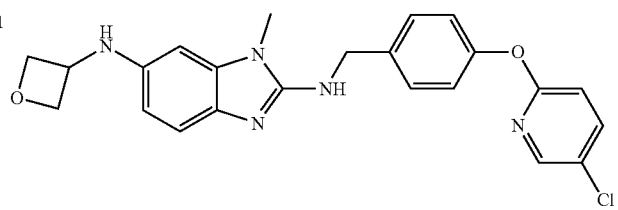 |
| 226 | 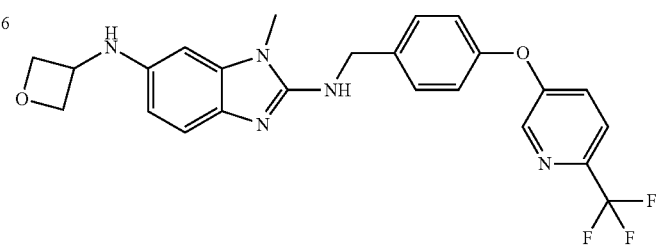 |
| 227 | 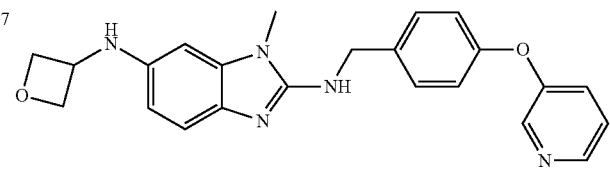 |

| No. | Structure |
|---|---|
| 251 | 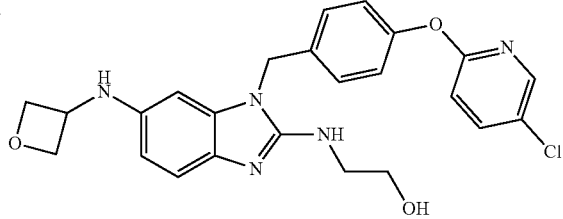 [SMILES: OCCNc1nc2ccc(NC3COC3)cc2n1Cc1ccc(Oc2ccc(Cl)cn2)cc1] |
| 256 | 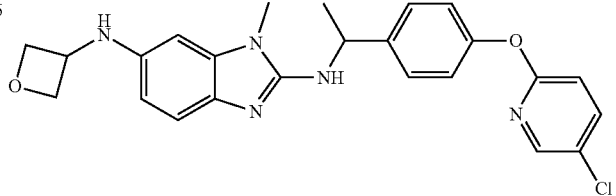 |
| 268 | 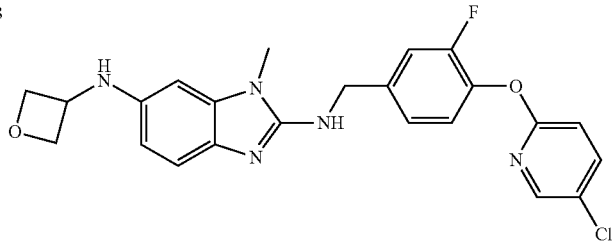 |
| 269 | 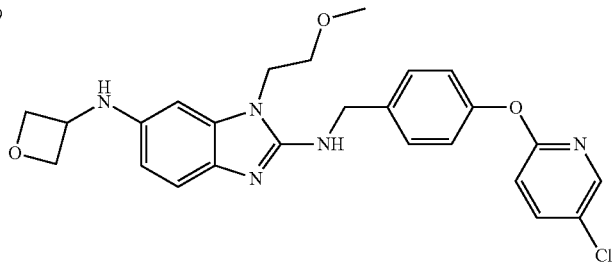 |
| 270 | 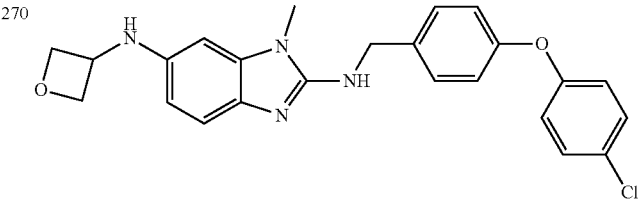 |
| 271 | 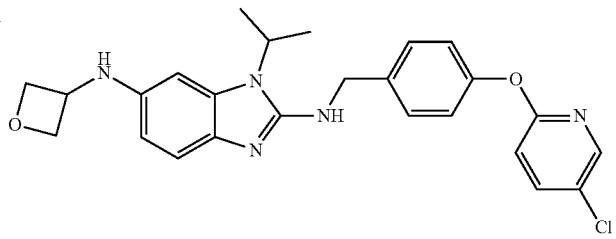 [SMILES: CC(C)n1c(NCc2ccc(Oc3ccc(Cl)cn3)cc2)nc2ccc(NC3COC3)cc21] |

| No. | Structure |
|---|---|
| 275 | 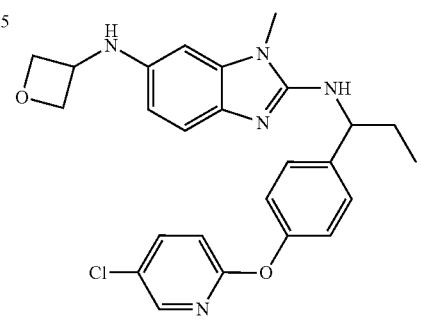 |
| 279 | 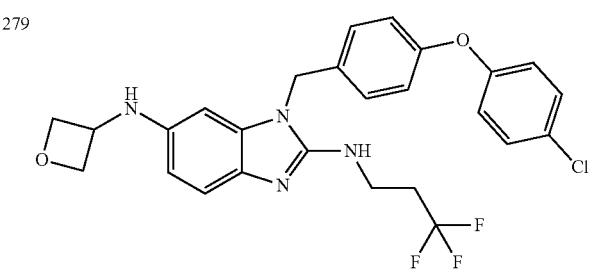 |
| 281 | 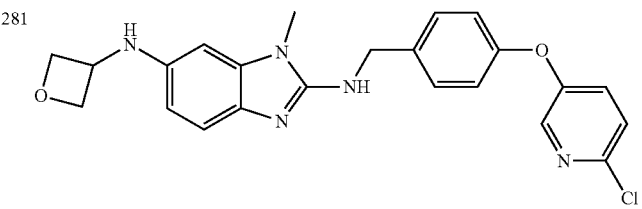 |
| 284 | 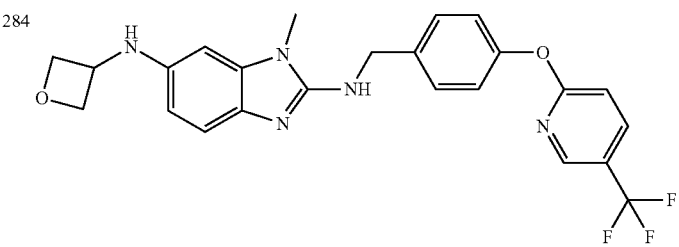 |
| 289 | 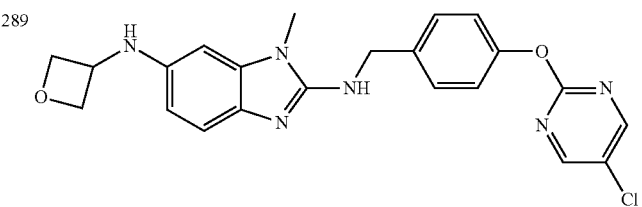 |
| 296 | 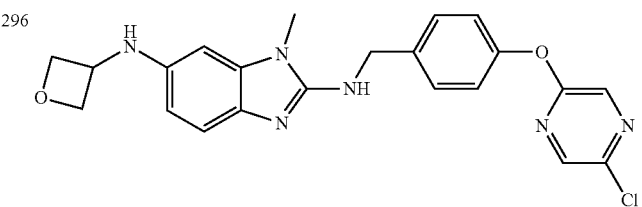 |

| No. | Structure |
|---|---|
| 306 | 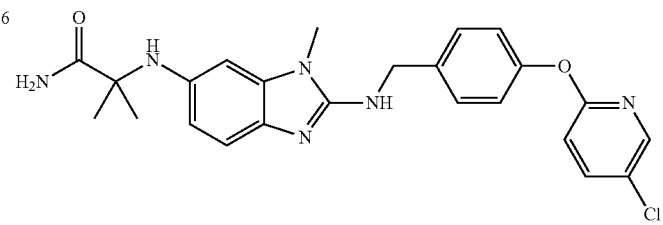 |
| 324 | 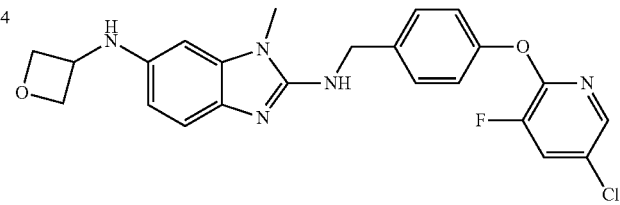 |
| 328 | 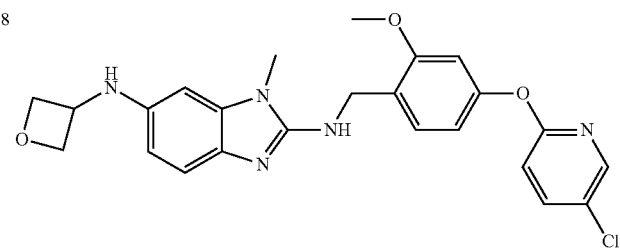 |
| 341 | 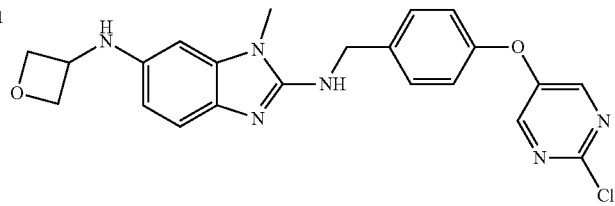 |
| 345 | 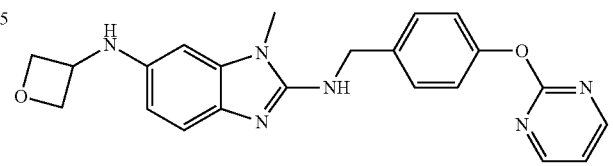 |
| 351 | 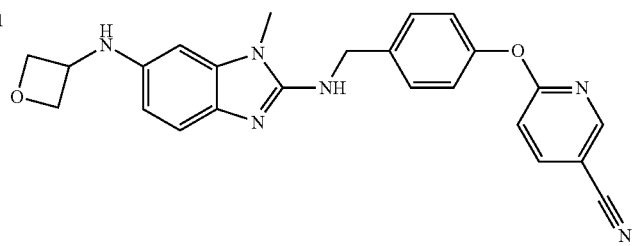 |
| 358 | 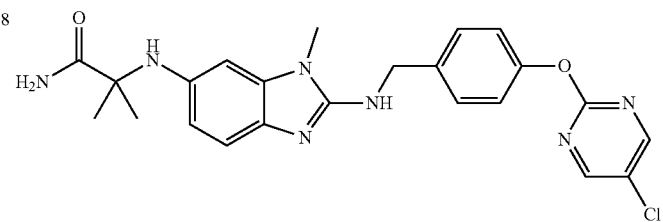 |

| No. | Structure |
|---|---|
| 362 | 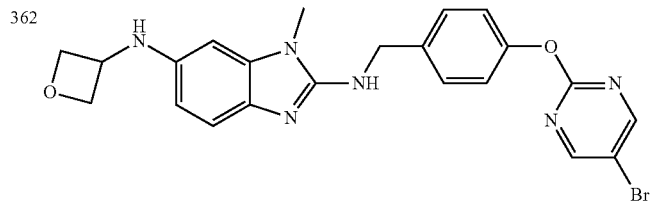 |
| 368 | 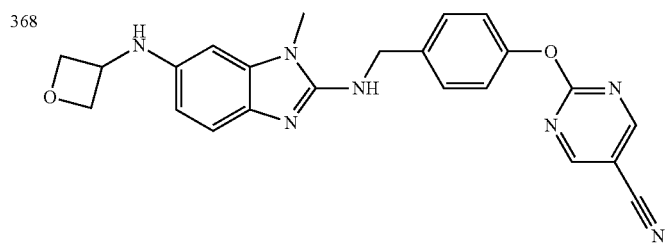 |
| 369 | 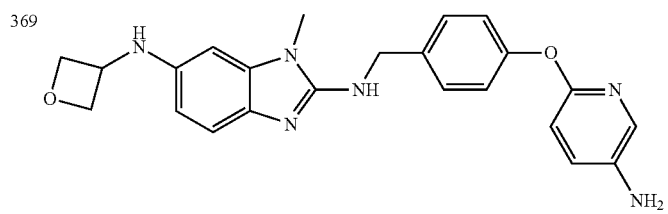 |
| 374 | 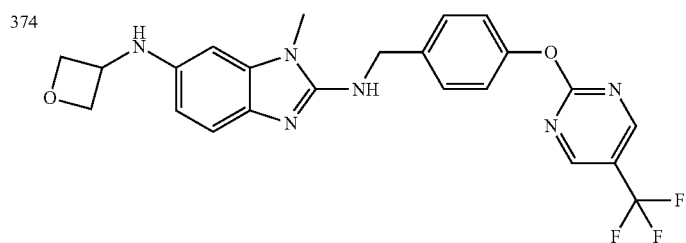 |
| 378 | 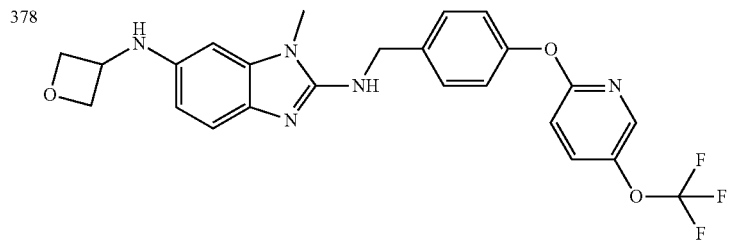 |
| 381 | 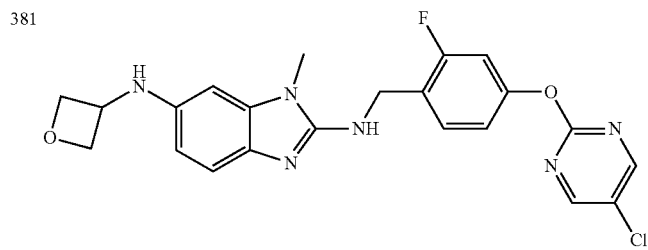 |

| No. | Structure |
|---|---|
| 392 | 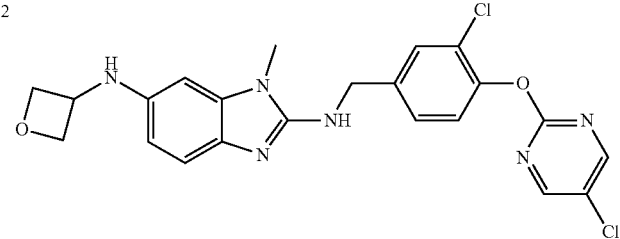 |
| 412 | 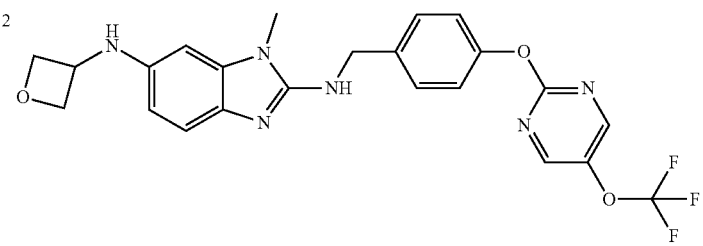 |
| 413 | 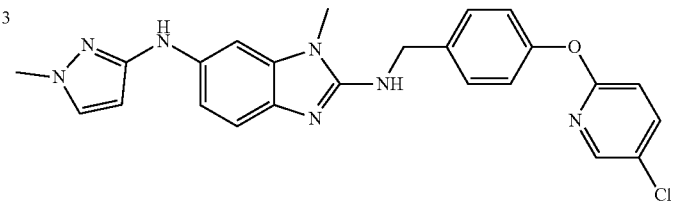 |
| 414 | 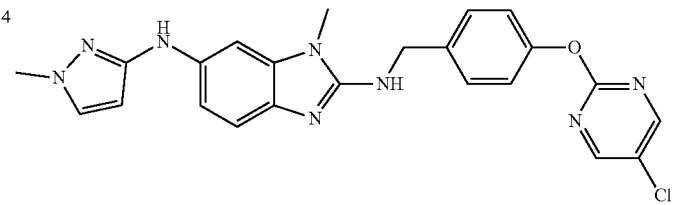 |
| 415 | 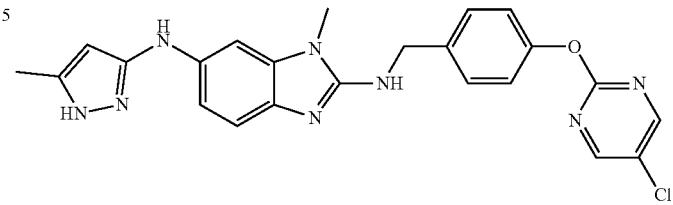 |
| 431 | 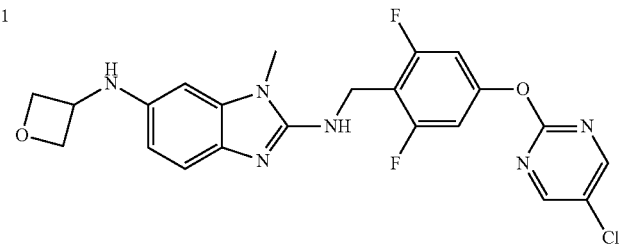 |

-continued
| No. | Structure |
|---|---|
| 433 | 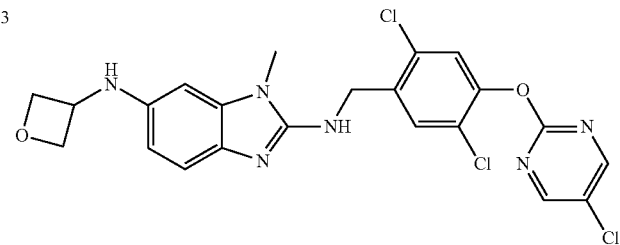 |
| 447 | 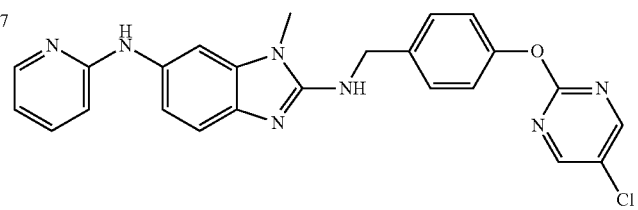 |
| 448 | 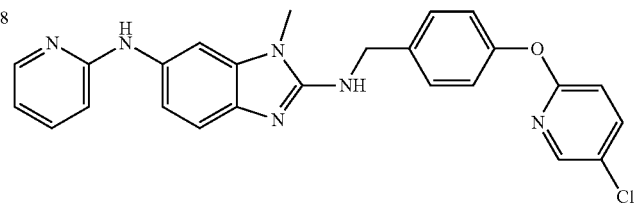 |
| 449 | 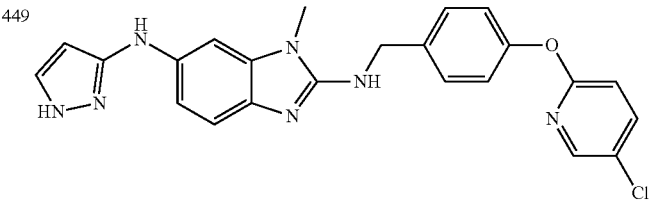 |
| 450 | 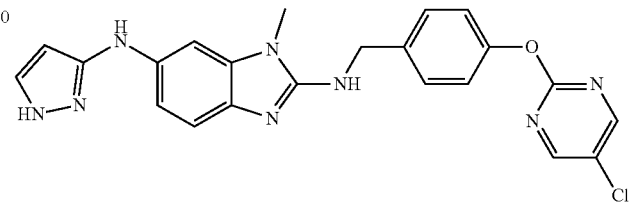 |
| 461 | 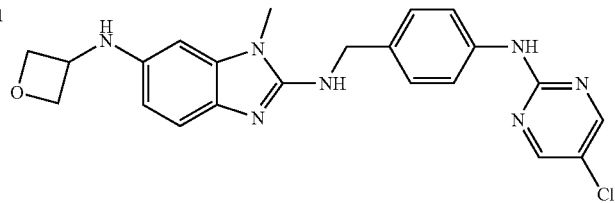 |
| 464 | 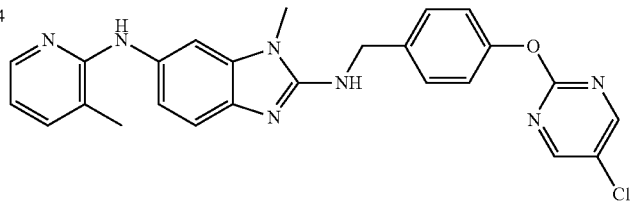 |

| No. | Structure |
|---|---|
| 465 | 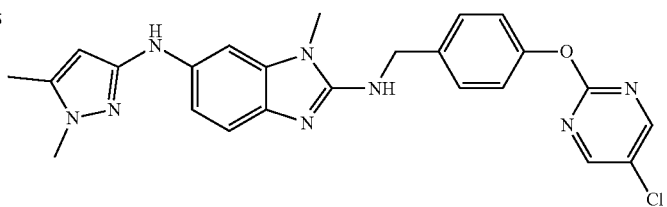 |
| 466 | 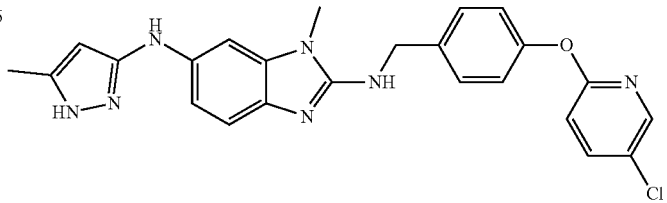 |
| 468 | 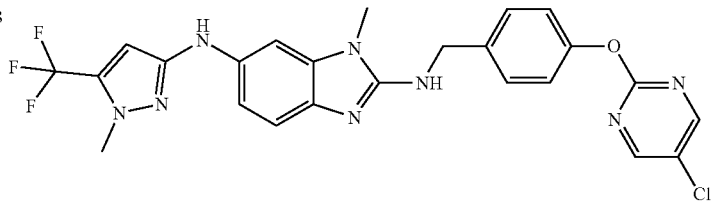 |
| 469 | 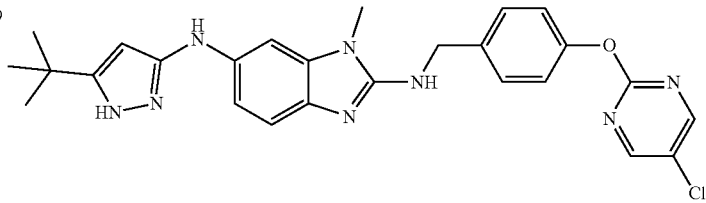 |
| 471 | 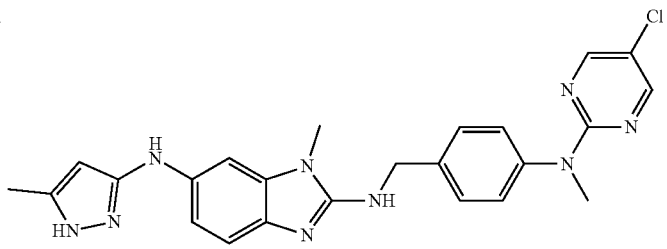 [SMILES: Cc1cc(Nc2ccc3nc(NCc4ccc(N(C)c5ncc(Cl)cn5)cc4)n(C)c3c2)n[nH]1] |
| 473 | 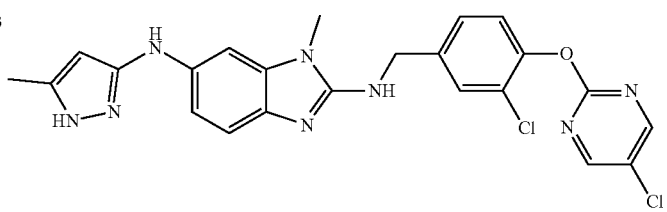 |
| 474 | 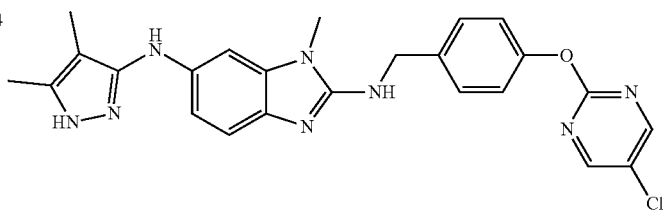 |

| No. | Structure |
|---|---|
| 475 | 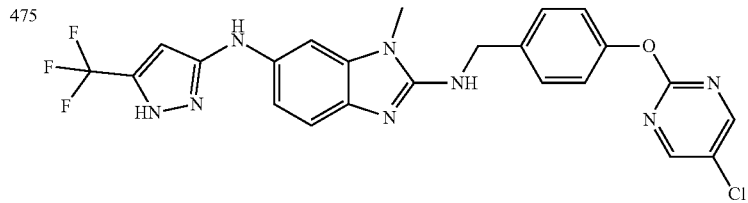 |
| 476 | 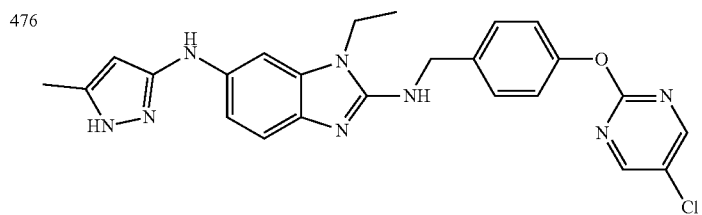 |
| 477 | 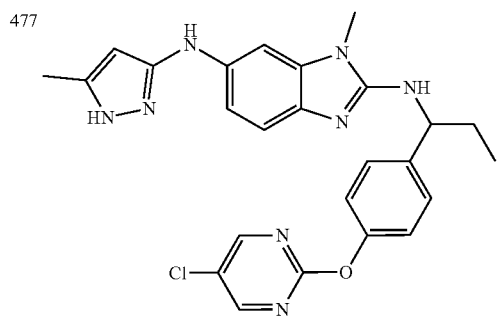 |
| 479 | 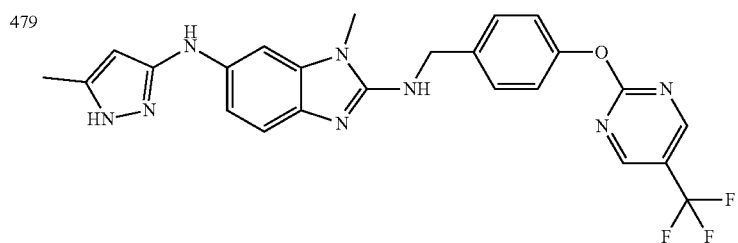 |
| 481 | 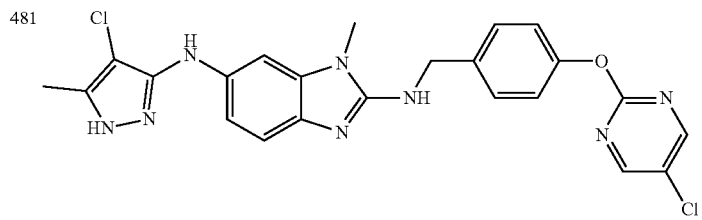 |
| 482 | 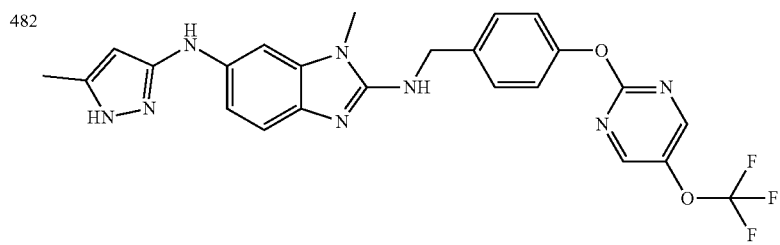 |

| No. | Structure |
|---|---|
| 486 | 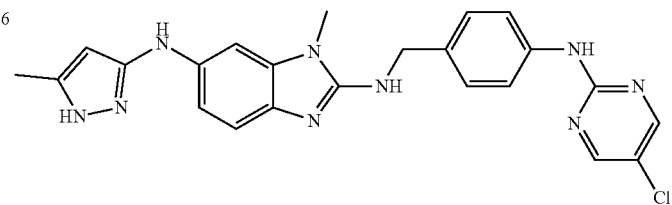 |
| 487 | 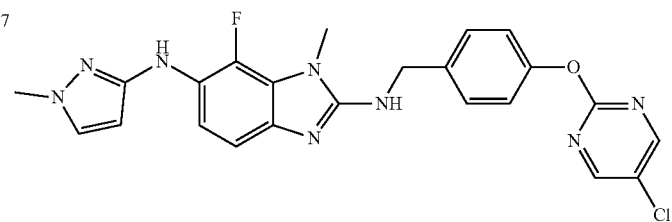 |
| 489 | 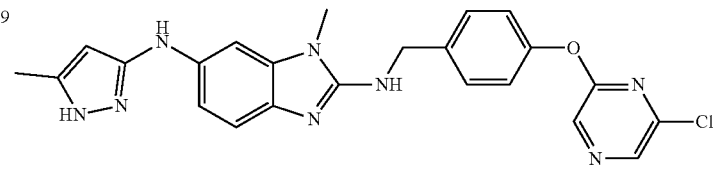 |
| 490 | 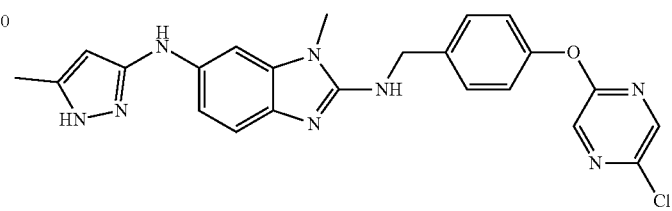 |
| 491 | 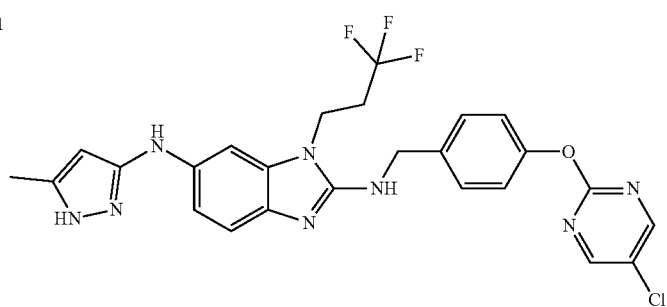 |
| 492 | 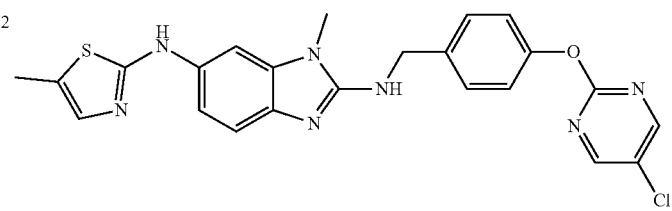 |
| 493 | 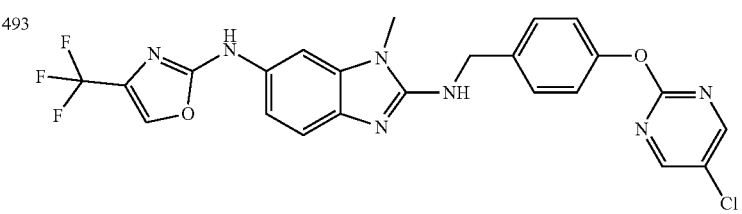 |

| No. | Structure |
|---|---|
| 494 | 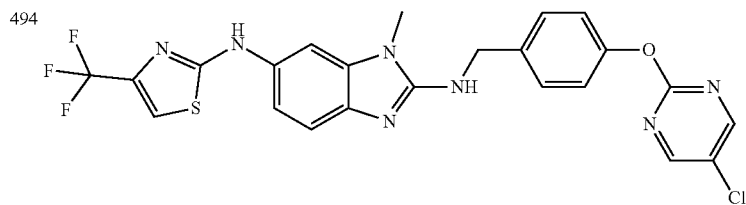 |
| 495 | 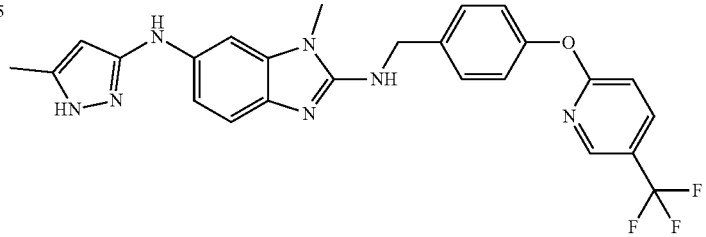 |
| 496 | 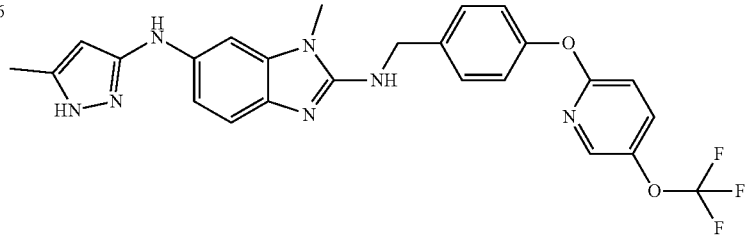 |
| 498 | 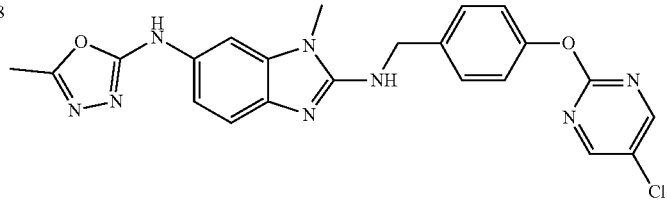 |
| 499 | 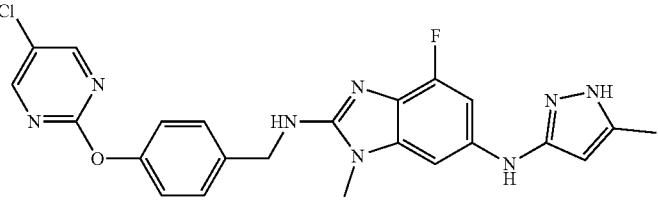 |
| 501 | 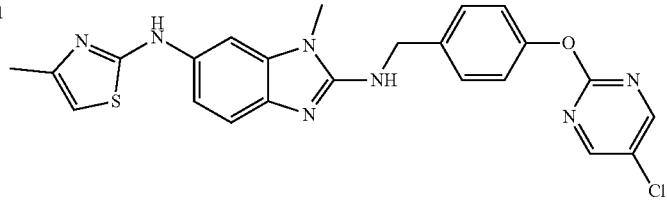 |
| 502 | 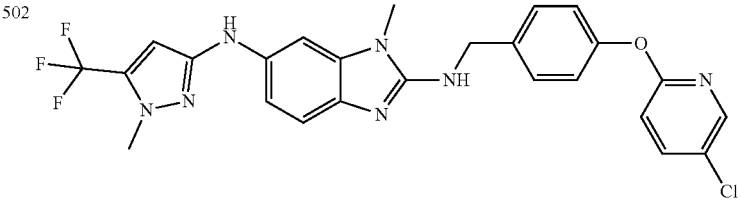 |

| No. | Structure |
|---|---|
| 503 | 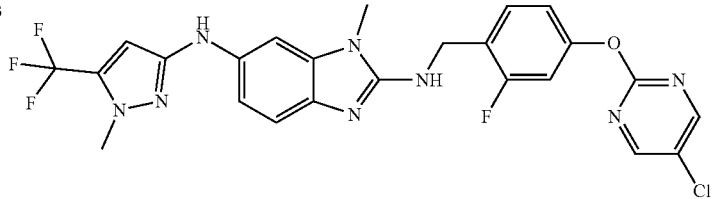 |
| 504 | 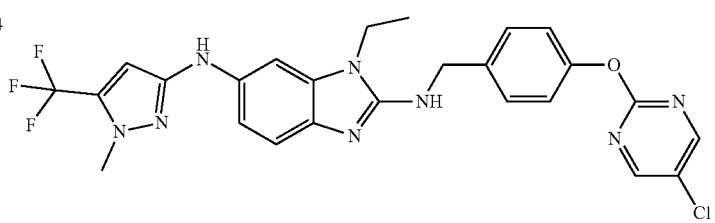 |
| 505 | 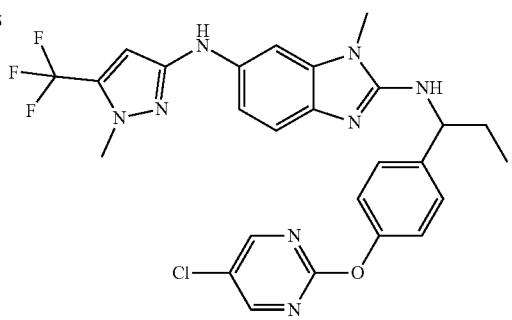 |
| 506 | 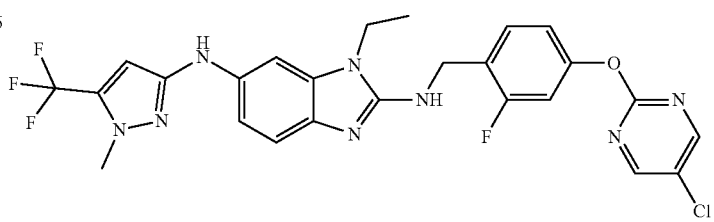 |
| 508 | 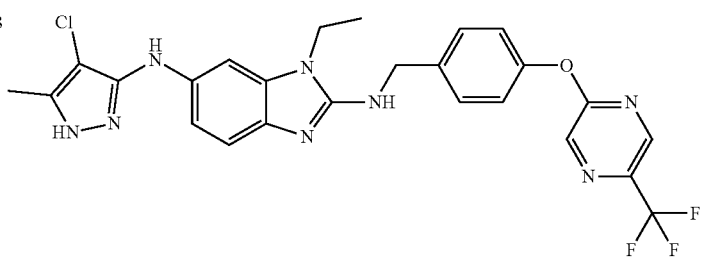 |
| 509 | 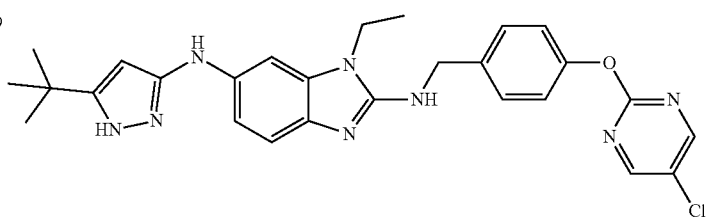 |

| No. | Structure |
|---|---|
| 512 | 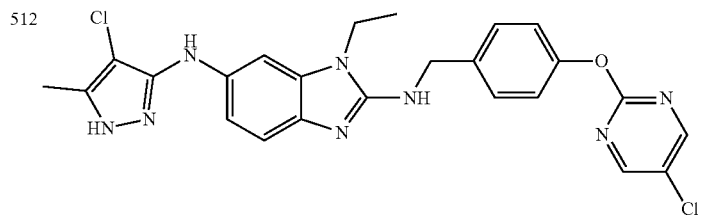 |
| 513 | 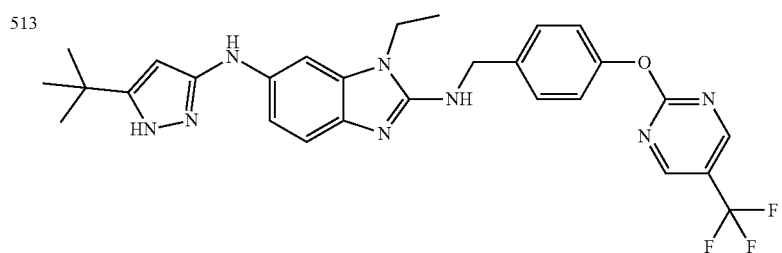 |
| 514 | 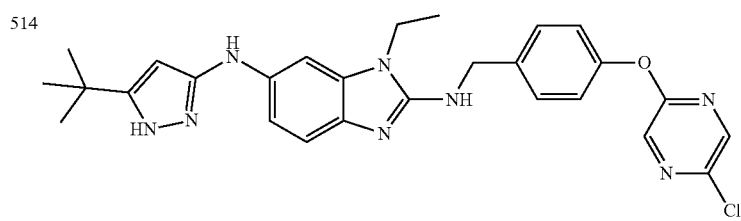 |
| 516 | 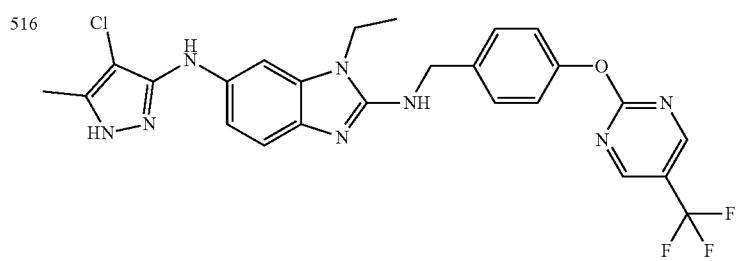 |
| 517 | 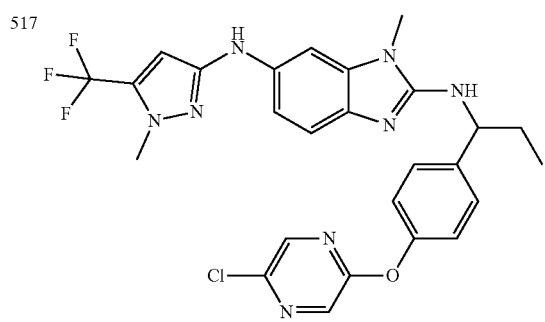 |
| 518 | 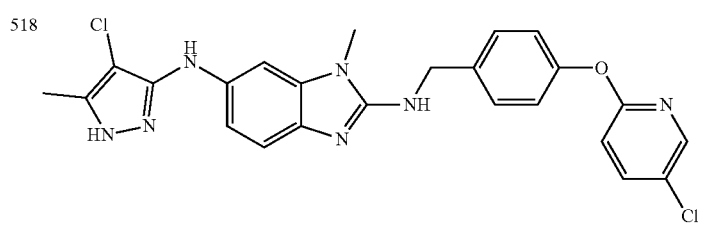 |

| No. | Structure |
|---|---|
| 519 | 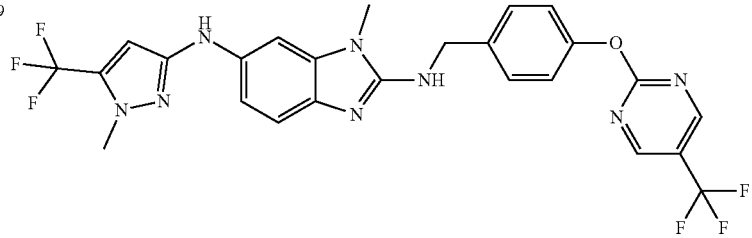 |
| 525 | 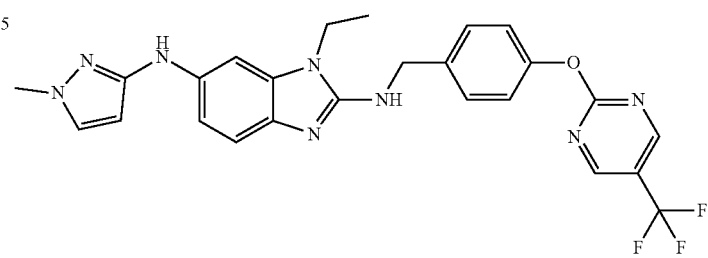 |
| 526 | 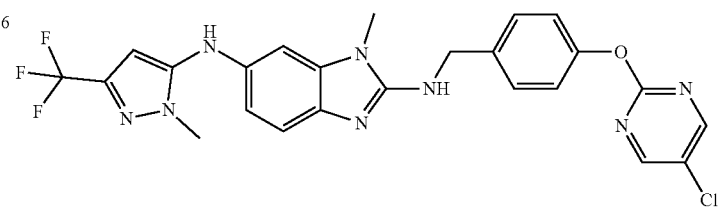 |
| 527 | 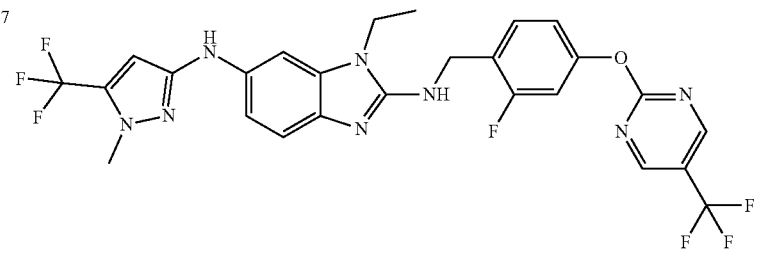 |
| 528 | 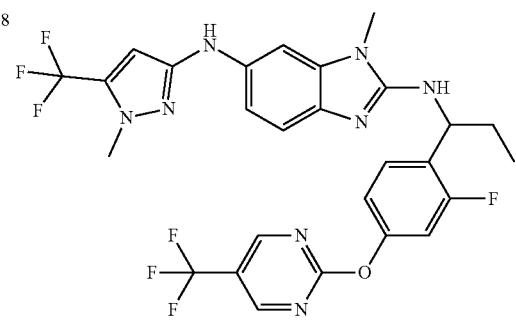 |
| 529 | 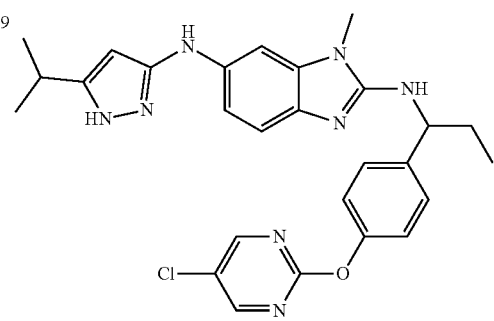 |

| No. | Structure |
|---|---|
| 530 | 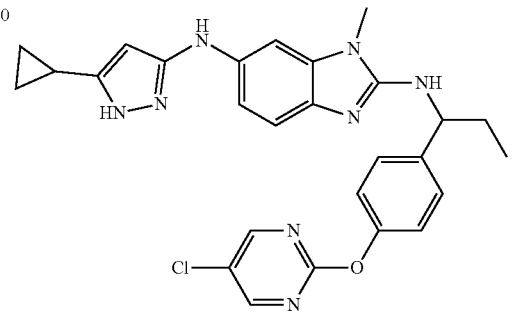 |
| 531 | 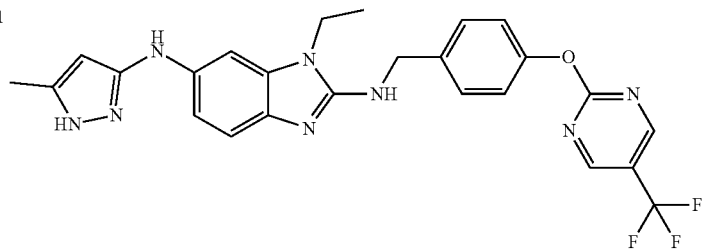 |
| 532 | 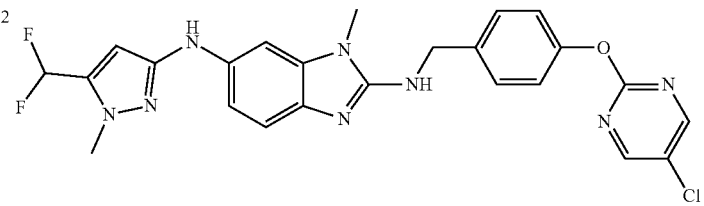 |
| 533 | 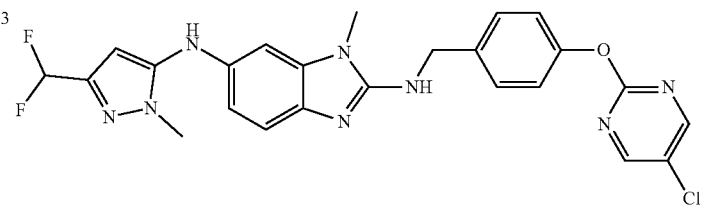 |
| 534 | 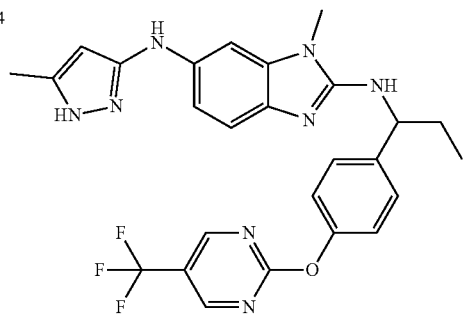 |

| No. | Structure |
|---|---|
| 535 | 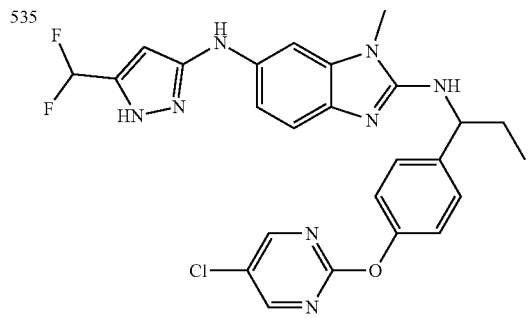 |
| 536 | 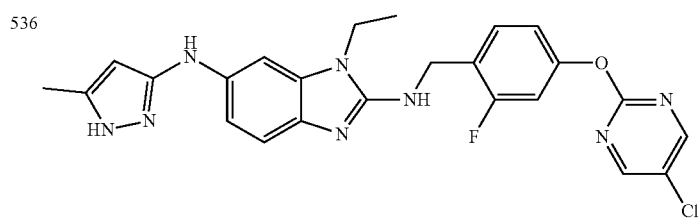 |
| 537 | 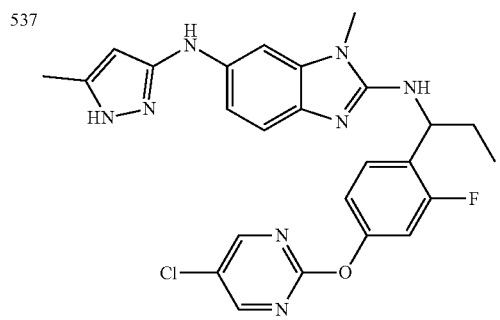 |
| 538 | 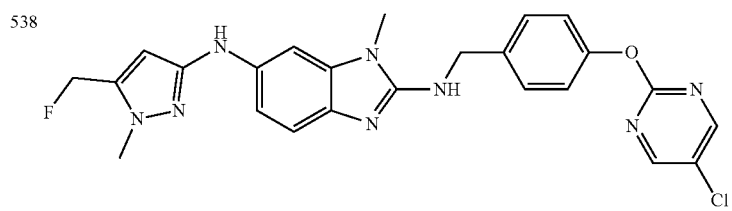 |
| 540 | 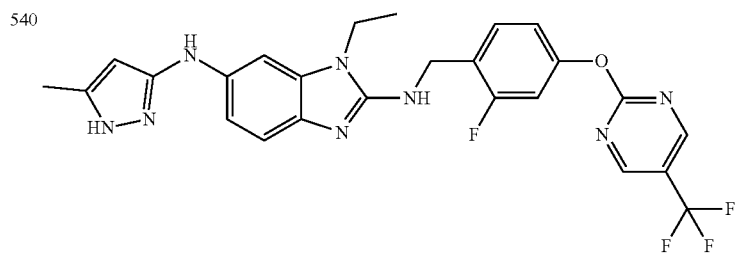 |

| No. | Structure |
|---|---|
| 541 | 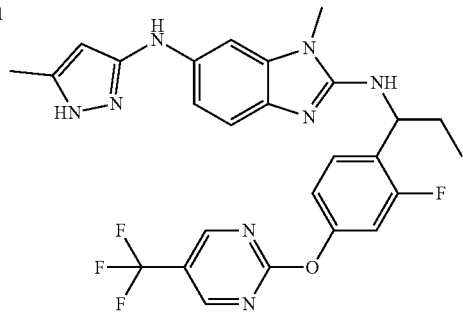 |
| 542 | 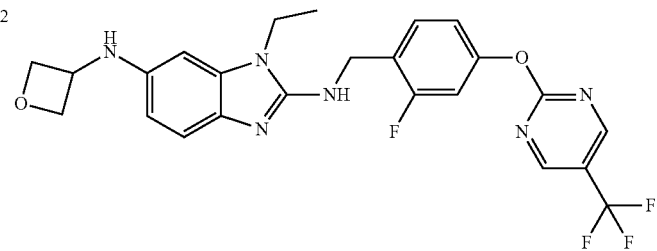 |
| 543 | 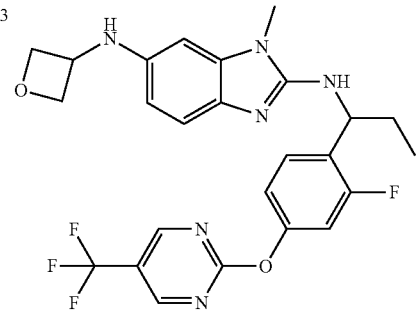 |
| 544 | 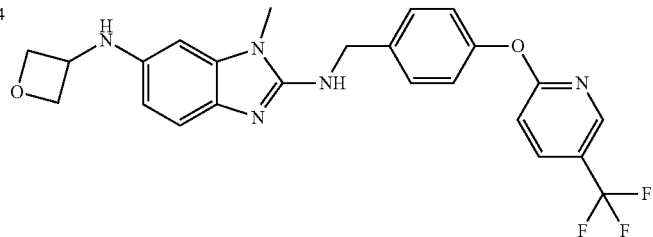 |
| 545 | 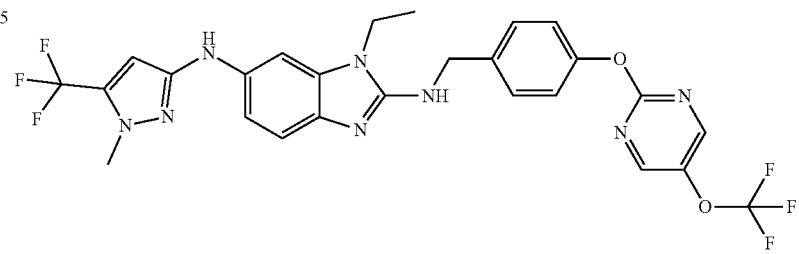 |

-continued
| No. | Structure |
|---|---|
| 546 | 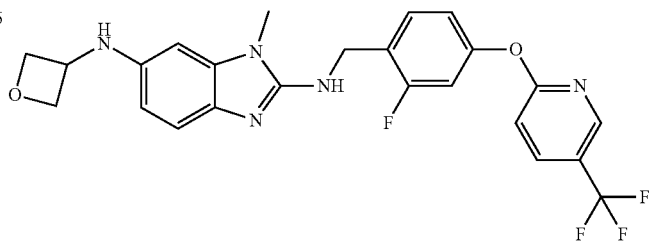 |
| 547 | 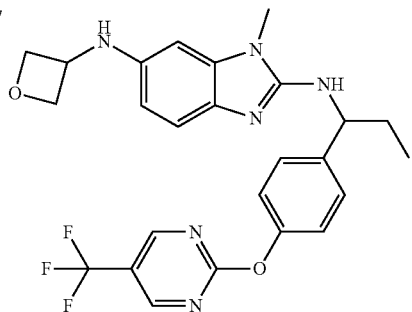 |
| 550 | 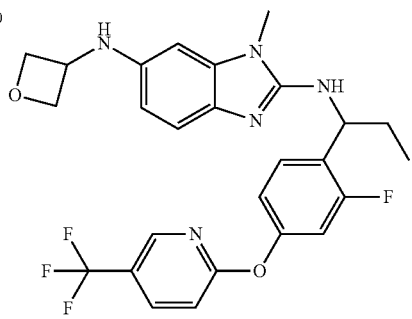 |
| 553 | 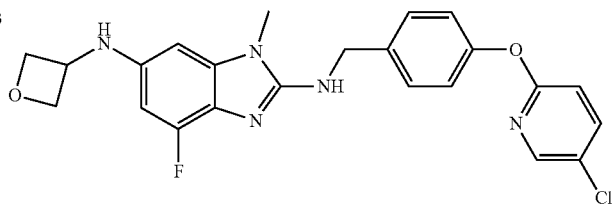 |
| 554 | 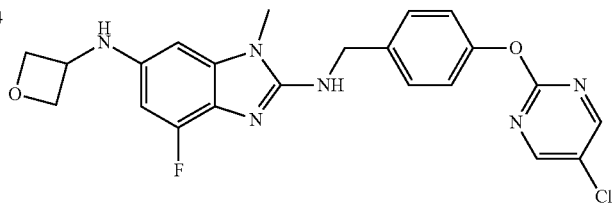 |
or a pharmaceutically acceptable salt thereof.
* * * * *

UNITED STATES PATENT AND TRADEMARK OFFICE
CERTIFICATE OF CORRECTION

PATENT NO. : 11,447,486 B2  Page 1 of 8
APPLICATION NO. : 15/327560
DATED : September 20, 2022
INVENTOR(S) : Kim et al.

It is certified that error appears in the above-identified patent and that said Letters Patent is hereby corrected as shown below:

In the Specification

Column 1,

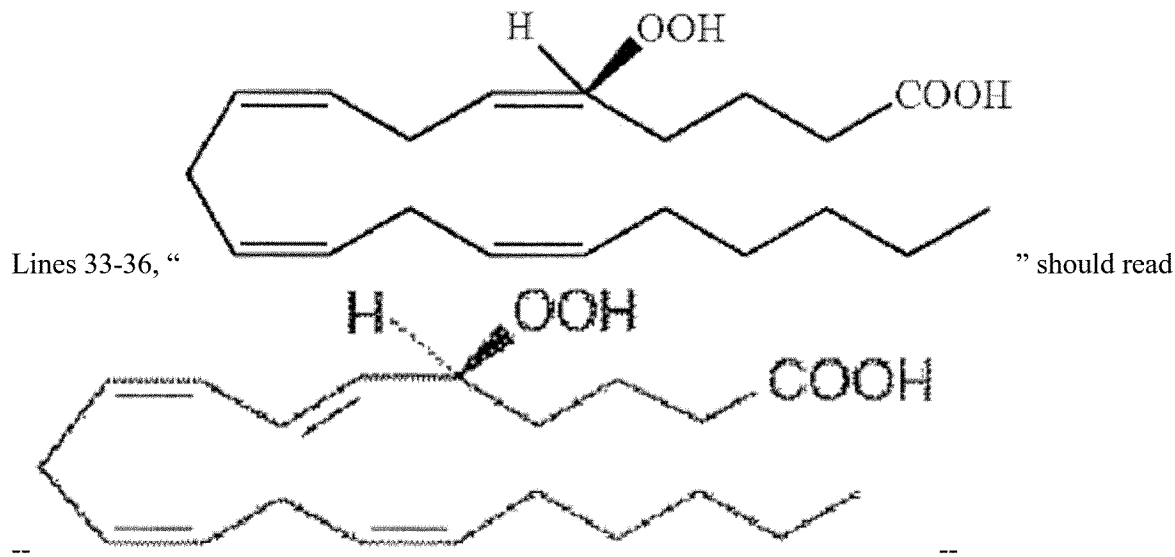

Lines 33-36, " " should read -- --

Column 9,

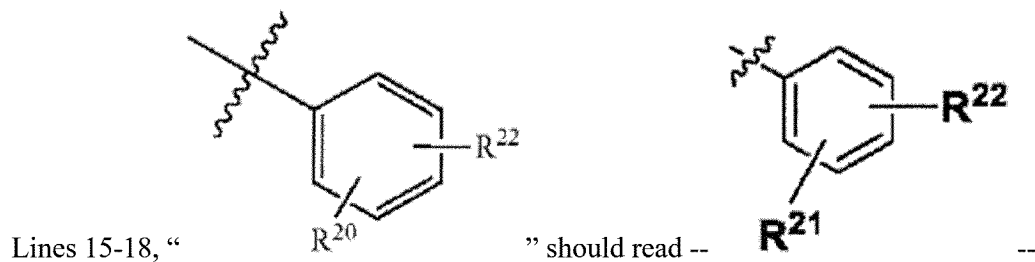

Lines 15-18, " " should read -- --

Signed and Sealed this
Twenty-seventh Day of June, 2023

Katherine Kelly Vidal
*Director of the United States Patent and Trademark Office*

Column 28,
Lines 59-66, " 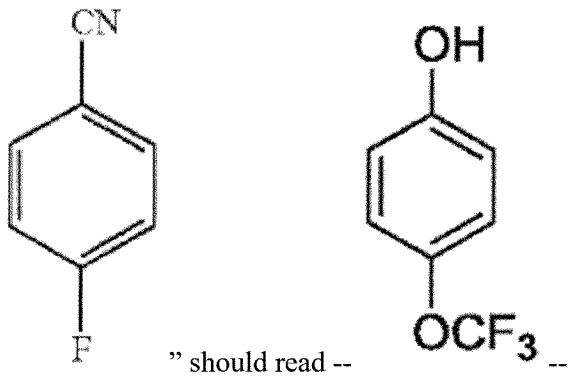 " should read -- --
Column 34,
Lines 22-26, " 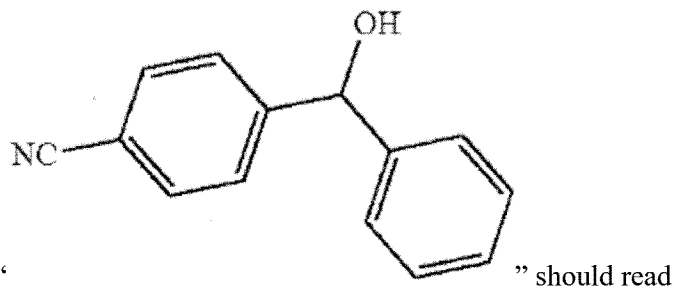 " should read
-- 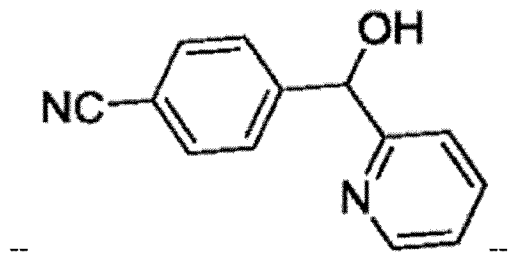 --
Column 34,
Lines 32-36, " 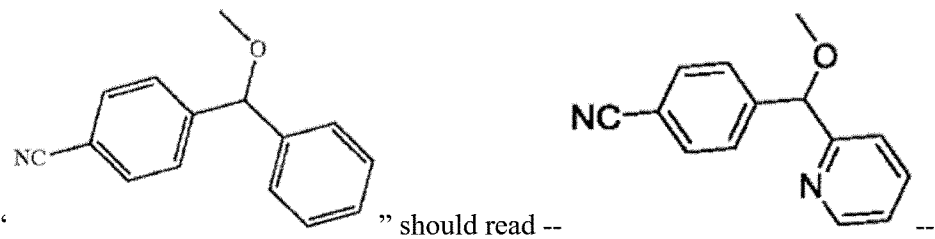 " should read -- --
Column 36,
Line 13, "with 1μM NaOH" should read --with 12M NaOH--
Column 37,
Line 54, "afford a crude," should read --afford a crude product,--
Column 40,

CERTIFICATE OF CORRECTION (continued)
U.S. Pat. No. 11,447,486 B2

Lines 56-59, scheme 15 " 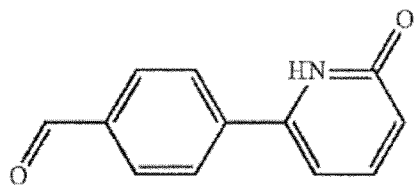 O1 " should read

-- 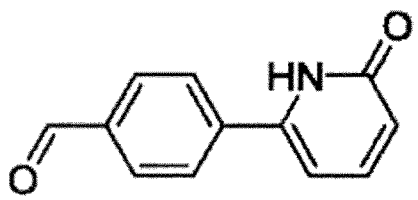 O1 --

Column 44,
Line 19, "solution of R4" should read --solution of R3--

Column 45,
Lines 36-37, scheme 20 "  " should read --  --

Column 47,

Lines 55-59, scheme 21 " 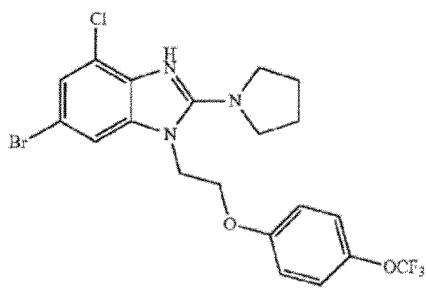 U6 " should read

-- 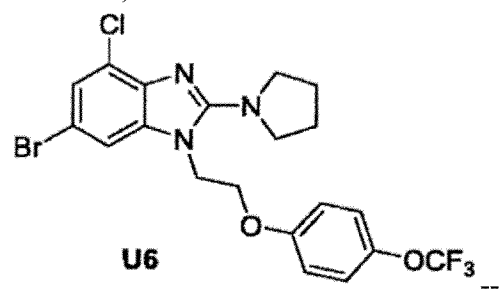 U6 --

Column 53,

Line 10, "extracts was" should read --extracts were--
Column 93,
Lines 16-20, chemical drawing 37 " 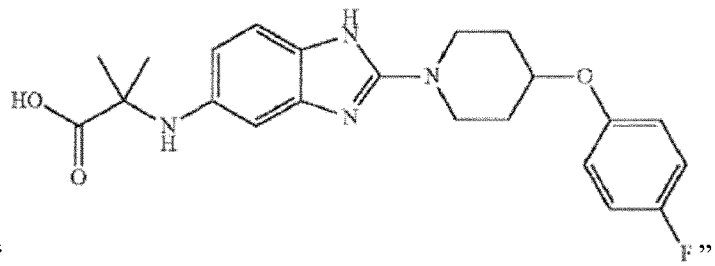"
should read -- 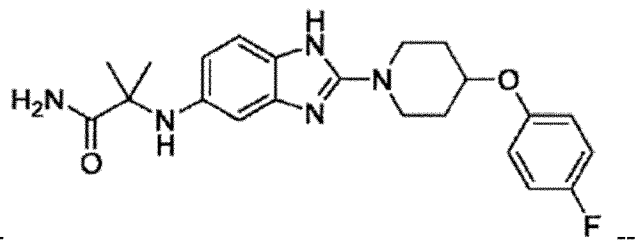 --
Column 105,
Lines 21-25, chemical drawing 76
" 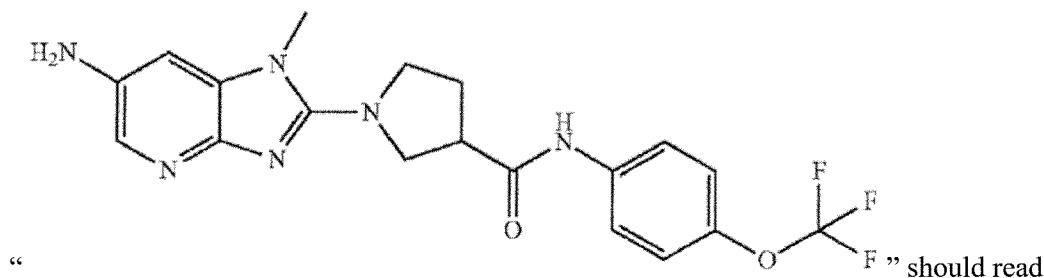 " should read
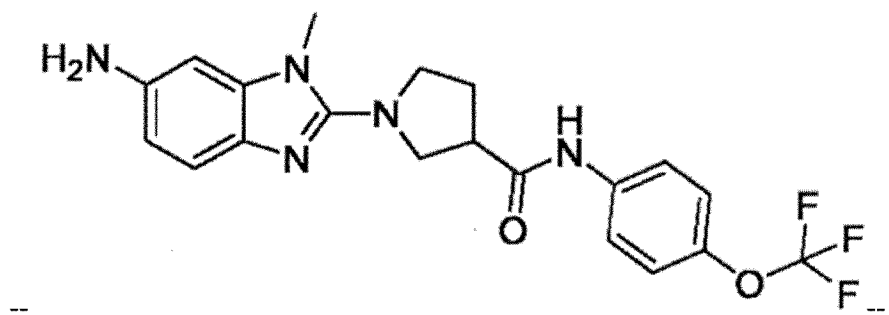
--
Column 187,

CERTIFICATE OF CORRECTION (continued)
U.S. Pat. No. 11,447,486 B2

Lines 20-24, chemical drawing 354 " 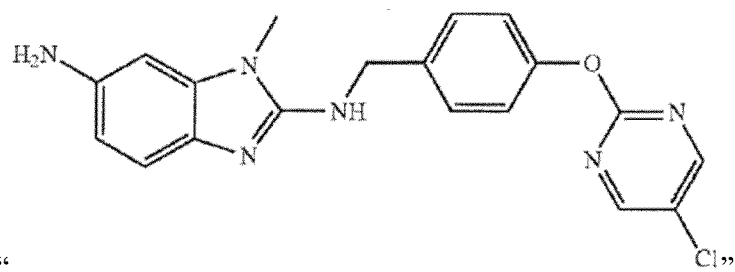

should read -- 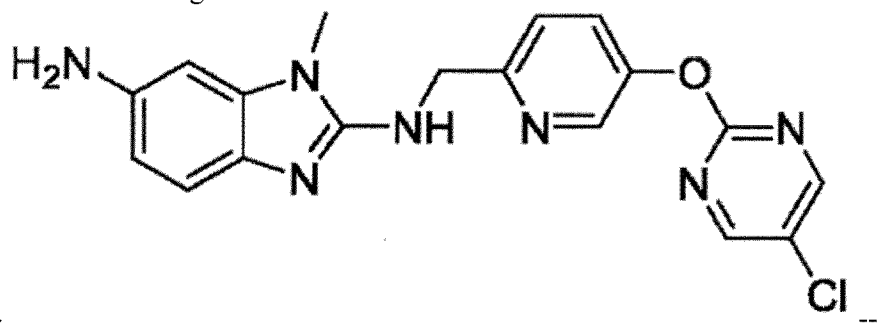 --

Column 229,
Lines 32-34, chemical drawing 486

" 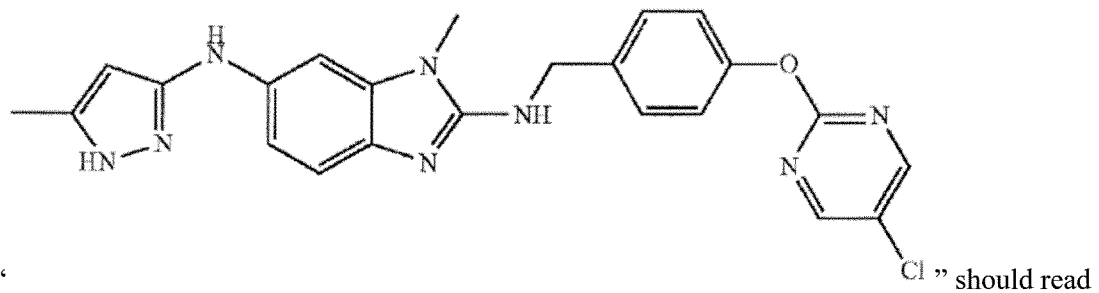 " should read

-- 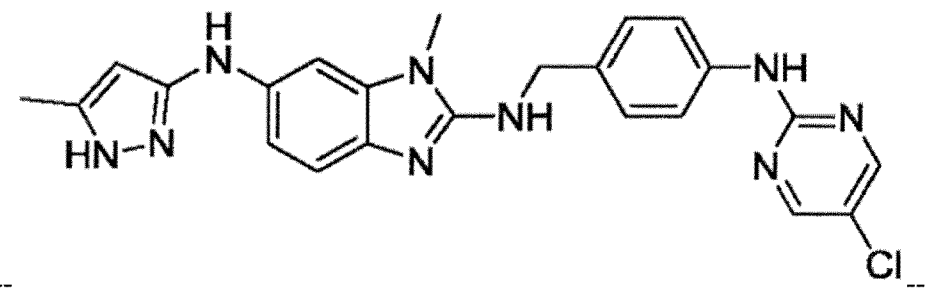 --

Column 233,

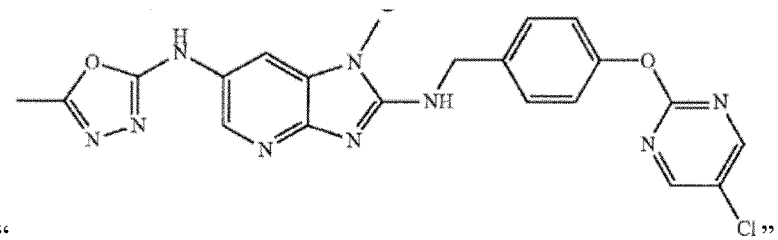

Lines 14-19, chemical drawing 498 "

CERTIFICATE OF CORRECTION (continued)
U.S. Pat. No. 11,447,486 B2

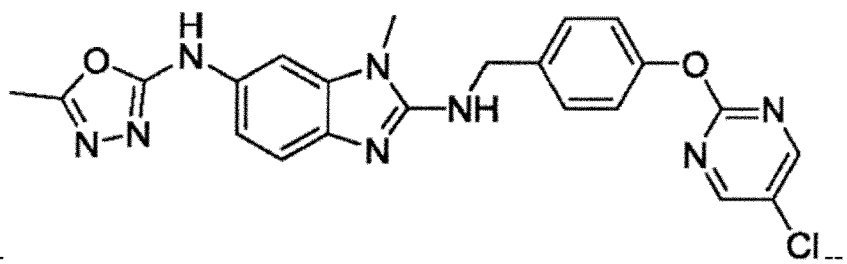

should read --

Column 247,
Lines 56-60, chemical drawing 544

" 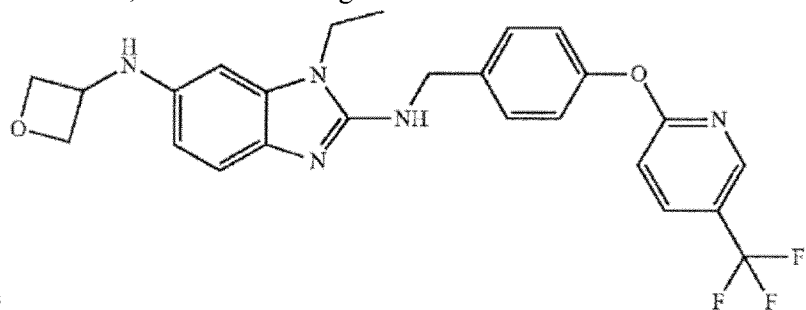 " should read

-- 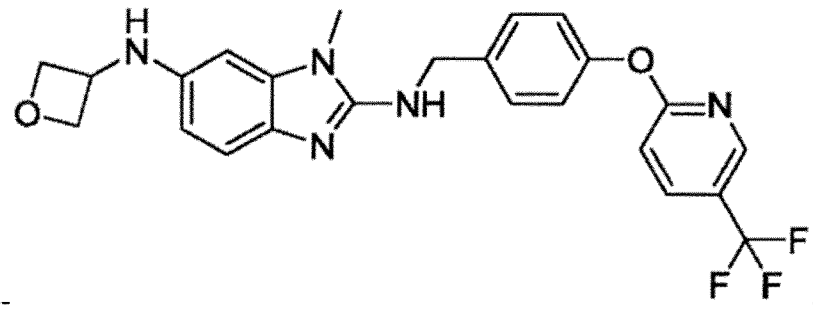 --

Column 259,
Line 15, paragraph #52 "m/z 366.9" should read --m/z 336.9--

Column 265,
Line 21, paragraph #110 "m/z 379.0" should read --m/z 379.0 [M+H] +.--

Column 299,
Line 17, paragraph #340 "381 [M+H]+." should read --381.0 [M+H]+.--

Column 305,
Line 79, paragraph #393 "381.00 [M+H]+." should read --381.0 [M+H]+.--

Column 307,
Line 54, paragraph #402 "420 [M+H]+." should read --420.1 [M+H]+.--

CERTIFICATE OF CORRECTION (continued)
U.S. Pat. No. 11,447,486 B2

In the Claims

Column 336,
Line 61, Claim 3, "R14 is" should read --$R^{14}$ is--

Column 341,

Lines 45-47, Claim 11, " 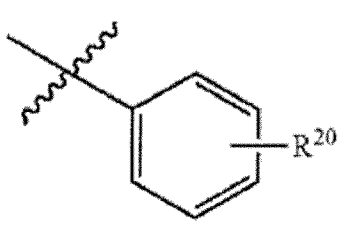 " should read -- 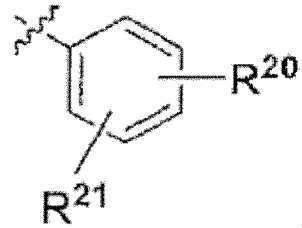 --

Column 349,
Claim 13, structure #144 is missing in patent

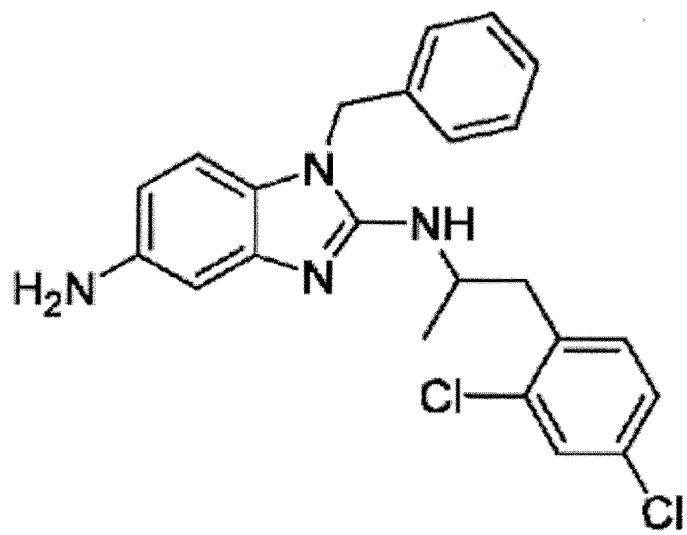

Column 407,

Claim 13, structure #527 " 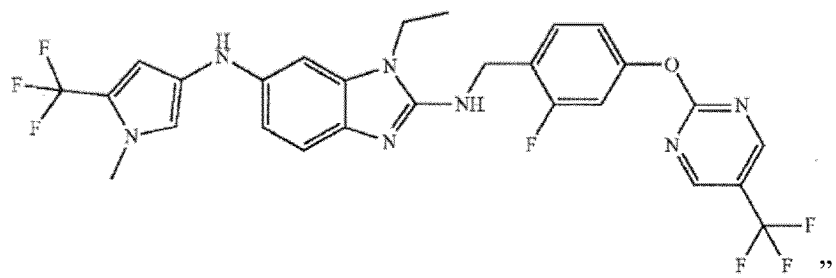 "

CERTIFICATE OF CORRECTION (continued)
U.S. Pat. No. 11,447,486 B2

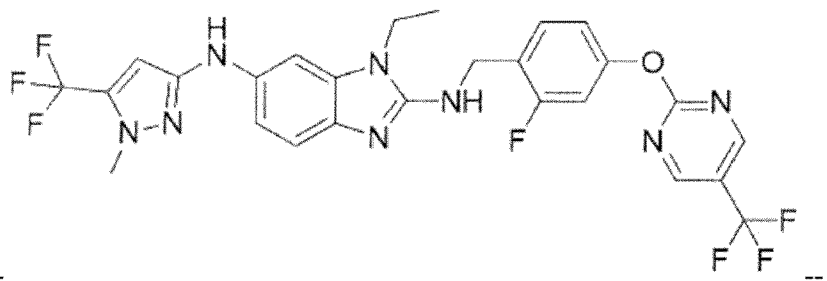

should read --

Column 407,

Claim 13, structure 528 " 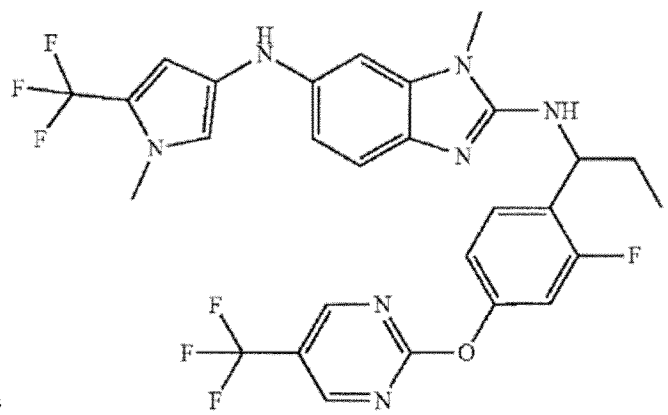 " should read

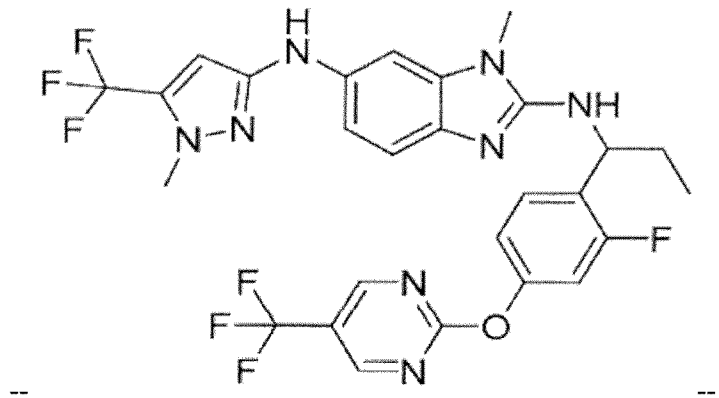

-- --

Column 417,
Lines 48-49, Claim 14, "and-NH-($R^9$), -$R^{10}$" should read --and-NH-($R^9$)$_n$-$R^{10}$,--

Column 420,
Line 66, Claim 14, "$C_3$-$C_1$ cycloalkenyl," should read --$C_3$-$C_{10}$ cycloalkenyl,--